(12) United States Patent
Parris et al.

(10) Patent No.: US 6,684,162 B2
(45) Date of Patent: Jan. 27, 2004

(54) METHODS FOR IDENTIFYING AGENTS THAT INTERACT WITH AN ACTIVE SITE OF ACYL CARRIER PROTEIN SYNTHASE-ACYL CARRIER PROTEIN COMPLEX

(75) Inventors: Kevin Delos Parris, Auburndale, MA (US); William Stuart Somers, Cambridge, MA (US); Amy Szepui Tam, Framingham, MA (US); Laura Long Lin, Weston, MA (US); Mark Lloyd Stahl, Lexington, MA (US); Robert Powers, Westford, MA (US); Guang-Yi Xu, Medford, MA (US)

(73) Assignees: Wyeth, Madison, NY (US); Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/770,834

(22) Filed: Jan. 25, 2001

(65) Prior Publication Data

US 2003/0211588 A1 Nov. 13, 2003

Related U.S. Application Data

(60) Provisional application No. 60/202,466, filed on May 8, 2000.

(51) Int. Cl.[7] .......................... G06F 19/00; G01N 33/53; G01N 31/00
(52) U.S. Cl. .............................. 702/27; 436/4; 435/7.1; 435/7.2
(58) Field of Search ............................... 702/27; 436/4, 436/7.1, 7.2

(56) References Cited

U.S. PATENT DOCUMENTS 6,160,092 A * 12/2000 Chen et al. .................. 530/350

OTHER PUBLICATIONS

Drenth, Principles of Protein X–ray Crystallography. 1995, Springer–Verlag, Second Edition, pp. 1–18.*

Huang et al., Crystal structure of B–ketoacyl–acyl carrier protein synthase II from *E. coli* reveals the molecular architecture of condensing enzymes. EMBO J., 17(5):1183–91, 1998.

Meurer and Hutchinson, Functional analysis of putative B–ketoacyl:acyl carrier protein synthase and acyltransferase active site motifs in a type II polyketide synthase of *Streptomyces glaucescens*. Journal of Bacteriology, 177(2):477–81, Jan. 1995.

Moche et al., Structure of the complex between the antibiotic cerulenin and its target, B–ketoacyl–acyl carrier protein synthase. The Journal of Biological Chemistry, 274(10):6031–34, Mar. 5, 1999.

Olsen et al., The X–ray crystal structure of B–ketoacyl [acyl carrier protein] synthase I. FEBS Letters, 460:46–52, 1999.

* cited by examiner

*Primary Examiner*—Ardin H. Marschel
*Assistant Examiner*—Carolyn Smith
(74) *Attorney, Agent, or Firm*—Amster, Rothstein & Ebenstein LLP

(57) ABSTRACT

This invention is directed to the crystal structure of Acyl Carrier Protein Synthase (ACPS) complexed with Acyl Carrier Protein (ACP), the solution structure of *B. subtilis* ACP, and to the use of these structures in rational drug design methods to identify agents that may interact with active sites of ACPS and ACP, and to the testing of these agents to identify agents that may represent novel antibiotics.

36 Claims, 98 Drawing Sheets

ACP

```
              10          20          30          40
GPLGS   ADTLERVTKI  IVDRLGVDEA  DVKLEASFKE  DLGADSLDVV
              50          60          70          76
        ELVMELEDEF  DMEISDEDAE  KIATVGDAVN  YIQNQQ
```

ACPS

```
              10          20          30          40
        AYGIGLDIT   ELKRIASMAG  RQKRFAERIL  TRSELDQYYE
              50          60          70          80
        LSEKRKNEFL  AGRFAAKEAF  SKAFGTGIGR  QLSFQDIEIR
              90         100         110         120
        KDQNGKPYII  CTKLSQAAVH  VSITHTKEYA  AAQVVIERLS
        121
        S
```

ACP

```
                10          20          30          40
GPLGS   ADTLERVTKI   IVDRLGVDEA   DVKLEASFKE   DLGADSLDVV
                50          60          70          76
        ELVMELEDEF   DMEISDEDAE   KIATVGDAVN   YIQNQQ
```

ACPS

```
            10          20          30          40
AYGIGLDIT   ELKRIASMAG   RQKRFAERIL   TRSELDQYYE
            50          60          70          80
LSEKRKNEFL  AGRFAAKEAF   SKAFGTGIGR   QLSFQDIEIR
            90          100         110         120
KDQNGKPYII  CTKLSQAAVH   VSITHTKEYA   AAQVVIERLS
121
S
```

FIG. 1

```
Aquifex           1  ----MIGVDIVKNERIKDALERFGDKFLDRIYTKRELEYCY----AHCDFLPCLAARWAG
Chlamydophila     1  MEIIHIGTDIIEISRIREAIATHGNRLLNRIFTEAEQKYCL----EKTDPIPSFAGRFAG
Helicobacter      1  ----MIGIDIVSIARIEKCVKRFKMKFLERFLSPSEIVLCK----DKSS---SIAGFFAL
Staphylococcus    1  -MIHGIGVDLIEIDRIQALYSKQ-PKLVERILTKNEQHKFNN-FTHEQRKIEFLAGRFAT
Thermotoga        1  -MIVGVGIDVLEVERVP-------EKFAERILGESEKRLF---LTRKRRR-EFIAGRFAL
Escherichia       1  MAILGLGTDIVEIARIEAVIARSGDRLARRVLSDNEWAIWK---THHQPV-RFLAKRFAV
Rickettsia        1  -MLIGVGTDIVQIPRIEKILNIYQELFAKKILALKELKQFT--LLNKTNHATFLAKRFSA
Streptomyces      1  MSIIGVGIDVAEVERFGA-ALERTPALAGRLFLESELLLP----GGERRGVASLAARFAA
Treponema         1  -MIIGVGIDIVEIERFVS-WTHNVRLLR-RFFHQEEIVDF----FKNHMRAQFLATRFAA
Bacillus          1  -MIYGIGLDITELKRIAS-MAGRQKRFAERILTRSELDQYY--ELSEKRKNEFLAGRFAA
Bradyrhizobium    1  -MIIGIGSDLIDITRYGKVIERHGERFLDRIFTAAERAKAERRAKNEKMVVATYAKRFAA
Mycobacterium     1  MGIVGVGIDLVSIPDFAEQVSQPGTVFM-TIFTPGERRDAS---VKSSSAVCHLAARWAV
consensus                  G D                          E                A
                  1  1........10........20........30........40........50........

Aquifex          53  KEAVLKAFYTEFKIFL------RFKEIEILGNRGRPPTVVINRE--GVEEILKNY----E
Chlamydophila    57  KEAVAKALGTGIGSVV------AWKDIEVFKVSHGPEVLLPS----HVYAKIGIS----K
Helicobacter     50  KEACSKALQVGIGKEL------SFLDIKISKSPKNAPLITLSK---EKMDYFNIQ----S
Staphylococcus   58  KEAFSKALGTGLGKHV------AFNDIDCYNDELGKPKI---------DYEGF-----I
Thermotoga       49  KEAFFKALGTGLNGH-------SFTDVEFLESN-GKPVLCVH------KDFGFFN----Y
Escherichia      57  KEAAAKAFGTGIRNGL------AFNQFEVFNDELGKPRLRLWGEALKLAEKLGVA----N
Rickettsia       58  KEAVSKAFGVGIGRGI------NFKDITILNDNLGKPTVEISS---HYTNKLAPF----N
Streptomyces     56  KEALAKALGAPAG--L------LWTDAEVWVEAGGRPRLRVTGTVAARAAELGVA----S
Treponema        54  KEAFGKALGTGLRN-M------ELRNIRVCQNGWGKPRLEVYGAAQAMLAATGGT----H
Bacillus         57  KEAFSKAFGTGIGRQL------SFQDIEIRKDQNGKPYIICT--------KLSQA----A
Bradyrhizobium   60  KEACSKALGTGIRRGV------WWRDMGVVNLPGGRPTMQLTGGALARLQALTPDGFEAR
Mycobacterium    57  KEAVIKAWSGSRFAQRPMLPENIHRDIEVVNDMWGRPRVRLTG---AIAKHLTDV----T
consensus        61  KEA KA
                  61  61.......70........80........90........100.......110........

Aquifex         101  VIVSLSHERDYSVAVAYIKKKS--------------------------------------
Chlamydophila   103  VILSISHCKEYATATAIALA----------------------------------------
Helicobacter     97  LSASISHDAGFAIAVVVSSSNE--------------------------------------
Staphylococcus   97  VHVSISHTEHYAMSQVVLEK----------SAF---------------------------
Thermotoga       91  AHVSLSH-DRFAVALVVLEKRKGDIIVEGDESFLRKRFEVLERSVEGWEIETSLPPFTLK
Escherichia     107  MHVTLADERHYACATVIIES----------------------------------------
Rickettsia      105  IHLSLSDDYPICIAFAIIESNC--------------------------------------
Streptomyces    104  WHVSLSHDAGIASAVVIAEG----------------------------------------
Treponema       103  IQVSLTHEREVASAIVIIEGEPL-------------------------------------
Bacillus         99  VHVSITHTKEYAAAQVVIERLSS-------------------------------------
Bradyrhizobium  114  IDVSITDDWPLAQAFVIISAVPLAKS----------------------------------
Mycobacterium   110  IHVSLTHEGDIAAAVVILEVL---------------------------------------
consensus       121
                 121 121......130.......140.......150.......160.......170........

Aquifex              --------------------
Chlamydophila        --------------------
Helicobacter         --------------------
Staphylococcus       --------------------
Thermotoga      150  KLLESSGCRLVRYGNILIGE
Escherichia          --------------------
Rickettsia           --------------------
Streptomyces         --------------------
Treponema            --------------------
Bacillus             --------------------
Bradyrhizobium       --------------------
Mycobacterium        --------------------
consensus       181
                181  181......190........
```

| ATOM | 50 | N | ILE | 9 | 21.471 | 32.072 | 16.618 | 1.00 | 32.83 | A1 |
|---|---|---|---|---|---|---|---|---|---|---|
| ATOM | 51 | CA | ILE | 9 | 21.247 | 31.006 | 17.589 | 1.00 | 34.13 | A1 |
| ATOM | 52 | CB | ILE | 9 | 22.570 | 30.453 | 18.178 | 1.00 | 34.00 | A1 |
| ATOM | 53 | CG2 | ILE | 9 | 22.296 | 29.317 | 19.164 | 1.00 | 33.87 | A1 |
| ATOM | 54 | CG1 | ILE | 9 | 23.444 | 29.887 | 17.067 | 1.00 | 34.24 | A1 |
| ATOM | 55 | CD1 | ILE | 9 | 24.893 | 29.598 | 17.566 | 1.00 | 35.11 | A1 |
| ATOM | 56 | C | ILE | 9 | 20.398 | 31.673 | 18.684 | 1.00 | 35.95 | A1 |
| ATOM | 57 | O | ILE | 9 | 20.706 | 32.779 | 19.152 | 1.00 | 35.83 | A1 |
| ATOM | 58 | N | THR | 10 | 19.276 | 31.027 | 19.009 | 1.00 | 37.57 | A1 |
| ATOM | 59 | CA | THR | 10 | 18.319 | 31.517 | 20.012 | 1.00 | 38.92 | A1 |
| ATOM | 60 | CB | THR | 10 | 16.963 | 31.852 | 19.371 | 1.00 | 39.79 | A1 |
| ATOM | 61 | OG1 | THR | 10 | 17.071 | 33.055 | 18.597 | 1.00 | 42.44 | A1 |
| ATOM | 62 | CG2 | THR | 10 | 15.920 | 32.030 | 20.438 | 1.00 | 41.04 | A1 |
| ATOM | 63 | C | THR | 10 | 18.074 | 30.409 | 21.053 | 1.00 | 38.98 | A1 |
| ATOM | 64 | O | THR | 10 | 17.705 | 29.273 | 20.707 | 1.00 | 38.16 | A1 |
| ATOM | 65 | N | GLU | 11 | 18.303 | 30.762 | 22.311 | 1.00 | 39.04 | A1 |
| ATOM | 66 | CA | GLU | 11 | 18.128 | 29.873 | 23.458 | 1.00 | 39.06 | A1 |
| ATOM | 67 | CB | GLU | 11 | 18.697 | 30.562 | 24.706 | 1.00 | 40.96 | A1 |
| ATOM | 68 | CG | GLU | 11 | 20.091 | 31.151 | 24.425 | 1.00 | 44.69 | A1 |
| ATOM | 69 | CD | GLU | 11 | 20.728 | 31.947 | 25.576 | 1.00 | 47.14 | A1 |
| ATOM | 70 | OE1 | GLU | 11 | 20.543 | 33.201 | 25.664 | 1.00 | 47.18 | A1 |
| ATOM | 71 | OE2 | GLU | 11 | 21.434 | 31.302 | 26.391 | 1.00 | 49.53 | A1 |
| ATOM | 72 | C | GLU | 11 | 16.634 | 29.571 | 23.662 | 1.00 | 37.28 | A1 |
| ATOM | 73 | O | GLU | 11 | 15.819 | 30.487 | 23.748 | 1.00 | 35.93 | A1 |
| ATOM | 74 | N | LEU | 12 | 16.296 | 28.287 | 23.677 | 1.00 | 35.49 | A1 |
| ATOM | 75 | CA | LEU | 12 | 14.929 | 27.816 | 23.913 | 1.00 | 36.05 | A1 |
| ATOM | 76 | CB | LEU | 12 | 14.929 | 26.279 | 24.073 | 1.00 | 36.45 | A1 |
| ATOM | 77 | CG | LEU | 12 | 14.421 | 25.319 | 23.017 | 1.00 | 37.15 | A1 |
| ATOM | 78 | CD1 | LEU | 12 | 14.235 | 23.997 | 23.690 | 1.00 | 37.38 | A1 |
| ATOM | 79 | CD2 | LEU | 12 | 13.096 | 25.759 | 22.439 | 1.00 | 37.94 | A1 |
| ATOM | 80 | C | LEU | 12 | 14.254 | 28.379 | 25.179 | 1.00 | 35.86 | A1 |
| ATOM | 81 | O | LEU | 12 | 13.059 | 28.765 | 25.161 | 1.00 | 36.02 | A1 |
| ATOM | 82 | N | ALA | 13 | 14.998 | 28.370 | 26.289 | 1.00 | 35.85 | A1 |
| ATOM | 83 | CA | ALA | 13 | 14.455 | 28.819 | 27.586 | 1.00 | 37.01 | A1 |
| ATOM | 84 | CB | ALA | 13 | 15.543 | 28.726 | 28.723 | 1.00 | 37.35 | A1 |
| ATOM | 85 | C | ALA | 13 | 13.903 | 30.209 | 27.518 | 1.00 | 37.53 | A1 |
| ATOM | 86 | O | ALA | 13 | 12.893 | 30.486 | 28.116 | 1.00 | 37.21 | A1 |
| ATOM | 87 | N | ARG | 14 | 14.550 | 31.087 | 26.772 | 1.00 | 38.91 | A1 |
| ATOM | 88 | CA | ARG | 14 | 14.041 | 32.440 | 26.670 | 1.00 | 40.95 | A1 |
| ATOM | 89 | CB | ARG | 14 | 15.044 | 33.320 | 25.940 | 1.00 | 41.35 | A1 |
| ATOM | 90 | CG | ARG | 14 | 16.138 | 33.808 | 26.853 | 1.00 | 43.91 | A1 |
| ATOM | 91 | CD | ARG | 14 | 16.385 | 35.294 | 26.635 | 1.00 | 44.07 | A1 |
| ATOM | 92 | NE | ARG | 14 | 17.184 | 35.440 | 25.443 | 1.00 | 44.98 | A1 |
| ATOM | 93 | CZ | ARG | 14 | 17.473 | 36.595 | 24.859 | 1.00 | 45.66 | A1 |
| ATOM | 94 | NH1 | ARG | 14 | 17.033 | 37.741 | 25.356 | 1.00 | 45.42 | A1 |
| ATOM | 95 | NH2 | ARG | 14 | 18.192 | 36.586 | 23.746 | 1.00 | 45.86 | A1 |
| ATOM | 96 | C | ARG | 14 | 12.679 | 32.515 | 25.986 | 1.00 | 42.15 | A1 |
| ATOM | 97 | O | ARG | 14 | 11.887 | 33.419 | 26.262 | 1.00 | 41.07 | A1 |
| ATOM | 98 | N | ILE | 15 | 12.398 | 31.578 | 25.077 | 1.00 | 43.69 | A1 |
| ATOM | 99 | CA | ILE | 15 | 11.088 | 31.604 | 24.409 | 1.00 | 45.37 | A1 |
| ATOM | 100 | CB | ILE | 15 | 11.022 | 30.801 | 23.055 | 1.00 | 44.97 | A1 |
| ATOM | 101 | CG2 | ILE | 15 | 9.634 | 30.994 | 22.442 | 1.00 | 44.72 | A1 |
| ATOM | 102 | CG1 | ILE | 15 | 12.119 | 31.219 | 22.074 | 1.00 | 44.89 | A1 |
| ATOM | 103 | CD1 | ILE | 15 | 11.983 | 32.621 | 21.518 | 1.00 | 45.11 | A1 |
| ATOM | 104 | C | ILE | 15 | 10.125 | 30.881 | 25.330 | 1.00 | 46.54 | A1 |
| ATOM | 105 | O | ILE | 15 | 8.955 | 31.170 | 25.337 | 1.00 | 46.55 | A1 |
| ATOM | 106 | N | ALA | 16 | 10.613 | 29.897 | 26.073 | 1.00 | 48.62 | A1 |

FIG. 3A-2

| ATOM | 107 | CA | ALA | 16 | 9.710 | 29.148 | 26.928 | 1.00 | 51.99 | A1 |
| --- | --- | --- | --- | --- | --- | --- | --- | --- | --- | --- |
| ATOM | 108 | CB | ALA | 16 | 10.375 | 27.891 | 27.447 | 1.00 | 51.52 | A1 |
| ATOM | 109 | C | ALA | 16 | 9.247 | 30.000 | 28.084 | 1.00 | 54.29 | A1 |
| ATOM | 110 | O | ALA | 16 | 8.119 | 29.878 | 28.544 | 1.00 | 55.04 | A1 |
| ATOM | 111 | N | SER | 17 | 10.122 | 30.877 | 28.545 | 1.00 | 56.66 | A1 |
| ATOM | 112 | CA | SER | 17 | 9.797 | 31.752 | 29.653 | 1.00 | 58.77 | A1 |
| ATOM | 113 | CB | SER | 17 | 11.064 | 32.402 | 30.169 | 1.00 | 58.15 | A1 |
| ATOM | 114 | OG | SER | 17 | 11.864 | 31.409 | 30.758 | 1.00 | 58.99 | A1 |
| ATOM | 115 | C | SER | 17 | 8.807 | 32.836 | 29.283 | 1.00 | 60.67 | A1 |
| ATOM | 116 | O | SER | 17 | 9.034 | 34.013 | 29.587 | 1.00 | 61.61 | A1 |
| ATOM | 117 | N | MET | 18 | 7.719 | 32.463 | 28.620 | 1.00 | 61.88 | A1 |
| ATOM | 118 | CA | MET | 18 | 6.711 | 33.457 | 28.252 | 1.00 | 63.20 | A1 |
| ATOM | 119 | CB | MET | 18 | 6.411 | 33.397 | 26.760 | 1.00 | 63.45 | A1 |
| ATOM | 120 | CG | MET | 18 | 7.629 | 33.473 | 25.982 | 1.00 | 63.73 | A1 |
| ATOM | 121 | SD | MET | 18 | 8.431 | 34.930 | 26.488 | 1.00 | 64.97 | A1 |
| ATOM | 122 | CE | MET | 18 | 8.882 | 35.588 | 24.735 | 1.00 | 64.08 | A1 |
| ATOM | 123 | C | MET | 18 | 5.434 | 33.205 | 28.994 | 1.00 | 63.31 | A1 |
| ATOM | 124 | O | MET | 18 | 4.815 | 34.127 | 29.506 | 1.00 | 63.03 | A1 |
| ATOM | 125 | N | ALA | 19 | 5.054 | 31.933 | 29.017 | 1.00 | 64.24 | A1 |
| ATOM | 126 | CA | ALA | 19 | 3.827 | 31.469 | 29.670 | 1.00 | 65.18 | A1 |
| ATOM | 127 | CB | ALA | 19 | 4.036 | 31.349 | 31.198 | 1.00 | 65.29 | A1 |
| ATOM | 128 | C | ALA | 19 | 2.685 | 32.425 | 29.352 | 1.00 | 65.24 | A1 |
| ATOM | 129 | O | ALA | 19 | 1.899 | 32.199 | 28.419 | 1.00 | 66.10 | A1 |
| ATOM | 130 | N | GLY | 20 | 2.606 | 33.507 | 30.110 | 1.00 | 64.64 | A1 |
| ATOM | 131 | CA | GLY | 20 | 1.548 | 34.460 | 29.857 | 1.00 | 64.00 | A1 |
| ATOM | 132 | C | GLY | 20 | 1.725 | 35.165 | 28.534 | 1.00 | 63.02 | A1 |
| ATOM | 133 | O | GLY | 20 | 0.789 | 35.248 | 27.741 | 1.00 | 64.04 | A1 |
| ATOM | 134 | N | ALA | 21 | 2.943 | 35.638 | 28.288 | 1.00 | 61.60 | A1 |
| ATOM | 135 | CA | ALA | 21 | 3.280 | 36.392 | 27.085 | 1.00 | 59.98 | A1 |
| ATOM | 136 | CB | ALA | 21 | 4.525 | 37.225 | 27.378 | 1.00 | 59.25 | A1 |
| ATOM | 137 | C | ALA | 21 | 3.453 | 35.663 | 25.725 | 1.00 | 59.06 | A1 |
| ATOM | 138 | O | ALA | 21 | 3.425 | 36.310 | 24.675 | 1.00 | 58.46 | A1 |
| ATOM | 139 | N | GLN | 22 | 3.612 | 34.339 | 25.722 | 1.00 | 57.78 | A1 |
| ATOM | 140 | CA | GLN | 22 | 3.861 | 33.642 | 24.461 | 1.00 | 56.31 | A1 |
| ATOM | 141 | CB | GLN | 22 | 4.120 | 32.160 | 24.707 | 1.00 | 56.11 | A1 |
| ATOM | 142 | CG | GLN | 22 | 4.701 | 31.498 | 23.464 | 1.00 | 54.61 | A1 |
| ATOM | 143 | CD | GLN | 22 | 5.154 | 30.063 | 23.674 | 1.00 | 54.11 | A1 |
| ATOM | 144 | OE1 | GLN | 22 | 4.417 | 29.108 | 23.357 | 1.00 | 52.66 | A1 |
| ATOM | 145 | NE2 | GLN | 22 | 6.384 | 29.901 | 24.212 | 1.00 | 52.51 | A1 |
| ATOM | 146 | C | GLN | 22 | 2.877 | 33.786 | 23.305 | 1.00 | 55.31 | A1 |
| ATOM | 147 | O | GLN | 22 | 3.279 | 33.751 | 22.136 | 1.00 | 54.38 | A1 |
| ATOM | 148 | N | LYS | 23 | 1.599 | 33.950 | 23.625 | 1.00 | 54.54 | A1 |
| ATOM | 149 | CA | LYS | 23 | 0.587 | 34.102 | 22.597 | 1.00 | 53.74 | A1 |
| ATOM | 150 | CB | LYS | 23 | -0.816 | 34.126 | 23.192 | 1.00 | 54.52 | A1 |
| ATOM | 151 | CG | LYS | 23 | -1.908 | 34.428 | 22.158 | 1.00 | 55.45 | A1 |
| ATOM | 152 | CD | LYS | 23 | -3.280 | 34.438 | 22.820 | 1.00 | 56.61 | A1 |
| ATOM | 153 | CE | LYS | 23 | -4.342 | 35.093 | 21.932 | 1.00 | 57.55 | A1 |
| ATOM | 154 | NZ | LYS | 23 | -4.631 | 34.292 | 20.715 | 1.00 | 58.20 | A1 |
| ATOM | 155 | C | LYS | 23 | 0.795 | 35.387 | 21.819 | 1.00 | 52.72 | A1 |
| ATOM | 156 | O | LYS | 23 | 0.775 | 35.377 | 20.578 | 1.00 | 52.28 | A1 |
| ATOM | 157 | N | ARG | 24 | 0.966 | 36.494 | 22.530 | 1.00 | 50.67 | A1 |
| ATOM | 158 | CA | ARG | 24 | 1.151 | 37.730 | 21.811 | 1.00 | 49.83 | A1 |
| ATOM | 159 | CB | ARG | 24 | 1.027 | 38.929 | 22.746 | 1.00 | 52.03 | A1 |
| ATOM | 160 | CG | ARG | 24 | -0.442 | 39.179 | 23.140 | 1.00 | 54.86 | A1 |
| ATOM | 161 | CD | ARG | 24 | -0.689 | 40.544 | 23.779 | 1.00 | 57.57 | A1 |
| ATOM | 162 | NE | ARG | 24 | -0.708 | 41.626 | 22.799 | 1.00 | 59.50 | A1 |
| ATOM | 163 | CZ | ARG | 24 | 0.284 | 42.496 | 22.638 | 1.00 | 60.97 | A1 |

FIG. 3A-3

| ATOM | 164 | NH1 | ARG | 24 | 1.378 | 42.411 | 23.403 | 1.00 | 61.46 | A1 |
| --- | --- | --- | --- | --- | --- | --- | --- | --- | --- | --- |
| ATOM | 165 | NH2 | ARG | 24 | 0.179 | 43.448 | 21.714 | 1.00 | 61.28 | A1 |
| ATOM | 166 | C | ARG | 24 | 2.473 | 37.735 | 21.070 | 1.00 | 47.89 | A1 |
| ATOM | 167 | O | ARG | 24 | 2.596 | 38.349 | 20.014 | 1.00 | 47.33 | A1 |
| ATOM | 168 | N | PHE | 25 | 3.456 | 37.039 | 21.622 | 1.00 | 45.04 | A1 |
| ATOM | 169 | CA | PHE | 25 | 4.748 | 36.965 | 20.992 | 1.00 | 42.60 | A1 |
| ATOM | 170 | CB | PHE | 25 | 5.757 | 36.301 | 21.927 | 1.00 | 41.19 | A1 |
| ATOM | 171 | CG | PHE | 25 | 7.107 | 36.071 | 21.294 | 1.00 | 39.72 | A1 |
| ATOM | 172 | CD1 | PHE | 25 | 7.945 | 37.133 | 21.010 | 1.00 | 39.39 | A1 |
| ATOM | 173 | CD2 | PHE | 25 | 7.538 | 34.791 | 21.010 | 1.00 | 39.13 | A1 |
| ATOM | 174 | CE1 | PHE | 25 | 9.198 | 36.924 | 20.460 | 1.00 | 39.53 | A1 |
| ATOM | 175 | CE2 | PHE | 25 | 8.776 | 34.578 | 20.469 | 1.00 | 39.73 | A1 |
| ATOM | 176 | CZ | PHE | 25 | 9.616 | 35.648 | 20.187 | 1.00 | 39.05 | A1 |
| ATOM | 177 | C | PHE | 25 | 4.617 | 36.143 | 19.701 | 1.00 | 41.96 | A1 |
| ATOM | 178 | O | PHE | 25 | 5.236 | 36.459 | 18.664 | 1.00 | 40.61 | A1 |
| ATOM | 179 | N | ALA | 26 | 3.824 | 35.078 | 19.771 | 1.00 | 40.74 | A1 |
| ATOM | 180 | CA | ALA | 26 | 3.635 | 34.237 | 18.597 | 1.00 | 40.86 | A1 |
| ATOM | 181 | CB | ALA | 26 | 2.786 | 32.993 | 18.948 | 1.00 | 39.28 | A1 |
| ATOM | 182 | C | ALA | 26 | 2.965 | 35.034 | 17.463 | 1.00 | 40.94 | A1 |
| ATOM | 183 | O | ALA | 26 | 3.380 | 34.940 | 16.293 | 1.00 | 40.38 | A1 |
| ATOM | 184 | N | GLU | 27 | 1.940 | 35.802 | 17.821 | 1.00 | 40.51 | A1 |
| ATOM | 185 | CA | GLU | 27 | 1.198 | 36.598 | 16.870 | 1.00 | 41.68 | A1 |
| ATOM | 186 | CB | GLU | 27 | -0.003 | 37.269 | 17.537 | 1.00 | 44.31 | A1 |
| ATOM | 187 | CG | GLU | 27 | -1.076 | 36.311 | 18.027 | 1.00 | 49.27 | A1 |
| ATOM | 188 | CD | GLU | 27 | -2.143 | 36.968 | 18.903 | 1.00 | 52.19 | A1 |
| ATOM | 189 | OE1 | GLU | 27 | -1.939 | 38.106 | 19.431 | 1.00 | 53.39 | A1 |
| ATOM | 190 | OE2 | GLU | 27 | -3.196 | 36.314 | 19.081 | 1.00 | 54.05 | A1 |
| ATOM | 191 | C | GLU | 27 | 2.059 | 37.672 | 16.245 | 1.00 | 40.55 | A1 |
| ATOM | 192 | O | GLU | 27 | 1.819 | 38.065 | 15.125 | 1.00 | 41.26 | A1 |
| ATOM | 193 | N | ARG | 28 | 3.043 | 38.172 | 16.971 | 1.00 | 39.83 | A1 |
| ATOM | 194 | CA | ARG | 28 | 3.907 | 39.216 | 16.433 | 1.00 | 39.44 | A1 |
| ATOM | 195 | CB | ARG | 28 | 4.712 | 39.897 | 17.558 | 1.00 | 39.37 | A1 |
| ATOM | 196 | CG | ARG | 28 | 5.203 | 41.267 | 17.199 | 1.00 | 40.38 | A1 |
| ATOM | 197 | CD | ARG | 28 | 6.175 | 41.850 | 18.199 | 1.00 | 42.61 | A1 |
| ATOM | 198 | NE | ARG | 28 | 6.730 | 43.108 | 17.671 | 1.00 | 45.42 | A1 |
| ATOM | 199 | CZ | ARG | 28 | 6.148 | 44.304 | 17.774 | 1.00 | 46.09 | A1 |
| ATOM | 200 | NH1 | ARG | 28 | 4.980 | 44.429 | 18.417 | 1.00 | 46.55 | A1 |
| ATOM | 201 | NH2 | ARG | 28 | 6.699 | 45.370 | 17.184 | 1.00 | 46.78 | A1 |
| ATOM | 202 | C | ARG | 28 | 4.901 | 38.628 | 15.428 | 1.00 | 38.17 | A1 |
| ATOM | 203 | O | ARG | 28 | 5.202 | 39.233 | 14.423 | 1.00 | 37.71 | A1 |
| ATOM | 204 | N | ILE | 29 | 5.344 | 37.416 | 15.728 | 1.00 | 37.47 | A1 |
| ATOM | 205 | CA | ILE | 29 | 6.364 | 36.675 | 14.989 | 1.00 | 37.22 | A1 |
| ATOM | 206 | CB | ILE | 29 | 7.140 | 35.756 | 16.013 | 1.00 | 38.04 | A1 |
| ATOM | 207 | CG2 | ILE | 29 | 8.353 | 35.033 | 15.400 | 1.00 | 40.19 | A1 |
| ATOM | 208 | CG1 | ILE | 29 | 7.740 | 36.634 | 17.113 | 1.00 | 38.36 | A1 |
| ATOM | 209 | CD1 | ILE | 29 | 8.363 | 37.896 | 16.573 | 1.00 | 37.14 | A1 |
| ATOM | 210 | C | ILE | 29 | 5.937 | 35.851 | 13.804 | 1.00 | 35.77 | A1 |
| ATOM | 211 | O | ILE | 29 | 6.646 | 35.793 | 12.827 | 1.00 | 35.39 | A1 |
| ATOM | 212 | N | LEU | 30 | 4.760 | 35.243 | 13.883 | 1.00 | 35.34 | A1 |
| ATOM | 213 | CA | LEU | 30 | 4.285 | 34.351 | 12.846 | 1.00 | 33.85 | A1 |
| ATOM | 214 | CB | LEU | 30 | 3.627 | 33.129 | 13.464 | 1.00 | 33.02 | A1 |
| ATOM | 215 | CG | LEU | 30 | 4.509 | 32.589 | 14.575 | 1.00 | 33.23 | A1 |
| ATOM | 216 | CD1 | LEU | 30 | 3.813 | 31.411 | 15.244 | 1.00 | 32.55 | A1 |
| ATOM | 217 | CD2 | LEU | 30 | 5.894 | 32.205 | 13.972 | 1.00 | 32.98 | A1 |
| ATOM | 218 | C | LEU | 30 | 3.322 | 34.899 | 11.877 | 1.00 | 33.78 | A1 |
| ATOM | 219 | O | LEU | 30 | 2.576 | 35.820 | 12.199 | 1.00 | 34.57 | A1 |
| ATOM | 220 | N | THR | 31 | 3.338 | 34.325 | 10.678 | 1.00 | 33.02 | A1 |

FIG. 3A-4

| ATOM | 221 | CA  | THR | 31 | 2.369  | 34.702 | 9.662  | 1.00 | 33.03 | A1 |
| ---- | --- | --- | --- | -- | ------ | ------ | ------ | ---- | ----- | -- |
| ATOM | 222 | CB  | THR | 31 | 2.847  | 34.320 | 8.247  | 1.00 | 31.42 | A1 |
| ATOM | 223 | OG1 | THR | 31 | 3.043  | 32.896 | 8.180  | 1.00 | 28.99 | A1 |
| ATOM | 224 | CG2 | THR | 31 | 4.120  | 35.093 | 7.903  | 1.00 | 28.16 | A1 |
| ATOM | 225 | C   | THR | 31 | 1.108  | 33.863 | 9.996  | 1.00 | 33.87 | A1 |
| ATOM | 226 | O   | THR | 31 | 1.130  | 33.022 | 10.924 | 1.00 | 32.70 | A1 |
| ATOM | 227 | N   | ALA | 32 | 0.042  | 34.064 | 9.211  | 1.00 | 34.24 | A1 |
| ATOM | 228 | CA  | ALA | 32 | -1.226 | 33.341 | 9.401  | 1.00 | 34.08 | A1 |
| ATOM | 229 | CB  | ALA | 32 | -2.259 | 33.767 | 8.340  | 1.00 | 34.11 | A1 |
| ATOM | 230 | C   | ALA | 32 | -1.056 | 31.816 | 9.352  | 1.00 | 33.63 | A1 |
| ATOM | 231 | O   | ALA | 32 | -1.506 | 31.094 | 10.258 | 1.00 | 33.02 | A1 |
| ATOM | 232 | N   | SER | 33 | -0.421 | 31.306 | 8.303  | 1.00 | 33.11 | A1 |
| ATOM | 233 | CA  | SER | 33 | -0.279 | 29.854 | 8.239  | 1.00 | 32.41 | A1 |
| ATOM | 234 | CB  | SER | 33 | 0.204  | 29.411 | 6.884  | 1.00 | 31.81 | A1 |
| ATOM | 235 | OG  | SER | 33 | 1.557  | 29.762 | 6.706  | 1.00 | 33.87 | A1 |
| ATOM | 236 | C   | SER | 33 | 0.675  | 29.300 | 9.296  | 1.00 | 32.48 | A1 |
| ATOM | 237 | O   | SER | 33 | 0.516  | 28.143 | 9.700  | 1.00 | 32.22 | A1 |
| ATOM | 238 | N   | GLU | 34 | 1.653  | 30.100 | 9.736  | 1.00 | 31.47 | A1 |
| ATOM | 239 | CA  | GLU | 34 | 2.591  | 29.616 | 10.750 | 1.00 | 32.82 | A1 |
| ATOM | 240 | CB  | GLU | 34 | 3.806  | 30.539 | 10.893 | 1.00 | 32.38 | A1 |
| ATOM | 241 | CG  | GLU | 34 | 4.740  | 30.472 | 9.705  | 1.00 | 33.34 | A1 |
| ATOM | 242 | CD  | GLU | 34 | 5.726  | 31.605 | 9.716  | 1.00 | 34.32 | A1 |
| ATOM | 243 | OE1 | GLU | 34 | 5.342  | 32.743 | 10.078 | 1.00 | 36.26 | A1 |
| ATOM | 244 | OE2 | GLU | 34 | 6.877  | 31.352 | 9.349  | 1.00 | 34.55 | A1 |
| ATOM | 245 | C   | GLU | 34 | 1.893  | 29.482 | 12.104 | 1.00 | 32.92 | A1 |
| ATOM | 246 | O   | GLU | 34 | 2.113  | 28.522 | 12.821 | 1.00 | 33.23 | A1 |
| ATOM | 247 | N   | LEU | 35 | 1.042  | 30.445 | 12.407 | 1.00 | 33.04 | A1 |
| ATOM | 248 | CA  | LEU | 35 | 0.296  | 30.458 | 13.639 | 1.00 | 34.42 | A1 |
| ATOM | 249 | CB  | LEU | 35 | -0.535 | 31.724 | 13.721 | 1.00 | 35.37 | A1 |
| ATOM | 250 | CG  | LEU | 35 | -0.151 | 33.010 | 14.442 | 1.00 | 36.15 | A1 |
| ATOM | 251 | CD1 | LEU | 35 | -1.425 | 33.899 | 14.346 | 1.00 | 34.90 | A1 |
| ATOM | 252 | CD2 | LEU | 35 | 0.223  | 32.778 | 15.929 | 1.00 | 34.49 | A1 |
| ATOM | 253 | C   | LEU | 35 | -0.643 | 29.237 | 13.764 | 1.00 | 34.43 | A1 |
| ATOM | 254 | O   | LEU | 35 | -0.785 | 28.684 | 14.855 | 1.00 | 33.54 | A1 |
| ATOM | 255 | N   | ASP | 36 | -1.286 | 28.862 | 12.650 | 1.00 | 33.79 | A1 |
| ATOM | 256 | CA  | ASP | 36 | -2.192 | 27.710 | 12.582 | 1.00 | 33.66 | A1 |
| ATOM | 257 | CB  | ASP | 36 | -2.764 | 27.472 | 11.161 | 1.00 | 33.07 | A1 |
| ATOM | 258 | CG  | ASP | 36 | -3.803 | 28.533 | 10.727 | 1.00 | 34.30 | A1 |
| ATOM | 259 | OD1 | ASP | 36 | -4.410 | 29.136 | 11.612 | 1.00 | 33.98 | A1 |
| ATOM | 260 | OD2 | ASP | 36 | -4.048 | 28.748 | 9.492  | 1.00 | 33.61 | A1 |
| ATOM | 261 | C   | ASP | 36 | -1.397 | 26.468 | 12.935 | 1.00 | 34.25 | A1 |
| ATOM | 262 | O   | ASP | 36 | -1.900 | 25.564 | 13.582 | 1.00 | 34.41 | A1 |
| ATOM | 263 | N   | GLN | 37 | -0.152 | 26.398 | 12.494 | 1.00 | 35.24 | A1 |
| ATOM | 264 | CA  | GLN | 37 | 0.652  | 25.202 | 12.793 | 1.00 | 36.17 | A1 |
| ATOM | 265 | CB  | GLN | 37 | 1.939  | 25.189 | 11.972 | 1.00 | 35.40 | A1 |
| ATOM | 266 | CG  | GLN | 37 | 1.671  | 25.154 | 10.533 | 1.00 | 38.15 | A1 |
| ATOM | 267 | CD  | GLN | 37 | 2.956  | 25.046 | 9.717  | 1.00 | 40.58 | A1 |
| ATOM | 268 | OE1 | GLN | 37 | 3.812  | 24.195 | 10.009 | 1.00 | 43.09 | A1 |
| ATOM | 269 | NE2 | GLN | 37 | 3.095  | 25.889 | 8.696  | 1.00 | 37.84 | A1 |
| ATOM | 270 | C   | GLN | 37 | 1.003  | 25.162 | 14.254 | 1.00 | 35.48 | A1 |
| ATOM | 271 | O   | GLN | 37 | 1.002  | 24.095 | 14.874 | 1.00 | 35.73 | A1 |
| ATOM | 272 | N   | TYR | 38 | 1.269  | 26.346 | 14.790 | 1.00 | 34.97 | A1 |
| ATOM | 273 | CA  | TYR | 38 | 1.669  | 26.510 | 16.176 | 1.00 | 34.85 | A1 |
| ATOM | 274 | CB  | TYR | 38 | 2.143  | 27.952 | 16.370 | 1.00 | 33.46 | A1 |
| ATOM | 275 | CG  | TYR | 38 | 2.273  | 28.458 | 17.781 | 1.00 | 32.73 | A1 |
| ATOM | 276 | CD1 | TYR | 38 | 1.208  | 29.115 | 18.405 | 1.00 | 32.82 | A1 |
| ATOM | 277 | CE1 | TYR | 38 | 1.348  | 29.645 | 19.682 | 1.00 | 34.21 | A1 |

FIG. 3A-5

| ATOM | 278 | CD2 | TYR | 38 | 3.463 | 28.341 | 18.465 | 1.00 | 31.00 | A1 |
| --- | --- | --- | --- | --- | --- | --- | --- | --- | --- | --- |
| ATOM | 279 | CE2 | TYR | 38 | 3.620 | 28.873 | 19.744 | 1.00 | 33.46 | A1 |
| ATOM | 280 | CZ | TYR | 38 | 2.577 | 29.522 | 20.346 | 1.00 | 34.00 | A1 |
| ATOM | 281 | OH | TYR | 38 | 2.761 | 30.111 | 21.570 | 1.00 | 37.22 | A1 |
| ATOM | 282 | C | TYR | 38 | 0.564 | 26.117 | 17.130 | 1.00 | 36.15 | A1 |
| ATOM | 283 | O | TYR | 38 | 0.804 | 25.382 | 18.089 | 1.00 | 35.82 | A1 |
| ATOM | 284 | N | TYR | 39 | -0.662 | 26.546 | 16.849 | 1.00 | 37.88 | A1 |
| ATOM | 285 | CA | TYR | 39 | -1.782 | 26.204 | 17.725 | 1.00 | 39.63 | A1 |
| ATOM | 286 | CB | TYR | 39 | -3.037 | 27.013 | 17.357 | 1.00 | 39.03 | A1 |
| ATOM | 287 | CG | TYR | 39 | -2.913 | 28.438 | 17.829 | 1.00 | 39.74 | A1 |
| ATOM | 288 | CD1 | TYR | 39 | -2.533 | 28.713 | 19.154 | 1.00 | 40.42 | A1 |
| ATOM | 289 | CE1 | TYR | 39 | -2.338 | 30.051 | 19.600 | 1.00 | 41.11 | A1 |
| ATOM | 290 | CD2 | TYR | 39 | -3.108 | 29.523 | 16.956 | 1.00 | 39.84 | A1 |
| ATOM | 291 | CE2 | TYR | 39 | -2.923 | 30.852 | 17.384 | 1.00 | 39.73 | A1 |
| ATOM | 292 | CZ | TYR | 39 | -2.538 | 31.112 | 18.721 | 1.00 | 41.24 | A1 |
| ATOM | 293 | OH | TYR | 39 | -2.435 | 32.412 | 19.217 | 1.00 | 41.44 | A1 |
| ATOM | 294 | C | TYR | 39 | -2.062 | 24.720 | 17.762 | 1.00 | 40.63 | A1 |
| ATOM | 295 | O | TYR | 39 | -2.604 | 24.206 | 18.747 | 1.00 | 42.50 | A1 |
| ATOM | 296 | N | ALA | 40 | -1.665 | 24.017 | 16.716 | 1.00 | 41.27 | A1 |
| ATOM | 297 | CA | ALA | 40 | -1.847 | 22.573 | 16.649 | 1.00 | 41.86 | A1 |
| ATOM | 298 | CB | ALA | 40 | -1.759 | 22.100 | 15.196 | 1.00 | 41.73 | A1 |
| ATOM | 299 | C | ALA | 40 | -0.789 | 21.837 | 17.473 | 1.00 | 42.96 | A1 |
| ATOM | 300 | O | ALA | 40 | -0.908 | 20.618 | 17.703 | 1.00 | 43.10 | A1 |
| ATOM | 301 | N | LEU | 41 | 0.252 | 22.539 | 17.927 | 1.00 | 42.81 | A1 |
| ATOM | 302 | CA | LEU | 41 | 1.301 | 21.833 | 18.650 | 1.00 | 42.81 | A1 |
| ATOM | 303 | CB | LEU | 41 | 2.665 | 22.466 | 18.339 | 1.00 | 42.41 | A1 |
| ATOM | 304 | CG | LEU | 41 | 3.140 | 22.361 | 16.875 | 1.00 | 43.61 | A1 |
| ATOM | 305 | CD1 | LEU | 41 | 4.395 | 23.238 | 16.638 | 1.00 | 41.82 | A1 |
| ATOM | 306 | CD2 | LEU | 41 | 3.425 | 20.898 | 16.550 | 1.00 | 42.33 | A1 |
| ATOM | 307 | C | LEU | 41 | 1.126 | 21.698 | 20.170 | 1.00 | 42.93 | A1 |
| ATOM | 308 | O | LEU | 41 | 0.363 | 22.432 | 20.778 | 1.00 | 41.85 | A1 |
| ATOM | 309 | N | SER | 42 | 1.859 | 20.733 | 20.748 | 1.00 | 43.71 | A1 |
| ATOM | 310 | CA | SER | 42 | 1.885 | 20.488 | 22.188 | 1.00 | 44.05 | A1 |
| ATOM | 311 | CB | SER | 42 | 2.659 | 19.246 | 22.461 | 1.00 | 43.73 | A1 |
| ATOM | 312 | OG | SER | 42 | 4.019 | 19.536 | 22.239 | 1.00 | 44.18 | A1 |
| ATOM | 313 | C | SER | 42 | 2.684 | 21.644 | 22.763 | 1.00 | 44.62 | A1 |
| ATOM | 314 | O | SER | 42 | 3.416 | 22.292 | 22.028 | 1.00 | 44.29 | A1 |
| ATOM | 315 | N | GLU | 43 | 2.603 | 21.884 | 24.068 | 1.00 | 45.05 | A1 |
| ATOM | 316 | CA | GLU | 43 | 3.332 | 23.019 | 24.607 | 1.00 | 45.94 | A1 |
| ATOM | 317 | CB | GLU | 43 | 2.971 | 23.259 | 26.071 | 1.00 | 48.60 | A1 |
| ATOM | 318 | CG | GLU | 43 | 1.444 | 23.613 | 26.267 | 1.00 | 52.40 | A1 |
| ATOM | 319 | CD | GLU | 43 | 0.995 | 24.887 | 25.505 | 1.00 | 54.53 | A1 |
| ATOM | 320 | OE1 | GLU | 43 | 1.696 | 25.925 | 25.631 | 1.00 | 55.13 | A1 |
| ATOM | 321 | OE2 | GLU | 43 | -0.062 | 24.845 | 24.800 | 1.00 | 55.25 | A1 |
| ATOM | 322 | C | GLU | 43 | 4.848 | 23.048 | 24.432 | 1.00 | 44.63 | A1 |
| ATOM | 323 | O | GLU | 43 | 5.401 | 24.132 | 24.209 | 1.00 | 44.60 | A1 |
| ATOM | 324 | N | ALA | 44 | 5.523 | 21.902 | 24.531 | 1.00 | 43.03 | A1 |
| ATOM | 325 | CA | ALA | 44 | 6.981 | 21.880 | 24.350 | 1.00 | 42.00 | A1 |
| ATOM | 326 | CB | ALA | 44 | 7.581 | 20.509 | 24.772 | 1.00 | 42.03 | A1 |
| ATOM | 327 | C | ALA | 44 | 7.253 | 22.130 | 22.850 | 1.00 | 41.00 | A1 |
| ATOM | 328 | O | ALA | 44 | 8.188 | 22.836 | 22.483 | 1.00 | 40.92 | A1 |
| ATOM | 329 | N | ARG | 45 | 6.415 | 21.548 | 21.996 | 1.00 | 39.12 | A1 |
| ATOM | 330 | CA | ARG | 45 | 6.575 | 21.735 | 20.588 | 1.00 | 38.05 | A1 |
| ATOM | 331 | CB | ARG | 45 | 5.695 | 20.782 | 19.825 | 1.00 | 39.12 | A1 |
| ATOM | 332 | CG | ARG | 45 | 6.067 | 19.368 | 20.050 | 1.00 | 42.02 | A1 |
| ATOM | 333 | CD | ARG | 45 | 7.460 | 19.066 | 19.559 | 1.00 | 45.74 | A1 |
| ATOM | 334 | NE | ARG | 45 | 7.673 | 19.650 | 18.247 | 1.00 | 49.41 | A1 |

FIG. 3A-6

| ATOM | 335 | CZ | ARG | 45 | 8.773 | 19.489 | 17.522 | 1.00 | 51.27 | A1 |
| ATOM | 336 | NH1 | ARG | 45 | 9.776 | 18.733 | 17.986 | 1.00 | 52.41 | A1 |
| ATOM | 337 | NH2 | ARG | 45 | 8.884 | 20.129 | 16.351 | 1.00 | 51.44 | A1 |
| ATOM | 338 | C | ARG | 45 | 6.305 | 23.174 | 20.185 | 1.00 | 36.52 | A1 |
| ATOM | 339 | O | ARG | 45 | 6.871 | 23.626 | 19.211 | 1.00 | 35.97 | A1 |
| ATOM | 340 | N | LYS | 46 | 5.480 | 23.896 | 20.929 | 1.00 | 34.62 | A1 |
| ATOM | 341 | CA | LYS | 46 | 5.249 | 25.294 | 20.610 | 1.00 | 34.21 | A1 |
| ATOM | 342 | CB | LYS | 46 | 4.171 | 25.906 | 21.474 | 1.00 | 33.14 | A1 |
| ATOM | 343 | CG | LYS | 46 | 2.738 | 25.639 | 21.025 | 1.00 | 35.37 | A1 |
| ATOM | 344 | CD | LYS | 46 | 1.803 | 26.461 | 21.945 | 1.00 | 35.71 | A1 |
| ATOM | 345 | CE | LYS | 46 | 0.356 | 26.339 | 21.546 | 1.00 | 37.07 | A1 |
| ATOM | 346 | NZ | LYS | 46 | -0.432 | 27.391 | 22.270 | 1.00 | 37.31 | A1 |
| ATOM | 347 | C | LYS | 46 | 6.524 | 26.132 | 20.803 | 1.00 | 33.86 | A1 |
| ATOM | 348 | O | LYS | 46 | 6.812 | 27.016 | 20.004 | 1.00 | 32.48 | A1 |
| ATOM | 349 | N | ASN | 47 | 7.278 | 25.865 | 21.871 | 1.00 | 33.74 | A1 |
| ATOM | 350 | CA | ASN | 47 | 8.477 | 26.646 | 22.098 | 1.00 | 34.19 | A1 |
| ATOM | 351 | CB | ASN | 47 | 9.005 | 26.388 | 23.480 | 1.00 | 35.68 | A1 |
| ATOM | 352 | CG | ASN | 47 | 7.983 | 26.734 | 24.497 | 1.00 | 39.69 | A1 |
| ATOM | 353 | OD1 | ASN | 47 | 7.324 | 27.795 | 24.363 | 1.00 | 41.09 | A1 |
| ATOM | 354 | ND2 | ASN | 47 | 7.802 | 25.867 | 25.513 | 1.00 | 38.62 | A1 |
| ATOM | 355 | C | ASN | 47 | 9.553 | 26.396 | 21.065 | 1.00 | 32.89 | A1 |
| ATOM | 356 | O | ASN | 47 | 10.276 | 27.324 | 20.693 | 1.00 | 30.94 | A1 |
| ATOM | 357 | N | GLU | 48 | 9.656 | 25.138 | 20.629 | 1.00 | 31.98 | A1 |
| ATOM | 358 | CA | GLU | 48 | 10.642 | 24.769 | 19.638 | 1.00 | 32.98 | A1 |
| ATOM | 359 | CB | GLU | 48 | 10.629 | 23.269 | 19.413 | 1.00 | 35.91 | A1 |
| ATOM | 360 | CG | GLU | 48 | 11.585 | 22.498 | 20.276 | 1.00 | 41.51 | A1 |
| ATOM | 361 | CD | GLU | 48 | 11.124 | 21.078 | 20.397 | 1.00 | 44.62 | A1 |
| ATOM | 362 | OE1 | GLU | 48 | 10.860 | 20.463 | 19.319 | 1.00 | 45.75 | A1 |
| ATOM | 363 | OE2 | GLU | 48 | 11.009 | 20.603 | 21.568 | 1.00 | 46.32 | A1 |
| ATOM | 364 | C | GLU | 48 | 10.346 | 25.455 | 18.301 | 1.00 | 31.14 | A1 |
| ATOM | 365 | O | GLU | 48 | 11.241 | 26.036 | 17.676 | 1.00 | 31.58 | A1 |
| ATOM | 366 | N | PHE | 49 | 9.087 | 25.344 | 17.892 | 1.00 | 28.29 | A1 |
| ATOM | 367 | CA | PHE | 49 | 8.574 | 25.895 | 16.666 | 1.00 | 26.99 | A1 |
| ATOM | 368 | CB | PHE | 49 | 7.059 | 25.633 | 16.566 | 1.00 | 26.28 | A1 |
| ATOM | 369 | CG | PHE | 49 | 6.461 | 26.100 | 15.286 | 1.00 | 25.52 | A1 |
| ATOM | 370 | CD1 | PHE | 49 | 6.587 | 25.339 | 14.120 | 1.00 | 26.28 | A1 |
| ATOM | 371 | CD2 | PHE | 49 | 5.823 | 27.313 | 15.212 | 1.00 | 24.67 | A1 |
| ATOM | 372 | CE1 | PHE | 49 | 6.071 | 25.798 | 12.878 | 1.00 | 25.84 | A1 |
| ATOM | 373 | CE2 | PHE | 49 | 5.303 | 27.773 | 13.960 | 1.00 | 26.00 | A1 |
| ATOM | 374 | CZ | PHE | 49 | 5.440 | 26.994 | 12.800 | 1.00 | 24.44 | A1 |
| ATOM | 375 | C | PHE | 49 | 8.827 | 27.399 | 16.672 | 1.00 | 26.54 | A1 |
| ATOM | 376 | O | PHE | 49 | 9.327 | 27.949 | 15.700 | 1.00 | 24.86 | A1 |
| ATOM | 377 | N | LEU | 50 | 8.504 | 28.034 | 17.794 | 1.00 | 25.76 | A1 |
| ATOM | 378 | CA | LEU | 50 | 8.667 | 29.452 | 17.929 | 1.00 | 26.80 | A1 |
| ATOM | 379 | CB | LEU | 50 | 8.013 | 29.905 | 19.205 | 1.00 | 26.47 | A1 |
| ATOM | 380 | CG | LEU | 50 | 7.184 | 31.173 | 19.245 | 1.00 | 26.96 | A1 |
| ATOM | 381 | CD1 | LEU | 50 | 6.188 | 31.085 | 18.097 | 1.00 | 28.27 | A1 |
| ATOM | 382 | CD2 | LEU | 50 | 6.427 | 31.298 | 20.634 | 1.00 | 26.53 | A1 |
| ATOM | 383 | C | LEU | 50 | 10.132 | 29.899 | 17.920 | 1.00 | 27.42 | A1 |
| ATOM | 384 | O | LEU | 50 | 10.477 | 30.897 | 17.298 | 1.00 | 28.25 | A1 |
| ATOM | 385 | N | ALA | 51 | 11.008 | 29.164 | 18.577 | 1.00 | 26.72 | A1 |
| ATOM | 386 | CA | ALA | 51 | 12.399 | 29.586 | 18.589 | 1.00 | 26.62 | A1 |
| ATOM | 387 | CB | ALA | 51 | 13.161 | 28.786 | 19.583 | 1.00 | 24.82 | A1 |
| ATOM | 388 | C | ALA | 51 | 13.009 | 29.369 | 17.187 | 1.00 | 26.71 | A1 |
| ATOM | 389 | O | ALA | 51 | 13.871 | 30.115 | 16.785 | 1.00 | 26.84 | A1 |
| ATOM | 390 | N | GLY | 52 | 12.564 | 28.333 | 16.475 | 1.00 | 26.28 | A1 |
| ATOM | 391 | CA | GLY | 52 | 13.120 | 28.049 | 15.160 | 1.00 | 27.58 | A1 |

FIG. 3A-7

| ATOM | 392 | C | GLY | 52 | 12.723 | 29.141 | 14.167 | 1.00 | 27.43 | A1 |
|---|---|---|---|---|---|---|---|---|---|---|
| ATOM | 393 | O | GLY | 52 | 13.537 | 29.588 | 13.353 | 1.00 | 27.16 | A1 |
| ATOM | 394 | N | ARG | 53 | 11.468 | 29.577 | 14.259 | 1.00 | 27.33 | A1 |
| ATOM | 395 | CA | ARG | 53 | 10.963 | 30.626 | 13.382 | 1.00 | 28.47 | A1 |
| ATOM | 396 | CB | ARG | 53 | 9.416 | 30.743 | 13.508 | 1.00 | 28.93 | A1 |
| ATOM | 397 | CG | ARG | 53 | 8.635 | 29.550 | 12.916 | 1.00 | 31.06 | A1 |
| ATOM | 398 | CD | ARG | 53 | 8.966 | 29.452 | 11.454 | 1.00 | 33.23 | A1 |
| ATOM | 399 | NE | ARG | 53 | 7.949 | 28.823 | 10.619 | 1.00 | 34.72 | A1 |
| ATOM | 400 | CZ | ARG | 53 | 7.853 | 27.509 | 10.417 | 1.00 | 34.64 | A1 |
| ATOM | 401 | NH1 | ARG | 53 | 8.712 | 26.691 | 11.017 | 1.00 | 33.41 | A1 |
| ATOM | 402 | NH2 | ARG | 53 | 6.959 | 27.037 | 9.551 | 1.00 | 32.59 | A1 |
| ATOM | 403 | C | ARG | 53 | 11.647 | 31.989 | 13.724 | 1.00 | 27.67 | A1 |
| ATOM | 404 | O | ARG | 53 | 11.960 | 32.741 | 12.810 | 1.00 | 27.77 | A1 |
| ATOM | 405 | N | PHE | 54 | 11.847 | 32.294 | 15.011 | 1.00 | 25.56 | A1 |
| ATOM | 406 | CA | PHE | 54 | 12.470 | 33.544 | 15.395 | 1.00 | 25.41 | A1 |
| ATOM | 407 | CB | PHE | 54 | 12.419 | 33.737 | 16.937 | 1.00 | 25.84 | A1 |
| ATOM | 408 | CG | PHE | 54 | 13.035 | 35.038 | 17.412 | 1.00 | 26.15 | A1 |
| ATOM | 409 | CD1 | PHE | 54 | 14.326 | 35.068 | 17.855 | 1.00 | 25.57 | A1 |
| ATOM | 410 | CD2 | PHE | 54 | 12.335 | 36.247 | 17.285 | 1.00 | 27.42 | A1 |
| ATOM | 411 | CE1 | PHE | 54 | 14.962 | 36.279 | 18.163 | 1.00 | 27.84 | A1 |
| ATOM | 412 | CE2 | PHE | 54 | 12.931 | 37.477 | 17.589 | 1.00 | 27.70 | A1 |
| ATOM | 413 | CZ | PHE | 54 | 14.245 | 37.507 | 18.023 | 1.00 | 29.21 | A1 |
| ATOM | 414 | C | PHE | 54 | 13.918 | 33.499 | 14.883 | 1.00 | 25.07 | A1 |
| ATOM | 415 | O | PHE | 54 | 14.416 | 34.481 | 14.315 | 1.00 | 24.66 | A1 |
| ATOM | 416 | N | ALA | 55 | 14.589 | 32.354 | 15.061 | 1.00 | 24.76 | A1 |
| ATOM | 417 | CA | ALA | 55 | 15.960 | 32.232 | 14.566 | 1.00 | 24.79 | A1 |
| ATOM | 418 | CB | ALA | 55 | 16.565 | 30.896 | 14.966 | 1.00 | 23.37 | A1 |
| ATOM | 419 | C | ALA | 55 | 16.000 | 32.384 | 13.036 | 1.00 | 24.40 | A1 |
| ATOM | 420 | O | ALA | 55 | 16.761 | 33.188 | 12.506 | 1.00 | 25.92 | A1 |
| ATOM | 421 | N | ALA | 56 | 15.201 | 31.612 | 12.332 | 1.00 | 23.65 | A1 |
| ATOM | 422 | CA | ALA | 56 | 15.178 | 31.705 | 10.873 | 1.00 | 23.88 | A1 |
| ATOM | 423 | CB | ALA | 56 | 14.184 | 30.759 | 10.314 | 1.00 | 21.79 | A1 |
| ATOM | 424 | C | ALA | 56 | 14.885 | 33.113 | 10.391 | 1.00 | 24.13 | A1 |
| ATOM | 425 | O | ALA | 56 | 15.510 | 33.572 | 9.449 | 1.00 | 24.31 | A1 |
| ATOM | 426 | N | LYS | 57 | 13.974 | 33.816 | 11.060 | 1.00 | 24.20 | A1 |
| ATOM | 427 | CA | LYS | 57 | 13.613 | 35.168 | 10.647 | 1.00 | 25.22 | A1 |
| ATOM | 428 | CB | LYS | 57 | 12.217 | 35.576 | 11.224 | 1.00 | 25.77 | A1 |
| ATOM | 429 | CG | LYS | 57 | 11.047 | 34.738 | 10.632 | 1.00 | 24.59 | A1 |
| ATOM | 430 | CD | LYS | 57 | 9.646 | 35.359 | 10.830 | 1.00 | 24.83 | A1 |
| ATOM | 431 | CE | LYS | 57 | 8.552 | 34.359 | 10.417 | 1.00 | 25.92 | A1 |
| ATOM | 432 | NZ | LYS | 57 | 7.084 | 34.830 | 10.452 | 1.00 | 26.32 | A1 |
| ATOM | 433 | C | LYS | 57 | 14.633 | 36.214 | 11.026 | 1.00 | 26.40 | A1 |
| ATOM | 434 | O | LYS | 57 | 14.705 | 37.245 | 10.355 | 1.00 | 26.87 | A1 |
| ATOM | 435 | N | GLU | 58 | 15.351 | 36.000 | 12.147 | 1.00 | 26.28 | A1 |
| ATOM | 436 | CA | GLU | 58 | 16.384 | 36.941 | 12.581 | 1.00 | 26.02 | A1 |
| ATOM | 437 | CB | GLU | 58 | 16.871 | 36.639 | 13.992 | 1.00 | 27.63 | A1 |
| ATOM | 438 | CG | GLU | 58 | 15.889 | 37.012 | 15.062 | 1.00 | 30.56 | A1 |
| ATOM | 439 | CD | GLU | 58 | 15.832 | 38.528 | 15.219 | 1.00 | 32.92 | A1 |
| ATOM | 440 | OE1 | GLU | 58 | 16.876 | 39.092 | 15.600 | 1.00 | 34.30 | A1 |
| ATOM | 441 | OE2 | GLU | 58 | 14.775 | 39.151 | 14.929 | 1.00 | 33.64 | A1 |
| ATOM | 442 | C | GLU | 58 | 17.553 | 36.768 | 11.611 | 1.00 | 25.11 | A1 |
| ATOM | 443 | O | GLU | 58 | 18.159 | 37.739 | 11.168 | 1.00 | 24.66 | A1 |
| ATOM | 444 | N | ALA | 59 | 17.865 | 35.529 | 11.276 | 1.00 | 24.85 | A1 |
| ATOM | 445 | CA | ALA | 59 | 18.928 | 35.272 | 10.327 | 1.00 | 23.99 | A1 |
| ATOM | 446 | CB | ALA | 59 | 19.128 | 33.764 | 10.154 | 1.00 | 23.99 | A1 |
| ATOM | 447 | C | ALA | 59 | 18.606 | 35.912 | 8.952 | 1.00 | 24.17 | A1 |
| ATOM | 448 | O | ALA | 59 | 19.459 | 36.540 | 8.315 | 1.00 | 21.87 | A1 |

FIG. 3A-8

| ATOM | 449 | N   | PHE | 60 | 17.370 | 35.737 | 8.505  | 1.00 | 24.88 | A1 |
|------|-----|-----|-----|----|--------|--------|--------|------|-------|----|
| ATOM | 450 | CA  | PHE | 60 | 16.968 | 36.251 | 7.218  | 1.00 | 25.44 | A1 |
| ATOM | 451 | CB  | PHE | 60 | 15.521 | 35.895 | 6.879  | 1.00 | 24.96 | A1 |
| ATOM | 452 | CG  | PHE | 60 | 15.037 | 36.546 | 5.586  | 1.00 | 26.06 | A1 |
| ATOM | 453 | CD1 | PHE | 60 | 15.193 | 35.904 | 4.363  | 1.00 | 25.13 | A1 |
| ATOM | 454 | CD2 | PHE | 60 | 14.474 | 37.831 | 5.598  | 1.00 | 25.99 | A1 |
| ATOM | 455 | CE1 | PHE | 60 | 14.804 | 36.507 | 3.170  | 1.00 | 24.37 | A1 |
| ATOM | 456 | CE2 | PHE | 60 | 14.078 | 38.450 | 4.391  | 1.00 | 25.81 | A1 |
| ATOM | 457 | CZ  | PHE | 60 | 14.251 | 37.766 | 3.185  | 1.00 | 24.62 | A1 |
| ATOM | 458 | C   | PHE | 60 | 17.114 | 37.770 | 7.207  | 1.00 | 27.27 | A1 |
| ATOM | 459 | O   | PHE | 60 | 17.691 | 38.352 | 6.242  | 1.00 | 27.79 | A1 |
| ATOM | 460 | N   | SER | 61 | 16.627 | 38.413 | 8.260  | 1.00 | 27.40 | A1 |
| ATOM | 461 | CA  | SER | 61 | 16.721 | 39.846 | 8.294  | 1.00 | 29.82 | A1 |
| ATOM | 462 | CB  | SER | 61 | 16.005 | 40.461 | 9.533  | 1.00 | 29.61 | A1 |
| ATOM | 463 | OG  | SER | 61 | 16.679 | 40.092 | 10.727 | 1.00 | 31.10 | A1 |
| ATOM | 464 | C   | SER | 61 | 18.191 | 40.242 | 8.294  | 1.00 | 31.09 | A1 |
| ATOM | 465 | O   | SER | 61 | 18.517 | 41.316 | 7.832  | 1.00 | 31.02 | A1 |
| ATOM | 466 | N   | LYS | 62 | 19.071 | 39.389 | 8.819  | 1.00 | 32.53 | A1 |
| ATOM | 467 | CA  | LYS | 62 | 20.508 | 39.723 | 8.828  | 1.00 | 34.06 | A1 |
| ATOM | 468 | CB  | LYS | 62 | 21.307 | 38.729 | 9.698  | 1.00 | 35.23 | A1 |
| ATOM | 469 | CG  | LYS | 62 | 21.305 | 38.975 | 11.242 | 1.00 | 37.56 | A1 |
| ATOM | 470 | CD  | LYS | 62 | 22.349 | 38.019 | 11.845 | 1.00 | 41.31 | A1 |
| ATOM | 471 | CE  | LYS | 62 | 22.427 | 38.038 | 13.347 | 1.00 | 43.94 | A1 |
| ATOM | 472 | NZ  | LYS | 62 | 21.213 | 37.446 | 14.089 | 1.00 | 46.69 | A1 |
| ATOM | 473 | C   | LYS | 62 | 21.066 | 39.710 | 7.382  | 1.00 | 34.27 | A1 |
| ATOM | 474 | O   | LYS | 62 | 21.760 | 40.641 | 6.956  | 1.00 | 34.53 | A1 |
| ATOM | 475 | N   | ALA | 63 | 20.746 | 38.649 | 6.651  | 1.00 | 33.34 | A1 |
| ATOM | 476 | CA  | ALA | 63 | 21.177 | 38.496 | 5.297  | 1.00 | 33.47 | A1 |
| ATOM | 477 | CB  | ALA | 63 | 20.751 | 37.106 | 4.756  | 1.00 | 32.08 | A1 |
| ATOM | 478 | C   | ALA | 63 | 20.563 | 39.610 | 4.459  | 1.00 | 33.97 | A1 |
| ATOM | 479 | O   | ALA | 63 | 21.230 | 40.142 | 3.616  | 1.00 | 34.33 | A1 |
| ATOM | 480 | N   | PHE | 64 | 19.291 | 39.945 | 4.700  | 1.00 | 35.12 | A1 |
| ATOM | 481 | CA  | PHE | 64 | 18.585 | 40.987 | 3.955  | 1.00 | 35.58 | A1 |
| ATOM | 482 | CB  | PHE | 64 | 17.097 | 41.040 | 4.371  | 1.00 | 33.83 | A1 |
| ATOM | 483 | CG  | PHE | 64 | 16.211 | 41.767 | 3.393  | 1.00 | 32.65 | A1 |
| ATOM | 484 | CD1 | PHE | 64 | 15.901 | 41.190 | 2.164  | 1.00 | 32.40 | A1 |
| ATOM | 485 | CD2 | PHE | 64 | 15.671 | 43.012 | 3.708  | 1.00 | 32.51 | A1 |
| ATOM | 486 | CE1 | PHE | 64 | 15.073 | 41.824 | 1.274  | 1.00 | 32.68 | A1 |
| ATOM | 487 | CE2 | PHE | 64 | 14.826 | 43.682 | 2.829  | 1.00 | 32.56 | A1 |
| ATOM | 488 | CZ  | PHE | 64 | 14.517 | 43.085 | 1.593  | 1.00 | 33.86 | A1 |
| ATOM | 489 | C   | PHE | 64 | 19.259 | 42.334 | 4.236  | 1.00 | 36.82 | A1 |
| ATOM | 490 | O   | PHE | 64 | 19.007 | 43.330 | 3.554  | 1.00 | 37.04 | A1 |
| ATOM | 491 | N   | GLY | 65 | 20.092 | 42.350 | 5.265  | 1.00 | 38.68 | A1 |
| ATOM | 492 | CA  | GLY | 65 | 20.837 | 43.542 | 5.636  | 1.00 | 41.46 | A1 |
| ATOM | 493 | C   | GLY | 65 | 20.119 | 44.748 | 6.216  | 1.00 | 43.07 | A1 |
| ATOM | 494 | O   | GLY | 65 | 20.749 | 45.793 | 6.427  | 1.00 | 42.77 | A1 |
| ATOM | 495 | N   | THR | 66 | 18.821 | 44.628 | 6.487  | 1.00 | 44.10 | A1 |
| ATOM | 496 | CA  | THR | 66 | 18.062 | 45.767 | 7.032  | 1.00 | 45.54 | A1 |
| ATOM | 497 | CB  | THR | 66 | 16.769 | 46.091 | 6.194  | 1.00 | 45.56 | A1 |
| ATOM | 498 | OG1 | THR | 66 | 15.854 | 44.992 | 6.288  | 1.00 | 46.47 | A1 |
| ATOM | 499 | CG2 | THR | 66 | 17.093 | 46.322 | 4.730  | 1.00 | 45.39 | A1 |
| ATOM | 500 | C   | THR | 66 | 17.579 | 45.503 | 8.463  | 1.00 | 46.31 | A1 |
| ATOM | 501 | O   | THR | 66 | 17.262 | 46.453 | 9.195  | 1.00 | 45.86 | A1 |
| ATOM | 502 | N   | GLY | 67 | 17.509 | 44.221 | 8.857  | 1.00 | 46.67 | A1 |
| ATOM | 503 | CA  | GLY | 67 | 16.994 | 43.912 | 10.186 | 1.00 | 46.27 | A1 |
| ATOM | 504 | C   | GLY | 67 | 15.487 | 44.210 | 10.210 | 1.00 | 46.15 | A1 |
| ATOM | 505 | O   | GLY | 67 | 14.938 | 44.754 | 9.254  | 1.00 | 46.00 | A1 |

FIG. 3A-9

| ATOM | 506 | N   | ILE | 68 | 14.813 | 43.892 | 11.310 | 1.00 | 45.81 | A1 |
|------|-----|-----|-----|----|--------|--------|--------|------|-------|-----|
| ATOM | 507 | CA  | ILE | 68 | 13.380 | 44.098 | 11.393 | 1.00 | 45.27 | A1 |
| ATOM | 508 | CB  | ILE | 68 | 12.744 | 43.185 | 12.478 | 1.00 | 44.45 | A1 |
| ATOM | 509 | CG2 | ILE | 68 | 11.221 | 43.417 | 12.518 | 1.00 | 42.62 | A1 |
| ATOM | 510 | CG1 | ILE | 68 | 13.043 | 41.716 | 12.159 | 1.00 | 43.31 | A1 |
| ATOM | 511 | CD1 | ILE | 68 | 12.415 | 41.217 | 10.850 | 1.00 | 42.83 | A1 |
| ATOM | 512 | C   | ILE | 68 | 12.989 | 45.544 | 11.650 | 1.00 | 45.87 | A1 |
| ATOM | 513 | O   | ILE | 68 | 13.490 | 46.188 | 12.572 | 1.00 | 46.37 | A1 |
| ATOM | 514 | N   | GLY | 69 | 12.065 | 46.047 | 10.843 | 1.00 | 45.69 | A1 |
| ATOM | 515 | CA  | GLY | 69 | 11.643 | 47.426 | 10.988 | 1.00 | 45.78 | A1 |
| ATOM | 516 | C   | GLY | 69 | 10.838 | 47.891 | 9.789  | 1.00 | 46.78 | A1 |
| ATOM | 517 | O   | GLY | 69 | 9.977  | 47.182 | 9.252  | 1.00 | 46.20 | A1 |
| ATOM | 518 | N   | ARG | 70 | 11.120 | 49.108 | 9.360  | 1.00 | 47.73 | A1 |
| ATOM | 519 | CA  | ARG | 70 | 10.415 | 49.684 | 8.236  | 1.00 | 48.39 | A1 |
| ATOM | 520 | CB  | ARG | 70 | 10.932 | 51.108 | 8.026  | 1.00 | 51.49 | A1 |
| ATOM | 521 | CG  | ARG | 70 | 10.084 | 51.897 | 7.059  | 1.00 | 55.58 | A1 |
| ATOM | 522 | CD  | ARG | 70 | 10.755 | 53.199 | 6.589  | 1.00 | 59.37 | A1 |
| ATOM | 523 | NE  | ARG | 70 | 9.972  | 53.806 | 5.496  | 1.00 | 62.26 | A1 |
| ATOM | 524 | CZ  | ARG | 70 | 9.714  | 55.111 | 5.385  | 1.00 | 63.78 | A1 |
| ATOM | 525 | NH1 | ARG | 70 | 8.985  | 55.551 | 4.353  | 1.00 | 64.14 | A1 |
| ATOM | 526 | NH2 | ARG | 70 | 10.181 | 55.975 | 6.303  | 1.00 | 63.87 | A1 |
| ATOM | 527 | C   | ARG | 70 | 10.499 | 48.871 | 6.914  | 1.00 | 47.02 | A1 |
| ATOM | 528 | O   | ARG | 70 | 9.480  | 48.606 | 6.250  | 1.00 | 46.19 | A1 |
| ATOM | 529 | N   | GLN | 71 | 11.705 | 48.471 | 6.532  | 1.00 | 45.11 | A1 |
| ATOM | 530 | CA  | GLN | 71 | 11.875 | 47.743 | 5.279  | 1.00 | 43.56 | A1 |
| ATOM | 531 | CB  | GLN | 71 | 13.336 | 47.854 | 4.821  | 1.00 | 44.43 | A1 |
| ATOM | 532 | CG  | GLN | 71 | 13.896 | 49.308 | 4.720  | 1.00 | 45.80 | A1 |
| ATOM | 533 | CD  | GLN | 71 | 15.391 | 49.319 | 4.344  | 1.00 | 47.82 | A1 |
| ATOM | 534 | OE1 | GLN | 71 | 15.764 | 48.917 | 3.228  | 1.00 | 48.24 | A1 |
| ATOM | 535 | NE2 | GLN | 71 | 16.253 | 49.751 | 5.276  | 1.00 | 47.27 | A1 |
| ATOM | 536 | C   | GLN | 71 | 11.483 | 46.275 | 5.387  | 1.00 | 42.01 | A1 |
| ATOM | 537 | O   | GLN | 71 | 11.186 | 45.639 | 4.395  | 1.00 | 42.31 | A1 |
| ATOM | 538 | N   | LEU | 72 | 11.425 | 45.743 | 6.601  | 1.00 | 39.83 | A1 |
| ATOM | 539 | CA  | LEU | 72 | 11.117 | 44.324 | 6.779  | 1.00 | 38.04 | A1 |
| ATOM | 540 | CB  | LEU | 72 | 12.420 | 43.528 | 6.713  | 1.00 | 36.85 | A1 |
| ATOM | 541 | CG  | LEU | 72 | 12.382 | 42.017 | 6.775  | 1.00 | 35.82 | A1 |
| ATOM | 542 | CD1 | LEU | 72 | 11.605 | 41.559 | 5.607  | 1.00 | 36.04 | A1 |
| ATOM | 543 | CD2 | LEU | 72 | 13.812 | 41.440 | 6.753  | 1.00 | 35.98 | A1 |
| ATOM | 544 | C   | LEU | 72 | 10.400 | 43.984 | 8.086  | 1.00 | 37.03 | A1 |
| ATOM | 545 | O   | LEU | 72 | 10.920 | 44.215 | 9.166  | 1.00 | 36.11 | A1 |
| ATOM | 546 | N   | SER | 73 | 9.214  | 43.406 | 7.980  | 1.00 | 36.72 | A1 |
| ATOM | 547 | CA  | SER | 73 | 8.461  | 43.031 | 9.175  | 1.00 | 36.31 | A1 |
| ATOM | 548 | CB  | SER | 73 | 7.003  | 43.440 | 9.032  | 1.00 | 36.91 | A1 |
| ATOM | 549 | OG  | SER | 73 | 6.222  | 42.756 | 10.003 | 1.00 | 39.16 | A1 |
| ATOM | 550 | C   | SER | 73 | 8.518  | 41.529 | 9.333  | 1.00 | 34.81 | A1 |
| ATOM | 551 | O   | SER | 73 | 8.730  | 40.849 | 8.353  | 1.00 | 34.46 | A1 |
| ATOM | 552 | N   | PHE | 74 | 8.368  | 41.023 | 10.565 | 1.00 | 33.65 | A1 |
| ATOM | 553 | CA  | PHE | 74 | 8.342  | 39.578 | 10.825 | 1.00 | 31.90 | A1 |
| ATOM | 554 | CB  | PHE | 74 | 7.948  | 39.298 | 12.282 | 1.00 | 30.13 | A1 |
| ATOM | 555 | CG  | PHE | 74 | 9.046  | 39.532 | 13.283 | 1.00 | 29.47 | A1 |
| ATOM | 556 | CD1 | PHE | 74 | 10.153 | 38.660 | 13.341 | 1.00 | 27.35 | A1 |
| ATOM | 557 | CD2 | PHE | 74 | 8.983  | 40.633 | 14.167 | 1.00 | 28.21 | A1 |
| ATOM | 558 | CE1 | PHE | 74 | 11.195 | 38.867 | 14.254 | 1.00 | 28.79 | A1 |
| ATOM | 559 | CE2 | PHE | 74 | 10.021 | 40.878 | 15.100 | 1.00 | 28.83 | A1 |
| ATOM | 560 | CZ  | PHE | 74 | 11.146 | 39.992 | 15.160 | 1.00 | 29.18 | A1 |
| ATOM | 561 | C   | PHE | 74 | 7.240  | 38.948 | 9.935  | 1.00 | 32.18 | A1 |
| ATOM | 562 | O   | PHE | 74 | 7.334  | 37.801 | 9.490  | 1.00 | 31.91 | A1 |

FIG. 3A-10

| ATOM | 563 | N | GLN | 75 | 6.168 | 39.704 | 9.731 | 1.00 | 32.36 | A1 |
| ATOM | 564 | CA | GLN | 75 | 5.018 | 39.257 | 8.956 | 1.00 | 32.59 | A1 |
| ATOM | 565 | CB | GLN | 75 | 3.847 | 40.223 | 9.188 | 1.00 | 34.01 | A1 |
| ATOM | 566 | CG | GLN | 75 | 3.335 | 40.256 | 10.616 | 1.00 | 36.12 | A1 |
| ATOM | 567 | CD | GLN | 75 | 2.919 | 38.876 | 11.112 | 1.00 | 38.23 | A1 |
| ATOM | 568 | OE1 | GLN | 75 | 3.282 | 38.496 | 12.227 | 1.00 | 39.11 | A1 |
| ATOM | 569 | NE2 | GLN | 75 | 2.148 | 38.118 | 10.290 | 1.00 | 37.65 | A1 |
| ATOM | 570 | C | GLN | 75 | 5.270 | 39.153 | 7.450 | 1.00 | 32.64 | A1 |
| ATOM | 571 | O | GLN | 75 | 4.418 | 38.625 | 6.744 | 1.00 | 32.25 | A1 |
| ATOM | 572 | N | ASP | 76 | 6.407 | 39.681 | 6.958 | 1.00 | 31.97 | A1 |
| ATOM | 573 | CA | ASP | 76 | 6.732 | 39.636 | 5.535 | 1.00 | 32.18 | A1 |
| ATOM | 574 | CB | ASP | 76 | 7.584 | 40.808 | 5.066 | 1.00 | 32.18 | A1 |
| ATOM | 575 | CG | ASP | 76 | 6.939 | 42.171 | 5.288 | 1.00 | 35.33 | A1 |
| ATOM | 576 | OD1 | ASP | 76 | 5.748 | 42.417 | 4.914 | 1.00 | 35.87 | A1 |
| ATOM | 577 | OD2 | ASP | 76 | 7.669 | 43.031 | 5.842 | 1.00 | 36.61 | A1 |
| ATOM | 578 | C | ASP | 76 | 7.530 | 38.395 | 5.203 | 1.00 | 32.20 | A1 |
| ATOM | 579 | O | ASP | 76 | 7.811 | 38.130 | 4.021 | 1.00 | 31.47 | A1 |
| ATOM | 580 | N | ILE | 77 | 7.901 | 37.632 | 6.229 | 1.00 | 31.49 | A1 |
| ATOM | 581 | CA | ILE | 77 | 8.744 | 36.421 | 6.006 | 1.00 | 31.71 | A1 |
| ATOM | 582 | CB | ILE | 77 | 10.005 | 36.477 | 6.882 | 1.00 | 30.86 | A1 |
| ATOM | 583 | CG2 | ILE | 77 | 10.951 | 35.376 | 6.513 | 1.00 | 29.76 | A1 |
| ATOM | 584 | CG1 | ILE | 77 | 10.629 | 37.868 | 6.771 | 1.00 | 31.47 | A1 |
| ATOM | 585 | CD1 | ILE | 77 | 11.497 | 38.255 | 7.981 | 1.00 | 30.84 | A1 |
| ATOM | 586 | C | ILE | 77 | 8.010 | 35.164 | 6.420 | 1.00 | 31.37 | A1 |
| ATOM | 587 | O | ILE | 77 | 7.504 | 35.095 | 7.534 | 1.00 | 33.09 | A1 |
| ATOM | 588 | N | GLU | 78 | 7.959 | 34.169 | 5.565 | 1.00 | 29.65 | A1 |
| ATOM | 589 | CA | GLU | 78 | 7.306 | 32.952 | 5.971 | 1.00 | 28.49 | A1 |
| ATOM | 590 | CB | GLU | 78 | 5.947 | 32.856 | 5.315 | 1.00 | 30.42 | A1 |
| ATOM | 591 | CG | GLU | 78 | 5.133 | 31.599 | 5.646 | 1.00 | 31.45 | A1 |
| ATOM | 592 | CD | GLU | 78 | 3.797 | 31.681 | 4.955 | 1.00 | 33.67 | A1 |
| ATOM | 593 | OE1 | GLU | 78 | 2.890 | 32.370 | 5.501 | 1.00 | 34.85 | A1 |
| ATOM | 594 | OE2 | GLU | 78 | 3.656 | 31.116 | 3.848 | 1.00 | 33.40 | A1 |
| ATOM | 595 | C | GLU | 78 | 8.161 | 31.740 | 5.648 | 1.00 | 27.82 | A1 |
| ATOM | 596 | O | GLU | 78 | 8.708 | 31.588 | 4.535 | 1.00 | 28.34 | A1 |
| ATOM | 597 | N | ILE | 79 | 8.322 | 30.880 | 6.639 | 1.00 | 26.70 | A1 |
| ATOM | 598 | CA | ILE | 79 | 9.097 | 29.671 | 6.433 | 1.00 | 25.67 | A1 |
| ATOM | 599 | CB | ILE | 79 | 9.902 | 29.208 | 7.739 | 1.00 | 25.60 | A1 |
| ATOM | 600 | CG2 | ILE | 79 | 10.224 | 27.693 | 7.636 | 1.00 | 23.34 | A1 |
| ATOM | 601 | CG1 | ILE | 79 | 11.187 | 30.053 | 7.937 | 1.00 | 23.66 | A1 |
| ATOM | 602 | CD1 | ILE | 79 | 10.943 | 31.531 | 8.226 | 1.00 | 22.51 | A1 |
| ATOM | 603 | C | ILE | 79 | 8.058 | 28.619 | 6.131 | 1.00 | 26.47 | A1 |
| ATOM | 604 | O | ILE | 79 | 7.055 | 28.501 | 6.836 | 1.00 | 26.91 | A1 |
| ATOM | 605 | N | ARG | 80 | 8.258 | 27.879 | 5.062 | 1.00 | 27.30 | A1 |
| ATOM | 606 | CA | ARG | 80 | 7.350 | 26.794 | 4.712 | 1.00 | 28.19 | A1 |
| ATOM | 607 | CB | ARG | 80 | 6.641 | 27.089 | 3.351 | 1.00 | 28.49 | A1 |
| ATOM | 608 | CG | ARG | 80 | 5.673 | 28.304 | 3.313 | 1.00 | 28.49 | A1 |
| ATOM | 609 | CD | ARG | 80 | 4.975 | 28.383 | 1.922 | 1.00 | 30.89 | A1 |
| ATOM | 610 | NE | ARG | 80 | 4.356 | 29.680 | 1.634 | 1.00 | 31.32 | A1 |
| ATOM | 611 | CZ | ARG | 80 | 3.847 | 30.049 | 0.460 | 1.00 | 31.60 | A1 |
| ATOM | 612 | NH1 | ARG | 80 | 3.865 | 29.226 | -0.584 | 1.00 | 31.89 | A1 |
| ATOM | 613 | NH2 | ARG | 80 | 3.354 | 31.272 | 0.320 | 1.00 | 31.19 | A1 |
| ATOM | 614 | C | ARG | 80 | 8.252 | 25.547 | 4.575 | 1.00 | 29.13 | A1 |
| ATOM | 615 | O | ARG | 80 | 9.503 | 25.666 | 4.493 | 1.00 | 27.83 | A1 |
| ATOM | 616 | N | LYS | 81 | 7.636 | 24.366 | 4.581 | 1.00 | 30.40 | A1 |
| ATOM | 617 | CA | LYS | 81 | 8.358 | 23.104 | 4.392 | 1.00 | 32.40 | A1 |
| ATOM | 618 | CB | LYS | 81 | 8.193 | 22.210 | 5.612 | 1.00 | 33.34 | A1 |
| ATOM | 619 | CG | LYS | 81 | 9.194 | 22.540 | 6.717 | 1.00 | 37.90 | A1 |

FIG. 3A-11

| ATOM | 620 | CD | LYS | 81 | 9.035 | 21.611 | 7.935 | 1.00 | 41.46 | A1 |
| ATOM | 621 | CE | LYS | 81 | 10.236 | 21.723 | 8.948 | 1.00 | 43.94 | A1 |
| ATOM | 622 | NZ | LYS | 81 | 9.836 | 21.172 | 10.319 | 1.00 | 44.22 | A1 |
| ATOM | 623 | C | LYS | 81 | 7.874 | 22.337 | 3.126 | 1.00 | 33.26 | A1 |
| ATOM | 624 | O | LYS | 81 | 6.669 | 22.225 | 2.875 | 1.00 | 32.50 | A1 |
| ATOM | 625 | N | ASP | 82 | 8.791 | 21.799 | 2.335 | 1.00 | 33.89 | A1 |
| ATOM | 626 | CA | ASP | 82 | 8.331 | 21.071 | 1.185 | 1.00 | 36.78 | A1 |
| ATOM | 627 | CB | ASP | 82 | 9.332 | 21.153 | 0.011 | 1.00 | 37.31 | A1 |
| ATOM | 628 | CG | ASP | 82 | 10.635 | 20.442 | 0.269 | 1.00 | 38.63 | A1 |
| ATOM | 629 | OD1 | ASP | 82 | 10.690 | 19.498 | 1.077 | 1.00 | 38.49 | A1 |
| ATOM | 630 | OD2 | ASP | 82 | 11.633 | 20.826 | -0.398 | 1.00 | 41.14 | A1 |
| ATOM | 631 | C | ASP | 82 | 7.962 | 19.627 | 1.512 | 1.00 | 37.29 | A1 |
| ATOM | 632 | O | ASP | 82 | 7.892 | 19.242 | 2.676 | 1.00 | 36.84 | A1 |
| ATOM | 633 | N | ALA | 83 | 7.688 | 18.840 | 0.481 | 1.00 | 38.27 | A1 |
| ATOM | 634 | CA | ALA | 83 | 7.281 | 17.446 | 0.677 | 1.00 | 40.15 | A1 |
| ATOM | 635 | CB | ALA | 83 | 7.085 | 16.751 | -0.707 | 1.00 | 41.30 | A1 |
| ATOM | 636 | C | ALA | 83 | 8.261 | 16.634 | 1.559 | 1.00 | 40.22 | A1 |
| ATOM | 637 | O | ALA | 83 | 7.842 | 15.798 | 2.359 | 1.00 | 40.09 | A1 |
| ATOM | 638 | N | ASN | 84 | 9.554 | 16.887 | 1.386 | 1.00 | 40.04 | A1 |
| ATOM | 639 | CA | ASN | 84 | 10.607 | 16.221 | 2.157 | 1.00 | 40.28 | A1 |
| ATOM | 640 | CB | ASN | 84 | 11.908 | 16.209 | 1.345 | 1.00 | 41.08 | A1 |
| ATOM | 641 | CG | ASN | 84 | 11.773 | 15.434 | 0.049 | 1.00 | 42.63 | A1 |
| ATOM | 642 | OD1 | ASN | 84 | 12.401 | 15.778 | -0.966 | 1.00 | 43.70 | A1 |
| ATOM | 643 | ND2 | ASN | 84 | 10.957 | 14.373 | 0.072 | 1.00 | 42.72 | A1 |
| ATOM | 644 | C | ASN | 84 | 10.897 | 16.895 | 3.513 | 1.00 | 39.63 | A1 |
| ATOM | 645 | O | ASN | 84 | 11.838 | 16.500 | 4.199 | 1.00 | 40.43 | A1 |
| ATOM | 646 | N | GLY | 85 | 10.114 | 17.899 | 3.903 | 1.00 | 38.52 | A1 |
| ATOM | 647 | CA | GLY | 85 | 10.365 | 18.584 | 5.172 | 1.00 | 37.04 | A1 |
| ATOM | 648 | C | GLY | 85 | 11.517 | 19.616 | 5.151 | 1.00 | 36.50 | A1 |
| ATOM | 649 | O | GLY | 85 | 11.921 | 20.112 | 6.201 | 1.00 | 37.45 | A1 |
| ATOM | 650 | N | LYS | 86 | 12.047 | 19.933 | 3.966 | 1.00 | 35.00 | A1 |
| ATOM | 651 | CA | LYS | 86 | 13.139 | 20.921 | 3.778 | 1.00 | 32.22 | A1 |
| ATOM | 652 | CB | LYS | 86 | 13.754 | 20.797 | 2.369 | 1.00 | 31.49 | A1 |
| ATOM | 653 | CG | LYS | 86 | 14.854 | 21.784 | 2.068 | 1.00 | 32.53 | A1 |
| ATOM | 654 | CD | LYS | 86 | 15.943 | 21.629 | 3.134 | 1.00 | 35.38 | A1 |
| ATOM | 655 | CE | LYS | 86 | 17.218 | 22.403 | 2.881 | 1.00 | 35.96 | A1 |
| ATOM | 656 | NZ | LYS | 86 | 16.966 | 23.771 | 3.262 | 1.00 | 37.11 | A1 |
| ATOM | 657 | C | LYS | 86 | 12.456 | 22.275 | 3.885 | 1.00 | 30.60 | A1 |
| ATOM | 658 | O | LYS | 86 | 11.489 | 22.523 | 3.193 | 1.00 | 29.77 | A1 |
| ATOM | 659 | N | PRO | 87 | 12.976 | 23.172 | 4.727 | 1.00 | 29.10 | A1 |
| ATOM | 660 | CD | PRO | 87 | 14.082 | 22.948 | 5.699 | 1.00 | 28.74 | A1 |
| ATOM | 661 | CA | PRO | 87 | 12.351 | 24.486 | 4.876 | 1.00 | 27.83 | A1 |
| ATOM | 662 | CB | PRO | 87 | 12.765 | 24.891 | 6.297 | 1.00 | 27.32 | A1 |
| ATOM | 663 | CG | PRO | 87 | 14.256 | 24.309 | 6.370 | 1.00 | 27.78 | A1 |
| ATOM | 664 | C | PRO | 87 | 12.783 | 25.517 | 3.801 | 1.00 | 27.06 | A1 |
| ATOM | 665 | O | PRO | 87 | 13.890 | 25.471 | 3.333 | 1.00 | 27.38 | A1 |
| ATOM | 666 | N | TYR | 88 | 11.883 | 26.395 | 3.374 | 1.00 | 25.32 | A1 |
| ATOM | 667 | CA | TYR | 88 | 12.248 | 27.448 | 2.411 | 1.00 | 25.06 | A1 |
| ATOM | 668 | CB | TYR | 88 | 11.917 | 27.069 | 0.947 | 1.00 | 24.22 | A1 |
| ATOM | 669 | CG | TYR | 88 | 10.463 | 26.735 | 0.656 | 1.00 | 23.29 | A1 |
| ATOM | 670 | CD1 | TYR | 88 | 9.599 | 27.704 | 0.100 | 1.00 | 22.42 | A1 |
| ATOM | 671 | CE1 | TYR | 88 | 8.247 | 27.406 | -0.174 | 1.00 | 23.37 | A1 |
| ATOM | 672 | CD2 | TYR | 88 | 9.952 | 25.460 | 0.937 | 1.00 | 23.26 | A1 |
| ATOM | 673 | CE2 | TYR | 88 | 8.615 | 25.141 | 0.686 | 1.00 | 23.66 | A1 |
| ATOM | 674 | CZ | TYR | 88 | 7.762 | 26.132 | 0.126 | 1.00 | 25.22 | A1 |
| ATOM | 675 | OH | TYR | 88 | 6.421 | 25.901 | -0.045 | 1.00 | 26.63 | A1 |
| ATOM | 676 | C | TYR | 88 | 11.520 | 28.712 | 2.850 | 1.00 | 24.33 | A1 |

FIG. 3A-12

| ATOM | 677 | O | TYR | 88 | 10.546 | 28.651 | 3.582 | 1.00 | 23.08 | A1 |
| ATOM | 678 | N | ILE | 89 | 12.029 | 29.856 | 2.443 | 1.00 | 24.80 | A1 |
| ATOM | 679 | CA | ILE | 89 | 11.453 | 31.120 | 2.833 | 1.00 | 24.53 | A1 |
| ATOM | 680 | CB | ILE | 89 | 12.525 | 32.056 | 3.375 | 1.00 | 24.83 | A1 |
| ATOM | 681 | CG2 | ILE | 89 | 12.086 | 33.554 | 3.208 | 1.00 | 24.50 | A1 |
| ATOM | 682 | CG1 | ILE | 89 | 12.788 | 31.742 | 4.864 | 1.00 | 24.97 | A1 |
| ATOM | 683 | CD1 | ILE | 89 | 14.217 | 32.125 | 5.316 | 1.00 | 25.39 | A1 |
| ATOM | 684 | C | ILE | 89 | 10.809 | 31.826 | 1.679 | 1.00 | 26.13 | A1 |
| ATOM | 685 | O | ILE | 89 | 11.378 | 31.920 | 0.600 | 1.00 | 26.39 | A1 |
| ATOM | 686 | N | ILE | 90 | 9.590 | 32.304 | 1.907 | 1.00 | 27.30 | A1 |
| ATOM | 687 | CA | ILE | 90 | 8.905 | 33.116 | 0.911 | 1.00 | 27.73 | A1 |
| ATOM | 688 | CB | ILE | 90 | 7.457 | 32.697 | 0.679 | 1.00 | 27.77 | A1 |
| ATOM | 689 | CG2 | ILE | 90 | 6.777 | 33.777 | -0.198 | 1.00 | 26.69 | A1 |
| ATOM | 690 | CG1 | ILE | 90 | 7.379 | 31.283 | 0.073 | 1.00 | 27.36 | A1 |
| ATOM | 691 | CD1 | ILE | 90 | 8.309 | 31.055 | -1.121 | 1.00 | 25.23 | A1 |
| ATOM | 692 | C | ILE | 90 | 8.863 | 34.461 | 1.619 | 1.00 | 28.64 | A1 |
| ATOM | 693 | O | ILE | 90 | 8.375 | 34.534 | 2.750 | 1.00 | 28.70 | A1 |
| ATOM | 694 | N | CYS | 91 | 9.368 | 35.500 | 0.979 | 1.00 | 29.78 | A1 |
| ATOM | 695 | CA | CYS | 91 | 9.394 | 36.846 | 1.529 | 1.00 | 31.18 | A1 |
| ATOM | 696 | CB | CYS | 91 | 10.822 | 37.284 | 1.840 | 1.00 | 31.71 | A1 |
| ATOM | 697 | SG | CYS | 91 | 10.958 | 39.042 | 2.467 | 1.00 | 33.30 | A1 |
| ATOM | 698 | C | CYS | 91 | 8.795 | 37.798 | 0.492 | 1.00 | 32.78 | A1 |
| ATOM | 699 | O | CYS | 91 | 9.160 | 37.750 | -0.701 | 1.00 | 32.93 | A1 |
| ATOM | 700 | N | THR | 92 | 7.890 | 38.652 | 0.961 | 1.00 | 33.89 | A1 |
| ATOM | 701 | CA | THR | 92 | 7.169 | 39.654 | 0.161 | 1.00 | 35.68 | A1 |
| ATOM | 702 | CB | THR | 92 | 5.956 | 40.205 | 0.980 | 1.00 | 35.88 | A1 |
| ATOM | 703 | OG1 | THR | 92 | 6.424 | 40.914 | 2.147 | 1.00 | 35.36 | A1 |
| ATOM | 704 | CG2 | THR | 92 | 5.071 | 39.048 | 1.463 | 1.00 | 35.26 | A1 |
| ATOM | 705 | C | THR | 92 | 8.007 | 40.867 | -0.298 | 1.00 | 37.04 | A1 |
| ATOM | 706 | O | THR | 92 | 7.635 | 41.567 | -1.234 | 1.00 | 38.47 | A1 |
| ATOM | 707 | N | LYS | 93 | 9.132 | 41.099 | 0.361 | 1.00 | 38.09 | A1 |
| ATOM | 708 | CA | LYS | 93 | 10.018 | 42.238 | 0.091 | 1.00 | 39.21 | A1 |
| ATOM | 709 | CB | LYS | 93 | 10.455 | 42.831 | 1.410 | 1.00 | 38.83 | A1 |
| ATOM | 710 | CG | LYS | 93 | 9.355 | 43.459 | 2.165 | 1.00 | 41.82 | A1 |
| ATOM | 711 | CD | LYS | 93 | 9.133 | 44.850 | 1.659 | 1.00 | 43.77 | A1 |
| ATOM | 712 | CE | LYS | 93 | 8.287 | 45.660 | 2.603 | 1.00 | 45.90 | A1 |
| ATOM | 713 | NZ | LYS | 93 | 6.866 | 45.285 | 2.448 | 1.00 | 48.15 | A1 |
| ATOM | 714 | C | LYS | 93 | 11.277 | 41.938 | -0.700 | 1.00 | 39.21 | A1 |
| ATOM | 715 | O | LYS | 93 | 12.037 | 42.843 | -1.033 | 1.00 | 38.83 | A1 |
| ATOM | 716 | N | LEU | 94 | 11.495 | 40.663 | -0.980 | 1.00 | 40.77 | A1 |
| ATOM | 717 | CA | LEU | 94 | 12.692 | 40.202 | -1.677 | 1.00 | 42.19 | A1 |
| ATOM | 718 | CB | LEU | 94 | 13.065 | 38.808 | -1.152 | 1.00 | 41.91 | A1 |
| ATOM | 719 | CG | LEU | 94 | 14.332 | 38.116 | -1.637 | 1.00 | 41.65 | A1 |
| ATOM | 720 | CD1 | LEU | 94 | 15.550 | 38.970 | -1.401 | 1.00 | 42.73 | A1 |
| ATOM | 721 | CD2 | LEU | 94 | 14.464 | 36.818 | -0.891 | 1.00 | 41.81 | A1 |
| ATOM | 722 | C | LEU | 94 | 12.467 | 40.185 | -3.186 | 1.00 | 43.24 | A1 |
| ATOM | 723 | O | LEU | 94 | 11.555 | 39.532 | -3.688 | 1.00 | 42.50 | A1 |
| ATOM | 724 | N | SER | 95 | 13.329 | 40.899 | -3.897 | 1.00 | 45.02 | A1 |
| ATOM | 725 | CA | SER | 95 | 13.229 | 41.029 | -5.343 | 1.00 | 47.26 | A1 |
| ATOM | 726 | CB | SER | 95 | 13.094 | 42.524 | -5.673 | 1.00 | 47.88 | A1 |
| ATOM | 727 | OG | SER | 95 | 13.153 | 42.763 | -7.070 | 1.00 | 50.21 | A1 |
| ATOM | 728 | C | SER | 95 | 14.401 | 40.414 | -6.130 | 1.00 | 47.86 | A1 |
| ATOM | 729 | O | SER | 95 | 15.558 | 40.660 | -5.815 | 1.00 | 47.15 | A1 |
| ATOM | 730 | N | GLN | 96 | 14.079 | 39.602 | -7.138 | 1.00 | 48.90 | A1 |
| ATOM | 731 | CA | GLN | 96 | 15.075 | 38.957 | -8.016 | 1.00 | 49.92 | A1 |
| ATOM | 732 | CB | GLN | 96 | 15.506 | 39.944 | -9.123 | 1.00 | 52.77 | A1 |
| ATOM | 733 | CG | GLN | 96 | 14.362 | 40.551 | -9.970 | 1.00 | 57.47 | A1 |

FIG. 3A-13

| ATOM | 734 | CD | GLN | 96 | 13.996 | 39.744 | -11.255 | 1.00 | 60.94 | A1 |
| ATOM | 735 | OE1 | GLN | 96 | 12.988 | 40.062 | -11.934 | 1.00 | 63.96 | A1 |
| ATOM | 736 | NE2 | GLN | 96 | 14.802 | 38.727 | -11.597 | 1.00 | 60.89 | A1 |
| ATOM | 737 | C | GLN | 96 | 16.335 | 38.405 | -7.322 | 1.00 | 48.68 | A1 |
| ATOM | 738 | O | GLN | 96 | 17.465 | 38.849 | -7.592 | 1.00 | 48.55 | A1 |
| ATOM | 739 | N | ALA | 97 | 16.150 | 37.427 | -6.443 | 1.00 | 46.14 | A1 |
| ATOM | 740 | CA | ALA | 97 | 17.279 | 36.849 | -5.738 | 1.00 | 43.43 | A1 |
| ATOM | 741 | CB | ALA | 97 | 17.720 | 37.792 | -4.625 | 1.00 | 42.90 | A1 |
| ATOM | 742 | C | ALA | 97 | 16.834 | 35.512 | -5.174 | 1.00 | 41.43 | A1 |
| ATOM | 743 | O | ALA | 97 | 15.649 | 35.275 | -5.016 | 1.00 | 42.26 | A1 |
| ATOM | 744 | N | ALA | 98 | 17.781 | 34.633 | -4.888 | 1.00 | 38.63 | A1 |
| ATOM | 745 | CA | ALA | 98 | 17.491 | 33.320 | -4.333 | 1.00 | 35.46 | A1 |
| ATOM | 746 | CB | ALA | 98 | 18.340 | 32.283 | -5.027 | 1.00 | 34.45 | A1 |
| ATOM | 747 | C | ALA | 98 | 17.829 | 33.355 | -2.843 | 1.00 | 33.41 | A1 |
| ATOM | 748 | O | ALA | 98 | 18.818 | 33.969 | -2.447 | 1.00 | 32.79 | A1 |
| ATOM | 749 | N | VAL | 99 | 17.005 | 32.711 | -2.034 | 1.00 | 31.25 | A1 |
| ATOM | 750 | CA | VAL | 99 | 17.213 | 32.600 | -0.581 | 1.00 | 30.34 | A1 |
| ATOM | 751 | CB | VAL | 99 | 15.994 | 32.977 | 0.278 | 1.00 | 32.21 | A1 |
| ATOM | 752 | CG1 | VAL | 99 | 16.452 | 33.374 | 1.688 | 1.00 | 30.41 | A1 |
| ATOM | 753 | CG2 | VAL | 99 | 15.153 | 33.979 | -0.393 | 1.00 | 32.69 | A1 |
| ATOM | 754 | C | VAL | 99 | 17.339 | 31.136 | -0.206 | 1.00 | 29.01 | A1 |
| ATOM | 755 | O | VAL | 99 | 16.558 | 30.319 | -0.680 | 1.00 | 27.15 | A1 |
| ATOM | 756 | N | HIS | 100 | 18.299 | 30.810 | 0.651 | 1.00 | 28.69 | A1 |
| ATOM | 757 | CA | HIS | 100 | 18.435 | 29.432 | 1.141 | 1.00 | 28.94 | A1 |
| ATOM | 758 | CB | HIS | 100 | 19.735 | 28.813 | 0.699 | 1.00 | 31.55 | A1 |
| ATOM | 759 | CG | HIS | 100 | 19.904 | 28.757 | -0.780 | 1.00 | 35.62 | A1 |
| ATOM | 760 | CD2 | HIS | 100 | 20.725 | 29.452 | -1.610 | 1.00 | 36.22 | A1 |
| ATOM | 761 | ND1 | HIS | 100 | 19.196 | 27.881 | -1.578 | 1.00 | 37.27 | A1 |
| ATOM | 762 | CE1 | HIS | 100 | 19.575 | 28.041 | -2.836 | 1.00 | 36.95 | A1 |
| ATOM | 763 | NE2 | HIS | 100 | 20.497 | 28.987 | -2.881 | 1.00 | 37.02 | A1 |
| ATOM | 764 | C | HIS | 100 | 18.416 | 29.518 | 2.680 | 1.00 | 28.21 | A1 |
| ATOM | 765 | O | HIS | 100 | 18.921 | 30.477 | 3.274 | 1.00 | 28.01 | A1 |
| ATOM | 766 | N | VAL | 101 | 17.819 | 28.534 | 3.320 | 1.00 | 26.49 | A1 |
| ATOM | 767 | CA | VAL | 101 | 17.731 | 28.521 | 4.755 | 1.00 | 25.36 | A1 |
| ATOM | 768 | CB | VAL | 101 | 16.321 | 28.961 | 5.171 | 1.00 | 25.72 | A1 |
| ATOM | 769 | CG1 | VAL | 101 | 15.312 | 27.810 | 4.830 | 1.00 | 25.91 | A1 |
| ATOM | 770 | CG2 | VAL | 101 | 16.249 | 29.263 | 6.693 | 1.00 | 24.55 | A1 |
| ATOM | 771 | C | VAL | 101 | 17.974 | 27.082 | 5.284 | 1.00 | 24.98 | A1 |
| ATOM | 772 | O | VAL | 101 | 17.731 | 26.114 | 4.577 | 1.00 | 23.99 | A1 |
| ATOM | 773 | N | SER | 102 | 18.460 | 26.968 | 6.525 | 1.00 | 25.05 | A1 |
| ATOM | 774 | CA | SER | 102 | 18.654 | 25.705 | 7.218 | 1.00 | 25.32 | A1 |
| ATOM | 775 | CB | SER | 102 | 20.016 | 25.077 | 6.943 | 1.00 | 25.69 | A1 |
| ATOM | 776 | OG | SER | 102 | 20.078 | 23.796 | 7.570 | 1.00 | 26.81 | A1 |
| ATOM | 777 | C | SER | 102 | 18.474 | 25.991 | 8.715 | 1.00 | 26.24 | A1 |
| ATOM | 778 | O | SER | 102 | 18.990 | 26.948 | 9.279 | 1.00 | 26.44 | A1 |
| ATOM | 779 | N | ILE | 103 | 17.727 | 25.118 | 9.347 | 1.00 | 27.73 | A1 |
| ATOM | 780 | CA | ILE | 103 | 17.348 | 25.250 | 10.733 | 1.00 | 28.05 | A1 |
| ATOM | 781 | CB | ILE | 103 | 15.823 | 25.429 | 10.771 | 1.00 | 28.38 | A1 |
| ATOM | 782 | CG2 | ILE | 103 | 15.257 | 25.564 | 12.273 | 1.00 | 26.15 | A1 |
| ATOM | 783 | CG1 | ILE | 103 | 15.482 | 26.676 | 9.967 | 1.00 | 27.93 | A1 |
| ATOM | 784 | CD1 | ILE | 103 | 13.976 | 26.855 | 9.714 | 1.00 | 27.56 | A1 |
| ATOM | 785 | C | ILE | 103 | 17.743 | 23.982 | 11.474 | 1.00 | 29.39 | A1 |
| ATOM | 786 | O | ILE | 103 | 17.594 | 22.882 | 10.953 | 1.00 | 28.59 | A1 |
| ATOM | 787 | N | THR | 104 | 18.279 | 24.133 | 12.679 | 1.00 | 31.06 | A1 |
| ATOM | 788 | CA | THR | 104 | 18.659 | 22.963 | 13.470 | 1.00 | 32.26 | A1 |
| ATOM | 789 | CB | THR | 104 | 20.156 | 22.640 | 13.288 | 1.00 | 33.13 | A1 |
| ATOM | 790 | OG1 | THR | 104 | 20.417 | 21.334 | 13.796 | 1.00 | 36.05 | A1 |

FIG. 3A-14

| ATOM | 791 | CG2 | THR | 104 | 21.040 | 23.653 | 14.041 | 1.00 | 34.05 | A1 |
|---|---|---|---|---|---|---|---|---|---|---|
| ATOM | 792 | C | THR | 104 | 18.337 | 23.236 | 14.945 | 1.00 | 32.20 | A1 |
| ATOM | 793 | O | THR | 104 | 18.251 | 24.383 | 15.375 | 1.00 | 32.07 | A1 |
| ATOM | 794 | N | HIS | 105 | 18.207 | 22.175 | 15.718 | 1.00 | 32.17 | A1 |
| ATOM | 795 | CA | HIS | 105 | 17.868 | 22.318 | 17.112 | 1.00 | 33.14 | A1 |
| ATOM | 796 | CB | HIS | 105 | 16.419 | 21.857 | 17.378 | 1.00 | 33.42 | A1 |
| ATOM | 797 | CG | HIS | 105 | 15.361 | 22.740 | 16.785 | 1.00 | 33.41 | A1 |
| ATOM | 798 | CD2 | HIS | 105 | 14.776 | 22.728 | 15.563 | 1.00 | 33.17 | A1 |
| ATOM | 799 | ND1 | HIS | 105 | 14.806 | 23.799 | 17.468 | 1.00 | 33.56 | A1 |
| ATOM | 800 | CE1 | HIS | 105 | 13.930 | 24.410 | 16.684 | 1.00 | 33.55 | A1 |
| ATOM | 801 | NE2 | HIS | 105 | 13.898 | 23.784 | 15.524 | 1.00 | 31.70 | A1 |
| ATOM | 802 | C | HIS | 105 | 18.732 | 21.440 | 17.955 | 1.00 | 33.28 | A1 |
| ATOM | 803 | O | HIS | 105 | 19.219 | 20.423 | 17.495 | 1.00 | 34.01 | A1 |
| ATOM | 804 | N | THR | 106 | 18.913 | 21.866 | 19.188 | 1.00 | 33.82 | A1 |
| ATOM | 805 | CA | THR | 106 | 19.571 | 21.079 | 20.231 | 1.00 | 35.50 | A1 |
| ATOM | 806 | CB | THR | 106 | 20.888 | 21.669 | 20.699 | 1.00 | 34.97 | A1 |
| ATOM | 807 | OG1 | THR | 106 | 20.649 | 23.006 | 21.184 | 1.00 | 35.76 | A1 |
| ATOM | 808 | CG2 | THR | 106 | 21.896 | 21.675 | 19.560 | 1.00 | 34.11 | A1 |
| ATOM | 809 | C | THR | 106 | 18.534 | 21.271 | 21.372 | 1.00 | 36.77 | A1 |
| ATOM | 810 | O | THR | 106 | 17.583 | 22.050 | 21.232 | 1.00 | 36.77 | A1 |
| ATOM | 811 | N | LYS | 107 | 18.705 | 20.579 | 22.488 | 1.00 | 38.69 | A1 |
| ATOM | 812 | CA | LYS | 107 | 17.766 | 20.700 | 23.606 | 1.00 | 39.45 | A1 |
| ATOM | 813 | CB | LYS | 107 | 18.217 | 19.791 | 24.744 | 1.00 | 41.81 | A1 |
| ATOM | 814 | CG | LYS | 107 | 18.548 | 18.426 | 24.200 | 1.00 | 45.50 | A1 |
| ATOM | 815 | CD | LYS | 107 | 17.376 | 17.906 | 23.316 | 1.00 | 48.48 | A1 |
| ATOM | 816 | CE | LYS | 107 | 17.726 | 16.573 | 22.670 | 1.00 | 49.87 | A1 |
| ATOM | 817 | NZ | LYS | 107 | 19.034 | 16.767 | 21.979 | 1.00 | 51.62 | A1 |
| ATOM | 818 | C | LYS | 107 | 17.629 | 22.131 | 24.102 | 1.00 | 38.70 | A1 |
| ATOM | 819 | O | LYS | 107 | 16.549 | 22.546 | 24.447 | 1.00 | 38.83 | A1 |
| ATOM | 820 | N | GLU | 108 | 18.717 | 22.890 | 24.129 | 1.00 | 38.25 | A1 |
| ATOM | 821 | CA | GLU | 108 | 18.634 | 24.266 | 24.600 | 1.00 | 38.46 | A1 |
| ATOM | 822 | CB | GLU | 108 | 19.784 | 24.546 | 25.551 | 1.00 | 41.56 | A1 |
| ATOM | 823 | CG | GLU | 108 | 19.689 | 23.806 | 26.905 | 1.00 | 46.25 | A1 |
| ATOM | 824 | CD | GLU | 108 | 21.046 | 23.723 | 27.532 | 1.00 | 49.16 | A1 |
| ATOM | 825 | OE1 | GLU | 108 | 21.297 | 22.804 | 28.359 | 1.00 | 51.02 | A1 |
| ATOM | 826 | OE2 | GLU | 108 | 21.875 | 24.583 | 27.165 | 1.00 | 50.23 | A1 |
| ATOM | 827 | C | GLU | 108 | 18.599 | 25.342 | 23.511 | 1.00 | 37.27 | A1 |
| ATOM | 828 | O | GLU | 108 | 18.241 | 26.490 | 23.775 | 1.00 | 37.57 | A1 |
| ATOM | 829 | N | TYR | 109 | 18.882 | 24.972 | 22.272 | 1.00 | 35.87 | A1 |
| ATOM | 830 | CA | TYR | 109 | 18.903 | 25.983 | 21.205 | 1.00 | 34.61 | A1 |
| ATOM | 831 | CB | TYR | 109 | 20.347 | 26.276 | 20.786 | 1.00 | 35.12 | A1 |
| ATOM | 832 | CG | TYR | 109 | 21.247 | 26.738 | 21.886 | 1.00 | 37.02 | A1 |
| ATOM | 833 | CD1 | TYR | 109 | 21.082 | 27.983 | 22.469 | 1.00 | 37.99 | A1 |
| ATOM | 834 | CE1 | TYR | 109 | 21.878 | 28.388 | 23.506 | 1.00 | 39.54 | A1 |
| ATOM | 835 | CD2 | TYR | 109 | 22.238 | 25.905 | 22.370 | 1.00 | 38.09 | A1 |
| ATOM | 836 | CE2 | TYR | 109 | 23.033 | 26.284 | 23.413 | 1.00 | 40.11 | A1 |
| ATOM | 837 | CZ | TYR | 109 | 22.848 | 27.524 | 23.983 | 1.00 | 40.67 | A1 |
| ATOM | 838 | OH | TYR | 109 | 23.585 | 27.851 | 25.080 | 1.00 | 42.84 | A1 |
| ATOM | 839 | C | TYR | 109 | 18.178 | 25.739 | 19.900 | 1.00 | 32.13 | A1 |
| ATOM | 840 | O | TYR | 109 | 17.993 | 24.593 | 19.476 | 1.00 | 31.90 | A1 |
| ATOM | 841 | N | ALA | 110 | 17.817 | 26.857 | 19.272 | 1.00 | 30.38 | A1 |
| ATOM | 842 | CA | ALA | 110 | 17.290 | 26.885 | 17.897 | 1.00 | 28.86 | A1 |
| ATOM | 843 | CB | ALA | 110 | 15.995 | 27.591 | 17.836 | 1.00 | 28.37 | A1 |
| ATOM | 844 | C | ALA | 110 | 18.370 | 27.712 | 17.127 | 1.00 | 29.23 | A1 |
| ATOM | 845 | O | ALA | 110 | 18.794 | 28.810 | 17.575 | 1.00 | 29.93 | A1 |
| ATOM | 846 | N | ALA | 111 | 18.882 | 27.187 | 16.022 | 1.00 | 27.52 | A1 |
| ATOM | 847 | CA | ALA | 111 | 19.837 | 27.950 | 15.237 | 1.00 | 25.45 | A1 |

FIG. 3A-15

| ATOM | 848 | CB  | ALA | 111 | 21.158 | 27.349 | 15.323 | 1.00 | 24.00 | A1 |
| ---- | --- | --- | --- | --- | ------ | ------ | ------ | ---- | ----- | -- |
| ATOM | 849 | C   | ALA | 111 | 19.368 | 27.907 | 13.778 | 1.00 | 25.60 | A1 |
| ATOM | 850 | O   | ALA | 111 | 18.808 | 26.889 | 13.333 | 1.00 | 25.88 | A1 |
| ATOM | 851 | N   | ALA | 112 | 19.592 | 29.004 | 13.048 | 1.00 | 24.52 | A1 |
| ATOM | 852 | CA  | ALA | 112 | 19.264 | 29.091 | 11.617 | 1.00 | 24.43 | A1 |
| ATOM | 853 | CB  | ALA | 112 | 17.946 | 29.749 | 11.434 | 1.00 | 21.58 | A1 |
| ATOM | 854 | C   | ALA | 112 | 20.339 | 29.907 | 10.848 | 1.00 | 25.57 | A1 |
| ATOM | 855 | O   | ALA | 112 | 20.956 | 30.820 | 11.398 | 1.00 | 26.18 | A1 |
| ATOM | 856 | N   | GLN | 113 | 20.556 | 29.564 | 9.586  | 1.00 | 25.23 | A1 |
| ATOM | 857 | CA  | GLN | 113 | 21.470 | 30.320 | 8.770  | 1.00 | 26.13 | A1 |
| ATOM | 858 | CB  | GLN | 113 | 22.760 | 29.543 | 8.517  | 1.00 | 26.47 | A1 |
| ATOM | 859 | CG  | GLN | 113 | 22.662 | 28.453 | 7.592  | 1.00 | 29.75 | A1 |
| ATOM | 860 | CD  | GLN | 113 | 23.958 | 27.673 | 7.572  | 1.00 | 32.50 | A1 |
| ATOM | 861 | OE1 | GLN | 113 | 24.926 | 28.054 | 8.255  | 1.00 | 36.57 | A1 |
| ATOM | 862 | NE2 | GLN | 113 | 23.992 | 26.573 | 6.829  | 1.00 | 31.90 | A1 |
| ATOM | 863 | C   | GLN | 113 | 20.694 | 30.579 | 7.471  | 1.00 | 25.66 | A1 |
| ATOM | 864 | O   | GLN | 113 | 19.859 | 29.755 | 7.045  | 1.00 | 24.97 | A1 |
| ATOM | 865 | N   | VAL | 114 | 20.925 | 31.745 | 6.882  | 1.00 | 24.78 | A1 |
| ATOM | 866 | CA  | VAL | 114 | 20.225 | 32.103 | 5.673  | 1.00 | 25.47 | A1 |
| ATOM | 867 | CB  | VAL | 114 | 19.161 | 33.207 | 5.911  | 1.00 | 24.56 | A1 |
| ATOM | 868 | CG1 | VAL | 114 | 18.648 | 33.687 | 4.571  | 1.00 | 24.37 | A1 |
| ATOM | 869 | CG2 | VAL | 114 | 18.009 | 32.716 | 6.747  | 1.00 | 22.99 | A1 |
| ATOM | 870 | C   | VAL | 114 | 21.192 | 32.670 | 4.638  | 1.00 | 26.69 | A1 |
| ATOM | 871 | O   | VAL | 114 | 22.091 | 33.446 | 4.989  | 1.00 | 26.92 | A1 |
| ATOM | 872 | N   | VAL | 115 | 21.018 | 32.286 | 3.371  | 1.00 | 27.22 | A1 |
| ATOM | 873 | CA  | VAL | 115 | 21.834 | 32.879 | 2.303  | 1.00 | 28.03 | A1 |
| ATOM | 874 | CB  | VAL | 115 | 22.795 | 31.856 | 1.613  | 1.00 | 27.69 | A1 |
| ATOM | 875 | CG1 | VAL | 115 | 23.605 | 32.534 | 0.410  | 1.00 | 25.99 | A1 |
| ATOM | 876 | CG2 | VAL | 115 | 23.795 | 31.316 | 2.637  | 1.00 | 27.55 | A1 |
| ATOM | 877 | C   | VAL | 115 | 20.865 | 33.507 | 1.254  | 1.00 | 29.18 | A1 |
| ATOM | 878 | O   | VAL | 115 | 19.864 | 32.900 | 0.824  | 1.00 | 27.88 | A1 |
| ATOM | 879 | N   | ILE | 116 | 21.131 | 34.767 | 0.932  | 1.00 | 30.60 | A1 |
| ATOM | 880 | CA  | ILE | 116 | 20.367 | 35.486 | -0.076 | 1.00 | 32.32 | A1 |
| ATOM | 881 | CB  | ILE | 116 | 19.787 | 36.777 | 0.501  | 1.00 | 31.54 | A1 |
| ATOM | 882 | CG2 | ILE | 116 | 19.258 | 37.657 | -0.621 | 1.00 | 30.92 | A1 |
| ATOM | 883 | CG1 | ILE | 116 | 18.651 | 36.419 | 1.510  | 1.00 | 30.97 | A1 |
| ATOM | 884 | CD1 | ILE | 116 | 17.956 | 37.568 | 2.088  | 1.00 | 29.63 | A1 |
| ATOM | 885 | C   | ILE | 116 | 21.423 | 35.756 | -1.170 | 1.00 | 36.07 | A1 |
| ATOM | 886 | O   | ILE | 116 | 22.425 | 36.468 | -0.958 | 1.00 | 35.04 | A1 |
| ATOM | 887 | N   | GLU | 117 | 21.201 | 35.130 | -2.316 | 1.00 | 39.41 | A1 |
| ATOM | 888 | CA  | GLU | 117 | 22.104 | 35.182 | -3.479 | 1.00 | 44.07 | A1 |
| ATOM | 889 | CB  | GLU | 117 | 22.420 | 33.781 | -4.007 | 1.00 | 44.80 | A1 |
| ATOM | 890 | CG  | GLU | 117 | 23.090 | 32.856 | -3.087 | 1.00 | 47.54 | A1 |
| ATOM | 891 | CD  | GLU | 117 | 23.439 | 31.583 | -3.800 | 1.00 | 49.39 | A1 |
| ATOM | 892 | OE1 | GLU | 117 | 22.506 | 30.829 | -4.213 | 1.00 | 49.67 | A1 |
| ATOM | 893 | OE2 | GLU | 117 | 24.661 | 31.354 | -3.953 | 1.00 | 50.54 | A1 |
| ATOM | 894 | C   | GLU | 117 | 21.527 | 35.833 | -4.701 | 1.00 | 45.98 | A1 |
| ATOM | 895 | O   | GLU | 117 | 20.347 | 36.079 | -4.779 | 1.00 | 46.28 | A1 |
| ATOM | 896 | N   | ALA | 118 | 22.396 | 36.016 | -5.696 | 1.00 | 49.81 | A1 |
| ATOM | 897 | CA  | ALA | 118 | 22.012 | 36.546 | -7.004 | 1.00 | 53.49 | A1 |
| ATOM | 898 | CB  | ALA | 118 | 23.271 | 36.985 | -7.787 | 1.00 | 53.10 | A1 |
| ATOM | 899 | C   | ALA | 118 | 21.344 | 35.312 | -7.683 | 1.00 | 56.40 | A1 |
| ATOM | 900 | O   | ALA | 118 | 21.759 | 34.156 | -7.466 | 1.00 | 56.33 | A1 |
| ATOM | 901 | N   | LEU | 119 | 20.314 | 35.556 | -8.485 | 1.00 | 58.93 | A1 |
| ATOM | 902 | CA  | LEU | 119 | 19.614 | 34.475 | -9.176 | 1.00 | 62.13 | A1 |
| ATOM | 903 | CB  | LEU | 119 | 18.385 | 35.046 | -9.902 | 1.00 | 62.98 | A1 |
| ATOM | 904 | CG  | LEU | 119 | 17.128 | 35.145 | -9.029 | 1.00 | 64.50 | A1 |

FIG. 3A-16

| ATOM | 905 | CD1 | LEU | 119 | 15.976 | 35.783 | -9.797 | 1.00 | 64.92 | A1 |
| --- | --- | --- | --- | --- | --- | --- | --- | --- | --- | --- |
| ATOM | 906 | CD2 | LEU | 119 | 16.746 | 33.722 | -8.584 | 1.00 | 65.21 | A1 |
| ATOM | 907 | C | LEU | 119 | 20.484 | 33.670 | -10.164 | 1.00 | 63.60 | A1 |
| ATOM | 908 | OT1 | LEU | 119 | 21.489 | 34.207 | -10.695 | 1.00 | 64.51 | A1 |
| ATOM | 909 | OT2 | LEU | 119 | 20.141 | 32.490 | -10.403 | 1.00 | 64.56 | A1 |
| ATOM | 910 | CB | ALA | 2 | 31.204 | 30.268 | -1.737 | 1.00 | 26.39 | B1 |
| ATOM | 911 | C | ALA | 2 | 33.074 | 29.689 | -3.244 | 1.00 | 25.91 | B1 |
| ATOM | 912 | O | ALA | 2 | 33.105 | 28.570 | -3.739 | 1.00 | 26.11 | B1 |
| ATOM | 913 | N | ALA | 2 | 30.781 | 29.877 | -4.115 | 1.00 | 25.73 | B1 |
| ATOM | 914 | CA | ALA | 2 | 31.761 | 30.434 | -3.139 | 1.00 | 25.92 | B1 |
| ATOM | 915 | N | TYR | 3 | 34.150 | 30.270 | -2.707 | 1.00 | 25.88 | B1 |
| ATOM | 916 | CA | TYR | 3 | 35.481 | 29.614 | -2.742 | 1.00 | 26.08 | B1 |
| ATOM | 917 | CB | TYR | 3 | 36.575 | 30.662 | -2.886 | 1.00 | 26.57 | B1 |
| ATOM | 918 | CG | TYR | 3 | 36.421 | 31.481 | -4.102 | 1.00 | 27.82 | B1 |
| ATOM | 919 | CD1 | TYR | 3 | 36.818 | 32.814 | -4.122 | 1.00 | 29.29 | B1 |
| ATOM | 920 | CE1 | TYR | 3 | 36.734 | 33.556 | -5.296 | 1.00 | 28.29 | B1 |
| ATOM | 921 | CD2 | TYR | 3 | 35.931 | 30.921 | -5.281 | 1.00 | 29.34 | B1 |
| ATOM | 922 | CE2 | TYR | 3 | 35.840 | 31.655 | -6.439 | 1.00 | 28.63 | B1 |
| ATOM | 923 | CZ | TYR | 3 | 36.243 | 32.960 | -6.437 | 1.00 | 28.80 | B1 |
| ATOM | 924 | OH | TYR | 3 | 36.164 | 33.677 | -7.609 | 1.00 | 30.80 | B1 |
| ATOM | 925 | C | TYR | 3 | 35.772 | 28.792 | -1.465 | 1.00 | 25.12 | B1 |
| ATOM | 926 | O | TYR | 3 | 36.490 | 27.795 | -1.518 | 1.00 | 23.25 | B1 |
| ATOM | 927 | N | GLY | 4 | 35.235 | 29.257 | -0.326 | 1.00 | 25.05 | B1 |
| ATOM | 928 | CA | GLY | 4 | 35.397 | 28.565 | 0.958 | 1.00 | 23.80 | B1 |
| ATOM | 929 | C | GLY | 4 | 34.387 | 29.073 | 1.990 | 1.00 | 24.49 | B1 |
| ATOM | 930 | O | GLY | 4 | 33.838 | 30.213 | 1.843 | 1.00 | 23.38 | B1 |
| ATOM | 931 | N | ILE | 5 | 34.096 | 28.253 | 3.014 | 1.00 | 24.35 | B1 |
| ATOM | 932 | CA | ILE | 5 | 33.215 | 28.684 | 4.077 | 1.00 | 24.74 | B1 |
| ATOM | 933 | CB | ILE | 5 | 31.806 | 28.117 | 3.996 | 1.00 | 25.07 | B1 |
| ATOM | 934 | CG2 | ILE | 5 | 31.156 | 28.471 | 2.641 | 1.00 | 24.89 | B1 |
| ATOM | 935 | CG1 | ILE | 5 | 31.819 | 26.585 | 4.228 | 1.00 | 26.94 | B1 |
| ATOM | 936 | CD1 | ILE | 5 | 30.415 | 25.916 | 4.024 | 1.00 | 25.53 | B1 |
| ATOM | 937 | C | ILE | 5 | 33.812 | 28.256 | 5.382 | 1.00 | 25.64 | B1 |
| ATOM | 938 | O | ILE | 5 | 34.669 | 27.397 | 5.431 | 1.00 | 26.38 | B1 |
| ATOM | 939 | N | GLY | 6 | 33.356 | 28.860 | 6.457 | 1.00 | 25.30 | B1 |
| ATOM | 940 | CA | GLY | 6 | 33.864 | 28.495 | 7.752 | 1.00 | 25.02 | B1 |
| ATOM | 941 | C | GLY | 6 | 32.887 | 28.860 | 8.862 | 1.00 | 25.03 | B1 |
| ATOM | 942 | O | GLY | 6 | 32.180 | 29.886 | 8.809 | 1.00 | 24.21 | B1 |
| ATOM | 943 | N | LEU | 7 | 32.882 | 28.022 | 9.892 | 1.00 | 25.45 | B1 |
| ATOM | 944 | CA | LEU | 7 | 32.023 | 28.217 | 11.036 | 1.00 | 26.13 | B1 |
| ATOM | 945 | CB | LEU | 7 | 30.893 | 27.176 | 11.031 | 1.00 | 27.37 | B1 |
| ATOM | 946 | CG | LEU | 7 | 29.911 | 27.230 | 12.202 | 1.00 | 27.44 | B1 |
| ATOM | 947 | CD1 | LEU | 7 | 29.025 | 28.487 | 12.083 | 1.00 | 28.47 | B1 |
| ATOM | 948 | CD2 | LEU | 7 | 29.047 | 26.014 | 12.156 | 1.00 | 27.61 | B1 |
| ATOM | 949 | C | LEU | 7 | 32.836 | 28.022 | 12.306 | 1.00 | 26.61 | B1 |
| ATOM | 950 | O | LEU | 7 | 33.773 | 27.217 | 12.350 | 1.00 | 26.23 | B1 |
| ATOM | 951 | N | ASP | 8 | 32.474 | 28.777 | 13.338 | 1.00 | 27.29 | B1 |
| ATOM | 952 | CA | ASP | 8 | 33.126 | 28.645 | 14.649 | 1.00 | 28.31 | B1 |
| ATOM | 953 | CB | ASP | 8 | 34.444 | 29.445 | 14.775 | 1.00 | 29.82 | B1 |
| ATOM | 954 | CG | ASP | 8 | 35.210 | 29.094 | 16.096 | 1.00 | 32.76 | B1 |
| ATOM | 955 | OD1 | ASP | 8 | 35.069 | 29.848 | 17.084 | 1.00 | 32.47 | B1 |
| ATOM | 956 | OD2 | ASP | 8 | 35.929 | 28.040 | 16.138 | 1.00 | 33.99 | B1 |
| ATOM | 957 | C | ASP | 8 | 32.194 | 29.076 | 15.750 | 1.00 | 26.75 | B1 |
| ATOM | 958 | O | ASP | 8 | 31.471 | 30.067 | 15.628 | 1.00 | 25.85 | B1 |
| ATOM | 959 | N | ILE | 9 | 32.193 | 28.280 | 16.805 | 1.00 | 26.88 | B1 |
| ATOM | 960 | CA | ILE | 9 | 31.379 | 28.564 | 17.999 | 1.00 | 27.43 | B1 |
| ATOM | 961 | CB | ILE | 9 | 30.312 | 27.446 | 18.244 | 1.00 | 27.59 | B1 |

FIG. 3A-17

| ATOM | 962 | CG2 | ILE | 9 | 29.559 | 27.658 | 19.599 | 1.00 | 27.04 | B1 |
| ATOM | 963 | CG1 | ILE | 9 | 29.318 | 27.430 | 17.044 | 1.00 | 28.13 | B1 |
| ATOM | 964 | CD1 | ILE | 9 | 28.148 | 26.387 | 17.150 | 1.00 | 27.19 | B1 |
| ATOM | 965 | C | ILE | 9 | 32.382 | 28.611 | 19.145 | 1.00 | 28.24 | B1 |
| ATOM | 966 | O | ILE | 9 | 33.151 | 27.690 | 19.321 | 1.00 | 28.60 | B1 |
| ATOM | 967 | N | THR | 10 | 32.353 | 29.685 | 19.926 | 1.00 | 29.28 | B1 |
| ATOM | 968 | CA | THR | 10 | 33.249 | 29.864 | 21.057 | 1.00 | 30.48 | B1 |
| ATOM | 969 | CB | THR | 10 | 34.188 | 31.052 | 20.742 | 1.00 | 31.33 | B1 |
| ATOM | 970 | OG1 | THR | 10 | 35.169 | 30.594 | 19.789 | 1.00 | 34.42 | B1 |
| ATOM | 971 | CG2 | THR | 10 | 34.917 | 31.538 | 21.956 | 1.00 | 32.00 | B1 |
| ATOM | 972 | C | THR | 10 | 32.526 | 30.036 | 22.419 | 1.00 | 29.95 | B1 |
| ATOM | 973 | O | THR | 10 | 31.531 | 30.720 | 22.529 | 1.00 | 28.39 | B1 |
| ATOM | 974 | N | GLU | 11 | 33.048 | 29.399 | 23.464 | 1.00 | 31.32 | B1 |
| ATOM | 975 | CA | GLU | 11 | 32.403 | 29.472 | 24.801 | 1.00 | 31.87 | B1 |
| ATOM | 976 | CB | GLU | 11 | 32.835 | 28.289 | 25.676 | 1.00 | 33.64 | B1 |
| ATOM | 977 | CG | GLU | 11 | 31.716 | 27.784 | 26.547 | 1.00 | 40.24 | B1 |
| ATOM | 978 | CD | GLU | 11 | 32.181 | 27.028 | 27.821 | 1.00 | 43.39 | B1 |
| ATOM | 979 | OE1 | GLU | 11 | 33.344 | 26.499 | 27.873 | 1.00 | 44.86 | B1 |
| ATOM | 980 | OE2 | GLU | 11 | 31.343 | 26.941 | 28.766 | 1.00 | 45.49 | B1 |
| ATOM | 981 | C | GLU | 11 | 32.804 | 30.770 | 25.481 | 1.00 | 30.40 | B1 |
| ATOM | 982 | O | GLU | 11 | 33.992 | 31.004 | 25.678 | 1.00 | 29.17 | B1 |
| ATOM | 983 | N | LEU | 12 | 31.823 | 31.610 | 25.801 | 1.00 | 29.04 | B1 |
| ATOM | 984 | CA | LEU | 12 | 32.089 | 32.876 | 26.454 | 1.00 | 31.07 | B1 |
| ATOM | 985 | CB | LEU | 12 | 30.801 | 33.681 | 26.662 | 1.00 | 32.99 | B1 |
| ATOM | 986 | CG | LEU | 12 | 30.053 | 34.021 | 25.359 | 1.00 | 35.90 | B1 |
| ATOM | 987 | CD1 | LEU | 12 | 28.665 | 34.596 | 25.624 | 1.00 | 35.82 | B1 |
| ATOM | 988 | CD2 | LEU | 12 | 30.901 | 35.004 | 24.552 | 1.00 | 36.85 | B1 |
| ATOM | 989 | C | LEU | 12 | 32.815 | 32.740 | 27.816 | 1.00 | 31.80 | B1 |
| ATOM | 990 | O | LEU | 12 | 33.708 | 33.553 | 28.106 | 1.00 | 31.13 | B1 |
| ATOM | 991 | N | ALA | 13 | 32.448 | 31.741 | 28.634 | 1.00 | 31.23 | B1 |
| ATOM | 992 | CA | ALA | 13 | 33.123 | 31.588 | 29.927 | 1.00 | 32.54 | B1 |
| ATOM | 993 | CB | ALA | 13 | 32.413 | 30.507 | 30.881 | 1.00 | 32.09 | B1 |
| ATOM | 994 | C | ALA | 13 | 34.588 | 31.260 | 29.733 | 1.00 | 31.41 | B1 |
| ATOM | 995 | O | ALA | 13 | 35.431 | 31.793 | 30.433 | 1.00 | 30.77 | B1 |
| ATOM | 996 | N | ARG | 14 | 34.891 | 30.414 | 28.754 | 1.00 | 31.73 | B1 |
| ATOM | 997 | CA | ARG | 14 | 36.286 | 30.039 | 28.459 | 1.00 | 30.99 | B1 |
| ATOM | 998 | CB | ARG | 14 | 36.259 | 29.020 | 27.327 | 1.00 | 30.57 | B1 |
| ATOM | 999 | CG | ARG | 14 | 37.526 | 28.328 | 27.173 | 1.00 | 31.14 | B1 |
| ATOM | 1000 | CD | ARG | 14 | 37.522 | 27.371 | 26.023 | 1.00 | 32.79 | B1 |
| ATOM | 1001 | NE | ARG | 14 | 38.887 | 26.847 | 25.848 | 1.00 | 32.33 | B1 |
| ATOM | 1002 | CZ | ARG | 14 | 39.262 | 25.977 | 24.925 | 1.00 | 31.66 | B1 |
| ATOM | 1003 | NH1 | ARG | 14 | 38.383 | 25.511 | 24.042 | 1.00 | 31.62 | B1 |
| ATOM | 1004 | NH2 | ARG | 14 | 40.513 | 25.543 | 24.926 | 1.00 | 31.83 | B1 |
| ATOM | 1005 | C | ARG | 14 | 37.125 | 31.325 | 28.076 | 1.00 | 30.35 | B1 |
| ATOM | 1006 | O | ARG | 14 | 38.204 | 31.580 | 28.588 | 1.00 | 29.54 | B1 |
| ATOM | 1007 | N | ILE | 15 | 36.585 | 32.141 | 27.185 | 1.00 | 30.11 | B1 |
| ATOM | 1008 | CA | ILE | 15 | 37.218 | 33.400 | 26.814 | 1.00 | 30.69 | B1 |
| ATOM | 1009 | CB | ILE | 15 | 36.361 | 34.204 | 25.754 | 1.00 | 30.02 | B1 |
| ATOM | 1010 | CG2 | ILE | 15 | 36.816 | 35.678 | 25.717 | 1.00 | 28.67 | B1 |
| ATOM | 1011 | CG1 | ILE | 15 | 36.417 | 33.502 | 24.393 | 1.00 | 28.37 | B1 |
| ATOM | 1012 | CD1 | ILE | 15 | 37.778 | 33.454 | 23.791 | 1.00 | 27.34 | B1 |
| ATOM | 1013 | C | ILE | 15 | 37.362 | 34.280 | 28.074 | 1.00 | 30.92 | B1 |
| ATOM | 1014 | O | ILE | 15 | 38.439 | 34.823 | 28.358 | 1.00 | 31.82 | B1 |
| ATOM | 1015 | N | ALA | 16 | 36.283 | 34.443 | 28.805 | 1.00 | 30.39 | B1 |
| ATOM | 1016 | CA | ALA | 16 | 36.326 | 35.247 | 30.020 | 1.00 | 31.94 | B1 |
| ATOM | 1017 | CB | ALA | 16 | 34.941 | 35.199 | 30.765 | 1.00 | 29.82 | B1 |
| ATOM | 1018 | C | ALA | 16 | 37.475 | 34.791 | 30.969 | 1.00 | 32.80 | B1 |

FIG. 3A-18

| ATOM | 1019 | O | ALA | 16 | 38.254 | 35.621 | 31.429 | 1.00 | 34.32 | B1 |
|---|---|---|---|---|---|---|---|---|---|---|
| ATOM | 1020 | N | SER | 17 | 37.568 | 33.501 | 31.267 | 1.00 | 32.89 | B1 |
| ATOM | 1021 | CA | SER | 17 | 38.629 | 32.978 | 32.125 | 1.00 | 34.00 | B1 |
| ATOM | 1022 | CB | SER | 17 | 38.517 | 31.476 | 32.260 | 1.00 | 32.84 | B1 |
| ATOM | 1023 | OG | SER | 17 | 37.194 | 31.136 | 32.461 | 1.00 | 35.05 | B1 |
| ATOM | 1024 | C | SER | 17 | 40.018 | 33.242 | 31.561 | 1.00 | 34.86 | B1 |
| ATOM | 1025 | O | SER | 17 | 40.946 | 33.597 | 32.273 | 1.00 | 33.03 | B1 |
| ATOM | 1026 | N | MET | 18 | 40.160 | 32.993 | 30.270 | 1.00 | 37.22 | B1 |
| ATOM | 1027 | CA | MET | 18 | 41.450 | 33.205 | 29.637 | 1.00 | 39.40 | B1 |
| ATOM | 1028 | CB | MET | 18 | 41.446 | 32.790 | 28.186 | 1.00 | 41.45 | B1 |
| ATOM | 1029 | CG | MET | 18 | 41.697 | 31.321 | 27.987 | 1.00 | 45.54 | B1 |
| ATOM | 1030 | SD | MET | 18 | 41.922 | 31.024 | 26.211 | 1.00 | 50.43 | B1 |
| ATOM | 1031 | CE | MET | 18 | 40.247 | 30.845 | 25.782 | 1.00 | 48.09 | B1 |
| ATOM | 1032 | C | MET | 18 | 41.878 | 34.643 | 29.726 | 1.00 | 39.53 | B1 |
| ATOM | 1033 | O | MET | 18 | 43.020 | 34.910 | 30.119 | 1.00 | 40.11 | B1 |
| ATOM | 1034 | N | ALA | 19 | 41.003 | 35.574 | 29.376 | 1.00 | 39.08 | B1 |
| ATOM | 1035 | CA | ALA | 19 | 41.412 | 36.973 | 29.473 | 1.00 | 39.54 | B1 |
| ATOM | 1036 | CB | ALA | 19 | 40.327 | 37.933 | 28.907 | 1.00 | 38.99 | B1 |
| ATOM | 1037 | C | ALA | 19 | 41.715 | 37.317 | 30.925 | 1.00 | 39.55 | B1 |
| ATOM | 1038 | O | ALA | 19 | 42.608 | 38.115 | 31.168 | 1.00 | 40.32 | B1 |
| ATOM | 1039 | N | GLY | 20 | 41.005 | 36.718 | 31.888 | 1.00 | 39.22 | B1 |
| ATOM | 1040 | CA | GLY | 20 | 41.269 | 37.037 | 33.277 | 1.00 | 39.09 | B1 |
| ATOM | 1041 | C | GLY | 20 | 42.655 | 36.569 | 33.713 | 1.00 | 39.90 | B1 |
| ATOM | 1042 | O | GLY | 20 | 43.421 | 37.278 | 34.382 | 1.00 | 39.40 | B1 |
| ATOM | 1043 | N | ARG | 21 | 42.957 | 35.353 | 33.288 | 1.00 | 39.88 | B1 |
| ATOM | 1044 | CA | ARG | 21 | 44.192 | 34.626 | 33.543 | 1.00 | 40.39 | B1 |
| ATOM | 1045 | CB | ARG | 21 | 43.920 | 33.149 | 33.162 | 1.00 | 39.16 | B1 |
| ATOM | 1046 | CG | ARG | 21 | 44.701 | 32.071 | 33.882 | 1.00 | 37.29 | B1 |
| ATOM | 1047 | CD | ARG | 21 | 44.013 | 30.718 | 33.776 | 1.00 | 35.14 | B1 |
| ATOM | 1048 | NE | ARG | 21 | 43.669 | 30.325 | 32.393 | 1.00 | 33.14 | B1 |
| ATOM | 1049 | CZ | ARG | 21 | 42.451 | 29.918 | 32.010 | 1.00 | 32.97 | B1 |
| ATOM | 1050 | NH1 | ARG | 21 | 41.444 | 29.861 | 32.898 | 1.00 | 32.98 | B1 |
| ATOM | 1051 | NH2 | ARG | 21 | 42.234 | 29.515 | 30.767 | 1.00 | 30.26 | B1 |
| ATOM | 1052 | C | ARG | 21 | 45.383 | 35.225 | 32.728 | 1.00 | 41.48 | B1 |
| ATOM | 1053 | O | ARG | 21 | 46.556 | 35.161 | 33.147 | 1.00 | 41.49 | B1 |
| ATOM | 1054 | N | GLN | 22 | 45.086 | 35.851 | 31.590 | 1.00 | 42.70 | B1 |
| ATOM | 1055 | CA | GLN | 22 | 46.149 | 36.426 | 30.758 | 1.00 | 43.56 | B1 |
| ATOM | 1056 | CB | GLN | 22 | 46.536 | 35.439 | 29.664 | 1.00 | 45.80 | B1 |
| ATOM | 1057 | CG | GLN | 22 | 47.813 | 35.827 | 28.972 | 1.00 | 49.05 | B1 |
| ATOM | 1058 | CD | GLN | 22 | 48.970 | 35.490 | 29.843 | 1.00 | 50.23 | B1 |
| ATOM | 1059 | OE1 | GLN | 22 | 49.851 | 36.326 | 30.101 | 1.00 | 50.93 | B1 |
| ATOM | 1060 | NE2 | GLN | 22 | 48.977 | 34.246 | 30.334 | 1.00 | 51.27 | B1 |
| ATOM | 1061 | C | GLN | 22 | 45.786 | 37.747 | 30.114 | 1.00 | 43.68 | B1 |
| ATOM | 1062 | O | GLN | 22 | 45.133 | 37.782 | 29.071 | 1.00 | 43.58 | B1 |
| ATOM | 1063 | N | LYS | 23 | 46.234 | 38.841 | 30.721 | 1.00 | 44.50 | B1 |
| ATOM | 1064 | CA | LYS | 23 | 45.932 | 40.197 | 30.213 | 1.00 | 45.41 | B1 |
| ATOM | 1065 | CB | LYS | 23 | 46.577 | 41.263 | 31.174 | 1.00 | 46.07 | B1 |
| ATOM | 1066 | C | LYS | 23 | 46.286 | 40.529 | 28.721 | 1.00 | 45.13 | B1 |
| ATOM | 1067 | O | LYS | 23 | 45.670 | 41.419 | 28.111 | 1.00 | 45.95 | B1 |
| ATOM | 1068 | N | ARG | 24 | 47.252 | 39.828 | 28.137 | 1.00 | 44.79 | B1 |
| ATOM | 1069 | CA | ARG | 24 | 47.647 | 40.066 | 26.734 | 1.00 | 44.30 | B1 |
| ATOM | 1070 | CB | ARG | 24 | 49.161 | 39.813 | 26.558 | 1.00 | 45.66 | B1 |
| ATOM | 1071 | CG | ARG | 24 | 50.091 | 40.916 | 27.138 | 1.00 | 48.65 | B1 |
| ATOM | 1072 | CD | ARG | 24 | 51.545 | 40.424 | 27.439 | 1.00 | 51.04 | B1 |
| ATOM | 1073 | NE | ARG | 24 | 52.170 | 39.768 | 26.281 | 1.00 | 53.16 | B1 |
| ATOM | 1074 | CZ | ARG | 24 | 52.409 | 38.460 | 26.181 | 1.00 | 52.98 | B1 |
| ATOM | 1075 | NH1 | ARG | 24 | 52.098 | 37.631 | 27.176 | 1.00 | 52.77 | B1 |

FIG. 3A-19

| ATOM | 1076 | NH2 | ARG | 24 | 52.911 | 37.976 | 25.050 | 1.00 | 53.75 | B1 |
| ATOM | 1077 | C | ARG | 24 | 46.862 | 39.224 | 25.682 | 1.00 | 43.41 | B1 |
| ATOM | 1078 | O | ARG | 24 | 47.117 | 39.342 | 24.476 | 1.00 | 41.77 | B1 |
| ATOM | 1079 | N | PHE | 25 | 45.904 | 38.396 | 26.122 | 1.00 | 41.98 | B1 |
| ATOM | 1080 | CA | PHE | 25 | 45.153 | 37.588 | 25.159 | 1.00 | 41.18 | B1 |
| ATOM | 1081 | CB | PHE | 25 | 44.145 | 36.674 | 25.866 | 1.00 | 40.68 | B1 |
| ATOM | 1082 | CG | PHE | 25 | 43.188 | 35.966 | 24.926 | 1.00 | 41.90 | B1 |
| ATOM | 1083 | CD1 | PHE | 25 | 43.657 | 35.222 | 23.852 | 1.00 | 40.31 | B1 |
| ATOM | 1084 | CD2 | PHE | 25 | 41.796 | 35.990 | 25.168 | 1.00 | 42.65 | B1 |
| ATOM | 1085 | CE1 | PHE | 25 | 42.793 | 34.515 | 23.047 | 1.00 | 40.58 | B1 |
| ATOM | 1086 | CE2 | PHE | 25 | 40.904 | 35.265 | 24.342 | 1.00 | 42.06 | B1 |
| ATOM | 1087 | CZ | PHE | 25 | 41.403 | 34.532 | 23.290 | 1.00 | 41.02 | B1 |
| ATOM | 1088 | C | PHE | 25 | 44.432 | 38.438 | 24.128 | 1.00 | 39.93 | B1 |
| ATOM | 1089 | O | PHE | 25 | 44.489 | 38.151 | 22.944 | 1.00 | 40.29 | B1 |
| ATOM | 1090 | N | ALA | 26 | 43.778 | 39.500 | 24.569 | 1.00 | 39.38 | B1 |
| ATOM | 1091 | CA | ALA | 26 | 43.052 | 40.358 | 23.659 | 1.00 | 39.11 | B1 |
| ATOM | 1092 | CB | ALA | 26 | 42.214 | 41.368 | 24.439 | 1.00 | 39.81 | B1 |
| ATOM | 1093 | C | ALA | 26 | 43.943 | 41.073 | 22.667 | 1.00 | 39.48 | B1 |
| ATOM | 1094 | O | ALA | 26 | 43.532 | 41.289 | 21.525 | 1.00 | 39.36 | B1 |
| ATOM | 1095 | N | GLU | 27 | 45.151 | 41.446 | 23.090 | 1.00 | 39.52 | B1 |
| ATOM | 1096 | CA | GLU | 27 | 46.105 | 42.137 | 22.214 | 1.00 | 39.44 | B1 |
| ATOM | 1097 | CB | GLU | 27 | 47.359 | 42.618 | 22.972 | 1.00 | 42.26 | B1 |
| ATOM | 1098 | CG | GLU | 27 | 47.153 | 43.846 | 23.880 | 1.00 | 46.62 | B1 |
| ATOM | 1099 | CD | GLU | 27 | 48.453 | 44.311 | 24.546 | 1.00 | 49.04 | B1 |
| ATOM | 1100 | OE1 | GLU | 27 | 48.791 | 43.779 | 25.635 | 1.00 | 49.32 | B1 |
| ATOM | 1101 | OE2 | GLU | 27 | 49.145 | 45.198 | 23.959 | 1.00 | 51.13 | B1 |
| ATOM | 1102 | C | GLU | 27 | 46.572 | 41.231 | 21.114 | 1.00 | 37.83 | B1 |
| ATOM | 1103 | O | GLU | 27 | 46.871 | 41.700 | 20.010 | 1.00 | 36.89 | B1 |
| ATOM | 1104 | N | ARG | 28 | 46.660 | 39.938 | 21.414 | 1.00 | 35.85 | B1 |
| ATOM | 1105 | CA | ARG | 28 | 47.092 | 38.981 | 20.403 | 1.00 | 35.38 | B1 |
| ATOM | 1106 | CB | ARG | 28 | 47.359 | 37.617 | 21.011 | 1.00 | 35.61 | B1 |
| ATOM | 1107 | CG | ARG | 28 | 48.442 | 36.892 | 20.272 | 1.00 | 37.83 | B1 |
| ATOM | 1108 | CD | ARG | 28 | 48.482 | 35.423 | 20.638 | 1.00 | 40.08 | B1 |
| ATOM | 1109 | NE | ARG | 28 | 49.440 | 34.762 | 19.763 | 1.00 | 41.90 | B1 |
| ATOM | 1110 | CZ | ARG | 28 | 50.761 | 34.831 | 19.905 | 1.00 | 43.04 | B1 |
| ATOM | 1111 | NH1 | ARG | 28 | 51.318 | 35.525 | 20.919 | 1.00 | 42.06 | B1 |
| ATOM | 1112 | NH2 | ARG | 28 | 51.532 | 34.225 | 18.999 | 1.00 | 43.51 | B1 |
| ATOM | 1113 | C | ARG | 28 | 46.041 | 38.782 | 19.314 | 1.00 | 34.81 | B1 |
| ATOM | 1114 | O | ARG | 28 | 46.384 | 38.692 | 18.146 | 1.00 | 34.82 | B1 |
| ATOM | 1115 | N | ILE | 29 | 44.770 | 38.705 | 19.727 | 1.00 | 34.29 | B1 |
| ATOM | 1116 | CA | ILE | 29 | 43.608 | 38.476 | 18.854 | 1.00 | 33.36 | B1 |
| ATOM | 1117 | CB | ILE | 29 | 42.388 | 38.009 | 19.716 | 1.00 | 32.64 | B1 |
| ATOM | 1118 | CG2 | ILE | 29 | 41.199 | 37.626 | 18.834 | 1.00 | 33.38 | B1 |
| ATOM | 1119 | CG1 | ILE | 29 | 42.790 | 36.826 | 20.581 | 1.00 | 32.81 | B1 |
| ATOM | 1120 | CD1 | ILE | 29 | 43.503 | 35.659 | 19.828 | 1.00 | 33.12 | B1 |
| ATOM | 1121 | C | ILE | 29 | 43.135 | 39.669 | 18.008 | 1.00 | 33.56 | B1 |
| ATOM | 1122 | O | ILE | 29 | 42.800 | 39.519 | 16.818 | 1.00 | 33.84 | B1 |
| ATOM | 1123 | N | LEU | 30 | 43.132 | 40.849 | 18.624 | 1.00 | 33.60 | B1 |
| ATOM | 1124 | CA | LEU | 30 | 42.591 | 42.069 | 18.017 | 1.00 | 34.10 | B1 |
| ATOM | 1125 | CB | LEU | 30 | 41.805 | 42.837 | 19.103 | 1.00 | 31.55 | B1 |
| ATOM | 1126 | CG | LEU | 30 | 40.805 | 41.980 | 19.917 | 1.00 | 30.29 | B1 |
| ATOM | 1127 | CD1 | LEU | 30 | 40.166 | 42.792 | 21.065 | 1.00 | 27.41 | B1 |
| ATOM | 1128 | CD2 | LEU | 30 | 39.717 | 41.460 | 18.934 | 1.00 | 28.50 | B1 |
| ATOM | 1129 | C | LEU | 30 | 43.577 | 43.006 | 17.365 | 1.00 | 35.65 | B1 |
| ATOM | 1130 | O | LEU | 30 | 44.731 | 43.105 | 17.773 | 1.00 | 37.79 | B1 |
| ATOM | 1131 | N | THR | 31 | 43.140 | 43.704 | 16.340 | 1.00 | 36.42 | B1 |
| ATOM | 1132 | CA | THR | 31 | 44.028 | 44.678 | 15.724 | 1.00 | 37.57 | B1 |

FIG. 3A-20

| ATOM | 1133 | CB | THR | 31 | 43.492 | 45.135 | 14.355 | 1.00 | 36.44 | B1 |
| ATOM | 1134 | OG1 | THR | 31 | 42.186 | 45.710 | 14.536 | 1.00 | 36.56 | B1 |
| ATOM | 1135 | CG2 | THR | 31 | 43.453 | 43.974 | 13.400 | 1.00 | 34.20 | B1 |
| ATOM | 1136 | C | THR | 31 | 43.988 | 45.866 | 16.684 | 1.00 | 38.90 | B1 |
| ATOM | 1137 | O | THR | 31 | 43.210 | 45.852 | 17.633 | 1.00 | 39.30 | B1 |
| ATOM | 1138 | N | ARG | 32 | 44.783 | 46.912 | 16.445 | 1.00 | 40.92 | B1 |
| ATOM | 1139 | CA | ARG | 32 | 44.761 | 48.057 | 17.370 | 1.00 | 42.16 | B1 |
| ATOM | 1140 | CB | ARG | 32 | 45.849 | 49.077 | 17.034 | 1.00 | 43.63 | B1 |
| ATOM | 1141 | CG | ARG | 32 | 46.249 | 49.896 | 18.307 | 1.00 | 45.88 | B1 |
| ATOM | 1142 | CD | ARG | 32 | 47.069 | 51.105 | 17.912 | 1.00 | 47.41 | B1 |
| ATOM | 1143 | NE | ARG | 32 | 47.817 | 50.791 | 16.700 | 1.00 | 49.09 | B1 |
| ATOM | 1144 | CZ | ARG | 32 | 49.068 | 50.357 | 16.675 | 1.00 | 49.50 | B1 |
| ATOM | 1145 | NH1 | ARG | 32 | 49.733 | 50.188 | 17.810 | 1.00 | 49.69 | B1 |
| ATOM | 1146 | NH2 | ARG | 32 | 49.650 | 50.097 | 15.506 | 1.00 | 50.68 | B1 |
| ATOM | 1147 | C | ARG | 32 | 43.402 | 48.763 | 17.353 | 1.00 | 42.65 | B1 |
| ATOM | 1148 | O | ARG | 32 | 42.878 | 49.222 | 18.391 | 1.00 | 41.41 | B1 |
| ATOM | 1149 | N | SER | 33 | 42.838 | 48.852 | 16.151 | 1.00 | 42.81 | B1 |
| ATOM | 1150 | CA | SER | 33 | 41.550 | 49.464 | 16.015 | 1.00 | 43.76 | B1 |
| ATOM | 1151 | CB | SER | 33 | 41.261 | 49.643 | 14.540 | 1.00 | 43.52 | B1 |
| ATOM | 1152 | OG | SER | 33 | 39.873 | 49.782 | 14.386 | 1.00 | 46.24 | B1 |
| ATOM | 1153 | C | SER | 33 | 40.438 | 48.629 | 16.733 | 1.00 | 43.65 | B1 |
| ATOM | 1154 | O | SER | 33 | 39.574 | 49.182 | 17.415 | 1.00 | 44.48 | B1 |
| ATOM | 1155 | N | GLU | 34 | 40.475 | 47.305 | 16.607 | 1.00 | 42.94 | B1 |
| ATOM | 1156 | CA | GLU | 34 | 39.470 | 46.465 | 17.259 | 1.00 | 41.95 | B1 |
| ATOM | 1157 | CB | GLU | 34 | 39.628 | 45.001 | 16.835 | 1.00 | 40.95 | B1 |
| ATOM | 1158 | CG | GLU | 34 | 39.348 | 44.750 | 15.393 | 1.00 | 40.15 | B1 |
| ATOM | 1159 | CD | GLU | 34 | 39.605 | 43.309 | 14.967 | 1.00 | 40.92 | B1 |
| ATOM | 1160 | OE1 | GLU | 34 | 40.597 | 42.695 | 15.431 | 1.00 | 40.90 | B1 |
| ATOM | 1161 | OE2 | GLU | 34 | 38.823 | 42.793 | 14.150 | 1.00 | 40.87 | B1 |
| ATOM | 1162 | C | GLU | 34 | 39.687 | 46.593 | 18.753 | 1.00 | 41.77 | B1 |
| ATOM | 1163 | O | GLU | 34 | 38.749 | 46.677 | 19.535 | 1.00 | 41.48 | B1 |
| ATOM | 1164 | N | LEU | 35 | 40.956 | 46.623 | 19.125 | 1.00 | 42.42 | B1 |
| ATOM | 1165 | CA | LEU | 35 | 41.393 | 46.745 | 20.504 | 1.00 | 43.24 | B1 |
| ATOM | 1166 | CB | LEU | 35 | 42.904 | 46.713 | 20.538 | 1.00 | 43.31 | B1 |
| ATOM | 1167 | CG | LEU | 35 | 43.622 | 45.884 | 21.580 | 1.00 | 43.75 | B1 |
| ATOM | 1168 | CD1 | LEU | 35 | 44.944 | 46.592 | 21.876 | 1.00 | 43.54 | B1 |
| ATOM | 1169 | CD2 | LEU | 35 | 42.805 | 45.720 | 22.833 | 1.00 | 43.33 | B1 |
| ATOM | 1170 | C | LEU | 35 | 40.897 | 48.053 | 21.130 | 1.00 | 43.93 | B1 |
| ATOM | 1171 | O | LEU | 35 | 40.421 | 48.060 | 22.280 | 1.00 | 43.01 | B1 |
| ATOM | 1172 | N | ASP | 36 | 41.005 | 49.157 | 20.387 | 1.00 | 44.72 | B1 |
| ATOM | 1173 | CA | ASP | 36 | 40.522 | 50.411 | 20.939 | 1.00 | 46.43 | B1 |
| ATOM | 1174 | CB | ASP | 36 | 40.834 | 51.625 | 20.047 | 1.00 | 46.32 | B1 |
| ATOM | 1175 | CG | ASP | 36 | 42.328 | 51.962 | 20.034 | 1.00 | 47.18 | B1 |
| ATOM | 1176 | OD1 | ASP | 36 | 43.011 | 51.676 | 21.042 | 1.00 | 47.46 | B1 |
| ATOM | 1177 | OD2 | ASP | 36 | 42.831 | 52.504 | 19.025 | 1.00 | 48.14 | B1 |
| ATOM | 1178 | C | ASP | 36 | 39.040 | 50.269 | 21.131 | 1.00 | 47.36 | B1 |
| ATOM | 1179 | O | ASP | 36 | 38.519 | 50.720 | 22.138 | 1.00 | 48.13 | B1 |
| ATOM | 1180 | N | GLN | 37 | 38.355 | 49.630 | 20.183 | 1.00 | 47.84 | B1 |
| ATOM | 1181 | CA | GLN | 37 | 36.918 | 49.445 | 20.333 | 1.00 | 48.02 | B1 |
| ATOM | 1182 | CB | GLN | 37 | 36.354 | 48.755 | 19.100 | 1.00 | 48.62 | B1 |
| ATOM | 1183 | CG | GLN | 37 | 36.416 | 49.589 | 17.849 | 1.00 | 50.60 | B1 |
| ATOM | 1184 | CD | GLN | 37 | 36.137 | 48.763 | 16.597 | 1.00 | 51.12 | B1 |
| ATOM | 1185 | OE1 | GLN | 37 | 35.145 | 48.050 | 16.531 | 1.00 | 51.75 | B1 |
| ATOM | 1186 | NE2 | GLN | 37 | 37.023 | 48.853 | 15.606 | 1.00 | 52.14 | B1 |
| ATOM | 1187 | C | GLN | 37 | 36.585 | 48.632 | 21.596 | 1.00 | 47.78 | B1 |
| ATOM | 1188 | O | GLN | 37 | 35.640 | 48.946 | 22.299 | 1.00 | 48.37 | B1 |
| ATOM | 1189 | N | TYR | 38 | 37.374 | 47.603 | 21.885 | 1.00 | 47.54 | B1 |

FIG. 3A-21

| | | | | | | | | | | |
|---|---|---|---|---|---|---|---|---|---|---|
| ATOM | 1190 | CA | TYR | 38 | 37.161 | 46.732 | 23.046 | 1.00 | 47.74 | B1 |
| ATOM | 1191 | CB | TYR | 38 | 38.165 | 45.551 | 22.941 | 1.00 | 46.60 | B1 |
| ATOM | 1192 | CG | TYR | 38 | 38.527 | 44.738 | 24.195 | 1.00 | 45.26 | B1 |
| ATOM | 1193 | CD1 | TYR | 38 | 39.691 | 45.014 | 24.905 | 1.00 | 44.68 | B1 |
| ATOM | 1194 | CE1 | TYR | 38 | 40.084 | 44.229 | 25.991 | 1.00 | 44.13 | B1 |
| ATOM | 1195 | CD2 | TYR | 38 | 37.749 | 43.647 | 24.616 | 1.00 | 44.67 | B1 |
| ATOM | 1196 | CE2 | TYR | 38 | 38.123 | 42.863 | 25.703 | 1.00 | 43.73 | B1 |
| ATOM | 1197 | CZ | TYR | 38 | 39.298 | 43.160 | 26.382 | 1.00 | 44.36 | B1 |
| ATOM | 1198 | OH | TYR | 38 | 39.717 | 42.401 | 27.450 | 1.00 | 44.63 | B1 |
| ATOM | 1199 | C | TYR | 38 | 37.287 | 47.487 | 24.373 | 1.00 | 48.96 | B1 |
| ATOM | 1200 | O | TYR | 38 | 36.502 | 47.282 | 25.296 | 1.00 | 48.92 | B1 |
| ATOM | 1201 | N | TYR | 39 | 38.268 | 48.377 | 24.449 | 1.00 | 50.35 | B1 |
| ATOM | 1202 | CA | TYR | 39 | 38.539 | 49.177 | 25.645 | 1.00 | 52.19 | B1 |
| ATOM | 1203 | CB | TYR | 39 | 39.867 | 49.908 | 25.465 | 1.00 | 52.76 | B1 |
| ATOM | 1204 | CG | TYR | 39 | 41.044 | 49.009 | 25.696 | 1.00 | 53.28 | B1 |
| ATOM | 1205 | CD1 | TYR | 39 | 42.182 | 49.086 | 24.901 | 1.00 | 52.99 | B1 |
| ATOM | 1206 | CE1 | TYR | 39 | 43.276 | 48.261 | 25.147 | 1.00 | 53.92 | B1 |
| ATOM | 1207 | CD2 | TYR | 39 | 41.023 | 48.084 | 26.742 | 1.00 | 53.93 | B1 |
| ATOM | 1208 | CE2 | TYR | 39 | 42.102 | 47.267 | 26.994 | 1.00 | 54.12 | B1 |
| ATOM | 1209 | CZ | TYR | 39 | 43.222 | 47.355 | 26.204 | 1.00 | 54.32 | B1 |
| ATOM | 1210 | OH | TYR | 39 | 44.295 | 46.532 | 26.502 | 1.00 | 56.15 | B1 |
| ATOM | 1211 | C | TYR | 39 | 37.467 | 50.187 | 26.053 | 1.00 | 52.72 | B1 |
| ATOM | 1212 | O | TYR | 39 | 37.457 | 50.646 | 27.185 | 1.00 | 53.04 | B1 |
| ATOM | 1213 | N | ALA | 40 | 36.570 | 50.517 | 25.129 | 1.00 | 53.49 | B1 |
| ATOM | 1214 | CA | ALA | 40 | 35.507 | 51.473 | 25.379 | 1.00 | 53.72 | B1 |
| ATOM | 1215 | CB | ALA | 40 | 35.097 | 52.154 | 24.063 | 1.00 | 52.69 | B1 |
| ATOM | 1216 | C | ALA | 40 | 34.293 | 50.818 | 26.013 | 1.00 | 54.49 | B1 |
| ATOM | 1217 | O | ALA | 40 | 33.388 | 51.526 | 26.451 | 1.00 | 55.28 | B1 |
| ATOM | 1218 | N | LEU | 41 | 34.268 | 49.483 | 26.073 | 1.00 | 54.98 | B1 |
| ATOM | 1219 | CA | LEU | 41 | 33.107 | 48.746 | 26.622 | 1.00 | 55.00 | B1 |
| ATOM | 1220 | CB | LEU | 41 | 32.825 | 47.481 | 25.789 | 1.00 | 53.64 | B1 |
| ATOM | 1221 | CG | LEU | 41 | 33.130 | 47.485 | 24.293 | 1.00 | 53.38 | B1 |
| ATOM | 1222 | CD1 | LEU | 41 | 33.180 | 46.027 | 23.794 | 1.00 | 52.52 | B1 |
| ATOM | 1223 | CD2 | LEU | 41 | 32.103 | 48.303 | 23.537 | 1.00 | 52.98 | B1 |
| ATOM | 1224 | C | LEU | 41 | 33.224 | 48.311 | 28.082 | 1.00 | 55.16 | B1 |
| ATOM | 1225 | O | LEU | 41 | 34.318 | 48.191 | 28.616 | 1.00 | 55.63 | B1 |
| ATOM | 1226 | N | SER | 42 | 32.076 | 48.041 | 28.695 | 1.00 | 55.74 | B1 |
| ATOM | 1227 | CA | SER | 42 | 31.983 | 47.578 | 30.089 | 1.00 | 56.51 | B1 |
| ATOM | 1228 | CB | SER | 42 | 30.520 | 47.412 | 30.508 | 1.00 | 57.31 | B1 |
| ATOM | 1229 | OG | SER | 42 | 29.991 | 46.181 | 29.993 | 1.00 | 57.63 | B1 |
| ATOM | 1230 | C | SER | 42 | 32.622 | 46.208 | 30.229 | 1.00 | 56.49 | B1 |
| ATOM | 1231 | O | SER | 42 | 32.986 | 45.575 | 29.236 | 1.00 | 56.57 | B1 |
| ATOM | 1232 | N | ALA | 43 | 32.715 | 45.734 | 31.466 | 1.00 | 56.33 | B1 |
| ATOM | 1233 | CA | ALA | 43 | 33.291 | 44.420 | 31.713 | 1.00 | 56.63 | B1 |
| ATOM | 1234 | CB | ALA | 43 | 33.418 | 44.151 | 33.257 | 1.00 | 56.01 | B1 |
| ATOM | 1235 | C | ALA | 43 | 32.439 | 43.328 | 31.024 | 1.00 | 56.37 | B1 |
| ATOM | 1236 | O | ALA | 43 | 32.973 | 42.344 | 30.504 | 1.00 | 56.24 | B1 |
| ATOM | 1237 | N | ALA | 44 | 31.122 | 43.511 | 30.995 | 1.00 | 56.00 | B1 |
| ATOM | 1238 | CA | ALA | 44 | 30.263 | 42.517 | 30.361 | 1.00 | 55.31 | B1 |
| ATOM | 1239 | CB | ALA | 44 | 28.793 | 42.867 | 30.547 | 1.00 | 55.66 | B1 |
| ATOM | 1240 | C | ALA | 44 | 30.583 | 42.505 | 28.887 | 1.00 | 55.23 | B1 |
| ATOM | 1241 | O | ALA | 44 | 31.264 | 41.581 | 28.378 | 1.00 | 55.55 | B1 |
| ATOM | 1242 | N | ALA | 45 | 30.083 | 43.546 | 28.222 | 1.00 | 52.94 | B1 |
| ATOM | 1243 | CA | ALA | 45 | 30.242 | 43.735 | 26.799 | 1.00 | 51.15 | B1 |
| ATOM | 1244 | CB | ALA | 45 | 29.909 | 45.174 | 26.441 | 1.00 | 51.88 | B1 |
| ATOM | 1245 | C | ALA | 45 | 31.628 | 43.379 | 26.283 | 1.00 | 49.53 | B1 |
| ATOM | 1246 | O | ALA | 45 | 31.789 | 43.067 | 25.112 | 1.00 | 49.20 | B1 |

FIG. 3A-22

| ATOM | 1247 | N | LYS | 46 | 32.630 | 43.412 | 27.144 | 1.00 | 47.53 | B1 |
|---|---|---|---|---|---|---|---|---|---|---|
| ATOM | 1248 | CA | LYS | 46 | 33.972 | 43.088 | 26.686 | 1.00 | 45.73 | B1 |
| ATOM | 1249 | CB | LYS | 46 | 35.019 | 43.433 | 27.731 | 1.00 | 46.26 | B1 |
| ATOM | 1250 | CG | LYS | 46 | 35.557 | 44.825 | 27.647 | 1.00 | 48.50 | B1 |
| ATOM | 1251 | CD | LYS | 46 | 36.731 | 44.962 | 28.607 | 1.00 | 49.81 | B1 |
| ATOM | 1252 | CE | LYS | 46 | 37.403 | 46.296 | 28.457 | 1.00 | 52.00 | B1 |
| ATOM | 1253 | NZ | LYS | 46 | 38.669 | 46.353 | 29.255 | 1.00 | 53.15 | B1 |
| ATOM | 1254 | C | LYS | 46 | 34.206 | 41.644 | 26.283 | 1.00 | 43.73 | B1 |
| ATOM | 1255 | O | LYS | 46 | 34.819 | 41.413 | 25.245 | 1.00 | 43.15 | B1 |
| ATOM | 1256 | N | ASN | 47 | 33.769 | 40.688 | 27.107 | 1.00 | 41.38 | B1 |
| ATOM | 1257 | CA | ASN | 47 | 34.007 | 39.285 | 26.798 | 1.00 | 39.96 | B1 |
| ATOM | 1258 | CB | ASN | 47 | 33.735 | 38.375 | 28.015 | 1.00 | 41.11 | B1 |
| ATOM | 1259 | CG | ASN | 47 | 34.884 | 38.447 | 29.069 | 1.00 | 45.19 | B1 |
| ATOM | 1260 | OD1 | ASN | 47 | 34.648 | 38.357 | 30.307 | 1.00 | 46.49 | B1 |
| ATOM | 1261 | ND2 | ASN | 47 | 36.136 | 38.607 | 28.584 | 1.00 | 44.51 | B1 |
| ATOM | 1262 | C | ASN | 47 | 33.248 | 38.821 | 25.561 | 1.00 | 37.98 | B1 |
| ATOM | 1263 | O | ASN | 47 | 33.771 | 38.012 | 24.780 | 1.00 | 36.13 | B1 |
| ATOM | 1264 | N | GLU | 48 | 32.048 | 39.353 | 25.351 | 1.00 | 36.77 | B1 |
| ATOM | 1265 | CA | GLU | 48 | 31.310 | 38.951 | 24.177 | 1.00 | 37.17 | B1 |
| ATOM | 1266 | CB | GLU | 48 | 29.812 | 39.230 | 24.325 | 1.00 | 40.44 | B1 |
| ATOM | 1267 | CG | GLU | 48 | 29.446 | 40.643 | 24.622 | 1.00 | 44.46 | B1 |
| ATOM | 1268 | CD | GLU | 48 | 28.807 | 40.796 | 26.024 | 1.00 | 47.35 | B1 |
| ATOM | 1269 | OE1 | GLU | 48 | 29.591 | 40.785 | 27.020 | 1.00 | 48.12 | B1 |
| ATOM | 1270 | OE2 | GLU | 48 | 27.546 | 40.917 | 26.113 | 1.00 | 46.80 | B1 |
| ATOM | 1271 | C | GLU | 48 | 31.884 | 39.621 | 22.921 | 1.00 | 35.12 | B1 |
| ATOM | 1272 | O | GLU | 48 | 31.886 | 39.015 | 21.866 | 1.00 | 34.22 | B1 |
| ATOM | 1273 | N | PHE | 49 | 32.396 | 40.851 | 23.042 | 1.00 | 33.28 | B1 |
| ATOM | 1274 | CA | PHE | 49 | 33.003 | 41.492 | 21.891 | 1.00 | 31.67 | B1 |
| ATOM | 1275 | CB | PHE | 49 | 33.407 | 42.921 | 22.201 | 1.00 | 31.19 | B1 |
| ATOM | 1276 | CG | PHE | 49 | 34.157 | 43.604 | 21.082 | 1.00 | 28.77 | B1 |
| ATOM | 1277 | CD1 | PHE | 49 | 33.480 | 44.281 | 20.078 | 1.00 | 28.58 | B1 |
| ATOM | 1278 | CD2 | PHE | 49 | 35.531 | 43.583 | 21.040 | 1.00 | 29.27 | B1 |
| ATOM | 1279 | CE1 | PHE | 49 | 34.173 | 44.935 | 19.041 | 1.00 | 26.85 | B1 |
| ATOM | 1280 | CE2 | PHE | 49 | 36.236 | 44.245 | 20.004 | 1.00 | 28.19 | B1 |
| ATOM | 1281 | CZ | PHE | 49 | 35.545 | 44.913 | 19.017 | 1.00 | 26.97 | B1 |
| ATOM | 1282 | C | PHE | 49 | 34.273 | 40.685 | 21.527 | 1.00 | 30.94 | B1 |
| ATOM | 1283 | O | PHE | 49 | 34.521 | 40.391 | 20.353 | 1.00 | 29.62 | B1 |
| ATOM | 1284 | N | LEU | 50 | 35.052 | 40.308 | 22.540 | 1.00 | 29.25 | B1 |
| ATOM | 1285 | CA | LEU | 50 | 36.289 | 39.561 | 22.297 | 1.00 | 28.26 | B1 |
| ATOM | 1286 | CB | LEU | 50 | 37.112 | 39.473 | 23.575 | 1.00 | 27.33 | B1 |
| ATOM | 1287 | CG | LEU | 50 | 38.423 | 38.692 | 23.483 | 1.00 | 28.33 | B1 |
| ATOM | 1288 | CD1 | LEU | 50 | 39.317 | 39.237 | 22.326 | 1.00 | 26.30 | B1 |
| ATOM | 1289 | CD2 | LEU | 50 | 39.121 | 38.763 | 24.889 | 1.00 | 26.85 | B1 |
| ATOM | 1290 | C | LEU | 50 | 35.956 | 38.170 | 21.746 | 1.00 | 27.90 | B1 |
| ATOM | 1291 | O | LEU | 50 | 36.501 | 37.755 | 20.732 | 1.00 | 27.63 | B1 |
| ATOM | 1292 | N | ALA | 51 | 35.024 | 37.466 | 22.388 | 1.00 | 26.98 | B1 |
| ATOM | 1293 | CA | ALA | 51 | 34.645 | 36.140 | 21.915 | 1.00 | 25.11 | B1 |
| ATOM | 1294 | CB | ALA | 51 | 33.603 | 35.538 | 22.857 | 1.00 | 23.27 | B1 |
| ATOM | 1295 | C | ALA | 51 | 34.098 | 36.194 | 20.453 | 1.00 | 24.63 | B1 |
| ATOM | 1296 | O | ALA | 51 | 34.356 | 35.291 | 19.621 | 1.00 | 23.74 | B1 |
| ATOM | 1297 | N | GLY | 52 | 33.343 | 37.244 | 20.147 | 1.00 | 24.05 | B1 |
| ATOM | 1298 | CA | GLY | 52 | 32.795 | 37.346 | 18.817 | 1.00 | 23.42 | B1 |
| ATOM | 1299 | C | GLY | 52 | 33.874 | 37.557 | 17.775 | 1.00 | 24.52 | B1 |
| ATOM | 1300 | O | GLY | 52 | 33.850 | 36.942 | 16.711 | 1.00 | 25.82 | B1 |
| ATOM | 1301 | N | ARG | 53 | 34.833 | 38.430 | 18.052 | 1.00 | 25.23 | B1 |
| ATOM | 1302 | CA | ARG | 53 | 35.856 | 38.701 | 17.061 | 1.00 | 26.47 | B1 |
| ATOM | 1303 | CB | ARG | 53 | 36.676 | 39.970 | 17.419 | 1.00 | 27.84 | B1 |

FIG. 3A-23

| ATOM | 1304 | CG | ARG | 53 | 36.193 | 41.286 | 16.713 | 1.00 | 29.04 | B1 |
| ATOM | 1305 | CD | ARG | 53 | 34.753 | 41.748 | 17.040 | 1.00 | 32.70 | B1 |
| ATOM | 1306 | NE | ARG | 53 | 34.323 | 42.926 | 16.256 | 1.00 | 33.45 | B1 |
| ATOM | 1307 | CZ | ARG | 53 | 33.040 | 43.280 | 16.076 | 1.00 | 36.40 | B1 |
| ATOM | 1308 | NH1 | ARG | 53 | 32.065 | 42.555 | 16.620 | 1.00 | 37.75 | B1 |
| ATOM | 1309 | NH2 | ARG | 53 | 32.696 | 44.350 | 15.348 | 1.00 | 37.36 | B1 |
| ATOM | 1310 | C | ARG | 53 | 36.727 | 37.503 | 16.895 | 1.00 | 25.54 | B1 |
| ATOM | 1311 | O | ARG | 53 | 37.185 | 37.225 | 15.798 | 1.00 | 25.97 | B1 |
| ATOM | 1312 | N | PHE | 54 | 36.971 | 36.790 | 17.989 | 1.00 | 25.78 | B1 |
| ATOM | 1313 | CA | PHE | 54 | 37.782 | 35.573 | 17.916 | 1.00 | 24.70 | B1 |
| ATOM | 1314 | CB | PHE | 54 | 37.986 | 34.967 | 19.304 | 1.00 | 23.11 | B1 |
| ATOM | 1315 | CG | PHE | 54 | 38.758 | 33.676 | 19.275 | 1.00 | 23.50 | B1 |
| ATOM | 1316 | CD1 | PHE | 54 | 38.105 | 32.443 | 19.349 | 1.00 | 23.28 | B1 |
| ATOM | 1317 | CD2 | PHE | 54 | 40.143 | 33.685 | 19.117 | 1.00 | 24.40 | B1 |
| ATOM | 1318 | CE1 | PHE | 54 | 38.818 | 31.251 | 19.274 | 1.00 | 23.13 | B1 |
| ATOM | 1319 | CE2 | PHE | 54 | 40.874 | 32.486 | 19.037 | 1.00 | 23.88 | B1 |
| ATOM | 1320 | CZ | PHE | 54 | 40.189 | 31.262 | 19.120 | 1.00 | 23.28 | B1 |
| ATOM | 1321 | C | PHE | 54 | 37.030 | 34.564 | 17.021 | 1.00 | 24.85 | B1 |
| ATOM | 1322 | O | PHE | 54 | 37.614 | 33.926 | 16.151 | 1.00 | 25.96 | B1 |
| ATOM | 1323 | N | ALA | 55 | 35.723 | 34.433 | 17.238 | 1.00 | 23.60 | B1 |
| ATOM | 1324 | CA | ALA | 55 | 34.921 | 33.500 | 16.443 | 1.00 | 22.67 | B1 |
| ATOM | 1325 | CB | ALA | 55 | 33.412 | 33.474 | 16.986 | 1.00 | 19.81 | B1 |
| ATOM | 1326 | C | ALA | 55 | 34.957 | 33.917 | 14.955 | 1.00 | 21.88 | B1 |
| ATOM | 1327 | O | ALA | 55 | 35.168 | 33.087 | 14.064 | 1.00 | 22.44 | B1 |
| ATOM | 1328 | N | ALA | 56 | 34.750 | 35.198 | 14.678 | 1.00 | 21.17 | B1 |
| ATOM | 1329 | CA | ALA | 56 | 34.773 | 35.644 | 13.281 | 1.00 | 21.94 | B1 |
| ATOM | 1330 | CB | ALA | 56 | 34.447 | 37.053 | 13.217 | 1.00 | 21.38 | B1 |
| ATOM | 1331 | C | ALA | 56 | 36.141 | 35.385 | 12.634 | 1.00 | 23.12 | B1 |
| ATOM | 1332 | O | ALA | 56 | 36.212 | 35.050 | 11.455 | 1.00 | 25.01 | B1 |
| ATOM | 1333 | N | LYS | 57 | 37.225 | 35.473 | 13.411 | 1.00 | 22.35 | B1 |
| ATOM | 1334 | CA | LYS | 57 | 38.527 | 35.253 | 12.814 | 1.00 | 23.06 | B1 |
| ATOM | 1335 | CB | LYS | 57 | 39.679 | 35.933 | 13.598 | 1.00 | 21.11 | B1 |
| ATOM | 1336 | CG | LYS | 57 | 39.543 | 37.437 | 13.622 | 1.00 | 19.67 | B1 |
| ATOM | 1337 | CD | LYS | 57 | 40.779 | 38.119 | 14.201 | 1.00 | 19.94 | B1 |
| ATOM | 1338 | CE | LYS | 57 | 40.524 | 39.636 | 14.269 | 1.00 | 21.28 | B1 |
| ATOM | 1339 | NZ | LYS | 57 | 41.711 | 40.419 | 14.731 | 1.00 | 21.24 | B1 |
| ATOM | 1340 | C | LYS | 57 | 38.794 | 33.786 | 12.657 | 1.00 | 23.67 | B1 |
| ATOM | 1341 | O | LYS | 57 | 39.442 | 33.390 | 11.703 | 1.00 | 24.22 | B1 |
| ATOM | 1342 | N | GLU | 58 | 38.314 | 32.966 | 13.581 | 1.00 | 23.83 | B1 |
| ATOM | 1343 | CA | GLU | 58 | 38.519 | 31.539 | 13.370 | 1.00 | 24.27 | B1 |
| ATOM | 1344 | CB | GLU | 58 | 38.056 | 30.755 | 14.590 | 1.00 | 26.87 | B1 |
| ATOM | 1345 | CG | GLU | 58 | 39.034 | 30.808 | 15.772 | 1.00 | 32.81 | B1 |
| ATOM | 1346 | CD | GLU | 58 | 40.209 | 29.836 | 15.554 | 1.00 | 36.83 | B1 |
| ATOM | 1347 | OE1 | GLU | 58 | 39.913 | 28.628 | 15.293 | 1.00 | 40.26 | B1 |
| ATOM | 1348 | OE2 | GLU | 58 | 41.398 | 30.262 | 15.628 | 1.00 | 36.84 | B1 |
| ATOM | 1349 | C | GLU | 58 | 37.718 | 31.083 | 12.104 | 1.00 | 22.49 | B1 |
| ATOM | 1350 | O | GLU | 58 | 38.230 | 30.372 | 11.253 | 1.00 | 21.87 | B1 |
| ATOM | 1351 | N | ALA | 59 | 36.488 | 31.542 | 11.971 | 1.00 | 20.35 | B1 |
| ATOM | 1352 | CA | ALA | 59 | 35.684 | 31.094 | 10.867 | 1.00 | 21.36 | B1 |
| ATOM | 1353 | CB | ALA | 59 | 34.240 | 31.652 | 11.021 | 1.00 | 19.54 | B1 |
| ATOM | 1354 | C | ALA | 59 | 36.326 | 31.557 | 9.513 | 1.00 | 22.84 | B1 |
| ATOM | 1355 | O | ALA | 59 | 36.373 | 30.805 | 8.536 | 1.00 | 22.04 | B1 |
| ATOM | 1356 | N | PHE | 60 | 36.795 | 32.801 | 9.490 | 1.00 | 22.02 | B1 |
| ATOM | 1357 | CA | PHE | 60 | 37.420 | 33.345 | 8.316 | 1.00 | 22.50 | B1 |
| ATOM | 1358 | CB | PHE | 60 | 37.822 | 34.807 | 8.572 | 1.00 | 23.42 | B1 |
| ATOM | 1359 | CG | PHE | 60 | 38.562 | 35.379 | 7.442 | 1.00 | 23.85 | B1 |
| ATOM | 1360 | CD1 | PHE | 60 | 37.867 | 35.934 | 6.361 | 1.00 | 23.20 | B1 |

FIG. 3A-24

| ATOM | 1361 | CD2 | PHE | 60 | 39.942 | 35.274 | 7.402 | 1.00 | 23.36 | B1 |
| --- | --- | --- | --- | --- | --- | --- | --- | --- | --- | --- |
| ATOM | 1362 | CE1 | PHE | 60 | 38.535 | 36.377 | 5.240 | 1.00 | 24.53 | B1 |
| ATOM | 1363 | CE2 | PHE | 60 | 40.662 | 35.710 | 6.283 | 1.00 | 26.01 | B1 |
| ATOM | 1364 | CZ | PHE | 60 | 39.936 | 36.277 | 5.170 | 1.00 | 24.87 | B1 |
| ATOM | 1365 | C | PHE | 60 | 38.659 | 32.529 | 7.946 | 1.00 | 22.51 | B1 |
| ATOM | 1366 | O | PHE | 60 | 38.842 | 32.106 | 6.776 | 1.00 | 22.37 | B1 |
| ATOM | 1367 | N | SER | 61 | 39.521 | 32.301 | 8.931 | 1.00 | 22.91 | B1 |
| ATOM | 1368 | CA | SER | 61 | 40.732 | 31.509 | 8.660 | 1.00 | 23.52 | B1 |
| ATOM | 1369 | CB | SER | 61 | 41.560 | 31.290 | 9.953 | 1.00 | 23.83 | B1 |
| ATOM | 1370 | OG | SER | 61 | 40.958 | 30.284 | 10.809 | 1.00 | 25.53 | B1 |
| ATOM | 1371 | C | SER | 61 | 40.343 | 30.136 | 8.063 | 1.00 | 23.43 | B1 |
| ATOM | 1372 | O | SER | 61 | 41.105 | 29.571 | 7.304 | 1.00 | 24.15 | B1 |
| ATOM | 1373 | N | LYS | 62 | 39.167 | 29.599 | 8.405 | 1.00 | 22.88 | B1 |
| ATOM | 1374 | CA | LYS | 62 | 38.758 | 28.286 | 7.858 | 1.00 | 24.47 | B1 |
| ATOM | 1375 | CB | LYS | 62 | 37.679 | 27.642 | 8.757 | 1.00 | 25.68 | B1 |
| ATOM | 1376 | CG | LYS | 62 | 38.126 | 27.199 | 10.182 | 1.00 | 29.50 | B1 |
| ATOM | 1377 | CD | LYS | 62 | 36.846 | 26.907 | 11.071 | 1.00 | 32.07 | B1 |
| ATOM | 1378 | CE | LYS | 62 | 37.165 | 26.114 | 12.368 | 1.00 | 33.86 | B1 |
| ATOM | 1379 | NZ | LYS | 62 | 36.250 | 26.459 | 13.585 | 1.00 | 36.00 | B1 |
| ATOM | 1380 | C | LYS | 62 | 38.225 | 28.428 | 6.398 | 1.00 | 24.82 | B1 |
| ATOM | 1381 | O | LYS | 62 | 38.453 | 27.602 | 5.552 | 1.00 | 23.97 | B1 |
| ATOM | 1382 | N | ALA | 63 | 37.481 | 29.490 | 6.151 | 1.00 | 25.40 | B1 |
| ATOM | 1383 | CA | ALA | 63 | 36.950 | 29.827 | 4.839 | 1.00 | 26.03 | B1 |
| ATOM | 1384 | CB | ALA | 63 | 36.122 | 31.106 | 4.995 | 1.00 | 23.81 | B1 |
| ATOM | 1385 | C | ALA | 63 | 38.193 | 30.109 | 3.936 | 1.00 | 26.63 | B1 |
| ATOM | 1386 | O | ALA | 63 | 38.228 | 29.752 | 2.774 | 1.00 | 25.61 | B1 |
| ATOM | 1387 | N | PHE | 64 | 39.186 | 30.795 | 4.498 | 1.00 | 27.51 | B1 |
| ATOM | 1388 | CA | PHE | 64 | 40.422 | 31.136 | 3.772 | 1.00 | 29.24 | B1 |
| ATOM | 1389 | CB | PHE | 64 | 41.315 | 32.016 | 4.664 | 1.00 | 29.05 | B1 |
| ATOM | 1390 | CG | PHE | 64 | 42.531 | 32.577 | 3.977 | 1.00 | 30.71 | B1 |
| ATOM | 1391 | CD1 | PHE | 64 | 42.432 | 33.666 | 3.092 | 1.00 | 29.37 | B1 |
| ATOM | 1392 | CD2 | PHE | 64 | 43.808 | 32.082 | 4.293 | 1.00 | 30.61 | B1 |
| ATOM | 1393 | CE1 | PHE | 64 | 43.594 | 34.243 | 2.552 | 1.00 | 29.64 | B1 |
| ATOM | 1394 | CE2 | PHE | 64 | 44.978 | 32.657 | 3.761 | 1.00 | 30.30 | B1 |
| ATOM | 1395 | CZ | PHE | 64 | 44.879 | 33.744 | 2.891 | 1.00 | 29.10 | B1 |
| ATOM | 1396 | C | PHE | 64 | 41.147 | 29.851 | 3.386 | 1.00 | 30.09 | B1 |
| ATOM | 1397 | O | PHE | 64 | 41.897 | 29.864 | 2.444 | 1.00 | 30.68 | B1 |
| ATOM | 1398 | N | GLY | 65 | 40.926 | 28.756 | 4.139 | 1.00 | 30.98 | B1 |
| ATOM | 1399 | CA | GLY | 65 | 41.527 | 27.472 | 3.815 | 1.00 | 31.37 | B1 |
| ATOM | 1400 | C | GLY | 65 | 42.753 | 26.964 | 4.562 | 1.00 | 33.20 | B1 |
| ATOM | 1401 | O | GLY | 65 | 43.211 | 25.837 | 4.342 | 1.00 | 33.31 | B1 |
| ATOM | 1402 | N | THR | 66 | 43.274 | 27.738 | 5.498 | 1.00 | 32.35 | B1 |
| ATOM | 1403 | CA | THR | 66 | 44.491 | 27.293 | 6.148 | 1.00 | 32.11 | B1 |
| ATOM | 1404 | CB | THR | 66 | 45.613 | 28.232 | 5.794 | 1.00 | 30.57 | B1 |
| ATOM | 1405 | OG1 | THR | 66 | 45.290 | 29.511 | 6.364 | 1.00 | 28.59 | B1 |
| ATOM | 1406 | CG2 | THR | 66 | 45.747 | 28.354 | 4.300 | 1.00 | 30.33 | B1 |
| ATOM | 1407 | C | THR | 66 | 44.470 | 27.332 | 7.652 | 1.00 | 33.04 | B1 |
| ATOM | 1408 | O | THR | 66 | 45.398 | 26.826 | 8.260 | 1.00 | 33.53 | B1 |
| ATOM | 1409 | N | GLY | 67 | 43.459 | 27.992 | 8.232 | 1.00 | 33.38 | B1 |
| ATOM | 1410 | CA | GLY | 67 | 43.391 | 28.178 | 9.668 | 1.00 | 33.05 | B1 |
| ATOM | 1411 | C | GLY | 67 | 44.432 | 29.247 | 9.963 | 1.00 | 33.13 | B1 |
| ATOM | 1412 | O | GLY | 67 | 45.166 | 29.634 | 9.055 | 1.00 | 31.39 | B1 |
| ATOM | 1413 | N | ILE | 68 | 44.479 | 29.728 | 11.207 | 1.00 | 33.97 | B1 |
| ATOM | 1414 | CA | ILE | 68 | 45.444 | 30.751 | 11.657 | 1.00 | 33.80 | B1 |
| ATOM | 1415 | CB | ILE | 68 | 45.022 | 31.343 | 13.056 | 1.00 | 32.72 | B1 |
| ATOM | 1416 | CG2 | ILE | 68 | 46.167 | 32.173 | 13.668 | 1.00 | 30.94 | B1 |
| ATOM | 1417 | CG1 | ILE | 68 | 43.746 | 32.163 | 12.916 | 1.00 | 32.01 | B1 |

FIG. 3A-25

| ATOM | 1418 | CD1 | ILE | 68 | 43.901 | 33.419 | 12.019 | 1.00 | 29.71 | B1 |
| --- | --- | --- | --- | --- | --- | --- | --- | --- | --- | --- |
| ATOM | 1419 | C | ILE | 68 | 46.855 | 30.146 | 11.788 | 1.00 | 35.01 | B1 |
| ATOM | 1420 | O | ILE | 68 | 47.015 | 29.005 | 12.185 | 1.00 | 34.63 | B1 |
| ATOM | 1421 | N | GLY | 69 | 47.874 | 30.926 | 11.429 | 1.00 | 36.79 | B1 |
| ATOM | 1422 | CA | GLY | 69 | 49.249 | 30.469 | 11.521 | 1.00 | 38.01 | B1 |
| ATOM | 1423 | C | GLY | 69 | 50.230 | 31.161 | 10.578 | 1.00 | 39.61 | B1 |
| ATOM | 1424 | O | GLY | 69 | 50.264 | 32.393 | 10.460 | 1.00 | 38.05 | B1 |
| ATOM | 1425 | N | ALA | 70 | 51.023 | 30.327 | 9.900 | 1.00 | 41.65 | B1 |
| ATOM | 1426 | CA | ALA | 70 | 52.024 | 30.765 | 8.944 | 1.00 | 43.14 | B1 |
| ATOM | 1427 | CB | ALA | 70 | 52.822 | 29.536 | 8.415 | 1.00 | 43.37 | B1 |
| ATOM | 1428 | C | ALA | 70 | 51.432 | 31.568 | 7.775 | 1.00 | 43.45 | B1 |
| ATOM | 1429 | O | ALA | 70 | 51.935 | 32.625 | 7.446 | 1.00 | 44.06 | B1 |
| ATOM | 1430 | N | GLN | 71 | 50.345 | 31.101 | 7.172 | 1.00 | 43.42 | B1 |
| ATOM | 1431 | CA | GLN | 71 | 49.782 | 31.872 | 6.033 | 1.00 | 43.43 | B1 |
| ATOM | 1432 | CB | GLN | 71 | 49.130 | 30.925 | 5.004 | 1.00 | 45.18 | B1 |
| ATOM | 1433 | CG | GLN | 71 | 50.095 | 29.867 | 4.411 | 1.00 | 48.80 | B1 |
| ATOM | 1434 | CD | GLN | 71 | 49.429 | 28.485 | 4.153 | 1.00 | 51.39 | B1 |
| ATOM | 1435 | OE1 | GLN | 71 | 49.030 | 28.175 | 3.023 | 1.00 | 54.02 | B1 |
| ATOM | 1436 | NE2 | GLN | 71 | 49.308 | 27.663 | 5.202 | 1.00 | 50.54 | B1 |
| ATOM | 1437 | C | GLN | 71 | 48.776 | 32.960 | 6.449 | 1.00 | 40.86 | B1 |
| ATOM | 1438 | O | GLN | 71 | 48.323 | 33.754 | 5.614 | 1.00 | 39.98 | B1 |
| ATOM | 1439 | N | LEU | 72 | 48.480 | 33.045 | 7.744 | 1.00 | 37.98 | B1 |
| ATOM | 1440 | CA | LEU | 72 | 47.478 | 34.009 | 8.190 | 1.00 | 36.26 | B1 |
| ATOM | 1441 | CB | LEU | 72 | 46.102 | 33.522 | 7.777 | 1.00 | 34.40 | B1 |
| ATOM | 1442 | CG | LEU | 72 | 44.902 | 34.399 | 8.050 | 1.00 | 32.85 | B1 |
| ATOM | 1443 | CD1 | LEU | 72 | 44.843 | 35.468 | 6.992 | 1.00 | 32.54 | B1 |
| ATOM | 1444 | CD2 | LEU | 72 | 43.629 | 33.535 | 8.011 | 1.00 | 31.85 | B1 |
| ATOM | 1445 | C | LEU | 72 | 47.472 | 34.216 | 9.682 | 1.00 | 36.26 | B1 |
| ATOM | 1446 | O | LEU | 72 | 47.304 | 33.262 | 10.467 | 1.00 | 35.99 | B1 |
| ATOM | 1447 | N | SER | 73 | 47.615 | 35.474 | 10.052 | 1.00 | 35.30 | B1 |
| ATOM | 1448 | CA | SER | 73 | 47.639 | 35.883 | 11.439 | 1.00 | 35.78 | B1 |
| ATOM | 1449 | CB | SER | 73 | 48.729 | 36.924 | 11.647 | 1.00 | 35.81 | B1 |
| ATOM | 1450 | OG | SER | 73 | 48.610 | 37.488 | 12.952 | 1.00 | 38.65 | B1 |
| ATOM | 1451 | C | SER | 73 | 46.321 | 36.512 | 11.889 | 1.00 | 35.17 | B1 |
| ATOM | 1452 | O | SER | 73 | 45.537 | 36.964 | 11.061 | 1.00 | 35.80 | B1 |
| ATOM | 1453 | N | PHE | 74 | 46.101 | 36.549 | 13.200 | 1.00 | 34.10 | B1 |
| ATOM | 1454 | CA | PHE | 74 | 44.908 | 37.177 | 13.750 | 1.00 | 33.89 | B1 |
| ATOM | 1455 | CB | PHE | 74 | 44.890 | 37.046 | 15.278 | 1.00 | 32.52 | B1 |
| ATOM | 1456 | CG | PHE | 74 | 44.502 | 35.675 | 15.764 | 1.00 | 32.11 | B1 |
| ATOM | 1457 | CD1 | PHE | 74 | 43.182 | 35.231 | 15.658 | 1.00 | 31.77 | B1 |
| ATOM | 1458 | CD2 | PHE | 74 | 45.460 | 34.806 | 16.306 | 1.00 | 31.78 | B1 |
| ATOM | 1459 | CE1 | PHE | 74 | 42.819 | 33.934 | 16.090 | 1.00 | 32.33 | B1 |
| ATOM | 1460 | CE2 | PHE | 74 | 45.108 | 33.502 | 16.745 | 1.00 | 31.95 | B1 |
| ATOM | 1461 | CZ | PHE | 74 | 43.780 | 33.066 | 16.631 | 1.00 | 30.79 | B1 |
| ATOM | 1462 | C | PHE | 74 | 44.986 | 38.685 | 13.364 | 1.00 | 34.20 | B1 |
| ATOM | 1463 | O | PHE | 74 | 43.953 | 39.338 | 13.079 | 1.00 | 31.60 | B1 |
| ATOM | 1464 | N | GLN | 75 | 46.228 | 39.201 | 13.334 | 1.00 | 34.11 | B1 |
| ATOM | 1465 | CA | GLN | 75 | 46.485 | 40.607 | 13.032 | 1.00 | 34.43 | B1 |
| ATOM | 1466 | CB | GLN | 75 | 47.942 | 40.950 | 13.352 | 1.00 | 36.57 | B1 |
| ATOM | 1467 | CG | GLN | 75 | 48.293 | 40.925 | 14.862 | 1.00 | 35.45 | B1 |
| ATOM | 1468 | CD | GLN | 75 | 47.372 | 41.779 | 15.674 | 1.00 | 36.29 | B1 |
| ATOM | 1469 | OE1 | GLN | 75 | 46.929 | 41.389 | 16.775 | 1.00 | 36.74 | B1 |
| ATOM | 1470 | NE2 | GLN | 75 | 47.069 | 42.966 | 15.154 | 1.00 | 37.01 | B1 |
| ATOM | 1471 | C | GLN | 75 | 46.165 | 41.006 | 11.608 | 1.00 | 33.88 | B1 |
| ATOM | 1472 | O | GLN | 75 | 45.993 | 42.171 | 11.339 | 1.00 | 34.13 | B1 |
| ATOM | 1473 | N | ASP | 76 | 46.080 | 40.050 | 10.698 | 1.00 | 33.62 | B1 |
| ATOM | 1474 | CA | ASP | 76 | 45.739 | 40.354 | 9.301 | 1.00 | 33.82 | B1 |

FIG. 3A-26

| ATOM | 1475 | CB  | ASP | 76 | 46.322 | 39.270 | 8.395  | 1.00 | 35.57 | B1 |
| ---- | ---- | --- | --- | -- | ------ | ------ | ------ | ---- | ----- | -- |
| ATOM | 1476 | CG  | ASP | 76 | 47.852 | 39.128 | 8.534  | 1.00 | 37.11 | B1 |
| ATOM | 1477 | OD1 | ASP | 76 | 48.552 | 40.144 | 8.846  | 1.00 | 36.68 | B1 |
| ATOM | 1478 | OD2 | ASP | 76 | 48.328 | 37.987 | 8.309  | 1.00 | 37.48 | B1 |
| ATOM | 1479 | C   | ASP | 76 | 44.210 | 40.422 | 9.012  | 1.00 | 34.06 | B1 |
| ATOM | 1480 | O   | ASP | 76 | 43.787 | 40.732 | 7.888  | 1.00 | 32.89 | B1 |
| ATOM | 1481 | N   | ILE | 77 | 43.398 | 40.089 | 10.018 | 1.00 | 33.00 | B1 |
| ATOM | 1482 | CA  | ILE | 77 | 41.955 | 40.077 | 9.870  | 1.00 | 33.14 | B1 |
| ATOM | 1483 | CB  | ILE | 77 | 41.341 | 38.684 | 10.249 | 1.00 | 31.81 | B1 |
| ATOM | 1484 | CG2 | ILE | 77 | 39.856 | 38.611 | 9.840  | 1.00 | 30.14 | B1 |
| ATOM | 1485 | CG1 | ILE | 77 | 42.099 | 37.549 | 9.512  | 1.00 | 31.15 | B1 |
| ATOM | 1486 | CD1 | ILE | 77 | 41.911 | 36.136 | 10.200 | 1.00 | 29.63 | B1 |
| ATOM | 1487 | C   | ILE | 77 | 41.355 | 41.143 | 10.764 | 1.00 | 34.04 | B1 |
| ATOM | 1488 | O   | ILE | 77 | 41.608 | 41.201 | 11.980 | 1.00 | 34.59 | B1 |
| ATOM | 1489 | N   | GLU | 78 | 40.571 | 42.014 | 10.160 | 1.00 | 34.50 | B1 |
| ATOM | 1490 | CA  | GLU | 78 | 39.948 | 43.026 | 10.950 | 1.00 | 35.99 | B1 |
| ATOM | 1491 | CB  | GLU | 78 | 40.631 | 44.366 | 10.676 | 1.00 | 38.42 | B1 |
| ATOM | 1492 | CG  | GLU | 78 | 40.066 | 45.544 | 11.396 | 1.00 | 41.11 | B1 |
| ATOM | 1493 | CD  | GLU | 78 | 41.027 | 46.714 | 11.296 | 1.00 | 43.67 | B1 |
| ATOM | 1494 | OE1 | GLU | 78 | 41.755 | 46.939 | 12.283 | 1.00 | 44.57 | B1 |
| ATOM | 1495 | OE2 | GLU | 78 | 41.081 | 47.377 | 10.223 | 1.00 | 44.87 | B1 |
| ATOM | 1496 | C   | GLU | 78 | 38.454 | 43.114 | 10.676 | 1.00 | 36.02 | B1 |
| ATOM | 1497 | O   | GLU | 78 | 37.994 | 43.186 | 9.522  | 1.00 | 36.20 | B1 |
| ATOM | 1498 | N   | ILE | 79 | 37.708 | 43.094 | 11.758 | 1.00 | 35.68 | B1 |
| ATOM | 1499 | CA  | ILE | 79 | 36.296 | 43.225 | 11.696 | 1.00 | 37.08 | B1 |
| ATOM | 1500 | CB  | ILE | 79 | 35.639 | 42.374 | 12.814 | 1.00 | 36.74 | B1 |
| ATOM | 1501 | CG2 | ILE | 79 | 34.146 | 42.704 | 12.920 | 1.00 | 36.28 | B1 |
| ATOM | 1502 | CG1 | ILE | 79 | 35.822 | 40.878 | 12.489 | 1.00 | 36.49 | B1 |
| ATOM | 1503 | CD1 | ILE | 79 | 37.253 | 40.448 | 12.415 | 1.00 | 37.09 | B1 |
| ATOM | 1504 | C   | ILE | 79 | 35.970 | 44.714 | 11.870 | 1.00 | 38.48 | B1 |
| ATOM | 1505 | O   | ILE | 79 | 36.470 | 45.350 | 12.795 | 1.00 | 37.73 | B1 |
| ATOM | 1506 | N   | ARG | 80 | 35.185 | 45.273 | 10.953 | 1.00 | 40.54 | B1 |
| ATOM | 1507 | CA  | ARG | 80 | 34.776 | 46.679 | 11.031 | 1.00 | 43.90 | B1 |
| ATOM | 1508 | CB  | ARG | 80 | 35.337 | 47.451 | 9.842  | 1.00 | 44.69 | B1 |
| ATOM | 1509 | CG  | ARG | 80 | 36.851 | 47.544 | 9.830  | 1.00 | 46.15 | B1 |
| ATOM | 1510 | CD  | ARG | 80 | 37.368 | 48.230 | 8.579  | 1.00 | 47.22 | B1 |
| ATOM | 1511 | NE  | ARG | 80 | 38.813 | 48.036 | 8.469  | 1.00 | 48.93 | B1 |
| ATOM | 1512 | CZ  | ARG | 80 | 39.512 | 48.260 | 7.365  | 1.00 | 49.88 | B1 |
| ATOM | 1513 | NH1 | ARG | 80 | 38.887 | 48.692 | 6.270  | 1.00 | 49.30 | B1 |
| ATOM | 1514 | NH2 | ARG | 80 | 40.828 | 48.046 | 7.351  | 1.00 | 49.32 | B1 |
| ATOM | 1515 | C   | ARG | 80 | 33.242 | 46.839 | 11.048 | 1.00 | 46.39 | B1 |
| ATOM | 1516 | O   | ARG | 80 | 32.493 | 45.980 | 10.556 | 1.00 | 46.33 | B1 |
| ATOM | 1517 | N   | ALA | 81 | 32.770 | 47.949 | 11.607 | 1.00 | 49.26 | B1 |
| ATOM | 1518 | CA  | ALA | 81 | 31.331 | 48.203 | 11.671 | 1.00 | 52.06 | B1 |
| ATOM | 1519 | CB  | ALA | 81 | 30.969 | 48.850 | 13.018 | 1.00 | 51.83 | B1 |
| ATOM | 1520 | C   | ALA | 81 | 31.018 | 49.136 | 10.509 | 1.00 | 53.95 | B1 |
| ATOM | 1521 | O   | ALA | 81 | 31.826 | 50.014 | 10.202 | 1.00 | 54.91 | B1 |
| ATOM | 1522 | N   | ASP | 82 | 29.882 | 48.956 | 9.846  | 1.00 | 55.55 | B1 |
| ATOM | 1523 | CA  | ASP | 82 | 29.580 | 49.823 | 8.720  | 1.00 | 58.10 | B1 |
| ATOM | 1524 | CB  | ASP | 82 | 28.899 | 49.023 | 7.606  | 1.00 | 57.68 | B1 |
| ATOM | 1525 | CG  | ASP | 82 | 27.483 | 48.625 | 7.966  | 1.00 | 57.85 | B1 |
| ATOM | 1526 | OD1 | ASP | 82 | 26.738 | 48.149 | 7.077  | 1.00 | 57.82 | B1 |
| ATOM | 1527 | OD2 | ASP | 82 | 27.119 | 48.789 | 9.151  | 1.00 | 57.88 | B1 |
| ATOM | 1528 | C   | ASP | 82 | 28.691 | 51.021 | 9.099  | 1.00 | 59.84 | B1 |
| ATOM | 1529 | O   | ASP | 82 | 28.675 | 51.469 | 10.244 | 1.00 | 60.02 | B1 |
| ATOM | 1530 | N   | GLN | 83 | 27.964 | 51.538 | 8.107  | 1.00 | 61.97 | B1 |
| ATOM | 1531 | CA  | GLN | 83 | 27.035 | 52.666 | 8.293  | 1.00 | 63.65 | B1 |

FIG. 3A-27

| ATOM | 1532 | CB | GLN | 83 | 26.184 | 52.848 | 7.031 | 1.00 | 64.43 | B1 |
| ATOM | 1533 | CG | GLN | 83 | 27.006 | 52.812 | 5.757 | 1.00 | 66.77 | B1 |
| ATOM | 1534 | CD | GLN | 83 | 26.149 | 52.707 | 4.501 | 1.00 | 68.23 | B1 |
| ATOM | 1535 | OE1 | GLN | 83 | 25.367 | 53.619 | 4.188 | 1.00 | 68.35 | B1 |
| ATOM | 1536 | NE2 | GLN | 83 | 26.296 | 51.587 | 3.766 | 1.00 | 68.89 | B1 |
| ATOM | 1537 | C | GLN | 83 | 26.101 | 52.378 | 9.479 | 1.00 | 63.85 | B1 |
| ATOM | 1538 | O | GLN | 83 | 26.173 | 53.032 | 10.534 | 1.00 | 63.94 | B1 |
| ATOM | 1539 | N | ASN | 84 | 25.233 | 51.387 | 9.301 | 1.00 | 63.70 | B1 |
| ATOM | 1540 | CA | ASN | 84 | 24.304 | 51.037 | 10.353 | 1.00 | 63.32 | B1 |
| ATOM | 1541 | CB | ASN | 84 | 23.000 | 50.557 | 9.737 | 1.00 | 64.23 | B1 |
| ATOM | 1542 | CG | ASN | 84 | 21.798 | 51.287 | 10.326 | 1.00 | 65.77 | B1 |
| ATOM | 1543 | OD1 | ASN | 84 | 21.424 | 52.388 | 9.867 | 1.00 | 65.94 | B1 |
| ATOM | 1544 | ND2 | ASN | 84 | 21.204 | 50.699 | 11.376 | 1.00 | 66.01 | B1 |
| ATOM | 1545 | C | ASN | 84 | 24.771 | 50.040 | 11.429 | 1.00 | 62.56 | B1 |
| ATOM | 1546 | O | ASN | 84 | 23.942 | 49.406 | 12.103 | 1.00 | 62.52 | B1 |
| ATOM | 1547 | N | GLY | 85 | 26.084 | 49.874 | 11.581 | 1.00 | 61.17 | B1 |
| ATOM | 1548 | CA | GLY | 85 | 26.580 | 48.986 | 12.626 | 1.00 | 59.18 | B1 |
| ATOM | 1549 | C | GLY | 85 | 26.957 | 47.538 | 12.336 | 1.00 | 57.65 | B1 |
| ATOM | 1550 | O | GLY | 85 | 27.729 | 46.943 | 13.108 | 1.00 | 57.89 | B1 |
| ATOM | 1551 | N | ALA | 86 | 26.420 | 46.952 | 11.269 | 1.00 | 55.17 | B1 |
| ATOM | 1552 | CA | ALA | 86 | 26.739 | 45.563 | 10.911 | 1.00 | 53.38 | B1 |
| ATOM | 1553 | CB | ALA | 86 | 25.931 | 45.151 | 9.650 | 1.00 | 52.68 | B1 |
| ATOM | 1554 | C | ALA | 86 | 28.278 | 45.347 | 10.687 | 1.00 | 51.50 | B1 |
| ATOM | 1555 | O | ALA | 86 | 29.000 | 46.268 | 10.262 | 1.00 | 51.32 | B1 |
| ATOM | 1556 | N | PRO | 87 | 28.784 | 44.130 | 10.998 | 1.00 | 49.44 | B1 |
| ATOM | 1557 | CD | PRO | 87 | 27.948 | 43.003 | 11.480 | 1.00 | 48.99 | B1 |
| ATOM | 1558 | CA | PRO | 87 | 30.201 | 43.717 | 10.868 | 1.00 | 46.89 | B1 |
| ATOM | 1559 | CB | PRO | 87 | 30.310 | 42.543 | 11.836 | 1.00 | 47.60 | B1 |
| ATOM | 1560 | CG | PRO | 87 | 28.943 | 41.819 | 11.567 | 1.00 | 48.65 | B1 |
| ATOM | 1561 | C | PRO | 87 | 30.560 | 43.267 | 9.464 | 1.00 | 44.00 | B1 |
| ATOM | 1562 | O | PRO | 87 | 29.740 | 42.683 | 8.758 | 1.00 | 43.26 | B1 |
| ATOM | 1563 | N | TYR | 88 | 31.773 | 43.575 | 9.043 | 1.00 | 41.45 | B1 |
| ATOM | 1564 | CA | TYR | 88 | 32.244 | 43.126 | 7.740 | 1.00 | 39.15 | B1 |
| ATOM | 1565 | CB | TYR | 88 | 31.843 | 44.102 | 6.590 | 1.00 | 39.61 | B1 |
| ATOM | 1566 | CG | TYR | 88 | 32.482 | 45.487 | 6.604 | 1.00 | 41.06 | B1 |
| ATOM | 1567 | CD1 | TYR | 88 | 33.675 | 45.743 | 5.894 | 1.00 | 41.16 | B1 |
| ATOM | 1568 | CE1 | TYR | 88 | 34.313 | 47.007 | 5.953 | 1.00 | 41.19 | B1 |
| ATOM | 1569 | CD2 | TYR | 88 | 31.934 | 46.533 | 7.368 | 1.00 | 41.56 | B1 |
| ATOM | 1570 | CE2 | TYR | 88 | 32.567 | 47.807 | 7.440 | 1.00 | 41.61 | B1 |
| ATOM | 1571 | CZ | TYR | 88 | 33.756 | 48.024 | 6.727 | 1.00 | 42.13 | B1 |
| ATOM | 1572 | OH | TYR | 88 | 34.396 | 49.247 | 6.800 | 1.00 | 43.16 | B1 |
| ATOM | 1573 | C | TYR | 88 | 33.744 | 42.976 | 7.937 | 1.00 | 36.73 | B1 |
| ATOM | 1574 | O | TYR | 88 | 34.324 | 43.493 | 8.883 | 1.00 | 34.70 | B1 |
| ATOM | 1575 | N | ILE | 89 | 34.360 | 42.263 | 7.029 | 1.00 | 35.89 | B1 |
| ATOM | 1576 | CA | ILE | 89 | 35.757 | 41.973 | 7.131 | 1.00 | 35.67 | B1 |
| ATOM | 1577 | CB | ILE | 89 | 35.961 | 40.450 | 7.207 | 1.00 | 35.14 | B1 |
| ATOM | 1578 | CG2 | ILE | 89 | 37.473 | 40.080 | 6.887 | 1.00 | 33.43 | B1 |
| ATOM | 1579 | CG1 | ILE | 89 | 35.493 | 39.959 | 8.569 | 1.00 | 33.89 | B1 |
| ATOM | 1580 | CD1 | ILE | 89 | 35.498 | 38.495 | 8.693 | 1.00 | 34.14 | B1 |
| ATOM | 1581 | C | ILE | 89 | 36.706 | 42.462 | 6.060 | 1.00 | 36.44 | B1 |
| ATOM | 1582 | O | ILE | 89 | 36.451 | 42.305 | 4.864 | 1.00 | 36.42 | B1 |
| ATOM | 1583 | N | ILE | 90 | 37.837 | 42.974 | 6.527 | 1.00 | 36.77 | B1 |
| ATOM | 1584 | CA | ILE | 90 | 38.917 | 43.418 | 5.652 | 1.00 | 37.18 | B1 |
| ATOM | 1585 | CB | ILE | 90 | 39.256 | 44.903 | 5.835 | 1.00 | 37.91 | B1 |
| ATOM | 1586 | CG2 | ILE | 90 | 40.363 | 45.286 | 4.829 | 1.00 | 39.62 | B1 |
| ATOM | 1587 | CG1 | ILE | 90 | 38.033 | 45.775 | 5.513 | 1.00 | 38.16 | B1 |
| ATOM | 1588 | CD1 | ILE | 90 | 37.522 | 45.595 | 4.070 | 1.00 | 35.21 | B1 |

FIG. 3A-28

| ATOM | 1589 | C | ILE | 90 | 40.132 | 42.593 | 6.034 | 1.00 | 36.19 | B1 |
|------|------|------|-----|----|--------|--------|-------|------|-------|-----|
| ATOM | 1590 | O | ILE | 90 | 40.564 | 42.623 | 7.166 | 1.00 | 36.53 | B1 |
| ATOM | 1591 | N | CYS | 91 | 40.621 | 41.804 | 5.092 | 1.00 | 35.99 | B1 |
| ATOM | 1592 | CA | CYS | 91 | 41.776 | 40.955 | 5.323 | 1.00 | 35.74 | B1 |
| ATOM | 1593 | CB | CYS | 91 | 41.455 | 39.490 | 5.037 | 1.00 | 35.10 | B1 |
| ATOM | 1594 | SG | CYS | 91 | 42.926 | 38.466 | 5.170 | 1.00 | 33.12 | B1 |
| ATOM | 1595 | C | CYS | 91 | 42.920 | 41.359 | 4.415 | 1.00 | 36.16 | B1 |
| ATOM | 1596 | O | CYS | 91 | 42.750 | 41.390 | 3.189 | 1.00 | 35.07 | B1 |
| ATOM | 1597 | N | THR | 92 | 44.085 | 41.591 | 5.024 | 1.00 | 36.82 | B1 |
| ATOM | 1598 | CA | THR | 92 | 45.287 | 42.019 | 4.300 | 1.00 | 38.35 | B1 |
| ATOM | 1599 | CB | THR | 92 | 46.507 | 42.197 | 5.248 | 1.00 | 38.75 | B1 |
| ATOM | 1600 | OG1 | THR | 92 | 46.761 | 40.963 | 5.936 | 1.00 | 37.76 | B1 |
| ATOM | 1601 | CG2 | THR | 92 | 46.263 | 43.298 | 6.272 | 1.00 | 39.01 | B1 |
| ATOM | 1602 | C | THR | 92 | 45.716 | 41.027 | 3.231 | 1.00 | 39.26 | B1 |
| ATOM | 1603 | O | THR | 92 | 46.323 | 41.413 | 2.264 | 1.00 | 39.63 | B1 |
| ATOM | 1604 | N | LYS | 93 | 45.407 | 39.745 | 3.421 | 1.00 | 39.79 | B1 |
| ATOM | 1605 | CA | LYS | 93 | 45.810 | 38.723 | 2.484 | 1.00 | 39.52 | B1 |
| ATOM | 1606 | CB | LYS | 93 | 46.010 | 37.393 | 3.198 | 1.00 | 40.17 | B1 |
| ATOM | 1607 | CG | LYS | 93 | 47.006 | 37.426 | 4.332 | 1.00 | 40.94 | B1 |
| ATOM | 1608 | CD | LYS | 93 | 48.307 | 38.081 | 3.926 | 1.00 | 41.78 | B1 |
| ATOM | 1609 | CE | LYS | 93 | 49.388 | 37.905 | 4.982 | 1.00 | 42.27 | B1 |
| ATOM | 1610 | NZ | LYS | 93 | 50.633 | 38.699 | 4.664 | 1.00 | 44.42 | B1 |
| ATOM | 1611 | C | LYS | 93 | 44.867 | 38.495 | 1.341 | 1.00 | 39.75 | B1 |
| ATOM | 1612 | O | LYS | 93 | 45.155 | 37.671 | 0.493 | 1.00 | 39.68 | B1 |
| ATOM | 1613 | N | LEU | 94 | 43.748 | 39.203 | 1.304 | 1.00 | 40.01 | B1 |
| ATOM | 1614 | CA | LEU | 94 | 42.774 | 39.014 | 0.217 | 1.00 | 41.18 | B1 |
| ATOM | 1615 | CB | LEU | 94 | 41.353 | 38.899 | 0.778 | 1.00 | 40.88 | B1 |
| ATOM | 1616 | CG | LEU | 94 | 40.856 | 37.581 | 1.350 | 1.00 | 40.77 | B1 |
| ATOM | 1617 | CD1 | LEU | 94 | 39.413 | 37.749 | 1.726 | 1.00 | 39.19 | B1 |
| ATOM | 1618 | CD2 | LEU | 94 | 41.054 | 36.453 | 0.312 | 1.00 | 39.78 | B1 |
| ATOM | 1619 | C | LEU | 94 | 42.718 | 40.145 | -0.806 | 1.00 | 41.93 | B1 |
| ATOM | 1620 | O | LEU | 94 | 42.764 | 41.313 | -0.438 | 1.00 | 42.74 | B1 |
| ATOM | 1621 | N | SER | 95 | 42.526 | 39.815 | -2.072 | 1.00 | 42.58 | B1 |
| ATOM | 1622 | CA | SER | 95 | 42.421 | 40.876 | -3.069 | 1.00 | 42.96 | B1 |
| ATOM | 1623 | CB | SER | 95 | 43.778 | 41.109 | -3.754 | 1.00 | 43.94 | B1 |
| ATOM | 1624 | OG | SER | 95 | 44.020 | 40.115 | -4.746 | 1.00 | 43.87 | B1 |
| ATOM | 1625 | C | SER | 95 | 41.379 | 40.672 | -4.150 | 1.00 | 42.89 | B1 |
| ATOM | 1626 | O | SER | 95 | 40.905 | 41.627 | -4.730 | 1.00 | 44.24 | B1 |
| ATOM | 1627 | N | GLN | 96 | 41.009 | 39.450 | -4.471 | 1.00 | 43.07 | B1 |
| ATOM | 1628 | CA | GLN | 96 | 40.033 | 39.325 | -5.561 | 1.00 | 42.39 | B1 |
| ATOM | 1629 | CB | GLN | 96 | 40.750 | 38.755 | -6.780 | 1.00 | 44.77 | B1 |
| ATOM | 1630 | CG | GLN | 96 | 41.943 | 39.613 | -7.243 | 1.00 | 47.44 | B1 |
| ATOM | 1631 | CD | GLN | 96 | 41.569 | 40.542 | -8.395 | 1.00 | 49.06 | B1 |
| ATOM | 1632 | OE1 | GLN | 96 | 42.357 | 41.411 | -8.776 | 1.00 | 49.80 | B1 |
| ATOM | 1633 | NE2 | GLN | 96 | 40.363 | 40.344 | -8.977 | 1.00 | 49.46 | B1 |
| ATOM | 1634 | C | GLN | 96 | 38.854 | 38.456 | -5.173 | 1.00 | 40.56 | B1 |
| ATOM | 1635 | O | GLN | 96 | 38.375 | 37.620 | -5.947 | 1.00 | 40.17 | B1 |
| ATOM | 1636 | N | ALA | 97 | 38.367 | 38.690 | -3.962 | 1.00 | 38.47 | B1 |
| ATOM | 1637 | CA | ALA | 97 | 37.270 | 37.906 | -3.429 | 1.00 | 36.12 | B1 |
| ATOM | 1638 | CB | ALA | 97 | 37.845 | 36.736 | -2.643 | 1.00 | 34.36 | B1 |
| ATOM | 1639 | C | ALA | 97 | 36.388 | 38.735 | -2.535 | 1.00 | 35.07 | B1 |
| ATOM | 1640 | O | ALA | 97 | 36.870 | 39.615 | -1.833 | 1.00 | 36.55 | B1 |
| ATOM | 1641 | N | ALA | 98 | 35.092 | 38.472 | -2.550 | 1.00 | 33.28 | B1 |
| ATOM | 1642 | CA | ALA | 98 | 34.201 | 39.183 | -1.629 | 1.00 | 31.74 | B1 |
| ATOM | 1643 | CB | ALA | 98 | 32.803 | 39.328 | -2.228 | 1.00 | 30.40 | B1 |
| ATOM | 1644 | C | ALA | 98 | 34.130 | 38.316 | -0.337 | 1.00 | 30.10 | B1 |
| ATOM | 1645 | O | ALA | 98 | 34.182 | 37.094 | -0.387 | 1.00 | 28.07 | B1 |

FIG. 3A-29

| ATOM | 1646 | N | VAL | 99 | 33.978 | 38.966 | 0.799 | 1.00 | 30.22 | B1 |
| ATOM | 1647 | CA | VAL | 99 | 33.900 | 38.260 | 2.058 | 1.00 | 30.56 | B1 |
| ATOM | 1648 | CB | VAL | 99 | 35.113 | 38.595 | 2.968 | 1.00 | 30.62 | B1 |
| ATOM | 1649 | CG1 | VAL | 99 | 35.074 | 37.747 | 4.264 | 1.00 | 29.52 | B1 |
| ATOM | 1650 | CG2 | VAL | 99 | 36.397 | 38.287 | 2.246 | 1.00 | 31.07 | B1 |
| ATOM | 1651 | C | VAL | 99 | 32.621 | 38.611 | 2.814 | 1.00 | 30.85 | B1 |
| ATOM | 1652 | O | VAL | 99 | 32.270 | 39.801 | 2.952 | 1.00 | 30.29 | B1 |
| ATOM | 1653 | N | HIS | 100 | 31.932 | 37.576 | 3.300 | 1.00 | 30.10 | B1 |
| ATOM | 1654 | CA | HIS | 100 | 30.719 | 37.792 | 4.111 | 1.00 | 30.30 | B1 |
| ATOM | 1655 | CB | HIS | 100 | 29.465 | 37.206 | 3.469 | 1.00 | 30.39 | B1 |
| ATOM | 1656 | CG | HIS | 100 | 29.121 | 37.824 | 2.161 | 1.00 | 34.23 | B1 |
| ATOM | 1657 | CD2 | HIS | 100 | 29.355 | 37.408 | 0.894 | 1.00 | 34.42 | B1 |
| ATOM | 1658 | ND1 | HIS | 100 | 28.564 | 39.083 | 2.062 | 1.00 | 34.61 | B1 |
| ATOM | 1659 | CE1 | HIS | 100 | 28.476 | 39.420 | 0.787 | 1.00 | 36.03 | B1 |
| ATOM | 1660 | NE2 | HIS | 100 | 28.950 | 38.425 | 0.060 | 1.00 | 36.35 | B1 |
| ATOM | 1661 | C | HIS | 100 | 30.869 | 37.141 | 5.477 | 1.00 | 29.01 | B1 |
| ATOM | 1662 | O | HIS | 100 | 31.357 | 35.977 | 5.612 | 1.00 | 28.01 | B1 |
| ATOM | 1663 | N | VAL | 101 | 30.390 | 37.880 | 6.466 | 1.00 | 27.15 | B1 |
| ATOM | 1664 | CA | VAL | 101 | 30.432 | 37.420 | 7.803 | 1.00 | 27.02 | B1 |
| ATOM | 1665 | CB | VAL | 101 | 31.533 | 38.118 | 8.577 | 1.00 | 26.29 | B1 |
| ATOM | 1666 | CG1 | VAL | 101 | 31.179 | 39.597 | 8.765 | 1.00 | 24.61 | B1 |
| ATOM | 1667 | CG2 | VAL | 101 | 31.724 | 37.451 | 9.899 | 1.00 | 24.54 | B1 |
| ATOM | 1668 | C | VAL | 101 | 29.146 | 37.662 | 8.539 | 1.00 | 28.14 | B1 |
| ATOM | 1669 | O | VAL | 101 | 28.482 | 38.698 | 8.356 | 1.00 | 29.45 | B1 |
| ATOM | 1670 | N | SER | 102 | 28.766 | 36.707 | 9.379 | 1.00 | 28.04 | B1 |
| ATOM | 1671 | CA | SER | 102 | 27.616 | 36.957 | 10.208 | 1.00 | 28.42 | B1 |
| ATOM | 1672 | CB | SER | 102 | 26.399 | 36.166 | 9.718 | 1.00 | 27.56 | B1 |
| ATOM | 1673 | OG | SER | 102 | 25.295 | 36.440 | 10.575 | 1.00 | 29.02 | B1 |
| ATOM | 1674 | C | SER | 102 | 28.060 | 36.563 | 11.635 | 1.00 | 28.63 | B1 |
| ATOM | 1675 | O | SER | 102 | 28.699 | 35.524 | 11.824 | 1.00 | 28.25 | B1 |
| ATOM | 1676 | N | ILE | 103 | 27.749 | 37.392 | 12.630 | 1.00 | 28.89 | B1 |
| ATOM | 1677 | CA | ILE | 103 | 28.156 | 37.096 | 13.994 | 1.00 | 29.90 | B1 |
| ATOM | 1678 | CB | ILE | 103 | 29.152 | 38.131 | 14.536 | 1.00 | 30.84 | B1 |
| ATOM | 1679 | CG2 | ILE | 103 | 29.511 | 37.772 | 16.050 | 1.00 | 32.46 | B1 |
| ATOM | 1680 | CG1 | ILE | 103 | 30.430 | 38.125 | 13.682 | 1.00 | 30.85 | B1 |
| ATOM | 1681 | CD1 | ILE | 103 | 31.412 | 39.173 | 14.073 | 1.00 | 30.47 | B1 |
| ATOM | 1682 | C | ILE | 103 | 26.972 | 37.048 | 14.933 | 1.00 | 30.17 | B1 |
| ATOM | 1683 | O | ILE | 103 | 26.145 | 37.944 | 14.946 | 1.00 | 30.48 | B1 |
| ATOM | 1684 | N | THR | 104 | 26.866 | 36.004 | 15.731 | 1.00 | 30.81 | B1 |
| ATOM | 1685 | CA | THR | 104 | 25.712 | 35.941 | 16.635 | 1.00 | 31.45 | B1 |
| ATOM | 1686 | CB | THR | 104 | 24.677 | 34.929 | 16.131 | 1.00 | 31.80 | B1 |
| ATOM | 1687 | OG1 | THR | 104 | 23.467 | 35.108 | 16.863 | 1.00 | 32.62 | B1 |
| ATOM | 1688 | CG2 | THR | 104 | 25.190 | 33.488 | 16.319 | 1.00 | 30.80 | B1 |
| ATOM | 1689 | C | THR | 104 | 26.143 | 35.562 | 18.052 | 1.00 | 31.67 | B1 |
| ATOM | 1690 | O | THR | 104 | 27.209 | 34.983 | 18.234 | 1.00 | 30.85 | B1 |
| ATOM | 1691 | N | HIS | 105 | 25.285 | 35.878 | 19.028 | 1.00 | 32.96 | B1 |
| ATOM | 1692 | CA | HIS | 105 | 25.557 | 35.637 | 20.466 | 1.00 | 34.13 | B1 |
| ATOM | 1693 | CB | HIS | 105 | 25.928 | 36.950 | 21.166 | 1.00 | 34.78 | B1 |
| ATOM | 1694 | CG | HIS | 105 | 27.158 | 37.587 | 20.644 | 1.00 | 37.03 | B1 |
| ATOM | 1695 | CD2 | HIS | 105 | 27.335 | 38.645 | 19.814 | 1.00 | 38.51 | B1 |
| ATOM | 1696 | ND1 | HIS | 105 | 28.423 | 37.129 | 20.961 | 1.00 | 38.91 | B1 |
| ATOM | 1697 | CE1 | HIS | 105 | 29.328 | 37.869 | 20.346 | 1.00 | 38.37 | B1 |
| ATOM | 1698 | NE2 | HIS | 105 | 28.696 | 38.799 | 19.644 | 1.00 | 40.30 | B1 |
| ATOM | 1699 | C | HIS | 105 | 24.379 | 35.094 | 21.267 | 1.00 | 34.37 | B1 |
| ATOM | 1700 | O | HIS | 105 | 23.261 | 35.499 | 21.025 | 1.00 | 33.67 | B1 |
| ATOM | 1701 | N | THR | 106 | 24.659 | 34.189 | 22.209 | 1.00 | 34.82 | B1 |
| ATOM | 1702 | CA | THR | 106 | 23.665 | 33.685 | 23.164 | 1.00 | 35.49 | B1 |

FIG. 3A-30

| ATOM | 1703 | CB | THR | 106 | 23.475 | 32.156 | 23.182 | 1.00 | 35.09 | B1 |
| ATOM | 1704 | OG1 | THR | 106 | 24.707 | 31.544 | 23.546 | 1.00 | 34.36 | B1 |
| ATOM | 1705 | CG2 | THR | 106 | 22.953 | 31.632 | 21.823 | 1.00 | 35.91 | B1 |
| ATOM | 1706 | C | THR | 106 | 24.309 | 34.003 | 24.517 | 1.00 | 36.01 | B1 |
| ATOM | 1707 | O | THR | 106 | 25.409 | 34.565 | 24.562 | 1.00 | 35.69 | B1 |
| ATOM | 1708 | N | ALA | 107 | 23.663 | 33.602 | 25.613 | 1.00 | 36.11 | B1 |
| ATOM | 1709 | CA | ALA | 107 | 24.222 | 33.885 | 26.943 | 1.00 | 36.17 | B1 |
| ATOM | 1710 | CB | ALA | 107 | 23.182 | 33.498 | 28.093 | 1.00 | 36.40 | B1 |
| ATOM | 1711 | C | ALA | 107 | 25.560 | 33.172 | 27.162 | 1.00 | 35.49 | B1 |
| ATOM | 1712 | O | ALA | 107 | 26.469 | 33.727 | 27.769 | 1.00 | 35.34 | B1 |
| ATOM | 1713 | N | GLU | 108 | 25.706 | 31.971 | 26.625 | 1.00 | 35.10 | B1 |
| ATOM | 1714 | CA | GLU | 108 | 26.945 | 31.234 | 26.825 | 1.00 | 35.82 | B1 |
| ATOM | 1715 | CB | GLU | 108 | 26.639 | 29.789 | 27.251 | 1.00 | 38.90 | B1 |
| ATOM | 1716 | CG | GLU | 108 | 25.842 | 29.696 | 28.522 | 1.00 | 44.61 | B1 |
| ATOM | 1717 | CD | GLU | 108 | 25.599 | 28.262 | 28.937 | 1.00 | 48.58 | B1 |
| ATOM | 1718 | OE1 | GLU | 108 | 24.655 | 28.041 | 29.730 | 1.00 | 50.53 | B1 |
| ATOM | 1719 | OE2 | GLU | 108 | 26.362 | 27.357 | 28.489 | 1.00 | 51.47 | B1 |
| ATOM | 1720 | C | GLU | 108 | 27.922 | 31.137 | 25.666 | 1.00 | 34.54 | B1 |
| ATOM | 1721 | O | GLU | 108 | 29.067 | 30.773 | 25.877 | 1.00 | 33.82 | B1 |
| ATOM | 1722 | N | TYR | 109 | 27.475 | 31.424 | 24.445 | 1.00 | 33.83 | B1 |
| ATOM | 1723 | CA | TYR | 109 | 28.353 | 31.235 | 23.264 | 1.00 | 31.80 | B1 |
| ATOM | 1724 | CB | TYR | 109 | 27.875 | 30.013 | 22.503 | 1.00 | 31.67 | B1 |
| ATOM | 1725 | CG | TYR | 109 | 28.046 | 28.688 | 23.249 | 1.00 | 32.77 | B1 |
| ATOM | 1726 | CD1 | TYR | 109 | 29.273 | 28.051 | 23.250 | 1.00 | 33.33 | B1 |
| ATOM | 1727 | CE1 | TYR | 109 | 29.487 | 26.878 | 23.917 | 1.00 | 35.40 | B1 |
| ATOM | 1728 | CD2 | TYR | 109 | 27.005 | 28.103 | 23.962 | 1.00 | 33.45 | B1 |
| ATOM | 1729 | CE2 | TYR | 109 | 27.208 | 26.886 | 24.682 | 1.00 | 34.90 | B1 |
| ATOM | 1730 | CZ | TYR | 109 | 28.463 | 26.290 | 24.648 | 1.00 | 35.91 | B1 |
| ATOM | 1731 | OH | TYR | 109 | 28.808 | 25.152 | 25.354 | 1.00 | 37.81 | B1 |
| ATOM | 1732 | C | TYR | 109 | 28.417 | 32.380 | 22.310 | 1.00 | 30.50 | B1 |
| ATOM | 1733 | O | TYR | 109 | 27.554 | 33.228 | 22.303 | 1.00 | 30.99 | B1 |
| ATOM | 1734 | N | ALA | 110 | 29.461 | 32.420 | 21.505 | 1.00 | 29.56 | B1 |
| ATOM | 1735 | CA | ALA | 110 | 29.581 | 33.426 | 20.459 | 1.00 | 28.07 | B1 |
| ATOM | 1736 | CB | ALA | 110 | 30.834 | 34.276 | 20.657 | 1.00 | 28.86 | B1 |
| ATOM | 1737 | C | ALA | 110 | 29.738 | 32.524 | 19.210 | 1.00 | 27.13 | B1 |
| ATOM | 1738 | O | ALA | 110 | 30.402 | 31.493 | 19.291 | 1.00 | 26.29 | B1 |
| ATOM | 1739 | N | ALA | 111 | 29.118 | 32.894 | 18.081 | 1.00 | 25.13 | B1 |
| ATOM | 1740 | CA | ALA | 111 | 29.227 | 32.100 | 16.882 | 1.00 | 23.39 | B1 |
| ATOM | 1741 | CB | ALA | 111 | 28.013 | 31.175 | 16.746 | 1.00 | 22.39 | B1 |
| ATOM | 1742 | C | ALA | 111 | 29.356 | 33.008 | 15.679 | 1.00 | 22.70 | B1 |
| ATOM | 1743 | O | ALA | 111 | 28.867 | 34.126 | 15.682 | 1.00 | 22.85 | B1 |
| ATOM | 1744 | N | ALA | 112 | 30.089 | 32.558 | 14.686 | 1.00 | 21.46 | B1 |
| ATOM | 1745 | CA | ALA | 112 | 30.241 | 33.345 | 13.482 | 1.00 | 22.44 | B1 |
| ATOM | 1746 | CB | ALA | 112 | 31.486 | 34.252 | 13.589 | 1.00 | 21.22 | B1 |
| ATOM | 1747 | C | ALA | 112 | 30.398 | 32.430 | 12.266 | 1.00 | 23.59 | B1 |
| ATOM | 1748 | O | ALA | 112 | 30.879 | 31.293 | 12.375 | 1.00 | 24.32 | B1 |
| ATOM | 1749 | N | GLN | 113 | 29.993 | 32.935 | 11.115 | 1.00 | 23.66 | B1 |
| ATOM | 1750 | CA | GLN | 113 | 30.208 | 32.218 | 9.878 | 1.00 | 25.14 | B1 |
| ATOM | 1751 | CB | GLN | 113 | 28.908 | 31.534 | 9.383 | 1.00 | 25.14 | B1 |
| ATOM | 1752 | CG | GLN | 113 | 27.902 | 32.494 | 8.868 | 1.00 | 27.79 | B1 |
| ATOM | 1753 | CD | GLN | 113 | 26.589 | 31.847 | 8.350 | 1.00 | 28.98 | B1 |
| ATOM | 1754 | OE1 | GLN | 113 | 25.654 | 32.552 | 8.027 | 1.00 | 30.45 | B1 |
| ATOM | 1755 | NE2 | GLN | 113 | 26.531 | 30.530 | 8.284 | 1.00 | 30.54 | B1 |
| ATOM | 1756 | C | GLN | 113 | 30.776 | 33.195 | 8.822 | 1.00 | 24.53 | B1 |
| ATOM | 1757 | O | GLN | 113 | 30.519 | 34.401 | 8.807 | 1.00 | 23.39 | B1 |
| ATOM | 1758 | N | VAL | 114 | 31.571 | 32.644 | 7.944 | 1.00 | 24.96 | B1 |
| ATOM | 1759 | CA | VAL | 114 | 32.177 | 33.414 | 6.905 | 1.00 | 24.84 | B1 |

FIG. 3A-31

| ATOM | 1760 | CB  | VAL | 114 | 33.652 | 33.625 | 7.242  | 1.00 | 24.26 | B1 |
| ---- | ---- | --- | --- | --- | ------ | ------ | ------ | ---- | ----- | -- |
| ATOM | 1761 | CG1 | VAL | 114 | 34.423 | 34.152 | 6.006  | 1.00 | 22.12 | B1 |
| ATOM | 1762 | CG2 | VAL | 114 | 33.757 | 34.606 | 8.465  | 1.00 | 21.27 | B1 |
| ATOM | 1763 | C   | VAL | 114 | 32.030 | 32.714 | 5.545  | 1.00 | 26.84 | B1 |
| ATOM | 1764 | O   | VAL | 114 | 32.043 | 31.466 | 5.430  | 1.00 | 28.29 | B1 |
| ATOM | 1765 | N   | VAL | 115 | 31.806 | 33.504 | 4.513  | 1.00 | 27.25 | B1 |
| ATOM | 1766 | CA  | VAL | 115 | 31.771 | 32.953 | 3.166  | 1.00 | 27.22 | B1 |
| ATOM | 1767 | CB  | VAL | 115 | 30.349 | 33.016 | 2.574  | 1.00 | 28.50 | B1 |
| ATOM | 1768 | CG1 | VAL | 115 | 30.344 | 32.570 | 1.101  | 1.00 | 28.02 | B1 |
| ATOM | 1769 | CG2 | VAL | 115 | 29.410 | 32.124 | 3.431  | 1.00 | 28.89 | B1 |
| ATOM | 1770 | C   | VAL | 115 | 32.738 | 33.848 | 2.383  | 1.00 | 27.02 | B1 |
| ATOM | 1771 | O   | VAL | 115 | 32.711 | 35.075 | 2.508  | 1.00 | 26.76 | B1 |
| ATOM | 1772 | N   | ILE | 116 | 33.677 | 33.218 | 1.686  | 1.00 | 27.52 | B1 |
| ATOM | 1773 | CA  | ILE | 116 | 34.609 | 33.904 | 0.814  | 1.00 | 26.35 | B1 |
| ATOM | 1774 | CB  | ILE | 116 | 36.075 | 33.488 | 1.072  | 1.00 | 26.60 | B1 |
| ATOM | 1775 | CG2 | ILE | 116 | 36.983 | 33.957 | -0.072 | 1.00 | 21.90 | B1 |
| ATOM | 1776 | CG1 | ILE | 116 | 36.563 | 34.055 | 2.443  | 1.00 | 25.67 | B1 |
| ATOM | 1777 | CD1 | ILE | 116 | 37.846 | 33.375 | 2.910  | 1.00 | 23.92 | B1 |
| ATOM | 1778 | C   | ILE | 116 | 34.168 | 33.440 | -0.585 | 1.00 | 27.98 | B1 |
| ATOM | 1779 | O   | ILE | 116 | 34.019 | 32.231 | -0.862 | 1.00 | 27.19 | B1 |
| ATOM | 1780 | N   | GLU | 117 | 33.948 | 34.402 | -1.468 | 1.00 | 29.29 | B1 |
| ATOM | 1781 | CA  | GLU | 117 | 33.483 | 34.060 | -2.793 | 1.00 | 32.80 | B1 |
| ATOM | 1782 | CB  | GLU | 117 | 31.938 | 33.962 | -2.782 | 1.00 | 33.28 | B1 |
| ATOM | 1783 | CG  | GLU | 117 | 31.267 | 35.318 | -2.609 | 1.00 | 35.65 | B1 |
| ATOM | 1784 | CD  | GLU | 117 | 29.723 | 35.291 | -2.613 | 1.00 | 39.26 | B1 |
| ATOM | 1785 | OE1 | GLU | 117 | 29.134 | 36.419 | -2.643 | 1.00 | 39.69 | B1 |
| ATOM | 1786 | OE2 | GLU | 117 | 29.100 | 34.172 | -2.569 | 1.00 | 40.90 | B1 |
| ATOM | 1787 | C   | GLU | 117 | 33.915 | 35.103 | -3.843 | 1.00 | 34.11 | B1 |
| ATOM | 1788 | O   | GLU | 117 | 34.548 | 36.141 | -3.535 | 1.00 | 32.11 | B1 |
| ATOM | 1789 | N   | ALA | 118 | 33.485 | 34.819 | -5.066 | 1.00 | 36.51 | B1 |
| ATOM | 1790 | CA  | ALA | 118 | 33.783 | 35.630 | -6.233 | 1.00 | 40.20 | B1 |
| ATOM | 1791 | CB  | ALA | 118 | 33.338 | 34.887 | -7.482 | 1.00 | 39.39 | B1 |
| ATOM | 1792 | C   | ALA | 118 | 33.186 | 37.007 | -6.271 | 1.00 | 42.95 | B1 |
| ATOM | 1793 | O   | ALA | 118 | 32.180 | 37.281 | -5.640 | 1.00 | 43.48 | B1 |
| ATOM | 1794 | N   | LEU | 119 | 33.826 | 37.852 | -7.070 | 1.00 | 47.53 | B1 |
| ATOM | 1795 | CA  | LEU | 119 | 33.378 | 39.215 | -7.384 | 1.00 | 49.83 | B1 |
| ATOM | 1796 | CB  | LEU | 119 | 31.859 | 39.214 | -7.654 | 1.00 | 49.43 | B1 |
| ATOM | 1797 | CG  | LEU | 119 | 30.968 | 40.454 | -7.784 | 1.00 | 50.65 | B1 |
| ATOM | 1798 | CD1 | LEU | 119 | 31.476 | 41.381 | -8.912 | 1.00 | 51.06 | B1 |
| ATOM | 1799 | CD2 | LEU | 119 | 29.527 | 39.980 | -8.097 | 1.00 | 50.28 | B1 |
| ATOM | 1800 | C   | LEU | 119 | 33.756 | 40.162 | -6.277 | 1.00 | 51.63 | B1 |
| ATOM | 1801 | OT1 | LEU | 119 | 34.683 | 39.763 | -5.528 | 1.00 | 51.82 | B1 |
| ATOM | 1802 | OT2 | LEU | 119 | 33.142 | 41.276 | -6.215 | 1.00 | 53.62 | B1 |
| ATOM | 1803 | CB  | TYR | 3   | 22.353 | 25.516 | -5.379 | 1.00 | 52.68 | C1 |
| ATOM | 1804 | CG  | TYR | 3   | 23.167 | 26.530 | -4.597 | 1.00 | 55.12 | C1 |
| ATOM | 1805 | CD1 | TYR | 3   | 23.777 | 27.607 | -5.230 | 1.00 | 56.73 | C1 |
| ATOM | 1806 | CE1 | TYR | 3   | 24.534 | 28.530 | -4.502 | 1.00 | 57.50 | C1 |
| ATOM | 1807 | CD2 | TYR | 3   | 23.326 | 26.402 | -3.210 | 1.00 | 56.45 | C1 |
| ATOM | 1808 | CE2 | TYR | 3   | 24.059 | 27.308 | -2.471 | 1.00 | 56.85 | C1 |
| ATOM | 1809 | CZ  | TYR | 3   | 24.663 | 28.372 | -3.111 | 1.00 | 57.87 | C1 |
| ATOM | 1810 | OH  | TYR | 3   | 25.343 | 29.305 | -2.339 | 1.00 | 58.87 | C1 |
| ATOM | 1811 | C   | TYR | 3   | 21.336 | 24.385 | -3.370 | 1.00 | 47.65 | C1 |
| ATOM | 1812 | O   | TYR | 3   | 20.156 | 24.720 | -3.457 | 1.00 | 48.16 | C1 |
| ATOM | 1813 | N   | TYR | 3   | 21.618 | 23.132 | -5.551 | 1.00 | 50.61 | C1 |
| ATOM | 1814 | CA  | TYR | 3   | 22.181 | 24.174 | -4.640 | 1.00 | 50.00 | C1 |
| ATOM | 1815 | N   | GLY | 4   | 21.970 | 24.178 | -2.205 | 1.00 | 43.78 | C1 |
| ATOM | 1816 | CA  | GLY | 4   | 21.319 | 24.320 | -0.920 | 1.00 | 38.85 | C1 |

FIG. 3A-32

| ATOM | 1817 | C | GLY | 4 | 22.345 | 24.450 | 0.208 | 1.00 | 36.34 | C1 |
| ATOM | 1818 | O | GLY | 4 | 23.551 | 24.279 | -0.011 | 1.00 | 34.94 | C1 |
| ATOM | 1819 | N | ILE | 5 | 21.879 | 24.771 | 1.417 | 1.00 | 32.79 | C1 |
| ATOM | 1820 | CA | ILE | 5 | 22.812 | 24.856 | 2.499 | 1.00 | 30.68 | C1 |
| ATOM | 1821 | CB | ILE | 5 | 23.048 | 26.321 | 2.948 | 1.00 | 30.63 | C1 |
| ATOM | 1822 | CG2 | ILE | 5 | 23.451 | 27.158 | 1.751 | 1.00 | 30.56 | C1 |
| ATOM | 1823 | CG1 | ILE | 5 | 21.785 | 26.866 | 3.658 | 1.00 | 28.48 | C1 |
| ATOM | 1824 | CD1 | ILE | 5 | 21.859 | 28.351 | 3.966 | 1.00 | 29.65 | C1 |
| ATOM | 1825 | C | ILE | 5 | 22.278 | 24.030 | 3.675 | 1.00 | 30.17 | C1 |
| ATOM | 1826 | O | ILE | 5 | 21.067 | 23.869 | 3.858 | 1.00 | 28.91 | C1 |
| ATOM | 1827 | N | GLY | 6 | 23.204 | 23.501 | 4.470 | 1.00 | 28.77 | C1 |
| ATOM | 1828 | CA | GLY | 6 | 22.815 | 22.720 | 5.628 | 1.00 | 27.45 | C1 |
| ATOM | 1829 | C | GLY | 6 | 23.619 | 23.128 | 6.849 | 1.00 | 27.03 | C1 |
| ATOM | 1830 | O | GLY | 6 | 24.801 | 23.444 | 6.791 | 1.00 | 26.98 | C1 |
| ATOM | 1831 | N | LEU | 7 | 22.948 | 23.131 | 7.972 | 1.00 | 27.09 | C1 |
| ATOM | 1832 | CA | LEU | 7 | 23.572 | 23.483 | 9.217 | 1.00 | 27.34 | C1 |
| ATOM | 1833 | CB | LEU | 7 | 23.079 | 24.868 | 9.689 | 1.00 | 26.42 | C1 |
| ATOM | 1834 | CG | LEU | 7 | 23.524 | 25.173 | 11.136 | 1:00 | 25.33 | C1 |
| ATOM | 1835 | CD1 | LEU | 7 | 25.069 | 25.163 | 11.156 | 1.00 | 24.79 | C1 |
| ATOM | 1836 | CD2 | LEU | 7 | 22.967 | 26.502 | 11.651 | 1.00 | 23.18 | C1 |
| ATOM | 1837 | C | LEU | 7 | 23.155 | 22.464 | 10.256 | 1.00 | 28.20 | C1 |
| ATOM | 1838 | O | LEU | 7 | 21.971 | 22.130 | 10.349 | 1.00 | 27.84 | C1 |
| ATOM | 1839 | N | ASP | 8 | 24.102 | 21.939 | 11.023 | 1.00 | 29.28 | C1 |
| ATOM | 1840 | CA | ASP | 8 | 23.706 | 21.056 | 12.115 | 1.00 | 30.50 | C1 |
| ATOM | 1841 | CB | ASP | 8 | 23.763 | 19.571 | 11.768 | 1.00 | 31.66 | C1 |
| ATOM | 1842 | CG | ASP | 8 | 23.427 | 18.685 | 13.011 | 1.00 | 35.63 | C1 |
| ATOM | 1843 | OD1 | ASP | 8 | 24.372 | 18.151 | 13.645 | 1.00 | 37.39 | C1 |
| ATOM | 1844 | OD2 | ASP | 8 | 22.219 | 18.555 | 13.405 | 1.00 | 36.31 | C1 |
| ATOM | 1845 | C | ASP | 8 | 24.585 | 21.300 | 13.323 | 1.00 | 30.33 | C1 |
| ATOM | 1846 | O | ASP | 8 | 25.762 | 21.585 | 13.166 | 1.00 | 30.47 | C1 |
| ATOM | 1847 | N | ILE | 9 | 23.993 | 21.205 | 14.511 | 1.00 | 31.74 | C1 |
| ATOM | 1848 | CA | ILE | 9 | 24.678 | 21.363 | 15.784 | 1.00 | 32.84 | C1 |
| ATOM | 1849 | CB | ILE | 9 | 24.252 | 22.658 | 16.511 | 1.00 | 32.34 | C1 |
| ATOM | 1850 | CG2 | ILE | 9 | 25.067 | 22.797 | 17.803 | 1.00 | 30.24 | C1 |
| ATOM | 1851 | CG1 | ILE | 9 | 24.518 | 23.893 | 15.641 | 1.00 | 33.38 | C1 |
| ATOM | 1852 | CD1 | ILE | 9 | 24.043 | 25.227 | 16.283 | 1.00 | 33.77 | C1 |
| ATOM | 1853 | C | ILE | 9 | 24.296 | 20.145 | 16.673 | 1.00 | 34.79 | C1 |
| ATOM | 1854 | O | ILE | 9 | 23.122 | 19.971 | 17.004 | 1.00 | 35.36 | C1 |
| ATOM | 1855 | N | THR | 10 | 25.269 | 19.328 | 17.073 | 1.00 | 35.74 | C1 |
| ATOM | 1856 | CA | THR | 10 | 24.994 | 18.137 | 17.882 | 1.00 | 37.27 | C1 |
| ATOM | 1857 | CB | THR | 10 | 25.472 | 16.876 | 17.144 | 1.00 | 37.49 | C1 |
| ATOM | 1858 | OG1 | THR | 10 | 24.647 | 16.636 | 15.995 | 1.00 | 38.81 | C1 |
| ATOM | 1859 | CG2 | THR | 10 | 25.451 | 15.678 | 18.065 | 1.00 | 38.55 | C1 |
| ATOM | 1860 | C | THR | 10 | 25.681 | 18.138 | 19.248 | 1.00 | 38.47 | C1 |
| ATOM | 1861 | O | THR | 10 | 26.890 | 18.376 | 19.350 | 1.00 | 38.09 | C1 |
| ATOM | 1862 | N | GLU | 11 | 24.937 | 17.808 | 20.297 | 1.00 | 40.65 | C1 |
| ATOM | 1863 | CA | GLU | 11 | 25.517 | 17.796 | 21.641 | 1.00 | 42.07 | C1 |
| ATOM | 1864 | CB | GLU | 11 | 24.445 | 17.698 | 22.704 | 1.00 | 44.46 | C1 |
| ATOM | 1865 | CG | GLU | 11 | 23.399 | 18.780 | 22.608 | 1.00 | 47.87 | C1 |
| ATOM | 1866 | CD | GLU | 11 | 22.055 | 18.287 | 22.052 | 1.00 | 50.81 | C1 |
| ATOM | 1867 | OE1 | GLU | 11 | 21.992 | 17.793 | 20.875 | 1.00 | 52.69 | C1 |
| ATOM | 1868 | OE2 | GLU | 11 | 21.042 | 18.409 | 22.790 | 1.00 | 52.15 | C1 |
| ATOM | 1869 | C | GLU | 11 | 26.487 | 16.655 | 21.798 | 1.00 | 42.23 | C1 |
| ATOM | 1870 | O | GLU | 11 | 26.160 | 15.496 | 21.547 | 1.00 | 41.87 | C1 |
| ATOM | 1871 | N | LEU | 12 | 27.703 | 16.998 | 22.197 | 1.00 | 43.04 | C1 |
| ATOM | 1872 | CA | LEU | 12 | 28.755 | 16.015 | 22.402 | 1.00 | 44.92 | C1 |
| ATOM | 1873 | CB | LEU | 12 | 30.050 | 16.762 | 22.759 | 1.00 | 45.32 | C1 |

FIG. 3A-33

```
ATOM   1874  CG   LEU  12    31.373  16.017  22.645  1.00  45.47    C1
ATOM   1875  CD1  LEU  12    31.521  15.493  21.223  1.00  45.90    C1
ATOM   1876  CD2  LEU  12    32.531  16.952  22.988  1.00  45.63    C1
ATOM   1877  C    LEU  12    28.445  14.905  23.462  1.00  45.67    C1
ATOM   1878  O    LEU  12    28.808  13.750  23.266  1.00  46.27    C1
ATOM   1879  N    LYS  13    27.804  15.257  24.570  1.00  46.36    C1
ATOM   1880  CA   LYS  13    27.478  14.283  25.614  1.00  48.63    C1
ATOM   1881  CB   LYS  13    26.628  14.935  26.733  1.00  48.16    C1
ATOM   1882  CG   LYS  13    25.200  15.282  26.310  1.00  50.76    C1
ATOM   1883  CD   LYS  13    24.417  16.187  27.292  1.00  52.14    C1
ATOM   1884  CE   LYS  13    23.891  15.429  28.541  1.00  53.30    C1
ATOM   1885  NZ   LYS  13    22.991  16.264  29.447  1.00  53.41    C1
ATOM   1886  C    LYS  13    26.732  13.083  25.015  1.00  49.49    C1
ATOM   1887  O    LYS  13    27.108  11.942  25.199  1.00  49.68    C1
ATOM   1888  N    ARG  14    25.686  13.359  24.265  1.00  50.80    C1
ATOM   1889  CA   ARG  14    24.892  12.318  23.663  1.00  52.14    C1
ATOM   1890  CB   ARG  14    23.783  12.965  22.866  1.00  51.84    C1
ATOM   1891  CG   ARG  14    23.042  13.982  23.692  1.00  51.93    C1
ATOM   1892  CD   ARG  14    22.047  14.703  22.828  1.00  53.26    C1
ATOM   1893  NE   ARG  14    21.053  13.803  22.252  1.00  53.51    C1
ATOM   1894  CZ   ARG  14    20.340  14.101  21.171  1.00  54.68    C1
ATOM   1895  NH1  ARG  14    20.523  15.261  20.563  1.00  54.94    C1
ATOM   1896  NH2  ARG  14    19.444  13.245  20.687  1.00  55.74    C1
ATOM   1897  C    ARG  14    25.680  11.361  22.795  1.00  53.45    C1
ATOM   1898  O    ARG  14    25.363  10.183  22.741  1.00  54.19    C1
ATOM   1899  N    ILE  15    26.717  11.843  22.128  1.00  54.83    C1
ATOM   1900  CA   ILE  15    27.474  10.964  21.267  1.00  57.01    C1
ATOM   1901  CB   ILE  15    28.057  11.749  20.059  1.00  56.55    C1
ATOM   1902  CG2  ILE  15    29.188  10.976  19.391  1.00  56.26    C1
ATOM   1903  CG1  ILE  15    26.929  11.991  19.053  1.00  56.70    C1
ATOM   1904  CD1  ILE  15    27.329  12.663  17.774  1.00  56.92    C1
ATOM   1905  C    ILE  15    28.547  10.195  22.020  1.00  58.74    C1
ATOM   1906  O    ILE  15    28.958   9.114  21.606  1.00  59.22    C1
ATOM   1907  N    ALA  16    28.994  10.740  23.138  1.00  60.96    C1
ATOM   1908  CA   ALA  16    30.002  10.064  23.939  1.00  63.12    C1
ATOM   1909  CB   ALA  16    30.797  11.077  24.740  1.00  63.01    C1
ATOM   1910  C    ALA  16    29.254   9.132  24.881  1.00  64.75    C1
ATOM   1911  O    ALA  16    29.784   8.098  25.285  1.00  65.27    C1
ATOM   1912  N    SER  17    28.017   9.519  25.208  1.00  66.19    C1
ATOM   1913  CA   SER  17    27.134   8.793  26.118  1.00  67.59    C1
ATOM   1914  CB   SER  17    25.826   9.574  26.347  1.00  67.92    C1
ATOM   1915  OG   SER  17    26.016  10.786  27.054  1.00  67.73    C1
ATOM   1916  C    SER  17    26.757   7.405  25.628  1.00  68.66    C1
ATOM   1917  O    SER  17    26.132   6.640  26.376  1.00  68.47    C1
ATOM   1918  N    MET  18    27.093   7.094  24.375  1.00  69.63    C1
ATOM   1919  CA   MET  18    26.786   5.777  23.798  1.00  70.99    C1
ATOM   1920  CB   MET  18    26.851   5.853  22.277  1.00  71.06    C1
ATOM   1921  CG   MET  18    25.973   6.933  21.711  1.00  71.97    C1
ATOM   1922  SD   MET  18    26.030   6.980  19.905  1.00  73.05    C1
ATOM   1923  CE   MET  18    24.315   6.428  19.528  1.00  73.21    C1
ATOM   1924  C    MET  18    27.749   4.697  24.321  1.00  71.40    C1
ATOM   1925  O    MET  18    28.673   4.264  23.633  1.00  71.07    C1
ATOM   1926  N    ALA  19    27.506   4.270  25.551  1.00  72.22    C1
ATOM   1927  CA   ALA  19    28.341   3.281  26.219  1.00  73.14    C1
ATOM   1928  CB   ALA  19    27.573   2.671  27.415  1.00  73.41    C1
ATOM   1929  C    ALA  19    28.821   2.189  25.267  1.00  73.29    C1
ATOM   1930  O    ALA  19    29.755   2.402  24.496  1.00  73.21    C1
```

FIG. 3A-34

| ATOM | 1931 | N | GLY | 20 | 28.187 | 1.022 | 25.339 | 1.00 | 73.39 | C1 |
| ATOM | 1932 | CA | GLY | 20 | 28.550 | -0.088 | 24.468 | 1.00 | 73.28 | C1 |
| ATOM | 1933 | C | GLY | 20 | 27.835 | 0.042 | 23.133 | 1.00 | 72.78 | C1 |
| ATOM | 1934 | O | GLY | 20 | 28.124 | -0.687 | 22.172 | 1.00 | 73.18 | C1 |
| ATOM | 1935 | N | ALA | 21 | 26.909 | 0.994 | 23.074 | 1.00 | 72.11 | C1 |
| ATOM | 1936 | CA | ALA | 21 | 26.152 | 1.257 | 21.864 | 1.00 | 71.43 | C1 |
| ATOM | 1937 | CB | ALA | 21 | 24.775 | 1.796 | 22.230 | 1.00 | 71.48 | C1 |
| ATOM | 1938 | C | ALA | 21 | 26.869 | 2.234 | 20.915 | 1.00 | 70.86 | C1 |
| ATOM | 1939 | O | ALA | 21 | 26.378 | 2.496 | 19.814 | 1.00 | 71.29 | C1 |
| ATOM | 1940 | N | GLN | 22 | 28.026 | 2.767 | 21.310 | 1.00 | 69.99 | C1 |
| ATOM | 1941 | CA | GLN | 22 | 28.721 | 3.723 | 20.435 | 1.00 | 68.84 | C1 |
| ATOM | 1942 | CB | GLN | 22 | 29.765 | 4.560 | 21.216 | 1.00 | 69.02 | C1 |
| ATOM | 1943 | CG | GLN | 22 | 30.326 | 5.758 | 20.410 | 1.00 | 69.19 | C1 |
| ATOM | 1944 | CD | GLN | 22 | 31.497 | 6.497 | 21.087 | 1.00 | 69.34 | C1 |
| ATOM | 1945 | OE1 | GLN | 22 | 31.310 | 7.185 | 22.095 | 1.00 | 69.45 | C1 |
| ATOM | 1946 | NE2 | GLN | 22 | 32.709 | 6.356 | 20.521 | 1.00 | 68.39 | C1 |
| ATOM | 1947 | C | GLN | 22 | 29.391 | 3.081 | 19.218 | 1.00 | 67.50 | C1 |
| ATOM | 1948 | O | GLN | 22 | 29.385 | 3.660 | 18.117 | 1.00 | 67.29 | C1 |
| ATOM | 1949 | N | LYS | 23 | 29.960 | 1.887 | 19.405 | 1.00 | 66.01 | C1 |
| ATOM | 1950 | CA | LYS | 23 | 30.647 | 1.197 | 18.306 | 1.00 | 63.66 | C1 |
| ATOM | 1951 | CB | LYS | 23 | 31.376 | -0.048 | 18.820 | 1.00 | 63.88 | C1 |
| ATOM | 1952 | C | LYS | 23 | 29.697 | 0.828 | 17.178 | 1.00 | 61.94 | C1 |
| ATOM | 1953 | O | LYS | 23 | 30.024 | 1.040 | 16.009 | 1.00 | 61.92 | C1 |
| ATOM | 1954 | N | ALA | 24 | 28.531 | 0.276 | 17.501 | 1.00 | 59.42 | C1 |
| ATOM | 1955 | CA | ALA | 24 | 27.608 | -0.064 | 16.433 | 1.00 | 57.41 | C1 |
| ATOM | 1956 | CB | ALA | 24 | 26.401 | -0.809 | 16.978 | 1.00 | 58.14 | C1 |
| ATOM | 1957 | C | ALA | 24 | 27.188 | 1.243 | 15.774 | 1.00 | 55.96 | C1 |
| ATOM | 1958 | O | ALA | 24 | 26.959 | 1.309 | 14.560 | 1.00 | 55.56 | C1 |
| ATOM | 1959 | N | PHE | 25 | 27.096 | 2.293 | 16.585 | 1.00 | 54.55 | C1 |
| ATOM | 1960 | CA | PHE | 25 | 26.742 | 3.606 | 16.069 | 1.00 | 53.36 | C1 |
| ATOM | 1961 | CB | PHE | 25 | 26.589 | 4.605 | 17.206 | 1.00 | 54.38 | C1 |
| ATOM | 1962 | CG | PHE | 25 | 26.245 | 6.010 | 16.750 | 1.00 | 54.54 | C1 |
| ATOM | 1963 | CD1 | PHE | 25 | 25.001 | 6.302 | 16.224 | 1.00 | 53.95 | C1 |
| ATOM | 1964 | CD2 | PHE | 25 | 27.175 | 7.044 | 16.869 | 1.00 | 54.96 | C1 |
| ATOM | 1965 | CE1 | PHE | 25 | 24.690 | 7.594 | 15.826 | 1.00 | 54.26 | C1 |
| ATOM | 1966 | CE2 | PHE | 25 | 26.863 | 8.348 | 16.468 | 1.00 | 54.29 | C1 |
| ATOM | 1967 | CZ | PHE | 25 | 25.622 | 8.616 | 15.950 | 1.00 | 54.55 | C1 |
| ATOM | 1968 | C | PHE | 25 | 27.793 | 4.127 | 15.089 | 1.00 | 52.32 | C1 |
| ATOM | 1969 | O | PHE | 25 | 27.439 | 4.764 | 14.115 | 1.00 | 51.87 | C1 |
| ATOM | 1970 | N | ALA | 26 | 29.077 | 3.876 | 15.348 | 1.00 | 50.87 | C1 |
| ATOM | 1971 | CA | ALA | 26 | 30.116 | 4.333 | 14.436 | 1.00 | 49.99 | C1 |
| ATOM | 1972 | CB | ALA | 26 | 31.478 | 4.112 | 15.040 | 1.00 | 50.04 | C1 |
| ATOM | 1973 | C | ALA | 26 | 29.997 | 3.573 | 13.123 | 1.00 | 49.93 | C1 |
| ATOM | 1974 | O | ALA | 26 | 30.188 | 4.127 | 12.033 | 1.00 | 49.20 | C1 |
| ATOM | 1975 | N | GLU | 27 | 29.649 | 2.295 | 13.234 | 1.00 | 50.16 | C1 |
| ATOM | 1976 | CA | GLU | 27 | 29.496 | 1.448 | 12.070 | 1.00 | 50.47 | C1 |
| ATOM | 1977 | CB | GLU | 27 | 29.173 | 0.024 | 12.510 | 1.00 | 52.03 | C1 |
| ATOM | 1978 | CG | GLU | 27 | 30.367 | -0.815 | 12.987 | 1.00 | 54.33 | C1 |
| ATOM | 1979 | CD | GLU | 27 | 29.916 | -2.070 | 13.746 | 1.00 | 55.34 | C1 |
| ATOM | 1980 | OE1 | GLU | 27 | 28.944 | -2.729 | 13.292 | 1.00 | 56.02 | C1 |
| ATOM | 1981 | OE2 | GLU | 27 | 30.533 | -2.398 | 14.787 | 1.00 | 55.46 | C1 |
| ATOM | 1982 | C | GLU | 27 | 28.419 | 1.931 | 11.093 | 1.00 | 49.87 | C1 |
| ATOM | 1983 | O | GLU | 27 | 28.528 | 1.710 | 9.895 | 1.00 | 49.63 | C1 |
| ATOM | 1984 | N | ARG | 28 | 27.360 | 2.567 | 11.569 | 1.00 | 49.12 | C1 |
| ATOM | 1985 | CA | ARG | 28 | 26.371 | 2.984 | 10.596 | 1.00 | 49.19 | C1 |
| ATOM | 1986 | CB | ARG | 28 | 24.942 | 2.738 | 11.106 | 1.00 | 51.09 | C1 |
| ATOM | 1987 | CG | ARG | 28 | 24.450 | 3.590 | 12.237 | 1.00 | 54.01 | C1 |

FIG. 3A-35

| ATOM | 1988 | CD | ARG | 28 | 23.036 | 3.114 | 12.653 | 1.00 | 55.93 | C1 |
| ATOM | 1989 | NE | ARG | 28 | 22.209 | 2.863 | 11.476 | 1.00 | 57.95 | C1 |
| ATOM | 1990 | CZ | ARG | 28 | 20.924 | 2.507 | 11.517 | 1.00 | 58.79 | C1 |
| ATOM | 1991 | NH1 | ARG | 28 | 20.313 | 2.352 | 12.684 | 1.00 | 59.69 | C1 |
| ATOM | 1992 | NH2 | ARG | 28 | 20.243 | 2.340 | 10.389 | 1.00 | 58.73 | C1 |
| ATOM | 1993 | C | ARG | 28 | 26.553 | 4.409 | 10.124 | 1.00 | 48.21 | C1 |
| ATOM | 1994 | O | ARG | 28 | 26.098 | 4.762 | 9.053 | 1.00 | 47.43 | C1 |
| ATOM | 1995 | N | ILE | 29 | 27.272 | 5.201 | 10.912 | 1.00 | 47.42 | C1 |
| ATOM | 1996 | CA | ILE | 29 | 27.538 | 6.605 | 10.614 | 1.00 | 46.88 | C1 |
| ATOM | 1997 | CB | ILE | 29 | 27.707 | 7.408 | 11.976 | 1.00 | 47.32 | C1 |
| ATOM | 1998 | CG2 | ILE | 29 | 28.331 | 8.779 | 11.771 | 1.00 | 47.45 | C1 |
| ATOM | 1999 | CG1 | ILE | 29 | 26.334 | 7.637 | 12.586 | 1.00 | 48.41 | C1 |
| ATOM | 2000 | CD1 | ILE | 29 | 25.391 | 8.300 | 11.593 | 1.00 | 46.71 | C1 |
| ATOM | 2001 | C | ILE | 29 | 28.777 | 6.806 | 9.728 | 1.00 | 46.01 | C1 |
| ATOM | 2002 | O | ILE | 29 | 28.777 | 7.696 | 8.896 | 1.00 | 45.66 | C1 |
| ATOM | 2003 | N | LEU | 30 | 29.803 | 5.956 | 9.893 | 1.00 | 45.16 | C1 |
| ATOM | 2004 | CA | LEU | 30 | 31.074 | 6.085 | 9.173 | 1.00 | 44.13 | C1 |
| ATOM | 2005 | CB | LEU | 30 | 32.230 | 5.891 | 10.149 | 1.00 | 42.42 | C1 |
| ATOM | 2006 | CG | LEU | 30 | 32.220 | 6.792 | 11.380 | 1.00 | 40.57 | C1 |
| ATOM | 2007 | CD1 | LEU | 30 | 33.481 | 6.580 | 12.183 | 1.00 | 39.86 | C1 |
| ATOM | 2008 | CD2 | LEU | 30 | 32.155 | 8.253 | 10.937 | 1.00 | 40.97 | C1 |
| ATOM | 2009 | C | LEU | 30 | 31.314 | 5.199 | 7.983 | 1.00 | 44.93 | C1 |
| ATOM | 2010 | O | LEU | 30 | 30.702 | 4.163 | 7.832 | 1.00 | 46.00 | C1 |
| ATOM | 2011 | N | THR | 31 | 32.186 | 5.612 | 7.088 | 1.00 | 45.98 | C1 |
| ATOM | 2012 | CA | THR | 31 | 32.469 | 4.743 | 5.961 | 1.00 | 47.55 | C1 |
| ATOM | 2013 | CB | THR | 31 | 32.961 | 5.509 | 4.736 | 1.00 | 46.23 | C1 |
| ATOM | 2014 | OG1 | THR | 31 | 34.189 | 6.165 | 5.066 | 1.00 | 46.01 | C1 |
| ATOM | 2015 | CG2 | THR | 31 | 31.927 | 6.503 | 4.262 | 1.00 | 45.18 | C1 |
| ATOM | 2016 | C | THR | 31 | 33.632 | 3.869 | 6.463 | 1.00 | 49.42 | C1 |
| ATOM | 2017 | O | THR | 31 | 34.085 | 4.033 | 7.610 | 1.00 | 50.48 | C1 |
| ATOM | 2018 | N | ALA | 32 | 34.123 | 2.963 | 5.616 | 1.00 | 50.64 | C1 |
| ATOM | 2019 | CA | ALA | 32 | 35.253 | 2.106 | 5.991 | 1.00 | 51.68 | C1 |
| ATOM | 2020 | CB | ALA | 32 | 35.528 | 1.047 | 4.876 | 1.00 | 52.35 | C1 |
| ATOM | 2021 | C | ALA | 32 | 36.491 | 2.965 | 6.219 | 1.00 | 52.19 | C1 |
| ATOM | 2022 | O | ALA | 32 | 37.197 | 2.814 | 7.219 | 1.00 | 52.47 | C1 |
| ATOM | 2023 | N | SER | 33 | 36.759 | 3.875 | 5.290 | 1.00 | 52.78 | C1 |
| ATOM | 2024 | CA | SER | 33 | 37.923 | 4.754 | 5.443 | 1.00 | 53.37 | C1 |
| ATOM | 2025 | CB | SER | 33 | 38.091 | 5.616 | 4.192 | 1.00 | 54.79 | C1 |
| ATOM | 2026 | OG | SER | 33 | 39.472 | 5.820 | 3.917 | 1.00 | 57.32 | C1 |
| ATOM | 2027 | C | SER | 33 | 37.852 | 5.661 | 6.688 | 1.00 | 52.95 | C1 |
| ATOM | 2028 | O | SER | 33 | 38.883 | 6.095 | 7.211 | 1.00 | 53.00 | C1 |
| ATOM | 2029 | N | GLU | 34 | 36.635 | 5.958 | 7.152 | 1.00 | 52.41 | C1 |
| ATOM | 2030 | CA | GLU | 34 | 36.455 | 6.784 | 8.347 | 1.00 | 52.05 | C1 |
| ATOM | 2031 | CB | GLU | 34 | 35.114 | 7.540 | 8.280 | 1.00 | 51.02 | C1 |
| ATOM | 2032 | CG | GLU | 34 | 35.061 | 8.615 | 7.156 | 1.00 | 49.60 | C1 |
| ATOM | 2033 | CD | GLU | 34 | 33.753 | 9.410 | 7.130 | 1.00 | 48.95 | C1 |
| ATOM | 2034 | OE1 | GLU | 34 | 32.684 | 8.769 | 7.085 | 1.00 | 47.99 | C1 |
| ATOM | 2035 | OE2 | GLU | 34 | 33.787 | 10.666 | 7.156 | 1.00 | 47.77 | C1 |
| ATOM | 2036 | C | GLU | 34 | 36.537 | 5.909 | 9.618 | 1.00 | 52.70 | C1 |
| ATOM | 2037 | O | GLU | 34 | 36.952 | 6.377 | 10.666 | 1.00 | 52.35 | C1 |
| ATOM | 2038 | N | LEU | 35 | 36.139 | 4.639 | 9.531 | 1.00 | 53.84 | C1 |
| ATOM | 2039 | CA | LEU | 35 | 36.242 | 3.754 | 10.695 | 1.00 | 54.78 | C1 |
| ATOM | 2040 | CB | LEU | 35 | 35.546 | 2.420 | 10.432 | 1.00 | 55.12 | C1 |
| ATOM | 2041 | CG | LEU | 35 | 34.076 | 2.277 | 10.820 | 1.00 | 55.35 | C1 |
| ATOM | 2042 | CD1 | LEU | 35 | 33.600 | 0.893 | 10.406 | 1.00 | 55.25 | C1 |
| ATOM | 2043 | CD2 | LEU | 35 | 33.898 | 2.501 | 12.333 | 1.00 | 54.93 | C1 |
| ATOM | 2044 | C | LEU | 35 | 37.705 | 3.480 | 11.030 | 1.00 | 55.08 | C1 |

FIG. 3A-36

| ATOM | 2045 | O   | LEU | 35 | 38.115 | 3.573  | 12.191 | 1.00 | 55.65 | C1 |
|------|------|-----|-----|----|--------|--------|--------|------|-------|----|
| ATOM | 2046 | N   | ASP | 36 | 38.485 | 3.130  | 10.009 | 1.00 | 55.26 | C1 |
| ATOM | 2047 | CA  | ASP | 36 | 39.904 | 2.848  | 10.203 | 1.00 | 55.75 | C1 |
| ATOM | 2048 | CB  | ASP | 36 | 40.635 | 2.737  | 8.850  | 1.00 | 56.59 | C1 |
| ATOM | 2049 | CG  | ASP | 36 | 40.120 | 1.578  | 7.996  | 1.00 | 57.54 | C1 |
| ATOM | 2050 | OD1 | ASP | 36 | 39.855 | 0.505  | 8.576  | 1.00 | 57.49 | C1 |
| ATOM | 2051 | OD2 | ASP | 36 | 39.985 | 1.732  | 6.753  | 1.00 | 58.09 | C1 |
| ATOM | 2052 | C   | ASP | 36 | 40.478 | 3.993  | 11.016 | 1.00 | 55.72 | C1 |
| ATOM | 2053 | O   | ASP | 36 | 41.169 | 3.788  | 11.997 | 1.00 | 56.02 | C1 |
| ATOM | 2054 | N   | GLN | 37 | 40.166 | 5.210  | 10.600 | 1.00 | 55.73 | C1 |
| ATOM | 2055 | CA  | GLN | 37 | 40.619 | 6.405  | 11.283 | 1.00 | 55.71 | C1 |
| ATOM | 2056 | CB  | GLN | 37 | 40.149 | 7.628  | 10.521 | 1.00 | 54.93 | C1 |
| ATOM | 2057 | CG  | GLN | 37 | 41.213 | 8.381  | 9.795  | 1.00 | 54.35 | C1 |
| ATOM | 2058 | CD  | GLN | 37 | 40.631 | 9.593  | 9.112  | 1.00 | 54.07 | C1 |
| ATOM | 2059 | OE1 | GLN | 37 | 39.960 | 9.478  | 8.075  | 1.00 | 52.71 | C1 |
| ATOM | 2060 | NE2 | GLN | 37 | 40.858 | 10.764 | 9.705  | 1.00 | 52.34 | C1 |
| ATOM | 2061 | C   | GLN | 37 | 40.101 | 6.530  | 12.708 | 1.00 | 56.36 | C1 |
| ATOM | 2062 | O   | GLN | 37 | 40.839 | 6.929  | 13.607 | 1.00 | 56.00 | C1 |
| ATOM | 2063 | N   | TYR | 38 | 38.821 | 6.219  | 12.909 | 1.00 | 57.07 | C1 |
| ATOM | 2064 | CA  | TYR | 38 | 38.219 | 6.361  | 14.237 | 1.00 | 58.12 | C1 |
| ATOM | 2065 | CB  | TYR | 38 | 36.686 | 6.298  | 14.132 | 1.00 | 56.44 | C1 |
| ATOM | 2066 | CG  | TYR | 38 | 35.946 | 5.851  | 15.376 | 1.00 | 55.07 | C1 |
| ATOM | 2067 | CD1 | TYR | 38 | 35.634 | 4.492  | 15.577 | 1.00 | 54.58 | C1 |
| ATOM | 2068 | CE1 | TYR | 38 | 34.888 | 4.081  | 16.665 | 1.00 | 54.40 | C1 |
| ATOM | 2069 | CD2 | TYR | 38 | 35.495 | 6.775  | 16.309 | 1.00 | 54.17 | C1 |
| ATOM | 2070 | CE2 | TYR | 38 | 34.743 | 6.383  | 17.403 | 1.00 | 54.20 | C1 |
| ATOM | 2071 | CZ  | TYR | 38 | 34.434 | 5.031  | 17.579 | 1.00 | 55.06 | C1 |
| ATOM | 2072 | OH  | TYR | 38 | 33.624 | 4.643  | 18.637 | 1.00 | 54.94 | C1 |
| ATOM | 2073 | C   | TYR | 38 | 38.746 | 5.362  | 15.259 | 1.00 | 59.63 | C1 |
| ATOM | 2074 | O   | TYR | 38 | 38.891 | 5.689  | 16.444 | 1.00 | 59.42 | C1 |
| ATOM | 2075 | N   | TYR | 39 | 39.033 | 4.147  | 14.814 | 1.00 | 61.46 | C1 |
| ATOM | 2076 | CA  | TYR | 39 | 39.556 | 3.170  | 15.746 | 1.00 | 63.73 | C1 |
| ATOM | 2077 | CB  | TYR | 39 | 39.643 | 1.793  | 15.071 | 1.00 | 64.25 | C1 |
| ATOM | 2078 | CG  | TYR | 39 | 38.272 | 1.181  | 14.835 | 1.00 | 64.53 | C1 |
| ATOM | 2079 | CD1 | TYR | 39 | 37.344 | 1.080  | 15.881 | 1.00 | 64.91 | C1 |
| ATOM | 2080 | CE1 | TYR | 39 | 36.072 | 0.506  | 15.680 | 1.00 | 65.28 | C1 |
| ATOM | 2081 | CD2 | TYR | 39 | 37.905 | 0.696  | 13.577 | 1.00 | 64.93 | C1 |
| ATOM | 2082 | CE2 | TYR | 39 | 36.642 | 0.121  | 13.361 | 1.00 | 65.37 | C1 |
| ATOM | 2083 | CZ  | TYR | 39 | 35.729 | 0.030  | 14.418 | 1.00 | 65.70 | C1 |
| ATOM | 2084 | OH  | TYR | 39 | 34.476 | -0.536 | 14.209 | 1.00 | 66.41 | C1 |
| ATOM | 2085 | C   | TYR | 39 | 40.921 | 3.650  | 16.250 | 1.00 | 64.86 | C1 |
| ATOM | 2086 | O   | TYR | 39 | 41.182 | 3.658  | 17.456 | 1.00 | 65.10 | C1 |
| ATOM | 2087 | N   | GLU | 40 | 41.762 | 4.121  | 15.335 | 1.00 | 65.88 | C1 |
| ATOM | 2088 | CA  | GLU | 40 | 43.089 | 4.588  | 15.700 | 1.00 | 66.96 | C1 |
| ATOM | 2089 | CB  | GLU | 40 | 43.841 | 5.007  | 14.437 | 1.00 | 68.15 | C1 |
| ATOM | 2090 | CG  | GLU | 40 | 43.834 | 3.971  | 13.306 | 1.00 | 70.60 | C1 |
| ATOM | 2091 | CD  | GLU | 40 | 44.773 | 2.804  | 13.551 | 1.00 | 71.61 | C1 |
| ATOM | 2092 | OE1 | GLU | 40 | 45.990 | 3.062  | 13.726 | 1.00 | 72.41 | C1 |
| ATOM | 2093 | OE2 | GLU | 40 | 44.300 | 1.640  | 13.560 | 1.00 | 72.06 | C1 |
| ATOM | 2094 | C   | GLU | 40 | 43.169 | 5.739  | 16.718 | 1.00 | 67.18 | C1 |
| ATOM | 2095 | O   | GLU | 40 | 44.278 | 6.191  | 17.025 | 1.00 | 67.28 | C1 |
| ATOM | 2096 | N   | LEU | 41 | 42.041 | 6.217  | 17.254 | 1.00 | 67.17 | C1 |
| ATOM | 2097 | CA  | LEU | 41 | 42.099 | 7.348  | 18.199 | 1.00 | 66.97 | C1 |
| ATOM | 2098 | CB  | LEU | 41 | 41.165 | 8.493  | 17.752 | 1.00 | 68.22 | C1 |
| ATOM | 2099 | CG  | LEU | 41 | 40.458 | 8.591  | 16.389 | 1.00 | 69.08 | C1 |
| ATOM | 2100 | CD1 | LEU | 41 | 39.582 | 9.844  | 16.385 | 1.00 | 69.66 | C1 |
| ATOM | 2101 | CD2 | LEU | 41 | 41.463 | 8.646  | 15.253 | 1.00 | 68.80 | C1 |

FIG. 3A-37

| ATOM | 2102 | C   | LEU | 41 | 41.815 | 7.099   | 19.673 | 1.00 | 66.10 | C1 |
| ---- | ---- | --- | --- | -- | ------ | ------- | ------ | ---- | ----- | -- |
| ATOM | 2103 | O   | LEU | 41 | 41.316 | 6.049   | 20.056 | 1.00 | 65.84 | C1 |
| ATOM | 2104 | N   | SER | 42 | 42.121 | 8.118   | 20.481 | 1.00 | 65.38 | C1 |
| ATOM | 2105 | CA  | SER | 42 | 41.900 | 8.119   | 21.927 | 1.00 | 64.65 | C1 |
| ATOM | 2106 | CB  | SER | 42 | 42.509 | 9.379   | 22.550 | 1.00 | 65.06 | C1 |
| ATOM | 2107 | OG  | SER | 42 | 41.588 | 10.451  | 22.500 | 1.00 | 65.28 | C1 |
| ATOM | 2108 | C   | SER | 42 | 40.395 | 8.120   | 22.188 | 1.00 | 64.02 | C1 |
| ATOM | 2109 | O   | SER | 42 | 39.614 | 8.129   | 21.247 | 1.00 | 64.03 | C1 |
| ATOM | 2110 | N   | ALA | 43 | 39.982 | 8.135   | 23.453 | 1.00 | 63.26 | C1 |
| ATOM | 2111 | CA  | ALA | 43 | 38.548 | 8.115   | 23.771 | 1.00 | 62.62 | C1 |
| ATOM | 2112 | CB  | ALA | 43 | 38.320 | 7.715   | 25.241 | 1.00 | 63.05 | C1 |
| ATOM | 2113 | C   | ALA | 43 | 37.864 | 9.443   | 23.490 | 1.00 | 62.12 | C1 |
| ATOM | 2114 | O   | ALA | 43 | 36.805 | 9.473   | 22.853 | 1.00 | 61.61 | C1 |
| ATOM | 2115 | N   | ALA | 44 | 38.465 | 10.530  | 23.986 | 1.00 | 61.56 | C1 |
| ATOM | 2116 | CA  | ALA | 44 | 37.933 | 11.878  | 23.798 | 1.00 | 60.59 | C1 |
| ATOM | 2117 | CB  | ALA | 44 | 38.706 | 12.916  | 24.672 | 1.00 | 60.16 | C1 |
| ATOM | 2118 | C   | ALA | 44 | 37.978 | 12.284  | 22.326 | 1.00 | 59.80 | C1 |
| ATOM | 2119 | O   | ALA | 44 | 37.012 | 12.828  | 21.824 | 1.00 | 59.42 | C1 |
| ATOM | 2120 | N   | ARG | 45 | 39.098 | 12.030  | 21.649 | 1.00 | 59.45 | C1 |
| ATOM | 2121 | CA  | ARG | 45 | 39.235 | 12.370  | 20.232 | 1.00 | 58.82 | C1 |
| ATOM | 2122 | CB  | ARG | 45 | 40.678 | 12.131  | 19.761 | 1.00 | 59.70 | C1 |
| ATOM | 2123 | CG  | ARG | 45 | 41.752 | 12.782  | 20.644 | 1.00 | 62.25 | C1 |
| ATOM | 2124 | CD  | ARG | 45 | 41.628 | 14.315  | 20.713 | 1.00 | 64.07 | C1 |
| ATOM | 2125 | NE  | ARG | 45 | 42.275 | 14.966  | 19.581 | 1.00 | 65.16 | C1 |
| ATOM | 2126 | CZ  | ARG | 45 | 42.180 | 16.264  | 19.297 | 1.00 | 66.26 | C1 |
| ATOM | 2127 | NH1 | ARG | 45 | 41.458 | 17.081  | 20.062 | 1.00 | 66.17 | C1 |
| ATOM | 2128 | NH2 | ARG | 45 | 42.811 | 16.745  | 18.232 | 1.00 | 66.74 | C1 |
| ATOM | 2129 | C   | ARG | 45 | 38.265 | 11.541  | 19.367 | 1.00 | 57.52 | C1 |
| ATOM | 2130 | O   | ARG | 45 | 37.920 | 11.938  | 18.252 | 1.00 | 56.92 | C1 |
| ATOM | 2131 | N   | LYS | 46 | 37.847 | 10.387  | 19.894 | 1.00 | 56.06 | C1 |
| ATOM | 2132 | CA  | LYS | 46 | 36.907 | 9.486   | 19.224 | 1.00 | 54.03 | C1 |
| ATOM | 2133 | CB  | LYS | 46 | 36.846 | 8.128   | 19.929 | 1.00 | 54.55 | C1 |
| ATOM | 2134 | CG  | LYS | 46 | 37.435 | 6.971   | 19.164 | 1.00 | 54.57 | C1 |
| ATOM | 2135 | CD  | LYS | 46 | 37.268 | 5.714   | 19.992 | 1.00 | 55.22 | C1 |
| ATOM | 2136 | CE  | LYS | 46 | 38.104 | 4.549   | 19.478 | 1.00 | 55.72 | C1 |
| ATOM | 2137 | NZ  | LYS | 46 | 38.363 | 3.564   | 20.603 | 1.00 | 56.26 | C1 |
| ATOM | 2138 | C   | LYS | 46 | 35.520 | 10.089  | 19.273 | 1.00 | 52.55 | C1 |
| ATOM | 2139 | O   | LYS | 46 | 34.821 | 10.106  | 18.258 | 1.00 | 52.04 | C1 |
| ATOM | 2140 | N   | ASN | 47 | 35.121 | 10.569  | 20.454 | 1.00 | 51.04 | C1 |
| ATOM | 2141 | CA  | ASN | 47 | 33.793 | 11.169  | 20.611 | 1.00 | 50.28 | C1 |
| ATOM | 2142 | CB  | ASN | 47 | 33.479 | 11.536  | 22.077 | 1.00 | 50.72 | C1 |
| ATOM | 2143 | CG  | ASN | 47 | 33.383 | 10.309  | 23.007 | 1.00 | 51.16 | C1 |
| ATOM | 2144 | OD1 | ASN | 47 | 33.148 | 9.176   | 22.575 | 1.00 | 50.76 | C1 |
| ATOM | 2145 | ND2 | ASN | 47 | 33.551 | 10.552  | 24.298 | 1.00 | 51.61 | C1 |
| ATOM | 2146 | C   | ASN | 47 | 33.665 | 12.430  | 19.760 | 1.00 | 49.27 | C1 |
| ATOM | 2147 | O   | ASN | 47 | 32.597 | 12.715  | 19.215 | 1.00 | 49.62 | C1 |
| ATOM | 2148 | N   | GLU | 48 | 34.756 | 13.181  | 19.668 | 1.00 | 47.01 | C1 |
| ATOM | 2149 | CA  | GLU | 48 | 34.787 | 14.405  | 18.890 | 1.00 | 45.47 | C1 |
| ATOM | 2150 | CB  | GLU | 48 | 36.056 | 15.175  | 19.232 | 1.00 | 45.97 | C1 |
| ATOM | 2151 | CG  | GLU | 48 | 36.313 | 16.414  | 18.420 | 1.00 | 48.61 | C1 |
| ATOM | 2152 | CD  | GLU | 48 | 37.700 | 17.005  | 18.710 | 1.00 | 50.94 | C1 |
| ATOM | 2153 | OE1 | GLU | 48 | 37.954 | 17.311  | 19.905 | 1.00 | 51.25 | C1 |
| ATOM | 2154 | OE2 | GLU | 48 | 38.523 | 17.146  | 17.756 | 1.00 | 51.22 | C1 |
| ATOM | 2155 | C   | GLU | 48 | 34.710 | 14.105  | 17.385 | 1.00 | 43.65 | C1 |
| ATOM | 2156 | O   | GLU | 48 | 33.909 | 14.705  | 16.674 | 1.00 | 43.81 | C1 |
| ATOM | 2157 | N   | PHE | 49 | 35.530 | 13.169  | 16.924 | 1.00 | 41.45 | C1 |
| ATOM | 2158 | CA  | PHE | 49 | 35.583 | 12.746  | 15.520 | 1.00 | 40.40 | C1 |

FIG. 3A-38

```
ATOM  2159  CB   PHE  49   36.602  11.606  15.401  1.00  39.94   C1
ATOM  2160  CG   PHE  49   36.716  11.001  14.030  1.00  39.65   C1
ATOM  2161  CD1  PHE  49   37.568  11.557  13.076  1.00  39.24   C1
ATOM  2162  CD2  PHE  49   35.956   9.872  13.683  1.00  39.25   C1
ATOM  2163  CE1  PHE  49   37.664  10.995  11.786  1.00  39.19   C1
ATOM  2164  CE2  PHE  49   36.045   9.309  12.416  1.00  39.13   C1
ATOM  2165  CZ   PHE  49   36.898   9.870  11.465  1.00  39.13   C1
ATOM  2166  C    PHE  49   34.223  12.285  14.969  1.00  39.44   C1
ATOM  2167  O    PHE  49   33.853  12.569  13.837  1.00  38.77   C1
ATOM  2168  N    LEU  50   33.493  11.585  15.822  1.00  39.24   C1
ATOM  2169  CA   LEU  50   32.181  11.017  15.536  1.00  38.43   C1
ATOM  2170  CB   LEU  50   31.894   9.933  16.563  1.00  40.17   C1
ATOM  2171  CG   LEU  50   30.869   8.849  16.338  1.00  41.67   C1
ATOM  2172  CD1  LEU  50   31.036   8.226  14.967  1.00  41.34   C1
ATOM  2173  CD2  LEU  50   31.076   7.817  17.485  1.00  42.66   C1
ATOM  2174  C    LEU  50   31.096  12.080  15.584  1.00  36.53   C1
ATOM  2175  O    LEU  50   30.238  12.089  14.728  1.00  35.96   C1
ATOM  2176  N    ALA  51   31.122  12.964  16.574  1.00  34.40   C1
ATOM  2177  CA   ALA  51   30.119  14.037  16.624  1.00  33.68   C1
ATOM  2178  CB   ALA  51   30.253  14.848  17.916  1.00  32.94   C1
ATOM  2179  C    ALA  51   30.273  14.978  15.397  1.00  33.10   C1
ATOM  2180  O    ALA  51   29.285  15.500  14.898  1.00  32.94   C1
ATOM  2181  N    GLY  52   31.507  15.173  14.925  1.00  31.96   C1
ATOM  2182  CA   GLY  52   31.733  16.031  13.780  1.00  31.80   C1
ATOM  2183  C    GLY  52   31.252  15.353  12.494  1.00  31.78   C1
ATOM  2184  O    GLY  52   30.628  15.983  11.644  1.00  31.70   C1
ATOM  2185  N    ARG  53   31.541  14.069  12.343  1.00  30.89   C1
ATOM  2186  CA   ARG  53   31.095  13.360  11.178  1.00  30.82   C1
ATOM  2187  CB   ARG  53   31.696  11.955  11.140  1.00  31.36   C1
ATOM  2188  CG   ARG  53   33.218  11.928  10.921  1.00  32.07   C1
ATOM  2189  CD   ARG  53   33.616  12.890   9.806  1.00  32.32   C1
ATOM  2190  NE   ARG  53   34.692  12.368   8.969  1.00  33.86   C1
ATOM  2191  CZ   ARG  53   35.987  12.658   9.095  1.00  33.37   C1
ATOM  2192  NH1  ARG  53   36.428  13.486  10.054  1.00  33.63   C1
ATOM  2193  NH2  ARG  53   36.841  12.146   8.220  1.00  32.05   C1
ATOM  2194  C    ARG  53   29.569  13.319  11.182  1.00  31.61   C1
ATOM  2195  O    ARG  53   28.937  13.501  10.152  1.00  31.36   C1
ATOM  2196  N    PHE  54   28.962  13.127  12.347  1.00  31.34   C1
ATOM  2197  CA   PHE  54   27.525  13.108  12.372  1.00  31.44   C1
ATOM  2198  CB   PHE  54   27.029  12.706  13.743  1.00  31.60   C1
ATOM  2199  CG   PHE  54   25.526  12.607  13.832  1.00  31.67   C1
ATOM  2200  CD1  PHE  54   24.785  13.643  14.338  1.00  31.48   C1
ATOM  2201  CD2  PHE  54   24.872  11.431  13.469  1.00  33.28   C1
ATOM  2202  CE1  PHE  54   23.417  13.532  14.512  1.00  33.12   C1
ATOM  2203  CE2  PHE  54   23.498  11.304  13.636  1.00  33.43   C1
ATOM  2204  CZ   PHE  54   22.768  12.356  14.159  1.00  32.71   C1
ATOM  2205  C    PHE  54   26.956  14.500  12.004  1.00  31.59   C1
ATOM  2206  O    PHE  54   25.979  14.607  11.221  1.00  31.51   C1
ATOM  2207  N    ALA  55   27.557  15.561  12.556  1.00  30.03   C1
ATOM  2208  CA   ALA  55   27.078  16.901  12.244  1.00  28.91   C1
ATOM  2209  CB   ALA  55   27.818  17.954  13.085  1.00  27.86   C1
ATOM  2210  C    ALA  55   27.269  17.201  10.759  1.00  27.31   C1
ATOM  2211  O    ALA  55   26.382  17.727  10.093  1.00  27.19   C1
ATOM  2212  N    ALA  56   28.422  16.827  10.237  1.00  26.94   C1
ATOM  2213  CA   ALA  56   28.714  17.144   8.872  1.00  27.05   C1
ATOM  2214  CB   ALA  56   30.187  16.884   8.580  1.00  24.76   C1
ATOM  2215  C    ALA  56   27.795  16.412   7.896  1.00  27.88   C1
```

FIG. 3A-39

```
ATOM   2216  O    ALA   56      27.235  17.025   6.991  1.00 26.74      C1
ATOM   2217  N    LYS   57      27.608  15.107   8.109  1.00 29.56      C1
ATOM   2218  CA   LYS   57      26.730  14.322   7.225  1.00 31.03      C1
ATOM   2219  CB   LYS   57      26.852  12.839   7.583  1.00 31.20      C1
ATOM   2220  CG   LYS   57      28.325  12.401   7.540  1.00 32.34      C1
ATOM   2221  CD   LYS   57      28.512  10.871   7.527  1.00 32.86      C1
ATOM   2222  CE   LYS   57      29.964  10.523   7.125  1.00 32.77      C1
ATOM   2223  NZ   LYS   57      30.182   9.068   6.836  1.00 34.27      C1
ATOM   2224  C    LYS   57      25.274  14.819   7.324  1.00 31.24      C1
ATOM   2225  O    LYS   57      24.590  14.833   6.318  1.00 31.30      C1
ATOM   2226  N    GLU   58      24.818  15.223   8.521  1.00 31.14      C1
ATOM   2227  CA   GLU   58      23.469  15.773   8.701  1.00 32.92      C1
ATOM   2228  CB   GLU   58      23.160  16.046  10.174  1.00 36.48      C1
ATOM   2229  CG   GLU   58      22.886  14.782  11.009  1.00 41.69      C1
ATOM   2230  CD   GLU   58      21.613  14.062  10.525  1.00 45.03      C1
ATOM   2231  OE1  GLU   58      20.590  14.119  11.249  1.00 46.29      C1
ATOM   2232  OE2  GLU   58      21.642  13.468   9.407  1.00 47.23      C1
ATOM   2233  C    GLU   58      23.369  17.113   7.960  1.00 33.31      C1
ATOM   2234  O    GLU   58      22.386  17.346   7.263  1.00 33.22      C1
ATOM   2235  N    ALA   59      24.380  17.986   8.106  1.00 32.66      C1
ATOM   2236  CA   ALA   59      24.364  19.285   7.436  1.00 32.45      C1
ATOM   2237  CB   ALA   59      25.613  20.073   7.756  1.00 30.78      C1
ATOM   2238  C    ALA   59      24.309  19.048   5.937  1.00 32.54      C1
ATOM   2239  O    ALA   59      23.592  19.712   5.207  1.00 30.95      C1
ATOM   2240  N    PHE   60      25.109  18.110   5.483  1.00 33.43      C1
ATOM   2241  CA   PHE   60      25.158  17.816   4.065  1.00 35.36      C1
ATOM   2242  CB   PHE   60      26.240  16.789   3.766  1.00 35.51      C1
ATOM   2243  CG   PHE   60      26.301  16.398   2.312  1.00 37.38      C1
ATOM   2244  CD1  PHE   60      27.001  17.173   1.391  1.00 38.64      C1
ATOM   2245  CD2  PHE   60      25.663  15.256   1.863  1.00 37.90      C1
ATOM   2246  CE1  PHE   60      27.061  16.786   0.032  1.00 38.44      C1
ATOM   2247  CE2  PHE   60      25.715  14.871   0.532  1.00 37.72      C1
ATOM   2248  CZ   PHE   60.     26.411  15.626  -0.379  1.00 38.22      C1
ATOM   2249  C    PHE   60      23.815  17.239   3.606  1.00 35.65      C1
ATOM   2250  O    PHE   60      23.355  17.504   2.497  1.00 35.06      C1
ATOM   2251  N    SER   61      23.196  16.441   4.470  1.00 36.40      C1
ATOM   2252  CA   SER   61      21.940  15.852   4.072  1.00 37.14      C1
ATOM   2253  CB   SER   61      21.545  14.691   5.006  1.00 36.12      C1
ATOM   2254  OG   SER   61      20.814  15.139   6.126  1.00 35.05      C1
ATOM   2255  C    SER   61      20.869  16.940   4.016  1.00 37.16      C1
ATOM   2256  O    SER   61      19.964  16.870   3.190  1.00 38.46      C1
ATOM   2257  N    LYS   62      20.970  17.955   4.857  1.00 37.48      C1
ATOM   2258  CA   LYS   62      19.954  19.006   4.813  1.00 37.83      C1
ATOM   2259  CB   LYS   62      20.021  19.903   6.021  1.00 38.42      C1
ATOM   2260  CG   LYS   62      19.610  19.236   7.327  1.00 40.35      C1
ATOM   2261  CD   LYS   62      19.854  20.259   8.406  1.00 41.61      C1
ATOM   2262  CE   LYS   62      19.418  19.814   9.748  1.00 43.22      C1
ATOM   2263  NZ   LYS   62      18.737  20.988  10.385  1.00 44.06      C1
ATOM   2264  C    LYS   62      20.178  19.805   3.557  1.00 37.95      C1
ATOM   2265  O    LYS   62      19.233  20.045   2.826  1.00 37.84      C1
ATOM   2266  N    ALA   63      21.425  20.183   3.293  1.00 38.21      C1
ATOM   2267  CA   ALA   63      21.790  20.925   2.090  1.00 39.70      C1
ATOM   2268  CB   ALA   63      23.306  21.094   1.994  1.00 38.23      C1
ATOM   2269  C    ALA   63      21.308  20.245   0.811  1.00 40.64      C1
ATOM   2270  O    ALA   63      20.823  20.897  -0.098  1.00 40.84      C1
ATOM   2271  N    PHE   64      21.513  18.939   0.737  1.00 42.16      C1
ATOM   2272  CA   PHE   64      21.137  18.134  -0.423  1.00 43.43      C1
```

FIG. 3A-40

| ATOM | 2273 | CB | PHE | 64 | 21.748 | 16.747 | -0.186 | 1.00 | 44.71 | C1 |
|---|---|---|---|---|---|---|---|---|---|---|
| ATOM | 2274 | CG | PHE | 64 | 21.435 | 15.714 | -1.242 | 1.00 | 46.29 | C1 |
| ATOM | 2275 | CD1 | PHE | 64 | 22.246 | 15.577 | -2.371 | 1.00 | 47.02 | C1 |
| ATOM | 2276 | CD2 | PHE | 64 | 20.373 | 14.808 | -1.059 | 1.00 | 47.22 | C1 |
| ATOM | 2277 | CE1 | PHE | 64 | 22.019 | 14.543 | -3.300 | 1.00 | 47.15 | C1 |
| ATOM | 2278 | CE2 | PHE | 64 | 20.135 | 13.762 | -1.985 | 1.00 | 47.50 | C1 |
| ATOM | 2279 | CZ | PHE | 64 | 20.968 | 13.638 | -3.107 | 1.00 | 46.63 | C1 |
| ATOM | 2280 | C | PHE | 64 | 19.587 | 18.095 | -0.581 | 1.00 | 43.41 | C1 |
| ATOM | 2281 | O | PHE | 64 | 19.077 | 17.679 | -1.608 | 1.00 | 43.04 | C1 |
| ATOM | 2282 | N | GLY | 65 | 18.861 | 18.515 | 0.464 | 1.00 | 44.00 | C1 |
| ATOM | 2283 | CA | GLY | 65 | 17.401 | 18.551 | 0.442 | 1.00 | 44.61 | C1 |
| ATOM | 2284 | C | GLY | 65 | 16.547 | 17.360 | 0.900 | 1.00 | 45.23 | C1 |
| ATOM | 2285 | O | GLY | 65 | 15.319 | 17.481 | 1.024 | 1.00 | 44.77 | C1 |
| ATOM | 2286 | N | THR | 66 | 17.162 | 16.214 | 1.173 | 1.00 | 46.05 | C1 |
| ATOM | 2287 | CA | THR | 66 | 16.371 | 15.047 | 1.573 | 1.00 | 46.97 | C1 |
| ATOM | 2288 | CB | THR | 66 | 16.677 | 13.833 | 0.689 | 1.00 | 46.94 | C1 |
| ATOM | 2289 | OG1 | THR | 66 | 18.043 | 13.416 | 0.900 | 1.00 | 47.06 | C1 |
| ATOM | 2290 | CG2 | THR | 66 | 16.451 | 14.197 | -0.760 | 1.00 | 46.70 | C1 |
| ATOM | 2291 | C | THR | 66 | 16.499 | 14.540 | 2.986 | 1.00 | 47.71 | C1 |
| ATOM | 2292 | O | THR | 66 | 15.578 | 13.908 | 3.488 | 1.00 | 47.47 | C1 |
| ATOM | 2293 | N | GLY | 67 | 17.628 | 14.819 | 3.638 | 1.00 | 48.74 | C1 |
| ATOM | 2294 | CA | GLY | 67 | 17.816 | 14.259 | 4.966 | 1.00 | 49.20 | C1 |
| ATOM | 2295 | C | GLY | 67 | 18.312 | 12.825 | 4.726 | 1.00 | 49.52 | C1 |
| ATOM | 2296 | O | GLY | 67 | 18.463 | 12.380 | 3.569 | 1.00 | 49.17 | C1 |
| ATOM | 2297 | N | ILE | 68 | 18.599 | 12.106 | 5.802 | 1.00 | 50.08 | C1 |
| ATOM | 2298 | CA | ILE | 68 | 19.068 | 10.726 | 5.679 | 1.00 | 50.36 | C1 |
| ATOM | 2299 | CB | ILE | 68 | 19.859 | 10.258 | 6.956 | 1.00 | 49.26 | C1 |
| ATOM | 2300 | CG2 | ILE | 68 | 20.194 | 8.758 | 6.867 | 1.00 | 47.83 | C1 |
| ATOM | 2301 | CG1 | ILE | 68 | 21.154 | 11.072 | 7.095 | 1.00 | 48.45 | C1 |
| ATOM | 2302 | CD1 | ILE | 68 | 22.032 | 11.086 | 5.836 | 1.00 | 47.51 | C1 |
| ATOM | 2303 | C | ILE | 68 | 17.841 | 9.846 | 5.458 | 1.00 | 51.41 | C1 |
| ATOM | 2304 | O | ILE | 68 | 16.796 | 10.053 | 6.088 | 1.00 | 52.16 | C1 |
| ATOM | 2305 | N | GLY | 69 | 17.970 | 8.885 | 4.550 | 1.00 | 51.45 | C1 |
| ATOM | 2306 | CA | GLY | 69 | 16.876 | 7.988 | 4.246 | 1.00 | 51.52 | C1 |
| ATOM | 2307 | C | GLY | 69 | 17.034 | 7.313 | 2.887 | 1.00 | 51.85 | C1 |
| ATOM | 2308 | O | GLY | 69 | 18.136 | 6.957 | 2.487 | 1.00 | 51.77 | C1 |
| ATOM | 2309 | N | ALA | 70 | 15.921 | 7.156 | 2.174 | 1.00 | 52.21 | C1 |
| ATOM | 2310 | CA | ALA | 70 | 15.907 | 6.512 | 0.872 | 1.00 | 52.38 | C1 |
| ATOM | 2311 | CB | ALA | 70 | 14.459 | 6.445 | 0.355 | 1.00 | 52.35 | C1 |
| ATOM | 2312 | C | ALA | 70 | 16.806 | 7.202 | -0.156 | 1.00 | 52.84 | C1 |
| ATOM | 2313 | O | ALA | 70 | 17.647 | 6.563 | -0.801 | 1.00 | 53.61 | C1 |
| ATOM | 2314 | N | GLN | 71 | 16.641 | 8.512 | -0.300 | 1.00 | 52.78 | C1 |
| ATOM | 2315 | CA | GLN | 71 | 17.411 | 9.283 | -1.272 | 1.00 | 52.79 | C1 |
| ATOM | 2316 | CB | GLN | 71 | 16.740 | 10.668 | -1.450 | 1.00 | 53.71 | C1 |
| ATOM | 2317 | CG | GLN | 71 | 15.196 | 10.560 | -1.487 | 1.00 | 54.85 | C1 |
| ATOM | 2318 | CD | GLN | 71 | 14.471 | 11.904 | -1.600 | 1.00 | 56.44 | C1 |
| ATOM | 2319 | OE1 | GLN | 71 | 14.610 | 12.623 | -2.623 | 1.00 | 56.95 | C1 |
| ATOM | 2320 | NE2 | GLN | 71 | 13.689 | 12.262 | -0.548 | 1.00 | 55.97 | C1 |
| ATOM | 2321 | C | GLN | 71 | 18.910 | 9.433 | -0.974 | 1.00 | 51.80 | C1 |
| ATOM | 2322 | O | GLN | 71 | 19.691 | 9.693 | -1.900 | 1.00 | 52.03 | C1 |
| ATOM | 2323 | N | LEU | 72 | 19.316 | 9.270 | 0.293 | 1.00 | 50.94 | C1 |
| ATOM | 2324 | CA | LEU | 72 | 20.741 | 9.423 | 0.689 | 1.00 | 49.64 | C1 |
| ATOM | 2325 | CB | LEU | 72 | 21.143 | 10.909 | 0.726 | 1.00 | 48.92 | C1 |
| ATOM | 2326 | CG | LEU | 72 | 22.541 | 11.397 | 1.155 | 1.00 | 47.24 | C1 |
| ATOM | 2327 | CD1 | LEU | 72 | 23.540 | 11.368 | -0.012 | 1.00 | 45.52 | C1 |
| ATOM | 2328 | CD2 | LEU | 72 | 22.382 | 12.825 | 1.665 | 1.00 | 47.11 | C1 |
| ATOM | 2329 | C | LEU | 72 | 21.119 | 8.815 | 2.029 | 1.00 | 49.40 | C1 |

FIG. 3A-41

| ATOM | 2330 | O   | LEU | 72 | 20.426 | 9.008  | 3.057  | 1.00 | 48.89 | C1 |
| ATOM | 2331 | N   | SER | 73 | 22.256 | 8.120  | 2.004  | 1.00 | 48.75 | C1 |
| ATOM | 2332 | CA  | SER | 73 | 22.801 | 7.450  | 3.173  | 1.00 | 48.80 | C1 |
| ATOM | 2333 | CB  | SER | 73 | 23.008 | 5.952  | 2.845  | 1.00 | 49.54 | C1 |
| ATOM | 2334 | OG  | SER | 73 | 23.967 | 5.331  | 3.711  | 1.00 | 50.91 | C1 |
| ATOM | 2335 | C   | SER | 73 | 24.136 | 8.027  | 3.677  | 1.00 | 48.34 | C1 |
| ATOM | 2336 | O   | SER | 73 | 24.914 | 8.609  | 2.915  | 1.00 | 48.05 | C1 |
| ATOM | 2337 | N   | PHE | 74 | 24.390 | 7.813  | 4.967  | 1.00 | 47.81 | C1 |
| ATOM | 2338 | CA  | PHE | 74 | 25.625 | 8.201  | 5.636  | 1.00 | 47.50 | C1 |
| ATOM | 2339 | CB  | PHE | 74 | 25.664 | 7.615  | 7.041  | 1.00 | 47.20 | C1 |
| ATOM | 2340 | CG  | PHE | 74 | 24.715 | 8.259  | 8.002  | 1.00 | 47.29 | C1 |
| ATOM | 2341 | CD1 | PHE | 74 | 24.850 | 9.620  | 8.337  | 1.00 | 46.98 | C1 |
| ATOM | 2342 | CD2 | PHE | 74 | 23.726 | 7.508  | 8.627  | 1.00 | 46.60 | C1 |
| ATOM | 2343 | CE1 | PHE | 74 | 24.026 | 10.216 | 9.278  | 1.00 | 45.88 | C1 |
| ATOM | 2344 | CE2 | PHE | 74 | 22.893 | 8.104  | 9.572  | 1.00 | 46.36 | C1 |
| ATOM | 2345 | CZ  | PHE | 74 | 23.051 | 9.465  | 9.895  | 1.00 | 45.98 | C1 |
| ATOM | 2346 | C   | PHE | 74 | 26.798 | 7.608  | 4.893  | 1.00 | 48.02 | C1 |
| ATOM | 2347 | O   | PHE | 74 | 27.849 | 8.235  | 4.714  | 1.00 | 47.41 | C1 |
| ATOM | 2348 | N   | GLN | 75 | 26.615 | 6.364  | 4.472  | 1.00 | 48.84 | C1 |
| ATOM | 2349 | CA  | GLN | 75 | 27.666 | 5.644  | 3.785  | 1.00 | 49.52 | C1 |
| ATOM | 2350 | CB  | GLN | 75 | 27.278 | 4.168  | 3.684  | 1.00 | 50.19 | C1 |
| ATOM | 2351 | CG  | GLN | 75 | 27.029 | 3.513  | 5.046  | 1.00 | 50.48 | C1 |
| ATOM | 2352 | CD  | GLN | 75 | 28.285 | 3.526  | 5.886  | 1.00 | 51.73 | C1 |
| ATOM | 2353 | OE1 | GLN | 75 | 29.353 | 3.130  | 5.412  | 1.00 | 52.49 | C1 |
| ATOM | 2354 | NE2 | GLN | 75 | 28.180 | 3.985  | 7.126  | 1.00 | 51.45 | C1 |
| ATOM | 2355 | C   | GLN | 75 | 27.988 | 6.235  | 2.421  | 1.00 | 49.96 | C1 |
| ATOM | 2356 | O   | GLN | 75 | 29.017 | 5.907  | 1.825  | 1.00 | 50.48 | C1 |
| ATOM | 2357 | N   | ASP | 76 | 27.130 | 7.122  | 1.927  | 1.00 | 50.43 | C1 |
| ATOM | 2358 | CA  | ASP | 76 | 27.365 | 7.761  | 0.619  | 1.00 | 50.67 | C1 |
| ATOM | 2359 | CB  | ASP | 76 | 26.054 | 8.166  | -0.046 | 1.00 | 51.37 | C1 |
| ATOM | 2360 | CG  | ASP | 76 | 25.287 | 6.997  | -0.560 | 1.00 | 52.52 | C1 |
| ATOM | 2361 | OD1 | ASP | 76 | 25.891 | 6.193  | -1.301 | 1.00 | 52.95 | C1 |
| ATOM | 2362 | OD2 | ASP | 76 | 24.086 | 6.888  | -0.224 | 1.00 | 53.95 | C1 |
| ATOM | 2363 | C   | ASP | 76 | 28.184 | 9.026  | 0.765  | 1.00 | 50.43 | C1 |
| ATOM | 2364 | O   | ASP | 76 | 28.669 | 9.579  | -0.223 | 1.00 | 51.13 | C1 |
| ATOM | 2365 | N   | ILE | 77 | 28.317 | 9.481  | 2.006  | 1.00 | 49.70 | C1 |
| ATOM | 2366 | CA  | ILE | 77 | 29.031 | 10.701 | 2.309  | 1.00 | 48.67 | C1 |
| ATOM | 2367 | CB  | ILE | 77 | 28.211 | 11.559 | 3.253  | 1.00 | 47.95 | C1 |
| ATOM | 2368 | CG2 | ILE | 77 | 28.817 | 12.936 | 3.353  | 1.00 | 47.84 | C1 |
| ATOM | 2369 | CG1 | ILE | 77 | 26.746 | 11.564 | 2.789  | 1.00 | 48.00 | C1 |
| ATOM | 2370 | CD1 | ILE | 77 | 25.808 | 12.444 | 3.603  | 1.00 | 47.22 | C1 |
| ATOM | 2371 | C   | ILE | 77 | 30.368 | 10.440 | 2.978  | 1.00 | 48.96 | C1 |
| ATOM | 2372 | O   | ILE | 77 | 30.434 | 9.757  | 3.997  | 1.00 | 48.72 | C1 |
| ATOM | 2373 | N   | GLU | 78 | 31.440 | 10.969 | 2.408  | 1.00 | 48.68 | C1 |
| ATOM | 2374 | CA  | GLU | 78 | 32.704 | 10.799 | 3.073  | 1.00 | 49.55 | C1 |
| ATOM | 2375 | CB  | GLU | 78 | 33.621 | 9.823  | 2.333  | 1.00 | 51.11 | C1 |
| ATOM | 2376 | CG  | GLU | 78 | 34.970 | 9.720  | 3.028  | 1.00 | 52.90 | C1 |
| ATOM | 2377 | CD  | GLU | 78 | 35.794 | 8.537  | 2.593  | 1.00 | 54.48 | C1 |
| ATOM | 2378 | OE1 | GLU | 78 | 37.012 | 8.540  | 2.910  | 1.00 | 55.00 | C1 |
| ATOM | 2379 | OE2 | GLU | 78 | 35.224 | 7.615  | 1.953  | 1.00 | 55.86 | C1 |
| ATOM | 2380 | C   | GLU | 78 | 33.438 | 12.115 | 3.287  | 1.00 | 48.60 | C1 |
| ATOM | 2381 | O   | GLU | 78 | 33.607 | 12.901 | 2.361  | 1.00 | 48.62 | C1 |
| ATOM | 2382 | N   | ILE | 79 | 33.877 | 12.325 | 4.526  | 1.00 | 47.38 | C1 |
| ATOM | 2383 | CA  | ILE | 79 | 34.619 | 13.513 | 4.920  | 1.00 | 45.83 | C1 |
| ATOM | 2384 | CB  | ILE | 79 | 34.182 | 14.038 | 6.320  | 1.00 | 44.21 | C1 |
| ATOM | 2385 | CG2 | ILE | 79 | 35.248 | 15.001 | 6.849  | 1.00 | 43.54 | C1 |
| ATOM | 2386 | CG1 | ILE | 79 | 32.840 | 14.777 | 6.243  | 1.00 | 43.11 | C1 |

FIG. 3A-42

| ATOM | 2387 | CD1 | ILE | 79 | 31.649 | 13.923 | 6.253 | 1.00 | 42.90 | C1 |
|---|---|---|---|---|---|---|---|---|---|---|
| ATOM | 2388 | C | ILE | 79 | 36.115 | 13.204 | 5.008 | 1.00 | 46.28 | C1 |
| ATOM | 2389 | O | ILE | 79 | 36.524 | 12.284 | 5.704 | 1.00 | 46.25 | C1 |
| ATOM | 2390 | N | ARG | 80 | 36.931 | 13.978 | 4.308 | 1.00 | 47.15 | C1 |
| ATOM | 2391 | CA | ARG | 80 | 38.381 | 13.810 | 4.363 | 1.00 | 47.86 | C1 |
| ATOM | 2392 | CB | ARG | 80 | 38.918 | 13.306 | 3.023 | 1.00 | 49.91 | C1 |
| ATOM | 2393 | CG | ARG | 80 | 38.470 | 11.879 | 2.682 | 1.00 | 53.47 | C1 |
| ATOM | 2394 | CD | ARG | 80 | 39.177 | 11.328 | 1.415 | 1.00 | 56.60 | C1 |
| ATOM | 2395 | NE | ARG | 80 | 38.299 | 10.415 | 0.673 | 1.00 | 59.57 | C1 |
| ATOM | 2396 | CZ | ARG | 80 | 38.580 | 9.892 | -0.520 | 1.00 | 61.29 | C1 |
| ATOM | 2397 | NH1 | ARG | 80 | 37.705 | 9.082 | -1.102 | 1.00 | 62.00 | C1 |
| ATOM | 2398 | NH2 | ARG | 80 | 39.732 | 10.170 | -1.133 | 1.00 | 61.67 | C1 |
| ATOM | 2399 | C | ARG | 80 | 38.998 | 15.154 | 4.702 | 1.00 | 47.04 | C1 |
| ATOM | 2400 | O | ARG | 80 | 38.302 | 16.172 | 4.696 | 1.00 | 46.98 | C1 |
| ATOM | 2401 | N | LYS | 81 | 40.285 | 15.164 | 5.021 | 1.00 | 46.29 | C1 |
| ATOM | 2402 | CA | LYS | 81 | 40.969 | 16.429 | 5.316 | 1.00 | 46.35 | C1 |
| ATOM | 2403 | CB | LYS | 81 | 41.221 | 16.598 | 6.822 | 1.00 | 46.29 | C1 |
| ATOM | 2404 | CG | LYS | 81 | 40.018 | 17.101 | 7.625 | 1.00 | 46.61 | C1 |
| ATOM | 2405 | CD | LYS | 81 | 40.403 | 17.303 | 9.096 | 1.00 | 46.26 | C1 |
| ATOM | 2406 | CE | LYS | 81 | 39.246 | 17.784 | 9.958 | 1.00 | 46.08 | C1 |
| ATOM | 2407 | NZ | LYS | 81 | 39.660 | 17.771 | 11.416 | 1.00 | 46.72 | C1 |
| ATOM | 2408 | C | LYS | 81 | 42.312 | 16.573 | 4.592 | 1.00 | 46.05 | C1 |
| ATOM | 2409 | O | LYS | 81 | 43.110 | 15.630 | 4.573 | 1.00 | 45.90 | C1 |
| ATOM | 2410 | N | ASP | 82 | 42.576 | 17.753 | 4.017 | 1.00 | 45.41 | C1 |
| ATOM | 2411 | CA | ASP | 82 | 43.872 | 17.963 | 3.356 | 1.00 | 45.00 | C1 |
| ATOM | 2412 | CB | ASP | 82 | 43.782 | 19.022 | 2.231 | 1.00 | 43.78 | C1 |
| ATOM | 2413 | CG | ASP | 82 | 43.524 | 20.455 | 2.742 | 1.00 | 43.90 | C1 |
| ATOM | 2414 | OD1 | ASP | 82 | 43.895 | 20.840 | 3.884 | 1.00 | 42.17 | C1 |
| ATOM | 2415 | OD2 | ASP | 82 | 42.962 | 21.224 | 1.935 | 1.00 | 43.52 | C1 |
| ATOM | 2416 | C | ASP | 82 | 44.983 | 18.330 | 4.374 | 1.00 | 44.67 | C1 |
| ATOM | 2417 | O | ASP | 82 | 44.750 | 18.333 | 5.598 | 1.00 | 43.85 | C1 |
| ATOM | 2418 | N | GLN | 83 | 46.172 | 18.643 | 3.855 | 1.00 | 44.78 | C1 |
| ATOM | 2419 | CA | GLN | 83 | 47.359 | 18.986 | 4.671 | 1.00 | 45.33 | C1 |
| ATOM | 2420 | CB | GLN | 83 | 48.573 | 19.193 | 3.759 | 1.00 | 45.91 | C1 |
| ATOM | 2421 | CG | GLN | 83 | 49.490 | 18.021 | 3.641 | 1.00 | 46.80 | C1 |
| ATOM | 2422 | CD | GLN | 83 | 48.747 | 16.733 | 3.714 | 1.00 | 48.38 | C1 |
| ATOM | 2423 | OE1 | GLN | 83 | 48.676 | 16.113 | 4.793 | 1.00 | 49.41 | C1 |
| ATOM | 2424 | NE2 | GLN | 83 | 48.152 | 16.315 | 2.584 | 1.00 | 47.83 | C1 |
| ATOM | 2425 | C | GLN | 83 | 47.240 | 20.217 | 5.550 | 1.00 | 44.80 | C1 |
| ATOM | 2426 | O | GLN | 83 | 48.041 | 20.408 | 6.448 | 1.00 | 44.50 | C1 |
| ATOM | 2427 | N | ASN | 84 | 46.254 | 21.060 | 5.250 | 1.00 | 44.80 | C1 |
| ATOM | 2428 | CA | ASN | 84 | 46.013 | 22.296 | 5.991 | 1.00 | 44.29 | C1 |
| ATOM | 2429 | CB | ASN | 84 | 45.585 | 23.412 | 5.032 | 1.00 | 44.06 | C1 |
| ATOM | 2430 | CG | ASN | 84 | 46.747 | 24.027 | 4.289 | 1.00 | 44.62 | C1 |
| ATOM | 2431 | OD1 | ASN | 84 | 46.624 | 24.390 | 3.111 | 1.00 | 44.59 | C1 |
| ATOM | 2432 | ND2 | ASN | 84 | 47.874 | 24.174 | 4.969 | 1.00 | 43.72 | C1 |
| ATOM | 2433 | C | ASN | 84 | 44.898 | 22.048 | 6.995 | 1.00 | 43.71 | C1 |
| ATOM | 2434 | O | ASN | 84 | 44.510 | 22.956 | 7.742 | 1.00 | 43.04 | C1 |
| ATOM | 2435 | N | GLY | 85 | 44.389 | 20.814 | 6.978 | 1.00 | 43.44 | C1 |
| ATOM | 2436 | CA | GLY | 85 | 43.311 | 20.406 | 7.867 | 1.00 | 42.84 | C1 |
| ATOM | 2437 | C | GLY | 85 | 41.948 | 20.869 | 7.404 | 1.00 | 42.40 | C1 |
| ATOM | 2438 | O | GLY | 85 | 41.025 | 20.958 | 8.209 | 1.00 | 43.31 | C1 |
| ATOM | 2439 | N | LYS | 86 | 41.808 | 21.182 | 6.123 | 1.00 | 41.80 | C1 |
| ATOM | 2440 | CA | LYS | 86 | 40.519 | 21.633 | 5.609 | 1.00 | 42.19 | C1 |
| ATOM | 2441 | CB | LYS | 86 | 40.674 | 22.537 | 4.380 | 1.00 | 41.23 | C1 |
| ATOM | 2442 | CG | LYS | 86 | 39.386 | 23.217 | 3.952 | 1.00 | 41.66 | C1 |
| ATOM | 2443 | CD | LYS | 86 | 39.513 | 23.859 | 2.566 | 1.00 | 42.36 | C1 |

FIG. 3A-43

| ATOM | 2444 | CE | LYS | 86 | 38.541 | 23.239 | 1.522 | 1.00 | 43.64 | C1 |
| ATOM | 2445 | NZ | LYS | 86 | 38.374 | 24.125 | 0.287 | 1.00 | 44.71 | C1 |
| ATOM | 2446 | C | LYS | 86 | 39.738 | 20.396 | 5.231 | 1.00 | 42.58 | C1 |
| ATOM | 2447 | O | LYS | 86 | 40.219 | 19.540 | 4.495 | 1.00 | 42.76 | C1 |
| ATOM | 2448 | N | PRO | 87 | 38.516 | 20.282 | 5.743 | 1.00 | 43.20 | C1 |
| ATOM | 2449 | CD | PRO | 87 | 37.872 | 21.103 | 6.786 | 1.00 | 43.03 | C1 |
| ATOM | 2450 | CA | PRO | 87 | 37.715 | 19.113 | 5.422 | 1.00 | 43.26 | C1 |
| ATOM | 2451 | CB | PRO | 87 | 36.722 | 19.061 | 6.555 | 1.00 | 43.23 | C1 |
| ATOM | 2452 | CG | PRO | 87 | 36.488 | 20.526 | 6.838 | 1.00 | 43.31 | C1 |
| ATOM | 2453 | C | PRO | 87 | 37.056 | 19.322 | 4.111 | 1.00 | 43.97 | C1 |
| ATOM | 2454 | O | PRO | 87 | 36.907 | 20.464 | 3.651 | 1.00 | 43.98 | C1 |
| ATOM | 2455 | N | TYR | 88 | 36.711 | 18.214 | 3.484 | 1.00 | 44.08 | C1 |
| ATOM | 2456 | CA | TYR | 88 | 36.033 | 18.278 | 2.230 | 1.00 | 45.68 | C1 |
| ATOM | 2457 | CB | TYR | 88 | 37.015 | 18.472 | 1.034 | 1.00 | 47.43 | C1 |
| ATOM | 2458 | CG | TYR | 88 | 38.189 | 17.526 | 0.886 | 1.00 | 49.08 | C1 |
| ATOM | 2459 | CD1 | TYR | 88 | 38.194 | 16.521 | -0.107 | 1.00 | 50.60 | C1 |
| ATOM | 2460 | CE1 | TYR | 88 | 39.336 | 15.701 | -0.334 | 1.00 | 50.63 | C1 |
| ATOM | 2461 | CD2 | TYR | 88 | 39.341 | 17.681 | 1.660 | 1.00 | 49.84 | C1 |
| ATOM | 2462 | CE2 | TYR | 88 | 40.476 | 16.862 | 1.450 | 1.00 | 50.93 | C1 |
| ATOM | 2463 | CZ | TYR | 88 | 40.464 | 15.885 | 0.451 | 1.00 | 51.22 | C1 |
| ATOM | 2464 | OH | TYR | 88 | 41.590 | 15.120 | 0.244 | 1.00 | 52.41 | C1 |
| ATOM | 2465 | C | TYR | 88 | 35.215 | 17.026 | 2.127 | 1.00 | 46.37 | C1 |
| ATOM | 2466 | O | TYR | 88 | 35.549 | 16.010 | 2.721 | 1.00 | 45.65 | C1 |
| ATOM | 2467 | N | ILE | 89 | 34.103 | 17.124 | 1.419 | 1.00 | 47.63 | C1 |
| ATOM | 2468 | CA | ILE | 89 | 33.221 | 15.998 | 1.275 | 1.00 | 50.50 | C1 |
| ATOM | 2469 | CB | ILE | 89 | 31.754 | 16.402 | 1.541 | 1.00 | 49.66 | C1 |
| ATOM | 2470 | CG2 | ILE | 89 | 30.825 | 15.216 | 1.273 | 1.00 | 48.82 | C1 |
| ATOM | 2471 | CG1 | ILE | 89 | 31.627 | 16.905 | 2.972 | 1.00 | 49.02 | C1 |
| ATOM | 2472 | CD1 | ILE | 89 | 30.227 | 17.264 | 3.369 | 1.00 | 48.76 | C1 |
| ATOM | 2473 | C | ILE | 89 | 33.276 | 15.340 | -0.095 | 1.00 | 52.86 | C1 |
| ATOM | 2474 | O | ILE | 89 | 33.365 | 16.004 | -1.123 | 1.00 | 53.08 | C1 |
| ATOM | 2475 | N | ILE | 90 | 33.229 | 14.021 | -0.093 | 1.00 | 55.54 | C1 |
| ATOM | 2476 | CA | ILE | 90 | 33.199 | 13.295 | -1.334 | 1.00 | 58.03 | C1 |
| ATOM | 2477 | CB | ILE | 90 | 34.292 | 12.261 | -1.404 | 1.00 | 57.72 | C1 |
| ATOM | 2478 | CG2 | ILE | 90 | 34.455 | 11.818 | -2.851 | 1.00 | 57.78 | C1 |
| ATOM | 2479 | CG1 | ILE | 90 | 35.618 | 12.870 | -0.947 | 1.00 | 58.26 | C1 |
| ATOM | 2480 | CD1 | ILE | 90 | 36.152 | 13.997 | -1.880 | 1.00 | 58.15 | C1 |
| ATOM | 2481 | C | ILE | 90 | 31.843 | 12.610 | -1.309 | 1.00 | 59.92 | C1 |
| ATOM | 2482 | O | ILE | 90 | 31.460 | 12.005 | -0.309 | 1.00 | 60.54 | C1 |
| ATOM | 2483 | N | CYS | 91 | 31.085 | 12.767 | -2.375 | 1.00 | 62.06 | C1 |
| ATOM | 2484 | CA | CYS | 91 | 29.789 | 12.135 | -2.442 | 1.00 | 65.02 | C1 |
| ATOM | 2485 | CB | CYS | 91 | 28.729 | 12.879 | -1.636 | 1.00 | 64.53 | C1 |
| ATOM | 2486 | SG | CYS | 91 | 27.007 | 12.228 | -1.893 | 1.00 | 65.15 | C1 |
| ATOM | 2487 | C | CYS | 91 | 29.339 | 12.047 | -3.872 | 1.00 | 67.19 | C1 |
| ATOM | 2488 | O | CYS | 91 | 28.809 | 13.012 | -4.450 | 1.00 | 67.57 | C1 |
| ATOM | 2489 | N | THR | 92 | 29.597 | 10.892 | -4.463 | 1.00 | 69.14 | C1 |
| ATOM | 2490 | CA | THR | 92 | 29.160 | 10.677 | -5.812 | 1.00 | 71.19 | C1 |
| ATOM | 2491 | CB | THR | 92 | 29.946 | 9.525 | -6.462 | 1.00 | 71.08 | C1 |
| ATOM | 2492 | OG1 | THR | 92 | 29.521 | 8.282 | -5.894 | 1.00 | 71.32 | C1 |
| ATOM | 2493 | CG2 | THR | 92 | 31.453 | 9.721 | -6.224 | 1.00 | 70.41 | C1 |
| ATOM | 2494 | C | THR | 92 | 27.722 | 10.304 | -5.485 | 1.00 | 72.70 | C1 |
| ATOM | 2495 | O | THR | 92 | 27.446 | 9.328 | -4.768 | 1.00 | 73.09 | C1 |
| ATOM | 2496 | N | LYS | 93 | 26.842 | 11.183 | -5.932 | 1.00 | 74.04 | C1 |
| ATOM | 2497 | CA | LYS | 93 | 25.406 | 11.099 | -5.769 | 1.00 | 75.40 | C1 |
| ATOM | 2498 | CB | LYS | 93 | 24.979 | 11.225 | -4.318 | 1.00 | 75.38 | C1 |
| ATOM | 2499 | CG | LYS | 93 | 24.537 | 9.897 | -3.689 | 1.00 | 75.40 | C1 |
| ATOM | 2500 | CD | LYS | 93 | 23.074 | 9.583 | -3.977 | 1.00 | 75.01 | C1 |

FIG. 3A-44

| ATOM | 2501 | CE  | LYS | 93  | 22.649 | 8.273  | -3.321  | 1.00 | 75.18 | C1 |
|------|------|-----|-----|-----|--------|--------|---------|------|-------|----|
| ATOM | 2502 | NZ  | LYS | 93  | 21.168 | 8.059  | -3.343  | 1.00 | 74.81 | C1 |
| ATOM | 2503 | C   | LYS | 93  | 25.077 | 12.351 | -6.532  | 1.00 | 76.29 | C1 |
| ATOM | 2504 | O   | LYS | 93  | 24.070 | 13.017 | -6.326  | 1.00 | 76.31 | C1 |
| ATOM | 2505 | N   | LEU | 94  | 26.036 | 12.641 | -7.405  | 1.00 | 77.49 | C1 |
| ATOM | 2506 | CA  | LEU | 94  | 26.063 | 13.734 | -8.361  | 1.00 | 78.53 | C1 |
| ATOM | 2507 | CB  | LEU | 94  | 24.692 | 14.417 | -8.499  | 1.00 | 79.09 | C1 |
| ATOM | 2508 | CG  | LEU | 94  | 24.161 | 14.260 | -9.936  | 1.00 | 79.46 | C1 |
| ATOM | 2509 | CD1 | LEU | 94  | 25.097 | 14.972 | -10.908 | 1.00 | 79.49 | C1 |
| ATOM | 2510 | CD2 | LEU | 94  | 24.057 | 12.761 | -10.301 | 1.00 | 79.47 | C1 |
| ATOM | 2511 | C   | LEU | 94  | 27.140 | 14.797 | -8.236  | 1.00 | 78.47 | C1 |
| ATOM | 2512 | O   | LEU | 94  | 27.454 | 15.308 | -7.149  | 1.00 | 79.19 | C1 |
| ATOM | 2513 | N   | SER | 95  | 27.732 | 15.068 | -9.394  | 1.00 | 77.80 | C1 |
| ATOM | 2514 | CA  | SER | 95  | 28.721 | 16.095 | -9.540  | 1.00 | 77.11 | C1 |
| ATOM | 2515 | CB  | SER | 95  | 29.745 | 15.726 | -10.618 | 1.00 | 77.27 | C1 |
| ATOM | 2516 | OG  | SER | 95  | 31.066 | 15.770 | -10.095 | 1.00 | 77.30 | C1 |
| ATOM | 2517 | C   | SER | 95  | 27.801 | 17.221 | -10.024 | 1.00 | 76.59 | C1 |
| ATOM | 2518 | O   | SER | 95  | 26.679 | 17.383 | -9.499  | 1.00 | 76.68 | C1 |
| ATOM | 2519 | N   | ALA | 96  | 28.234 | 17.954 | -11.053 | 1.00 | 75.05 | C1 |
| ATOM | 2520 | CA  | ALA | 96  | 27.455 | 19.086 | -11.550 | 1.00 | 73.08 | C1 |
| ATOM | 2521 | CB  | ALA | 96  | 26.078 | 18.610 | -12.037 | 1.00 | 73.32 | C1 |
| ATOM | 2522 | C   | ALA | 96  | 27.318 | 20.027 | -10.330 | 1.00 | 71.45 | C1 |
| ATOM | 2523 | O   | ALA | 96  | 26.471 | 20.959 | -10.324 | 1.00 | 72.20 | C1 |
| ATOM | 2524 | N   | ALA | 97  | 28.182 | 19.779 | -9.323  | 1.00 | 68.24 | C1 |
| ATOM | 2525 | CA  | ALA | 97  | 28.200 | 20.528 | -8.066  | 1.00 | 64.53 | C1 |
| ATOM | 2526 | CB  | ALA | 97  | 26.974 | 20.148 | -7.236  | 1.00 | 64.01 | C1 |
| ATOM | 2527 | C   | ALA | 97  | 29.461 | 20.384 | -7.202  | 1.00 | 61.89 | C1 |
| ATOM | 2528 | O   | ALA | 97  | 29.994 | 19.301 | -7.005  | 1.00 | 61.20 | C1 |
| ATOM | 2529 | N   | ALA | 98  | 29.925 | 21.507 | -6.678  | 1.00 | 59.31 | C1 |
| ATOM | 2530 | CA  | ALA | 98  | 31.081 | 21.535 | -5.794  | 1.00 | 56.05 | C1 |
| ATOM | 2531 | CB  | ALA | 98  | 31.933 | 22.771 | -6.084  | 1.00 | 55.80 | C1 |
| ATOM | 2532 | C   | ALA | 98  | 30.465 | 21.618 | -4.400  | 1.00 | 53.71 | C1 |
| ATOM | 2533 | O   | ALA | 98  | 29.341 | 22.108 | -4.253  | 1.00 | 52.98 | C1 |
| ATOM | 2534 | N   | VAL | 99  | 31.195 | 21.146 | -3.391  | 1.00 | 50.77 | C1 |
| ATOM | 2535 | CA  | VAL | 99  | 30.700 | 21.160 | -2.017  | 1.00 | 47.45 | C1 |
| ATOM | 2536 | CB  | VAL | 99  | 30.513 | 19.706 | -1.466  | 1.00 | 47.53 | C1 |
| ATOM | 2537 | CG1 | VAL | 99  | 29.641 | 19.692 | -0.210  | 1.00 | 47.19 | C1 |
| ATOM | 2538 | CG2 | VAL | 99  | 29.933 | 18.819 | -2.529  | 1.00 | 46.70 | C1 |
| ATOM | 2539 | C   | VAL | 99  | 31.693 | 21.864 | -1.107  | 1.00 | 45.49 | C1 |
| ATOM | 2540 | O   | VAL | 99  | 32.904 | 21.743 | -1.284  | 1.00 | 44.20 | C1 |
| ATOM | 2541 | N   | HIS | 100 | 31.168 | 22.613 | -0.141  | 1.00 | 43.53 | C1 |
| ATOM | 2542 | CA  | HIS | 100 | 32.008 | 23.282 | 0.851   | 1.00 | 41.02 | C1 |
| ATOM | 2543 | CB  | HIS | 100 | 31.926 | 24.804 | 0.764   | 1.00 | 42.26 | C1 |
| ATOM | 2544 | CG  | HIS | 100 | 32.416 | 25.362 | -0.526  | 1.00 | 43.68 | C1 |
| ATOM | 2545 | CD2 | HIS | 100 | 33.671 | 25.597 | -0.971  | 1.00 | 44.46 | C1 |
| ATOM | 2546 | ND1 | HIS | 100 | 31.563 | 25.698 | -1.559  | 1.00 | 44.71 | C1 |
| ATOM | 2547 | CE1 | HIS | 100 | 32.278 | 26.112 | -2.593  | 1.00 | 45.41 | C1 |
| ATOM | 2548 | NE2 | HIS | 100 | 33.558 | 26.060 | -2.263  | 1.00 | 46.23 | C1 |
| ATOM | 2549 | C   | HIS | 100 | 31.487 | 22.853 | 2.227   | 1.00 | 39.34 | C1 |
| ATOM | 2550 | O   | HIS | 100 | 30.277 | 22.772 | 2.477   | 1.00 | 37.89 | C1 |
| ATOM | 2551 | N   | VAL | 101 | 32.423 | 22.599 | 3.124   | 1.00 | 37.22 | C1 |
| ATOM | 2552 | CA  | VAL | 101 | 32.081 | 22.169 | 4.463   | 1.00 | 35.34 | C1 |
| ATOM | 2553 | CB  | VAL | 101 | 32.273 | 20.644 | 4.612   | 1.00 | 34.50 | C1 |
| ATOM | 2554 | CG1 | VAL | 101 | 33.691 | 20.325 | 4.422   | 1.00 | 34.09 | C1 |
| ATOM | 2555 | CG2 | VAL | 101 | 31.847 | 20.179 | 5.973   | 1.00 | 33.26 | C1 |
| ATOM | 2556 | C   | VAL | 101 | 32.994 | 22.813 | 5.450   | 1.00 | 33.51 | C1 |
| ATOM | 2557 | O   | VAL | 101 | 34.133 | 23.106 | 5.139   | 1.00 | 33.22 | C1 |

FIG. 3A-45

```
ATOM   2558  N    SER  102      32.488  23.006   6.655  1.00 32.89           C1
ATOM   2559  CA   SER  102      33.282  23.547   7.750  1.00 31.81           C1
ATOM   2560  CB   SER  102      33.077  25.044   7.919  1.00 32.65           C1
ATOM   2561  OG   SER  102      34.008  25.557   8.884  1.00 32.76           C1
ATOM   2562  C    SER  102      32.786  22.837   8.993  1.00 32.14           C1
ATOM   2563  O    SER  102      31.595  22.633   9.145  1.00 31.51           C1
ATOM   2564  N    ILE  103      33.708  22.478   9.887  1.00 32.69           C1
ATOM   2565  CA   ILE  103      33.383  21.774  11.127  1.00 32.36           C1
ATOM   2566  CB   ILE  103      33.837  20.322  11.005  1.00 32.02           C1
ATOM   2567  CG2  ILE  103      33.518  19.539  12.311  1.00 30.43           C1
ATOM   2568  CG1  ILE  103      33.186  19.731   9.757  1.00 29.77           C1
ATOM   2569  CD1  ILE  103      33.800  18.433   9.328  1.00 31.21           C1
ATOM   2570  C    ILE  103      34.097  22.437  12.308  1.00 33.22           C1
ATOM   2571  O    ILE  103      35.255  22.798  12.203  1.00 33.37           C1
ATOM   2572  N    THR  104      33.402  22.589  13.425  1.00 33.89           C1
ATOM   2573  CA   THR  104      33.952  23.222  14.592  1.00 34.64           C1
ATOM   2574  CB   THR  104      33.523  24.685  14.643  1.00 35.31           C1
ATOM   2575  OG1  THR  104      34.073  25.322  15.805  1.00 36.64           C1
ATOM   2576  CG2  THR  104      32.025  24.774  14.697  1.00 35.83           C1
ATOM   2577  C    THR  104      33.484  22.531  15.865  1.00 34.82           C1
ATOM   2578  O    THR  104      32.392  21.970  15.930  1.00 35.84           C1
ATOM   2579  N    HIS  105      34.305  22.606  16.894  1.00 34.86           C1
ATOM   2580  CA   HIS  105      33.998  21.958  18.158  1.00 35.82           C1
ATOM   2581  CB   HIS  105      34.956  20.792  18.452  1.00 34.73           C1
ATOM   2582  CG   HIS  105      34.945  19.743  17.398  1.00 34.83           C1
ATOM   2583  CD2  HIS  105      35.695  19.603  16.277  1.00 33.18           C1
ATOM   2584  ND1  HIS  105      34.027  18.711  17.391  1.00 34.52           C1
ATOM   2585  CE1  HIS  105      34.213  17.979  16.306  1.00 35.06           C1
ATOM   2586  NE2  HIS  105      35.217  18.497  15.615  1.00 34.71           C1
ATOM   2587  C    HIS  105      34.158  22.908  19.280  1.00 35.73           C1
ATOM   2588  O    HIS  105      34.987  23.794  19.246  1.00 33.92           C1
ATOM   2589  N    THR  106      33.390  22.611  20.299  1.00 36.77           C1
ATOM   2590  CA   THR  106      33.355  23.348  21.524  1.00 40.09           C1
ATOM   2591  CB   THR  106      32.082  24.176  21.508  1.00 40.79           C1
ATOM   2592  OG1  THR  106      32.299  25.425  22.156  1.00 43.54           C1
ATOM   2593  CG2  THR  106      30.992  23.443  22.156  1.00 42.68           C1
ATOM   2594  C    THR  106      33.358  22.224  22.608  1.00 41.25           C1
ATOM   2595  O    THR  106      33.425  21.023  22.265  1.00 41.69           C1
ATOM   2596  N    ALA  107      33.304  22.574  23.894  1.00 42.12           C1
ATOM   2597  CA   ALA  107      33.328  21.526  24.912  1.00 42.01           C1
ATOM   2598  CB   ALA  107      33.557  22.131  26.311  1.00 43.25           C1
ATOM   2599  C    ALA  107      32.003  20.768  24.874  1.00 42.28           C1
ATOM   2600  O    ALA  107      31.972  19.556  25.012  1.00 42.24           C1
ATOM   2601  N    GLU  108      30.907  21.482  24.667  1.00 42.09           C1
ATOM   2602  CA   GLU  108      29.604  20.842  24.612  1.00 41.95           C1
ATOM   2603  CB   GLU  108      28.538  21.761  25.204  1.00 44.03           C1
ATOM   2604  CG   GLU  108      28.709  22.065  26.689  1.00 48.57           C1
ATOM   2605  CD   GLU  108      27.406  21.949  27.467  1.00 50.64           C1
ATOM   2606  OE1  GLU  108      27.493  21.903  28.720  1.00 52.40           C1
ATOM   2607  OE2  GLU  108      26.306  21.905  26.838  1.00 51.79           C1
ATOM   2608  C    GLU  108      29.115  20.438  23.226  1.00 40.76           C1
ATOM   2609  O    GLU  108      28.259  19.572  23.112  1.00 40.77           C1
ATOM   2610  N    TYR  109      29.660  21.031  22.173  1.00 38.80           C1
ATOM   2611  CA   TYR  109      29.118  20.760  20.851  1.00 36.61           C1
ATOM   2612  CB   TYR  109      28.242  21.950  20.431  1.00 37.49           C1
ATOM   2613  CG   TYR  109      27.115  22.270  21.350  1.00 39.09           C1
ATOM   2614  CD1  TYR  109      25.930  21.532  21.323  1.00 39.55           C1
```

FIG. 3A-46

| ATOM | 2615 | CE1 | TYR | 109 | 24.865 | 21.844 | 22.169 | 1.00 | 40.62 | C1 |
| ATOM | 2616 | CD2 | TYR | 109 | 27.215 | 23.324 | 22.242 | 1.00 | 40.44 | C1 |
| ATOM | 2617 | CE2 | TYR | 109 | 26.166 | 23.652 | 23.088 | 1.00 | 40.89 | C1 |
| ATOM | 2618 | CZ | TYR | 109 | 24.997 | 22.913 | 23.050 | 1.00 | 41.89 | C1 |
| ATOM | 2619 | OH | TYR | 109 | 23.958 | 23.262 | 23.905 | 1.00 | 44.16 | C1 |
| ATOM | 2620 | C | TYR | 109 | 30.033 | 20.503 | 19.682 | 1.00 | 34.46 | C1 |
| ATOM | 2621 | O | TYR | 109 | 31.192 | 20.822 | 19.708 | 1.00 | 33.77 | C1 |
| ATOM | 2622 | N | ALA | 110 | 29.456 | 19.905 | 18.642 | 1.00 | 32.46 | C1 |
| ATOM | 2623 | CA | ALA | 110 | 30.128 | 19.719 | 17.376 | 1.00 | 30.31 | C1 |
| ATOM | 2624 | CB | ALA | 110 | 30.296 | 18.263 | 17.029 | 1.00 | 30.67 | C1 |
| ATOM | 2625 | C | ALA | 110 | 29.083 | 20.384 | 16.474 | 1.00 | 29.65 | C1 |
| ATOM | 2626 | O | ALA | 110 | 27.879 | 20.217 | 16.667 | 1.00 | 29.10 | C1 |
| ATOM | 2627 | N | ALA | 111 | 29.540 | 21.163 | 15.512 | 1.00 | 28.10 | C1 |
| ATOM | 2628 | CA | ALA | 111 | 28.639 | 21.853 | 14.609 | 1.00 | 26.34 | C1 |
| ATOM | 2629 | CB | ALA | 111 | 28.478 | 23.284 | 15.055 | 1.00 | 26.00 | C1 |
| ATOM | 2630 | C | ALA | 111 | 29.257 | 21.788 | 13.211 | 1.00 | 25.08 | C1 |
| ATOM | 2631 | O | ALA | 111 | 30.464 | 21.589 | 13.065 | 1.00 | 24.72 | C1 |
| ATOM | 2632 | N | ALA | 112 | 28.441 | 21.946 | 12.185 | 1.00 | 24.25 | C1 |
| ATOM | 2633 | CA | ALA | 112 | 28.974 | 21.875 | 10.820 | 1.00 | 24.68 | C1 |
| ATOM | 2634 | CB | ALA | 112 | 29.189 | 20.419 | 10.395 | 1.00 | 21.72 | C1 |
| ATOM | 2635 | C | ALA | 112 | 28.044 | 22.566 | 9.838 | 1.00 | 25.11 | C1 |
| ATOM | 2636 | O | ALA | 112 | 26.848 | 22.689 | 10.058 | 1.00 | 25.98 | C1 |
| ATOM | 2637 | N | GLN | 113 | 28.597 | 23.045 | 8.753 | 1.00 | 26.72 | C1 |
| ATOM | 2638 | CA | GLN | 113 | 27.749 | 23.684 | 7.781 | 1.00 | 28.89 | C1 |
| ATOM | 2639 | CB | GLN | 113 | 27.860 | 25.200 | 7.850 | 1.00 | 29.76 | C1 |
| ATOM | 2640 | CG | GLN | 113 | 29.227 | 25.758 | 7.596 | 1.00 | 32.46 | C1 |
| ATOM | 2641 | CD | GLN | 113 | 29.173 | 27.298 | 7.531 | 1.00 | 33.88 | C1 |
| ATOM | 2642 | OE1 | GLN | 113 | 28.130 | 27.865 | 7.233 | 1.00 | 36.87 | C1 |
| ATOM | 2643 | NE2 | GLN | 113 | 30.276 | 27.955 | 7.797 | 1.00 | 34.55 | C1 |
| ATOM | 2644 | C | GLN | 113 | 28.204 | 23.199 | 6.447 | 1.00 | 28.78 | C1 |
| ATOM | 2645 | O | GLN | 113 | 29.369 | 22.848 | 6.248 | 1.00 | 27.81 | C1 |
| ATOM | 2646 | N | VAL | 114 | 27.259 | 23.153 | 5.535 | 1.00 | 29.54 | C1 |
| ATOM | 2647 | CA | VAL | 114 | 27.572 | 22.712 | 4.204 | 1.00 | 29.98 | C1 |
| ATOM | 2648 | CB | VAL | 114 | 27.078 | 21.237 | 3.967 | 1.00 | 30.15 | C1 |
| ATOM | 2649 | CG1 | VAL | 114 | 27.057 | 20.936 | 2.442 | 1.00 | 29.05 | C1 |
| ATOM | 2650 | CG2 | VAL | 114 | 27.992 | 20.250 | 4.686 | 1.00 | 28.96 | C1 |
| ATOM | 2651 | C | VAL | 114 | 26.876 | 23.603 | 3.177 | 1.00 | 29.81 | C1 |
| ATOM | 2652 | O | VAL | 114 | 25.766 | 24.049 | 3.378 | 1.00 | 29.57 | C1 |
| ATOM | 2653 | N | VAL | 115 | 27.560 | 23.858 | 2.086 | 1.00 | 30.84 | C1 |
| ATOM | 2654 | CA | VAL | 115 | 26.971 | 24.574 | 0.986 | 1.00 | 32.60 | C1 |
| ATOM | 2655 | CB | VAL | 115 | 27.618 | 25.931 | 0.695 | 1.00 | 32.10 | C1 |
| ATOM | 2656 | CG1 | VAL | 115 | 27.048 | 26.474 | -0.664 | 1.00 | 32.24 | C1 |
| ATOM | 2657 | CG2 | VAL | 115 | 27.301 | 26.925 | 1.848 | 1.00 | 32.42 | C1 |
| ATOM | 2658 | C | VAL | 115 | 27.195 | 23.691 | -0.241 | 1.00 | 34.20 | C1 |
| ATOM | 2659 | O | VAL | 115 | 28.337 | 23.287 | -0.547 | 1.00 | 34.19 | C1 |
| ATOM | 2660 | N | ILE | 116 | 26.108 | 23.355 | -0.916 | 1.00 | 35.87 | C1 |
| ATOM | 2661 | CA | ILE | 116 | 26.244 | 22.600 | -2.154 | 1.00 | 38.89 | C1 |
| ATOM | 2662 | CB | ILE | 116 | 25.349 | 21.370 | -2.186 | 1.00 | 38.31 | C1 |
| ATOM | 2663 | CG2 | ILE | 116 | 25.267 | 20.863 | -3.656 | 1.00 | 38.34 | C1 |
| ATOM | 2664 | CG1 | ILE | 116 | 25.881 | 20.292 | -1.237 | 1.00 | 36.78 | C1 |
| ATOM | 2665 | CD1 | ILE | 116 | 24.830 | 19.301 | -0.953 | 1.00 | 36.94 | C1 |
| ATOM | 2666 | C | ILE | 116 | 25.753 | 23.555 | -3.263 | 1.00 | 40.86 | C1 |
| ATOM | 2667 | O | ILE | 116 | 24.616 | 24.034 | -3.217 | 1.00 | 40.74 | C1 |
| ATOM | 2668 | N | GLU | 117 | 26.584 | 23.844 | -4.243 | 1.00 | 43.03 | C1 |
| ATOM | 2669 | CA | GLU | 117 | 26.142 | 24.728 | -5.316 | 1.00 | 45.86 | C1 |
| ATOM | 2670 | CB | GLU | 117 | 26.865 | 26.075 | -5.184 | 1.00 | 47.20 | C1 |
| ATOM | 2671 | CG | GLU | 117 | 28.404 | 25.981 | -5.155 | 1.00 | 48.86 | C1 |

FIG. 3A-47

| | | | | | | | | | | |
|---|---|---|---|---|---|---|---|---|---|---|
| ATOM | 2672 | CD | GLU | 117 | 29.015 | 27.249 | -4.545 | 1.00 | 49.86 | C1 |
| ATOM | 2673 | OE1 | GLU | 117 | 28.231 | 28.110 | -4.057 | 1.00 | 51.10 | C1 |
| ATOM | 2674 | OE2 | GLU | 117 | 30.261 | 27.380 | -4.527 | 1.00 | 50.18 | C1 |
| ATOM | 2675 | C | GLU | 117 | 26.395 | 24.073 | -6.677 | 1.00 | 46.30 | C1 |
| ATOM | 2676 | O | GLU | 117 | 27.005 | 23.029 | -6.745 | 1.00 | 45.75 | C1 |
| ATOM | 2677 | N | ALA | 118 | 25.930 | 24.667 | -7.772 | 1.00 | 48.77 | C1 |
| ATOM | 2678 | CA | ALA | 118 | 26.148 | 24.030 | -9.086 | 1.00 | 50.57 | C1 |
| ATOM | 2679 | CB | ALA | 118 | 24.913 | 24.136 | -9.897 | 1.00 | 50.60 | C1 |
| ATOM | 2680 | C | ALA | 118 | 27.371 | 24.456 | -9.924 | 1.00 | 52.10 | C1 |
| ATOM | 2681 | OT1 | ALA | 118 | 28.273 | 25.169 | -9.411 | 1.00 | 53.16 | C1 |
| ATOM | 2682 | OT2 | ALA | 118 | 27.454 | 24.034 | -11.108 | 1.00 | 54.02 | C1 |
| ATOM | 2683 | N | SER | 0 | 68.967 | 23.776 | 26.894 | 1.00 | 20.00 | AP1 |
| ATOM | 2684 | CA | SER | 0 | 68.672 | 23.405 | 28.273 | 1.00 | 20.00 | AP1 |
| ATOM | 2685 | C | SER | 0 | 68.067 | 22.002 | 28.361 | 1.00 | 20.00 | AP1 |
| ATOM | 2686 | O | SER | 0 | 68.040 | 21.159 | 27.474 | 1.00 | 20.00 | AP1 |
| ATOM | 2687 | CB | SER | 0 | 68.207 | 24.675 | 28.953 | 1.00 | 20.00 | AP1 |
| ATOM | 2688 | OG | SER | 0 | 69.266 | 25.630 | 29.017 | 1.00 | 20.00 | AP1 |
| ATOM | 2689 | CB | ALA | 1 | 68.176 | 19.343 | 30.518 | 1.00 | 84.05 | AP1 |
| ATOM | 2690 | C | ALA | 1 | 66.353 | 20.967 | 31.144 | 1.00 | 83.83 | AP1 |
| ATOM | 2691 | O | ALA | 1 | 65.915 | 20.207 | 32.017 | 1.00 | 83.53 | AP1 |
| ATOM | 2692 | N | ALA | 1 | 68.040 | 21.577 | 29.427 | 1.00 | 84.15 | AP1 |
| ATOM | 2693 | CA | ALA | 1 | 67.243 | 20.455 | 30.009 | 1.00 | 84.11 | AP1 |
| ATOM | 2694 | N | ASP | 2 | 66.766 | 22.112 | 31.200 | 1.00 | 83.55 | AP1 |
| ATOM | 2695 | CA | ASP | 2 | 66.164 | 23.057 | 32.134 | 1.00 | 83.11 | AP1 |
| ATOM | 2696 | CB | ASP | 2 | 67.112 | 24.243 | 32.351 | 1.00 | 83.20 | AP1 |
| ATOM | 2697 | CG | ASP | 2 | 66.448 | 25.416 | 33.064 | 1.00 | 83.58 | AP1 |
| ATOM | 2698 | OD1 | ASP | 2 | 65.906 | 25.229 | 34.181 | 1.00 | 83.39 | AP1 |
| ATOM | 2699 | OD2 | ASP | 2 | 66.481 | 26.536 | 32.505 | 1.00 | 83.39 | AP1 |
| ATOM | 2700 | C | ASP | 2 | 64.857 | 23.534 | 31.486 | 1.00 | 82.74 | AP1 |
| ATOM | 2701 | O | ASP | 2 | 63.759 | 23.407 | 32.062 | 1.00 | 82.60 | AP1 |
| ATOM | 2702 | N | THR | 3 | 64.988 | 24.067 | 30.273 | 1.00 | 81.72 | AP1 |
| ATOM | 2703 | CA | THR | 3 | 63.836 | 24.561 | 29.539 | 1.00 | 80.65 | AP1 |
| ATOM | 2704 | CB | THR | 3 | 64.230 | 25.062 | 28.148 | 1.00 | 80.87 | AP1 |
| ATOM | 2705 | OG1 | THR | 3 | 64.460 | 23.941 | 27.283 | 1.00 | 81.31 | AP1 |
| ATOM | 2706 | CG2 | THR | 3 | 65.495 | 25.900 | 28.237 | 1.00 | 80.59 | AP1 |
| ATOM | 2707 | C | THR | 3 | 62.793 | 23.467 | 29.379 | 1.00 | 79.71 | AP1 |
| ATOM | 2708 | O | THR | 3 | 61.605 | 23.759 | 29.317 | 1.00 | 79.30 | AP1 |
| ATOM | 2709 | N | LEU | 4 | 63.222 | 22.208 | 29.321 | 1.00 | 78.77 | AP1 |
| ATOM | 2710 | CA | LEU | 4 | 62.251 | 21.132 | 29.156 | 1.00 | 78.22 | AP1 |
| ATOM | 2711 | CB | LEU | 4 | 62.923 | 19.801 | 28.851 | 1.00 | 77.88 | AP1 |
| ATOM | 2712 | CG | LEU | 4 | 61.828 | 18.727 | 28.731 | 1.00 | 77.68 | AP1 |
| ATOM | 2713 | CD1 | LEU | 4 | 60.998 | 19.049 | 27.513 | 1.00 | 77.33 | AP1 |
| ATOM | 2714 | CD2 | LEU | 4 | 62.403 | 17.321 | 28.629 | 1.00 | 77.20 | AP1 |
| ATOM | 2715 | C | LEU | 4 | 61.331 | 20.916 | 30.346 | 1.00 | 78.03 | AP1 |
| ATOM | 2716 | O | LEU | 4 | 60.136 | 20.639 | 30.178 | 1.00 | 77.68 | AP1 |
| ATOM | 2717 | N | ALA | 5 | 61.886 | 21.017 | 31.549 | 1.00 | 77.86 | AP1 |
| ATOM | 2718 | CA | ALA | 5 | 61.085 | 20.810 | 32.747 | 1.00 | 77.70 | AP1 |
| ATOM | 2719 | CB | ALA | 5 | 62.017 | 20.587 | 33.932 | 1.00 | 78.40 | AP1 |
| ATOM | 2720 | C | ALA | 5 | 60.210 | 22.036 | 33.016 | 1.00 | 76.70 | AP1 |
| ATOM | 2721 | O | ALA | 5 | 59.170 | 21.935 | 33.663 | 1.00 | 76.78 | AP1 |
| ATOM | 2722 | N | ARG | 6 | 60.632 | 23.190 | 32.514 | 1.00 | 75.48 | AP1 |
| ATOM | 2723 | CA | ARG | 6 | 59.832 | 24.397 | 32.661 | 1.00 | 74.44 | AP1 |
| ATOM | 2724 | CB | ARG | 6 | 60.684 | 25.657 | 32.435 | 1.00 | 73.87 | AP1 |
| ATOM | 2725 | CG | ARG | 6 | 61.473 | 26.120 | 33.670 | 1.00 | 73.31 | AP1 |
| ATOM | 2726 | CD | ARG | 6 | 61.862 | 27.604 | 33.562 | 1.00 | 72.64 | AP1 |
| ATOM | 2727 | NE | ARG | 6 | 63.062 | 27.818 | 32.760 | 1.00 | 71.95 | AP1 |
| ATOM | 2728 | CZ | ARG | 6 | 63.467 | 28.995 | 32.277 | 1.00 | 71.96 | AP1 |

FIG. 3A-48

| ATOM | 2729 | NH1 | ARG | 6 | 62.761 | 30.091 | 32.501 | 1.00 | 71.89 | AP1 |
|------|------|-----|-----|---|--------|--------|--------|------|-------|-----|
| ATOM | 2730 | NH2 | ARG | 6 | 64.600 | 29.082 | 31.580 | 1.00 | 71.79 | AP1 |
| ATOM | 2731 | C | ARG | 6 | 58.668 | 24.341 | 31.640 | 1.00 | 74.00 | AP1 |
| ATOM | 2732 | O | ARG | 6 | 57.600 | 24.921 | 31.880 | 1.00 | 74.10 | AP1 |
| ATOM | 2733 | N | VAL | 7 | 58.882 | 23.635 | 30.519 | 1.00 | 72.52 | AP1 |
| ATOM | 2734 | CA | VAL | 7 | 57.875 | 23.476 | 29.474 | 1.00 | 71.13 | AP1 |
| ATOM | 2735 | CB | VAL | 7 | 58.528 | 23.150 | 28.081 | 1.00 | 70.76 | AP1 |
| ATOM | 2736 | CG1 | VAL | 7 | 57.473 | 22.682 | 27.082 | 1.00 | 69.94 | AP1 |
| ATOM | 2737 | CG2 | VAL | 7 | 59.224 | 24.379 | 27.531 | 1.00 | 70.02 | AP1 |
| ATOM | 2738 | C | VAL | 7 | 56.880 | 22.362 | 29.842 | 1.00 | 70.99 | AP1 |
| ATOM | 2739 | O | VAL | 7 | 55.696 | 22.448 | 29.487 | 1.00 | 70.50 | AP1 |
| ATOM | 2740 | N | THR | 8 | 57.343 | 21.315 | 30.532 | 1.00 | 70.31 | AP1 |
| ATOM | 2741 | CA | THR | 8 | 56.437 | 20.228 | 30.924 | 1.00 | 69.89 | AP1 |
| ATOM | 2742 | CB | THR | 8 | 57.207 | 19.000 | 31.436 | 1.00 | 70.39 | AP1 |
| ATOM | 2743 | OG1 | THR | 8 | 58.176 | 18.604 | 30.455 | 1.00 | 71.27 | AP1 |
| ATOM | 2744 | CG2 | THR | 8 | 56.258 | 17.844 | 31.677 | 1.00 | 69.84 | AP1 |
| ATOM | 2745 | C | THR | 8 | 55.496 | 20.740 | 32.028 | 1.00 | 69.21 | AP1 |
| ATOM | 2746 | O | THR | 8 | 54.310 | 20.395 | 32.074 | 1.00 | 68.80 | AP1 |
| ATOM | 2747 | N | LYS | 9 | 56.033 | 21.588 | 32.902 | 1.00 | 68.48 | AP1 |
| ATOM | 2748 | CA | LYS | 9 | 55.243 | 22.183 | 33.976 | 1.00 | 67.55 | AP1 |
| ATOM | 2749 | CB | LYS | 9 | 56.112 | 23.128 | 34.830 | 1.00 | 67.47 | AP1 |
| ATOM | 2750 | CG | LYS | 9 | 55.319 | 23.931 | 35.878 | 1.00 | 68.25 | AP1 |
| ATOM | 2751 | CD | LYS | 9 | 56.210 | 24.545 | 36.983 | 1.00 | 68.59 | AP1 |
| ATOM | 2752 | CE | LYS | 9 | 55.418 | 25.517 | 37.861 | 1.00 | 68.36 | AP1 |
| ATOM | 2753 | NZ | LYS | 9 | 54.123 | 24.921 | 38.323 | 1.00 | 68.66 | AP1 |
| ATOM | 2754 | C | LYS | 9 | 54.103 | 22.966 | 33.329 | 1.00 | 66.72 | AP1 |
| ATOM | 2755 | O | LYS | 9 | 52.939 | 22.773 | 33.659 | 1.00 | 66.23 | AP1 |
| ATOM | 2756 | N | ILE | 10 | 54.468 | 23.841 | 32.395 | 1.00 | 66.18 | AP1 |
| ATOM | 2757 | CA | ILE | 10 | 53.531 | 24.685 | 31.660 | 1.00 | 65.16 | AP1 |
| ATOM | 2758 | CB | ILE | 10 | 54.291 | 25.543 | 30.628 | 1.00 | 65.28 | AP1 |
| ATOM | 2759 | CG2 | ILE | 10 | 53.314 | 26.400 | 29.843 | 1.00 | 64.89 | AP1 |
| ATOM | 2760 | CG1 | ILE | 10 | 55.385 | 26.357 | 31.319 | 1.00 | 64.70 | AP1 |
| ATOM | 2761 | CD1 | ILE | 10 | 55.044 | 27.783 | 31.590 | 1.00 | 65.19 | AP1 |
| ATOM | 2762 | C | ILE | 10 | 52.441 | 23.904 | 30.912 | 1.00 | 64.66 | AP1 |
| ATOM | 2763 | O | ILE | 10 | 51.287 | 24.308 | 30.896 | 1.00 | 64.47 | AP1 |
| ATOM | 2764 | N | ILE | 11 | 52.815 | 22.789 | 30.298 | 1.00 | 64.80 | AP1 |
| ATOM | 2765 | CA | ILE | 11 | 51.889 | 21.963 | 29.521 | 1.00 | 65.01 | AP1 |
| ATOM | 2766 | CB | ILE | 11 | 52.663 | 20.931 | 28.676 | 1.00 | 64.05 | AP1 |
| ATOM | 2767 | CG2 | ILE | 11 | 51.740 | 19.861 | 28.151 | 1.00 | 63.58 | AP1 |
| ATOM | 2768 | CG1 | ILE | 11 | 53.380 | 21.657 | 27.546 | 1.00 | 63.60 | AP1 |
| ATOM | 2769 | CD1 | ILE | 11 | 54.255 | 20.768 | 26.702 | 1.00 | 63.69 | AP1 |
| ATOM | 2770 | C | ILE | 11 | 50.898 | 21.251 | 30.405 | 1.00 | 66.13 | AP1 |
| ATOM | 2771 | O | ILE | 11 | 49.685 | 21.345 | 30.202 | 1.00 | 65.72 | AP1 |
| ATOM | 2772 | N | VAL | 12 | 51.428 | 20.538 | 31.395 | 1.00 | 67.85 | AP1 |
| ATOM | 2773 | CA | VAL | 12 | 50.607 | 19.799 | 32.342 | 1.00 | 69.32 | AP1 |
| ATOM | 2774 | CB | VAL | 12 | 51.492 | 19.164 | 33.428 | 1.00 | 70.03 | AP1 |
| ATOM | 2775 | CG1 | VAL | 12 | 50.641 | 18.275 | 34.359 | 1.00 | 70.41 | AP1 |
| ATOM | 2776 | CG2 | VAL | 12 | 52.600 | 18.352 | 32.763 | 1.00 | 70.07 | AP1 |
| ATOM | 2777 | C | VAL | 12 | 49.586 | 20.734 | 32.992 | 1.00 | 70.16 | AP1 |
| ATOM | 2778 | O | VAL | 12 | 48.399 | 20.418 | 33.059 | 1.00 | 69.91 | AP1 |
| ATOM | 2779 | N | ASP | 13 | 50.056 | 21.890 | 33.455 | 1.00 | 71.30 | AP1 |
| ATOM | 2780 | CA | ASP | 13 | 49.181 | 22.866 | 34.085 | 1.00 | 72.67 | AP1 |
| ATOM | 2781 | CB | ASP | 13 | 49.946 | 24.159 | 34.443 | 1.00 | 73.98 | AP1 |
| ATOM | 2782 | CG | ASP | 13 | 50.819 | 24.015 | 35.704 | 1.00 | 75.23 | AP1 |
| ATOM | 2783 | OD1 | ASP | 13 | 50.890 | 22.888 | 36.255 | 1.00 | 76.30 | AP1 |
| ATOM | 2784 | OD2 | ASP | 13 | 51.440 | 25.026 | 36.144 | 1.00 | 75.56 | AP1 |
| ATOM | 2785 | C | ASP | 13 | 48.043 | 23.214 | 33.148 | 1.00 | 72.95 | AP1 |

FIG. 3A-49

| ATOM | 2786 | O | ASP | 13 | 46.876 | 23.099 | 33.513 | 1.00 | 73.09 | AP1 |
|---|---|---|---|---|---|---|---|---|---|---|
| ATOM | 2787 | N | ARG | 14 | 48.398 | 23.620 | 31.931 | 1.00 | 73.49 | AP1 |
| ATOM | 2788 | CA | ARG | 14 | 47.429 | 24.028 | 30.931 | 1.00 | 73.84 | AP1 |
| ATOM | 2789 | CB | ARG | 14 | 48.141 | 24.758 | 29.814 | 1.00 | 73.31 | AP1 |
| ATOM | 2790 | CG | ARG | 14 | 48.317 | 26.230 | 30.103 | 1.00 | 72.15 | AP1 |
| ATOM | 2791 | CD | ARG | 14 | 47.264 | 27.078 | 29.385 | 1.00 | 70.90 | AP1 |
| ATOM | 2792 | NE | ARG | 14 | 45.891 | 26.836 | 29.822 | 1.00 | 69.36 | AP1 |
| ATOM | 2793 | CZ | ARG | 14 | 45.389 | 27.215 | 30.997 | 1.00 | 68.61 | AP1 |
| ATOM | 2794 | NH1 | ARG | 14 | 46.138 | 27.869 | 31.883 | 1.00 | 66.65 | AP1 |
| ATOM | 2795 | NH2 | ARG | 14 | 44.123 | 26.925 | 31.282 | 1.00 | 67.78 | AP1 |
| ATOM | 2796 | C | ARG | 14 | 46.515 | 22.990 | 30.332 | 1.00 | 74.92 | AP1 |
| ATOM | 2797 | O | ARG | 14 | 45.306 | 23.073 | 30.506 | 1.00 | 75.02 | AP1 |
| ATOM | 2798 | N | LEU | 15 | 47.073 | 22.020 | 29.621 | 1.00 | 76.33 | AP1 |
| ATOM | 2799 | CA | LEU | 15 | 46.254 | 20.988 | 28.980 | 1.00 | 77.82 | AP1 |
| ATOM | 2800 | CB | LEU | 15 | 47.016 | 20.345 | 27.824 | 1.00 | 77.66 | AP1 |
| ATOM | 2801 | CG | LEU | 15 | 47.558 | 21.237 | 26.711 | 1.00 | 77.79 | AP1 |
| ATOM | 2802 | CD1 | LEU | 15 | 48.132 | 20.348 | 25.613 | 1.00 | 77.88 | AP1 |
| ATOM | 2803 | CD2 | LEU | 15 | 46.455 | 22.123 | 26.158 | 1.00 | 77.57 | AP1 |
| ATOM | 2804 | C | LEU | 15 | 45.773 | 19.869 | 29.899 | 1.00 | 79.19 | AP1 |
| ATOM | 2805 | O | LEU | 15 | 46.049 | 19.859 | 31.110 | 1.00 | 79.28 | AP1 |
| ATOM | 2806 | N | GLY | 16 | 45.048 | 18.922 | 29.306 | 1.00 | 80.67 | AP1 |
| ATOM | 2807 | CA | GLY | 16 | 44.559 | 17.789 | 30.071 | 1.00 | 82.85 | AP1 |
| ATOM | 2808 | C | GLY | 16 | 45.767 | 17.061 | 30.637 | 1.00 | 84.35 | AP1 |
| ATOM | 2809 | O | GLY | 16 | 45.945 | 16.974 | 31.855 | 1.00 | 84.11 | AP1 |
| ATOM | 2810 | N | VAL | 17 | 46.607 | 16.578 | 29.721 | 1.00 | 85.77 | AP1 |
| ATOM | 2811 | CA | VAL | 17 | 47.844 | 15.839 | 30.001 | 1.00 | 87.22 | AP1 |
| ATOM | 2812 | CB | VAL | 17 | 49.070 | 16.474 | 29.301 | 1.00 | 87.11 | AP1 |
| ATOM | 2813 | CG1 | VAL | 17 | 48.710 | 16.869 | 27.893 | 1.00 | 87.54 | AP1 |
| ATOM | 2814 | CG2 | VAL | 17 | 49.584 | 17.663 | 30.103 | 1.00 | 87.15 | AP1 |
| ATOM | 2815 | C | VAL | 17 | 48.289 | 15.579 | 31.429 | 1.00 | 88.17 | AP1 |
| ATOM | 2816 | O | VAL | 17 | 48.000 | 16.321 | 32.373 | 1.00 | 88.26 | AP1 |
| ATOM | 2817 | N | ASP | 18 | 49.056 | 14.505 | 31.537 | 1.00 | 89.54 | AP1 |
| ATOM | 2818 | CA | ASP | 18 | 49.619 | 14.041 | 32.787 | 1.00 | 90.63 | AP1 |
| ATOM | 2819 | CB | ASP | 18 | 49.655 | 12.509 | 32.759 | 1.00 | 91.40 | AP1 |
| ATOM | 2820 | CG | ASP | 18 | 48.388 | 11.910 | 32.118 | 1.00 | 92.34 | AP1 |
| ATOM | 2821 | OD1 | ASP | 18 | 47.900 | 10.854 | 32.597 | 1.00 | 92.79 | AP1 |
| ATOM | 2822 | OD2 | ASP | 18 | 47.881 | 12.497 | 31.128 | 1.00 | 92.45 | AP1 |
| ATOM | 2823 | C | ASP | 18 | 51.017 | 14.660 | 32.913 | 1.00 | 90.91 | AP1 |
| ATOM | 2824 | O | ASP | 18 | 51.150 | 15.889 | 32.892 | 1.00 | 91.13 | AP1 |
| ATOM | 2825 | N | GLU | 19 | 52.053 | 13.839 | 33.037 | 1.00 | 90.94 | AP1 |
| ATOM | 2826 | CA | GLU | 19 | 53.415 | 14.359 | 33.152 | 1.00 | 91.05 | AP1 |
| ATOM | 2827 | CB | GLU | 19 | 53.824 | 14.457 | 34.628 | 1.00 | 91.09 | AP1 |
| ATOM | 2828 | CG | GLU | 19 | 54.855 | 15.536 | 34.961 | 1.00 | 91.09 | AP1 |
| ATOM | 2829 | CD | GLU | 19 | 56.226 | 15.279 | 34.357 | 1.00 | 91.30 | AP1 |
| ATOM | 2830 | OE1 | GLU | 19 | 56.573 | 14.093 | 34.145 | 1.00 | 91.36 | AP1 |
| ATOM | 2831 | OE2 | GLU | 19 | 56.966 | 16.263 | 34.117 | 1.00 | 91.19 | AP1 |
| ATOM | 2832 | C | GLU | 19 | 54.284 | 13.352 | 32.409 | 1.00 | 91.17 | AP1 |
| ATOM | 2833 | O | GLU | 19 | 55.365 | 13.670 | 31.906 | 1.00 | 91.03 | AP1 |
| ATOM | 2834 | N | ALA | 20 | 53.787 | 12.122 | 32.352 | 1.00 | 91.10 | AP1 |
| ATOM | 2835 | CA | ALA | 20 | 54.470 | 11.056 | 31.650 | 1.00 | 90.83 | AP1 |
| ATOM | 2836 | CB | ALA | 20 | 54.346 | 9.742 | 32.422 | 1.00 | 90.97 | AP1 |
| ATOM | 2837 | C | ALA | 20 | 53.745 | 10.975 | 30.319 | 1.00 | 90.53 | AP1 |
| ATOM | 2838 | O | ALA | 20 | 53.250 | 9.921 | 29.921 | 1.00 | 90.54 | AP1 |
| ATOM | 2839 | N | ASP | 21 | 53.673 | 12.120 | 29.649 | 1.00 | 90.01 | AP1 |
| ATOM | 2840 | CA | ASP | 21 | 53.011 | 12.240 | 28.356 | 1.00 | 89.51 | AP1 |
| ATOM | 2841 | CB | ASP | 21 | 51.573 | 12.703 | 28.540 | 1.00 | 90.00 | AP1 |
| ATOM | 2842 | CG | ASP | 21 | 50.671 | 11.607 | 29.018 | 1.00 | 90.37 | AP1 |

FIG. 3A-50

| ATOM | 2843 | OD1 | ASP | 21 | 51.172 | 10.479 | 29.200 | 1.00 | 90.49 | AP1 |
|------|------|-----|-----|----|--------|--------|--------|------|-------|-----|
| ATOM | 2844 | OD2 | ASP | 21 | 49.463 | 11.878 | 29.201 | 1.00 | 90.73 | AP1 |
| ATOM | 2845 | C | ASP | 21 | 53.742 | 13.265 | 27.512 | 1.00 | 88.90 | AP1 |
| ATOM | 2846 | O | ASP | 21 | 53.788 | 13.161 | 26.288 | 1.00 | 88.82 | AP1 |
| ATOM | 2847 | N | VAL | 22 | 54.287 | 14.273 | 28.186 | 1.00 | 88.02 | AP1 |
| ATOM | 2848 | CA | VAL | 22 | 55.034 | 15.336 | 27.534 | 1.00 | 86.78 | AP1 |
| ATOM | 2849 | CB | VAL | 22 | 55.323 | 16.508 | 28.529 | 1.00 | 87.06 | AP1 |
| ATOM | 2850 | CG1 | VAL | 22 | 56.038 | 17.662 | 27.822 | 1.00 | 86.97 | AP1 |
| ATOM | 2851 | CG2 | VAL | 22 | 54.014 | 16.997 | 29.147 | 1.00 | 87.18 | AP1 |
| ATOM | 2852 | C | VAL | 22 | 56.348 | 14.744 | 27.032 | 1.00 | 85.76 | AP1 |
| ATOM | 2853 | O | VAL | 22 | 57.414 | 14.993 | 27.596 | 1.00 | 85.65 | AP1 |
| ATOM | 2854 | N | LYS | 23 | 56.253 | 13.930 | 25.985 | 1.00 | 84.59 | AP1 |
| ATOM | 2855 | CA | LYS | 23 | 57.427 | 13.314 | 25.382 | 1.00 | 83.57 | AP1 |
| ATOM | 2856 | CB | LYS | 23 | 57.121 | 11.861 | 24.978 | 1.00 | 83.52 | AP1 |
| ATOM | 2857 | C | LYS | 23 | 57.719 | 14.171 | 24.154 | 1.00 | 82.69 | AP1 |
| ATOM | 2858 | O | LYS | 23 | 56.838 | 14.353 | 23.317 | 1.00 | 82.89 | AP1 |
| ATOM | 2859 | N | LEU | 24 | 58.943 | 14.691 | 24.056 | 1.00 | 81.40 | AP1 |
| ATOM | 2860 | CA | LEU | 24 | 59.356 | 15.573 | 22.955 | 1.00 | 80.08 | AP1 |
| ATOM | 2861 | CB | LEU | 24 | 60.872 | 15.489 | 22.737 | 1.00 | 79.75 | AP1 |
| ATOM | 2862 | CG | LEU | 24 | 61.731 | 16.258 | 23.739 | 1.00 | 79.50 | AP1 |
| ATOM | 2863 | CD1 | LEU | 24 | 61.624 | 15.608 | 25.106 | 1.00 | 79.62 | AP1 |
| ATOM | 2864 | CD2 | LEU | 24 | 63.163 | 16.267 | 23.275 | 1.00 | 79.59 | AP1 |
| ATOM | 2865 | C | LEU | 24 | 58.655 | 15.423 | 21.610 | 1.00 | 79.43 | AP1 |
| ATOM | 2866 | O | LEU | 24 | 58.428 | 16.416 | 20.920 | 1.00 | 79.17 | AP1 |
| ATOM | 2867 | N | GLU | 25 | 58.306 | 14.198 | 21.235 | 1.00 | 78.68 | AP1 |
| ATOM | 2868 | CA | GLU | 25 | 57.650 | 13.981 | 19.952 | 1.00 | 78.37 | AP1 |
| ATOM | 2869 | CB | GLU | 25 | 57.965 | 12.579 | 19.408 | 1.00 | 78.68 | AP1 |
| ATOM | 2870 | CG | GLU | 25 | 59.443 | 12.271 | 19.291 | 1.00 | 79.23 | AP1 |
| ATOM | 2871 | CD | GLU | 25 | 59.891 | 11.221 | 20.293 | 1.00 | 79.42 | AP1 |
| ATOM | 2872 | OE1 | GLU | 25 | 59.178 | 11.021 | 21.303 | 1.00 | 79.38 | AP1 |
| ATOM | 2873 | OE2 | GLU | 25 | 60.956 | 10.606 | 20.072 | 1.00 | 79.41 | AP1 |
| ATOM | 2874 | C | GLU | 25 | 56.138 | 14.163 | 19.977 | 1.00 | 77.58 | AP1 |
| ATOM | 2875 | O | GLU | 25 | 55.499 | 14.132 | 18.931 | 1.00 | 77.72 | AP1 |
| ATOM | 2876 | N | ALA | 26 | 55.566 | 14.345 | 21.161 | 1.00 | 76.67 | AP1 |
| ATOM | 2877 | CA | ALA | 26 | 54.123 | 14.513 | 21.286 | 1.00 | 75.78 | AP1 |
| ATOM | 2878 | CB | ALA | 26 | 53.695 | 14.309 | 22.740 | 1.00 | 75.80 | AP1 |
| ATOM | 2879 | C | ALA | 26 | 53.625 | 15.869 | 20.790 | 1.00 | 75.27 | AP1 |
| ATOM | 2880 | O | ALA | 26 | 54.006 | 16.920 | 21.328 | 1.00 | 75.04 | AP1 |
| ATOM | 2881 | N | SER | 27 | 52.783 | 15.839 | 19.755 | 1.00 | 74.60 | AP1 |
| ATOM | 2882 | CA | SER | 27 | 52.188 | 17.064 | 19.214 | 1.00 | 73.92 | AP1 |
| ATOM | 2883 | CB | SER | 27 | 51.502 | 16.804 | 17.874 | 1.00 | 73.95 | AP1 |
| ATOM | 2884 | OG | SER | 27 | 50.754 | 17.940 | 17.470 | 1.00 | 73.19 | AP1 |
| ATOM | 2885 | C | SER | 27 | 51.141 | 17.561 | 20.205 | 1.00 | 73.32 | AP1 |
| ATOM | 2886 | O | SER | 27 | 50.448 | 16.765 | 20.839 | 1.00 | 73.44 | AP1 |
| ATOM | 2887 | N | PHE | 28 | 51.020 | 18.874 | 20.333 | 1.00 | 72.76 | AP1 |
| ATOM | 2888 | CA | PHE | 28 | 50.057 | 19.439 | 21.264 | 1.00 | 72.39 | AP1 |
| ATOM | 2889 | CB | PHE | 28 | 50.196 | 20.969 | 21.345 | 1.00 | 71.67 | AP1 |
| ATOM | 2890 | CG | PHE | 28 | 51.538 | 21.431 | 21.825 | 1.00 | 70.96 | AP1 |
| ATOM | 2891 | CD1 | PHE | 28 | 51.948 | 21.175 | 23.131 | 1.00 | 70.16 | AP1 |
| ATOM | 2892 | CD2 | PHE | 28 | 52.407 | 22.105 | 20.962 | 1.00 | 70.39 | AP1 |
| ATOM | 2893 | CE1 | PHE | 28 | 53.207 | 21.579 | 23.571 | 1.00 | 69.79 | AP1 |
| ATOM | 2894 | CE2 | PHE | 28 | 53.668 | 22.515 | 21.393 | 1.00 | 69.61 | AP1 |
| ATOM | 2895 | CZ | PHE | 28 | 54.068 | 22.251 | 22.697 | 1.00 | 69.78 | AP1 |
| ATOM | 2896 | C | PHE | 28 | 48.635 | 19.090 | 20.870 | 1.00 | 72.17 | AP1 |
| ATOM | 2897 | O | PHE | 28 | 47.913 | 18.445 | 21.628 | 1.00 | 71.91 | AP1 |
| ATOM | 2898 | N | LYS | 29 | 48.239 | 19.499 | 19.675 | 1.00 | 72.50 | AP1 |
| ATOM | 2899 | CA | LYS | 29 | 46.877 | 19.262 | 19.244 | 1.00 | 73.27 | AP1 |

FIG. 3A-51

| | | | | | | | | | |
|---|---|---|---|---|---|---|---|---|---|
| ATOM | 2900 | CB | LYS | 29 | 46.622 | 19.945 | 17.898 | 1.00 73.40 | AP1 |
| ATOM | 2901 | CG | LYS | 29 | 47.348 | 21.272 | 17.766 | 1.00 73.52 | AP1 |
| ATOM | 2902 | CD | LYS | 29 | 46.788 | 22.164 | 16.669 | 1.00 73.98 | AP1 |
| ATOM | 2903 | CE | LYS | 29 | 45.573 | 22.953 | 17.146 | 1.00 74.17 | AP1 |
| ATOM | 2904 | NZ | LYS | 29 | 45.197 | 24.052 | 16.207 | 1.00 73.83 | AP1 |
| ATOM | 2905 | C | LYS | 29 | 46.551 | 17.782 | 19.170 | 1.00 73.71 | AP1 |
| ATOM | 2906 | O | LYS | 29 | 45.597 | 17.329 | 19.805 | 1.00 73.88 | AP1 |
| ATOM | 2907 | N | GLU | 30 | 47.368 | 17.023 | 18.446 | 1.00 74.16 | AP1 |
| ATOM | 2908 | CA | GLU | 30 | 47.126 | 15.590 | 18.271 | 1.00 74.65 | AP1 |
| ATOM | 2909 | CB | GLU | 30 | 48.023 | 15.049 | 17.170 | 1.00 75.07 | AP1 |
| ATOM | 2910 | CG | GLU | 30 | 47.947 | 15.852 | 15.929 | 1.00 76.86 | AP1 |
| ATOM | 2911 | CD | GLU | 30 | 48.057 | 14.977 | 14.718 | 1.00 78.78 | AP1 |
| ATOM | 2912 | OE1 | GLU | 30 | 49.056 | 14.212 | 14.642 | 1.00 79.54 | AP1 |
| ATOM | 2913 | OE2 | GLU | 30 | 47.147 | 15.046 | 13.847 | 1.00 79.33 | AP1 |
| ATOM | 2914 | C | GLU | 30 | 47.257 | 14.667 | 19.484 | 1.00 74.38 | AP1 |
| ATOM | 2915 | O | GLU | 30 | 46.340 | 13.875 | 19.775 | 1.00 74.75 | AP1 |
| ATOM | 2916 | N | ASP | 31 | 48.381 | 14.769 | 20.192 | 1.00 73.09 | AP1 |
| ATOM | 2917 | CA | ASP | 31 | 48.636 | 13.897 | 21.328 | 1.00 71.86 | AP1 |
| ATOM | 2918 | CB | ASP | 31 | 50.132 | 13.566 | 21.384 | 1.00 72.88 | AP1 |
| ATOM | 2919 | CG | ASP | 31 | 50.652 | 13.051 | 20.069 | 1.00 73.78 | AP1 |
| ATOM | 2920 | OD1 | ASP | 31 | 50.012 | 12.137 | 19.501 | 1.00 74.25 | AP1 |
| ATOM | 2921 | OD2 | ASP | 31 | 51.695 | 13.561 | 19.601 | 1.00 75.05 | AP1 |
| ATOM | 2922 | C | ASP | 31 | 48.184 | 14.360 | 22.706 | 1.00 70.61 | AP1 |
| ATOM | 2923 | O | ASP | 31 | 47.738 | 13.543 | 23.527 | 1.00 70.48 | AP1 |
| ATOM | 2924 | N | LEU | 32 | 48.286 | 15.659 | 22.970 | 1.00 68.61 | AP1 |
| ATOM | 2925 | CA | LEU | 32 | 47.934 | 16.158 | 24.296 | 1.00 66.10 | AP1 |
| ATOM | 2926 | CB | LEU | 32 | 48.990 | 17.177 | 24.745 | 1.00 65.45 | AP1 |
| ATOM | 2927 | CG | LEU | 32 | 50.426 | 16.633 | 24.584 | 1.00 64.39 | AP1 |
| ATOM | 2928 | CD1 | LEU | 32 | 51.434 | 17.693 | 24.928 | 1.00 64.02 | AP1 |
| ATOM | 2929 | CD2 | LEU | 32 | 50.618 | 15.417 | 25.477 | 1.00 63.67 | AP1 |
| ATOM | 2930 | C | LEU | 32 | 46.542 | 16.731 | 24.419 | 1.00 64.48 | AP1 |
| ATOM | 2931 | O | LEU | 32 | 46.238 | 17.395 | 25.403 | 1.00 65.05 | AP1 |
| ATOM | 2932 | N | GLY | 33 | 45.704 | 16.464 | 23.422 | 1.00 62.24 | AP1 |
| ATOM | 2933 | CA | GLY | 33 | 44.326 | 16.944 | 23.434 | 1.00 59.99 | AP1 |
| ATOM | 2934 | C | GLY | 33 | 44.083 | 18.452 | 23.397 | 1.00 58.02 | AP1 |
| ATOM | 2935 | O | GLY | 33 | 43.140 | 18.960 | 24.018 | 1.00 57.75 | AP1 |
| ATOM | 2936 | N | ALA | 34 | 44.904 | 19.172 | 22.639 | 1.00 55.70 | AP1 |
| ATOM | 2937 | CA | ALA | 34 | 44.774 | 20.612 | 22.568 | 1.00 53.12 | AP1 |
| ATOM | 2938 | CB | ALA | 34 | 46.160 | 21.243 | 22.618 | 1.00 51.50 | AP1 |
| ATOM | 2939 | C | ALA | 34 | 43.996 | 21.131 | 21.357 | 1.00 51.67 | AP1 |
| ATOM | 2940 | O | ALA | 34 | 44.030 | 20.555 | 20.265 | 1.00 52.46 | AP1 |
| ATOM | 2941 | N | ASP | 35 | 43.254 | 22.203 | 21.577 | 1.00 49.18 | AP1 |
| ATOM | 2942 | CA | ASP | 35 | 42.542 | 22.835 | 20.495 | 1.00 47.71 | AP1 |
| ATOM | 2943 | CB | ASP | 35 | 41.047 | 23.038 | 20.817 | 1.00 47.47 | AP1 |
| ATOM | 2944 | CG | ASP | 35 | 40.800 | 23.937 | 22.053 | 1.00 48.06 | AP1 |
| ATOM | 2945 | OD1 | ASP | 35 | 41.772 | 24.521 | 22.632 | 1.00 47.16 | AP1 |
| ATOM | 2946 | OD2 | ASP | 35 | 39.605 | 24.042 | 22.435 | 1.00 47.60 | AP1 |
| ATOM | 2947 | C | ASP | 35 | 43.241 | 24.178 | 20.327 | 1.00 46.40 | AP1 |
| ATOM | 2948 | O | ASP | 35 | 44.248 | 24.448 | 21.002 | 1.00 45.96 | AP1 |
| ATOM | 2949 | CA | PAN | 36 | 43.266 | 26.327 | 19.165 | 1.00 43.36 | AP1 |
| ATOM | 2950 | N | PAN | 36 | 42.705 | 25.005 | 19.437 | 1.00 44.57 | AP1 |
| ATOM | 2951 | C | PAN | 36 | 43.389 | 27.308 | 20.387 | 1.00 41.47 | AP1 |
| ATOM | 2952 | O | PAN | 36 | 44.435 | 27.948 | 20.563 | 1.00 39.31 | AP1 |
| ATOM | 2953 | O5 | PAN | 36 | 43.295 | 28.035 | 17.578 | 1.00 47.40 | AP1 |
| ATOM | 2954 | P6 | PAN | 36 | 44.014 | 27.865 | 16.147 | 1.00 49.84 | AP1 |
| ATOM | 2955 | O7 | PAN | 36 | 43.369 | 29.013 | 15.282 | 1.00 47.80 | AP1 |
| ATOM | 2956 | O8 | PAN | 36 | 43.594 | 26.426 | 15.540 | 1.00 47.32 | AP1 |

FIG. 3A-52

| ATOM | 2957 | O9 | PAN | 36 | 45.529 | 28.004 | 16.288 | 1.00 | 48.61 | AP1 |
| ATOM | 2958 | CB | PAN | 36 | 42.468 | 26.996 | 18.055 | 1.00 | 43.60 | AP1 |
| ATOM | 2959 | N | LEU | 37 | 42.317 | 27.456 | 21.167 | 1.00 | 38.73 | AP1 |
| ATOM | 2960 | CA | LEU | 37 | 42.342 | 28.307 | 22.361 | 1.00 | 38.63 | AP1 |
| ATOM | 2961 | CB | LEU | 37 | 40.970 | 28.384 | 23.033 | 1.00 | 38.45 | AP1 |
| ATOM | 2962 | CG | LEU | 37 | 40.084 | 29.491 | 22.490 | 1.00 | 39.46 | AP1 |
| ATOM | 2963 | CD1 | LEU | 37 | 38.726 | 29.397 | 23.139 | 1.00 | 40.89 | AP1 |
| ATOM | 2964 | CD2 | LEU | 37 | 40.730 | 30.853 | 22.756 | 1.00 | 39.88 | AP1 |
| ATOM | 2965 | C | LEU | 37 | 43.362 | 27.750 | 23.371 | 1.00 | 38.10 | AP1 |
| ATOM | 2966 | O | LEU | 37 | 44.001 | 28.511 | 24.055 | 1.00 | 37.69 | AP1 |
| ATOM | 2967 | N | ASP | 38 | 43.508 | 26.424 | 23.440 | 1.00 | 37.30 | AP1 |
| ATOM | 2968 | CA | ASP | 38 | 44.480 | 25.846 | 24.318 | 1.00 | 37.41 | AP1 |
| ATOM | 2969 | CB | ASP | 38 | 44.312 | 24.319 | 24.400 | 1.00 | 39.77 | AP1 |
| ATOM | 2970 | CG | ASP | 38 | 43.138 | 23.905 | 25.321 | 1.00 | 43.20 | AP1 |
| ATOM | 2971 | OD1 | ASP | 38 | 42.294 | 23.072 | 24.867 | 1.00 | 44.70 | AP1 |
| ATOM | 2972 | OD2 | ASP | 38 | 43.061 | 24.418 | 26.492 | 1.00 | 44.13 | AP1 |
| ATOM | 2973 | C | ASP | 38 | 45.895 | 26.193 | 23.881 | 1.00 | 36.29 | AP1 |
| ATOM | 2974 | O | ASP | 38 | 46.726 | 26.520 | 24.719 | 1.00 | 35.72 | AP1 |
| ATOM | 2975 | N | VAL | 39 | 46.185 | 26.160 | 22.578 | 1.00 | 34.94 | AP1 |
| ATOM | 2976 | CA | VAL | 39 | 47.551 | 26.435 | 22.162 | 1.00 | 33.47 | AP1 |
| ATOM | 2977 | CB | VAL | 39 | 47.891 | 25.854 | 20.691 | 1.00 | 33.86 | AP1 |
| ATOM | 2978 | CG1 | VAL | 39 | 46.700 | 25.967 | 19.759 | 1.00 | 33.20 | AP1 |
| ATOM | 2979 | CG2 | VAL | 39 | 49.064 | 26.630 | 20.071 | 1.00 | 34.16 | AP1 |
| ATOM | 2980 | C | VAL | 39 | 47.880 | 27.918 | 22.250 | 1.00 | 33.32 | AP1 |
| ATOM | 2981 | O | VAL | 39 | 49.011 | 28.262 | 22.562 | 1.00 | 32.10 | AP1 |
| ATOM | 2982 | N | VAL | 40 | 46.934 | 28.826 | 22.015 | 1.00 | 33.82 | AP1 |
| ATOM | 2983 | CA | VAL | 40 | 47.407 | 30.174 | 22.138 | 1.00 | 36.01 | AP1 |
| ATOM | 2984 | CB | VAL | 40 | 46.499 | 31.306 | 21.493 | 1.00 | 36.85 | AP1 |
| ATOM | 2985 | CG1 | VAL | 40 | 45.532 | 30.732 | 20.402 | 1.00 | 37.16 | AP1 |
| ATOM | 2986 | CG2 | VAL | 40 | 45.841 | 32.142 | 22.569 | 1.00 | 37.08 | AP1 |
| ATOM | 2987 | C | VAL | 40 | 47.660 | 30.465 | 23.597 | 1.00 | 36.87 | AP1 |
| ATOM | 2988 | O | VAL | 40 | 48.564 | 31.235 | 23.899 | 1.00 | 36.77 | AP1 |
| ATOM | 2989 | N | GLU | 41 | 46.904 | 29.854 | 24.505 | 1.00 | 36.94 | AP1 |
| ATOM | 2990 | CA | GLU | 41 | 47.171 | 30.150 | 25.886 | 1.00 | 38.60 | AP1 |
| ATOM | 2991 | CB | GLU | 41 | 46.139 | 29.525 | 26.818 | 1.00 | 39.00 | AP1 |
| ATOM | 2992 | CG | GLU | 41 | 46.536 | 29.747 | 28.282 | 1.00 | 40.88 | AP1 |
| ATOM | 2993 | CD | GLU | 41 | 45.374 | 30.037 | 29.249 | 1.00 | 41.76 | AP1 |
| ATOM | 2994 | OE1 | GLU | 41 | 44.188 | 29.696 | 28.971 | 1.00 | 40.79 | AP1 |
| ATOM | 2995 | OE2 | GLU | 41 | 45.683 | 30.631 | 30.315 | 1.00 | 42.76 | AP1 |
| ATOM | 2996 | C | GLU | 41 | 48.580 | 29.659 | 26.229 | 1.00 | 38.97 | AP1 |
| ATOM | 2997 | O | GLU | 41 | 49.363 | 30.383 | 26.838 | 1.00 | 38.23 | AP1 |
| ATOM | 2998 | N | LEU | 42 | 48.861 | 28.430 | 25.796 | 1.00 | 39.97 | AP1 |
| ATOM | 2999 | CA | LEU | 42 | 50.133 | 27.723 | 25.954 | 1.00 | 40.75 | AP1 |
| ATOM | 3000 | CB | LEU | 42 | 50.101 | 26.447 | 25.109 | 1.00 | 41.63 | AP1 |
| ATOM | 3001 | CG | LEU | 42 | 50.783 | 25.184 | 25.623 | 1.00 | 43.50 | AP1 |
| ATOM | 3002 | CD1 | LEU | 42 | 50.961 | 25.237 | 27.132 | 1.00 | 44.32 | AP1 |
| ATOM | 3003 | CD2 | LEU | 42 | 49.923 | 23.986 | 25.254 | 1.00 | 44.23 | AP1 |
| ATOM | 3004 | C | LEU | 42 | 51.248 | 28.618 | 25.448 | 1.00 | 41.88 | AP1 |
| ATOM | 3005 | O | LEU | 42 | 52.310 | 28.774 | 26.107 | 1.00 | 41.87 | AP1 |
| ATOM | 3006 | N | VAL | 43 | 51.019 | 29.192 | 24.271 | 1.00 | 41.61 | AP1 |
| ATOM | 3007 | CA | VAL | 43 | 52.002 | 30.099 | 23.698 | 1.00 | 43.10 | AP1 |
| ATOM | 3008 | CB | VAL | 43 | 51.573 | 30.626 | 22.280 | 1.00 | 41.95 | AP1 |
| ATOM | 3009 | CG1 | VAL | 43 | 52.461 | 31.773 | 21.849 | 1.00 | 42.05 | AP1 |
| ATOM | 3010 | CG2 | VAL | 43 | 51.683 | 29.525 | 21.272 | 1.00 | 41.68 | AP1 |
| ATOM | 3011 | C | VAL | 43 | 52.205 | 31.299 | 24.642 | 1.00 | 44.58 | AP1 |
| ATOM | 3012 | O | VAL | 43 | 53.334 | 31.710 | 24.885 | 1.00 | 44.40 | AP1 |
| ATOM | 3013 | N | MET | 44 | 51.129 | 31.846 | 25.198 | 1.00 | 46.55 | AP1 |

FIG. 3A-53

| ATOM | 3014 | CA | MET | 44 | 51.271 | 33.002 | 26.081 | 1.00 | 48.50 | AP1 |
|---|---|---|---|---|---|---|---|---|---|---|
| ATOM | 3015 | CB | MET | 44 | 49.903 | 33.596 | 26.411 | 1.00 | 50.62 | AP1 |
| ATOM | 3016 | CG | MET | 44 | 49.036 | 33.830 | 25.191 | 1.00 | 53.31 | AP1 |
| ATOM | 3017 | SD | MET | 44 | 48.010 | 35.308 | 25.274 | 1.00 | 56.48 | AP1 |
| ATOM | 3018 | CE | MET | 44 | 49.023 | 36.381 | 24.091 | 1.00 | 56.10 | AP1 |
| ATOM | 3019 | C | MET | 44 | 52.030 | 32.673 | 27.367 | 1.00 | 48.61 | AP1 |
| ATOM | 3020 | O | MET | 44 | 52.746 | 33.505 | 27.895 | 1.00 | 47.98 | AP1 |
| ATOM | 3021 | N | GLU | 45 | 51.862 | 31.456 | 27.850 | 1.00 | 49.57 | AP1 |
| ATOM | 3022 | CA | GLU | 45 | 52.537 | 30.979 | 29.047 | 1.00 | 51.80 | AP1 |
| ATOM | 3023 | CB | GLU | 45 | 52.109 | 29.544 | 29.311 | 1.00 | 53.29 | AP1 |
| ATOM | 3024 | CG | GLU | 45 | 51.852 | 29.175 | 30.731 | 1.00 | 56.51 | AP1 |
| ATOM | 3025 | CD | GLU | 45 | 50.397 | 29.315 | 31.099 | 1.00 | 58.24 | AP1 |
| ATOM | 3026 | OE1 | GLU | 45 | 50.000 | 30.403 | 31.586 | 1.00 | 60.07 | AP1 |
| ATOM | 3027 | OE2 | GLU | 45 | 49.646 | 28.331 | 30.896 | 1.00 | 59.11 | AP1 |
| ATOM | 3028 | C | GLU | 45 | 54.058 | 31.013 | 28.761 | 1.00 | 52.25 | AP1 |
| ATOM | 3029 | O | GLU | 45 | 54.836 | 31.596 | 29.526 | 1.00 | 52.28 | AP1 |
| ATOM | 3030 | N | LEU | 46 | 54.456 | 30.385 | 27.647 | 1.00 | 52.33 | AP1 |
| ATOM | 3031 | CA | LEU | 46 | 55.846 | 30.334 | 27.202 | 1.00 | 52.07 | AP1 |
| ATOM | 3032 | CB | LEU | 46 | 55.940 | 29.537 | 25.901 | 1.00 | 50.17 | AP1 |
| ATOM | 3033 | CG | LEU | 46 | 55.566 | 28.059 | 26.106 | 1.00 | 49.48 | AP1 |
| ATOM | 3034 | CD1 | LEU | 46 | 55.363 | 27.370 | 24.784 | 1.00 | 47.80 | AP1 |
| ATOM | 3035 | CD2 | LEU | 46 | 56.621 | 27.370 | 26.902 | 1.00 | 47.59 | AP1 |
| ATOM | 3036 | C | LEU | 46 | 56.453 | 31.735 | 27.029 | 1.00 | 53.27 | AP1 |
| ATOM | 3037 | O | LEU | 46 | 57.541 | 31.975 | 27.531 | 1.00 | 53.30 | AP1 |
| ATOM | 3038 | N | GLU | 47 | 55.760 | 32.656 | 26.344 | 1.00 | 54.28 | AP1 |
| ATOM | 3039 | CA | GLU | 47 | 56.254 | 34.042 | 26.152 | 1.00 | 55.41 | AP1 |
| ATOM | 3040 | CB | GLU | 47 | 55.254 | 34.859 | 25.313 | 1.00 | 55.37 | AP1 |
| ATOM | 3041 | CG | GLU | 47 | 54.558 | 34.403 | 24.030 | 1.00 | 20.00 | AP1 |
| ATOM | 3042 | CD | GLU | 47 | 53.941 | 35.658 | 23.455 | 1.00 | 20.00 | AP1 |
| ATOM | 3043 | OE1 | GLU | 47 | 53.223 | 36.026 | 24.374 | 1.00 | 20.00 | AP1 |
| ATOM | 3044 | OE2 | GLU | 47 | 53.948 | 36.198 | 22.351 | 1.00 | 20.00 | AP1 |
| ATOM | 3045 | C | GLU | 47 | 56.579 | 34.717 | 27.501 | 1.00 | 56.17 | AP1 |
| ATOM | 3046 | O | GLU | 47 | 57.556 | 35.469 | 27.650 | 1.00 | 55.04 | AP1 |
| ATOM | 3047 | N | ASP | 48 | 55.699 | 34.470 | 28.460 | 1.00 | 57.41 | AP1 |
| ATOM | 3048 | CA | ASP | 48 | 55.841 | 35.008 | 29.798 | 1.00 | 58.55 | AP1 |
| ATOM | 3049 | CB | ASP | 48 | 54.522 | 34.865 | 30.572 | 1.00 | 59.09 | AP1 |
| ATOM | 3050 | CG | ASP | 48 | 53.486 | 35.890 | 30.153 | 1.00 | 60.41 | AP1 |
| ATOM | 3051 | OD1 | ASP | 48 | 53.856 | 36.825 | 29.408 | 1.00 | 60.98 | AP1 |
| ATOM | 3052 | OD2 | ASP | 48 | 52.308 | 35.775 | 30.581 | 1.00 | 61.28 | AP1 |
| ATOM | 3053 | C | ASP | 48 | 56.959 | 34.278 | 30.523 | 1.00 | 58.58 | AP1 |
| ATOM | 3054 | O | ASP | 48 | 57.880 | 34.911 | 31.005 | 1.00 | 58.57 | AP1 |
| ATOM | 3055 | N | GLU | 49 | 56.888 | 32.952 | 30.565 | 1.00 | 59.20 | AP1 |
| ATOM | 3056 | CA | GLU | 49 | 57.884 | 32.133 | 31.251 | 1.00 | 60.01 | AP1 |
| ATOM | 3057 | CB | GLU | 49 | 57.414 | 30.677 | 31.237 | 1.00 | 60.67 | AP1 |
| ATOM | 3058 | CG | GLU | 49 | 58.437 | 29.655 | 31.732 | 1.00 | 61.95 | AP1 |
| ATOM | 3059 | CD | GLU | 49 | 58.960 | 30.013 | 33.107 | 1.00 | 62.06 | AP1 |
| ATOM | 3060 | OE1 | GLU | 49 | 58.130 | 30.354 | 33.981 | 1.00 | 62.53 | AP1 |
| ATOM | 3061 | OE2 | GLU | 49 | 60.188 | 29.960 | 33.313 | 1.00 | 61.75 | AP1 |
| ATOM | 3062 | C | GLU | 49 | 59.333 | 32.194 | 30.737 | 1.00 | 60.39 | AP1 |
| ATOM | 3063 | O | GLU | 49 | 60.240 | 31.675 | 31.382 | 1.00 | 60.33 | AP1 |
| ATOM | 3064 | N | PHE | 50 | 59.566 | 32.832 | 29.597 | 1.00 | 60.48 | AP1 |
| ATOM | 3065 | CA | PHE | 50 | 60.908 | 32.856 | 29.019 | 1.00 | 61.05 | AP1 |
| ATOM | 3066 | CB | PHE | 50 | 61.071 | 31.784 | 27.935 | 1.00 | 59.10 | AP1 |
| ATOM | 3067 | CG | PHE | 50 | 61.038 | 30.362 | 28.437 | 1.00 | 57.27 | AP1 |
| ATOM | 3068 | CD1 | PHE | 50 | 62.133 | 29.808 | 29.079 | 1.00 | 56.58 | AP1 |
| ATOM | 3069 | CD2 | PHE | 50 | 59.922 | 29.563 | 28.224 | 1.00 | 56.22 | AP1 |
| ATOM | 3070 | CE1 | PHE | 50 | 62.110 | 28.478 | 29.496 | 1.00 | 56.30 | AP1 |

FIG. 3A-54

| ATOM | 3071 | CE2 | PHE | 50 | 59.897 | 28.235 | 28.642 | 1.00 | 55.50 | AP1 |
|------|------|-----|-----|-----|--------|--------|--------|------|-------|-----|
| ATOM | 3072 | CZ  | PHE | 50 | 60.992 | 27.693 | 29.276 | 1.00 | 55.77 | AP1 |
| ATOM | 3073 | C   | PHE | 50 | 61.159 | 34.167 | 28.353 | 1.00 | 62.82 | AP1 |
| ATOM | 3074 | O   | PHE | 50 | 62.021 | 34.265 | 27.484 | 1.00 | 63.54 | AP1 |
| ATOM | 3075 | N   | ASP | 51 | 60.379 | 35.173 | 28.711 | 1.00 | 64.37 | AP1 |
| ATOM | 3076 | CA  | ASP | 51 | 60.579 | 36.477 | 28.118 | 1.00 | 66.05 | AP1 |
| ATOM | 3077 | CB  | ASP | 51 | 61.683 | 37.213 | 28.893 | 1.00 | 66.72 | AP1 |
| ATOM | 3078 | CG  | ASP | 51 | 62.056 | 38.540 | 28.265 | 1.00 | 67.40 | AP1 |
| ATOM | 3079 | OD1 | ASP | 51 | 61.179 | 39.425 | 28.226 | 1.00 | 68.03 | AP1 |
| ATOM | 3080 | OD2 | ASP | 51 | 63.215 | 38.699 | 27.808 | 1.00 | 67.55 | AP1 |
| ATOM | 3081 | C   | ASP | 51 | 60.932 | 36.430 | 26.618 | 1.00 | 66.81 | AP1 |
| ATOM | 3082 | O   | ASP | 51 | 62.073 | 36.731 | 26.236 | 1.00 | 67.47 | AP1 |
| ATOM | 3083 | N   | MET | 52 | 59.968 | 36.028 | 25.780 | 1.00 | 67.15 | AP1 |
| ATOM | 3084 | CA  | MET | 52 | 60.145 | 36.013 | 24.317 | 1.00 | 66.82 | AP1 |
| ATOM | 3085 | CB  | MET | 52 | 60.497 | 34.615 | 23.776 | 1.00 | 68.05 | AP1 |
| ATOM | 3086 | CG  | MET | 52 | 60.181 | 33.433 | 24.675 | 1.00 | 69.70 | AP1 |
| ATOM | 3087 | SD  | MET | 52 | 60.796 | 31.866 | 23.923 | 1.00 | 72.25 | AP1 |
| ATOM | 3088 | CE  | MET | 52 | 62.181 | 31.386 | 25.057 | 1.00 | 71.72 | AP1 |
| ATOM | 3089 | C   | MET | 52 | 58.877 | 36.557 | 23.637 | 1.00 | 65.95 | AP1 |
| ATOM | 3090 | O   | MET | 52 | 57.921 | 36.956 | 24.315 | 1.00 | 65.80 | AP1 |
| ATOM | 3091 | N   | GLU | 53 | 58.861 | 36.580 | 22.310 | 1.00 | 64.45 | AP1 |
| ATOM | 3092 | CA  | GLU | 53 | 57.714 | 37.128 | 21.607 | 1.00 | 63.42 | AP1 |
| ATOM | 3093 | CB  | GLU | 53 | 58.201 | 38.195 | 20.621 | 1.00 | 64.63 | AP1 |
| ATOM | 3094 | CG  | GLU | 53 | 57.177 | 39.291 | 20.326 | 1.00 | 66.71 | AP1 |
| ATOM | 3095 | CD  | GLU | 53 | 57.823 | 40.623 | 19.911 | 1.00 | 67.92 | AP1 |
| ATOM | 3096 | OE1 | GLU | 53 | 58.632 | 40.625 | 18.944 | 1.00 | 68.49 | AP1 |
| ATOM | 3097 | OE2 | GLU | 53 | 57.517 | 41.663 | 20.559 | 1.00 | 68.15 | AP1 |
| ATOM | 3098 | C   | GLU | 53 | 57.754 | 35.920 | 20.646 | 1.00 | 61.78 | AP1 |
| ATOM | 3099 | O   | GLU | 53 | 58.839 | 35.510 | 20.228 | 1.00 | 62.18 | AP1 |
| ATOM | 3100 | N   | ILE | 54 | 56.598 | 35.363 | 20.297 | 1.00 | 59.09 | AP1 |
| ATOM | 3101 | CA  | ILE | 54 | 56.484 | 34.192 | 19.385 | 1.00 | 56.93 | AP1 |
| ATOM | 3102 | CB  | ILE | 54 | 56.061 | 32.975 | 20.277 | 1.00 | 55.84 | AP1 |
| ATOM | 3103 | CG2 | ILE | 54 | 55.752 | 31.773 | 19.377 | 1.00 | 55.47 | AP1 |
| ATOM | 3104 | CG1 | ILE | 54 | 57.196 | 32.570 | 21.220 | 1.00 | 56.28 | AP1 |
| ATOM | 3105 | CD1 | ILE | 54 | 56.839 | 31.459 | 22.208 | 1.00 | 56.74 | AP1 |
| ATOM | 3106 | C   | ILE | 54 | 55.225 | 34.629 | 18.600 | 1.00 | 55.56 | AP1 |
| ATOM | 3107 | O   | ILE | 54 | 54.095 | 34.632 | 19.122 | 1.00 | 55.94 | AP1 |
| ATOM | 3108 | N   | SER | 55 | 55.424 | 34.947 | 17.328 | 1.00 | 53.24 | AP1 |
| ATOM | 3109 | CA  | SER | 55 | 54.345 | 35.363 | 16.445 | 1.00 | 51.67 | AP1 |
| ATOM | 3110 | CB  | SER | 55 | 54.957 | 35.881 | 15.149 | 1.00 | 51.59 | AP1 |
| ATOM | 3111 | OG  | SER | 55 | 55.754 | 34.843 | 14.601 | 1.00 | 50.98 | AP1 |
| ATOM | 3112 | C   | SER | 55 | 53.396 | 34.188 | 16.111 | 1.00 | 50.89 | AP1 |
| ATOM | 3113 | O   | SER | 55 | 53.686 | 33.025 | 16.427 | 1.00 | 50.20 | AP1 |
| ATOM | 3114 | N   | ASP | 56 | 52.263 | 34.505 | 15.477 | 1.00 | 50.52 | AP1 |
| ATOM | 3115 | CA  | ASP | 56 | 51.301 | 33.486 | 15.055 | 1.00 | 50.73 | AP1 |
| ATOM | 3116 | CB  | ASP | 56 | 50.115 | 34.112 | 14.282 | 1.00 | 51.39 | AP1 |
| ATOM | 3117 | CG  | ASP | 56 | 49.076 | 34.796 | 15.193 | 1.00 | 52.27 | AP1 |
| ATOM | 3118 | OD1 | ASP | 56 | 48.939 | 34.396 | 16.388 | 1.00 | 53.22 | AP1 |
| ATOM | 3119 | OD2 | ASP | 56 | 48.379 | 35.718 | 14.699 | 1.00 | 50.84 | AP1 |
| ATOM | 3120 | C   | ASP | 56 | 52.062 | 32.536 | 14.109 | 1.00 | 50.93 | AP1 |
| ATOM | 3121 | O   | ASP | 56 | 51.741 | 31.347 | 13.989 | 1.00 | 49.65 | AP1 |
| ATOM | 3122 | N   | GLU | 57 | 53.073 | 33.080 | 13.430 | 1.00 | 51.57 | AP1 |
| ATOM | 3123 | CA  | GLU | 57 | 53.881 | 32.285 | 12.510 | 1.00 | 52.66 | AP1 |
| ATOM | 3124 | CB  | GLU | 57 | 54.800 | 33.183 | 11.681 | 1.00 | 53.96 | AP1 |
| ATOM | 3125 | CG  | GLU | 57 | 55.384 | 32.498 | 10.470 | 1.00 | 56.75 | AP1 |
| ATOM | 3126 | CD  | GLU | 57 | 56.048 | 33.482 | 9.499  | 1.00 | 58.76 | AP1 |
| ATOM | 3127 | OE1 | GLU | 57 | 57.233 | 33.860 | 9.730  | 1.00 | 59.00 | AP1 |

FIG. 3A-55

| ATOM | 3128 | OE2 | GLU | 57 | 55.365 | 33.881 | 8.511 | 1.00 | 59.50 | AP1 |
|------|------|-----|-----|----|--------|--------|-------|------|-------|-----|
| ATOM | 3129 | C | GLU | 57 | 54.702 | 31.276 | 13.309 | 1.00 | 52.17 | AP1 |
| ATOM | 3130 | O | GLU | 57 | 54.669 | 30.082 | 13.030 | 1.00 | 50.84 | AP1 |
| ATOM | 3131 | N | ASP | 58 | 55.404 | 31.757 | 14.325 | 1.00 | 52.81 | AP1 |
| ATOM | 3132 | CA | ASP | 58 | 56.208 | 30.863 | 15.154 | 1.00 | 54.03 | AP1 |
| ATOM | 3133 | CB | ASP | 58 | 57.101 | 31.661 | 16.094 | 1.00 | 53.98 | AP1 |
| ATOM | 3134 | CG | ASP | 58 | 58.039 | 32.606 | 15.349 | 1.00 | 55.50 | AP1 |
| ATOM | 3135 | OD1 | ASP | 58 | 58.353 | 32.363 | 14.146 | 1.00 | 54.46 | AP1 |
| ATOM | 3136 | OD2 | ASP | 58 | 58.468 | 33.599 | 15.993 | 1.00 | 57.16 | AP1 |
| ATOM | 3137 | C | ASP | 58 | 55.328 | 29.901 | 15.960 | 1.00 | 54.50 | AP1 |
| ATOM | 3138 | O | ASP | 58 | 55.769 | 28.803 | 16.345 | 1.00 | 54.65 | AP1 |
| ATOM | 3139 | N | ALA | 59 | 54.083 | 30.294 | 16.215 | 1.00 | 54.12 | AP1 |
| ATOM | 3140 | CA | ALA | 59 | 53.206 | 29.405 | 16.957 | 1.00 | 54.32 | AP1 |
| ATOM | 3141 | CB | ALA | 59 | 51.865 | 30.091 | 17.249 | 1.00 | 54.13 | AP1 |
| ATOM | 3142 | C | ALA | 59 | 52.997 | 28.171 | 16.096 | 1.00 | 54.49 | AP1 |
| ATOM | 3143 | O | ALA | 59 | 53.039 | 27.045 | 16.571 | 1.00 | 53.95 | AP1 |
| ATOM | 3144 | N | GLU | 60 | 52.803 | 28.376 | 14.805 | 1.00 | 55.25 | AP1 |
| ATOM | 3145 | CA | GLU | 60 | 52.573 | 27.223 | 13.962 | 1.00 | 56.49 | AP1 |
| ATOM | 3146 | CB | GLU | 60 | 52.040 | 27.639 | 12.596 | 1.00 | 56.75 | AP1 |
| ATOM | 3147 | CG | GLU | 60 | 51.899 | 26.484 | 11.628 | 1.00 | 58.07 | AP1 |
| ATOM | 3148 | CD | GLU | 60 | 51.013 | 26.849 | 10.463 | 1.00 | 59.05 | AP1 |
| ATOM | 3149 | OE1 | GLU | 60 | 49.784 | 26.570 | 10.543 | 1.00 | 60.39 | AP1 |
| ATOM | 3150 | OE2 | GLU | 60 | 51.540 | 27.436 | 9.490 | 1.00 | 58.55 | AP1 |
| ATOM | 3151 | C | GLU | 60 | 53.820 | 26.367 | 13.820 | 1.00 | 56.93 | AP1 |
| ATOM | 3152 | O | GLU | 60 | 53.703 | 25.155 | 13.593 | 1.00 | 57.48 | AP1 |
| ATOM | 3153 | N | LYS | 61 | 55.014 | 26.947 | 13.965 | 1.00 | 56.79 | AP1 |
| ATOM | 3154 | CA | LYS | 61 | 56.174 | 26.073 | 13.861 | 1.00 | 57.27 | AP1 |
| ATOM | 3155 | CB | LYS | 61 | 57.519 | 26.797 | 13.840 | 1.00 | 57.94 | AP1 |
| ATOM | 3156 | CG | LYS | 61 | 58.612 | 25.719 | 13.702 | 1.00 | 59.35 | AP1 |
| ATOM | 3157 | CD | LYS | 61 | 60.038 | 26.222 | 13.793 | 1.00 | 61.65 | AP1 |
| ATOM | 3158 | CE | LYS | 61 | 61.023 | 25.049 | 13.679 | 1.00 | 61.95 | AP1 |
| ATOM | 3159 | NZ | LYS | 61 | 62.451 | 25.504 | 13.695 | 1.00 | 62.10 | AP1 |
| ATOM | 3160 | C | LYS | 61 | 56.246 | 25.084 | 15.005 | 1.00 | 56.70 | AP1 |
| ATOM | 3161 | O | LYS | 61 | 56.534 | 23.906 | 14.792 | 1.00 | 56.75 | AP1 |
| ATOM | 3162 | N | ILE | 62 | 55.985 | 25.552 | 16.224 | 1.00 | 56.23 | AP1 |
| ATOM | 3163 | CA | ILE | 62 | 56.084 | 24.651 | 17.355 | 1.00 | 55.58 | AP1 |
| ATOM | 3164 | CB | ILE | 62 | 56.520 | 25.434 | 18.608 | 1.00 | 55.21 | AP1 |
| ATOM | 3165 | CG2 | ILE | 62 | 57.819 | 26.184 | 18.284 | 1.00 | 54.70 | AP1 |
| ATOM | 3166 | CG1 | ILE | 62 | 55.491 | 26.474 | 19.002 | 1.00 | 54.99 | AP1 |
| ATOM | 3167 | CD1 | ILE | 62 | 55.913 | 27.242 | 20.214 | 1.00 | 54.20 | AP1 |
| ATOM | 3168 | C | ILE | 62 | 54.887 | 23.723 | 17.593 | 1.00 | 55.31 | AP1 |
| ATOM | 3169 | O | ILE | 62 | 54.109 | 23.854 | 18.542 | 1.00 | 55.02 | AP1 |
| ATOM | 3170 | N | ALA | 63 | 54.799 | 22.741 | 16.704 | 1.00 | 55.03 | AP1 |
| ATOM | 3171 | CA | ALA | 63 | 53.758 | 21.722 | 16.726 | 1.00 | 54.72 | AP1 |
| ATOM | 3172 | CB | ALA | 63 | 53.658 | 21.063 | 15.349 | 1.00 | 54.68 | AP1 |
| ATOM | 3173 | C | ALA | 63 | 53.950 | 20.640 | 17.790 | 1.00 | 54.19 | AP1 |
| ATOM | 3174 | O | ALA | 63 | 52.979 | 20.028 | 18.223 | 1.00 | 54.15 | AP1 |
| ATOM | 3175 | N | THR | 64 | 55.192 | 20.381 | 18.195 | 1.00 | 53.96 | AP1 |
| ATOM | 3176 | CA | THR | 64 | 55.457 | 19.358 | 19.222 | 1.00 | 53.49 | AP1 |
| ATOM | 3177 | CB | THR | 64 | 56.341 | 18.195 | 18.695 | 1.00 | 52.92 | AP1 |
| ATOM | 3178 | OG1 | THR | 64 | 57.656 | 18.696 | 18.412 | 1.00 | 51.65 | AP1 |
| ATOM | 3179 | CG2 | THR | 64 | 55.731 | 17.563 | 17.439 | 1.00 | 53.03 | AP1 |
| ATOM | 3180 | C | THR | 64 | 56.194 | 19.899 | 20.439 | 1.00 | 53.33 | AP1 |
| ATOM | 3181 | O | THR | 64 | 56.707 | 21.012 | 20.438 | 1.00 | 52.73 | AP1 |
| ATOM | 3182 | N | VAL | 65 | 56.262 | 19.067 | 21.472 | 1.00 | 53.66 | AP1 |
| ATOM | 3183 | CA | VAL | 65 | 56.961 | 19.426 | 22.696 | 1.00 | 54.06 | AP1 |
| ATOM | 3184 | CB | VAL | 65 | 56.907 | 18.244 | 23.702 | 1.00 | 54.27 | AP1 |

FIG. 3A-56

| ATOM | 3185 | CG1 | VAL | 65 | 57.520 | 18.646 | 25.030 | 1.00 | 54.06 | AP1 |
| --- | --- | --- | --- | --- | --- | --- | --- | --- | --- | --- |
| ATOM | 3186 | CG2 | VAL | 65 | 55.465 | 17.803 | 23.892 | 1.00 | 54.41 | AP1 |
| ATOM | 3187 | C | VAL | 65 | 58.439 | 19.770 | 22.380 | 1.00 | 53.79 | AP1 |
| ATOM | 3188 | O | VAL | 65 | 58.992 | 20.727 | 22.922 | 1.00 | 53.70 | AP1 |
| ATOM | 3189 | N | GLY | 66 | 59.058 | 18.982 | 21.497 | 1.00 | 53.49 | AP1 |
| ATOM | 3190 | CA | GLY | 66 | 60.448 | 19.199 | 21.126 | 1.00 | 52.65 | AP1 |
| ATOM | 3191 | C | GLY | 66 | 60.633 | 20.472 | 20.339 | 1.00 | 52.63 | AP1 |
| ATOM | 3192 | O | GLY | 66 | 61.672 | 21.145 | 20.420 | 1.00 | 51.80 | AP1 |
| ATOM | 3193 | N | ASP | 67 | 59.607 | 20.815 | 19.575 | 1.00 | 53.18 | AP1 |
| ATOM | 3194 | CA | ASP | 67 | 59.631 | 22.031 | 18.778 | 1.00 | 53.33 | AP1 |
| ATOM | 3195 | CB | ASP | 67 | 58.347 | 22.085 | 17.939 | 1.00 | 54.43 | AP1 |
| ATOM | 3196 | CG | ASP | 67 | 58.291 | 20.970 | 16.900 | 1.00 | 55.53 | AP1 |
| ATOM | 3197 | OD1 | ASP | 67 | 57.211 | 20.358 | 16.671 | 1.00 | 55.75 | AP1 |
| ATOM | 3198 | OD2 | ASP | 67 | 59.353 | 20.719 | 16.294 | 1.00 | 56.16 | AP1 |
| ATOM | 3199 | C | ASP | 67 | 59.745 | 23.248 | 19.715 | 1.00 | 53.22 | AP1 |
| ATOM | 3200 | O | ASP | 67 | 60.588 | 24.156 | 19.528 | 1.00 | 52.14 | AP1 |
| ATOM | 3201 | N | ALA | 68 | 58.905 | 23.270 | 20.741 | 1.00 | 53.13 | AP1 |
| ATOM | 3202 | CA | ALA | 68 | 58.971 | 24.384 | 21.666 | 1.00 | 53.88 | AP1 |
| ATOM | 3203 | CB | ALA | 68 | 57.936 | 24.246 | 22.742 | 1.00 | 52.72 | AP1 |
| ATOM | 3204 | C | ALA | 68 | 60.367 | 24.425 | 22.280 | 1.00 | 53.95 | AP1 |
| ATOM | 3205 | O | ALA | 68 | 61.017 | 25.454 | 22.264 | 1.00 | 54.56 | AP1 |
| ATOM | 3206 | N | VAL | 69 | 60.833 | 23.309 | 22.807 | 1.00 | 54.46 | AP1 |
| ATOM | 3207 | CA | VAL | 69 | 62.161 | 23.283 | 23.417 | 1.00 | 55.62 | AP1 |
| ATOM | 3208 | CB | VAL | 69 | 62.548 | 21.836 | 23.806 | 1.00 | 55.19 | AP1 |
| ATOM | 3209 | CG1 | VAL | 69 | 63.998 | 21.787 | 24.255 | 1.00 | 56.16 | AP1 |
| ATOM | 3210 | CG2 | VAL | 69 | 61.638 | 21.338 | 24.923 | 1.00 | 54.08 | AP1 |
| ATOM | 3211 | C | VAL | 69 | 63.223 | 23.905 | 22.491 | 1.00 | 56.45 | AP1 |
| ATOM | 3212 | O | VAL | 69 | 63.865 | 24.895 | 22.849 | 1.00 | 55.15 | AP1 |
| ATOM | 3213 | N | ASN | 70 | 63.387 | 23.335 | 21.298 | 1.00 | 58.25 | AP1 |
| ATOM | 3214 | CA | ASN | 70 | 64.356 | 23.856 | 20.326 | 1.00 | 60.36 | AP1 |
| ATOM | 3215 | CB | ASN | 70 | 64.185 | 23.230 | 18.930 | 1.00 | 60.51 | AP1 |
| ATOM | 3216 | CG | ASN | 70 | 64.407 | 21.739 | 18.914 | 1.00 | 60.64 | AP1 |
| ATOM | 3217 | OD1 | ASN | 70 | 65.442 | 21.254 | 19.343 | 1.00 | 61.77 | AP1 |
| ATOM | 3218 | ND2 | ASN | 70 | 63.432 | 21.003 | 18.404 | 1.00 | 60.71 | AP1 |
| ATOM | 3219 | C | ASN | 70 | 64.174 | 25.345 | 20.137 | 1.00 | 61.62 | AP1 |
| ATOM | 3220 | O | ASN | 70 | 65.157 | 26.080 | 20.052 | 1.00 | 61.81 | AP1 |
| ATOM | 3221 | N | TYR | 71 | 62.915 | 25.776 | 20.037 | 1.00 | 63.25 | AP1 |
| ATOM | 3222 | CA | TYR | 71 | 62.599 | 27.181 | 19.821 | 1.00 | 65.19 | AP1 |
| ATOM | 3223 | CB | TYR | 71 | 61.097 | 27.371 | 19.585 | 1.00 | 65.08 | AP1 |
| ATOM | 3224 | CG | TYR | 71 | 60.728 | 28.814 | 19.325 | 1.00 | 64.90 | AP1 |
| ATOM | 3225 | CD1 | TYR | 71 | 60.413 | 29.668 | 20.377 | 1.00 | 64.71 | AP1 |
| ATOM | 3226 | CE1 | TYR | 71 | 60.151 | 31.008 | 20.160 | 1.00 | 65.27 | AP1 |
| ATOM | 3227 | CD2 | TYR | 71 | 60.769 | 29.342 | 18.034 | 1.00 | 64.62 | AP1 |
| ATOM | 3228 | CE2 | TYR | 71 | 60.508 | 30.683 | 17.800 | 1.00 | 64.75 | AP1 |
| ATOM | 3229 | CZ | TYR | 71 | 60.197 | 31.517 | 18.866 | 1.00 | 65.04 | AP1 |
| ATOM | 3230 | OH | TYR | 71 | 59.928 | 32.854 | 18.650 | 1.00 | 64.43 | AP1 |
| ATOM | 3231 | C | TYR | 71 | 63.069 | 28.048 | 20.980 | 1.00 | 66.81 | AP1 |
| ATOM | 3232 | O | TYR | 71 | 63.375 | 29.238 | 20.803 | 1.00 | 66.70 | AP1 |
| ATOM | 3233 | N | ILE | 72 | 63.138 | 27.440 | 22.161 | 1.00 | 68.59 | AP1 |
| ATOM | 3234 | CA | ILE | 72 | 63.609 | 28.126 | 23.354 | 1.00 | 70.76 | AP1 |
| ATOM | 3235 | CB | ILE | 72 | 62.898 | 27.583 | 24.594 | 1.00 | 70.58 | AP1 |
| ATOM | 3236 | CG2 | ILE | 72 | 63.445 | 28.260 | 25.878 | 1.00 | 70.73 | AP1 |
| ATOM | 3237 | CG1 | ILE | 72 | 61.394 | 27.804 | 24.416 | 1.00 | 70.49 | AP1 |
| ATOM | 3238 | CD1 | ILE | 72 | 60.562 | 27.205 | 25.496 | 1.00 | 69.78 | AP1 |
| ATOM | 3239 | C | ILE | 72 | 65.130 | 27.925 | 23.466 | 1.00 | 72.57 | AP1 |
| ATOM | 3240 | O | ILE | 72 | 65.684 | 27.630 | 24.533 | 1.00 | 73.27 | AP1 |
| ATOM | 3241 | N | GLN | 73 | 65.791 | 28.072 | 22.325 | 1.00 | 74.34 | AP1 |

FIG. 3A-57

| ATOM | 3242 | CA | GLN | 73 | 67.235 | 27.953 | 22.214 | 1.00 | 75.70 | AP1 |
| ATOM | 3243 | CB | GLN | 73 | 67.636 | 26.483 | 22.085 | 1.00 | 76.75 | AP1 |
| ATOM | 3244 | CG | GLN | 73 | 67.369 | 25.611 | 23.306 | 1.00 | 79.08 | AP1 |
| ATOM | 3245 | CD | GLN | 73 | 67.842 | 24.174 | 23.089 | 1.00 | 80.59 | AP1 |
| ATOM | 3246 | OE1 | GLN | 73 | 68.958 | 23.944 | 22.606 | 1.00 | 81.29 | AP1 |
| ATOM | 3247 | NE2 | GLN | 73 | 67.006 | 23.201 | 23.449 | 1.00 | 80.77 | AP1 |
| ATOM | 3248 | C | GLN | 73 | 67.593 | 28.719 | 20.931 | 1.00 | 76.07 | AP1 |
| ATOM | 3249 | OT1 | GLN | 73 | 67.901 | 29.933 | 21.027 | 1.00 | 76.06 | AP1 |
| ATOM | 3250 | OT2 | GLN | 73 | 67.520 | 28.109 | 19.835 | 1.00 | 76.30 | AP1 |
| ATOM | 3251 | CB | ALA | 1 | 6.645 | 63.605 | 34.695 | 1.00 | 86.31 | AP2 |
| ATOM | 3252 | C | ALA | 1 | 6.820 | 61.130 | 34.410 | 1.00 | 86.49 | AP2 |
| ATOM | 3253 | O | ALA | 1 | 7.722 | 60.410 | 34.845 | 1.00 | 86.43 | AP2 |
| ATOM | 3254 | N | ALA | 1 | 6.500 | 62.631 | 32.424 | 1.00 | 86.34 | AP2 |
| ATOM | 3255 | CA | ALA | 1 | 7.130 | 62.486 | 33.774 | 1.00 | 86.44 | AP2 |
| ATOM | 3256 | N | ASP | 2 | 5.531 | 60.806 | 34.476 | 1.00 | 86.48 | AP2 |
| ATOM | 3257 | CA | ASP | 2 | 5.054 | 59.549 | 35.054 | 1.00 | 86.12 | AP2 |
| ATOM | 3258 | CB | ASP | 2 | 3.540 | 59.631 | 35.306 | 1.00 | 86.68 | AP2 |
| ATOM | 3259 | CG | ASP | 2 | 2.875 | 58.258 | 35.366 | 1.00 | 87.31 | AP2 |
| ATOM | 3260 | OD1 | ASP | 2 | 3.170 | 57.480 | 36.303 | 1.00 | 87.86 | AP2 |
| ATOM | 3261 | OD2 | ASP | 2 | 2.057 | 57.953 | 34.466 | 1.00 | 87.63 | AP2 |
| ATOM | 3262 | C | ASP | 2 | 5.355 | 58.396 | 34.108 | 1.00 | 85.41 | AP2 |
| ATOM | 3263 | O | ASP | 2 | 5.719 | 57.291 | 34.538 | 1.00 | 85.00 | AP2 |
| ATOM | 3264 | N | THR | 3 | 5.199 | 58.662 | 32.815 | 1.00 | 84.56 | AP2 |
| ATOM | 3265 | CA | THR | 3 | 5.455 | 57.639 | 31.824 | 1.00 | 83.93 | AP2 |
| ATOM | 3266 | CB | THR | 3 | 5.146 | 58.144 | 30.366 | 1.00 | 84.30 | AP2 |
| ATOM | 3267 | OG1 | THR | 3 | 6.165 | 59.047 | 29.927 | 1.00 | 84.66 | AP2 |
| ATOM | 3268 | CG2 | THR | 3 | 3.779 | 58.857 | 30.315 | 1.00 | 83.94 | AP2 |
| ATOM | 3269 | C | THR | 3 | 6.905 | 57.162 | 31.967 | 1.00 | 83.08 | AP2 |
| ATOM | 3270 | O | THR | 3 | 7.174 | 55.971 | 31.831 | 1.00 | 83.08 | AP2 |
| ATOM | 3271 | N | LEU | 4 | 7.827 | 58.073 | 32.275 | 1.00 | 82.05 | AP2 |
| ATOM | 3272 | CA | LEU | 4 | 9.230 | 57.688 | 32.450 | 1.00 | 81.45 | AP2 |
| ATOM | 3273 | CB | LEU | 4 | 10.132 | 58.918 | 32.629 | 1.00 | 81.43 | AP2 |
| ATOM | 3274 | CG | LEU | 4 | 11.604 | 58.706 | 33.043 | 1.00 | 81.05 | AP2 |
| ATOM | 3275 | CD1 | LEU | 4 | 12.368 | 57.866 | 32.045 | 1.00 | 80.62 | AP2 |
| ATOM | 3276 | CD2 | LEU | 4 | 12.262 | 60.051 | 33.161 | 1.00 | 80.98 | AP2 |
| ATOM | 3277 | C | LEU | 4 | 9.405 | 56.766 | 33.649 | 1.00 | 80.96 | AP2 |
| ATOM | 3278 | O | LEU | 4 | 10.243 | 55.866 | 33.634 | 1.00 | 80.86 | AP2 |
| ATOM | 3279 | N | GLU | 5 | 8.621 | 56.992 | 34.695 | 1.00 | 80.52 | AP2 |
| ATOM | 3280 | CA | GLU | 5 | 8.711 | 56.149 | 35.875 | 1.00 | 80.14 | AP2 |
| ATOM | 3281 | CB | GLU | 5 | 7.842 | 56.718 | 37.013 | 1.00 | 81.37 | AP2 |
| ATOM | 3282 | CG | GLU | 5 | 8.638 | 57.408 | 38.133 | 1.00 | 83.32 | AP2 |
| ATOM | 3283 | CD | GLU | 5 | 9.550 | 58.535 | 37.610 | 1.00 | 84.89 | AP2 |
| ATOM | 3284 | OE1 | GLU | 5 | 9.007 | 59.558 | 37.117 | 1.00 | 85.35 | AP2 |
| ATOM | 3285 | OE2 | GLU | 5 | 10.805 | 58.395 | 37.682 | 1.00 | 85.07 | AP2 |
| ATOM | 3286 | C | GLU | 5 | 8.264 | 54.733 | 35.502 | 1.00 | 79.23 | AP2 |
| ATOM | 3287 | O | GLU | 5 | 8.918 | 53.746 | 35.863 | 1.00 | 78.62 | AP2 |
| ATOM | 3288 | N | ARG | 6 | 7.155 | 54.635 | 34.769 | 1.00 | 78.13 | AP2 |
| ATOM | 3289 | CA | ARG | 6 | 6.658 | 53.331 | 34.355 | 1.00 | 77.16 | AP2 |
| ATOM | 3290 | CB | ARG | 6 | 5.225 | 53.430 | 33.827 | 1.00 | 77.18 | AP2 |
| ATOM | 3291 | CG | ARG | 6 | 4.171 | 53.413 | 34.942 | 1.00 | 77.34 | AP2 |
| ATOM | 3292 | CD | ARG | 6 | 2.764 | 53.134 | 34.408 | 1.00 | 76.80 | AP2 |
| ATOM | 3293 | NE | ARG | 6 | 2.136 | 54.303 | 33.801 | 1.00 | 75.86 | AP2 |
| ATOM | 3294 | CZ | ARG | 6 | 1.053 | 54.245 | 33.030 | 1.00 | 75.80 | AP2 |
| ATOM | 3295 | NH1 | ARG | 6 | 0.482 | 53.071 | 32.771 | 1.00 | 75.17 | AP2 |
| ATOM | 3296 | NH2 | ARG | 6 | 0.532 | 55.361 | 32.523 | 1.00 | 75.41 | AP2 |
| ATOM | 3297 | C | ARG | 6 | 7.571 | 52.706 | 33.310 | 1.00 | 76.44 | AP2 |
| ATOM | 3298 | O | ARG | 6 | 7.896 | 51.521 | 33.405 | 1.00 | 76.54 | AP2 |

FIG. 3A-58

| ATOM | 3299 | N | VAL | 7 | 7.995 | 53.493 | 32.324 | 1.00 | 75.18 | AP2 |
|---|---|---|---|---|---|---|---|---|---|---|
| ATOM | 3300 | CA | VAL | 7 | 8.894 | 52.981 | 31.306 | 1.00 | 74.11 | AP2 |
| ATOM | 3301 | CB | VAL | 7 | 9.345 | 54.067 | 30.323 | 1.00 | 73.72 | AP2 |
| ATOM | 3302 | CG1 | VAL | 7 | 10.514 | 53.549 | 29.513 | 1.00 | 73.33 | AP2 |
| ATOM | 3303 | CG2 | VAL | 7 | 8.216 | 54.462 | 29.404 | 1.00 | 72.85 | AP2 |
| ATOM | 3304 | C | VAL | 7 | 10.149 | 52.453 | 31.966 | 1.00 | 74.07 | AP2 |
| ATOM | 3305 | O | VAL | 7 | 10.634 | 51.386 | 31.626 | 1.00 | 74.04 | AP2 |
| ATOM | 3306 | N | THR | 8 | 10.680 | 53.209 | 32.916 | 1.00 | 74.19 | AP2 |
| ATOM | 3307 | CA | THR | 8 | 11.906 | 52.802 | 33.583 | 1.00 | 74.59 | AP2 |
| ATOM | 3308 | CB | THR | 8 | 12.395 | 53.893 | 34.580 | 1.00 | 74.78 | AP2 |
| ATOM | 3309 | OG1 | THR | 8 | 12.916 | 55.016 | 33.852 | 1.00 | 74.74 | AP2 |
| ATOM | 3310 | CG2 | THR | 8 | 13.493 | 53.348 | 35.489 | 1.00 | 74.82 | AP2 |
| ATOM | 3311 | C | THR | 8 | 11.721 | 51.488 | 34.315 | 1.00 | 74.86 | AP2 |
| ATOM | 3312 | O | THR | 8 | 12.585 | 50.603 | 34.259 | 1.00 | 74.74 | AP2 |
| ATOM | 3313 | N | LYS | 9 | 10.590 | 51.368 | 35.001 | 1.00 | 75.13 | AP2 |
| ATOM | 3314 | CA | LYS | 9 | 10.279 | 50.166 | 35.758 | 1.00 | 75.62 | AP2 |
| ATOM | 3315 | CB | LYS | 9 | 8.920 | 50.345 | 36.462 | 1.00 | 76.59 | AP2 |
| ATOM | 3316 | CG | LYS | 9 | 8.406 | 49.178 | 37.316 | 1.00 | 77.37 | AP2 |
| ATOM | 3317 | CD | LYS | 9 | 6.994 | 49.508 | 37.828 | 1.00 | 78.26 | AP2 |
| ATOM | 3318 | CE | LYS | 9 | 6.274 | 48.308 | 38.446 | 1.00 | 78.59 | AP2 |
| ATOM | 3319 | NZ | LYS | 9 | 6.887 | 47.838 | 39.724 | 1.00 | 79.09 | AP2 |
| ATOM | 3320 | C | LYS | 9 | 10.263 | 48.983 | 34.790 | 1.00 | 75.49 | AP2 |
| ATOM | 3321 | O | LYS | 9 | 10.794 | 47.921 | 35.094 | 1.00 | 75.37 | AP2 |
| ATOM | 3322 | N | ILE | 10 | 9.673 | 49.176 | 33.613 | 1.00 | 75.59 | AP2 |
| ATOM | 3323 | CA | ILE | 10 | 9.609 | 48.111 | 32.607 | 1.00 | 75.37 | AP2 |
| ATOM | 3324 | CB | ILE | 10 | 8.897 | 48.569 | 31.322 | 1.00 | 74.85 | AP2 |
| ATOM | 3325 | CG2 | ILE | 10 | 8.826 | 47.408 | 30.363 | 1.00 | 75.13 | AP2 |
| ATOM | 3326 | CG1 | ILE | 10 | 7.499 | 49.103 | 31.621 | 1.00 | 74.65 | AP2 |
| ATOM | 3327 | CD1 | ILE | 10 | 6.486 | 48.042 | 31.950 | 1.00 | 74.86 | AP2 |
| ATOM | 3328 | C | ILE | 10 | 11.024 | 47.697 | 32.203 | 1.00 | 75.44 | AP2 |
| ATOM | 3329 | O | ILE | 10 | 11.367 | 46.515 | 32.216 | 1.00 | 74.81 | AP2 |
| ATOM | 3330 | N | ILE | 11 | 11.831 | 48.689 | 31.836 | 1.00 | 76.08 | AP2 |
| ATOM | 3331 | CA | ILE | 11 | 13.208 | 48.459 | 31.408 | 1.00 | 77.08 | AP2 |
| ATOM | 3332 | CB | ILE | 11 | 13.918 | 49.787 | 31.105 | 1.00 | 76.69 | AP2 |
| ATOM | 3333 | CG2 | ILE | 11 | 15.360 | 49.522 | 30.722 | 1.00 | 76.30 | AP2 |
| ATOM | 3334 | CG1 | ILE | 11 | 13.187 | 50.514 | 29.974 | 1.00 | 76.78 | AP2 |
| ATOM | 3335 | CD1 | ILE | 11 | 13.840 | 51.819 | 29.527 | 1.00 | 76.66 | AP2 |
| ATOM | 3336 | C | ILE | 11 | 14.039 | 47.696 | 32.431 | 1.00 | 78.04 | AP2 |
| ATOM | 3337 | O | ILE | 11 | 14.696 | 46.706 | 32.102 | 1.00 | 77.63 | AP2 |
| ATOM | 3338 | N | VAL | 12 | 14.009 | 48.172 | 33.672 | 1.00 | 79.25 | AP2 |
| ATOM | 3339 | CA | VAL | 12 | 14.761 | 47.547 | 34.755 | 1.00 | 80.48 | AP2 |
| ATOM | 3340 | CB | VAL | 12 | 14.604 | 48.343 | 36.088 | 1.00 | 80.56 | AP2 |
| ATOM | 3341 | CG1 | VAL | 12 | 15.410 | 47.676 | 37.191 | 1.00 | 80.75 | AP2 |
| ATOM | 3342 | CG2 | VAL | 12 | 15.063 | 49.779 | 35.899 | 1.00 | 80.30 | AP2 |
| ATOM | 3343 | C | VAL | 12 | 14.298 | 46.116 | 34.989 | 1.00 | 81.20 | AP2 |
| ATOM | 3344 | O | VAL | 12 | 15.101 | 45.194 | 35.041 | 1.00 | 81.20 | AP2 |
| ATOM | 3345 | N | ASP | 13 | 12.992 | 45.942 | 35.121 | 1.00 | 82.40 | AP2 |
| ATOM | 3346 | CA | ASP | 13 | 12.402 | 44.634 | 35.375 | 1.00 | 83.84 | AP2 |
| ATOM | 3347 | CB | ASP | 13 | 10.901 | 44.804 | 35.657 | 1.00 | 84.55 | AP2 |
| ATOM | 3348 | CG | ASP | 13 | 10.618 | 45.767 | 36.829 | 1.00 | 85.50 | AP2 |
| ATOM | 3349 | OD1 | ASP | 13 | 11.513 | 46.577 | 37.182 | 1.00 | 85.54 | AP2 |
| ATOM | 3350 | OD2 | ASP | 13 | 9.491 | 45.726 | 37.386 | 1.00 | 85.79 | AP2 |
| ATOM | 3351 | C | ASP | 13 | 12.627 | 43.600 | 34.256 | 1.00 | 84.60 | AP2 |
| ATOM | 3352 | O | ASP | 13 | 12.466 | 42.395 | 34.485 | 1.00 | 84.91 | AP2 |
| ATOM | 3353 | N | ARG | 14 | 12.993 | 44.060 | 33.056 | 1.00 | 85.13 | AP2 |
| ATOM | 3354 | CA | ARG | 14 | 13.252 | 43.158 | 31.915 | 1.00 | 85.53 | AP2 |
| ATOM | 3355 | CB | ARG | 14 | 12.667 | 43.725 | 30.602 | 1.00 | 85.39 | AP2 |

FIG. 3A-59

| ATOM | 3356 | CG | ARG | 14 | 11.133 | 43.788 | 30.506 | 1.00 | 85.43 | AP2 |
| --- | --- | --- | --- | --- | --- | --- | --- | --- | --- | --- |
| ATOM | 3357 | CD | ARG | 14 | 10.493 | 42.407 | 30.616 | 1.00 | 85.43 | AP2 |
| ATOM | 3358 | NE | ARG | 14 | 11.253 | 41.397 | 29.883 | 1.00 | 85.32 | AP2 |
| ATOM | 3359 | CZ | ARG | 14 | 10.950 | 40.102 | 29.862 | 1.00 | 85.25 | AP2 |
| ATOM | 3360 | NH1 | ARG | 14 | 9.894 | 39.663 | 30.536 | 1.00 | 85.24 | AP2 |
| ATOM | 3361 | NH2 | ARG | 14 | 11.707 | 39.246 | 29.182 | 1.00 | 84.65 | AP2 |
| ATOM | 3362 | C | ARG | 14 | 14.760 | 42.939 | 31.717 | 1.00 | 85.76 | AP2 |
| ATOM | 3363 | O | ARG | 14 | 15.315 | 41.907 | 32.112 | 1.00 | 85.85 | AP2 |
| ATOM | 3364 | N | LEU | 15 | 15.405 | 43.929 | 31.106 | 1.00 | 85.73 | AP2 |
| ATOM | 3365 | CA | LEU | 15 | 16.828 | 43.896 | 30.831 | 1.00 | 86.03 | AP2 |
| ATOM | 3366 | CB | LEU | 15 | 17.192 | 45.082 | 29.947 | 1.00 | 85.82 | AP2 |
| ATOM | 3367 | CG | LEU | 15 | 16.136 | 45.523 | 28.925 | 1.00 | 85.68 | AP2 |
| ATOM | 3368 | CD1 | LEU | 15 | 16.630 | 46.758 | 28.206 | 1.00 | 85.55 | AP2 |
| ATOM | 3369 | CD2 | LEU | 15 | 15.843 | 44.414 | 27.933 | 1.00 | 85.29 | AP2 |
| ATOM | 3370 | C | LEU | 15 | 17.686 | 43.935 | 32.096 | 1.00 | 86.63 | AP2 |
| ATOM | 3371 | O | LEU | 15 | 18.914 | 43.909 | 32.005 | 1.00 | 86.53 | AP2 |
| ATOM | 3372 | N | GLY | 16 | 17.045 | 44.012 | 33.264 | 1.00 | 87.36 | AP2 |
| ATOM | 3373 | CA | GLY | 16 | 17.775 | 44.064 | 34.527 | 1.00 | 88.66 | AP2 |
| ATOM | 3374 | C | GLY | 16 | 19.053 | 44.883 | 34.456 | 1.00 | 89.59 | AP2 |
| ATOM | 3375 | O | GLY | 16 | 20.143 | 44.321 | 34.326 | 1.00 | 89.42 | AP2 |
| ATOM | 3376 | N | VAL | 17 | 18.928 | 46.207 | 34.553 | 1.00 | 90.59 | AP2 |
| ATOM | 3377 | CA | VAL | 17 | 20.092 | 47.092 | 34.452 | 1.00 | 91.73 | AP2 |
| ATOM | 3378 | CB | VAL | 17 | 20.148 | 47.718 | 33.034 | 1.00 | 91.33 | AP2 |
| ATOM | 3379 | CG1 | VAL | 17 | 20.461 | 46.641 | 32.006 | 1.00 | 91.06 | AP2 |
| ATOM | 3380 | CG2 | VAL | 17 | 18.816 | 48.361 | 32.700 | 1.00 | 91.16 | AP2 |
| ATOM | 3381 | C | VAL | 17 | 20.228 | 48.205 | 35.521 | 1.00 | 92.74 | AP2 |
| ATOM | 3382 | O | VAL | 17 | 20.108 | 49.412 | 35.233 | 1.00 | 92.96 | AP2 |
| ATOM | 3383 | N | ASP | 18 | 20.496 | 47.780 | 36.755 | 1.00 | 93.61 | AP2 |
| ATOM | 3384 | CA | ASP | 18 | 20.682 | 48.690 | 37.887 | 1.00 | 94.45 | AP2 |
| ATOM | 3385 | CB | ASP | 18 | 21.912 | 49.587 | 37.648 | 1.00 | 94.58 | AP2 |
| ATOM | 3386 | CG | ASP | 18 | 23.091 | 49.238 | 38.562 | 1.00 | 94.83 | AP2 |
| ATOM | 3387 | OD1 | ASP | 18 | 23.038 | 48.187 | 39.248 | 1.00 | 94.73 | AP2 |
| ATOM | 3388 | OD2 | ASP | 18 | 24.074 | 50.017 | 38.586 | 1.00 | 94.69 | AP2 |
| ATOM | 3389 | C | ASP | 18 | 19.486 | 49.575 | 38.233 | 1.00 | 94.87 | AP2 |
| ATOM | 3390 | O | ASP | 18 | 18.648 | 49.220 | 39.072 | 1.00 | 95.08 | AP2 |
| ATOM | 3391 | N | GLU | 19 | 19.428 | 50.725 | 37.569 | 1.00 | 95.17 | AP2 |
| ATOM | 3392 | CA | GLU | 19 | 18.406 | 51.745 | 37.786 | 1.00 | 95.47 | AP2 |
| ATOM | 3393 | CB | GLU | 19 | 17.856 | 51.675 | 39.219 | 1.00 | 95.60 | AP2 |
| ATOM | 3394 | CG | GLU | 19 | 16.350 | 51.546 | 39.320 | 1.00 | 96.31 | AP2 |
| ATOM | 3395 | CD | GLU | 19 | 15.637 | 52.864 | 39.091 | 1.00 | 96.93 | AP2 |
| ATOM | 3396 | OE1 | GLU | 19 | 16.190 | 53.720 | 38.362 | 1.00 | 97.29 | AP2 |
| ATOM | 3397 | OE2 | GLU | 19 | 14.518 | 53.040 | 39.629 | 1.00 | 97.32 | AP2 |
| ATOM | 3398 | C | GLU | 19 | 19.290 | 52.971 | 37.638 | 1.00 | 95.49 | AP2 |
| ATOM | 3399 | O | GLU | 19 | 20.496 | 52.819 | 37.420 | 1.00 | 95.65 | AP2 |
| ATOM | 3400 | N | ALA | 20 | 18.725 | 54.168 | 37.753 | 1.00 | 95.26 | AP2 |
| ATOM | 3401 | CA | ALA | 20 | 19.529 | 55.383 | 37.627 | 1.00 | 95.13 | AP2 |
| ATOM | 3402 | CB | ALA | 20 | 20.298 | 55.638 | 38.919 | 1.00 | 94.92 | AP2 |
| ATOM | 3403 | C | ALA | 20 | 20.503 | 55.217 | 36.464 | 1.00 | 94.92 | AP2 |
| ATOM | 3404 | O | ALA | 20 | 21.551 | 55.865 | 36.407 | 1.00 | 94.78 | AP2 |
| ATOM | 3405 | N | ASP | 21 | 20.133 | 54.333 | 35.542 | 1.00 | 94.78 | AP2 |
| ATOM | 3406 | CA | ASP | 21 | 20.946 | 54.030 | 34.376 | 1.00 | 94.36 | AP2 |
| ATOM | 3407 | CB | ASP | 21 | 21.514 | 52.619 | 34.503 | 1.00 | 94.73 | AP2 |
| ATOM | 3408 | CG | ASP | 21 | 22.692 | 52.402 | 33.603 | 1.00 | 95.30 | AP2 |
| ATOM | 3409 | OD1 | ASP | 21 | 23.821 | 52.771 | 34.000 | 1.00 | 95.81 | AP2 |
| ATOM | 3410 | OD2 | ASP | 21 | 22.486 | 51.887 | 32.487 | 1.00 | 95.82 | AP2 |
| ATOM | 3411 | C | ASP | 21 | 20.055 | 54.120 | 33.141 | 1.00 | 93.80 | AP2 |
| ATOM | 3412 | O | ASP | 21 | 20.425 | 53.706 | 32.037 | 1.00 | 93.62 | AP2 |

FIG. 3A-60

| ATOM | 3413 | N | VAL | 22 | 18.877 | 54.690 | 33.354 | 1.00 | 92.94 | AP2 |
| ATOM | 3414 | CA | VAL | 22 | 17.878 | 54.846 | 32.315 | 1.00 | 92.17 | AP2 |
| ATOM | 3415 | CB | VAL | 22 | 16.523 | 54.320 | 32.855 | 1.00 | 92.24 | AP2 |
| ATOM | 3416 | CG1 | VAL | 22 | 15.484 | 54.285 | 31.758 | 1.00 | 92.28 | AP2 |
| ATOM | 3417 | CG2 | VAL | 22 | 16.722 | 52.933 | 33.472 | 1.00 | 91.98 | AP2 |
| ATOM | 3418 | C | VAL | 22 | 17.741 | 56.308 | 31.843 | 1.00 | 91.45 | AP2 |
| ATOM | 3419 | O | VAL | 22 | 16.783 | 56.992 | 32.194 | 1.00 | 91.67 | AP2 |
| ATOM | 3420 | N | LYS | 23 | 18.693 | 56.787 | 31.044 | 1.00 | 90.56 | AP2 |
| ATOM | 3421 | CA | LYS | 23 | 18.653 | 58.168 | 30.540 | 1.00 | 89.58 | AP2 |
| ATOM | 3422 | CB | LYS | 23 | 20.078 | 58.706 | 30.378 | 1.00 | 89.69 | AP2 |
| ATOM | 3423 | C | LYS | 23 | 17.899 | 58.274 | 29.211 | 1.00 | 88.74 | AP2 |
| ATOM | 3424 | O | LYS | 23 | 17.965 | 57.369 | 28.388 | 1.00 | 88.66 | AP2 |
| ATOM | 3425 | N | LEU | 24 | 17.193 | 59.381 | 28.996 | 1.00 | 87.78 | AP2 |
| ATOM | 3426 | CA | LEU | 24 | 16.423 | 59.565 | 27.760 | 1.00 | 86.87 | AP2 |
| ATOM | 3427 | CB | LEU | 24 | 15.801 | 60.976 | 27.689 | 1.00 | 86.41 | AP2 |
| ATOM | 3428 | CG | LEU | 24 | 14.684 | 61.499 | 28.603 | 1.00 | 86.03 | AP2 |
| ATOM | 3429 | CD1 | LEU | 24 | 13.613 | 60.437 | 28.744 | 1.00 | 86.18 | AP2 |
| ATOM | 3430 | CD2 | LEU | 24 | 15.231 | 61.899 | 29.956 | 1.00 | 85.71 | AP2 |
| ATOM | 3431 | C | LEU | 24 | 17.255 | 59.347 | 26.497 | 1.00 | 86.36 | AP2 |
| ATOM | 3432 | O | LEU | 24 | 16.716 | 59.246 | 25.396 | 1.00 | 86.46 | AP2 |
| ATOM | 3433 | N | GLU | 25 | 18.570 | 59.285 | 26.663 | 1.00 | 85.76 | AP2 |
| ATOM | 3434 | CA | GLU | 25 | 19.500 | 59.103 | 25.545 | 1.00 | 85.09 | AP2 |
| ATOM | 3435 | CB | GLU | 25 | 20.607 | 60.138 | 25.649 | 1.00 | 85.64 | AP2 |
| ATOM | 3436 | CG | GLU | 25 | 21.204 | 60.175 | 27.047 | 1.00 | 86.77 | AP2 |
| ATOM | 3437 | CD | GLU | 25 | 21.379 | 61.586 | 27.571 | 1.00 | 87.43 | AP2 |
| ATOM | 3438 | OE1 | GLU | 25 | 22.292 | 62.287 | 27.075 | 1.00 | 87.74 | AP2 |
| ATOM | 3439 | OE2 | GLU | 25 | 20.601 | 61.989 | 28.470 | 1.00 | 87.25 | AP2 |
| ATOM | 3440 | C | GLU | 25 | 20.117 | 57.713 | 25.561 | 1.00 | 84.14 | AP2 |
| ATOM | 3441 | O | GLU | 25 | 20.876 | 57.349 | 24.662 | 1.00 | 84.00 | AP2 |
| ATOM | 3442 | N | ALA | 26 | 19.798 | 56.957 | 26.607 | 1.00 | 83.18 | AP2 |
| ATOM | 3443 | CA | ALA | 26 | 20.289 | 55.591 | 26.776 | 1.00 | 82.20 | AP2 |
| ATOM | 3444 | CB | ALA | 26 | 19.927 | 55.065 | 28.174 | 1.00 | 81.62 | AP2 |
| ATOM | 3445 | C | ALA | 26 | 19.676 | 54.684 | 25.708 | 1.00 | 81.46 | AP2 |
| ATOM | 3446 | O | ALA | 26 | 18.469 | 54.418 | 25.724 | 1.00 | 81.38 | AP2 |
| ATOM | 3447 | N | SER | 27 | 20.508 | 54.236 | 24.771 | 1.00 | 80.43 | AP2 |
| ATOM | 3448 | CA | SER | 27 | 20.066 | 53.338 | 23.709 | 1.00 | 79.24 | AP2 |
| ATOM | 3449 | CB | SER | 27 | 21.121 | 53.254 | 22.598 | 1.00 | 78.96 | AP2 |
| ATOM | 3450 | OG | SER | 27 | 20.722 | 52.381 | 21.556 | 1.00 | 78.46 | AP2 |
| ATOM | 3451 | C | SER | 27 | 19.856 | 51.956 | 24.321 | 1.00 | 78.58 | AP2 |
| ATOM | 3452 | O | SER | 27 | 20.722 | 51.452 | 25.052 | 1.00 | 78.03 | AP2 |
| ATOM | 3453 | N | PHE | 28 | 18.697 | 51.365 | 24.033 | 1.00 | 77.69 | AP2 |
| ATOM | 3454 | CA | PHE | 28 | 18.364 | 50.046 | 24.537 | 1.00 | 77.23 | AP2 |
| ATOM | 3455 | CB | PHE | 28 | 17.005 | 49.606 | 24.002 | 1.00 | 77.11 | AP2 |
| ATOM | 3456 | CG | PHE | 28 | 15.874 | 50.490 | 24.413 | 1.00 | 76.99 | AP2 |
| ATOM | 3457 | CD1 | PHE | 28 | 15.477 | 50.556 | 25.750 | 1.00 | 76.84 | AP2 |
| ATOM | 3458 | CD2 | PHE | 28 | 15.194 | 51.248 | 23.466 | 1.00 | 76.77 | AP2 |
| ATOM | 3459 | CE1 | PHE | 28 | 14.422 | 51.357 | 26.137 | 1.00 | 76.38 | AP2 |
| ATOM | 3460 | CE2 | PHE | 28 | 14.136 | 52.056 | 23.835 | 1.00 | 76.78 | AP2 |
| ATOM | 3461 | CZ | PHE | 28 | 13.747 | 52.112 | 25.177 | 1.00 | 77.00 | AP2 |
| ATOM | 3462 | C | PHE | 28 | 19.412 | 49.034 | 24.082 | 1.00 | 77.03 | AP2 |
| ATOM | 3463 | O | PHE | 28 | 19.960 | 48.275 | 24.880 | 1.00 | 76.80 | AP2 |
| ATOM | 3464 | N | LYS | 29 | 19.683 | 49.039 | 22.785 | 1.00 | 76.69 | AP2 |
| ATOM | 3465 | CA | LYS | 29 | 20.625 | 48.109 | 22.197 | 1.00 | 76.65 | AP2 |
| ATOM | 3466 | CB | LYS | 29 | 20.549 | 48.208 | 20.671 | 1.00 | 77.14 | AP2 |
| ATOM | 3467 | CG | LYS | 29 | 19.127 | 48.454 | 20.149 | 1.00 | 77.87 | AP2 |
| ATOM | 3468 | CD | LYS | 29 | 18.817 | 47.607 | 18.923 | 1.00 | 78.22 | AP2 |
| ATOM | 3469 | CE | LYS | 29 | 19.009 | 46.118 | 19.223 | 1.00 | 77.99 | AP2 |

FIG. 3A-61

| ATOM | 3470 | NZ  | LYS | 29 | 18.729 | 45.262 | 18.028 | 1.00 | 77.84 | AP2 |
| --- | --- | --- | --- | --- | --- | --- | --- | --- | --- | --- |
| ATOM | 3471 | C   | LYS | 29 | 22.055 | 48.331 | 22.661 | 1.00 | 76.29 | AP2 |
| ATOM | 3472 | O   | LYS | 29 | 22.691 | 47.426 | 23.204 | 1.00 | 76.44 | AP2 |
| ATOM | 3473 | N   | GLU | 30 | 22.555 | 49.544 | 22.465 | 1.00 | 75.77 | AP2 |
| ATOM | 3474 | CA  | GLU | 30 | 23.925 | 49.864 | 22.831 | 1.00 | 74.94 | AP2 |
| ATOM | 3475 | CB  | GLU | 30 | 24.388 | 51.081 | 22.042 | 1.00 | 75.30 | AP2 |
| ATOM | 3476 | CG  | GLU | 30 | 24.388 | 50.883 | 20.545 | 1.00 | 76.33 | AP2 |
| ATOM | 3477 | CD  | GLU | 30 | 24.656 | 52.184 | 19.800 | 1.00 | 77.36 | AP2 |
| ATOM | 3478 | OE1 | GLU | 30 | 23.737 | 53.042 | 19.722 | 1.00 | 77.95 | AP2 |
| ATOM | 3479 | OE2 | GLU | 30 | 25.796 | 52.355 | 19.305 | 1.00 | 77.61 | AP2 |
| ATOM | 3480 | C   | GLU | 30 | 24.256 | 50.089 | 24.301 | 1.00 | 73.99 | AP2 |
| ATOM | 3481 | O   | GLU | 30 | 25.149 | 49.438 | 24.847 | 1.00 | 74.25 | AP2 |
| ATOM | 3482 | N   | ASP | 31 | 23.549 | 50.996 | 24.953 | 1.00 | 72.54 | AP2 |
| ATOM | 3483 | CA  | ASP | 31 | 23.873 | 51.311 | 26.335 | 1.00 | 71.31 | AP2 |
| ATOM | 3484 | CB  | ASP | 31 | 23.524 | 52.781 | 26.580 | 1.00 | 72.36 | AP2 |
| ATOM | 3485 | CG  | ASP | 31 | 24.270 | 53.725 | 25.619 | 1.00 | 73.52 | AP2 |
| ATOM | 3486 | OD1 | ASP | 31 | 25.514 | 53.605 | 25.518 | 1.00 | 74.32 | AP2 |
| ATOM | 3487 | OD2 | ASP | 31 | 23.632 | 54.585 | 24.965 | 1.00 | 73.71 | AP2 |
| ATOM | 3488 | C   | ASP | 31 | 23.284 | 50.417 | 27.429 | 1.00 | 70.06 | AP2 |
| ATOM | 3489 | O   | ASP | 31 | 23.823 | 50.337 | 28.536 | 1.00 | 69.24 | AP2 |
| ATOM | 3490 | N   | LEU | 32 | 22.205 | 49.711 | 27.110 | 1.00 | 68.91 | AP2 |
| ATOM | 3491 | CA  | LEU | 32 | 21.541 | 48.861 | 28.089 | 1.00 | 67.85 | AP2 |
| ATOM | 3492 | CB  | LEU | 32 | 20.073 | 49.255 | 28.110 | 1.00 | 68.54 | AP2 |
| ATOM | 3493 | CG  | LEU | 32 | 19.920 | 50.701 | 28.569 | 1.00 | 68.87 | AP2 |
| ATOM | 3494 | CD1 | LEU | 32 | 18.472 | 51.131 | 28.462 | 1.00 | 69.10 | AP2 |
| ATOM | 3495 | CD2 | LEU | 32 | 20.422 | 50.809 | 30.012 | 1.00 | 69.20 | AP2 |
| ATOM | 3496 | C   | LEU | 32 | 21.686 | 47.323 | 28.021 | 1.00 | 66.73 | AP2 |
| ATOM | 3497 | O   | LEU | 32 | 21.176 | 46.610 | 28.894 | 1.00 | 66.96 | AP2 |
| ATOM | 3498 | N   | GLY | 33 | 22.373 | 46.811 | 27.003 | 1.00 | 65.33 | AP2 |
| ATOM | 3499 | CA  | GLY | 33 | 22.581 | 45.370 | 26.884 | 1.00 | 63.55 | AP2 |
| ATOM | 3500 | C   | GLY | 33 | 21.416 | 44.529 | 26.372 | 1.00 | 62.11 | AP2 |
| ATOM | 3501 | O   | GLY | 33 | 21.169 | 43.428 | 26.874 | 1.00 | 62.07 | AP2 |
| ATOM | 3502 | N   | ALA | 34 | 20.704 | 45.039 | 25.370 | 1.00 | 60.47 | AP2 |
| ATOM | 3503 | CA  | ALA | 34 | 19.556 | 44.331 | 24.810 | 1.00 | 58.47 | AP2 |
| ATOM | 3504 | CB  | ALA | 34 | 18.316 | 45.248 | 24.802 | 1.00 | 58.39 | AP2 |
| ATOM | 3505 | C   | ALA | 34 | 19.805 | 43.797 | 23.407 | 1.00 | 56.71 | AP2 |
| ATOM | 3506 | O   | ALA | 34 | 20.259 | 44.534 | 22.516 | 1.00 | 56.50 | AP2 |
| ATOM | 3507 | N   | ASP | 35 | 19.526 | 42.507 | 23.225 | 1.00 | 54.43 | AP2 |
| ATOM | 3508 | CA  | ASP | 35 | 19.663 | 41.882 | 21.910 | 1.00 | 52.45 | AP2 |
| ATOM | 3509 | CB  | ASP | 35 | 19.991 | 40.383 | 22.019 | 1.00 | 51.39 | AP2 |
| ATOM | 3510 | CG  | ASP | 35 | 18.982 | 39.589 | 22.864 | 1.00 | 50.25 | AP2 |
| ATOM | 3511 | OD1 | ASP | 35 | 17.860 | 40.067 | 23.129 | 1.00 | 48.54 | AP2 |
| ATOM | 3512 | OD2 | ASP | 35 | 19.338 | 38.455 | 23.241 | 1.00 | 48.62 | AP2 |
| ATOM | 3513 | C   | ASP | 35 | 18.324 | 42.080 | 21.226 | 1.00 | 52.01 | AP2 |
| ATOM | 3514 | O   | ASP | 35 | 17.462 | 42.783 | 21.770 | 1.00 | 52.08 | AP2 |
| ATOM | 3515 | CA  | PAN | 36 | 16.850 | 41.659 | 19.373 | 1.00 | 50.23 | AP2 |
| ATOM | 3516 | N   | PAN | 36 | 18.121 | 41.475 | 20.056 | 1.00 | 51.20 | AP2 |
| ATOM | 3517 | C   | PAN | 36 | 15.682 | 41.035 | 20.163 | 1.00 | 49.09 | AP2 |
| ATOM | 3518 | O   | PAN | 36 | 14.624 | 41.642 | 20.258 | 1.00 | 47.77 | AP2 |
| ATOM | 3519 | O5  | PAN | 36 | 15.669 | 41.227 | 17.265 | 1.00 | 54.25 | AP2 |
| ATOM | 3520 | P6  | PAN | 36 | 15.526 | 42.266 | 16.074 | 1.00 | 55.70 | AP2 |
| ATOM | 3521 | O7  | PAN | 36 | 15.304 | 41.457 | 14.765 | 1.00 | 55.98 | AP2 |
| ATOM | 3522 | O8  | PAN | 36 | 16.936 | 43.007 | 15.954 | 1.00 | 55.85 | AP2 |
| ATOM | 3523 | O9  | PAN | 36 | 14.356 | 43.189 | 16.312 | 1.00 | 55.46 | AP2 |
| ATOM | 3524 | CB  | PAN | 36 | 16.941 | 41.113 | 17.950 | 1.00 | 51.54 | AP2 |
| ATOM | 3525 | N   | LEU | 37 | 15.865 | 39.849 | 20.737 | 1.00 | 48.10 | AP2 |
| ATOM | 3526 | CA  | LEU | 37 | 14.782 | 39.240 | 21.505 | 1.00 | 47.87 | AP2 |

FIG. 3A-62

| ATOM | 3527 | CB  | LEU | 37 | 15.158 | 37.825 | 21.961 | 1.00 | 47.41 | AP2 |
| --- | --- | --- | --- | --- | --- | --- | --- | --- | --- | --- |
| ATOM | 3528 | CG  | LEU | 37 | 14.000 | 37.054 | 22.630 | 1.00 | 49.24 | AP2 |
| ATOM | 3529 | CD1 | LEU | 37 | 12.869 | 36.789 | 21.613 | 1.00 | 48.71 | AP2 |
| ATOM | 3530 | CD2 | LEU | 37 | 14.491 | 35.718 | 23.189 | 1.00 | 49.58 | AP2 |
| ATOM | 3531 | C   | LEU | 37 | 14.382 | 40.114 | 22.731 | 1.00 | 47.82 | AP2 |
| ATOM | 3532 | O   | LEU | 37 | 13.201 | 40.221 | 23.046 | 1.00 | 46.87 | AP2 |
| ATOM | 3533 | N   | ASP | 38 | 15.349 | 40.772 | 23.388 | 1.00 | 47.86 | AP2 |
| ATOM | 3534 | CA  | ASP | 38 | 15.015 | 41.602 | 24.551 | 1.00 | 47.84 | AP2 |
| ATOM | 3535 | CB  | ASP | 38 | 16.264 | 42.164 | 25.278 | 1.00 | 47.82 | AP2 |
| ATOM | 3536 | CG  | ASP | 38 | 17.157 | 41.078 | 25.909 | 1.00 | 47.77 | AP2 |
| ATOM | 3537 | OD1 | ASP | 38 | 18.384 | 41.221 | 25.817 | 1.00 | 47.55 | AP2 |
| ATOM | 3538 | OD2 | ASP | 38 | 16.663 | 40.095 | 26.506 | 1.00 | 48.56 | AP2 |
| ATOM | 3539 | C   | ASP | 38 | 14.176 | 42.767 | 24.072 | 1.00 | 47.53 | AP2 |
| ATOM | 3540 | O   | ASP | 38 | 13.221 | 43.171 | 24.728 | 1.00 | 47.07 | AP2 |
| ATOM | 3541 | N   | VAL | 39 | 14.505 | 43.295 | 22.905 | 1.00 | 47.99 | AP2 |
| ATOM | 3542 | CA  | VAL | 39 | 13.747 | 44.441 | 22.426 | 1.00 | 47.95 | AP2 |
| ATOM | 3543 | CB  | VAL | 39 | 14.466 | 45.138 | 21.301 | 1.00 | 47.96 | AP2 |
| ATOM | 3544 | CG1 | VAL | 39 | 14.203 | 44.460 | 19.969 | 1.00 | 49.07 | AP2 |
| ATOM | 3545 | CG2 | VAL | 39 | 14.002 | 46.543 | 21.270 | 1.00 | 49.98 | AP2 |
| ATOM | 3546 | C   | VAL | 39 | 12.291 | 44.172 | 22.034 | 1.00 | 47.86 | AP2 |
| ATOM | 3547 | O   | VAL | 39 | 11.438 | 45.056 | 22.217 | 1.00 | 47.51 | AP2 |
| ATOM | 3548 | N   | VAL | 40 | 11.976 | 42.981 | 21.505 | 1.00 | 47.55 | AP2 |
| ATOM | 3549 | CA  | VAL | 40 | 10.564 | 42.723 | 21.185 | 1.00 | 48.42 | AP2 |
| ATOM | 3550 | CB  | VAL | 40 | 10.296 | 41.526 | 20.144 | 1.00 | 47.99 | AP2 |
| ATOM | 3551 | CG1 | VAL | 40 | 11.559 | 40.997 | 19.585 | 1.00 | 48.02 | AP2 |
| ATOM | 3552 | CG2 | VAL | 40 | 9.484  | 40.438 | 20.758 | 1.00 | 48.83 | AP2 |
| ATOM | 3553 | C   | VAL | 40 | 9.766  | 42.494 | 22.480 | 1.00 | 48.47 | AP2 |
| ATOM | 3554 | O   | VAL | 40 | 8.618  | 42.879 | 22.549 | 1.00 | 47.57 | AP2 |
| ATOM | 3555 | N   | GLU | 41 | 10.370 | 41.886 | 23.502 | 1.00 | 49.18 | AP2 |
| ATOM | 3556 | CA  | GLU | 41 | 9.643  | 41.685 | 24.753 | 1.00 | 50.93 | AP2 |
| ATOM | 3557 | CB  | GLU | 41 | 10.387 | 40.718 | 25.673 | 1.00 | 53.01 | AP2 |
| ATOM | 3558 | CG  | GLU | 41 | 10.074 | 39.232 | 25.400 | 1.00 | 56.63 | AP2 |
| ATOM | 3559 | CD  | GLU | 41 | 10.552 | 38.329 | 26.536 | 1.00 | 58.01 | AP2 |
| ATOM | 3560 | OE1 | GLU | 41 | 11.776 | 38.066 | 26.609 | 1.00 | 59.21 | AP2 |
| ATOM | 3561 | OE2 | GLU | 41 | 9.704  | 37.902 | 27.366 | 1.00 | 59.16 | AP2 |
| ATOM | 3562 | C   | GLU | 41 | 9.440  | 43.020 | 25.451 | 1.00 | 50.42 | AP2 |
| ATOM | 3563 | O   | GLU | 41 | 8.452  | 43.233 | 26.134 | 1.00 | 49.86 | AP2 |
| ATOM | 3564 | N   | LEU | 42 | 10.393 | 43.923 | 25.248 | 1.00 | 50.66 | AP2 |
| ATOM | 3565 | CA  | LEU | 42 | 10.331 | 45.247 | 25.822 | 1.00 | 50.65 | AP2 |
| ATOM | 3566 | CB  | LEU | 42 | 11.630 | 45.984 | 25.529 | 1.00 | 51.48 | AP2 |
| ATOM | 3567 | CG  | LEU | 42 | 11.958 | 47.238 | 26.337 | 1.00 | 52.85 | AP2 |
| ATOM | 3568 | CD1 | LEU | 42 | 11.999 | 46.858 | 27.818 | 1.00 | 53.64 | AP2 |
| ATOM | 3569 | CD2 | LEU | 42 | 13.327 | 47.821 | 25.899 | 1.00 | 52.34 | AP2 |
| ATOM | 3570 | C   | LEU | 42 | 9.143  | 45.946 | 25.167 | 1.00 | 50.78 | AP2 |
| ATOM | 3571 | O   | LEU | 42 | 8.256  | 46.454 | 25.860 | 1.00 | 50.87 | AP2 |
| ATOM | 3572 | N   | VAL | 43 | 9.109  | 45.933 | 23.839 | 1.00 | 50.50 | AP2 |
| ATOM | 3573 | CA  | VAL | 43 | 8.026  | 46.554 | 23.081 | 1.00 | 51.44 | AP2 |
| ATOM | 3574 | CB  | VAL | 43 | 8.222  | 46.359 | 21.529 | 1.00 | 50.86 | AP2 |
| ATOM | 3575 | CG1 | VAL | 43 | 6.963  | 46.746 | 20.762 | 1.00 | 50.60 | AP2 |
| ATOM | 3576 | CG2 | VAL | 43 | 9.376  | 47.197 | 21.041 | 1.00 | 50.67 | AP2 |
| ATOM | 3577 | C   | VAL | 43 | 6.679  | 45.964 | 23.480 | 1.00 | 52.40 | AP2 |
| ATOM | 3578 | O   | VAL | 43 | 5.695  | 46.665 | 23.618 | 1.00 | 51.57 | AP2 |
| ATOM | 3579 | N   | MET | 44 | 6.633  | 44.656 | 23.658 | 1.00 | 54.33 | AP2 |
| ATOM | 3580 | CA  | MET | 44 | 5.383  | 44.020 | 24.030 | 1.00 | 56.33 | AP2 |
| ATOM | 3581 | CB  | MET | 44 | 5.557  | 42.509 | 24.002 | 1.00 | 56.08 | AP2 |
| ATOM | 3582 | CG  | MET | 44 | 6.120  | 42.014 | 22.700 | 1.00 | 57.30 | AP2 |
| ATOM | 3583 | SD  | MET | 44 | 5.978  | 40.248 | 22.480 | 1.00 | 57.38 | AP2 |

FIG. 3A-63

| ATOM | 3584 | CE | MET | 44 | 4.348 | 40.338 | 21.654 | 1.00 | 57.15 | AP2 |
|---|---|---|---|---|---|---|---|---|---|---|
| ATOM | 3585 | C | MET | 44 | 4.916 | 44.501 | 25.414 | 1.00 | 57.88 | AP2 |
| ATOM | 3586 | O | MET | 44 | 3.734 | 44.764 | 25.619 | 1.00 | 57.09 | AP2 |
| ATOM | 3587 | N | GLU | 45 | 5.863 | 44.646 | 26.341 | 1.00 | 59.93 | AP2 |
| ATOM | 3588 | CA | GLU | 45 | 5.554 | 45.105 | 27.691 | 1.00 | 62.06 | AP2 |
| ATOM | 3589 | CB | GLU | 45 | 6.834 | 45.156 | 28.544 | 1.00 | 63.72 | AP2 |
| ATOM | 3590 | CG | GLU | 45 | 6.613 | 44.808 | 30.038 | 1.00 | 67.19 | AP2 |
| ATOM | 3591 | CD | GLU | 45 | 6.406 | 43.296 | 30.299 | 1.00 | 69.02 | AP2 |
| ATOM | 3592 | OE1 | GLU | 45 | 5.445 | 42.704 | 29.729 | 1.00 | 69.48 | AP2 |
| ATOM | 3593 | OE2 | GLU | 45 | 7.212 | 42.701 | 31.074 | 1.00 | 69.81 | AP2 |
| ATOM | 3594 | C | GLU | 45 | 4.927 | 46.491 | 27.580 | 1.00 | 62.29 | AP2 |
| ATOM | 3595 | O | GLU | 45 | 3.927 | 46.777 | 28.232 | 1.00 | 62.46 | AP2 |
| ATOM | 3596 | N | LEU | 46 | 5.508 | 47.338 | 26.730 | 1.00 | 62.52 | AP2 |
| ATOM | 3597 | CA | LEU | 46 | 4.998 | 48.686 | 26.514 | 1.00 | 62.72 | AP2 |
| ATOM | 3598 | CB | LEU | 46 | 5.938 | 49.485 | 25.595 | 1.00 | 62.51 | AP2 |
| ATOM | 3599 | CG | LEU | 46 | 7.442 | 49.583 | 25.906 | 1.00 | 62.73 | AP2 |
| ATOM | 3600 | CD1 | LEU | 46 | 8.093 | 50.528 | 24.900 | 1.00 | 61.98 | AP2 |
| ATOM | 3601 | CD2 | LEU | 46 | 7.673 | 50.082 | 27.318 | 1.00 | 62.24 | AP2 |
| ATOM | 3602 | C | LEU | 46 | 3.604 | 48.629 | 25.884 | 1.00 | 63.09 | AP2 |
| ATOM | 3603 | O | LEU | 46 | 2.758 | 49.481 | 26.150 | 1.00 | 62.76 | AP2 |
| ATOM | 3604 | N | GLU | 47 | 3.373 | 47.617 | 25.050 | 1.00 | 63.87 | AP2 |
| ATOM | 3605 | CA | GLU | 47 | 2.090 | 47.440 | 24.372 | 1.00 | 64.51 | AP2 |
| ATOM | 3606 | CB | GLU | 47 | 2.157 | 46.295 | 23.344 | 1.00 | 64.64 | AP2 |
| ATOM | 3607 | CG | GLU | 47 | 2.460 | 46.416 | 21.850 | 1.00 | 20.00 | AP2 |
| ATOM | 3608 | CD | GLU | 47 | 2.451 | 45.221 | 20.924 | 1.00 | 20.00 | AP2 |
| ATOM | 3609 | OE1 | GLU | 47 | 2.262 | 44.023 | 21.080 | 1.00 | 20.00 | AP2 |
| ATOM | 3610 | OE2 | GLU | 47 | 2.447 | 45.762 | 19.820 | 1.00 | 20.00 | AP2 |
| ATOM | 3611 | C | GLU | 47 | 0.990 | 47.250 | 25.411 | 1.00 | 64.90 | AP2 |
| ATOM | 3612 | O | GLU | 47 | -0.092 | 47.818 | 25.292 | 1.00 | 64.70 | AP2 |
| ATOM | 3613 | N | ASP | 48 | 1.282 | 46.458 | 26.431 | 1.00 | 65.21 | AP2 |
| ATOM | 3614 | CA | ASP | 48 | 0.311 | 46.171 | 27.460 | 1.00 | 66.10 | AP2 |
| ATOM | 3615 | CB | ASP | 48 | 0.675 | 44.868 | 28.155 | 1.00 | 66.99 | AP2 |
| ATOM | 3616 | CG | ASP | 48 | 0.739 | 43.704 | 27.175 | 1.00 | 68.14 | AP2 |
| ATOM | 3617 | OD1 | ASP | 48 | -0.039 | 43.720 | 26.181 | 1.00 | 68.23 | AP2 |
| ATOM | 3618 | OD2 | ASP | 48 | 1.561 | 42.782 | 27.394 | 1.00 | 68.71 | AP2 |
| ATOM | 3619 | C | ASP | 48 | 0.198 | 47.284 | 28.451 | 1.00 | 66.30 | AP2 |
| ATOM | 3620 | O | ASP | 48 | -0.862 | 47.863 | 28.609 | 1.00 | 66.33 | AP2 |
| ATOM | 3621 | N | GLU | 49 | 1.310 | 47.593 | 29.094 | 1.00 | 66.84 | AP2 |
| ATOM | 3622 | CA | GLU | 49 | 1.390 | 48.652 | 30.085 | 1.00 | 67.24 | AP2 |
| ATOM | 3623 | CB | GLU | 49 | 2.852 | 48.913 | 30.425 | 1.00 | 68.55 | AP2 |
| ATOM | 3624 | CG | GLU | 49 | 3.081 | 49.967 | 31.498 | 1.00 | 70.53 | AP2 |
| ATOM | 3625 | CD | GLU | 49 | 2.745 | 49.446 | 32.885 | 1.00 | 71.90 | AP2 |
| ATOM | 3626 | OE1 | GLU | 49 | 3.012 | 48.237 | 33.122 | 1.00 | 72.29 | AP2 |
| ATOM | 3627 | OE2 | GLU | 49 | 2.234 | 50.237 | 33.725 | 1.00 | 72.12 | AP2 |
| ATOM | 3628 | C | GLU | 49 | 0.769 | 49.977 | 29.678 | 1.00 | 67.07 | AP2 |
| ATOM | 3629 | O | GLU | 49 | 0.421 | 50.778 | 30.542 | 1.00 | 67.58 | AP2 |
| ATOM | 3630 | N | PHE | 50 | 0.636 | 50.235 | 28.381 | 1.00 | 66.27 | AP2 |
| ATOM | 3631 | CA | PHE | 50 | 0.084 | 51.515 | 27.953 | 1.00 | 65.90 | AP2 |
| ATOM | 3632 | CB | PHE | 50 | 1.183 | 52.350 | 27.295 | 1.00 | 65.47 | AP2 |
| ATOM | 3633 | CG | PHE | 50 | 2.157 | 52.959 | 28.271 | 1.00 | 65.11 | AP2 |
| ATOM | 3634 | CD1 | PHE | 50 | 1.881 | 54.185 | 28.882 | 1.00 | 64.59 | AP2 |
| ATOM | 3635 | CD2 | PHE | 50 | 3.343 | 52.306 | 28.595 | 1.00 | 64.67 | AP2 |
| ATOM | 3636 | CE1 | PHE | 50 | 2.767 | 54.745 | 29.791 | 1.00 | 64.20 | AP2 |
| ATOM | 3637 | CE2 | PHE | 50 | 4.237 | 52.870 | 29.512 | 1.00 | 64.53 | AP2 |
| ATOM | 3638 | CZ | PHE | 50 | 3.947 | 54.086 | 30.105 | 1.00 | 64.19 | AP2 |
| ATOM | 3639 | C | PHE | 50 | -1.081 | 51.349 | 27.001 | 1.00 | 66.10 | AP2 |
| ATOM | 3640 | O | PHE | 50 | -1.685 | 52.316 | 26.534 | 1.00 | 66.26 | AP2 |

FIG. 3A-64

| ATOM | 3641 | N | ASP | 51 | -1.402 | 50.103 | 26.713 | 1.00 | 66.29 | AP2 |
|---|---|---|---|---|---|---|---|---|---|---|
| ATOM | 3642 | CA | ASP | 51 | -2.487 | 49.794 | 25.809 | 1.00 | 66.30 | AP2 |
| ATOM | 3643 | CB | ASP | 51 | -3.818 | 50.201 | 26.427 | 1.00 | 67.89 | AP2 |
| ATOM | 3644 | CG | ASP | 51 | -4.959 | 49.359 | 25.908 | 1.00 | 68.99 | AP2 |
| ATOM | 3645 | OD1 | ASP | 51 | -4.916 | 48.131 | 26.144 | 1.00 | 69.70 | AP2 |
| ATOM | 3646 | OD2 | ASP | 51 | -5.881 | 49.909 | 25.252 | 1.00 | 70.00 | AP2 |
| ATOM | 3647 | C | ASP | 51 | -2.360 | 50.406 | 24.412 | 1.00 | 65.79 | AP2 |
| ATOM | 3648 | O | ASP | 51 | -3.275 | 51.088 | 23.938 | 1.00 | 65.17 | AP2 |
| ATOM | 3649 | N | MET | 52 | -1.215 | 50.155 | 23.766 | 1.00 | 65.48 | AP2 |
| ATOM | 3650 | CA | MET | 52 | -0.951 | 50.606 | 22.400 | 1.00 | 65.07 | AP2 |
| ATOM | 3651 | CB | MET | 52 | 0.032 | 51.782 | 22.387 | 1.00 | 65.16 | AP2 |
| ATOM | 3652 | CG | MET | 52 | 1.226 | 51.618 | 23.307 | 1.00 | 65.99 | AP2 |
| ATOM | 3653 | SD | MET | 52 | 2.324 | 53.078 | 23.241 | 1.00 | 66.46 | AP2 |
| ATOM | 3654 | CE | MET | 52 | 1.109 | 54.407 | 23.535 | 1.00 | 66.61 | AP2 |
| ATOM | 3655 | C | MET | 52 | -0.413 | 49.420 | 21.577 | 1.00 | 64.74 | AP2 |
| ATOM | 3656 | O | MET | 52 | -0.176 | 48.338 | 22.124 | 1.00 | 64.50 | AP2 |
| ATOM | 3657 | N | GLU | 53 | -0.233 | 49.621 | 20.270 | 1.00 | 64.21 | AP2 |
| ATOM | 3658 | CA | GLU | 53 | 0.240 | 48.561 | 19.383 | 1.00 | 63.66 | AP2 |
| ATOM | 3659 | CB | GLU | 53 | -0.438 | 48.681 | 18.021 | 1.00 | 65.03 | AP2 |
| ATOM | 3660 | CG | GLU | 53 | -1.947 | 48.589 | 18.025 | 1.00 | 67.15 | AP2 |
| ATOM | 3661 | CD | GLU | 53 | -2.502 | 48.558 | 16.606 | 1.00 | 68.94 | AP2 |
| ATOM | 3662 | OE1 | GLU | 53 | -1.772 | 49.026 | 15.698 | 1.00 | 69.75 | AP2 |
| ATOM | 3663 | OE2 | GLU | 53 | -3.651 | 48.077 | 16.391 | 1.00 | 69.40 | AP2 |
| ATOM | 3664 | C | GLU | 53 | 1.370 | 49.384 | 18.714 | 1.00 | 62.69 | AP2 |
| ATOM | 3665 | O | GLU | 53 | 1.138 | 50.531 | 18.242 | 1.00 | 62.84 | AP2 |
| ATOM | 3666 | N | ILE | 54 | 2.577 | 48.811 | 18.703 | 1.00 | 60.28 | AP2 |
| ATOM | 3667 | CA | ILE | 54 | 3.777 | 49.462 | 18.159 | 1.00 | 58.22 | AP2 |
| ATOM | 3668 | CB | ILE | 54 | 4.722 | 49.262 | 19.364 | 1.00 | 58.17 | AP2 |
| ATOM | 3669 | CG2 | ILE | 54 | 6.177 | 49.590 | 18.924 | 1.00 | 58.30 | AP2 |
| ATOM | 3670 | CG1 | ILE | 54 | 4.302 | 50.170 | 20.534 | 1.00 | 58.24 | AP2 |
| ATOM | 3671 | CD1 | ILE | 54 | 5.286 | 50.195 | 21.696 | 1.00 | 57.29 | AP2 |
| ATOM | 3672 | C | ILE | 54 | 4.147 | 48.405 | 17.101 | 1.00 | 56.70 | AP2 |
| ATOM | 3673 | O | ILE | 54 | 4.502 | 47.272 | 17.413 | 1.00 | 56.48 | AP2 |
| ATOM | 3674 | N | SER | 55 | 4.053 | 48.804 | 15.842 | 1.00 | 54.79 | AP2 |
| ATOM | 3675 | CA | SER | 55 | 4.389 | 47.968 | 14.704 | 1.00 | 52.52 | AP2 |
| ATOM | 3676 | CB | SER | 55 | 4.019 | 48.705 | 13.434 | 1.00 | 52.24 | AP2 |
| ATOM | 3677 | OG | SER | 55 | 4.831 | 49.876 | 13.340 | 1.00 | 50.08 | AP2 |
| ATOM | 3678 | C | SER | 55 | 5.896 | 47.742 | 14.651 | 1.00 | 52.02 | AP2 |
| ATOM | 3679 | O | SER | 55 | 6.653 | 48.361 | 15.400 | 1.00 | 50.47 | AP2 |
| ATOM | 3680 | N | ASP | 56 | 6.316 | 46.870 | 13.734 | 1.00 | 51.52 | AP2 |
| ATOM | 3681 | CA | ASP | 56 | 7.734 | 46.611 | 13.526 | 1.00 | 51.65 | AP2 |
| ATOM | 3682 | CB | ASP | 56 | 7.955 | 45.432 | 12.561 | 1.00 | 51.39 | AP2 |
| ATOM | 3683 | CG | ASP | 56 | 7.585 | 44.072 | 13.173 | 1.00 | 51.27 | AP2 |
| ATOM | 3684 | OD1 | ASP | 56 | 7.718 | 43.888 | 14.397 | 1.00 | 50.03 | AP2 |
| ATOM | 3685 | OD2 | ASP | 56 | 7.180 | 43.173 | 12.405 | 1.00 | 51.66 | AP2 |
| ATOM | 3686 | C | ASP | 56 | 8.335 | 47.897 | 12.926 | 1.00 | 51.59 | AP2 |
| ATOM | 3687 | O | ASP | 56 | 9.470 | 48.254 | 13.208 | 1.00 | 50.53 | AP2 |
| ATOM | 3688 | N | GLU | 57 | 7.549 | 48.608 | 12.127 | 1.00 | 52.32 | AP2 |
| ATOM | 3689 | CA | GLU | 57 | 8.036 | 49.834 | 11.523 | 1.00 | 54.22 | AP2 |
| ATOM | 3690 | CB | GLU | 57 | 6.990 | 50.414 | 10.550 | 1.00 | 55.66 | AP2 |
| ATOM | 3691 | CG | GLU | 57 | 7.397 | 51.743 | 9.901 | 1.00 | 57.60 | AP2 |
| ATOM | 3692 | CD | GLU | 57 | 6.659 | 52.010 | 8.598 | 1.00 | 59.28 | AP2 |
| ATOM | 3693 | OE1 | GLU | 57 | 5.490 | 52.440 | 8.637 | 1.00 | 59.81 | AP2 |
| ATOM | 3694 | OE2 | GLU | 57 | 7.244 | 51.779 | 7.516 | 1.00 | 60.85 | AP2 |
| ATOM | 3695 | C | GLU | 57 | 8.353 | 50.849 | 12.606 | 1.00 | 54.45 | AP2 |
| ATOM | 3696 | O | GLU | 57 | 9.366 | 51.522 | 12.541 | 1.00 | 54.39 | AP2 |
| ATOM | 3697 | N | ASP | 58 | 7.465 | 50.933 | 13.596 | 1.00 | 55.48 | AP2 |

FIG. 3A-65

| ATOM | 3698 | CA | ASP | 58 | 7.567 | 51.848 | 14.737 | 1.00 | 55.90 | AP2 |
|---|---|---|---|---|---|---|---|---|---|---|
| ATOM | 3699 | CB | ASP | 58 | 6.199 | 51.991 | 15.409 | 1.00 | 56.10 | AP2 |
| ATOM | 3700 | CG | ASP | 58 | 5.191 | 52.738 | 14.539 | 1.00 | 56.92 | AP2 |
| ATOM | 3701 | OD1 | ASP | 58 | 5.622 | 53.558 | 13.695 | 1.00 | 57.78 | AP2 |
| ATOM | 3702 | OD2 | ASP | 58 | 3.968 | 52.527 | 14.712 | 1.00 | 57.12 | AP2 |
| ATOM | 3703 | C | ASP | 58 | 8.597 | 51.449 | 15.790 | 1.00 | 56.08 | AP2 |
| ATOM | 3704 | O | ASP | 58 | 9.222 | 52.309 | 16.422 | 1.00 | 56.33 | AP2 |
| ATOM | 3705 | N | ALA | 59 | 8.762 | 50.154 | 15.999 | 1.00 | 56.24 | AP2 |
| ATOM | 3706 | CA | ALA | 59 | 9.727 | 49.677 | 16.970 | 1.00 | 57.11 | AP2 |
| ATOM | 3707 | CB | ALA | 59 | 9.596 | 48.172 | 17.133 | 1.00 | 56.29 | AP2 |
| ATOM | 3708 | C | ALA | 59 | 11.151 | 50.041 | 16.537 | 1.00 | 58.31 | AP2 |
| ATOM | 3709 | O | ALA | 59 | 12.033 | 50.211 | 17.370 | 1.00 | 58.41 | AP2 |
| ATOM | 3710 | N | GLU | 60 | 11.385 | 50.149 | 15.235 | 1.00 | 59.58 | AP2 |
| ATOM | 3711 | CA | GLU | 60 | 12.716 | 50.510 | 14.759 | 1.00 | 61.45 | AP2 |
| ATOM | 3712 | CB | GLU | 60 | 12.863 | 50.206 | 13.261 | 1.00 | 62.21 | AP2 |
| ATOM | 3713 | CG | GLU | 60 | 14.185 | 50.674 | 12.636 | 1.00 | 62.75 | AP2 |
| ATOM | 3714 | CD | GLU | 60 | 14.216 | 50.448 | 11.142 | 1.00 | 63.75 | AP2 |
| ATOM | 3715 | OE1 | GLU | 60 | 14.397 | 49.285 | 10.719 | 1.00 | 65.16 | AP2 |
| ATOM | 3716 | OE2 | GLU | 60 | 14.045 | 51.419 | 10.380 | 1.00 | 64.13 | AP2 |
| ATOM | 3717 | C | GLU | 60 | 12.928 | 52.000 | 15.006 | 1.00 | 62.56 | AP2 |
| ATOM | 3718 | O | GLU | 60 | 14.036 | 52.442 | 15.314 | 1.00 | 62.46 | AP2 |
| ATOM | 3719 | N | LYS | 61 | 11.845 | 52.762 | 14.886 | 1.00 | 63.87 | AP2 |
| ATOM | 3720 | CA | LYS | 61 | 11.887 | 54.200 | 15.086 | 1.00 | 65.19 | AP2 |
| ATOM | 3721 | CB | LYS | 61 | 10.522 | 54.809 | 14.761 | 1.00 | 66.28 | AP2 |
| ATOM | 3722 | CG | LYS | 61 | 10.507 | 56.330 | 14.791 | 1.00 | 67.81 | AP2 |
| ATOM | 3723 | CD | LYS | 61 | 9.102 | 56.930 | 15.010 | 1.00 | 68.60 | AP2 |
| ATOM | 3724 | CE | LYS | 61 | 9.225 | 58.430 | 15.426 | 1.00 | 69.32 | AP2 |
| ATOM | 3725 | NZ | LYS | 61 | 7.943 | 59.126 | 15.786 | 1.00 | 68.93 | AP2 |
| ATOM | 3726 | C | LYS | 61 | 12.289 | 54.577 | 16.510 | 1.00 | 65.76 | AP2 |
| ATOM | 3727 | O | LYS | 61 | 12.885 | 55.619 | 16.719 | 1.00 | 66.25 | AP2 |
| ATOM | 3728 | N | ILE | 62 | 11.979 | 53.744 | 17.499 | 1.00 | 66.49 | AP2 |
| ATOM | 3729 | CA | ILE | 62 | 12.341 | 54.089 | 18.872 | 1.00 | 66.91 | AP2 |
| ATOM | 3730 | CB | ILE | 62 | 11.135 | 53.957 | 19.833 | 1.00 | 66.83 | AP2 |
| ATOM | 3731 | CG2 | ILE | 62 | 10.425 | 55.289 | 19.929 | 1.00 | 67.42 | AP2 |
| ATOM | 3732 | CG1 | ILE | 62 | 10.154 | 52.896 | 19.349 | 1.00 | 66.56 | AP2 |
| ATOM | 3733 | CD1 | ILE | 62 | 8.929 | 52.796 | 20.241 | 1.00 | 65.95 | AP2 |
| ATOM | 3734 | C | ILE | 62 | 13.535 | 53.360 | 19.467 | 1.00 | 67.38 | AP2 |
| ATOM | 3735 | O | ILE | 62 | 13.415 | 52.271 | 20.038 | 1.00 | 67.69 | AP2 |
| ATOM | 3736 | N | ALA | 63 | 14.691 | 54.010 | 19.360 | 1.00 | 68.00 | AP2 |
| ATOM | 3737 | CA | ALA | 63 | 15.958 | 53.465 | 19.847 | 1.00 | 68.34 | AP2 |
| ATOM | 3738 | CB | ALA | 63 | 17.099 | 53.977 | 18.965 | 1.00 | 68.67 | AP2 |
| ATOM | 3739 | C | ALA | 63 | 16.286 | 53.741 | 21.322 | 1.00 | 68.26 | AP2 |
| ATOM | 3740 | O | ALA | 63 | 16.791 | 52.851 | 22.025 | 1.00 | 68.25 | AP2 |
| ATOM | 3741 | N | THR | 64 | 16.016 | 54.966 | 21.780 | 1.00 | 67.85 | AP2 |
| ATOM | 3742 | CA | THR | 64 | 16.312 | 55.352 | 23.164 | 1.00 | 67.48 | AP2 |
| ATOM | 3743 | CB | THR | 64 | 16.968 | 56.751 | 23.239 | 1.00 | 67.62 | AP2 |
| ATOM | 3744 | OG1 | THR | 64 | 16.115 | 57.709 | 22.594 | 1.00 | 68.15 | AP2 |
| ATOM | 3745 | CG2 | THR | 64 | 18.340 | 56.749 | 22.572 | 1.00 | 67.72 | AP2 |
| ATOM | 3746 | C | THR | 64 | 15.098 | 55.379 | 24.092 | 1.00 | 67.10 | AP2 |
| ATOM | 3747 | O | THR | 64 | 13.941 | 55.343 | 23.651 | 1.00 | 67.12 | AP2 |
| ATOM | 3748 | N | VAL | 65 | 15.392 | 55.448 | 25.386 | 1.00 | 66.32 | AP2 |
| ATOM | 3749 | CA | VAL | 65 | 14.378 | 55.500 | 26.414 | 1.00 | 65.55 | AP2 |
| ATOM | 3750 | CB | VAL | 65 | 15.018 | 55.579 | 27.777 | 1.00 | 65.53 | AP2 |
| ATOM | 3751 | CG1 | VAL | 65 | 13.940 | 55.593 | 28.848 | 1.00 | 65.46 | AP2 |
| ATOM | 3752 | CG2 | VAL | 65 | 15.967 | 54.392 | 27.959 | 1.00 | 65.23 | AP2 |
| ATOM | 3753 | C | VAL | 65 | 13.534 | 56.731 | 26.180 | 1.00 | 65.33 | AP2 |
| ATOM | 3754 | O | VAL | 65 | 12.315 | 56.705 | 26.308 | 1.00 | 64.73 | AP2 |

FIG. 3A-66

| ATOM | 3755 | N | GLY | 66 | 14.198 | 57.814 | 25.813 | 1.00 | 65.45 | AP2 |
| ATOM | 3756 | CA | GLY | 66 | 13.488 | 59.043 | 25.533 | 1.00 | 65.51 | AP2 |
| ATOM | 3757 | C | GLY | 66 | 12.603 | 58.856 | 24.320 | 1.00 | 65.64 | AP2 |
| ATOM | 3758 | O | GLY | 66 | 11.508 | 59.419 | 24.261 | 1.00 | 65.65 | AP2 |
| ATOM | 3759 | N | ASP | 67 | 13.085 | 58.078 | 23.347 | 1.00 | 65.58 | AP2 |
| ATOM | 3760 | CA | ASP | 67 | 12.322 | 57.797 | 22.139 | 1.00 | 65.56 | AP2 |
| ATOM | 3761 | CB | ASP | 67 | 13.137 | 56.932 | 21.176 | 1.00 | 66.26 | AP2 |
| ATOM | 3762 | CG | ASP | 67 | 14.045 | 57.744 | 20.277 | 1.00 | 66.73 | AP2 |
| ATOM | 3763 | OD1 | ASP | 67 | 14.975 | 57.140 | 19.697 | 1.00 | 66.67 | AP2 |
| ATOM | 3764 | OD2 | ASP | 67 | 13.822 | 58.972 | 20.141 | 1.00 | 67.11 | AP2 |
| ATOM | 3765 | C | ASP | 67 | 11.076 | 57.037 | 22.548 | 1.00 | 65.28 | AP2 |
| ATOM | 3766 | O | ASP | 67 | 9.992 | 57.248 | 22.002 | 1.00 | 65.07 | AP2 |
| ATOM | 3767 | N | ALA | 68 | 11.246 | 56.136 | 23.511 | 1.00 | 65.21 | AP2 |
| ATOM | 3768 | CA | ALA | 68 | 10.136 | 55.333 | 24.014 | 1.00 | 65.16 | AP2 |
| ATOM | 3769 | CB | ALA | 68 | 10.649 | 54.312 | 25.014 | 1.00 | 64.87 | AP2 |
| ATOM | 3770 | C | ALA | 68 | 9.122 | 56.259 | 24.670 | 1.00 | 65.09 | AP2 |
| ATOM | 3771 | O | ALA | 68 | 7.935 | 56.235 | 24.355 | 1.00 | 64.84 | AP2 |
| ATOM | 3772 | N | VAL | 69 | 9.611 | 57.096 | 25.570 | 1.00 | 65.44 | AP2 |
| ATOM | 3773 | CA | VAL | 69 | 8.762 | 58.038 | 26.271 | 1.00 | 65.98 | AP2 |
| ATOM | 3774 | CB | VAL | 69 | 9.615 | 58.912 | 27.239 | 1.00 | 66.24 | AP2 |
| ATOM | 3775 | CG1 | VAL | 69 | 8.723 | 59.905 | 27.975 | 1.00 | 66.37 | AP2 |
| ATOM | 3776 | CG2 | VAL | 69 | 10.340 | 58.011 | 28.258 | 1.00 | 66.23 | AP2 |
| ATOM | 3777 | C | VAL | 69 | 8.010 | 58.911 | 25.261 | 1.00 | 66.16 | AP2 |
| ATOM | 3778 | O | VAL | 69 | 6.786 | 59.030 | 25.314 | 1.00 | 66.01 | AP2 |
| ATOM | 3779 | N | ASN | 70 | 8.738 | 59.491 | 24.318 | 1.00 | 66.66 | AP2 |
| ATOM | 3780 | CA | ASN | 70 | 8.119 | 60.343 | 23.304 | 1.00 | 67.53 | AP2 |
| ATOM | 3781 | CB | ASN | 70 | 9.173 | 60.910 | 22.360 | 1.00 | 67.86 | AP2 |
| ATOM | 3782 | CG | ASN | 70 | 9.775 | 62.168 | 22.887 | 1.00 | 68.32 | AP2 |
| ATOM | 3783 | OD1 | ASN | 70 | 9.102 | 62.932 | 23.581 | 1.00 | 68.33 | AP2 |
| ATOM | 3784 | ND2 | ASN | 70 | 11.040 | 62.412 | 22.561 | 1.00 | 68.72 | AP2 |
| ATOM | 3785 | C | ASN | 70 | 7.041 | 59.667 | 22.472 | 1.00 | 67.96 | AP2 |
| ATOM | 3786 | O | ASN | 70 | 6.031 | 60.300 | 22.118 | 1.00 | 67.43 | AP2 |
| ATOM | 3787 | N | TYR | 71 | 7.275 | 58.395 | 22.141 | 1.00 | 68.35 | AP2 |
| ATOM | 3788 | CA | TYR | 71 | 6.321 | 57.643 | 21.357 | 1.00 | 68.79 | AP2 |
| ATOM | 3789 | CB | TYR | 71 | 6.846 | 56.259 | 21.032 | 1.00 | 68.30 | AP2 |
| ATOM | 3790 | CG | TYR | 71 | 5.923 | 55.514 | 20.104 | 1.00 | 68.05 | AP2 |
| ATOM | 3791 | CD1 | TYR | 71 | 4.870 | 54.753 | 20.601 | 1.00 | 67.75 | AP2 |
| ATOM | 3792 | CE1 | TYR | 71 | 4.015 | 54.060 | 19.743 | 1.00 | 67.76 | AP2 |
| ATOM | 3793 | CD2 | TYR | 71 | 6.095 | 55.574 | 18.724 | 1.00 | 67.68 | AP2 |
| ATOM | 3794 | CE2 | TYR | 71 | 5.244 | 54.891 | 17.862 | 1.00 | 67.56 | AP2 |
| ATOM | 3795 | CZ | TYR | 71 | 4.209 | 54.130 | 18.375 | 1.00 | 67.54 | AP2 |
| ATOM | 3796 | OH | TYR | 71 | 3.398 | 53.405 | 17.526 | 1.00 | 67.12 | AP2 |
| ATOM | 3797 | C | TYR | 71 | 5.050 | 57.547 | 22.167 | 1.00 | 69.54 | AP2 |
| ATOM | 3798 | O | TYR | 71 | 3.972 | 57.833 | 21.665 | 1.00 | 69.15 | AP2 |
| ATOM | 3799 | N | ILE | 72 | 5.178 | 57.137 | 23.421 | 1.00 | 70.67 | AP2 |
| ATOM | 3800 | CA | ILE | 72 | 4.019 | 57.064 | 24.291 | 1.00 | 72.16 | AP2 |
| ATOM | 3801 | CB | ILE | 72 | 4.409 | 56.482 | 25.638 | 1.00 | 71.69 | AP2 |
| ATOM | 3802 | CG2 | ILE | 72 | 3.192 | 56.337 | 26.507 | 1.00 | 71.53 | AP2 |
| ATOM | 3803 | CG1 | ILE | 72 | 5.075 | 55.120 | 25.433 | 1.00 | 71.64 | AP2 |
| ATOM | 3804 | CD1 | ILE | 72 | 5.828 | 54.632 | 26.651 | 1.00 | 70.95 | AP2 |
| ATOM | 3805 | C | ILE | 72 | 3.613 | 58.528 | 24.461 | 1.00 | 73.58 | AP2 |
| ATOM | 3806 | O | ILE | 72 | 4.055 | 59.183 | 25.401 | 1.00 | 73.89 | AP2 |
| ATOM | 3807 | N | GLN | 73 | 2.811 | 59.025 | 23.510 | 1.00 | 74.98 | AP2 |
| ATOM | 3808 | CA | GLN | 73 | 2.308 | 60.418 | 23.421 | 1.00 | 75.56 | AP2 |
| ATOM | 3809 | CB | GLN | 73 | 3.282 | 61.415 | 24.068 | 1.00 | 76.72 | AP2 |
| ATOM | 3810 | CG | GLN | 73 | 3.248 | 61.493 | 25.597 | 1.00 | 78.78 | AP2 |
| ATOM | 3811 | CD | GLN | 73 | 4.435 | 62.272 | 26.189 | 1.00 | 79.69 | AP2 |

FIG. 3A-67

| ATOM | 3812 | OE1 | GLN | 73 | 4.730 | 63.398 | 25.764 | 1.00 | 80.13 | AP2 |
|------|------|-----|-----|----|-------|--------|--------|------|-------|-----|
| ATOM | 3813 | NE2 | GLN | 73 | 5.100 | 61.685 | 27.188 | 1.00 | 79.77 | AP2 |
| ATOM | 3814 | C | GLN | 73 | 2.171 | 60.766 | 21.921 | 1.00 | 75.34 | AP2 |
| ATOM | 3815 | OT1 | GLN | 73 | 1.145 | 60.381 | 21.304 | 1.00 | 74.80 | AP2 |
| ATOM | 3816 | OT2 | GLN | 73 | 3.114 | 61.391 | 21.370 | 1.00 | 75.08 | AP2 |
| ATOM | 3817 | CB | ALA | 1 | 1.800 | -6.041 | 21.213 | 1.00 | 80.30 | AP3 |
| ATOM | 3818 | C | ALA | 1 | 2.577 | -6.903 | 23.453 | 1.00 | 80.06 | AP3 |
| ATOM | 3819 | O | ALA | 1 | 2.622 | -5.935 | 24.217 | 1.00 | 80.11 | AP3 |
| ATOM | 3820 | N | ALA | 1 | 0.099 | -6.809 | 22.864 | 1.00 | 80.88 | AP3 |
| ATOM | 3821 | CA | ALA | 1 | 1.493 | -7.021 | 22.374 | 1.00 | 80.41 | AP3 |
| ATOM | 3822 | N | ASP | 2 | 3.439 | -7.912 | 23.516 | 1.00 | 79.63 | AP3 |
| ATOM | 3823 | CA | ASP | 2 | 4.556 | -7.909 | 24.444 | 1.00 | 79.28 | AP3 |
| ATOM | 3824 | CB | ASP | 2 | 4.998 | -9.318 | 24.788 | 1.00 | 78.93 | AP3 |
| ATOM | 3825 | CG | ASP | 2 | 6.087 | -9.342 | 25.821 | 1.00 | 78.75 | AP3 |
| ATOM | 3826 | OD1 | ASP | 2 | 5.841 | -8.839 | 26.940 | 1.00 | 78.53 | AP3 |
| ATOM | 3827 | OD2 | ASP | 2 | 7.181 | -9.868 | 25.520 | 1.00 | 78.56 | AP3 |
| ATOM | 3828 | C | ASP | 2 | 5.634 | -7.256 | 23.609 | 1.00 | 79.40 | AP3 |
| ATOM | 3829 | O | ASP | 2 | 6.715 | -6.942 | 24.100 | 1.00 | 79.66 | AP3 |
| ATOM | 3830 | N | THR | 3 | 5.337 | -7.089 | 22.322 | 1.00 | 78.88 | AP3 |
| ATOM | 3831 | CA | THR | 3 | 6.260 | -6.440 | 21.413 | 1.00 | 78.63 | AP3 |
| ATOM | 3832 | CB | THR | 3 | 5.832 | -6.637 | 19.947 | 1.00 | 77.90 | AP3 |
| ATOM | 3833 | OG1 | THR | 3 | 6.193 | -7.955 | 19.528 | 1.00 | 77.32 | AP3 |
| ATOM | 3834 | CG2 | THR | 3 | 6.513 | -5.630 | 19.039 | 1.00 | 77.44 | AP3 |
| ATOM | 3835 | C | THR | 3 | 6.239 | -4.957 | 21.783 | 1.00 | 79.14 | AP3 |
| ATOM | 3836 | O | THR | 3 | 7.285 | -4.310 | 21.858 | 1.00 | 79.19 | AP3 |
| ATOM | 3837 | N | LEU | 4 | 5.040 | -4.435 | 22.035 | 1.00 | 79.46 | AP3 |
| ATOM | 3838 | CA | LEU | 4 | 4.856 | -3.039 | 22.419 | 1.00 | 79.70 | AP3 |
| ATOM | 3839 | CB | LEU | 4 | 3.379 | -2.702 | 22.486 | 1.00 | 79.44 | AP3 |
| ATOM | 3840 | CG | LEU | 4 | 3.055 | -1.299 | 22.973 | 1.00 | 79.41 | AP3 |
| ATOM | 3841 | CD1 | LEU | 4 | 3.240 | -0.335 | 21.815 | 1.00 | 78.99 | AP3 |
| ATOM | 3842 | CD2 | LEU | 4 | 1.611 | -1.253 | 23.493 | 1.00 | 79.05 | AP3 |
| ATOM | 3843 | C | LEU | 4 | 5.458 | -2.832 | 23.792 | 1.00 | 79.95 | AP3 |
| ATOM | 3844 | O | LEU | 4 | 6.116 | -1.832 | 24.040 | 1.00 | 79.62 | AP3 |
| ATOM | 3845 | N | GLU | 5 | 5.220 | -3.789 | 24.682 | 1.00 | 80.50 | AP3 |
| ATOM | 3846 | CA | GLU | 5 | 5.744 | -3.725 | 26.043 | 1.00 | 81.25 | AP3 |
| ATOM | 3847 | CB | GLU | 5 | 5.352 | -4.988 | 26.828 | 1.00 | 82.17 | AP3 |
| ATOM | 3848 | CG | GLU | 5 | 4.862 | -4.727 | 28.256 | 1.00 | 83.74 | AP3 |
| ATOM | 3849 | CD | GLU | 5 | 3.754 | -3.667 | 28.302 | 1.00 | 84.88 | AP3 |
| ATOM | 3850 | OE1 | GLU | 5 | 2.717 | -3.846 | 27.619 | 1.00 | 85.02 | AP3 |
| ATOM | 3851 | OE2 | GLU | 5 | 3.921 | -2.649 | 29.016 | 1.00 | 85.43 | AP3 |
| ATOM | 3852 | C | GLU | 5 | 7.267 | -3.595 | 25.998 | 1.00 | 81.11 | AP3 |
| ATOM | 3853 | O | GLU | 5 | 7.869 | -2.915 | 26.835 | 1.00 | 81.30 | AP3 |
| ATOM | 3854 | N | ARG | 6 | 7.881 | -4.248 | 25.011 | 1.00 | 80.60 | AP3 |
| ATOM | 3855 | CA | ARG | 6 | 9.325 | -4.221 | 24.843 | 1.00 | 79.96 | AP3 |
| ATOM | 3856 | CB | ARG | 6 | 9.816 | -5.499 | 24.149 | 1.00 | 79.81 | AP3 |
| ATOM | 3857 | CG | ARG | 6 | 9.847 | -6.716 | 25.055 | 1.00 | 79.18 | AP3 |
| ATOM | 3858 | CD | ARG | 6 | 10.927 | -7.684 | 24.616 | 1.00 | 79.45 | AP3 |
| ATOM | 3859 | NE | ARG | 6 | 10.589 | -8.357 | 23.372 | 1.00 | 78.96 | AP3 |
| ATOM | 3860 | CZ | ARG | 6 | 11.448 | -9.047 | 22.629 | 1.00 | 78.97 | AP3 |
| ATOM | 3861 | NH1 | ARG | 6 | 12.713 | -9.163 | 22.991 | 1.00 | 79.03 | AP3 |
| ATOM | 3862 | NH2 | ARG | 6 | 11.038 | -9.629 | 21.514 | 1.00 | 79.17 | AP3 |
| ATOM | 3863 | C | ARG | 6 | 9.762 | -2.999 | 24.058 | 1.00 | 79.85 | AP3 |
| ATOM | 3864 | O | ARG | 6 | 10.894 | -2.527 | 24.204 | 1.00 | 79.66 | AP3 |
| ATOM | 3865 | N | VAL | 7 | 8.862 | -2.491 | 23.225 | 1.00 | 79.59 | AP3 |
| ATOM | 3866 | CA | VAL | 7 | 9.152 | -1.308 | 22.439 | 1.00 | 79.61 | AP3 |
| ATOM | 3867 | CB | VAL | 7 | 8.142 | -1.136 | 21.275 | 1.00 | 79.79 | AP3 |
| ATOM | 3868 | CG1 | VAL | 7 | 7.714 | 0.317 | 21.147 | 1.00 | 79.88 | AP3 |

FIG. 3A-68

| ATOM | 3869 | CG2 | VAL | 7 | 8.779 | -1.601 | 19.960 | 1.00 | 79.63 | AP3 |
| ATOM | 3870 | C | VAL | 7 | 9.084 | -0.107 | 23.359 | 1.00 | 79.59 | AP3 |
| ATOM | 3871 | O | VAL | 7 | 9.918 | 0.788 | 23.282 | 1.00 | 79.69 | AP3 |
| ATOM | 3872 | N | THR | 8 | 8.099 | -0.104 | 24.246 | 1.00 | 79.81 | AP3 |
| ATOM | 3873 | CA | THR | 8 | 7.924 | 1.002 | 25.177 | 1.00 | 80.35 | AP3 |
| ATOM | 3874 | CB | THR | 8 | 6.535 | 0.924 | 25.869 | 1.00 | 80.28 | AP3 |
| ATOM | 3875 | OG1 | THR | 8 | 5.510 | 1.227 | 24.908 | 1.00 | 80.23 | AP3 |
| ATOM | 3876 | CG2 | THR | 8 | 6.440 | 1.913 | 27.020 | 1.00 | 80.18 | AP3 |
| ATOM | 3877 | C | THR | 8 | 9.048 | 1.087 | 26.214 | 1.00 | 80.61 | AP3 |
| ATOM | 3878 | O | THR | 8 | 9.490 | 2.180 | 26.567 | 1.00 | 80.23 | AP3 |
| ATOM | 3879 | N | LYS | 9 | 9.527 | -0.061 | 26.683 | 1.00 | 80.99 | AP3 |
| ATOM | 3880 | CA | LYS | 9 | 10.610 | -0.062 | 27.656 | 1.00 | 81.53 | AP3 |
| ATOM | 3881 | CB | LYS | 9 | 10.917 | -1.493 | 28.130 | 1.00 | 81.32 | AP3 |
| ATOM | 3882 | CG | LYS | 9 | 12.160 | -1.594 | 29.023 | 1.00 | 81.21 | AP3 |
| ATOM | 3883 | CD | LYS | 9 | 12.144 | -2.839 | 29.918 | 1.00 | 81.53 | AP3 |
| ATOM | 3884 | CE | LYS | 9 | 13.543 | -3.165 | 30.484 | 1.00 | 81.08 | AP3 |
| ATOM | 3885 | NZ | LYS | 9 | 14.162 | -2.051 | 31.270 | 1.00 | 80.56 | AP3 |
| ATOM | 3886 | C | LYS | 9 | 11.860 | 0.579 | 27.041 | 1.00 | 81.86 | AP3 |
| ATOM | 3887 | O | LYS | 9 | 12.609 | 1.287 | 27.715 | 1.00 | 82.11 | AP3 |
| ATOM | 3888 | N | ILE | 10 | 12.075 | 0.334 | 25.753 | 1.00 | 81.96 | AP3 |
| ATOM | 3889 | CA | ILE | 10 | 13.225 | 0.885 | 25.048 | 1.00 | 81.82 | AP3 |
| ATOM | 3890 | CB | ILE | 10 | 13.390 | 0.203 | 23.654 | 1.00 | 81.28 | AP3 |
| ATOM | 3891 | CG2 | ILE | 10 | 14.375 | 0.966 | 22.795 | 1.00 | 81.09 | AP3 |
| ATOM | 3892 | CG1 | ILE | 10 | 13.783 | -1.272 | 23.838 | 1.00 | 81.30 | AP3 |
| ATOM | 3893 | CD1 | ILE | 10 | 14.806 | -1.554 | 24.964 | 1.00 | 81.09 | AP3 |
| ATOM | 3894 | C | ILE | 10 | 13.093 | 2.401 | 24.871 | 1.00 | 82.11 | AP3 |
| ATOM | 3895 | O | ILE | 10 | 14.082 | 3.136 | 24.999 | 1.00 | 81.77 | AP3 |
| ATOM | 3896 | N | ILE | 11 | 11.867 | 2.849 | 24.589 | 1.00 | 82.41 | AP3 |
| ATOM | 3897 | CA | ILE | 11 | 11.562 | 4.262 | 24.368 | 1.00 | 82.78 | AP3 |
| ATOM | 3898 | CB | ILE | 11 | 10.186 | 4.426 | 23.670 | 1.00 | 82.33 | AP3 |
| ATOM | 3899 | CG2 | ILE | 11 | 9.797 | 5.896 | 23.575 | 1.00 | 82.07 | AP3 |
| ATOM | 3900 | CG1 | ILE | 11 | 10.255 | 3.827 | 22.270 | 1.00 | 82.32 | AP3 |
| ATOM | 3901 | CD1 | ILE | 11 | 8.945 | 3.876 | 21.506 | 1.00 | 82.44 | AP3 |
| ATOM | 3902 | C | ILE | 11 | 11.568 | 5.098 | 25.644 | 1.00 | 83.20 | AP3 |
| ATOM | 3903 | O | ILE | 11 | 11.935 | 6.269 | 25.620 | 1.00 | 83.45 | AP3 |
| ATOM | 3904 | N | VAL | 12 | 11.164 | 4.501 | 26.760 | 1.00 | 83.91 | AP3 |
| ATOM | 3905 | CA | VAL | 12 | 11.127 | 5.227 | 28.019 | 1.00 | 84.43 | AP3 |
| ATOM | 3906 | CB | VAL | 12 | 10.158 | 4.540 | 29.031 | 1.00 | 84.31 | AP3 |
| ATOM | 3907 | CG1 | VAL | 12 | 10.373 | 5.070 | 30.435 | 1.00 | 84.17 | AP3 |
| ATOM | 3908 | CG2 | VAL | 12 | 8.724 | 4.811 | 28.623 | 1.00 | 84.03 | AP3 |
| ATOM | 3909 | C | VAL | 12 | 12.520 | 5.340 | 28.619 | 1.00 | 84.94 | AP3 |
| ATOM | 3910 | O | VAL | 12 | 12.701 | 5.944 | 29.678 | 1.00 | 85.35 | AP3 |
| ATOM | 3911 | N | ASP | 13 | 13.513 | 4.783 | 27.936 | 1.00 | 85.34 | AP3 |
| ATOM | 3912 | CA | ASP | 13 | 14.878 | 4.833 | 28.454 | 1.00 | 86.04 | AP3 |
| ATOM | 3913 | CB | ASP | 13 | 15.334 | 3.420 | 28.853 | 1.00 | 86.48 | AP3 |
| ATOM | 3914 | CG | ASP | 13 | 14.386 | 2.767 | 29.869 | 1.00 | 87.14 | AP3 |
| ATOM | 3915 | OD1 | ASP | 13 | 13.717 | 3.520 | 30.620 | 1.00 | 87.08 | AP3 |
| ATOM | 3916 | OD2 | ASP | 13 | 14.317 | 1.511 | 29.929 | 1.00 | 87.02 | AP3 |
| ATOM | 3917 | C | ASP | 13 | 15.878 | 5.476 | 27.490 | 1.00 | 86.16 | AP3 |
| ATOM | 3918 | O | ASP | 13 | 17.056 | 5.644 | 27.812 | 1.00 | 86.06 | AP3 |
| ATOM | 3919 | N | ARG | 14 | 15.395 | 5.850 | 26.313 | 1.00 | 86.23 | AP3 |
| ATOM | 3920 | CA | ARG | 14 | 16.233 | 6.481 | 25.310 | 1.00 | 86.55 | AP3 |
| ATOM | 3921 | CB | ARG | 14 | 16.109 | 5.733 | 23.987 | 1.00 | 86.57 | AP3 |
| ATOM | 3922 | CG | ARG | 14 | 16.725 | 4.339 | 23.997 | 1.00 | 86.67 | AP3 |
| ATOM | 3923 | CD | ARG | 14 | 18.206 | 4.391 | 23.645 | 1.00 | 86.53 | AP3 |
| ATOM | 3924 | NE | ARG | 14 | 19.027 | 5.031 | 24.669 | 1.00 | 86.50 | AP3 |
| ATOM | 3925 | CZ | ARG | 14 | 19.365 | 4.472 | 25.828 | 1.00 | 86.59 | AP3 |

FIG. 3A-69

| ATOM | 3926 | NH1 | ARG | 14 | 18.960 | 3.245 | 26.142 | 1.00 | 86.74 | AP3 |
| ATOM | 3927 | NH2 | ARG | 14 | 20.117 | 5.145 | 26.682 | 1.00 | 86.67 | AP3 |
| ATOM | 3928 | C | ARG | 14 | 15.761 | 7.914 | 25.143 | 1.00 | 86.71 | AP3 |
| ATOM | 3929 | O | ARG | 14 | 16.544 | 8.812 | 24.823 | 1.00 | 86.83 | AP3 |
| ATOM | 3930 | N | LEU | 15 | 14.468 | 8.111 | 25.371 | 1.00 | 86.78 | AP3 |
| ATOM | 3931 | CA | LEU | 15 | 13.847 | 9.419 | 25.263 | 1.00 | 87.14 | AP3 |
| ATOM | 3932 | CB | LEU | 15 | 12.632 | 9.351 | 24.343 | 1.00 | 86.46 | AP3 |
| ATOM | 3933 | CG | LEU | 15 | 12.945 | 9.019 | 22.895 | 1.00 | 85.94 | AP3 |
| ATOM | 3934 | CD1 | LEU | 15 | 11.689 | 9.228 | 22.079 | 1.00 | 86.10 | AP3 |
| ATOM | 3935 | CD2 | LEU | 15 | 14.064 | 9.913 | 22.386 | 1.00 | 85.45 | AP3 |
| ATOM | 3936 | C | LEU | 15 | 13.421 | 9.930 | 26.634 | 1.00 | 87.71 | AP3 |
| ATOM | 3937 | O | LEU | 15 | 13.111 | 11.111 | 26.798 | 1.00 | 87.66 | AP3 |
| ATOM | 3938 | N | GLY | 16 | 13.401 | 9.028 | 27.609 | 1.00 | 88.38 | AP3 |
| ATOM | 3939 | CA | GLY | 16 | 13.024 | 9.387 | 28.962 | 1.00 | 89.57 | AP3 |
| ATOM | 3940 | C | GLY | 16 | 11.685 | 10.083 | 29.141 | 1.00 | 90.52 | AP3 |
| ATOM | 3941 | O | GLY | 16 | 11.634 | 11.185 | 29.686 | 1.00 | 90.64 | AP3 |
| ATOM | 3942 | N | VAL | 17 | 10.606 | 9.456 | 28.680 | 1.00 | 91.37 | AP3 |
| ATOM | 3943 | CA | VAL | 17 | 9.260 | 10.011 | 28.830 | 1.00 | 92.27 | AP3 |
| ATOM | 3944 | CB | VAL | 17 | 8.411 | 9.821 | 27.510 | 1.00 | 92.11 | AP3 |
| ATOM | 3945 | CG1 | VAL | 17 | 8.673 | 10.969 | 26.535 | 1.00 | 91.59 | AP3 |
| ATOM | 3946 | CG2 | VAL | 17 | 8.763 | 8.495 | 26.833 | 1.00 | 91.92 | AP3 |
| ATOM | 3947 | C | VAL | 17 | 8.617 | 9.272 | 30.025 | 1.00 | 93.10 | AP3 |
| ATOM | 3948 | O | VAL | 17 | 9.327 | 8.596 | 30.778 | 1.00 | 93.19 | AP3 |
| ATOM | 3949 | N | ASP | 18 | 7.302 | 9.407 | 30.219 | 1.00 | 94.20 | AP3 |
| ATOM | 3950 | CA | ASP | 18 | 6.603 | 8.720 | 31.325 | 1.00 | 95.26 | AP3 |
| ATOM | 3951 | CB | ASP | 18 | 5.262 | 9.404 | 31.641 | 1.00 | 95.83 | AP3 |
| ATOM | 3952 | CG | ASP | 18 | 5.430 | 10.780 | 32.271 | 1.00 | 96.39 | AP3 |
| ATOM | 3953 | OD1 | ASP | 18 | 6.051 | 10.865 | 33.360 | 1.00 | 96.57 | AP3 |
| ATOM | 3954 | OD2 | ASP | 18 | 4.936 | 11.774 | 31.679 | 1.00 | 96.48 | AP3 |
| ATOM | 3955 | C | ASP | 18 | 6.331 | 7.258 | 30.951 | 1.00 | 95.69 | AP3 |
| ATOM | 3956 | O | ASP | 18 | 7.187 | 6.389 | 31.122 | 1.00 | 96.20 | AP3 |
| ATOM | 3957 | N | GLU | 19 | 5.122 | 6.990 | 30.469 | 1.00 | 95.81 | AP3 |
| ATOM | 3958 | CA | GLU | 19 | 4.741 | 5.654 | 30.025 | 1.00 | 95.73 | AP3 |
| ATOM | 3959 | CB | GLU | 19 | 4.592 | 4.669 | 31.179 | 1.00 | 95.35 | AP3 |
| ATOM | 3960 | CG | GLU | 19 | 4.271 | 3.268 | 30.674 | 1.00 | 94.53 | AP3 |
| ATOM | 3961 | CD | GLU | 19 | 4.963 | 2.186 | 31.467 | 1.00 | 94.17 | AP3 |
| ATOM | 3962 | OE1 | GLU | 19 | 6.103 | 2.413 | 31.924 | 1.00 | 93.98 | AP3 |
| ATOM | 3963 | OE2 | GLU | 19 | 4.374 | 1.100 | 31.617 | 1.00 | 93.93 | AP3 |
| ATOM | 3964 | C | GLU | 19 | 3.432 | 5.744 | 29.279 | 1.00 | 95.95 | AP3 |
| ATOM | 3965 | O | GLU | 19 | 3.344 | 5.344 | 28.120 | 1.00 | 96.20 | AP3 |
| ATOM | 3966 | N | ALA | 20 | 2.405 | 6.265 | 29.938 | 1.00 | 96.02 | AP3 |
| ATOM | 3967 | CA | ALA | 20 | 1.123 | 6.407 | 29.269 | 1.00 | 96.23 | AP3 |
| ATOM | 3968 | CB | ALA | 20 | 0.082 | 6.948 | 30.227 | 1.00 | 96.45 | AP3 |
| ATOM | 3969 | C | ALA | 20 | 1.361 | 7.383 | 28.123 | 1.00 | 96.14 | AP3 |
| ATOM | 3970 | O | ALA | 20 | 0.504 | 7.580 | 27.255 | 1.00 | 96.23 | AP3 |
| ATOM | 3971 | N | ASP | 21 | 2.548 | 7.987 | 28.142 | 1.00 | 95.88 | AP3 |
| ATOM | 3972 | CA | ASP | 21 | 2.972 | 8.934 | 27.120 | 1.00 | 95.67 | AP3 |
| ATOM | 3973 | CB | ASP | 21 | 4.335 | 9.526 | 27.494 | 1.00 | 95.98 | AP3 |
| ATOM | 3974 | CG | ASP | 21 | 4.226 | 10.896 | 28.144 | 1.00 | 96.43 | AP3 |
| ATOM | 3975 | OD1 | ASP | 21 | 3.313 | 11.079 | 28.979 | 1.00 | 96.41 | AP3 |
| ATOM | 3976 | OD2 | ASP | 21 | 5.064 | 11.783 | 27.831 | 1.00 | 96.37 | AP3 |
| ATOM | 3977 | C | ASP | 21 | 3.093 | 8.192 | 25.798 | 1.00 | 95.36 | AP3 |
| ATOM | 3978 | O | ASP | 21 | 2.740 | 8.720 | 24.740 | 1.00 | 95.36 | AP3 |
| ATOM | 3979 | N | VAL | 22 | 3.593 | 6.959 | 25.877 | 1.00 | 95.01 | AP3 |
| ATOM | 3980 | CA | VAL | 22 | 3.802 | 6.107 | 24.706 | 1.00 | 94.72 | AP3 |
| ATOM | 3981 | CB | VAL | 22 | 4.975 | 5.105 | 24.935 | 1.00 | 94.84 | AP3 |
| ATOM | 3982 | CG1 | VAL | 22 | 5.062 | 4.115 | 23.777 | 1.00 | 94.84 | AP3 |

FIG. 3A-70

| ATOM | 3983 | CG2 | VAL | 22 | 6.294 | 5.861 | 25.076 | 1.00 | 95.01 | AP3 |
|------|------|-----|-----|----|-------|-------|--------|------|-------|-----|
| ATOM | 3984 | C | VAL | 22 | 2.580 | 5.297 | 24.301 | 1.00 | 94.29 | AP3 |
| ATOM | 3985 | O | VAL | 22 | 2.334 | 4.225 | 24.843 | 1.00 | 94.13 | AP3 |
| ATOM | 3986 | N | LYS | 23 | 1.822 | 5.815 | 23.343 | 1.00 | 94.07 | AP3 |
| ATOM | 3987 | CA | LYS | 23 | 0.642 | 5.120 | 22.847 | 1.00 | 93.68 | AP3 |
| ATOM | 3988 | CB | LYS | 23 | -0.524 | 6.087 | 22.694 | 1.00 | 93.74 | AP3 |
| ATOM | 3989 | C | LYS | 23 | 1.046 | 4.550 | 21.498 | 1.00 | 93.39 | AP3 |
| ATOM | 3990 | O | LYS | 23 | 2.170 | 4.759 | 21.050 | 1.00 | 93.48 | AP3 |
| ATOM | 3991 | N | LEU | 24 | 0.134 | 3.842 | 20.846 | 1.00 | 93.12 | AP3 |
| ATOM | 3992 | CA | LEU | 24 | 0.438 | 3.233 | 19.557 | 1.00 | 92.79 | AP3 |
| ATOM | 3993 | CB | LEU | 24 | -0.584 | 2.123 | 19.247 | 1.00 | 92.55 | AP3 |
| ATOM | 3994 | CG | LEU | 24 | -0.066 | 0.793 | 18.668 | 1.00 | 92.42 | AP3 |
| ATOM | 3995 | CD1 | LEU | 24 | 0.765 | 0.040 | 19.714 | 1.00 | 91.85 | AP3 |
| ATOM | 3996 | CD2 | LEU | 24 | -1.248 | -0.060 | 18.216 | 1.00 | 92.20 | AP3 |
| ATOM | 3997 | C | LEU | 24 | 0.489 | 4.239 | 18.405 | 1.00 | 92.49 | AP3 |
| ATOM | 3998 | O | LEU | 24 | 1.330 | 4.135 | 17.522 | 1.00 | 92.33 | AP3 |
| ATOM | 3999 | N | GLU | 25 | -0.400 | 5.219 | 18.407 | 1.00 | 92.48 | AP3 |
| ATOM | 4000 | CA | GLU | 25 | -0.389 | 6.189 | 17.325 | 1.00 | 92.80 | AP3 |
| ATOM | 4001 | CB | GLU | 25 | -1.810 | 6.654 | 17.015 | 1.00 | 93.44 | AP3 |
| ATOM | 4002 | CG | GLU | 25 | -2.765 | 5.516 | 16.729 | 1.00 | 94.57 | AP3 |
| ATOM | 4003 | CD | GLU | 25 | -4.153 | 6.007 | 16.407 | 1.00 | 95.36 | AP3 |
| ATOM | 4004 | OE1 | GLU | 25 | -4.514 | 7.089 | 16.930 | 1.00 | 95.95 | AP3 |
| ATOM | 4005 | OE2 | GLU | 25 | -4.879 | 5.311 | 15.650 | 1.00 | 95.66 | AP3 |
| ATOM | 4006 | C | GLU | 25 | 0.493 | 7.391 | 17.655 | 1.00 | 92.51 | AP3 |
| ATOM | 4007 | O | GLU | 25 | 0.436 | 8.419 | 16.973 | 1.00 | 92.63 | AP3 |
| ATOM | 4008 | N | ALA | 26 | 1.311 | 7.262 | 18.697 | 1.00 | 91.90 | AP3 |
| ATOM | 4009 | CA | ALA | 26 | 2.200 | 8.346 | 19.093 | 1.00 | 91.28 | AP3 |
| ATOM | 4010 | CB | ALA | 26 | 2.729 | 8.101 | 20.505 | 1.00 | 90.92 | AP3 |
| ATOM | 4011 | C | ALA | 26 | 3.360 | 8.459 | 18.100 | 1.00 | 91.07 | AP3 |
| ATOM | 4012 | O | ALA | 26 | 4.005 | 7.459 | 17.769 | 1.00 | 91.02 | AP3 |
| ATOM | 4013 | N | SER | 27 | 3.602 | 9.674 | 17.605 | 1.00 | 90.75 | AP3 |
| ATOM | 4014 | CA | SER | 27 | 4.702 | 9.924 | 16.666 | 1.00 | 90.16 | AP3 |
| ATOM | 4015 | CB | SER | 27 | 4.460 | 11.190 | 15.826 | 1.00 | 90.40 | AP3 |
| ATOM | 4016 | OG | SER | 27 | 5.623 | 11.544 | 15.080 | 1.00 | 90.09 | AP3 |
| ATOM | 4017 | C | SER | 27 | 6.001 | 10.095 | 17.427 | 1.00 | 89.59 | AP3 |
| ATOM | 4018 | O | SER | 27 | 6.040 | 10.694 | 18.501 | 1.00 | 89.05 | AP3 |
| ATOM | 4019 | N | PHE | 28 | 7.069 | 9.566 | 16.857 | 1.00 | 89.40 | AP3 |
| ATOM | 4020 | CA | PHE | 28 | 8.364 | 9.671 | 17.488 | 1.00 | 89.33 | AP3 |
| ATOM | 4021 | CB | PHE | 28 | 9.377 | 8.800 | 16.740 | 1.00 | 88.83 | AP3 |
| ATOM | 4022 | CG | PHE | 28 | 9.274 | 7.333 | 17.065 | 1.00 | 87.80 | AP3 |
| ATOM | 4023 | CD1 | PHE | 28 | 9.394 | 6.891 | 18.382 | 1.00 | 87.34 | AP3 |
| ATOM | 4024 | CD2 | PHE | 28 | 9.061 | 6.399 | 16.061 | 1.00 | 87.22 | AP3 |
| ATOM | 4025 | CE1 | PHE | 28 | 9.306 | 5.545 | 18.697 | 1.00 | 86.85 | AP3 |
| ATOM | 4026 | CE2 | PHE | 28 | 8.971 | 5.049 | 16.368 | 1.00 | 87.12 | AP3 |
| ATOM | 4027 | CZ | PHE | 28 | 9.095 | 4.624 | 17.693 | 1.00 | 86.87 | AP3 |
| ATOM | 4028 | C | PHE | 28 | 8.835 | 11.121 | 17.543 | 1.00 | 89.67 | AP3 |
| ATOM | 4029 | O | PHE | 28 | 9.341 | 11.566 | 18.573 | 1.00 | 89.45 | AP3 |
| ATOM | 4030 | N | LYS | 29 | 8.652 | 11.865 | 16.451 | 1.00 | 90.18 | AP3 |
| ATOM | 4031 | CA | LYS | 29 | 9.095 | 13.263 | 16.417 | 1.00 | 90.72 | AP3 |
| ATOM | 4032 | CB | LYS | 29 | 9.453 | 13.681 | 14.986 | 1.00 | 90.81 | AP3 |
| ATOM | 4033 | CG | LYS | 29 | 10.959 | 13.633 | 14.692 | 1.00 | 90.99 | AP3 |
| ATOM | 4034 | CD | LYS | 29 | 11.237 | 13.776 | 13.195 | 1.00 | 91.39 | AP3 |
| ATOM | 4035 | CE | LYS | 29 | 12.690 | 13.466 | 12.840 | 1.00 | 91.39 | AP3 |
| ATOM | 4036 | NZ | LYS | 29 | 12.835 | 13.201 | 11.371 | 1.00 | 91.17 | AP3 |
| ATOM | 4037 | C | LYS | 29 | 8.115 | 14.268 | 17.001 | 1.00 | 90.70 | AP3 |
| ATOM | 4038 | O | LYS | 29 | 8.477 | 15.063 | 17.869 | 1.00 | 90.68 | AP3 |
| ATOM | 4039 | N | GLU | 30 | 6.875 | 14.214 | 16.528 | 1.00 | 90.93 | AP3 |

FIG. 3A-71

| ATOM | 4040 | CA | GLU | 30 | 5.820 | 15.131 | 16.961 | 1.00 | 90.95 | AP3 |
| --- | --- | --- | --- | --- | --- | --- | --- | --- | --- | --- |
| ATOM | 4041 | CB | GLU | 30 | 4.680 | 15.046 | 15.936 | 1.00 | 91.42 | AP3 |
| ATOM | 4042 | CG | GLU | 30 | 5.175 | 15.444 | 14.528 | 1.00 | 93.07 | AP3 |
| ATOM | 4043 | CD | GLU | 30 | 6.132 | 16.654 | 14.488 | 1.00 | 93.86 | AP3 |
| ATOM | 4044 | OE1 | GLU | 30 | 6.077 | 17.504 | 15.408 | 1.00 | 94.24 | AP3 |
| ATOM | 4045 | OE2 | GLU | 30 | 6.921 | 16.768 | 13.512 | 1.00 | 94.24 | AP3 |
| ATOM | 4046 | C | GLU | 30 | 5.295 | 15.001 | 18.406 | 1.00 | 90.36 | AP3 |
| ATOM | 4047 | O | GLU | 30 | 5.120 | 16.014 | 19.091 | 1.00 | 90.24 | AP3 |
| ATOM | 4048 | N | ASP | 31 | 5.073 | 13.771 | 18.875 | 1.00 | 89.92 | AP3 |
| ATOM | 4049 | CA | ASP | 31 | 4.547 | 13.519 | 20.232 | 1.00 | 89.32 | AP3 |
| ATOM | 4050 | CB | ASP | 31 | 3.481 | 12.396 | 20.207 | 1.00 | 89.62 | AP3 |
| ATOM | 4051 | CG | ASP | 31 | 2.159 | 12.822 | 19.558 | 1.00 | 89.86 | AP3 |
| ATOM | 4052 | OD1 | ASP | 31 | 1.483 | 13.725 | 20.107 | 1.00 | 90.00 | AP3 |
| ATOM | 4053 | OD2 | ASP | 31 | 1.790 | 12.243 | 18.504 | 1.00 | 89.74 | AP3 |
| ATOM | 4054 | C | ASP | 31 | 5.598 | 13.141 | 21.286 | 1.00 | 88.79 | AP3 |
| ATOM | 4055 | O | ASP | 31 | 5.439 | 13.436 | 22.471 | 1.00 | 88.28 | AP3 |
| ATOM | 4056 | N | LEU | 32 | 6.662 | 12.467 | 20.864 | 1.00 | 88.48 | AP3 |
| ATOM | 4057 | CA | LEU | 32 | 7.696 | 12.039 | 21.808 | 1.00 | 88.08 | AP3 |
| ATOM | 4058 | CB | LEU | 32 | 8.178 | 10.628 | 21.443 | 1.00 | 88.20 | AP3 |
| ATOM | 4059 | CG | LEU | 32 | 7.092 | 9.545 | 21.393 | 1.00 | 88.29 | AP3 |
| ATOM | 4060 | CD1 | LEU | 32 | 7.714 | 8.208 | 21.024 | 1.00 | 88.43 | AP3 |
| ATOM | 4061 | CD2 | LEU | 32 | 6.399 | 9.453 | 22.747 | 1.00 | 88.22 | AP3 |
| ATOM | 4062 | C | LEU | 32 | 8.886 | 13.002 | 21.878 | 1.00 | 87.67 | AP3 |
| ATOM | 4063 | O | LEU | 32 | 9.632 | 13.015 | 22.877 | 1.00 | 87.89 | AP3 |
| ATOM | 4064 | N | GLY | 33 | 9.059 | 13.793 | 20.816 | 1.00 | 86.61 | AP3 |
| ATOM | 4065 | CA | GLY | 33 | 10.138 | 14.763 | 20.766 | 1.00 | 85.37 | AP3 |
| ATOM | 4066 | C | GLY | 33 | 11.502 | 14.142 | 20.557 | 1.00 | 84.27 | AP3 |
| ATOM | 4067 | O | GLY | 33 | 12.447 | 14.401 | 21.311 | 1.00 | 84.12 | AP3 |
| ATOM | 4068 | N | ALA | 34 | 11.595 | 13.307 | 19.532 | 1.00 | 83.28 | AP3 |
| ATOM | 4069 | CA | ALA | 34 | 12.843 | 12.649 | 19.198 | 1.00 | 82.21 | AP3 |
| ATOM | 4070 | CB | ALA | 34 | 12.614 | 11.151 | 18.992 | 1.00 | 81.82 | AP3 |
| ATOM | 4071 | C | ALA | 34 | 13.410 | 13.279 | 17.933 | 1.00 | 81.35 | AP3 |
| ATOM | 4072 | O | ALA | 34 | 12.691 | 13.478 | 16.953 | 1.00 | 81.03 | AP3 |
| ATOM | 4073 | N | ASP | 35 | 14.698 | 13.606 | 17.971 | 1.00 | 80.45 | AP3 |
| ATOM | 4074 | CA | ASP | 35 | 15.348 | 14.198 | 16.818 | 1.00 | 79.95 | AP3 |
| ATOM | 4075 | CB | ASP | 35 | 16.295 | 15.343 | 17.224 | 1.00 | 79.22 | AP3 |
| ATOM | 4076 | CG | ASP | 35 | 17.324 | 14.928 | 18.258 | 1.00 | 79.03 | AP3 |
| ATOM | 4077 | OD1 | ASP | 35 | 17.556 | 13.710 | 18.421 | 1.00 | 78.87 | AP3 |
| ATOM | 4078 | OD2 | ASP | 35 | 17.914 | 15.829 | 18.902 | 1.00 | 78.65 | AP3 |
| ATOM | 4079 | C | ASP | 35 | 16.117 | 13.146 | 16.049 | 1.00 | 79.63 | AP3 |
| ATOM | 4080 | O | ASP | 35 | 16.163 | 11.983 | 16.446 | 1.00 | 79.61 | AP3 |
| ATOM | 4081 | CA | PAN | 36 | 17.510 | 12.743 | 14.053 | 1.00 | 79.08 | AP3 |
| ATOM | 4082 | N | PAN | 36 | 16.721 | 13.582 | 14.947 | 1.00 | 79.50 | AP3 |
| ATOM | 4083 | C | PAN | 36 | 18.515 | 11.845 | 14.766 | 1.00 | 77.61 | AP3 |
| ATOM | 4084 | O | PAN | 36 | 18.825 | 10.763 | 14.288 | 1.00 | 77.16 | AP3 |
| ATOM | 4085 | O5 | PAN | 36 | 17.274 | 14.569 | 12.565 | 1.00 | 85.24 | AP3 |
| ATOM | 4086 | P6 | PAN | 36 | 16.757 | 14.374 | 11.104 | 1.00 | 88.14 | AP3 |
| ATOM | 4087 | O7 | PAN | 36 | 15.217 | 14.054 | 11.218 | 1.00 | 88.33 | AP3 |
| ATOM | 4088 | O8 | PAN | 36 | 17.499 | 13.109 | 10.488 | 1.00 | 87.44 | AP3 |
| ATOM | 4089 | O9 | PAN | 36 | 17.008 | 15.600 | 10.291 | 1.00 | 88.61 | AP3 |
| ATOM | 4090 | CB | PAN | 36 | 18.231 | 13.636 | 13.050 | 1.00 | 81.25 | AP3 |
| ATOM | 4091 | N | LEU | 37 | 19.032 | 12.297 | 15.902 | 1.00 | 76.08 | AP3 |
| ATOM | 4092 | CA | LEU | 37 | 19.979 | 11.494 | 16.647 | 1.00 | 74.58 | AP3 |
| ATOM | 4093 | CB | LEU | 37 | 20.902 | 12.393 | 17.496 | 1.00 | 73.85 | AP3 |
| ATOM | 4094 | CG | LEU | 37 | 22.259 | 11.862 | 18.031 | 1.00 | 72.85 | AP3 |
| ATOM | 4095 | CD1 | LEU | 37 | 22.125 | 11.234 | 19.393 | 1.00 | 72.07 | AP3 |
| ATOM | 4096 | CD2 | LEU | 37 | 22.841 | 10.874 | 17.044 | 1.00 | 72.39 | AP3 |

FIG. 3A-72

| ATOM | 4097 | C | LEU | 37 | 19.179 | 10.522 | 17.521 | 1.00 | 73.97 | AP3 |
|---|---|---|---|---|---|---|---|---|---|---|
| ATOM | 4098 | O | LEU | 37 | 19.524 | 9.352 | 17.628 | 1.00 | 73.50 | AP3 |
| ATOM | 4099 | N | ASP | 38 | 18.101 | 10.993 | 18.138 | 1.00 | 73.53 | AP3 |
| ATOM | 4100 | CA | ASP | 38 | 17.301 | 10.098 | 18.970 | 1.00 | 72.79 | AP3 |
| ATOM | 4101 | CB | ASP | 38 | 16.124 | 10.842 | 19.607 | 1.00 | 73.04 | AP3 |
| ATOM | 4102 | CG | ASP | 38 | 16.481 | 11.464 | 20.962 | 1.00 | 73.81 | AP3 |
| ATOM | 4103 | OD1 | ASP | 38 | 15.731 | 12.358 | 21.431 | 1.00 | 73.99 | AP3 |
| ATOM | 4104 | OD2 | ASP | 38 | 17.504 | 11.055 | 21.572 | 1.00 | 74.36 | AP3 |
| ATOM | 4105 | C | ASP | 38 | 16.799 | 8.959 | 18.094 | 1.00 | 72.08 | AP3 |
| ATOM | 4106 | O | ASP | 38 | 16.909 | 7.787 | 18.460 | 1.00 | 71.86 | AP3 |
| ATOM | 4107 | N | VAL | 39 | 16.287 | 9.300 | 16.919 | 1.00 | 71.14 | AP3 |
| ATOM | 4108 | CA | VAL | 39 | 15.779 | 8.277 | 16.025 | 1.00 | 71.01 | AP3 |
| ATOM | 4109 | CB | VAL | 39 | 15.220 | 8.869 | 14.664 | 1.00 | 71.24 | AP3 |
| ATOM | 4110 | CG1 | VAL | 39 | 16.325 | 9.539 | 13.844 | 1.00 | 71.90 | AP3 |
| ATOM | 4111 | CG2 | VAL | 39 | 14.602 | 7.764 | 13.839 | 1.00 | 71.08 | AP3 |
| ATOM | 4112 | C | VAL | 39 | 16.793 | 7.170 | 15.739 | 1.00 | 70.58 | AP3 |
| ATOM | 4113 | O | VAL | 39 | 16.450 | 5.996 | 15.879 | 1.00 | 70.63 | AP3 |
| ATOM | 4114 | N | VAL | 40 | 18.034 | 7.491 | 15.369 | 1.00 | 70.04 | AP3 |
| ATOM | 4115 | CA | VAL | 40 | 18.956 | 6.386 | 15.087 | 1.00 | 69.56 | AP3 |
| ATOM | 4116 | CB | VAL | 40 | 20.255 | 6.798 | 14.328 | 1.00 | 69.09 | AP3 |
| ATOM | 4117 | CG1 | VAL | 40 | 20.024 | 8.040 | 13.501 | 1.00 | 68.25 | AP3 |
| ATOM | 4118 | CG2 | VAL | 40 | 21.398 | 6.934 | 15.286 | 1.00 | 68.70 | AP3 |
| ATOM | 4119 | C | VAL | 40 | 19.355 | 5.609 | 16.330 | 1.00 | 69.75 | AP3 |
| ATOM | 4120 | O | VAL | 40 | 19.632 | 4.419 | 16.236 | 1.00 | 69.52 | AP3 |
| ATOM | 4121 | N | GLU | 41 | 19.394 | 6.251 | 17.494 | 1.00 | 70.53 | AP3 |
| ATOM | 4122 | CA | GLU | 41 | 19.750 | 5.501 | 18.691 | 1.00 | 71.26 | AP3 |
| ATOM | 4123 | CB | GLU | 41 | 20.063 | 6.413 | 19.881 | 1.00 | 71.93 | AP3 |
| ATOM | 4124 | CG | GLU | 41 | 20.212 | 5.583 | 21.164 | 1.00 | 74.01 | AP3 |
| ATOM | 4125 | CD | GLU | 41 | 20.933 | 6.295 | 22.307 | 1.00 | 75.35 | AP3 |
| ATOM | 4126 | OE1 | GLU | 41 | 20.488 | 7.410 | 22.704 | 1.00 | 76.32 | AP3 |
| ATOM | 4127 | OE2 | GLU | 41 | 21.938 | 5.723 | 22.815 | 1.00 | 74.88 | AP3 |
| ATOM | 4128 | C | GLU | 41 | 18.569 | 4.574 | 19.029 | 1.00 | 71.15 | AP3 |
| ATOM | 4129 | O | GLU | 41 | 18.753 | 3.453 | 19.535 | 1.00 | 71.23 | AP3 |
| ATOM | 4130 | N | LEU | 42 | 17.366 | 5.053 | 18.718 | 1.00 | 70.41 | AP3 |
| ATOM | 4131 | CA | LEU | 42 | 16.132 | 4.309 | 18.947 | 1.00 | 69.86 | AP3 |
| ATOM | 4132 | CB | LEU | 42 | 14.937 | 5.219 | 18.664 | 1.00 | 69.83 | AP3 |
| ATOM | 4133 | CG | LEU | 42 | 13.790 | 5.127 | 19.661 | 1.00 | 70.14 | AP3 |
| ATOM | 4134 | CD1 | LEU | 42 | 14.294 | 5.398 | 21.072 | 1.00 | 70.26 | AP3 |
| ATOM | 4135 | CD2 | LEU | 42 | 12.735 | 6.126 | 19.280 | 1.00 | 70.54 | AP3 |
| ATOM | 4136 | C | LEU | 42 | 16.081 | 3.076 | 18.033 | 1.00 | 69.20 | AP3 |
| ATOM | 4137 | O | LEU | 42 | 15.799 | 1.969 | 18.480 | 1.00 | 68.64 | AP3 |
| ATOM | 4138 | N | VAL | 43 | 16.352 | 3.287 | 16.751 | 1.00 | 68.63 | AP3 |
| ATOM | 4139 | CA | VAL | 43 | 16.371 | 2.211 | 15.783 | 1.00 | 68.57 | AP3 |
| ATOM | 4140 | CB | VAL | 43 | 16.651 | 2.761 | 14.361 | 1.00 | 68.12 | AP3 |
| ATOM | 4141 | CG1 | VAL | 43 | 17.349 | 1.716 | 13.520 | 1.00 | 68.00 | AP3 |
| ATOM | 4142 | CG2 | VAL | 43 | 15.357 | 3.167 | 13.691 | 1.00 | 67.66 | AP3 |
| ATOM | 4143 | C | VAL | 43 | 17.434 | 1.161 | 16.136 | 1.00 | 68.96 | AP3 |
| ATOM | 4144 | O | VAL | 43 | 17.221 | -0.025 | 15.965 | 1.00 | 69.09 | AP3 |
| ATOM | 4145 | N | MET | 44 | 18.584 | 1.584 | 16.634 | 1.00 | 69.75 | AP3 |
| ATOM | 4146 | CA | MET | 44 | 19.624 | 0.616 | 16.954 | 1.00 | 70.62 | AP3 |
| ATOM | 4147 | CB | MET | 44 | 20.955 | 1.333 | 17.165 | 1.00 | 70.97 | AP3 |
| ATOM | 4148 | CG | MET | 44 | 21.520 | 1.984 | 15.900 | 1.00 | 70.88 | AP3 |
| ATOM | 4149 | SD | MET | 44 | 23.026 | 2.871 | 16.329 | 1.00 | 71.36 | AP3 |
| ATOM | 4150 | CE | MET | 44 | 24.138 | 1.540 | 16.501 | 1.00 | 71.46 | AP3 |
| ATOM | 4151 | C | MET | 44 | 19.267 | -0.219 | 18.171 | 1.00 | 70.87 | AP3 |
| ATOM | 4152 | O | MET | 44 | 19.633 | -1.377 | 18.281 | 1.00 | 70.84 | AP3 |
| ATOM | 4153 | N | GLU | 45 | 18.550 | 0.374 | 19.098 | 1.00 | 71.61 | AP3 |

FIG. 3A-73

| ATOM | 4154 | CA | GLU | 45 | 18.148 | -0.364 | 20.265 | 1.00 | 72.72 | AP3 |
| --- | --- | --- | --- | --- | --- | --- | --- | --- | --- | --- |
| ATOM | 4155 | CB | GLU | 45 | 17.465 | 0.574 | 21.241 | 1.00 | 74.12 | AP3 |
| ATOM | 4156 | CG | GLU | 45 | 17.616 | 0.132 | 22.660 | 1.00 | 76.86 | AP3 |
| ATOM | 4157 | CD | GLU | 45 | 18.162 | 1.241 | 23.512 | 1.00 | 78.21 | AP3 |
| ATOM | 4158 | OE1 | GLU | 45 | 19.158 | 1.860 | 23.070 | 1.00 | 79.78 | AP3 |
| ATOM | 4159 | OE2 | GLU | 45 | 17.607 | 1.494 | 24.609 | 1.00 | 78.92 | AP3 |
| ATOM | 4160 | C | GLU | 45 | 17.176 | -1.470 | 19.830 | 1.00 | 72.48 | AP3 |
| ATOM | 4161 | O | GLU | 45 | 17.188 | -2.579 | 20.368 | 1.00 | 71.93 | AP3 |
| ATOM | 4162 | N | LEU | 46 | 16.332 | -1.148 | 18.856 | 1.00 | 72.22 | AP3 |
| ATOM | 4163 | CA | LEU | 46 | 15.369 | -2.101 | 18.338 | 1.00 | 72.56 | AP3 |
| ATOM | 4164 | CB | LEU | 46 | 14.345 | -1.402 | 17.434 | 1.00 | 71.96 | AP3 |
| ATOM | 4165 | CG | LEU | 46 | 13.399 | -0.406 | 18.112 | 1.00 | 71.81 | AP3 |
| ATOM | 4166 | CD1 | LEU | 46 | 12.653 | 0.403 | 17.061 | 1.00 | 71.44 | AP3 |
| ATOM | 4167 | CD2 | LEU | 46 | 12.434 | -1.141 | 19.030 | 1.00 | 71.22 | AP3 |
| ATOM | 4168 | C | LEU | 46 | 16.145 | -3.137 | 17.538 | 1.00 | 73.07 | AP3 |
| ATOM | 4169 | O | LEU | 46 | 15.716 | -4.281 | 17.407 | 1.00 | 73.17 | AP3 |
| ATOM | 4170 | N | GLU | 47 | 17.288 | -2.726 | 16.996 | 1.00 | 73.44 | AP3 |
| ATOM | 4171 | CA | GLU | 47 | 18.127 | -3.638 | 16.233 | 1.00 | 74.04 | AP3 |
| ATOM | 4172 | CB | GLU | 47 | 19.261 | -2.932 | 15.466 | 1.00 | 73.93 | AP3 |
| ATOM | 4173 | CG | GLU | 47 | 18.998 | -2.437 | 14.043 | 1.00 | 20.00 | AP3 |
| ATOM | 4174 | CD | GLU | 47 | 20.090 | -1.830 | 13.191 | 1.00 | 20.00 | AP3 |
| ATOM | 4175 | OE1 | GLU | 47 | 21.243 | -1.687 | 13.573 | 1.00 | 20.00 | AP3 |
| ATOM | 4176 | OE2 | GLU | 47 | 19.767 | -1.801 | 12.004 | 1.00 | 20.00 | AP3 |
| ATOM | 4177 | C | GLU | 47 | 18.578 | -4.672 | 17.245 | 1.00 | 74.60 | AP3 |
| ATOM | 4178 | O | GLU | 47 | 18.464 | -5.862 | 17.025 | 1.00 | 74.69 | AP3 |
| ATOM | 4179 | N | ASP | 48 | 19.077 | -4.191 | 18.373 | 1.00 | 75.61 | AP3 |
| ATOM | 4180 | CA | ASP | 48 | 19.559 | -5.051 | 19.446 | 1.00 | 76.66 | AP3 |
| ATOM | 4181 | CB | ASP | 48 | 20.135 | -4.162 | 20.574 | 1.00 | 76.52 | AP3 |
| ATOM | 4182 | CG | ASP | 48 | 21.552 | -4.573 | 21.002 | 1.00 | 76.90 | AP3 |
| ATOM | 4183 | OD1 | ASP | 48 | 22.385 | -4.922 | 20.131 | 1.00 | 76.48 | AP3 |
| ATOM | 4184 | OD2 | ASP | 48 | 21.840 | -4.527 | 22.221 | 1.00 | 76.87 | AP3 |
| ATOM | 4185 | C | ASP | 48 | 18.431 | -5.969 | 19.981 | 1.00 | 77.22 | AP3 |
| ATOM | 4186 | O | ASP | 48 | 18.467 | -7.186 | 19.792 | 1.00 | 77.42 | AP3 |
| ATOM | 4187 | N | GLU | 49 | 17.427 | -5.373 | 20.623 | 1.00 | 77.74 | AP3 |
| ATOM | 4188 | CA | GLU | 49 | 16.305 | -6.110 | 21.216 | 1.00 | 78.13 | AP3 |
| ATOM | 4189 | CB | GLU | 49 | 15.181 | -5.135 | 21.601 | 1.00 | 78.45 | AP3 |
| ATOM | 4190 | CG | GLU | 49 | 14.040 | -5.768 | 22.413 | 1.00 | 78.97 | AP3 |
| ATOM | 4191 | CD | GLU | 49 | 14.522 | -6.426 | 23.708 | 1.00 | 79.44 | AP3 |
| ATOM | 4192 | OE1 | GLU | 49 | 15.314 | -5.805 | 24.456 | 1.00 | 79.86 | AP3 |
| ATOM | 4193 | OE2 | GLU | 49 | 14.103 | -7.565 | 23.986 | 1.00 | 79.37 | AP3 |
| ATOM | 4194 | C | GLU | 49 | 15.702 | -7.248 | 20.394 | 1.00 | 78.17 | AP3 |
| ATOM | 4195 | O | GLU | 49 | 15.764 | -8.406 | 20.794 | 1.00 | 78.04 | AP3 |
| ATOM | 4196 | N | PHE | 50 | 15.112 | -6.899 | 19.258 | 1.00 | 78.28 | AP3 |
| ATOM | 4197 | CA | PHE | 50 | 14.457 | -7.854 | 18.378 | 1.00 | 78.51 | AP3 |
| ATOM | 4198 | CB | PHE | 50 | 13.297 | -7.153 | 17.675 | 1.00 | 78.05 | AP3 |
| ATOM | 4199 | CG | PHE | 50 | 12.305 | -6.526 | 18.616 | 1.00 | 77.86 | AP3 |
| ATOM | 4200 | CD1 | PHE | 50 | 11.336 | -7.298 | 19.249 | 1.00 | 77.75 | AP3 |
| ATOM | 4201 | CD2 | PHE | 50 | 12.349 | -5.166 | 18.884 | 1.00 | 77.65 | AP3 |
| ATOM | 4202 | CE1 | PHE | 50 | 10.429 | -6.727 | 20.134 | 1.00 | 77.49 | AP3 |
| ATOM | 4203 | CE2 | PHE | 50 | 11.446 | -4.588 | 19.767 | 1.00 | 77.81 | AP3 |
| ATOM | 4204 | CZ | PHE | 50 | 10.483 | -5.374 | 20.393 | 1.00 | 77.71 | AP3 |
| ATOM | 4205 | C | PHE | 50 | 15.390 | -8.485 | 17.338 | 1.00 | 79.21 | AP3 |
| ATOM | 4206 | O | PHE | 50 | 14.962 | -9.268 | 16.482 | 1.00 | 79.08 | AP3 |
| ATOM | 4207 | N | ASP | 51 | 16.666 | -8.141 | 17.406 | 1.00 | 79.94 | AP3 |
| ATOM | 4208 | CA | ASP | 51 | 17.650 | -8.677 | 16.469 | 1.00 | 80.87 | AP3 |
| ATOM | 4209 | CB | ASP | 51 | 17.937 | -10.141 | 16.782 | 1.00 | 81.48 | AP3 |
| ATOM | 4210 | CG | ASP | 51 | 19.097 | -10.683 | 15.970 | 1.00 | 82.44 | AP3 |

FIG. 3A-74

| ATOM | 4211 | OD1 | ASP | 51 | 20.252 | -10.277 | 16.260 | 1.00 | 82.50 | AP3 |
|---|---|---|---|---|---|---|---|---|---|---|
| ATOM | 4212 | OD2 | ASP | 51 | 18.856 | -11.499 | 15.041 | 1.00 | 82.89 | AP3 |
| ATOM | 4213 | C | ASP | 51 | 17.319 | -8.568 | 14.978 | 1.00 | 81.25 | AP3 |
| ATOM | 4214 | O | ASP | 51 | 17.156 | -9.580 | 14.299 | 1.00 | 81.47 | AP3 |
| ATOM | 4215 | N | MET | 52 | 17.212 | -7.350 | 14.462 | 1.00 | 81.48 | AP3 |
| ATOM | 4216 | CA | MET | 52 | 16.957 | -7.173 | 13.040 | 1.00 | 82.01 | AP3 |
| ATOM | 4217 | CB | MET | 52 | 15.510 | -6.750 | 12.775 | 1.00 | 82.14 | AP3 |
| ATOM | 4218 | CG | MET | 52 | 14.696 | -6.381 | 14.007 | 1.00 | 82.31 | AP3 |
| ATOM | 4219 | SD | MET | 52 | 13.071 | -5.722 | 13.542 | 1.00 | 82.25 | AP3 |
| ATOM | 4220 | CE | MET | 52 | 12.014 | -7.194 | 13.718 | 1.00 | 82.26 | AP3 |
| ATOM | 4221 | C | MET | 52 | 17.926 | -6.121 | 12.519 | 1.00 | 82.34 | AP3 |
| ATOM | 4222 | O | MET | 52 | 18.885 | -5.763 | 13.209 | 1.00 | 82.16 | AP3 |
| ATOM | 4223 | N | GLU | 53 | 17.702 | -5.627 | 11.308 | 1.00 | 82.90 | AP3 |
| ATOM | 4224 | CA | GLU | 53 | 18.610 | -4.614 | 10.779 | 1.00 | 83.60 | AP3 |
| ATOM | 4225 | CB | GLU | 53 | 19.123 | -5.031 | 9.393 | 1.00 | 84.21 | AP3 |
| ATOM | 4226 | CG | GLU | 53 | 20.382 | -5.919 | 9.461 | 1.00 | 85.24 | AP3 |
| ATOM | 4227 | CD | GLU | 53 | 20.835 | -6.458 | 8.097 | 1.00 | 85.76 | AP3 |
| ATOM | 4228 | OE1 | GLU | 53 | 21.136 | -5.656 | 7.182 | 1.00 | 85.78 | AP3 |
| ATOM | 4229 | OE2 | GLU | 53 | 20.899 | -7.696 | 7.942 | 1.00 | 86.03 | AP3 |
| ATOM | 4230 | C | GLU | 53 | 17.612 | -3.738 | 10.000 | 1.00 | 83.76 | AP3 |
| ATOM | 4231 | O | GLU | 53 | 16.959 | -4.220 | 9.060 | 1.00 | 84.12 | AP3 |
| ATOM | 4232 | N | ILE | 54 | 17.503 | -2.461 | 10.362 | 1.00 | 83.35 | AP3 |
| ATOM | 4233 | CA | ILE | 54 | 16.552 | -1.545 | 9.704 | 1.00 | 82.72 | AP3 |
| ATOM | 4234 | CB | ILE | 54 | 16.164 | -0.927 | 11.074 | 1.00 | 82.40 | AP3 |
| ATOM | 4235 | CG2 | ILE | 54 | 15.129 | 0.174 | 10.882 | 1.00 | 82.02 | AP3 |
| ATOM | 4236 | CG1 | ILE | 54 | 15.556 | -1.994 | 11.975 | 1.00 | 82.36 | AP3 |
| ATOM | 4237 | CD1 | ILE | 54 | 15.194 | -1.481 | 13.334 | 1.00 | 82.18 | AP3 |
| ATOM | 4238 | C | ILE | 54 | 17.561 | -0.609 | 9.007 | 1.00 | 82.25 | AP3 |
| ATOM | 4239 | O | ILE | 54 | 18.456 | -0.037 | 9.633 | 1.00 | 81.65 | AP3 |
| ATOM | 4240 | N | SER | 55 | 17.408 | -0.482 | 7.693 | 1.00 | 81.94 | AP3 |
| ATOM | 4241 | CA | SER | 55 | 18.277 | 0.359 | 6.884 | 1.00 | 81.54 | AP3 |
| ATOM | 4242 | CB | SER | 55 | 18.019 | 0.082 | 5.399 | 1.00 | 80.92 | AP3 |
| ATOM | 4243 | OG | SER | 55 | 16.645 | 0.198 | 5.090 | 1.00 | 79.92 | AP3 |
| ATOM | 4244 | C | SER | 55 | 18.010 | 1.824 | 7.202 | 1.00 | 81.54 | AP3 |
| ATOM | 4245 | O | SER | 55 | 17.098 | 2.137 | 7.970 | 1.00 | 81.30 | AP3 |
| ATOM | 4246 | N | ASP | 56 | 18.798 | 2.724 | 6.618 | 1.00 | 81.47 | AP3 |
| ATOM | 4247 | CA | ASP | 56 | 18.590 | 4.145 | 6.872 | 1.00 | 81.81 | AP3 |
| ATOM | 4248 | CB | ASP | 56 | 19.683 | 5.001 | 6.193 | 1.00 | 81.44 | AP3 |
| ATOM | 4249 | CG | ASP | 56 | 21.040 | 4.968 | 6.948 | 1.00 | 81.79 | AP3 |
| ATOM | 4250 | OD1 | ASP | 56 | 21.046 | 4.792 | 8.192 | 1.00 | 81.20 | AP3 |
| ATOM | 4251 | OD2 | ASP | 56 | 22.105 | 5.147 | 6.298 | 1.00 | 81.38 | AP3 |
| ATOM | 4252 | C | ASP | 56 | 17.193 | 4.522 | 6.353 | 1.00 | 82.06 | AP3 |
| ATOM | 4253 | O | ASP | 56 | 16.468 | 5.310 | 6.971 | 1.00 | 81.65 | AP3 |
| ATOM | 4254 | N | GLU | 57 | 16.812 | 3.922 | 5.231 | 1.00 | 82.50 | AP3 |
| ATOM | 4255 | CA | GLU | 57 | 15.519 | 4.181 | 4.617 | 1.00 | 83.23 | AP3 |
| ATOM | 4256 | CB | GLU | 57 | 15.489 | 3.600 | 3.212 | 1.00 | 83.97 | AP3 |
| ATOM | 4257 | CG | GLU | 57 | 14.093 | 3.344 | 2.663 | 1.00 | 85.29 | AP3 |
| ATOM | 4258 | CD | GLU | 57 | 14.151 | 2.565 | 1.360 | 1.00 | 86.35 | AP3 |
| ATOM | 4259 | OE1 | GLU | 57 | 14.973 | 1.619 | 1.297 | 1.00 | 86.59 | AP3 |
| ATOM | 4260 | OE2 | GLU | 57 | 13.388 | 2.891 | 0.414 | 1.00 | 86.49 | AP3 |
| ATOM | 4261 | C | GLU | 57 | 14.389 | 3.582 | 5.410 | 1.00 | 83.25 | AP3 |
| ATOM | 4262 | O | GLU | 57 | 13.307 | 4.140 | 5.485 | 1.00 | 83.37 | AP3 |
| ATOM | 4263 | N | ASP | 58 | 14.645 | 2.419 | 5.977 | 1.00 | 83.61 | AP3 |
| ATOM | 4264 | CA | ASP | 58 | 13.643 | 1.733 | 6.762 | 1.00 | 84.08 | AP3 |
| ATOM | 4265 | CB | ASP | 58 | 14.221 | 0.420 | 7.298 | 1.00 | 84.48 | AP3 |
| ATOM | 4266 | CG | ASP | 58 | 13.920 | -0.757 | 6.399 | 1.00 | 84.79 | AP3 |
| ATOM | 4267 | OD1 | ASP | 58 | 13.894 | -0.578 | 5.161 | 1.00 | 84.94 | AP3 |

FIG. 3A-75

| ATOM | 4268 | OD2 | ASP | 58 | 13.718 | -1.866 | 6.937 | 1.00 | 85.28 | AP3 |
|------|------|-----|-----|----|--------|--------|-------|------|-------|-----|
| ATOM | 4269 | C | ASP | 58 | 13.161 | 2.594 | 7.916 | 1.00 | 84.20 | AP3 |
| ATOM | 4270 | O | ASP | 58 | 11.956 | 2.768 | 8.106 | 1.00 | 84.18 | AP3 |
| ATOM | 4271 | N | ALA | 59 | 14.110 | 3.127 | 8.682 | 1.00 | 84.44 | AP3 |
| ATOM | 4272 | CA | ALA | 59 | 13.800 | 3.947 | 9.847 | 1.00 | 84.80 | AP3 |
| ATOM | 4273 | CB | ALA | 59 | 15.090 | 4.324 | 10.576 | 1.00 | 84.94 | AP3 |
| ATOM | 4274 | C | ALA | 59 | 13.012 | 5.196 | 9.490 | 1.00 | 85.16 | AP3 |
| ATOM | 4275 | O | ALA | 59 | 12.270 | 5.733 | 10.320 | 1.00 | 84.92 | AP3 |
| ATOM | 4276 | N | GLU | 60 | 13.179 | 5.649 | 8.251 | 1.00 | 85.66 | AP3 |
| ATOM | 4277 | CA | GLU | 60 | 12.491 | 6.829 | 7.756 | 1.00 | 86.22 | AP3 |
| ATOM | 4278 | CB | GLU | 60 | 13.172 | 7.307 | 6.472 | 1.00 | 86.31 | AP3 |
| ATOM | 4279 | CG | GLU | 60 | 12.273 | 7.576 | 5.288 | 1.00 | 86.31 | AP3 |
| ATOM | 4280 | CD | GLU | 60 | 13.066 | 8.014 | 4.068 | 1.00 | 86.35 | AP3 |
| ATOM | 4281 | OE1 | GLU | 60 | 13.683 | 9.096 | 4.127 | 1.00 | 86.38 | AP3 |
| ATOM | 4282 | OE2 | GLU | 60 | 13.086 | 7.277 | 3.056 | 1.00 | 86.60 | AP3 |
| ATOM | 4283 | C | GLU | 60 | 11.011 | 6.543 | 7.528 | 1.00 | 86.77 | AP3 |
| ATOM | 4284 | O | GLU | 60 | 10.228 | 7.453 | 7.250 | 1.00 | 87.01 | AP3 |
| ATOM | 4285 | N | LYS | 61 | 10.623 | 5.277 | 7.653 | 1.00 | 87.25 | AP3 |
| ATOM | 4286 | CA | LYS | 61 | 9.220 | 4.909 | 7.488 | 1.00 | 87.61 | AP3 |
| ATOM | 4287 | CB | LYS | 61 | 9.074 | 3.593 | 6.731 | 1.00 | 88.37 | AP3 |
| ATOM | 4288 | CG | LYS | 61 | 7.624 | 3.104 | 6.665 | 1.00 | 89.43 | AP3 |
| ATOM | 4289 | CD | LYS | 61 | 7.551 | 1.686 | 6.112 | 1.00 | 90.13 | AP3 |
| ATOM | 4290 | CE | LYS | 61 | 6.127 | 1.165 | 6.055 | 1.00 | 90.43 | AP3 |
| ATOM | 4291 | NZ | LYS | 61 | 6.108 | -0.219 | 5.489 | 1.00 | 90.66 | AP3 |
| ATOM | 4292 | C | LYS | 61 | 8.503 | 4.778 | 8.830 | 1.00 | 87.34 | AP3 |
| ATOM | 4293 | O | LYS | 61 | 7.396 | 5.299 | 8.987 | 1.00 | 87.16 | AP3 |
| ATOM | 4294 | N | ILE | 62 | 9.122 | 4.090 | 9.791 | 1.00 | 87.02 | AP3 |
| ATOM | 4295 | CA | ILE | 62 | 8.488 | 3.909 | 11.094 | 1.00 | 86.92 | AP3 |
| ATOM | 4296 | CB | ILE | 62 | 9.281 | 2.898 | 11.997 | 1.00 | 86.84 | AP3 |
| ATOM | 4297 | CG2 | ILE | 62 | 9.711 | 1.698 | 11.164 | 1.00 | 86.77 | AP3 |
| ATOM | 4298 | CG1 | ILE | 62 | 10.516 | 3.547 | 12.621 | 1.00 | 86.82 | AP3 |
| ATOM | 4299 | CD1 | ILE | 62 | 11.170 | 2.683 | 13.670 | 1.00 | 86.27 | AP3 |
| ATOM | 4300 | C | ILE | 62 | 8.285 | 5.258 | 11.802 | 1.00 | 86.84 | AP3 |
| ATOM | 4301 | O | ILE | 62 | 9.041 | 5.659 | 12.698 | 1.00 | 86.83 | AP3 |
| ATOM | 4302 | N | ALA | 63 | 7.228 | 5.941 | 11.373 | 1.00 | 86.40 | AP3 |
| ATOM | 4303 | CA | ALA | 63 | 6.847 | 7.255 | 11.876 | 1.00 | 85.95 | AP3 |
| ATOM | 4304 | CB | ALA | 63 | 5.758 | 7.850 | 10.975 | 1.00 | 86.18 | AP3 |
| ATOM | 4305 | C | ALA | 63 | 6.376 | 7.268 | 13.323 | 1.00 | 85.54 | AP3 |
| ATOM | 4306 | O | ALA | 63 | 6.790 | 8.124 | 14.109 | 1.00 | 85.58 | AP3 |
| ATOM | 4307 | N | THR | 64 | 5.494 | 6.335 | 13.670 | 1.00 | 84.92 | AP3 |
| ATOM | 4308 | CA | THR | 64 | 4.977 | 6.272 | 15.033 | 1.00 | 84.10 | AP3 |
| ATOM | 4309 | CB | THR | 64 | 3.462 | 6.508 | 15.069 | 1.00 | 84.08 | AP3 |
| ATOM | 4310 | OG1 | THR | 64 | 2.779 | 5.266 | 14.876 | 1.00 | 84.50 | AP3 |
| ATOM | 4311 | CG2 | THR | 64 | 3.052 | 7.468 | 13.959 | 1.00 | 84.49 | AP3 |
| ATOM | 4312 | C | THR | 64 | 5.279 | 4.911 | 15.638 | 1.00 | 83.31 | AP3 |
| ATOM | 4313 | O | THR | 64 | 5.930 | 4.074 | 15.008 | 1.00 | 83.15 | AP3 |
| ATOM | 4314 | N | VAL | 65 | 4.797 | 4.697 | 16.858 | 1.00 | 82.39 | AP3 |
| ATOM | 4315 | CA | VAL | 65 | 5.026 | 3.441 | 17.567 | 1.00 | 81.57 | AP3 |
| ATOM | 4316 | CB | VAL | 65 | 4.426 | 3.504 | 18.998 | 1.00 | 81.36 | AP3 |
| ATOM | 4317 | CG1 | VAL | 65 | 4.872 | 2.300 | 19.806 | 1.00 | 81.23 | AP3 |
| ATOM | 4318 | CG2 | VAL | 65 | 4.856 | 4.790 | 19.687 | 1.00 | 81.01 | AP3 |
| ATOM | 4319 | C | VAL | 65 | 4.435 | 2.246 | 16.807 | 1.00 | 81.21 | AP3 |
| ATOM | 4320 | O | VAL | 65 | 5.159 | 1.333 | 16.406 | 1.00 | 80.81 | AP3 |
| ATOM | 4321 | N | GLY | 66 | 3.118 | 2.270 | 16.603 | 1.00 | 80.94 | AP3 |
| ATOM | 4322 | CA | GLY | 66 | 2.440 | 1.198 | 15.887 | 1.00 | 80.21 | AP3 |
| ATOM | 4323 | C | GLY | 66 | 3.238 | 0.690 | 14.702 | 1.00 | 79.61 | AP3 |
| ATOM | 4324 | O | GLY | 66 | 3.559 | -0.492 | 14.644 | 1.00 | 80.05 | AP3 |

FIG. 3A-76

| ATOM | 4325 | N   | ASP | 67 | 3.560  | 1.586  | 13.768 | 1.00 | 78.67 | AP3 |
| ATOM | 4326 | CA  | ASP | 67 | 4.334  | 1.250  | 12.577 | 1.00 | 77.46 | AP3 |
| ATOM | 4327 | CB  | ASP | 67 | 4.810  | 2.527  | 11.866 | 1.00 | 78.12 | AP3 |
| ATOM | 4328 | CG  | ASP | 67 | 3.663  | 3.435  | 11.426 | 1.00 | 78.60 | AP3 |
| ATOM | 4329 | OD1 | ASP | 67 | 3.948  | 4.595  | 11.038 | 1.00 | 78.50 | AP3 |
| ATOM | 4330 | OD2 | ASP | 67 | 2.484  | 2.998  | 11.460 | 1.00 | 79.03 | AP3 |
| ATOM | 4331 | C   | ASP | 67 | 5.553  | 0.427  | 12.966 | 1.00 | 76.39 | AP3 |
| ATOM | 4332 | O   | ASP | 67 | 5.847  | -0.586 | 12.349 | 1.00 | 76.25 | AP3 |
| ATOM | 4333 | N   | ALA | 68 | 6.265  | 0.875  | 13.992 | 1.00 | 75.14 | AP3 |
| ATOM | 4334 | CA  | ALA | 68 | 7.461  | 0.177  | 14.443 | 1.00 | 74.09 | AP3 |
| ATOM | 4335 | CB  | ALA | 68 | 8.127  | 0.958  | 15.557 | 1.00 | 73.75 | AP3 |
| ATOM | 4336 | C   | ALA | 68 | 7.126  | -1.231 | 14.923 | 1.00 | 73.41 | AP3 |
| ATOM | 4337 | O   | ALA | 68 | 7.901  | -2.178 | 14.722 | 1.00 | 72.94 | AP3 |
| ATOM | 4338 | N   | VAL | 69 | 5.977  | -1.353 | 15.583 | 1.00 | 72.59 | AP3 |
| ATOM | 4339 | CA  | VAL | 69 | 5.516  | -2.640 | 16.078 | 1.00 | 71.94 | AP3 |
| ATOM | 4340 | CB  | VAL | 69 | 4.233  | -2.496 | 16.913 | 1.00 | 71.70 | AP3 |
| ATOM | 4341 | CG1 | VAL | 69 | 3.613  | -3.860 | 17.128 | 1.00 | 72.09 | AP3 |
| ATOM | 4342 | CG2 | VAL | 69 | 4.550  | -1.867 | 18.264 | 1.00 | 71.85 | AP3 |
| ATOM | 4343 | C   | VAL | 69 | 5.235  | -3.533 | 14.874 | 1.00 | 71.56 | AP3 |
| ATOM | 4344 | O   | VAL | 69 | 5.670  | -4.677 | 14.834 | 1.00 | 71.28 | AP3 |
| ATOM | 4345 | N   | ASN | 70 | 4.536  | -2.977 | 13.888 | 1.00 | 71.51 | AP3 |
| ATOM | 4346 | CA  | ASN | 70 | 4.173  | -3.684 | 12.670 | 1.00 | 71.50 | AP3 |
| ATOM | 4347 | CB  | ASN | 70 | 3.286  | -2.806 | 11.784 | 1.00 | 72.56 | AP3 |
| ATOM | 4348 | CG  | ASN | 70 | 1.985  | -2.388 | 12.481 | 1.00 | 74.31 | AP3 |
| ATOM | 4349 | OD1 | ASN | 70 | 1.333  | -3.194 | 13.183 | 1.00 | 74.53 | AP3 |
| ATOM | 4350 | ND2 | ASN | 70 | 1.591  | -1.124 | 12.279 | 1.00 | 74.65 | AP3 |
| ATOM | 4351 | C   | ASN | 70 | 5.365  | -4.164 | 11.864 | 1.00 | 70.88 | AP3 |
| ATOM | 4352 | O   | ASN | 70 | 5.292  | -5.213 | 11.226 | 1.00 | 71.14 | AP3 |
| ATOM | 4353 | N   | TYR | 71 | 6.457  | -3.405 | 11.887 | 1.00 | 69.74 | AP3 |
| ATOM | 4354 | CA  | TYR | 71 | 7.656  | -3.775 | 11.148 | 1.00 | 68.50 | AP3 |
| ATOM | 4355 | CB  | TYR | 71 | 8.579  | -2.564 | 10.985 | 1.00 | 68.49 | AP3 |
| ATOM | 4356 | CG  | TYR | 71 | 9.941  | -2.875 | 10.408 | 1.00 | 68.25 | AP3 |
| ATOM | 4357 | CD1 | TYR | 71 | 10.983 | -3.316 | 11.223 | 1.00 | 68.37 | AP3 |
| ATOM | 4358 | CE1 | TYR | 71 | 12.246 | -3.579 | 10.700 | 1.00 | 68.50 | AP3 |
| ATOM | 4359 | CD2 | TYR | 71 | 10.195 | -2.709 | 9.048  | 1.00 | 68.69 | AP3 |
| ATOM | 4360 | CE2 | TYR | 71 | 11.452 | -2.968 | 8.512  | 1.00 | 68.85 | AP3 |
| ATOM | 4361 | CZ  | TYR | 71 | 12.476 | -3.397 | 9.342  | 1.00 | 68.83 | AP3 |
| ATOM | 4362 | OH  | TYR | 71 | 13.740 | -3.604 | 8.823  | 1.00 | 68.91 | AP3 |
| ATOM | 4363 | C   | TYR | 71 | 8.381  | -4.890 | 11.876 | 1.00 | 67.81 | AP3 |
| ATOM | 4364 | O   | TYR | 71 | 9.000  | -5.753 | 11.250 | 1.00 | 67.59 | AP3 |
| ATOM | 4365 | N   | ILE | 72 | 8.307  | -4.867 | 13.201 | 1.00 | 66.78 | AP3 |
| ATOM | 4366 | CA  | ILE | 72 | 8.952  | -5.895 | 14.004 | 1.00 | 66.16 | AP3 |
| ATOM | 4367 | CB  | ILE | 72 | 8.971  | -5.479 | 15.475 | 1.00 | 65.95 | AP3 |
| ATOM | 4368 | CG2 | ILE | 72 | 9.601  | -6.577 | 16.323 | 1.00 | 65.37 | AP3 |
| ATOM | 4369 | CG1 | ILE | 72 | 9.738  | -4.161 | 15.605 | 1.00 | 65.65 | AP3 |
| ATOM | 4370 | CD1 | ILE | 72 | 9.745  | -3.580 | 16.986 | 1.00 | 65.29 | AP3 |
| ATOM | 4371 | C   | ILE | 72 | 8.254  | -7.259 | 13.831 | 1.00 | 65.87 | AP3 |
| ATOM | 4372 | O   | ILE | 72 | 8.826  | -8.301 | 14.112 | 1.00 | 65.61 | AP3 |
| ATOM | 4373 | N   | GLN | 73 | 7.015  | -7.235 | 13.361 | 1.00 | 65.77 | AP3 |
| ATOM | 4374 | CA  | GLN | 73 | 6.263  | -8.454 | 13.096 | 1.00 | 66.13 | AP3 |
| ATOM | 4375 | CB  | GLN | 73 | 4.798  | -8.278 | 13.581 | 1.00 | 65.55 | AP3 |
| ATOM | 4376 | CG  | GLN | 73 | 4.647  | -7.843 | 15.063 | 1.00 | 64.13 | AP3 |
| ATOM | 4377 | CD  | GLN | 73 | 3.220  | -7.421 | 15.452 | 1.00 | 64.08 | AP3 |
| ATOM | 4378 | OE1 | GLN | 73 | 2.478  | -6.865 | 14.644 | 1.00 | 63.85 | AP3 |
| ATOM | 4379 | NE2 | GLN | 73 | 2.847  | -7.663 | 16.704 | 1.00 | 63.21 | AP3 |
| ATOM | 4380 | C   | GLN | 73 | 6.332  | -8.670 | 11.555 | 1.00 | 66.46 | AP3 |
| ATOM | 4381 | OT1 | GLN | 73 | 7.311  | -9.301 | 11.073 | 1.00 | 66.98 | AP3 |

FIG. 3A-77

| ATOM | 4382 | OT2 | GLN | 73 | 5.443 | -8.169 | 10.822 | 1.00 | 66.91 | AP3 |
|------|------|-----|-----|----|-------|--------|--------|------|-------|-----|
| ATOM | 4383 | Na  | Na  | 74 | 20.764 | 19.142 | 15.649 | 1.00 | 20.00 | AP3 |
| ATOM | 4384 | Cl  | Cl  | 75 | 48.270 | 38.501 | 33.120 | 1.00 | 20.00 | AP3 |
| ATOM | 4385 | O   | HOH | 1  | 20.971 | 35.418 | 19.446 | 1.00 | 28.08 | W |
| ATOM | 4386 | O   | HOH | 3  | 17.476 | 26.774 | 26.314 | 1.00 | 30.37 | W |
| ATOM | 4387 | O   | HOH | 4  | 12.070 | 27.791 | 30.387 | 1.00 | 43.18 | W |
| ATOM | 4388 | O   | HOH | 6  | -0.243 | 36.108 | 7.284  | 1.00 | 29.98 | W |
| ATOM | 4389 | O   | HOH | 7  | 0.953  | 30.812 | 3.352  | 1.00 | 25.95 | W |
| ATOM | 4390 | O   | HOH | 8  | 4.210  | 27.477 | 6.553  | 1.00 | 39.30 | W |
| ATOM | 4391 | O   | HOH | 9  | 0.717  | 18.079 | 16.564 | 1.00 | 67.04 | W |
| ATOM | 4392 | O   | HOH | 11 | 15.048 | 43.095 | -2.130 | 1.00 | 39.40 | W |
| ATOM | 4393 | O   | HOH | 12 | 17.559 | 22.506 | 6.739  | 1.00 | 26.96 | W |
| ATOM | 4394 | O   | HOH | 13 | 12.217 | 24.755 | 13.778 | 1.00 | 46.52 | W |
| ATOM | 4395 | O   | HOH | 15 | 35.287 | 26.338 | 18.440 | 1.00 | 20.30 | W |
| ATOM | 4396 | O   | HOH | 17 | 18.594 | 25.738 | 2.095  | 1.00 | 35.11 | W |
| ATOM | 4397 | O   | HOH | 18 | 15.737 | 27.004 | 1.792  | 1.00 | 44.57 | W |
| ATOM | 4398 | O   | HOH | 19 | 17.787 | 25.982 | -0.493 | 1.00 | 47.08 | W |
| ATOM | 4399 | O   | HOH | 20 | 14.655 | 29.401 | 1.057  | 1.00 | 29.13 | W |
| ATOM | 4400 | O   | HOH | 22 | 10.016 | 35.007 | -1.744 | 1.00 | 28.29 | W |
| ATOM | 4401 | O   | HOH | 23 | 36.914 | 24.143 | 16.155 | 1.00 | 45.82 | W |
| ATOM | 4402 | O   | HOH | 25 | 50.466 | 41.898 | 3.162  | 1.00 | 51.46 | W |
| ATOM | 4403 | O   | HOH | 30 | 37.884 | 38.482 | 31.771 | 1.00 | 44.83 | W |
| ATOM | 4404 | O   | HOH | 33 | 2.929  | 18.357 | 18.770 | 1.00 | 39.37 | W |
| ATOM | 4405 | O   | HOH | 35 | 36.000 | 25.296 | 5.752  | 1.00 | 51.16 | W |
| ATOM | 4406 | O   | HOH | 36 | 36.246 | 24.282 | 8.528  | 1.00 | 26.38 | W |
| ATOM | 4407 | O   | HOH | 37 | 28.425 | 33.179 | 30.115 | 1.00 | 38.91 | W |
| ATOM | 4408 | O   | HOH | 41 | 21.454 | 21.279 | 24.073 | 1.00 | 42.35 | W |
| ATOM | 4409 | O   | HOH | 43 | 32.713 | 18.758 | 19.974 | 1.00 | 39.89 | W |
| ATOM | 4410 | O   | HOH | 45 | 27.158 | 17.997 | 25.229 | 1.00 | 42.25 | W |
| ATOM | 4411 | O   | HOH | 47 | 15.063 | 24.776 | 27.152 | 1.00 | 51.90 | W |
| ATOM | 4412 | O   | HOH | 48 | 3.825  | 36.800 | 4.340  | 1.00 | 34.80 | W |
| ATOM | 4413 | O   | HOH | 50 | 20.567 | 27.887 | 27.820 | 1.00 | 55.40 | W |
| ATOM | 4414 | O   | HOH | 51 | 4.233  | 27.038 | 25.001 | 1.00 | 46.58 | W |
| ATOM | 4415 | O   | HOH | 52 | 29.473 | 30.435 | 6.152  | 1.00 | 30.54 | W |
| ATOM | 4416 | O   | HOH | 53 | 35.273 | 26.999 | 22.829 | 1.00 | 20.05 | W |
| ATOM | 4417 | O   | HOH | 55 | 42.995 | 43.869 | 7.601  | 1.00 | 34.30 | W |
| ATOM | 4418 | O   | HOH | 56 | 44.770 | 43.791 | 9.728  | 1.00 | 38.02 | W |
| ATOM | 4419 | O   | HOH | 57 | 16.116 | 25.445 | 30.290 | 1.00 | 58.80 | W |
| ATOM | 4420 | O   | HOH | 58 | 0.147  | 32.556 | 5.561  | 1.00 | 35.33 | W |
| ATOM | 4421 | O   | HOH | 59 | -0.841 | 26.194 | 8.298  | 1.00 | 52.99 | W |
| ATOM | 4422 | O   | HOH | 60 | 10.370 | 26.637 | 13.493 | 1.00 | 36.98 | W |
| ATOM | 4423 | O   | HOH | 61 | 8.214  | 23.987 | 10.644 | 1.00 | 40.29 | W |
| ATOM | 4424 | O   | HOH | 62 | 7.673  | 46.913 | 8.463  | 1.00 | 47.90 | W |
| ATOM | 4425 | O   | HOH | 63 | 4.946  | 41.758 | 13.539 | 1.00 | 40.09 | W |
| ATOM | 4426 | O   | HOH | 64 | 2.008  | 26.400 | 4.288  | 1.00 | 44.86 | W |
| ATOM | 4427 | O   | HOH | 65 | 32.337 | 32.228 | -5.705 | 1.00 | 32.42 | W |
| ATOM | 4428 | O   | HOH | 66 | 27.158 | 29.103 | 4.575  | 1.00 | 46.49 | W |
| ATOM | 4429 | O   | HOH | 67 | 51.087 | 34.911 | 10.070 | 1.00 | 39.28 | W |
| ATOM | 4430 | O   | HOH | 68 | 32.466 | 40.888 | 5.401  | 1.00 | 33.93 | W |
| ATOM | 4431 | O   | HOH | 69 | 39.494 | 41.762 | 2.408  | 1.00 | 58.71 | W |
| ATOM | 4432 | O   | HOH | 70 | 38.446 | 9.804  | 5.548  | 1.00 | 44.19 | W |
| ATOM | 4433 | O   | HOH | 71 | 37.802 | 15.483 | 14.333 | 1.00 | 53.16 | W |
| ATOM | 4434 | O   | HOH | 72 | 36.104 | 17.125 | 13.465 | 1.00 | 49.31 | W |
| ATOM | 4435 | O   | HOH | 73 | 35.093 | 14.562 | 11.995 | 1.00 | 37.15 | W |
| ATOM | 4436 | O   | HOH | 74 | 39.249 | 13.856 | 9.700  | 1.00 | 43.73 | W |
| ATOM | 4437 | O   | HOH | 75 | 40.786 | 20.731 | -0.083 | 1.00 | 41.60 | W |
| ATOM | 4438 | O   | HOH | 76 | 42.538 | 13.280 | 2.142  | 1.00 | 53.85 | W |

FIG. 3A-78

| ATOM | 4439 | O | HOH | 77 | 43.889 | 24.163 | 2.388 | 1.00 | 37.18 | W |
|------|------|---|-----|----|--------|--------|-------|------|-------|---|
| ATOM | 4440 | O | HOH | 79 | 2.540 | 34.722 | 4.575 | 1.00 | 52.66 | W |
| ATOM | 4441 | O | HOH | 80 | 43.300 | 39.495 | 27.764 | 1.00 | 44.05 | W |
| ATOM | 4442 | O | HOH | 81 | 30.076 | 30.368 | 28.457 | 1.00 | 41.35 | W |
| ATOM | 4443 | O | HOH | 82 | 0.554 | 36.258 | 25.377 | 1.00 | 53.47 | W |
| ATOM | 4444 | O | HOH | 83 | 42.781 | 28.492 | 12.843 | 1.00 | 51.06 | W |
| ATOM | 4445 | O | HOH | 84 | 17.785 | 20.002 | 14.425 | 1.00 | 47.01 | W |
| ATOM | 4446 | O | HOH | 85 | 57.006 | 35.947 | 12.705 | 1.00 | 61.42 | W |
| ATOM | 4447 | O | HOH | 86 | 35.408 | 25.621 | 2.707 | 1.00 | 51.93 | W |
| ATOM | 4448 | O | HOH | 87 | 26.037 | 26.711 | 5.073 | 1.00 | 55.68 | W |
| ATOM | 4449 | O | HOH | 88 | -0.037 | 36.618 | 11.554 | 1.00 | 62.51 | W |
| ATOM | 4450 | O | HOH | 89 | 18.549 | 21.897 | -0.102 | 1.00 | 57.85 | W |
| ATOM | 4451 | O | HOH | 90 | 35.373 | 45.010 | 15.224 | 1.00 | 44.09 | W |
| ATOM | 4452 | O | HOH | 91 | 43.922 | 17.170 | -0.889 | 1.00 | 54.42 | W |
| ATOM | 4453 | O | HOH | 92 | 7.281 | 53.078 | 4.234 | 1.00 | 54.35 | W |
| ATOM | 4454 | O | HOH | 93 | 36.648 | -0.702 | 8.498 | 1.00 | 47.55 | W |
| ATOM | 4455 | O | HOH | 94 | 24.724 | 39.269 | 9.469 | 1.00 | 53.05 | W |
| ATOM | 4456 | O | HOH | 95 | 19.529 | 33.965 | 22.828 | 1.00 | 58.72 | W |
| ATOM | 4457 | O | HOH | 96 | 25.749 | 39.500 | 11.779 | 1.00 | 57.45 | W |
| ATOM | 4458 | O | HOH | 98 | 2.556 | 39.351 | 3.903 | 1.00 | 60.67 | W |
| ATOM | 4459 | O | HOH | 99 | 4.962 | 24.357 | 5.423 | 1.00 | 50.93 | W |
| ATOM | 4460 | O | HOH | 100 | 52.895 | 36.138 | 12.412 | 1.00 | 58.46 | W |
| ATOM | 4461 | O | HOH | 101 | 29.825 | 40.539 | 5.862 | 1.00 | 49.27 | W |
| ATOM | 4462 | O | HOH | 102 | 21.479 | 17.255 | 17.560 | 1.00 | 57.74 | W |
| ATOM | 4463 | O | HOH | 103 | 17.766 | 38.296 | 19.527 | 1.00 | 57.08 | W |
| ATOM | 4464 | O | HOH | 104 | 1.919 | 40.589 | 25.467 | 1.00 | 69.59 | W |
| ATOM | 4465 | O | HOH | 105 | 45.650 | 16.023 | 1.737 | 1.00 | 68.18 | W |
| ATOM | 4466 | O | HOH | 106 | 39.326 | 28.368 | 32.930 | 1.00 | 53.77 | W |
| ATOM | 4467 | O | HOH | 107 | 3.591 | 33.811 | 2.107 | 1.00 | 46.49 | W |
| ATOM | 4468 | O | HOH | 108 | 33.929 | 42.844 | 3.314 | 1.00 | 55.14 | W |
| ATOM | 4469 | O | HOH | 109 | 46.647 | 46.329 | 14.321 | 1.00 | 59.44 | W |
| ATOM | 4470 | O | HOH | 110 | 39.222 | 24.809 | 6.979 | 1.00 | 50.22 | W |
| ATOM | 4471 | O | HOH | 111 | 49.804 | 23.224 | 6.539 | 1.00 | 58.63 | W |
| ATOM | 4472 | O | HOH | 112 | -3.058 | 18.507 | 16.487 | 1.00 | 53.33 | W |
| ATOM | 4473 | O | HOH | 113 | 27.700 | 31.120 | -5.231 | 1.00 | 69.60 | W |
| ATOM | 4474 | O | HOH | 114 | 29.929 | 38.507 | -4.418 | 1.00 | 52.20 | W |
| ATOM | 4475 | O | HOH | 115 | 34.570 | 42.009 | 0.898 | 1.00 | 44.15 | W |
| ATOM | 4476 | O | HOH | 116 | 40.508 | 27.337 | 28.107 | 1.00 | 45.88 | W |
| ATOM | 4477 | O | HOH | 117 | 41.210 | 12.812 | -1.190 | 1.00 | 66.16 | W |
| ATOM | 4478 | O | HOH | 118 | 23.723 | 30.084 | 26.100 | 1.00 | 20.00 | W |
| ATOM | 4479 | O | HOH | 119 | 0.869 | 28.565 | 2.785 | 1.00 | 20.00 | W |
| ATOM | 4480 | O | HOH | 120 | 15.469 | 15.123 | 22.821 | 1.00 | 20.00 | W |
| ATOM | 4481 | O | HOH | 122 | 12.470 | 22.800 | 11.398 | 1.00 | 20.00 | W |
| ATOM | 4482 | O | HOH | 123 | 41.506 | 25.423 | 15.397 | 1.00 | 20.00 | W |
| ATOM | 4483 | O | HOH | 124 | 37.626 | 28.216 | 31.136 | 1.00 | 20.00 | W |
| ATOM | 4484 | O | HOH | 125 | 48.566 | 37.385 | 16.630 | 1.00 | 20.00 | W |
| ATOM | 4485 | O | HOH | 126 | 1.496 | 22.085 | 13.272 | 1.00 | 20.00 | W |
| ATOM | 4486 | O | HOH | 127 | 34.698 | 24.986 | 24.965 | 1.00 | 20.00 | W |
| ATOM | 4487 | O | HOH | 128 | -2.903 | 37.363 | 6.990 | 1.00 | 20.00 | W |
| ATOM | 4488 | O | HOH | 129 | 12.491 | -3.414 | 25.110 | 1.00 | 20.00 | W |
| ATOM | 4489 | O | HOH | 130 | 5.176 | -10.899 | 28.961 | 1.00 | 20.00 | W |
| ATOM | 4490 | O | HOH | 131 | 48.659 | 38.012 | 29.029 | 1.00 | 20.00 | W |
| ATOM | 4491 | O | HOH | 133 | 52.619 | 28.488 | 32.666 | 1.00 | 20.00 | W |
| ATOM | 4492 | O | HOH | 134 | 39.711 | 23.898 | 9.790 | 1.00 | 20.00 | W |
| ATOM | 4493 | O | HOH | 135 | 3.443 | 35.318 | -0.076 | 1.00 | 20.00 | W |
| ATOM | 4494 | O | HOH | 136 | 20.485 | 29.825 | -10.828 | 1.00 | 20.00 | W |
| ATOM | 4495 | O | HOH | 137 | 27.808 | 44.788 | 25.549 | 1.00 | 20.00 | W |

FIG. 3A-79

```
ATOM   4496  O  HOH  138    9.406  20.806  12.275  1.00  20.00   W
ATOM   4497  O  HOH  139   32.311  40.520  18.168  1.00  20.00   W
ATOM   4498  O  HOH  140   26.404  40.444   7.377  1.00  20.00   W
ATOM   4499  O  HOH  141   24.546  29.367  -7.098  1.00  20.00   W
ATOM   4500  O  HOH  142   64.483  32.976  23.998  1.00  20.00   W
ATOM   4501  O  HOH  143   59.735  33.731   8.443  1.00  20.00   W
END
```

|  |  | -5 | 1 | 10 |
|---|---|---|---|---|
| *B. subtillis* ACP |  | G P L G S | A D T L E | R V T K I |
| E. coli ACP |  |  | S T I E E | R V K K I |
| *Streptomyces coelicolor* A3(2) ACP | M A T L L T | T D D L R | R A L V E |

|  | 20 |  | 30 |  |
|---|---|---|---|---|
| I V D R L | G V D E A | D V K L E | A S F K E | D L G A D |
| I G E Q L | G V K Q E | E V T N N | A S F V E | D L G A D |
| C A G E T | D G T D L | S G D F L | D L R F E | D I G Y D |

| 40 |  | 50 |  | 60 |
|---|---|---|---|---|
| S L D V V | E L V M E | L E D E F | D M E I S | D E D A E |
| S L D T V | E L V M A | L E E E F | D T E I P | D E E A E |
| S L A L M | E T A A R | L E S R Y | G V S I P | D D V A G |

|  | 70 | 76 |
|---|---|---|
| K I A T V | G D A V N | Y I Q N Q | Q |
| K I T T V | Q A A I D | Y I N G H | Q A |
| R V D T P | R E L L D | L I N G A | L A E A A |

| | Atom No. | Atom Type | Residue | Res. No. | x | y | z | | |
|---|---|---|---|---|---|---|---|---|---|
| ATOM | 1 | N | GLY | -5 | 13.445 | 10.407 | 11.181 | 1.00 | 7.22 |
| ATOM | 2 | CA | GLY | -5 | 14.143 | 11.725 | 11.174 | 1.00 | 6.61 |
| ATOM | 3 | C | GLY | -5 | 14.807 | 11.951 | 9.811 | 1.00 | 5.70 |
| ATOM | 4 | O | GLY | -5 | 14.370 | 12.786 | 9.043 | 1.00 | 5.61 |
| ATOM | 5 | 1HA | GLY | -5 | 14.899 | 11.735 | 11.944 | 1.00 | 6.68 |
| ATOM | 6 | 2HA | GLY | -5 | 13.427 | 12.512 | 11.362 | 1.00 | 7.06 |
| ATOM | 7 | 1H | GLY | -5 | 13.304 | 10.082 | 10.204 | 1.00 | 7.45 |
| ATOM | 8 | 2H | GLY | -5 | 12.521 | 10.507 | 11.650 | 1.00 | 7.32 |
| ATOM | 9 | 3H | GLY | -5 | 14.022 | 9.712 | 11.696 | 1.00 | 7.59 |
| ATOM | 10 | N | PRO | -4 | 15.850 | 11.199 | 9.553 | 1.00 | 5.38 |
| ATOM | 11 | CA | PRO | -4 | 16.579 | 11.330 | 8.267 | 1.00 | 4.86 |
| ATOM | 12 | C | PRO | -4 | 15.735 | 10.796 | 7.104 | 1.00 | 4.19 |
| ATOM | 13 | O | PRO | -4 | 14.970 | 11.522 | 6.500 | 1.00 | 4.30 |
| ATOM | 14 | CB | PRO | -4 | 17.842 | 10.496 | 8.484 | 1.00 | 5.34 |
| ATOM | 15 | CG | PRO | -4 | 17.475 | 9.509 | 9.545 | 1.00 | 5.78 |
| ATOM | 16 | CD | PRO | -4 | 16.442 | 10.169 | 10.420 | 1.00 | 5.92 |
| ATOM | 17 | HA | PRO | -4 | 16.847 | 12.350 | 8.088 | 1.00 | 5.08 |
| ATOM | 18 | 1HB | PRO | -4 | 18.652 | 11.121 | 8.826 | 1.00 | 5.86 |
| ATOM | 19 | 2HB | PRO | -4 | 18.117 | 9.986 | 7.571 | 1.00 | 5.21 |
| ATOM | 20 | 1HG | PRO | -4 | 18.344 | 9.260 | 10.135 | 1.00 | 6.43 |
| ATOM | 21 | 2HG | PRO | -4 | 17.065 | 8.617 | 9.093 | 1.00 | 5.71 |
| ATOM | 22 | 2HD | PRO | -4 | 15.694 | 9.451 | 10.728 | 1.00 | 6.14 |
| ATOM | 23 | 1HD | PRO | -4 | 16.906 | 10.628 | 11.278 | 1.00 | 6.49 |
| ATOM | 24 | N | LEU | -3 | 15.866 | 9.543 | 6.782 | 1.00 | 3.93 |
| ATOM | 25 | CA | LEU | -3 | 15.072 | 8.976 | 5.655 | 1.00 | 3.68 |
| ATOM | 26 | C | LEU | -3 | 14.070 | 7.952 | 6.194 | 1.00 | 2.75 |
| ATOM | 27 | O | LEU | -3 | 13.707 | 7.972 | 7.353 | 1.00 | 2.91 |
| ATOM | 28 | CB | LEU | -3 | 16.012 | 8.295 | 4.657 | 1.00 | 4.75 |
| ATOM | 29 | CG | LEU | -3 | 15.555 | 8.610 | 3.231 | 1.00 | 5.69 |
| ATOM | 30 | CD1 | LEU | -3 | 16.304 | 9.840 | 2.715 | 1.00 | 6.59 |
| ATOM | 31 | CD2 | LEU | -3 | 15.856 | 7.414 | 2.324 | 1.00 | 6.39 |
| ATOM | 32 | HN | LEU | -3 | 16.487 | 8.977 | 7.275 | 1.00 | 4.25 |
| ATOM | 33 | HA | LEU | -3 | 14.537 | 9.772 | 5.159 | 1.00 | 3.87 |
| ATOM | 34 | 1HB | LEU | -3 | 15.991 | 7.227 | 4.812 | 1.00 | 4.81 |
| ATOM | 35 | 2HB | LEU | -3 | 17.018 | 8.662 | 4.803 | 1.00 | 5.14 |
| ATOM | 36 | HG | LEU | -3 | 14.493 | 8.808 | 3.229 | 1.00 | 5.59 |
| ATOM | 37 | 1HD1 | LEU | -3 | 16.849 | 10.297 | 3.527 | 1.00 | 6.91 |
| ATOM | 38 | 2HD1 | LEU | -3 | 15.596 | 10.550 | 2.313 | 1.00 | 6.87 |
| ATOM | 39 | 3HD1 | LEU | -3 | 16.995 | 9.542 | 1.940 | 1.00 | 6.92 |
| ATOM | 40 | 1HD2 | LEU | -3 | 15.148 | 7.394 | 1.509 | 1.00 | 6.75 |
| ATOM | 41 | 2HD2 | LEU | -3 | 15.774 | 6.501 | 2.894 | 1.00 | 6.70 |
| ATOM | 42 | 3HD2 | LEU | -3 | 16.857 | 7.504 | 1.929 | 1.00 | 6.55 |
| ATOM | 43 | N | GLY | -2 | 13.619 | 7.057 | 5.357 | 1.00 | 2.32 |
| ATOM | 44 | CA | GLY | -2 | 12.638 | 6.032 | 5.813 | 1.00 | 1.96 |
| ATOM | 45 | C | GLY | -2 | 11.651 | 5.742 | 4.682 | 1.00 | 1.44 |
| ATOM | 46 | O | GLY | -2 | 11.709 | 4.710 | 4.043 | 1.00 | 2.05 |
| ATOM | 47 | HN | GLY | -2 | 13.924 | 7.061 | 4.426 | 1.00 | 2.73 |
| ATOM | 48 | 1HA | GLY | -2 | 12.099 | 6.404 | 6.671 | 1.00 | 2.15 |
| ATOM | 49 | 2HA | GLY | -2 | 13.163 | 5.126 | 6.080 | 1.00 | 2.61 |
| ATOM | 50 | N | SER | -1 | 10.749 | 6.649 | 4.425 | 1.00 | 1.07 |
| ATOM | 51 | CA | SER | -1 | 9.760 | 6.434 | 3.331 | 1.00 | 0.77 |
| ATOM | 52 | C | SER | -1 | 9.611 | 7.726 | 2.524 | 1.00 | 0.80 |
| ATOM | 53 | O | SER | -1 | 8.568 | 8.007 | 1.971 | 1.00 | 1.03 |
| ATOM | 54 | CB | SER | -1 | 8.407 | 6.049 | 3.931 | 1.00 | 1.06 |
| ATOM | 55 | OG | SER | -1 | 7.911 | 7.134 | 4.704 | 1.00 | 1.57 |
| ATOM | 56 | HN | SER | -1 | 10.724 | 7.476 | 4.950 | 1.00 | 1.67 |
| ATOM | 57 | HA | SER | -1 | 10.104 | 5.641 | 2.683 | 1.00 | 0.86 |
| ATOM | 58 | 1HB | SER | -1 | 8.527 | 5.174 | 4.556 | 1.00 | 1.22 |
| ATOM | 59 | 2HB | SER | -1 | 7.709 | 5.826 | 3.140 | 1.00 | 1.21 |
| ATOM | 60 | HG | SER | -1 | 8.481 | 7.240 | 5.469 | 1.00 | 2.01 |
| ATOM | 61 | N | ALA | 1 | 10.648 | 8.520 | 2.454 | 1.00 | 0.84 |
| ATOM | 62 | CA | ALA | 1 | 10.567 | 9.797 | 1.687 | 1.00 | 0.86 |
| ATOM | 63 | C | ALA | 1 | 9.992 | 9.530 | 0.293 | 1.00 | 0.83 |
| ATOM | 64 | O | ALA | 1 | 8.843 | 9.816 | 0.019 | 1.00 | 0.87 |
| ATOM | 65 | CB | ALA | 1 | 11.967 | 10.400 | 1.556 | 1.00 | 0.91 |
| ATOM | 66 | HN | ALA | 1 | 11.478 | 8.281 | 2.909 | 1.00 | 1.01 |
| ATOM | 67 | HA | ALA | 1 | 9.930 | 10.484 | 2.212 | 1.00 | 0.92 |
| ATOM | 68 | 1HB | ALA | 1 | 12.031 | 11.295 | 2.156 | 1.00 | 1.45 |
| ATOM | 69 | 2HB | ALA | 1 | 12.158 | 10.645 | 0.521 | 1.00 | 1.12 |
| ATOM | 70 | 3HB | ALA | 1 | 12.700 | 9.684 | 1.898 | 1.00 | 1.48 |
| ATOM | 71 | N | ASP | 2 | 10.779 | 8.974 | -0.583 | 1.00 | 0.80 |
| ATOM | 72 | CA | ASP | 2 | 10.273 | 8.677 | -1.952 | 1.00 | 0.81 |
| ATOM | 73 | C | ASP | 2 | 9.341 | 7.469 | -1.879 | 1.00 | 0.76 |
| ATOM | 74 | O | ASP | 2 | 8.421 | 7.327 | -2.659 | 1.00 | 0.79 |
| ATOM | 75 | CB | ASP | 2 | 11.451 | 8.362 | -2.878 | 1.00 | 0.86 |
| ATOM | 76 | CG | ASP | 2 | 11.709 | 9.554 | -3.802 | 1.00 | 1.59 |
| ATOM | 77 | OD1 | ASP | 2 | 11.953 | 9.327 | -4.976 | 1.00 | 2.30 |

FIG. 5A-1

| | | | | | | | | |
|---|---|---|---|---|---|---|---|---|
| ATOM | 78 | OD2 | ASP | 2 | 11.658 | 10.674 | -3.321 | 1.00 | 2.20 |
| ATOM | 79 | HN | ASP | 2 | 11.697 | 8.745 | -0.338 | 1.00 | 0.81 |
| ATOM | 80 | HA | ASP | 2 | 9.732 | 9.531 | -2.331 | 1.00 | 0.85 |
| ATOM | 81 | 1HB | ASP | 2 | 11.219 | 7.492 | -3.473 | 1.00 | 1.31 |
| ATOM | 82 | 2HB | ASP | 2 | 12.333 | 8.168 | -2.285 | 1.00 | 1.14 |
| ATOM | 83 | N | THR | 3 | 9.573 | 6.601 | -0.933 | 1.00 | 0.73 |
| ATOM | 84 | CA | THR | 3 | 8.709 | 5.399 | -0.783 | 1.00 | 0.69 |
| ATOM | 85 | C | THR | 3 | 7.282 | 5.837 | -0.452 | 1.00 | 0.66 |
| ATOM | 86 | O | THR | 3 | 6.372 | 5.666 | -1.237 | 1.00 | 0.63 |
| ATOM | 87 | CB | THR | 3 | 9.253 | 4.534 | 0.355 | 1.00 | 0.71 |
| ATOM | 88 | OG1 | THR | 3 | 10.665 | 4.674 | 0.418 | 1.00 | 0.86 |
| ATOM | 89 | CG2 | THR | 3 | 8.895 | 3.070 | 0.110 | 1.00 | 0.75 |
| ATOM | 90 | HN | THR | 3 | 10.319 | 6.744 | -0.314 | 1.00 | 0.75 |
| ATOM | 91 | HA | THR | 3 | 8.708 | 4.830 | -1.699 | 1.00 | 0.68 |
| ATOM | 92 | HB | THR | 3 | 8.819 | 4.855 | 1.287 | 1.00 | 0.70 |
| ATOM | 93 | HG1 | THR | 3 | 10.946 | 4.453 | 1.309 | 1.00 | 1.08 |
| ATOM | 94 | 1HG2 | THR | 3 | 9.527 | 2.442 | 0.720 | 1.00 | 1.26 |
| ATOM | 95 | 2HG2 | THR | 3 | 9.046 | 2.830 | -0.932 | 1.00 | 1.33 |
| ATOM | 96 | 3HG2 | THR | 3 | 7.861 | 2.902 | 0.373 | 1.00 | 1.09 |
| ATOM | 97 | N | LEU | 4 | 7.086 | 6.404 | 0.709 | 1.00 | 0.68 |
| ATOM | 98 | CA | LEU | 4 | 5.721 | 6.862 | 1.118 | 1.00 | 0.68 |
| ATOM | 99 | C | LEU | 4 | 5.055 | 7.628 | -0.025 | 1.00 | 0.66 |
| ATOM | 100 | O | LEU | 4 | 4.006 | 7.254 | -0.507 | 1.00 | 0.66 |
| ATOM | 101 | CB | LEU | 4 | 5.838 | 7.776 | 2.340 | 1.00 | 0.73 |
| ATOM | 102 | CG | LEU | 4 | 4.566 | 7.670 | 3.182 | 1.00 | 0.77 |
| ATOM | 103 | CD1 | LEU | 4 | 4.435 | 6.250 | 3.730 | 1.00 | 1.60 |
| ATOM | 104 | CD2 | LEU | 4 | 4.643 | 8.660 | 4.346 | 1.00 | 1.36 |
| ATOM | 105 | HN | LEU | 4 | 7.842 | 6.528 | 1.317 | 1.00 | 0.71 |
| ATOM | 106 | HA | LEU | 4 | 5.119 | 6.006 | 1.370 | 1.00 | 0.67 |
| ATOM | 107 | 1HB | LEU | 4 | 5.970 | 8.797 | 2.016 | 1.00 | 0.83 |
| ATOM | 108 | 2HB | LEU | 4 | 6.688 | 7.473 | 2.933 | 1.00 | 0.83 |
| ATOM | 109 | HG | LEU | 4 | 3.708 | 7.900 | 2.567 | 1.00 | 1.32 |
| ATOM | 110 | 1HD1 | LEU | 4 | 3.887 | 5.642 | 3.027 | 1.00 | 2.12 |
| ATOM | 111 | 2HD1 | LEU | 4 | 3.907 | 6.274 | 4.672 | 1.00 | 2.07 |
| ATOM | 112 | 3HD1 | LEU | 4 | 5.418 | 5.829 | 3.880 | 1.00 | 2.15 |
| ATOM | 113 | 1HD2 | LEU | 4 | 4.357 | 8.163 | 5.261 | 1.00 | 1.85 |
| ATOM | 114 | 2HD2 | LEU | 4 | 3.974 | 9.486 | 4.160 | 1.00 | 1.90 |
| ATOM | 115 | 3HD2 | LEU | 4 | 5.654 | 9.030 | 4.438 | 1.00 | 1.95 |
| ATOM | 116 | N | GLU | 5 | 5.659 | 8.695 | -0.463 | 1.00 | 0.68 |
| ATOM | 117 | CA | GLU | 5 | 5.066 | 9.483 | -1.577 | 1.00 | 0.69 |
| ATOM | 118 | C | GLU | 5 | 4.786 | 8.555 | -2.760 | 1.00 | 0.64 |
| ATOM | 119 | O | GLU | 5 | 3.740 | 8.613 | -3.375 | 1.00 | 0.64 |
| ATOM | 120 | CB | GLU | 5 | 6.043 | 10.581 | -2.002 | 1.00 | 0.75 |
| ATOM | 121 | CG | GLU | 5 | 5.579 | 11.925 | -1.438 | 1.00 | 0.99 |
| ATOM | 122 | CD | GLU | 5 | 5.850 | 13.029 | -2.462 | 1.00 | 1.53 |
| ATOM | 123 | OE1 | GLU | 5 | 6.673 | 13.884 | -2.179 | 1.00 | 2.26 |
| ATOM | 124 | OE2 | GLU | 5 | 5.229 | 13.000 | -3.512 | 1.00 | 1.99 |
| ATOM | 125 | HN | GLU | 5 | 6.501 | 8.976 | -0.062 | 1.00 | 0.69 |
| ATOM | 126 | HA | GLU | 5 | 4.146 | 9.926 | -1.243 | 1.00 | 0.70 |
| ATOM | 127 | 1HB | GLU | 5 | 6.075 | 10.637 | -3.080 | 1.00 | 0.92 |
| ATOM | 128 | 2HB | GLU | 5 | 7.029 | 10.352 | -1.624 | 1.00 | 1.03 |
| ATOM | 129 | 1HG | GLU | 5 | 6.120 | 12.140 | -0.529 | 1.00 | 1.46 |
| ATOM | 130 | 2HG | GLU | 5 | 4.521 | 11.881 | -1.226 | 1.00 | 1.41 |
| ATOM | 131 | N | ARG | 6 | 5.709 | 7.688 | -3.071 | 1.00 | 0.62 |
| ATOM | 132 | CA | ARG | 6 | 5.489 | 6.744 | -4.201 | 1.00 | 0.60 |
| ATOM | 133 | C | ARG | 6 | 4.238 | 5.922 | -3.903 | 1.00 | 0.55 |
| ATOM | 134 | O | ARG | 6 | 3.258 | 5.972 | -4.619 | 1.00 | 0.57 |
| ATOM | 135 | CB | ARG | 6 | 6.707 | 5.815 | -4.337 | 1.00 | 0.61 |
| ATOM | 136 | CG | ARG | 6 | 6.411 | 4.687 | -5.334 | 1.00 | 0.59 |
| ATOM | 137 | CD | ARG | 6 | 5.997 | 5.283 | -6.680 | 1.00 | 0.64 |
| ATOM | 138 | NE | ARG | 6 | 6.941 | 4.821 | -7.736 | 1.00 | 0.73 |
| ATOM | 139 | CZ | ARG | 6 | 6.995 | 5.442 | -8.883 | 1.00 | 1.07 |
| ATOM | 140 | NH1 | ARG | 6 | 8.123 | 5.952 | -9.296 | 1.00 | 1.70 |
| ATOM | 141 | NH2 | ARG | 6 | 5.922 | 5.553 | -9.617 | 1.00 | 1.79 |
| ATOM | 142 | HN | ARG | 6 | 6.539 | 7.651 | -2.553 | 1.00 | 0.65 |
| ATOM | 143 | HA | ARG | 6 | 5.348 | 7.300 | -5.112 | 1.00 | 0.63 |
| ATOM | 144 | 1HB | ARG | 6 | 6.935 | 5.384 | -3.374 | 1.00 | 0.60 |
| ATOM | 145 | 2HB | ARG | 6 | 7.555 | 6.383 | -4.685 | 1.00 | 0.68 |
| ATOM | 146 | 1HG | ARG | 6 | 5.610 | 4.072 | -4.953 | 1.00 | 0.56 |
| ATOM | 147 | 2HG | ARG | 6 | 7.297 | 4.083 | -5.466 | 1.00 | 0.61 |
| ATOM | 148 | 1HD | ARG | 6 | 6.020 | 6.359 | -6.620 | 1.00 | 0.67 |
| ATOM | 149 | 2HD | ARG | 6 | 4.996 | 4.958 | -6.921 | 1.00 | 0.64 |
| ATOM | 150 | HE | ARG | 6 | 7.524 | 4.052 | -7.569 | 1.00 | 0.94 |
| ATOM | 151 | 1HH1 | ARG | 6 | 8.946 | 5.867 | -8.734 | 1.00 | 2.17 |
| ATOM | 152 | 2HH1 | ARG | 6 | 8.166 | 6.428 | -10.175 | 1.00 | 2.13 |
| ATOM | 153 | 1HH2 | ARG | 6 | 5.058 | 5.162 | -9.301 | 1.00 | 2.29 |
| ATOM | 154 | 2HH2 | ARG | 6 | 5.964 | 6.027 | -10.496 | 1.00 | 2.19 |

FIG. 5A-2

| | | | | | | | | |
|---|---|---|---|---|---|---|---|---|
| ATOM | 155 | N | VAL | 7 | 4.271 | 5.170 | -2.343 | 1.00 | 0.53 |
| ATOM | 156 | CA | VAL | 7 | 3.097 | 4.343 | -2.476 | 1.00 | 0.50 |
| ATOM | 157 | C | VAL | 7 | 1.864 | 5.236 | -2.365 | 1.00 | 0.50 |
| ATOM | 158 | O | VAL | 7 | 0.777 | 4.868 | -2.765 | 1.00 | 0.61 |
| ATOM | 159 | CB | VAL | 7 | 3.357 | 3.664 | -1.133 | 1.00 | 0.52 |
| ATOM | 160 | CG1 | VAL | 7 | 2.279 | 2.619 | -0.878 | 1.00 | 0.56 |
| ATOM | 161 | CG2 | VAL | 7 | 4.716 | 2.974 | -1.166 | 1.00 | 0.53 |
| ATOM | 162 | HN | VAL | 7 | 5.070 | 5.152 | -2.287 | 1.00 | 0.56 |
| ATOM | 163 | HA | VAL | 7 | 2.938 | 3.596 | -3.232 | 1.00 | 0.50 |
| ATOM | 164 | HB | VAL | 7 | 3.342 | 4.402 | -0.344 | 1.00 | 0.56 |
| ATOM | 165 | 1HG1 | VAL | 7 | 1.941 | 2.216 | -1.821 | 1.00 | 1.14 |
| ATOM | 166 | 2HG1 | VAL | 7 | 1.453 | 3.079 | -0.364 | 1.00 | 1.13 |
| ATOM | 167 | 3HG1 | VAL | 7 | 2.687 | 1.824 | -0.272 | 1.00 | 1.23 |
| ATOM | 168 | 1HG2 | VAL | 7 | 4.783 | 2.275 | -0.349 | 1.00 | 1.19 |
| ATOM | 169 | 2HG2 | VAL | 7 | 5.499 | 3.708 | -1.076 | 1.00 | 1.06 |
| ATOM | 170 | 3HG2 | VAL | 7 | 4.821 | 2.446 | -2.098 | 1.00 | 1.15 |
| ATOM | 171 | N | THR | 8 | 2.028 | 6.411 | -1.826 | 1.00 | 0.47 |
| ATOM | 172 | CA | THR | 8 | 0.871 | 7.335 | -1.689 | 1.00 | 0.49 |
| ATOM | 173 | C | THR | 8 | 0.287 | 7.613 | -3.071 | 1.00 | 0.47 |
| ATOM | 174 | O | THR | 8 | -0.913 | 7.667 | -3.250 | 1.00 | 0.50 |
| ATOM | 175 | CB | THR | 8 | 1.335 | 8.649 | -1.054 | 1.00 | 0.58 |
| ATOM | 176 | OG1 | THR | 8 | 1.898 | 8.384 | 0.223 | 1.00 | 0.63 |
| ATOM | 177 | CG2 | THR | 8 | 0.143 | 9.594 | -0.902 | 1.00 | 0.65 |
| ATOM | 178 | HN | THR | 8 | 2.915 | 6.685 | -1.514 | 1.00 | 0.50 |
| ATOM | 179 | HA | THR | 8 | 0.120 | 6.877 | -1.068 | 1.00 | 0.48 |
| ATOM | 180 | HB | THR | 8 | 2.077 | 9.112 | -1.685 | 1.00 | 0.60 |
| ATOM | 181 | HG1 | THR | 8 | 2.434 | 9.140 | 0.474 | 1.00 | 0.92 |
| ATOM | 182 | 1HG2 | THR | 8 | -0.152 | 9.961 | -1.874 | 1.00 | 1.18 |
| ATOM | 183 | 2HG2 | THR | 8 | 0.421 | 10.426 | -0.272 | 1.00 | 1.17 |
| ATOM | 184 | 3HG2 | THR | 8 | -0.683 | 9.062 | -0.453 | 1.00 | 1.30 |
| ATOM | 185 | N | LYS | 9 | 1.127 | 7.777 | -4.054 | 1.00 | 0.49 |
| ATOM | 186 | CA | LYS | 9 | 0.615 | 8.035 | -5.425 | 1.00 | 0.51 |
| ATOM | 187 | C | LYS | 9 | -0.093 | 6.777 | -5.919 | 1.00 | 0.46 |
| ATOM | 188 | O | LYS | 9 | -1.121 | 6.837 | -6.563 | 1.00 | 0.50 |
| ATOM | 189 | CB | LYS | 9 | 1.782 | 8.373 | -6.356 | 1.00 | 0.57 |
| ATOM | 190 | CG | LYS | 9 | 1.486 | 9.683 | -7.088 | 1.00 | 0.83 |
| ATOM | 191 | CD | LYS | 9 | 2.733 | 10.570 | -7.074 | 1.00 | 1.21 |
| ATOM | 192 | CE | LYS | 9 | 3.808 | 9.953 | -7.971 | 1.00 | 1.47 |
| ATOM | 193 | NZ | LYS | 9 | 4.135 | 10.898 | -9.075 | 1.00 | 2.31 |
| ATOM | 194 | HN | LYS | 9 | 2.091 | 7.718 | -3.890 | 1.00 | 0.53 |
| ATOM | 195 | HA | LYS | 9 | -0.083 | 8.857 | -5.402 | 1.00 | 0.54 |
| ATOM | 196 | 1HB | LYS | 9 | 1.909 | 7.580 | -7.077 | 1.00 | 0.71 |
| ATOM | 197 | 2HB | LYS | 9 | 2.686 | 8.480 | -5.774 | 1.00 | 0.75 |
| ATOM | 198 | 1HG | LYS | 9 | 0.676 | 10.198 | -6.594 | 1.00 | 1.43 |
| ATOM | 199 | 2HG | LYS | 9 | 1.208 | 9.469 | -8.110 | 1.00 | 1.41 |
| ATOM | 200 | 1HD | LYS | 9 | 3.110 | 10.646 | -6.065 | 1.00 | 1.82 |
| ATOM | 201 | 2HD | LYS | 9 | 2.479 | 11.554 | -7.440 | 1.00 | 1.93 |
| ATOM | 202 | 1HE | LYS | 9 | 3.441 | 9.026 | -8.387 | 1.00 | 1.92 |
| ATOM | 203 | 2HE | LYS | 9 | 4.696 | 9.759 | -7.388 | 1.00 | 1.77 |
| ATOM | 204 | 1HZ | LYS | 9 | 3.912 | 11.869 | -8.779 | 1.00 | 2.74 |
| ATOM | 205 | 2HZ | LYS | 9 | 3.575 | 10.653 | -9.918 | 1.00 | 2.83 |
| ATOM | 206 | 3HZ | LYS | 9 | 5.148 | 10.831 | -9.300 | 1.00 | 2.62 |
| ATOM | 207 | N | ILE | 10 | 0.451 | 5.634 | -5.608 | 1.00 | 0.43 |
| ATOM | 208 | CA | ILE | 10 | -0.176 | 4.364 | -6.036 | 1.00 | 0.44 |
| ATOM | 209 | C | ILE | 10 | -1.459 | 4.137 | -5.234 | 1.00 | 0.39 |
| ATOM | 210 | O | ILE | 10 | -2.527 | 3.977 | -5.787 | 1.00 | 0.43 |
| ATOM | 211 | CB | ILE | 10 | 0.809 | 3.227 | -5.777 | 1.00 | 0.48 |
| ATOM | 212 | CG1 | ILE | 10 | 2.071 | 3.447 | -6.615 | 1.00 | 0.57 |
| ATOM | 213 | CG2 | ILE | 10 | 0.167 | 1.902 | -6.165 | 1.00 | 0.53 |
| ATOM | 214 | CD1 | ILE | 10 | 3.198 | 2.559 | -6.086 | 1.00 | 0.73 |
| ATOM | 215 | HN | ILE | 10 | 1.276 | 5.610 | -5.084 | 1.00 | 0.45 |
| ATOM | 216 | HA | ILE | 10 | -0.409 | 4.410 | -7.085 | 1.00 | 0.48 |
| ATOM | 217 | HB | ILE | 10 | 1.069 | 3.207 | -4.729 | 1.00 | 0.47 |
| ATOM | 218 | 1HG1 | ILE | 10 | 2.370 | 4.483 | -6.548 | 1.00 | 0.65 |
| ATOM | 219 | 2HG1 | ILE | 10 | 1.866 | 3.197 | -7.646 | 1.00 | 0.65 |
| ATOM | 220 | 1HG2 | ILE | 10 | 0.064 | 1.856 | -7.238 | 1.00 | 1.15 |
| ATOM | 221 | 2HG2 | ILE | 10 | -0.806 | 1.829 | -5.704 | 1.00 | 1.10 |
| ATOM | 222 | 3HG2 | ILE | 10 | 0.791 | 1.090 | -5.825 | 1.00 | 1.22 |
| ATOM | 223 | 1HD1 | ILE | 10 | 3.988 | 3.178 | -5.689 | 1.00 | 1.17 |
| ATOM | 224 | 2HD1 | ILE | 10 | 3.585 | 1.952 | -6.891 | 1.00 | 1.28 |
| ATOM | 225 | 3HD1 | ILE | 10 | 2.815 | 1.919 | -5.305 | 1.00 | 1.36 |
| ATOM | 226 | N | ILE | 11 | -1.363 | 4.126 | -3.935 | 1.00 | 0.34 |
| ATOM | 227 | CA | ILE | 11 | -2.581 | 3.912 | -3.100 | 1.00 | 0.31 |
| ATOM | 228 | C | ILE | 11 | -3.628 | 4.971 | -3.443 | 1.00 | 0.33 |
| ATOM | 229 | O | ILE | 11 | -4.692 | 4.674 | -3.949 | 1.00 | 0.38 |
| ATOM | 230 | CB | ILE | 11 | -2.231 | 4.038 | -1.614 | 1.00 | 0.31 |
| ATOM | 231 | CG1 | ILE | 11 | -1.167 | 3.005 | -1.232 | 1.00 | 0.42 |

FIG. 5A-3

| | | | | | | | | |
|---|---|---|---|---|---|---|---|---|
| ATOM | 232 | CG2 | ILE | 11 | -3.490 | 3.793 | -0.782 | 1.00 | 0.37 |
| ATOM | 233 | CD1 | ILE | 11 | -0.869 | 3.106 | 0.267 | 1.00 | 0.43 |
| ATOM | 234 | HN | ILE | 11 | -0.492 | 4.260 | -3.510 | 1.00 | 0.36 |
| ATOM | 235 | HA | ILE | 11 | -2.985 | 2.933 | -3.294 | 1.00 | 0.32 |
| ATOM | 236 | HB | ILE | 11 | -1.859 | 5.033 | -1.417 | 1.00 | 0.33 |
| ATOM | 237 | 1HG1 | ILE | 11 | -0.263 | 3.194 | -1.791 | 1.00 | 0.58 |
| ATOM | 238 | 2HG1 | ILE | 11 | -1.531 | 2.016 | -1.458 | 1.00 | 0.69 |
| ATOM | 239 | 1HG2 | ILE | 11 | -3.237 | 3.817 | 0.267 | 1.00 | 1.09 |
| ATOM | 240 | 2HG2 | ILE | 11 | -3.903 | 2.826 | -1.031 | 1.00 | 1.07 |
| ATOM | 241 | 3HG2 | ILE | 11 | -4.218 | 4.561 | -0.996 | 1.00 | 1.08 |
| ATOM | 242 | 1HD1 | ILE | 11 | -0.273 | 2.259 | 0.572 | 1.00 | 0.99 |
| ATOM | 243 | 2HD1 | ILE | 11 | -1.797 | 3.109 | 0.820 | 1.00 | 1.22 |
| ATOM | 244 | 3HD1 | ILE | 11 | -0.328 | 4.018 | 0.466 | 1.00 | 1.12 |
| ATOM | 245 | N | VAL | 12 | -3.331 | 6.205 | -3.150 | 1.00 | 0.38 |
| ATOM | 246 | CA | VAL | 12 | -4.294 | 7.310 | -3.427 | 1.00 | 0.44 |
| ATOM | 247 | C | VAL | 12 | -4.862 | 7.187 | -4.844 | 1.00 | 0.48 |
| ATOM | 248 | O | VAL | 12 | -6.050 | 7.016 | -5.037 | 1.00 | 0.61 |
| ATOM | 249 | CB | VAL | 12 | -3.567 | 8.650 | -3.286 | 1.00 | 0.49 |
| ATOM | 250 | CG1 | VAL | 12 | -4.535 | 9.795 | -3.586 | 1.00 | 0.59 |
| ATOM | 251 | CG2 | VAL | 12 | -3.036 | 8.792 | -1.858 | 1.00 | 0.50 |
| ATOM | 252 | HN | VAL | 12 | -2.469 | 6.405 | -2.731 | 1.00 | 0.44 |
| ATOM | 253 | HA | VAL | 12 | -5.099 | 7.266 | -2.714 | 1.00 | 0.44 |
| ATOM | 254 | HB | VAL | 12 | -2.743 | 8.685 | -3.984 | 1.00 | 0.49 |
| ATOM | 255 | 1HG1 | VAL | 12 | -4.123 | 10.421 | -4.363 | 1.00 | 0.94 |
| ATOM | 256 | 2HG1 | VAL | 12 | -4.686 | 10.383 | -2.692 | 1.00 | 1.35 |
| ATOM | 257 | 3HG1 | VAL | 12 | -5.481 | 9.391 | -3.914 | 1.00 | 1.23 |
| ATOM | 258 | 1HG2 | VAL | 12 | -3.716 | 9.401 | -1.280 | 1.00 | 1.09 |
| ATOM | 259 | 2HG2 | VAL | 12 | -2.064 | 9.261 | -1.881 | 1.00 | 1.15 |
| ATOM | 260 | 3HG2 | VAL | 12 | -2.954 | 7.815 | -1.405 | 1.00 | 1.17 |
| ATOM | 261 | N | ASP | 13 | -4.023 | 7.287 | -5.833 | 1.00 | 0.45 |
| ATOM | 262 | CA | ASP | 13 | -4.502 | 7.193 | -7.244 | 1.00 | 0.50 |
| ATOM | 263 | C | ASP | 13 | -5.372 | 5.947 | -7.429 | 1.00 | 0.45 |
| ATOM | 264 | O | ASP | 13 | -6.222 | 5.898 | -8.296 | 1.00 | 0.49 |
| ATOM | 265 | CB | ASP | 13 | -3.296 | 7.112 | -8.184 | 1.00 | 0.57 |
| ATOM | 266 | CG | ASP | 13 | -3.751 | 7.364 | -9.623 | 1.00 | 1.25 |
| ATOM | 267 | OD1 | ASP | 13 | -2.914 | 7.729 | -10.432 | 1.00 | 1.87 |
| ATOM | 268 | OD2 | ASP | 13 | -4.927 | 7.187 | -9.892 | 1.00 | 1.93 |
| ATOM | 269 | HN | ASP | 13 | -3.073 | 7.433 | -5.648 | 1.00 | 0.46 |
| ATOM | 270 | HA | ASP | 13 | -5.081 | 8.068 | -7.484 | 1.00 | 0.55 |
| ATOM | 271 | 1HB | ASP | 13 | -2.851 | 6.132 | -8.115 | 1.00 | 0.87 |
| ATOM | 272 | 2HB | ASP | 13 | -2.569 | 7.859 | -7.899 | 1.00 | 0.86 |
| ATOM | 273 | N | ARG | 14 | -5.161 | 4.935 | -6.636 | 1.00 | 0.39 |
| ATOM | 274 | CA | ARG | 14 | -5.971 | 3.695 | -6.791 | 1.00 | 0.37 |
| ATOM | 275 | C | ARG | 14 | -7.082 | 3.633 | -5.736 | 1.00 | 0.32 |
| ATOM | 276 | O | ARG | 14 | -8.198 | 4.056 | -5.970 | 1.00 | 0.34 |
| ATOM | 277 | CB | ARG | 14 | -5.049 | 2.479 | -6.649 | 1.00 | 0.39 |
| ATOM | 278 | CG | ARG | 14 | -4.404 | 2.155 | -8.004 | 1.00 | 0.48 |
| ATOM | 279 | CD | ARG | 14 | -3.757 | 3.413 | -8.600 | 1.00 | 0.51 |
| ATOM | 280 | NE | ARG | 14 | -3.019 | 3.051 | -9.842 | 1.00 | 0.62 |
| ATOM | 281 | CZ | ARG | 14 | -1.795 | 3.466 | -10.019 | 1.00 | 0.95 |
| ATOM | 282 | NH1 | ARG | 14 | -0.833 | 2.603 | -10.203 | 1.00 | 1.69 |
| ATOM | 283 | NH2 | ARG | 14 | -1.532 | 4.744 | -10.014 | 1.00 | 1.63 |
| ATOM | 284 | HN | ARG | 14 | -4.465 | 4.986 | -5.949 | 1.00 | 0.37 |
| ATOM | 285 | HA | ARG | 14 | -6.417 | 3.685 | -7.774 | 1.00 | 0.42 |
| ATOM | 286 | 1HB | ARG | 14 | -5.625 | 1.630 | -6.314 | 1.00 | 0.38 |
| ATOM | 287 | 2HB | ARG | 14 | -4.279 | 2.697 | -5.923 | 1.00 | 0.37 |
| ATOM | 288 | 1HG | ARG | 14 | -5.160 | 1.788 | -8.682 | 1.00 | 0.51 |
| ATOM | 289 | 2HG | ARG | 14 | -3.648 | 1.395 | -7.866 | 1.00 | 0.53 |
| ATOM | 290 | 1HD | ARG | 14 | -3.071 | 3.841 | -7.885 | 1.00 | 0.50 |
| ATOM | 291 | 2HD | ARG | 14 | -4.525 | 4.136 | -8.836 | 1.00 | 0.50 |
| ATOM | 292 | HE | ARG | 14 | -3.453 | 2.500 | -10.526 | 1.00 | 0.87 |
| ATOM | 293 | 1HH1 | ARG | 14 | -1.035 | 1.623 | -10.207 | 1.00 | 2.25 |
| ATOM | 294 | 2HH1 | ARG | 14 | 0.105 | 2.921 | -10.340 | 1.00 | 2.08 |
| ATOM | 295 | 1HH2 | ARG | 14 | -2.269 | 5.405 | -9.874 | 1.00 | 2.17 |
| ATOM | 296 | 2HH2 | ARG | 14 | -0.594 | 5.062 | -10.150 | 1.00 | 2.01 |
| ATOM | 297 | N | LEU | 15 | -6.793 | 3.089 | -4.585 | 1.00 | 0.30 |
| ATOM | 298 | CA | LEU | 15 | -7.832 | 2.971 | -3.525 | 1.00 | 0.30 |
| ATOM | 299 | C | LEU | 15 | -8.196 | 4.357 | -2.977 | 1.00 | 0.31 |
| ATOM | 300 | O | LEU | 15 | -9.146 | 4.505 | -2.234 | 1.00 | 0.37 |
| ATOM | 301 | CB | LEU | 15 | -7.290 | 2.091 | -2.391 | 1.00 | 0.34 |
| ATOM | 302 | CG | LEU | 15 | -7.351 | 0.607 | -2.790 | 1.00 | 0.39 |
| ATOM | 303 | CD1 | LEU | 15 | -8.810 | 0.156 | -2.885 | 1.00 | 0.45 |
| ATOM | 304 | CD2 | LEU | 15 | -6.672 | 0.393 | -4.147 | 1.00 | 0.40 |
| ATOM | 305 | HN | LEU | 15 | -5.893 | 2.740 | -4.421 | 1.00 | 0.33 |
| ATOM | 306 | HA | LEU | 15 | -8.715 | 2.510 | -3.941 | 1.00 | 0.33 |
| ATOM | 307 | 1HB | LEU | 15 | -7.886 | 2.246 | -1.504 | 1.00 | 0.37 |
| ATOM | 308 | 2HB | LEU | 15 | -6.266 | 2.365 | -2.186 | 1.00 | 0.34 |

FIG. 5A-4

| | | | | | | | | |
|---|---|---|---|---|---|---|---|---|
| ATOM | 309 | HG | LEU | 15 | -6.843 | 0.017 | -2.039 | 1.00 | 0.46 |
| ATOM | 310 | 1HD1 | LEU | 15 | -8.986 | -0.644 | -2.180 | 1.00 | 1.16 |
| ATOM | 311 | 2HD1 | LEU | 15 | -9.013 | -0.197 | -3.886 | 1.00 | 1.04 |
| ATOM | 312 | 3HD1 | LEU | 15 | -9.459 | 0.987 | -2.658 | 1.00 | 1.03 |
| ATOM | 313 | 1HD2 | LEU | 15 | -6.598 | -0.665 | -4.349 | 1.00 | 1.06 |
| ATOM | 314 | 2HD2 | LEU | 15 | -5.684 | 0.826 | -4.127 | 1.00 | 1.08 |
| ATOM | 315 | 3HD2 | LEU | 15 | -7.258 | 0.867 | -4.920 | 1.00 | 1.10 |
| ATOM | 316 | N | GLY | 16 | -7.456 | 5.373 | -3.332 | 1.00 | 0.35 |
| ATOM | 317 | CA | GLY | 16 | -7.777 | 6.737 | -2.822 | 1.00 | 0.41 |
| ATOM | 318 | C | GLY | 16 | -9.065 | 7.239 | -3.474 | 1.00 | 0.47 |
| ATOM | 319 | O | GLY | 16 | -9.782 | 8.042 | -2.911 | 1.00 | 0.72 |
| ATOM | 320 | HN | GLY | 16 | -6.693 | 5.243 | -3.931 | 1.00 | 0.40 |
| ATOM | 321 | 1HA | GLY | 16 | -6.972 | 7.411 | -3.066 | 1.00 | 0.47 |
| ATOM | 322 | 2HA | GLY | 16 | -7.904 | 6.699 | -1.750 | 1.00 | 0.53 |
| ATOM | 323 | N | VAL | 17 | -9.364 | 6.771 | -4.656 | 1.00 | 0.45 |
| ATOM | 324 | CA | VAL | 17 | -10.606 | 7.220 | -5.348 | 1.00 | 0.66 |
| ATOM | 325 | C | VAL | 17 | -10.558 | 8.740 | -5.551 | 1.00 | 0.76 |
| ATOM | 326 | O | VAL | 17 | -10.142 | 9.222 | -6.586 | 1.00 | 0.89 |
| ATOM | 327 | CB | VAL | 17 | -11.826 | 6.835 | -4.504 | 1.00 | 0.86 |
| ATOM | 328 | CG1 | VAL | 17 | -13.099 | 7.397 | -5.144 | 1.00 | 1.16 |
| ATOM | 329 | CG2 | VAL | 17 | -11.930 | 5.310 | -4.433 | 1.00 | 1.06 |
| ATOM | 330 | HN | VAL | 17 | -8.771 | 6.123 | -5.089 | 1.00 | 0.44 |
| ATOM | 331 | HA | VAL | 17 | -10.671 | 6.737 | -6.310 | 1.00 | 0.75 |
| ATOM | 332 | HB | VAL | 17 | -11.717 | 7.235 | -3.507 | 1.00 | 1.21 |
| ATOM | 333 | 1HG1 | VAL | 17 | -13.187 | 8.447 | -4.908 | 1.00 | 1.72 |
| ATOM | 334 | 2HG1 | VAL | 17 | -13.958 | 6.868 | -4.759 | 1.00 | 1.62 |
| ATOM | 335 | 3HG1 | VAL | 17 | -13.048 | 7.272 | -6.215 | 1.00 | 1.56 |
| ATOM | 336 | 1HG2 | VAL | 17 | -11.288 | 4.942 | -3.646 | 1.00 | 1.40 |
| ATOM | 337 | 2HG2 | VAL | 17 | -11.624 | 4.884 | -5.377 | 1.00 | 1.46 |
| ATOM | 338 | 3HG2 | VAL | 17 | -12.952 | 5.028 | -4.225 | 1.00 | 1.47 |
| ATOM | 339 | N | ASP | 18 | -10.979 | 9.498 | -4.576 | 1.00 | 0.82 |
| ATOM | 340 | CA | ASP | 18 | -10.956 | 10.982 | -4.720 | 1.00 | 0.99 |
| ATOM | 341 | C | ASP | 18 | -9.777 | 11.555 | -3.930 | 1.00 | 0.95 |
| ATOM | 342 | O | ASP | 18 | -9.809 | 12.684 | -3.481 | 1.00 | 1.75 |
| ATOM | 343 | CB | ASP | 18 | -12.263 | 11.567 | -4.181 | 1.00 | 1.18 |
| ATOM | 344 | CG | ASP | 18 | -13.023 | 12.253 | -5.318 | 1.00 | 1.80 |
| ATOM | 345 | OD1 | ASP | 18 | -14.122 | 11.816 | -5.618 | 1.00 | 2.38 |
| ATOM | 346 | OD2 | ASP | 18 | -12.494 | 13.205 | -5.868 | 1.00 | 2.37 |
| ATOM | 347 | HN | ASP | 18 | -11.311 | 9.093 | -3.750 | 1.00 | 0.82 |
| ATOM | 348 | HA | ASP | 18 | -10.849 | 11.240 | -5.763 | 1.00 | 1.08 |
| ATOM | 349 | 1HB | ASP | 18 | -12.043 | 12.290 | -3.410 | 1.00 | 1.24 |
| ATOM | 350 | 2HB | ASP | 18 | -12.869 | 10.773 | -3.769 | 1.00 | 1.48 |
| ATOM | 351 | N | GLU | 19 | -8.735 | 10.787 | -3.758 | 1.00 | 0.64 |
| ATOM | 352 | CA | GLU | 19 | -7.554 | 11.288 | -2.998 | 1.00 | 0.62 |
| ATOM | 353 | C | GLU | 19 | -7.952 | 11.554 | -1.545 | 1.00 | 0.62 |
| ATOM | 354 | O | GLU | 19 | -8.124 | 12.685 | -1.134 | 1.00 | 0.75 |
| ATOM | 355 | CB | GLU | 19 | -7.048 | 12.585 | -3.635 | 1.00 | 0.77 |
| ATOM | 356 | CG | GLU | 19 | -6.935 | 12.402 | -5.149 | 1.00 | 1.61 |
| ATOM | 357 | CD | GLU | 19 | -6.329 | 13.661 | -5.772 | 1.00 | 2.10 |
| ATOM | 358 | OE1 | GLU | 19 | -7.074 | 14.420 | -6.371 | 1.00 | 2.44 |
| ATOM | 359 | OE2 | GLU | 19 | -5.130 | 13.846 | -5.639 | 1.00 | 2.74 |
| ATOM | 360 | HN | GLU | 19 | -8.729 | 9.880 | -4.129 | 1.00 | 1.15 |
| ATOM | 361 | HA | GLU | 19 | -6.771 | 10.545 | -3.023 | 1.00 | 0.58 |
| ATOM | 362 | 1HB | GLU | 19 | -6.078 | 12.830 | -3.230 | 1.00 | 0.89 |
| ATOM | 363 | 2HB | GLU | 19 | -7.741 | 13.386 | -3.419 | 1.00 | 1.28 |
| ATOM | 364 | 1HG | GLU | 19 | -7.917 | 12.234 | -5.566 | 1.00 | 2.13 |
| ATOM | 365 | 2HG | GLU | 19 | -6.302 | 11.553 | -5.363 | 1.00 | 2.05 |
| ATOM | 366 | N | ALA | 20 | -8.098 | 10.519 | -0.763 | 1.00 | 0.53 |
| ATOM | 367 | CA | ALA | 20 | -8.482 | 10.700 | 0.668 | 1.00 | 0.61 |
| ATOM | 368 | C | ALA | 20 | -8.820 | 9.337 | 1.269 | 1.00 | 0.58 |
| ATOM | 369 | O | ALA | 20 | -8.444 | 9.022 | 2.381 | 1.00 | 0.64 |
| ATOM | 370 | CB | ALA | 20 | -9.705 | 11.617 | 0.767 | 1.00 | 0.71 |
| ATOM | 371 | HN | ALA | 20 | -7.952 | 9.617 | -1.118 | 1.00 | 0.47 |
| ATOM | 372 | HA | ALA | 20 | -7.658 | 11.136 | 1.209 | 1.00 | 0.68 |
| ATOM | 373 | 1HB | ALA | 20 | -10.511 | 11.091 | 1.258 | 1.00 | 1.14 |
| ATOM | 374 | 2HB | ALA | 20 | -10.018 | 11.909 | -0.225 | 1.00 | 1.32 |
| ATOM | 375 | 3HB | ALA | 20 | -9.450 | 12.497 | 1.338 | 1.00 | 1.30 |
| ATOM | 376 | N | ASP | 21 | -9.531 | 8.527 | 0.536 | 1.00 | 0.54 |
| ATOM | 377 | CA | ASP | 21 | -9.906 | 7.180 | 1.043 | 1.00 | 0.58 |
| ATOM | 378 | C | ASP | 21 | -8.659 | 6.447 | 1.547 | 1.00 | 0.50 |
| ATOM | 379 | O | ASP | 21 | -8.733 | 5.602 | 2.418 | 1.00 | 0.53 |
| ATOM | 380 | CB | ASP | 21 | -10.544 | 6.378 | -0.094 | 1.00 | 0.64 |
| ATOM | 381 | CG | ASP | 21 | -12.062 | 6.564 | -0.065 | 1.00 | 0.76 |
| ATOM | 382 | OD1 | ASP | 21 | -12.679 | 6.398 | -1.105 | 1.00 | 1.29 |
| ATOM | 383 | OD2 | ASP | 21 | -12.582 | 6.869 | 0.995 | 1.00 | 1.52 |
| ATOM | 384 | HN | ASP | 21 | -9.821 | 8.807 | -0.352 | 1.00 | 0.53 |
| ATOM | 385 | HA | ASP | 21 | -10.614 | 7.287 | 1.847 | 1.00 | 0.70 |

FIG. 5A-5

```
ATOM   386  1HB  ASP   21    -10.308   5.332   0.027  1.00  0.92
ATOM   387  2HB  ASP   21    -10.156   6.726  -1.040  1.00  0.83
ATOM   388  N    VAL   22     -7.516   6.762   1.004  1.00  0.44
ATOM   389  CA   VAL   22     -6.263   6.084   1.445  1.00  0.41
ATOM   390  C    VAL   22     -6.097   6.233   2.960  1.00  0.48
ATOM   391  O    VAL   22     -6.123   7.325   3.493  1.00  0.64
ATOM   392  CB   VAL   22     -5.068   6.726   0.737  1.00  0.45
ATOM   393  CG1  VAL   22     -5.007   8.213   1.086  1.00  0.90
ATOM   394  CG2  VAL   22     -3.778   6.042   1.196  1.00  0.85
ATOM   395  HN   VAL   22     -7.481   7.445   0.302  1.00  0.45
ATOM   396  HA   VAL   22     -6.312   5.036   1.189  1.00  0.39
ATOM   397  HB   VAL   22     -5.179   6.612  -0.332  1.00  0.59
ATOM   398  1HG1 VAL   22     -4.269   8.699   0.465  1.00  1.54
ATOM   399  2HG1 VAL   22     -4.735   8.329   2.125  1.00  1.43
ATOM   400  3HG1 VAL   22     -5.973   8.663   0.915  1.00  1.37
ATOM   401  1HG2 VAL   22     -3.093   5.970   0.364  1.00  1.43
ATOM   402  2HG2 VAL   22     -4.006   5.051   1.561  1.00  1.32
ATOM   403  3HG2 VAL   22     -3.325   6.621   1.987  1.00  1.47
ATOM   404  N    LYS   23     -5.920   5.143   3.659  1.00  0.43
ATOM   405  CA   LYS   23     -5.745   5.225   5.138  1.00  0.54
ATOM   406  C    LYS   23     -4.981   3.996   5.638  1.00  0.62
ATOM   407  O    LYS   23     -5.383   2.870   5.424  1.00  1.44
ATOM   408  CB   LYS   23     -7.113   5.283   5.817  1.00  0.55
ATOM   409  CG   LYS   23     -7.843   6.559   5.396  1.00  0.67
ATOM   410  CD   LYS   23     -9.104   6.730   6.246  1.00  0.92
ATOM   411  CE   LYS   23     -9.214   8.183   6.713  1.00  1.09
ATOM   412  NZ   LYS   23    -10.431   8.342   7.558  1.00  1.65
ATOM   413  HN   LYS   23     -5.897   4.271   3.211  1.00  0.41
ATOM   414  HA   LYS   23     -5.187   6.117   5.382  1.00  0.69
ATOM   415  1HB  LYS   23     -6.980   5.282   6.888  1.00  0.72
ATOM   416  2HB  LYS   23     -7.694   4.422   5.525  1.00  0.65
ATOM   417  1HG  LYS   23     -8.119   6.490   4.355  1.00  0.82
ATOM   418  2HG  LYS   23     -7.192   7.410   5.541  1.00  0.94
ATOM   419  1HD  LYS   23     -9.048   6.081   7.107  1.00  1.18
ATOM   420  2HD  LYS   23     -9.972   6.473   5.657  1.00  1.22
ATOM   421  1HE  LYS   23     -9.285   8.833   5.854  1.00  1.63
ATOM   422  2HE  LYS   23     -8.339   8.443   7.290  1.00  1.47
ATOM   423  1HZ  LYS   23    -10.842   9.284   7.401  1.00  2.08
ATOM   424  2HZ  LYS   23    -10.173   8.239   8.561  1.00  2.13
ATOM   425  3HZ  LYS   23    -11.129   7.615   7.303  1.00  2.14
ATOM   426  N    LEU   24     -3.886   4.211   6.311  1.00  0.81
ATOM   427  CA   LEU   24     -3.081   3.069   6.840  1.00  0.73
ATOM   428  C    LEU   24     -3.867   2.357   7.942  1.00  0.69
ATOM   429  O    LEU   24     -4.023   1.152   7.930  1.00  0.70
ATOM   430  CB   LEU   24     -1.776   3.606   7.434  1.00  0.87
ATOM   431  CG   LEU   24     -1.115   4.577   6.451  1.00  1.53
ATOM   432  CD1  LEU   24     -1.244   6.008   6.977  1.00  2.04
ATOM   433  CD2  LEU   24      0.368   4.229   6.308  1.00  2.10
ATOM   434  HN   LEU   24     -3.593   5.130   6.474  1.00  1.52
ATOM   435  HA   LEU   24     -2.859   2.370   6.040  1.00  0.66
ATOM   436  1HB  LEU   24     -1.107   2.784   7.632  1.00  0.95
ATOM   437  2HB  LEU   24     -1.992   4.121   8.358  1.00  1.14
ATOM   438  HG   LEU   24     -1.600   4.502   5.489  1.00  1.99
ATOM   439  1HD1 LEU   24     -2.173   6.437   6.635  1.00  2.68
ATOM   440  2HD1 LEU   24     -0.418   6.601   6.611  1.00  2.35
ATOM   441  3HD1 LEU   24     -1.228   5.998   8.057  1.00  2.28
ATOM   442  1HD2 LEU   24      0.656   3.547   7.094  1.00  2.39
ATOM   443  2HD2 LEU   24      0.957   5.132   6.383  1.00  2.56
ATOM   444  3HD2 LEU   24      0.539   3.768   5.348  1.00  2.54
ATOM   445  N    GLU   25     -4.358   3.097   8.899  1.00  0.74
ATOM   446  CA   GLU   25     -5.129   2.472  10.011  1.00  0.78
ATOM   447  C    GLU   25     -6.410   1.828   9.471  1.00  0.72
ATOM   448  O    GLU   25     -7.072   1.081  10.162  1.00  0.82
ATOM   449  CB   GLU   25     -5.498   3.546  11.037  1.00  0.86
ATOM   450  CG   GLU   25     -6.178   4.718  10.327  1.00  1.58
ATOM   451  CD   GLU   25     -7.020   5.505  11.333  1.00  2.17
ATOM   452  OE1  GLU   25     -6.443   6.063  12.251  1.00  2.77
ATOM   453  OE2  GLU   25     -8.229   5.535  11.167  1.00  2.66
ATOM   454  HN   GLU   25     -4.214   4.066   8.889  1.00  0.78
ATOM   455  HA   GLU   25     -4.522   1.717  10.488  1.00  0.83
ATOM   456  1HB  GLU   25     -4.604   3.896  11.531  1.00  1.38
ATOM   457  2HB  GLU   25     -6.174   3.126  11.769  1.00  1.27
ATOM   458  1HG  GLU   25     -6.816   4.342   9.542  1.00  2.03
ATOM   459  2HG  GLU   25     -5.425   5.366   9.901  1.00  2.22
ATOM   460  N    ALA   26     -6.772   2.107   8.246  1.00  0.60
ATOM   461  CA   ALA   26     -8.011   1.502   7.689  1.00  0.57
ATOM   462  C    ALA   26     -7.709   0.089   7.197  1.00  0.56
```

FIG. 5A-6

| | | | | | | | | |
|---|---|---|---|---|---|---|---|---|
| ATOM | 463 | O | ALA | 26 | -6.605 | -0.216 | 6.792 | 1.00 | 0.53 |
| ATOM | 464 | CB | ALA | 26 | -8.509 | 2.348 | 6.518 | 1.00 | 0.53 |
| ATOM | 465 | HN | ALA | 26 | -6.233 | 2.711 | 7.694 | 1.00 | 0.57 |
| ATOM | 466 | HA | ALA | 26 | -8.771 | 1.464 | 8.456 | 1.00 | 0.65 |
| ATOM | 467 | 1HB | ALA | 26 | -9.309 | 1.828 | 6.013 | 1.00 | 0.97 |
| ATOM | 468 | 2HB | ALA | 26 | -7.698 | 2.516 | 5.826 | 1.00 | 1.13 |
| ATOM | 469 | 3HB | ALA | 26 | -8.871 | 3.297 | 6.986 | 1.00 | 1.13 |
| ATOM | 470 | N | SER | 27 | -8.685 | -0.776 | 7.217 | 1.00 | 0.60 |
| ATOM | 471 | CA | SER | 27 | -8.452 | -2.165 | 6.738 | 1.00 | 0.63 |
| ATOM | 472 | C | SER | 27 | -8.524 | -2.201 | 5.205 | 1.00 | 0.55 |
| ATOM | 473 | O | SER | 27 | -8.406 | -3.247 | 4.599 | 1.00 | 0.58 |
| ATOM | 474 | CB | SER | 27 | -9.521 | -3.091 | 7.320 | 1.00 | 0.74 |
| ATOM | 475 | OG | SER | 27 | -8.923 | -3.952 | 8.281 | 1.00 | 1.33 |
| ATOM | 476 | HN | SER | 27 | -9.571 | -0.509 | 7.540 | 1.00 | 0.65 |
| ATOM | 477 | HA | SER | 27 | -7.474 | -2.496 | 7.059 | 1.00 | 0.65 |
| ATOM | 478 | 1HB | SER | 27 | -9.963 | -3.674 | 6.523 | 1.00 | 0.90 |
| ATOM | 479 | 2HB | SER | 27 | -10.287 | -2.504 | 7.799 | 1.00 | 0.89 |
| ATOM | 480 | HG | SER | 27 | -9.122 | -3.606 | 9.154 | 1.00 | 1.74 |
| ATOM | 481 | N | PHE | 28 | -8.716 | -1.070 | 4.570 | 1.00 | 0.50 |
| ATOM | 482 | CA | PHE | 28 | -8.791 | -1.056 | 3.083 | 1.00 | 0.47 |
| ATOM | 483 | C | PHE | 28 | -9.968 | -1.918 | 2.623 | 1.00 | 0.54 |
| ATOM | 484 | O | PHE | 28 | -9.838 | -2.735 | 1.735 | 1.00 | 0.67 |
| ATOM | 485 | CB | PHE | 28 | -7.492 | -1.620 | 2.506 | 1.00 | 0.44 |
| ATOM | 486 | CG | PHE | 28 | -6.555 | -0.491 | 2.148 | 1.00 | 0.38 |
| ATOM | 487 | CD1 | PHE | 28 | -6.241 | -0.238 | 0.807 | 1.00 | 1.15 |
| ATOM | 488 | CD2 | PHE | 28 | -5.990 | 0.296 | 3.158 | 1.00 | 1.29 |
| ATOM | 489 | CE1 | PHE | 28 | -5.363 | 0.800 | 0.478 | 1.00 | 1.15 |
| ATOM | 490 | CE2 | PHE | 28 | -5.114 | 1.335 | 2.826 | 1.00 | 1.28 |
| ATOM | 491 | CZ | PHE | 28 | -4.799 | 1.586 | 1.487 | 1.00 | 0.36 |
| ATOM | 492 | HN | PHE | 28 | -8.811 | -0.234 | 5.067 | 1.00 | 0.51 |
| ATOM | 493 | HA | PHE | 28 | -8.928 | -0.042 | 2.739 | 1.00 | 0.46 |
| ATOM | 494 | 1HB | PHE | 28 | -7.713 | -2.196 | 1.622 | 1.00 | 0.45 |
| ATOM | 495 | 2HB | PHE | 28 | -7.020 | -2.257 | 3.240 | 1.00 | 0.49 |
| ATOM | 496 | HD1 | PHE | 28 | -6.674 | -0.844 | 0.027 | 1.00 | 2.03 |
| ATOM | 497 | HD2 | PHE | 28 | -6.231 | 0.103 | 4.192 | 1.00 | 2.17 |
| ATOM | 498 | HE1 | PHE | 28 | -5.118 | 0.991 | -0.555 | 1.00 | 2.03 |
| ATOM | 499 | HE2 | PHE | 28 | -4.672 | 1.937 | 3.605 | 1.00 | 2.16 |
| ATOM | 500 | HZ | PHE | 28 | -4.122 | 2.387 | 1.232 | 1.00 | 0.38 |
| ATOM | 501 | N | LYS | 29 | -11.117 | -1.744 | 3.219 | 1.00 | 0.54 |
| ATOM | 502 | CA | LYS | 29 | -12.293 | -2.561 | 2.806 | 1.00 | 0.61 |
| ATOM | 503 | C | LYS | 29 | -13.555 | -2.051 | 3.508 | 1.00 | 0.65 |
| ATOM | 504 | O | LYS | 29 | -14.595 | -1.901 | 2.899 | 1.00 | 0.69 |
| ATOM | 505 | CB | LYS | 29 | -12.056 | -4.024 | 3.187 | 1.00 | 0.69 |
| ATOM | 506 | CG | LYS | 29 | -11.661 | -4.114 | 4.662 | 1.00 | 0.73 |
| ATOM | 507 | CD | LYS | 29 | -10.890 | -5.413 | 4.905 | 1.00 | 0.88 |
| ATOM | 508 | CE | LYS | 29 | -11.648 | -6.277 | 5.915 | 1.00 | 1.61 |
| ATOM | 509 | NZ | LYS | 29 | -11.118 | -7.669 | 5.873 | 1.00 | 2.16 |
| ATOM | 510 | HN | LYS | 29 | -11.205 | -1.081 | 3.935 | 1.00 | 0.55 |
| ATOM | 511 | HA | LYS | 29 | -12.423 | -2.487 | 1.738 | 1.00 | 0.63 |
| ATOM | 512 | 1HB | LYS | 29 | -11.262 | -4.430 | 2.578 | 1.00 | 0.71 |
| ATOM | 513 | 2HB | LYS | 29 | -12.962 | -4.589 | 3.021 | 1.00 | 0.77 |
| ATOM | 514 | 1HG | LYS | 29 | -12.550 | -4.105 | 5.275 | 1.00 | 0.81 |
| ATOM | 515 | 2HG | LYS | 29 | -11.037 | -3.270 | 4.920 | 1.00 | 0.71 |
| ATOM | 516 | 1HD | LYS | 29 | -9.910 | -5.183 | 5.295 | 1.00 | 1.44 |
| ATOM | 517 | 2HD | LYS | 29 | -10.789 | -5.951 | 3.974 | 1.00 | 1.05 |
| ATOM | 518 | 1HE | LYS | 29 | -12.698 | -6.284 | 5.666 | 1.00 | 2.05 |
| ATOM | 519 | 2HE | LYS | 29 | -11.515 | -5.871 | 6.907 | 1.00 | 2.21 |
| ATOM | 520 | 1HZ | LYS | 29 | -10.140 | -7.658 | 5.521 | 1.00 | 2.49 |
| ATOM | 521 | 2HZ | LYS | 29 | -11.709 | -8.246 | 5.240 | 1.00 | 2.47 |
| ATOM | 522 | 3HZ | LYS | 29 | -11.134 | -8.076 | 6.829 | 1.00 | 2.66 |
| ATOM | 523 | N | GLU | 30 | -13.475 | -1.789 | 4.784 | 1.00 | 0.68 |
| ATOM | 524 | CA | GLU | 30 | -14.675 | -1.297 | 5.518 | 1.00 | 0.78 |
| ATOM | 525 | C | GLU | 30 | -14.489 | 0.176 | 5.885 | 1.00 | 0.79 |
| ATOM | 526 | O | GLU | 30 | -15.443 | 0.895 | 6.108 | 1.00 | 0.96 |
| ATOM | 527 | CB | GLU | 30 | -14.863 | -2.118 | 6.795 | 1.00 | 0.91 |
| ATOM | 528 | CG | GLU | 30 | -13.616 | -1.990 | 7.672 | 1.00 | 1.39 |
| ATOM | 529 | CD | GLU | 30 | -13.876 | -2.645 | 9.030 | 1.00 | 1.76 |
| ATOM | 530 | OE1 | GLU | 30 | -14.797 | -2.217 | 9.705 | 1.00 | 2.17 |
| ATOM | 531 | OE2 | GLU | 30 | -13.148 | -3.563 | 9.372 | 1.00 | 2.28 |
| ATOM | 532 | HN | GLU | 30 | -12.628 | -1.921 | 5.259 | 1.00 | 0.68 |
| ATOM | 533 | HA | GLU | 30 | -15.548 | -1.404 | 4.891 | 1.00 | 0.79 |
| ATOM | 534 | 1HB | GLU | 30 | -15.015 | -3.155 | 6.538 | 1.00 | 1.32 |
| ATOM | 535 | 2HB | GLU | 30 | -15.724 | -1.750 | 7.336 | 1.00 | 1.25 |
| ATOM | 536 | 1HG | GLU | 30 | -13.383 | -0.946 | 7.817 | 1.00 | 1.81 |
| ATOM | 537 | 2HG | GLU | 30 | -12.784 | -2.481 | 7.187 | 1.00 | 1.80 |
| ATOM | 538 | N | ASP | 31 | -13.269 | 0.632 | 5.956 | 1.00 | 0.73 |
| ATOM | 539 | CA | ASP | 31 | -13.029 | 2.057 | 6.316 | 1.00 | 0.75 |

FIG. 5A-7

| | | | | | | | | |
|---|---|---|---|---|---|---|---|---|
| ATOM | 540 | C | ASP | 31 | -13.291 | 2.949 | 5.101 | 1.00 | 0.72 |
| ATOM | 541 | O | ASP | 31 | -14.218 | 3.734 | 5.084 | 1.00 | 0.77 |
| ATOM | 542 | CB | ASP | 31 | -11.580 | 2.233 | 6.772 | 1.00 | 0.76 |
| ATOM | 543 | CG | ASP | 31 | -11.555 | 2.867 | 8.164 | 1.00 | 0.98 |
| ATOM | 544 | OD1 | ASP | 31 | -11.051 | 3.971 | 8.281 | 1.00 | 1.57 |
| ATOM | 545 | OD2 | ASP | 31 | -12.042 | 2.237 | 9.088 | 1.00 | 1.51 |
| ATOM | 546 | HN | ASP | 31 | -12.511 | 0.037 | 5.777 | 1.00 | 0.77 |
| ATOM | 547 | HA | ASP | 31 | -13.694 | 2.341 | 7.119 | 1.00 | 0.83 |
| ATOM | 548 | 1HB | ASP | 31 | -11.059 | 2.874 | 6.077 | 1.00 | 0.84 |
| ATOM | 549 | 2HB | ASP | 31 | -11.094 | 1.268 | 6.806 | 1.00 | 0.92 |
| ATOM | 550 | N | LEU | 32 | -12.479 | 2.840 | 4.085 | 1.00 | 0.66 |
| ATOM | 551 | CA | LEU | 32 | -12.683 | 3.690 | 2.878 | 1.00 | 0.68 |
| ATOM | 552 | C | LEU | 32 | -13.430 | 2.898 | 1.801 | 1.00 | 0.66 |
| ATOM | 553 | O | LEU | 32 | -13.403 | 3.242 | 0.636 | 1.00 | 0.69 |
| ATOM | 554 | CB | LEU | 32 | -11.324 | 4.140 | 2.335 | 1.00 | 0.67 |
| ATOM | 555 | CG | LEU | 32 | -10.498 | 2.919 | 1.926 | 1.00 | 0.51 |
| ATOM | 556 | CD1 | LEU | 32 | -10.282 | 2.930 | 0.411 | 1.00 | 0.49 |
| ATOM | 557 | CD2 | LEU | 32 | -9.139 | 2.967 | 2.629 | 1.00 | 0.57 |
| ATOM | 558 | HN | LEU | 32 | -11.733 | 2.205 | 4.117 | 1.00 | 0.65 |
| ATOM | 559 | HA | LEU | 32 | -13.264 | 4.559 | 3.149 | 1.00 | 0.75 |
| ATOM | 560 | 1HB | LEU | 32 | -10.796 | 4.690 | 3.099 | 1.00 | 0.77 |
| ATOM | 561 | 2HB | LEU | 32 | -11.476 | 4.775 | 1.476 | 1.00 | 0.74 |
| ATOM | 562 | HG | LEU | 32 | -11.022 | 2.017 | 2.210 | 1.00 | 0.56 |
| ATOM | 563 | 1HD1 | LEU | 32 | -9.459 | 3.585 | 0.170 | 1.00 | 1.07 |
| ATOM | 564 | 2HD1 | LEU | 32 | -11.178 | 3.282 | -0.078 | 1.00 | 1.15 |
| ATOM | 565 | 3HD1 | LEU | 32 | -10.057 | 1.930 | 0.073 | 1.00 | 1.12 |
| ATOM | 566 | 1HD2 | LEU | 32 | -9.200 | 3.620 | 3.487 | 1.00 | 1.17 |
| ATOM | 567 | 2HD2 | LEU | 32 | -8.393 | 3.341 | 1.944 | 1.00 | 1.18 |
| ATOM | 568 | 3HD2 | LEU | 32 | -8.865 | 1.973 | 2.952 | 1.00 | 1.13 |
| ATOM | 569 | N | GLY | 33 | -14.103 | 1.843 | 2.178 | 1.00 | 0.69 |
| ATOM | 570 | CA | GLY | 33 | -14.856 | 1.035 | 1.172 | 1.00 | 0.74 |
| ATOM | 571 | C | GLY | 33 | -13.937 | 0.672 | 0.002 | 1.00 | 0.68 |
| ATOM | 572 | O | GLY | 33 | -13.951 | 1.310 | -1.031 | 1.00 | 0.89 |
| ATOM | 573 | HN | GLY | 33 | -14.117 | 1.583 | 3.122 | 1.00 | 0.71 |
| ATOM | 574 | 1HA | GLY | 33 | -15.692 | 1.609 | 0.803 | 1.00 | 0.82 |
| ATOM | 575 | 2HA | GLY | 33 | -15.219 | 0.130 | 1.639 | 1.00 | 0.79 |
| ATOM | 576 | N | ALA | 34 | -13.139 | -0.347 | 0.158 | 1.00 | 0.60 |
| ATOM | 577 | CA | ALA | 34 | -12.220 | -0.751 | -0.944 | 1.00 | 0.59 |
| ATOM | 578 | C | ALA | 34 | -12.385 | -2.246 | -1.225 | 1.00 | 0.74 |
| ATOM | 579 | O | ALA | 34 | -12.732 | -3.016 | -0.352 | 1.00 | 1.25 |
| ATOM | 580 | CB | ALA | 34 | -10.776 | -0.467 | -0.531 | 1.00 | 0.58 |
| ATOM | 581 | HN | ALA | 34 | -13.144 | -0.848 | 0.999 | 1.00 | 0.70 |
| ATOM | 582 | HA | ALA | 34 | -12.456 | -0.188 | -1.836 | 1.00 | 0.61 |
| ATOM | 583 | 1HB | ALA | 34 | -10.160 | -1.322 | -0.767 | 1.00 | 1.11 |
| ATOM | 584 | 2HB | ALA | 34 | -10.736 | -0.277 | 0.532 | 1.00 | 1.13 |
| ATOM | 585 | 3HB | ALA | 34 | -10.411 | 0.397 | -1.065 | 1.00 | 1.26 |
| ATOM | 586 | N | ASP | 35 | -12.137 | -2.664 | -2.435 | 1.00 | 0.85 |
| ATOM | 587 | CA | ASP | 35 | -12.278 | -4.109 | -2.766 | 1.00 | 0.96 |
| ATOM | 588 | C | ASP | 35 | -10.994 | -4.844 | -2.373 | 1.00 | 0.88 |
| ATOM | 589 | O | ASP | 35 | -9.903 | -4.405 | -2.673 | 1.00 | 1.15 |
| ATOM | 590 | CB | ASP | 35 | -12.518 | -4.270 | -4.268 | 1.00 | 1.06 |
| ATOM | 591 | CG | ASP | 35 | -14.012 | -4.465 | -4.529 | 1.00 | 1.59 |
| ATOM | 592 | OD1 | ASP | 35 | -14.343 | -5.156 | -5.479 | 1.00 | 2.24 |
| ATOM | 593 | OD2 | ASP | 35 | -14.801 | -3.920 | -3.775 | 1.00 | 2.05 |
| ATOM | 594 | HN | ASP | 35 | -11.856 | -2.027 | -3.126 | 1.00 | 1.21 |
| ATOM | 595 | HA | ASP | 35 | -13.112 | -4.525 | -2.220 | 1.00 | 1.09 |
| ATOM | 596 | 1HB | ASP | 35 | -11.976 | -5.131 | -4.630 | 1.00 | 1.23 |
| ATOM | 597 | 2HB | ASP | 35 | -12.173 | -3.385 | -4.784 | 1.00 | 1.26 |
| ATOM | 598 | N | SER | 36 | -11.115 | -5.959 | -1.703 | 1.00 | 0.89 |
| ATOM | 599 | CA | SER | 36 | -9.900 | -6.722 | -1.287 | 1.00 | 0.81 |
| ATOM | 600 | C | SER | 36 | -8.959 | -6.897 | -2.484 | 1.00 | 0.68 |
| ATOM | 601 | O | SER | 36 | -7.754 | -6.968 | -2.334 | 1.00 | 0.59 |
| ATOM | 602 | CB | SER | 36 | -10.318 | -8.098 | -0.765 | 1.00 | 0.98 |
| ATOM | 603 | OG | SER | 36 | -9.565 | -8.406 | 0.401 | 1.00 | 1.69 |
| ATOM | 604 | HN | SER | 36 | -12.006 | -6.296 | -1.471 | 1.00 | 1.17 |
| ATOM | 605 | HA | SER | 36 | -9.388 | -6.182 | -0.504 | 1.00 | 0.77 |
| ATOM | 606 | 1HB | SER | 36 | -10.138 | -8.842 | -1.529 | 1.00 | 1.34 |
| ATOM | 607 | 2HB | SER | 36 | -11.366 | -8.088 | -0.517 | 1.00 | 1.43 |
| ATOM | 608 | HG | SER | 36 | -9.931 | -9.204 | 0.789 | 1.00 | 1.97 |
| ATOM | 609 | N | LEU | 37 | -9.500 | -6.962 | -3.669 | 1.00 | 0.75 |
| ATOM | 610 | CA | LEU | 37 | -8.639 | -7.128 | -4.873 | 1.00 | 0.71 |
| ATOM | 611 | C | LEU | 37 | -7.830 | -5.851 | -5.100 | 1.00 | 0.58 |
| ATOM | 612 | O | LEU | 37 | -6.627 | -5.829 | -4.932 | 1.00 | 0.48 |
| ATOM | 613 | CB | LEU | 37 | -9.519 | -7.400 | -6.095 | 1.00 | 0.89 |
| ATOM | 614 | CG | LEU | 37 | -9.382 | -8.867 | -6.506 | 1.00 | 1.19 |
| ATOM | 615 | CD1 | LEU | 37 | -10.764 | -9.524 | -6.524 | 1.00 | 1.60 |
| ATOM | 616 | CD2 | LEU | 37 | -8.761 | -8.950 | -7.902 | 1.00 | 1.59 |

FIG. 5A-8

| | | | | | | | |
|---|---|---|---|---|---|---|---|
| ATOM | 617 | HN | LEU | 37 | -10.473 | -6.899 | -3.768 | 1.00 | 0.86 |
| ATOM | 618 | HA | LEU | 37 | -7.967 | -7.955 | -4.723 | 1.00 | 0.69 |
| ATOM | 619 | 1HB | LEU | 37 | -9.205 | -6.769 | -6.913 | 1.00 | 1.09 |
| ATOM | 620 | 2HB | LEU | 37 | -10.550 | -7.188 | -5.850 | 1.00 | 1.05 |
| ATOM | 621 | HG | LEU | 37 | -8.749 | -9.381 | -5.797 | 1.00 | 1.47 |
| ATOM | 622 | 1HD1 | LEU | 37 | -10.858 | -10.190 | -5.680 | 1.00 | 1.91 |
| ATOM | 623 | 2HD1 | LEU | 37 | -10.884 | -10.084 | -7.440 | 1.00 | 1.89 |
| ATOM | 624 | 3HD1 | LEU | 37 | -11.526 | -8.760 | -6.467 | 1.00 | 2.22 |
| ATOM | 625 | 1HD2 | LEU | 37 | -7.695 | -9.098 | -7.814 | 1.00 | 2.04 |
| ATOM | 626 | 2HD2 | LEU | 37 | -8.954 | -8.031 | -8.436 | 1.00 | 2.00 |
| ATOM | 627 | 3HD2 | LEU | 37 | -9.197 | -9.778 | -8.441 | 1.00 | 1.94 |
| ATOM | 628 | N | ASP | 38 | -8.484 | -4.788 | -5.481 | 1.00 | 0.65 |
| ATOM | 629 | CA | ASP | 38 | -7.766 | -3.500 | -5.725 | 1.00 | 0.59 |
| ATOM | 630 | C | ASP | 38 | -6.831 | -3.189 | -4.553 | 1.00 | 0.44 |
| ATOM | 631 | O | ASP | 38 | -5.759 | -2.645 | -4.727 | 1.00 | 0.41 |
| ATOM | 632 | CB | ASP | 38 | -8.788 | -2.371 | -5.872 | 1.00 | 0.69 |
| ATOM | 633 | CG | ASP | 38 | -9.146 | -2.193 | -7.348 | 1.00 | 1.07 |
| ATOM | 634 | OD1 | ASP | 38 | -8.496 | -1.395 | -8.003 | 1.00 | 1.42 |
| ATOM | 635 | OD2 | ASP | 38 | -10.063 | -2.859 | -7.799 | 1.00 | 1.84 |
| ATOM | 636 | HN | ASP | 38 | -9.453 | -4.837 | -5.607 | 1.00 | 0.78 |
| ATOM | 637 | HA | ASP | 38 | -7.188 | -3.576 | -6.631 | 1.00 | 0.63 |
| ATOM | 638 | 1HB | ASP | 38 | -8.367 | -1.452 | -5.492 | 1.00 | 0.71 |
| ATOM | 639 | 2HB | ASP | 38 | -9.679 | -2.618 | -5.312 | 1.00 | 0.85 |
| ATOM | 640 | N | VAL | 39 | -7.233 | -3.531 | -3.364 | 1.00 | 0.40 |
| ATOM | 641 | CA | VAL | 39 | -6.377 | -3.258 | -2.176 | 1.00 | 0.28 |
| ATOM | 642 | C | VAL | 39 | -5.035 | -3.973 | -2.332 | 1.00 | 0.23 |
| ATOM | 643 | O | VAL | 39 | -4.023 | -3.363 | -2.622 | 1.00 | 0.24 |
| ATOM | 644 | CB | VAL | 39 | -7.091 | -3.771 | -0.925 | 1.00 | 0.36 |
| ATOM | 645 | CG1 | VAL | 39 | -6.191 | -3.593 | 0.300 | 1.00 | 0.35 |
| ATOM | 646 | CG2 | VAL | 39 | -8.387 | -2.982 | -0.732 | 1.00 | 0.44 |
| ATOM | 647 | HN | VAL | 39 | -8.102 | -3.968 | -3.250 | 1.00 | 0.48 |
| ATOM | 648 | HA | VAL | 39 | -6.208 | -2.197 | -2.086 | 1.00 | 0.26 |
| ATOM | 649 | HB | VAL | 39 | -7.324 | -4.819 | -1.049 | 1.00 | 0.43 |
| ATOM | 650 | 1HG1 | VAL | 39 | -5.837 | -2.575 | 0.342 | 1.00 | 1.08 |
| ATOM | 651 | 2HG1 | VAL | 39 | -5.347 | -4.263 | 0.226 | 1.00 | 1.05 |
| ATOM | 652 | 3HG1 | VAL | 39 | -6.751 | -3.817 | 1.195 | 1.00 | 1.09 |
| ATOM | 653 | 1HG2 | VAL | 39 | -8.832 | -2.782 | -1.695 | 1.00 | 1.04 |
| ATOM | 654 | 2HG2 | VAL | 39 | -8.171 | -2.047 | -0.238 | 1.00 | 1.11 |
| ATOM | 655 | 3HG2 | VAL | 39 | -9.074 | -3.558 | -0.131 | 1.00 | 1.17 |
| ATOM | 656 | N | VAL | 40 | -5.016 | -5.259 | -2.138 | 1.00 | 0.27 |
| ATOM | 657 | CA | VAL | 40 | -3.738 | -6.006 | -2.270 | 1.00 | 0.28 |
| ATOM | 658 | C | VAL | 40 | -3.217 | -5.866 | -3.701 | 1.00 | 0.34 |
| ATOM | 659 | O | VAL | 40 | -2.029 | -5.932 | -3.947 | 1.00 | 0.39 |
| ATOM | 660 | CB | VAL | 40 | -3.967 | -7.479 | -1.937 | 1.00 | 0.33 |
| ATOM | 661 | CG1 | VAL | 40 | -2.616 | -8.175 | -1.764 | 1.00 | 0.39 |
| ATOM | 662 | CG2 | VAL | 40 | -4.763 | -7.582 | -0.633 | 1.00 | 0.36 |
| ATOM | 663 | HN | VAL | 40 | -5.841 | -5.731 | -1.902 | 1.00 | 0.33 |
| ATOM | 664 | HA | VAL | 40 | -3.011 | -5.593 | -1.585 | 1.00 | 0.29 |
| ATOM | 665 | HB | VAL | 40 | -4.517 | -7.950 | -2.738 | 1.00 | 0.37 |
| ATOM | 666 | 1HG1 | VAL | 40 | -2.571 | -9.038 | -2.410 | 1.00 | 1.10 |
| ATOM | 667 | 2HG1 | VAL | 40 | -2.501 | -8.487 | -0.736 | 1.00 | 1.06 |
| ATOM | 668 | 3HG1 | VAL | 40 | -1.822 | -7.489 | -2.023 | 1.00 | 1.10 |
| ATOM | 669 | 1HG2 | VAL | 40 | -4.781 | -6.617 | -0.146 | 1.00 | 0.94 |
| ATOM | 670 | 2HG2 | VAL | 40 | -4.295 | -8.304 | 0.019 | 1.00 | 1.11 |
| ATOM | 671 | 3HG2 | VAL | 40 | -5.773 | -7.893 | -0.851 | 1.00 | 1.14 |
| ATOM | 672 | N | GLU | 41 | -4.092 | -5.659 | -4.648 | 1.00 | 0.41 |
| ATOM | 673 | CA | GLU | 41 | -3.631 | -5.500 | -6.055 | 1.00 | 0.51 |
| ATOM | 674 | C | GLU | 41 | -2.789 | -4.231 | -6.151 | 1.00 | 0.51 |
| ATOM | 675 | O | GLU | 41 | -1.819 | -4.167 | -6.880 | 1.00 | 0.58 |
| ATOM | 676 | CB | GLU | 41 | -4.835 | -5.384 | -6.993 | 1.00 | 0.61 |
| ATOM | 677 | CG | GLU | 41 | -5.390 | -6.780 | -7.288 | 1.00 | 1.01 |
| ATOM | 678 | CD | GLU | 41 | -5.370 | -7.028 | -8.798 | 1.00 | 1.59 |
| ATOM | 679 | OE1 | GLU | 41 | -6.230 | -7.753 | -9.270 | 1.00 | 2.19 |
| ATOM | 680 | OE2 | GLU | 41 | -4.495 | -6.489 | -9.455 | 1.00 | 2.21 |
| ATOM | 681 | HN | GLU | 41 | -5.047 | -5.598 | -4.433 | 1.00 | 0.44 |
| ATOM | 682 | HA | GLU | 41 | -3.032 | -6.352 | -6.337 | 1.00 | 0.56 |
| ATOM | 683 | 1HB | GLU | 41 | -4.526 | -4.920 | -7.917 | 1.00 | 0.94 |
| ATOM | 684 | 2HB | GLU | 41 | -5.599 | -4.781 | -6.525 | 1.00 | 1.01 |
| ATOM | 685 | 1HG | GLU | 41 | -6.405 | -6.848 | -6.927 | 1.00 | 1.36 |
| ATOM | 686 | 2HG | GLU | 41 | -4.780 | -7.521 | -6.792 | 1.00 | 1.61 |
| ATOM | 687 | N | LEU | 42 | -3.149 | -3.219 | -5.409 | 1.00 | 0.45 |
| ATOM | 688 | CA | LEU | 42 | -2.365 | -1.956 | -5.447 | 1.00 | 0.46 |
| ATOM | 689 | C | LEU | 42 | -1.024 | -2.187 | -4.737 | 1.00 | 0.43 |
| ATOM | 690 | O | LEU | 42 | -0.009 | -1.626 | -5.098 | 1.00 | 0.52 |
| ATOM | 691 | CB | LEU | 42 | -3.180 | -0.825 | -4.778 | 1.00 | 0.46 |
| ATOM | 692 | CG | LEU | 42 | -2.874 | -0.710 | -3.279 | 1.00 | 0.87 |
| ATOM | 693 | CD1 | LEU | 42 | -1.690 | 0.235 | -3.071 | 1.00 | 1.15 |

FIG. 5A-9

| | | | | | | | | |
|---|---|---|---|---|---|---|---|---|
| ATOM | 694 | CD2 | LEU | 42 | -4.092 | -0.147 | -2.560 | 1.00 | 1.39 |
| ATOM | 695 | HN | LEU | 42 | -3.930 | -3.296 | -4.822 | 1.00 | 0.43 |
| ATOM | 696 | HA | LEU | 42 | -2.178 | -1.691 | -6.473 | 1.00 | 0.52 |
| ATOM | 697 | 1HB | LEU | 42 | -4.234 | -1.027 | -4.907 | 1.00 | 0.85 |
| ATOM | 698 | 2HB | LEU | 42 | -2.942 | 0.112 | -5.257 | 1.00 | 0.83 |
| ATOM | 699 | HG | LEU | 42 | -2.637 | -1.684 | -2.880 | 1.00 | 1.56 |
| ATOM | 700 | 1HD1 | LEU | 42 | -2.027 | 1.256 | -3.162 | 1.00 | 1.75 |
| ATOM | 701 | 2HD1 | LEU | 42 | -0.934 | 0.040 | -3.816 | 1.00 | 1.50 |
| ATOM | 702 | 3HD1 | LEU | 42 | -1.274 | 0.081 | -2.086 | 1.00 | 1.69 |
| ATOM | 703 | 1HD2 | LEU | 42 | -3.938 | -0.210 | -1.495 | 1.00 | 1.86 |
| ATOM | 704 | 2HD2 | LEU | 42 | -4.965 | -0.718 | -2.835 | 1.00 | 1.81 |
| ATOM | 705 | 3HD2 | LEU | 42 | -4.230 | 0.886 | -2.845 | 1.00 | 1.85 |
| ATOM | 706 | N | VAL | 43 | -1.026 | -3.011 | -3.726 | 1.00 | 0.34 |
| ATOM | 707 | CA | VAL | 43 | 0.229 | -3.290 | -2.979 | 1.00 | 0.35 |
| ATOM | 708 | C | VAL | 43 | 1.149 | -4.160 | -3.844 | 1.00 | 0.41 |
| ATOM | 709 | O | VAL | 43 | 2.345 | -4.208 | -3.638 | 1.00 | 0.46 |
| ATOM | 710 | CB | VAL | 43 | -0.110 | -4.011 | -1.669 | 1.00 | 0.32 |
| ATOM | 711 | CG1 | VAL | 43 | 1.073 | -3.915 | -0.702 | 1.00 | 0.36 |
| ATOM | 712 | CG2 | VAL | 43 | -1.335 | -3.350 | -1.025 | 1.00 | 0.28 |
| ATOM | 713 | HN | VAL | 43 | -1.861 | -3.449 | -3.455 | 1.00 | 0.30 |
| ATOM | 714 | HA | VAL | 43 | 0.727 | -2.357 | -2.756 | 1.00 | 0.37 |
| ATOM | 715 | HB | VAL | 43 | -0.326 | -5.049 | -1.875 | 1.00 | 0.33 |
| ATOM | 716 | 1HG1 | VAL | 43 | 1.436 | -4.906 | -0.477 | 1.00 | 1.09 |
| ATOM | 717 | 2HG1 | VAL | 43 | 0.754 | -3.433 | 0.211 | 1.00 | 1.03 |
| ATOM | 718 | 3HG1 | VAL | 43 | 1.863 | -3.336 | -1.156 | 1.00 | 1.03 |
| ATOM | 719 | 1HG2 | VAL | 43 | -1.282 | -3.460 | 0.048 | 1.00 | 1.02 |
| ATOM | 720 | 2HG2 | VAL | 43 | -2.234 | -3.823 | -1.392 | 1.00 | 1.08 |
| ATOM | 721 | 3HG2 | VAL | 43 | -1.352 | -2.300 | -1.278 | 1.00 | 1.03 |
| ATOM | 722 | N | MET | 44 | 0.604 | -4.832 | -4.826 | 1.00 | 0.49 |
| ATOM | 723 | CA | MET | 44 | 1.459 | -5.671 | -5.714 | 1.00 | 0.57 |
| ATOM | 724 | C | MET | 44 | 2.190 | -4.745 | -6.681 | 1.00 | 0.55 |
| ATOM | 725 | O | MET | 44 | 3.393 | -4.811 | -6.839 | 1.00 | 0.56 |
| ATOM | 726 | CB | MET | 44 | 0.586 | -6.657 | -6.495 | 1.00 | 0.68 |
| ATOM | 727 | CG | MET | 44 | 0.221 | -7.839 | -5.595 | 1.00 | 1.06 |
| ATOM | 728 | SD | MET | 44 | -0.272 | -9.247 | -6.619 | 1.00 | 1.46 |
| ATOM | 729 | CE | MET | 44 | 1.352 | -9.575 | -7.347 | 1.00 | 1.81 |
| ATOM | 730 | HN | MET | 44 | -0.359 | -4.771 | -4.990 | 1.00 | 0.55 |
| ATOM | 731 | HA | MET | 44 | 2.181 | -6.210 | -5.119 | 1.00 | 0.58 |
| ATOM | 732 | 1HB | MET | 44 | 1.130 | -7.017 | -7.355 | 1.00 | 1.17 |
| ATOM | 733 | 2HB | MET | 44 | -0.316 | -6.159 | -6.821 | 1.00 | 1.16 |
| ATOM | 734 | 1HG | MET | 44 | -0.598 | -7.559 | -4.949 | 1.00 | 1.57 |
| ATOM | 735 | 2HG | MET | 44 | 1.076 | -8.112 | -4.994 | 1.00 | 1.52 |
| ATOM | 736 | 1HE | MET | 44 | 2.110 | -9.511 | -6.578 | 1.00 | 2.32 |
| ATOM | 737 | 2HE | MET | 44 | 1.558 | -8.846 | -8.113 | 1.00 | 2.24 |
| ATOM | 738 | 3HE | MET | 44 | 1.357 | -10.565 | -7.783 | 1.00 | 2.15 |
| ATOM | 739 | N | GLU | 45 | 1.481 | -3.839 | -7.294 | 1.00 | 0.58 |
| ATOM | 740 | CA | GLU | 45 | 2.154 | -2.876 | -8.203 | 1.00 | 0.59 |
| ATOM | 741 | C | GLU | 45 | 3.160 | -2.100 | -7.359 | 1.00 | 0.51 |
| ATOM | 742 | O | GLU | 45 | 4.171 | -1.625 | -7.838 | 1.00 | 0.52 |
| ATOM | 743 | CB | GLU | 45 | 1.123 | -1.914 | -8.799 | 1.00 | 0.67 |
| ATOM | 744 | CG | GLU | 45 | 0.611 | -2.473 | -10.127 | 1.00 | 0.96 |
| ATOM | 745 | CD | GLU | 45 | 0.712 | -1.395 | -11.207 | 1.00 | 1.53 |
| ATOM | 746 | OE1 | GLU | 45 | 0.872 | -1.754 | -12.362 | 1.00 | 2.25 |
| ATOM | 747 | OE2 | GLU | 45 | 0.629 | -0.228 | -10.861 | 1.00 | 2.10 |
| ATOM | 748 | HN | GLU | 45 | 0.525 | -3.766 | -7.122 | 1.00 | 0.63 |
| ATOM | 749 | HA | GLU | 45 | 2.666 | -3.408 | -8.992 | 1.00 | 0.64 |
| ATOM | 750 | 1HB | GLU | 45 | 1.583 | -0.953 | -8.968 | 1.00 | 0.84 |
| ATOM | 751 | 2HB | GLU | 45 | 0.296 | -1.803 | -8.112 | 1.00 | 0.90 |
| ATOM | 752 | 1HG | GLU | 45 | -0.420 | -2.775 | -10.018 | 1.00 | 1.52 |
| ATOM | 753 | 2HG | GLU | 45 | 1.209 | -3.327 | -10.412 | 1.00 | 1.38 |
| ATOM | 754 | N | LEU | 46 | 2.885 | -1.998 | -6.085 | 1.00 | 0.49 |
| ATOM | 755 | CA | LEU | 46 | 3.802 | -1.295 | -5.167 | 1.00 | 0.49 |
| ATOM | 756 | C | LEU | 46 | 5.087 | -2.123 | -5.049 | 1.00 | 0.51 |
| ATOM | 757 | O | LEU | 46 | 6.184 | -1.602 | -5.102 | 1.00 | 0.55 |
| ATOM | 758 | CB | LEU | 46 | 3.094 | -1.150 | -3.803 | 1.00 | 0.53 |
| ATOM | 759 | CG | LEU | 46 | 4.097 | -0.970 | -2.657 | 1.00 | 0.73 |
| ATOM | 760 | CD1 | LEU | 46 | 3.689 | 0.231 | -1.809 | 1.00 | 1.49 |
| ATOM | 761 | CD2 | LEU | 46 | 4.097 | -2.224 | -1.783 | 1.00 | 0.80 |
| ATOM | 762 | HN | LEU | 46 | 2.070 | -2.405 | -5.727 | 1.00 | 0.51 |
| ATOM | 763 | HA | LEU | 46 | 4.026 | -0.325 | -5.568 | 1.00 | 0.52 |
| ATOM | 764 | 1HB | LEU | 46 | 2.502 | -2.034 | -3.619 | 1.00 | 0.70 |
| ATOM | 765 | 2HB | LEU | 46 | 2.441 | -0.291 | -3.836 | 1.00 | 1.00 |
| ATOM | 766 | HG | LEU | 46 | 5.085 | -0.809 | -3.058 | 1.00 | 1.40 |
| ATOM | 767 | 1HD1 | LEU | 46 | 2.900 | -0.058 | -1.131 | 1.00 | 1.92 |
| ATOM | 768 | 2HD1 | LEU | 46 | 3.340 | 1.025 | -2.452 | 1.00 | 2.10 |
| ATOM | 769 | 3HD1 | LEU | 46 | 4.540 | 0.573 | -1.245 | 1.00 | 1.98 |
| ATOM | 770 | 1HD2 | LEU | 46 | 3.701 | -3.056 | -2.347 | 1.00 | 1.41 |

FIG. 5A-10

```
ATOM    771  2HD2 LEU    46       3.483   -2.055   -0.911  1.00  1.46
ATOM    772  3HD2 LEU    46       5.108   -2.448   -1.474  1.00  1.30
ATOM    773  N    GLU    47       4.953   -3.411   -4.893  1.00  0.52
ATOM    774  CA   GLU    47       6.159   -4.272   -4.774  1.00  0.59
ATOM    775  C    GLU    47       7.005   -4.126   -6.044  1.00  0.63
ATOM    776  O    GLU    47       8.201   -4.333   -6.036  1.00  0.72
ATOM    777  CB   GLU    47       5.730   -5.737   -4.544  1.00  0.63
ATOM    778  CG   GLU    47       5.269   -6.406   -5.847  1.00  0.80
ATOM    779  CD   GLU    47       6.145   -7.629   -6.129  1.00  1.30
ATOM    780  OE1  GLU    47       6.898   -7.585   -7.088  1.00  1.82
ATOM    781  OE2  GLU    47       6.046   -8.588   -5.383  1.00  1.94
ATOM    782  HN   GLU    47       4.059   -3.808   -4.855  1.00  0.52
ATOM    783  HA   GLU    47       6.742   -3.941   -3.928  1.00  0.62
ATOM    784  1HB  GLU    47       4.915   -5.754   -3.836  1.00  0.82
ATOM    785  2HB  GLU    47       6.561   -6.291   -4.139  1.00  1.08
ATOM    786  1HG  GLU    47       5.351   -5.713   -6.665  1.00  1.31
ATOM    787  2HG  GLU    47       4.241   -6.717   -5.742  1.00  1.15
ATOM    788  N    ASP    48       6.385   -3.762   -7.136  1.00  0.61
ATOM    789  CA   ASP    48       7.146   -3.595   -8.406  1.00  0.68
ATOM    790  C    ASP    48       7.796   -2.208   -8.433  1.00  0.68
ATOM    791  O    ASP    48       8.818   -2.005   -9.059  1.00  0.77
ATOM    792  CB   ASP    48       6.192   -3.735   -9.594  1.00  0.71
ATOM    793  CG   ASP    48       6.564   -4.978  -10.404  1.00  1.07
ATOM    794  OD1  ASP    48       7.450   -4.875  -11.236  1.00  1.68
ATOM    795  OD2  ASP    48       5.956   -6.011  -10.179  1.00  1.70
ATOM    796  HN   ASP    48       5.416   -3.599   -7.119  1.00  0.58
ATOM    797  HA   ASP    48       7.913   -4.353   -8.468  1.00  0.72
ATOM    798  1HB  ASP    48       6.270   -2.861  -10.223  1.00  0.96
ATOM    799  2HB  ASP    48       5.179   -3.830   -9.231  1.00  0.93
ATOM    800  N    GLU    49       7.213   -1.252   -7.760  1.00  0.62
ATOM    801  CA   GLU    49       7.802    0.119   -7.752  1.00  0.64
ATOM    802  C    GLU    49       9.142    0.095   -7.021  1.00  0.67
ATOM    803  O    GLU    49      10.146    0.557   -7.526  1.00  0.73
ATOM    804  CB   GLU    49       6.854    1.089   -7.036  1.00  0.60
ATOM    805  CG   GLU    49       6.170    1.991   -8.065  1.00  0.73
ATOM    806  CD   GLU    49       5.346    1.135   -9.027  1.00  1.80
ATOM    807  OE1  GLU    49       4.143    1.059   -8.840  1.00  2.54
ATOM    808  OE2  GLU    49       5.931    0.570   -9.936  1.00  2.46
ATOM    809  HN   GLU    49       6.390   -1.435   -7.262  1.00  0.58
ATOM    810  HA   GLU    49       7.954    0.449   -8.766  1.00  0.68
ATOM    811  1HB  GLU    49       7.418    1.699   -6.345  1.00  0.65
ATOM    812  2HB  GLU    49       6.106    0.529   -6.493  1.00  0.54
ATOM    813  1HG  GLU    49       6.919    2.535   -8.621  1.00  1.00
ATOM    814  2HG  GLU    49       5.521    2.689   -7.555  1.00  0.99
ATOM    815  N    PHE    50       9.164   -0.432   -5.832  1.00  0.63
ATOM    816  CA   PHE    50      10.441   -0.479   -5.058  1.00  0.67
ATOM    817  C    PHE    50      11.064   -1.877   -5.159  1.00  0.70
ATOM    818  O    PHE    50      11.991   -2.201   -4.445  1.00  0.76
ATOM    819  CB   PHE    50      10.178   -0.152   -3.579  1.00  0.64
ATOM    820  CG   PHE    50       9.051    0.851   -3.455  1.00  0.60
ATOM    821  CD1  PHE    50       9.313    2.223   -3.550  1.00  1.31
ATOM    822  CD2  PHE    50       7.743    0.401   -3.246  1.00  1.23
ATOM    823  CE1  PHE    50       8.264    3.145   -3.434  1.00  1.27
ATOM    824  CE2  PHE    50       6.697    1.322   -3.132  1.00  1.25
ATOM    825  CZ   PHE    50       6.954    2.693   -3.224  1.00  0.56
ATOM    826  HN   PHE    50       8.339   -0.793   -5.444  1.00  0.58
ATOM    827  HA   PHE    50      11.130    0.247   -5.466  1.00  0.72
ATOM    828  1HB  PHE    50      11.073    0.261   -3.140  1.00  0.70
ATOM    829  2HB  PHE    50       9.908   -1.057   -3.056  1.00  0.63
ATOM    830  HD1  PHE    50      10.322    2.571   -3.710  1.00  2.14
ATOM    831  HD2  PHE    50       7.541   -0.657   -3.174  1.00  2.03
ATOM    832  HE1  PHE    50       8.465    4.203   -3.508  1.00  2.08
ATOM    833  HE2  PHE    50       5.691    0.975   -2.971  1.00  2.07
ATOM    834  HZ   PHE    50       6.140    3.401   -3.131  1.00  0.57
ATOM    835  N    ASP    51      10.567   -2.710   -6.036  1.00  0.72
ATOM    836  CA   ASP    51      11.141   -4.079   -6.167  1.00  0.76
ATOM    837  C    ASP    51      11.055   -4.800   -4.820  1.00  0.74
ATOM    838  O    ASP    51      12.001   -4.829   -4.059  1.00  0.80
ATOM    839  CB   ASP    51      12.605   -3.980   -6.601  1.00  0.84
ATOM    840  CG   ASP    51      12.699   -4.125   -8.120  1.00  1.18
ATOM    841  OD1  ASP    51      12.863   -5.243   -8.580  1.00  1.68
ATOM    842  OD2  ASP    51      12.603   -3.116   -8.799  1.00  1.85
ATOM    843  HN   ASP    51       9.819   -2.438   -6.606  1.00  0.74
ATOM    844  HA   ASP    51      10.584   -4.633   -6.908  1.00  0.78
ATOM    845  1HB  ASP    51      13.174   -4.767   -6.130  1.00  0.97
ATOM    846  2HB  ASP    51      13.004   -3.020   -6.304  1.00  1.23
ATOM    847  N    MET    52       9.926   -5.381   -4.521  1.00  0.75
```

FIG. 5A-11

| | | | | | | | | |
|---|---|---|---|---|---|---|---|---|
| ATOM | 348 | CA | MET | 52 | 9.776 | -6.100 | -3.224 | 1.00 | 0.77 |
| ATOM | 349 | C | MET | 52 | 9.189 | -7.490 | -3.477 | 1.00 | 0.81 |
| ATOM | 350 | O | MET | 52 | 8.891 | -7.855 | -4.597 | 1.00 | 0.96 |
| ATOM | 851 | CB | MET | 52 | 8.836 | -5.310 | -2.311 | 1.00 | 0.79 |
| ATOM | 852 | CG | MET | 52 | 9.638 | -4.687 | -1.164 | 1.00 | 0.87 |
| ATOM | 853 | SD | MET | 52 | 9.104 | -5.399 | 0.412 | 1.00 | 1.42 |
| ATOM | 854 | CE | MET | 52 | 7.774 | -4.220 | 0.750 | 1.00 | 0.79 |
| ATOM | 855 | HN | MET | 52 | 9.175 | -5.344 | -5.150 | 1.00 | 0.82 |
| ATOM | 856 | HA | MET | 52 | 10.742 | -6.196 | -2.752 | 1.00 | 0.83 |
| ATOM | 857 | 1HB | MET | 52 | 8.086 | -5.974 | -1.907 | 1.00 | 1.31 |
| ATOM | 858 | 2HB | MET | 52 | 8.355 | -4.528 | -2.881 | 1.00 | 1.31 |
| ATOM | 859 | 1HG | MET | 52 | 9.473 | -3.620 | -1.150 | 1.00 | 1.43 |
| ATOM | 860 | 2HG | MET | 52 | 10.689 | -4.887 | -1.310 | 1.00 | 1.41 |
| ATOM | 861 | 1HE | MET | 52 | 7.413 | -3.809 | -0.183 | 1.00 | 1.28 |
| ATOM | 862 | 2HE | MET | 52 | 8.147 | -3.422 | 1.371 | 1.00 | 1.42 |
| ATOM | 863 | 3HE | MET | 52 | 6.968 | -4.726 | 1.264 | 1.00 | 1.29 |
| ATOM | 864 | N | GLU | 53 | 9.019 | -8.269 | -2.444 | 1.00 | 0.83 |
| ATOM | 865 | CA | GLU | 53 | 8.449 | -9.634 | -2.625 | 1.00 | 0.88 |
| ATOM | 866 | C | GLU | 53 | 7.073 | -9.701 | -1.959 | 1.00 | 0.75 |
| ATOM | 867 | O | GLU | 53 | 6.675 | -10.722 | -1.434 | 1.00 | 1.16 |
| ATOM | 868 | CB | GLU | 53 | 9.379 | -10.664 | -1.981 | 1.00 | 1.11 |
| ATOM | 869 | CG | GLU | 53 | 10.817 | -10.410 | -2.437 | 1.00 | 1.59 |
| ATOM | 870 | CD | GLU | 53 | 11.667 | -11.653 | -2.170 | 1.00 | 2.23 |
| ATOM | 871 | OE1 | GLU | 53 | 12.056 | -11.847 | -1.030 | 1.00 | 2.86 |
| ATOM | 872 | OE2 | GLU | 53 | 11.914 | -12.391 | -3.110 | 1.00 | 2.66 |
| ATOM | 873 | HN | GLU | 53 | 9.264 | -7.956 | -1.548 | 1.00 | 0.90 |
| ATOM | 874 | HA | GLU | 53 | 8.350 | -9.846 | -3.679 | 1.00 | 0.99 |
| ATOM | 875 | 1HB | GLU | 53 | 9.079 | -11.657 | -2.280 | 1.00 | 1.43 |
| ATOM | 876 | 2HB | GLU | 53 | 9.321 | -10.578 | -0.905 | 1.00 | 1.51 |
| ATOM | 877 | 1HG | GLU | 53 | 11.225 | -9.573 | -1.891 | 1.00 | 1.92 |
| ATOM | 878 | 2HG | GLU | 53 | 10.824 | -10.188 | -3.495 | 1.00 | 2.01 |
| ATOM | 879 | N | ILE | 54 | 6.344 | -8.619 | -1.976 | 1.00 | 0.66 |
| ATOM | 880 | CA | ILE | 54 | 4.995 | -8.618 | -1.343 | 1.00 | 0.55 |
| ATOM | 881 | C | ILE | 54 | 4.059 | -9.539 | -2.125 | 1.00 | 0.67 |
| ATOM | 882 | O | ILE | 54 | 3.737 | -9.286 | -3.269 | 1.00 | 1.56 |
| ATOM | 883 | CB | ILE | 54 | 4.431 | -7.197 | -1.356 | 1.00 | 0.50 |
| ATOM | 884 | CG1 | ILE | 54 | 5.379 | -6.267 | -0.599 | 1.00 | 0.56 |
| ATOM | 885 | CG2 | ILE | 54 | 3.056 | -7.179 | -0.683 | 1.00 | 0.60 |
| ATOM | 886 | CD1 | ILE | 54 | 4.865 | -4.831 | -0.698 | 1.00 | 0.63 |
| ATOM | 887 | HN | ILE | 54 | 6.684 | -7.806 | -2.404 | 1.00 | 1.02 |
| ATOM | 888 | HA | ILE | 54 | 5.074 | -8.965 | -0.324 | 1.00 | 0.62 |
| ATOM | 889 | HB | ILE | 54 | 4.333 | -6.861 | -2.376 | 1.00 | 0.59 |
| ATOM | 890 | 1HG1 | ILE | 54 | 6.365 | -6.325 | -1.035 | 1.00 | 0.66 |
| ATOM | 891 | 2HG1 | ILE | 54 | 5.424 | -6.565 | 0.439 | 1.00 | 0.67 |
| ATOM | 892 | 1HG2 | ILE | 54 | 3.170 | -6.927 | 0.361 | 1.00 | 1.07 |
| ATOM | 893 | 2HG2 | ILE | 54 | 2.598 | -8.153 | -0.771 | 1.00 | 1.34 |
| ATOM | 894 | 3HG2 | ILE | 54 | 2.430 | -6.443 | -1.165 | 1.00 | 1.14 |
| ATOM | 895 | 1HD1 | ILE | 54 | 4.877 | -4.517 | -1.731 | 1.00 | 1.19 |
| ATOM | 896 | 2HD1 | ILE | 54 | 5.499 | -4.179 | -0.116 | 1.00 | 1.07 |
| ATOM | 897 | 3HD1 | ILE | 54 | 3.855 | -4.783 | -0.319 | 1.00 | 1.27 |
| ATOM | 898 | N | SER | 55 | 3.612 | -10.601 | -1.516 | 1.00 | 0.75 |
| ATOM | 899 | CA | SER | 55 | 2.690 | -11.530 | -2.223 | 1.00 | 0.77 |
| ATOM | 900 | C | SER | 55 | 1.252 | -11.225 | -1.801 | 1.00 | 0.82 |
| ATOM | 901 | O | SER | 55 | 1.012 | -10.432 | -0.913 | 1.00 | 1.54 |
| ATOM | 902 | CB | SER | 55 | 3.037 | -12.974 | -1.859 | 1.00 | 0.90 |
| ATOM | 903 | OG | SER | 55 | 3.508 | -13.649 | -3.019 | 1.00 | 1.56 |
| ATOM | 904 | HN | SER | 55 | 3.878 | -10.784 | -0.590 | 1.00 | 1.43 |
| ATOM | 905 | HA | SER | 55 | 2.789 | -11.393 | -3.290 | 1.00 | 0.80 |
| ATOM | 906 | 1HB | SER | 55 | 2.155 | -13.470 | -1.475 | 1.00 | 1.37 |
| ATOM | 907 | 2HB | SER | 55 | 3.807 | -12.983 | -1.106 | 1.00 | 1.08 |
| ATOM | 908 | HG | SER | 55 | 4.169 | -14.288 | -2.742 | 1.00 | 1.79 |
| ATOM | 909 | N | ASP | 56 | 0.292 | -11.846 | -2.428 | 1.00 | 0.77 |
| ATOM | 910 | CA | ASP | 56 | -1.127 | -11.584 | -2.058 | 1.00 | 0.74 |
| ATOM | 911 | C | ASP | 56 | -1.325 | -11.844 | -0.563 | 1.00 | 0.73 |
| ATOM | 912 | O | ASP | 56 | -2.253 | -11.349 | 0.043 | 1.00 | 1.00 |
| ATOM | 913 | CB | ASP | 56 | -2.043 | -12.510 | -2.861 | 1.00 | 0.90 |
| ATOM | 914 | CG | ASP | 56 | -2.969 | -11.672 | -3.745 | 1.00 | 1.56 |
| ATOM | 915 | OD1 | ASP | 56 | -3.948 | -11.161 | -3.227 | 1.00 | 2.33 |
| ATOM | 916 | OD2 | ASP | 56 | -2.682 | -11.555 | -4.926 | 1.00 | 2.15 |
| ATOM | 917 | HN | ASP | 56 | 0.504 | -12.482 | -3.143 | 1.00 | 1.31 |
| ATOM | 918 | HA | ASP | 56 | -1.372 | -10.556 | -2.279 | 1.00 | 0.69 |
| ATOM | 919 | 1HB | ASP | 56 | -2.637 | -13.105 | -2.184 | 1.00 | 1.33 |
| ATOM | 920 | 2HB | ASP | 56 | -1.443 | -13.160 | -3.481 | 1.00 | 1.28 |
| ATOM | 921 | N | GLU | 57 | -0.462 | -12.618 | 0.038 | 1.00 | 0.66 |
| ATOM | 922 | CA | GLU | 57 | -0.607 | -12.907 | 1.492 | 1.00 | 0.70 |
| ATOM | 923 | C | GLU | 57 | -0.097 | -11.718 | 2.310 | 1.00 | 0.59 |
| ATOM | 924 | O | GLU | 57 | -0.450 | -11.548 | 3.460 | 1.00 | 0.65 |

FIG. 5A-12

| | | | | | | | | |
|---|---|---|---|---|---|---|---|---|
| ATOM | 925 | CB | GLU | 57 | 0.205 | -14.154 | 1.946 | 1.00 | 0.82 |
| ATOM | 926 | CG | GLU | 57 | 1.654 | -13.966 | 1.392 | 1.00 | 0.74 |
| ATOM | 927 | CD | GLU | 57 | 2.541 | -15.013 | 2.066 | 1.00 | 1.01 |
| ATOM | 928 | OE1 | GLU | 57 | 3.487 | -14.621 | 2.730 | 1.00 | 1.45 |
| ATOM | 929 | OE2 | GLU | 57 | 2.260 | -16.190 | 1.907 | 1.00 | 1.65 |
| ATOM | 930 | HN | GLU | 57 | 0.280 | -13.011 | -0.467 | 1.00 | 0.78 |
| ATOM | 931 | HA | GLU | 57 | -1.648 | -13.080 | 1.721 | 1.00 | 0.79 |
| ATOM | 932 | 1HB | GLU | 57 | -0.218 | -15.013 | 1.348 | 1.00 | 1.04 |
| ATOM | 933 | 2HB | GLU | 57 | 0.179 | -14.308 | 2.916 | 1.00 | 1.02 |
| ATOM | 934 | 1HG | GLU | 57 | 1.993 | -12.978 | 1.667 | 1.00 | 0.91 |
| ATOM | 935 | 2HG | GLU | 57 | 1.711 | -14.080 | 0.319 | 1.00 | 0.91 |
| ATOM | 936 | N | ASP | 58 | 0.735 | -10.894 | 1.732 | 1.00 | 0.48 |
| ATOM | 937 | CA | ASP | 58 | 1.266 | -9.722 | 2.486 | 1.00 | 0.43 |
| ATOM | 938 | C | ASP | 58 | 0.157 | -8.688 | 2.683 | 1.00 | 0.40 |
| ATOM | 939 | O | ASP | 58 | -0.414 | -8.577 | 3.744 | 1.00 | 0.45 |
| ATOM | 940 | CB | ASP | 58 | 2.422 | -9.090 | 1.708 | 1.00 | 0.42 |
| ATOM | 941 | CG | ASP | 58 | 3.751 | -9.511 | 2.338 | 1.00 | 0.79 |
| ATOM | 942 | OD1 | ASP | 58 | 3.790 | -10.573 | 2.936 | 1.00 | 1.45 |
| ATOM | 943 | OD2 | ASP | 58 | 4.706 | -8.762 | 2.213 | 1.00 | 1.46 |
| ATOM | 944 | HN | ASP | 58 | 1.013 | -11.047 | 0.805 | 1.00 | 0.51 |
| ATOM | 945 | HA | ASP | 58 | 1.622 | -10.050 | 3.450 | 1.00 | 0.48 |
| ATOM | 946 | 1HB | ASP | 58 | 2.335 | -8.015 | 1.742 | 1.00 | 0.63 |
| ATOM | 947 | 2HB | ASP | 58 | 2.389 | -9.423 | 0.681 | 1.00 | 0.57 |
| ATOM | 948 | N | ALA | 59 | -0.149 | -7.932 | 1.665 | 1.00 | 0.41 |
| ATOM | 949 | CA | ALA | 59 | -1.221 | -6.889 | 1.775 | 1.00 | 0.43 |
| ATOM | 950 | C | ALA | 59 | -2.458 | -7.440 | 2.503 | 1.00 | 0.49 |
| ATOM | 951 | O | ALA | 59 | -3.224 | -6.695 | 3.082 | 1.00 | 0.53 |
| ATOM | 952 | CB | ALA | 59 | -1.624 | -6.444 | 0.370 | 1.00 | 0.54 |
| ATOM | 953 | HN | ALA | 59 | 0.331 | -8.046 | 0.820 | 1.00 | 0.47 |
| ATOM | 954 | HA | ALA | 59 | -0.840 | -6.034 | 2.318 | 1.00 | 0.42 |
| ATOM | 955 | 1HB | ALA | 59 | -0.987 | -6.927 | -0.357 | 1.00 | 1.28 |
| ATOM | 956 | 2HB | ALA | 59 | -1.516 | -5.375 | 0.288 | 1.00 | 1.06 |
| ATOM | 957 | 3HB | ALA | 59 | -2.651 | -6.718 | 0.186 | 1.00 | 1.14 |
| ATOM | 958 | N | GLU | 60 | -2.670 | -8.728 | 2.471 | 1.00 | 0.55 |
| ATOM | 959 | CA | GLU | 60 | -3.868 | -9.300 | 3.154 | 1.00 | 0.68 |
| ATOM | 960 | C | GLU | 60 | -3.558 | -9.603 | 4.624 | 1.00 | 0.70 |
| ATOM | 961 | O | GLU | 60 | -4.322 | -9.271 | 5.508 | 1.00 | 0.80 |
| ATOM | 962 | CB | GLU | 60 | -4.285 | -10.591 | 2.448 | 1.00 | 0.79 |
| ATOM | 963 | CG | GLU | 60 | -5.768 | -10.515 | 2.079 | 1.00 | 1.03 |
| ATOM | 964 | CD | GLU | 60 | -6.450 | -11.838 | 2.431 | 1.00 | 1.32 |
| ATOM | 965 | OE1 | GLU | 60 | -5.791 | -12.862 | 2.349 | 1.00 | 1.83 |
| ATOM | 966 | OE2 | GLU | 60 | -7.620 | -11.806 | 2.776 | 1.00 | 1.97 |
| ATOM | 967 | HN | GLU | 60 | -2.053 | -9.317 | 1.991 | 1.00 | 0.54 |
| ATOM | 968 | HA | GLU | 60 | -4.676 | -8.591 | 3.103 | 1.00 | 0.75 |
| ATOM | 969 | 1HB | GLU | 60 | -4.122 | -11.431 | 3.106 | 1.00 | 1.01 |
| ATOM | 970 | 2HB | GLU | 60 | -3.697 | -10.716 | 1.551 | 1.00 | 0.99 |
| ATOM | 971 | 1HG | GLU | 60 | -5.867 | -10.332 | 1.020 | 1.00 | 1.37 |
| ATOM | 972 | 2HG | GLU | 60 | -6.235 | -9.711 | 2.629 | 1.00 | 1.60 |
| ATOM | 973 | N | LYS | 61 | -2.455 | -10.243 | 4.893 | 1.00 | 0.65 |
| ATOM | 974 | CA | LYS | 61 | -2.114 | -10.580 | 6.309 | 1.00 | 0.73 |
| ATOM | 975 | C | LYS | 61 | -1.365 | -9.417 | 6.968 | 1.00 | 0.70 |
| ATOM | 976 | O | LYS | 61 | -1.291 | -9.322 | 8.177 | 1.00 | 0.97 |
| ATOM | 977 | CB | LYS | 61 | -1.230 | -11.828 | 6.336 | 1.00 | 0.81 |
| ATOM | 978 | CG | LYS | 61 | -1.407 | -12.548 | 7.674 | 1.00 | 1.30 |
| ATOM | 979 | CD | LYS | 61 | -1.016 | -14.018 | 7.519 | 1.00 | 1.75 |
| ATOM | 980 | CE | LYS | 61 | 0.509 | -14.139 | 7.498 | 1.00 | 2.14 |
| ATOM | 981 | NZ | LYS | 61 | 0.913 | -15.427 | 8.131 | 1.00 | 2.62 |
| ATOM | 982 | HN | LYS | 61 | -1.859 | -10.512 | 4.166 | 1.00 | 0.59 |
| ATOM | 983 | HA | LYS | 61 | -3.023 | -10.776 | 6.858 | 1.00 | 0.85 |
| ATOM | 984 | 1HB | LYS | 61 | -0.197 | -11.540 | 6.218 | 1.00 | 1.08 |
| ATOM | 985 | 2HB | LYS | 61 | -1.515 | -12.488 | 5.530 | 1.00 | 1.02 |
| ATOM | 986 | 1HG | LYS | 61 | -2.439 | -12.483 | 7.984 | 1.00 | 1.80 |
| ATOM | 987 | 2HG | LYS | 61 | -0.777 | -12.083 | 8.419 | 1.00 | 1.76 |
| ATOM | 988 | 1HD | LYS | 61 | -1.418 | -14.402 | 6.594 | 1.00 | 2.22 |
| ATOM | 989 | 2HD | LYS | 61 | -1.412 | -14.585 | 8.348 | 1.00 | 2.08 |
| ATOM | 990 | 1HE | LYS | 61 | 0.943 | -13.316 | 8.047 | 1.00 | 2.32 |
| ATOM | 991 | 2HE | LYS | 61 | 0.858 | -14.115 | 6.477 | 1.00 | 2.47 |
| ATOM | 992 | 1HZ | LYS | 61 | 1.131 | -15.267 | 9.134 | 1.00 | 2.92 |
| ATOM | 993 | 2HZ | LYS | 61 | 1.755 | -15.800 | 7.647 | 1.00 | 2.99 |
| ATOM | 994 | 3HZ | LYS | 61 | 0.135 | -16.111 | 8.053 | 1.00 | 2.94 |
| ATOM | 995 | N | ILE | 62 | -0.806 | -8.537 | 6.187 | 1.00 | 0.57 |
| ATOM | 996 | CA | ILE | 62 | -0.058 | -7.386 | 6.767 | 1.00 | 0.54 |
| ATOM | 997 | C | ILE | 62 | -0.962 | -6.642 | 7.761 | 1.00 | 0.59 |
| ATOM | 998 | O | ILE | 62 | -2.163 | -6.577 | 7.587 | 1.00 | 1.32 |
| ATOM | 999 | CB | ILE | 62 | 0.397 | -6.458 | 5.621 | 1.00 | 0.46 |
| ATOM | 1000 | CG1 | ILE | 62 | 1.569 | -5.596 | 6.093 | 1.00 | 0.56 |
| ATOM | 1001 | CG2 | ILE | 62 | -0.751 | -5.549 | 5.150 | 1.00 | 0.67 |

FIG. 5A-13

```
ATOM   1002  CD1  ILE  62    2.130  -4.818   4.903  1.00  0.60
ATOM   1003  HN   ILE  62   -0.873  -8.633   5.215  1.00  0.68
ATOM   1004  HA   ILE  62    0.811  -7.758   7.291  1.00  0.62
ATOM   1005  HB   ILE  62    0.723  -7.065   4.790  1.00  0.51
ATOM   1006  1HG1 ILE  62    2.343  -6.230   6.500  1.00  0.74
ATOM   1007  2HG1 ILE  62    1.230  -4.906   6.850  1.00  0.90
ATOM   1008  1HG2 ILE  62   -0.534  -5.178   4.159  1.00  1.33
ATOM   1009  2HG2 ILE  62   -0.854  -4.716   5.830  1.00  1.12
ATOM   1010  3HG2 ILE  62   -1.672  -6.112   5.129  1.00  1.31
ATOM   1011  1HD1 ILE  62    2.337  -5.500   4.091  1.00  1.15
ATOM   1012  2HD1 ILE  62    3.042  -4.318   5.195  1.00  1.18
ATOM   1013  3HD1 ILE  62    1.405  -4.085   4.580  1.00  1.17
ATOM   1014  N    ALA  63   -0.397  -6.086   8.801  1.00  0.80
ATOM   1015  CA   ALA  63   -1.231  -5.352   9.802  1.00  0.75
ATOM   1016  C    ALA  63   -2.146  -4.363   9.078  1.00  0.75
ATOM   1017  O    ALA  63   -3.285  -4.165   9.451  1.00  1.33
ATOM   1018  CB   ALA  63   -0.318  -4.593  10.767  1.00  0.77
ATOM   1019  HN   ALA  63    0.572  -6.151   8.926  1.00  1.44
ATOM   1020  HA   ALA  63   -1.831  -6.058  10.355  1.00  0.77
ATOM   1021  1HB  ALA  63    0.683  -4.995  10.708  1.00  1.10
ATOM   1022  2HB  ALA  63   -0.690  -4.701  11.775  1.00  1.34
ATOM   1023  3HB  ALA  63   -0.302  -3.546  10.500  1.00  1.30
ATOM   1024  N    THR  64   -1.652  -3.754   8.037  1.00  0.54
ATOM   1025  CA   THR  64   -2.473  -2.782   7.264  1.00  0.48
ATOM   1026  C    THR  64   -1.699  -2.346   6.020  1.00  0.41
ATOM   1027  O    THR  64   -0.488  -2.449   5.960  1.00  0.42
ATOM   1028  CB   THR  64   -2.769  -1.550   8.126  1.00  0.56
ATOM   1029  OG1  THR  64   -1.747  -1.400   9.102  1.00  0.63
ATOM   1030  CG2  THR  64   -4.118  -1.726   8.820  1.00  0.61
ATOM   1031  HN   THR  64   -0.737  -3.943   7.758  1.00  0.91
ATOM   1032  HA   THR  64   -3.401  -3.247   6.968  1.00  0.48
ATOM   1033  HB   THR  64   -2.804  -0.666   7.500  1.00  0.64
ATOM   1034  HG1  THR  64   -1.163  -0.695   8.815  1.00  1.07
ATOM   1035  1HG2 THR  64   -4.683  -2.494   8.315  1.00  1.12
ATOM   1036  2HG2 THR  64   -4.663  -0.795   8.788  1.00  1.18
ATOM   1037  3HG2 THR  64   -3.957  -2.014   9.848  1.00  1.16
ATOM   1038  N    VAL  65   -2.390  -1.839   5.034  1.00  0.36
ATOM   1039  CA   VAL  65   -1.712  -1.363   3.791  1.00  0.31
ATOM   1040  C    VAL  65   -0.527  -0.472   4.188  1.00  0.36
ATOM   1041  O    VAL  65    0.546  -0.542   3.619  1.00  0.38
ATOM   1042  CB   VAL  65   -2.731  -0.558   2.979  1.00  0.30
ATOM   1043  CG1  VAL  65   -2.031   0.276   1.901  1.00  0.37
ATOM   1044  CG2  VAL  65   -3.717  -1.523   2.315  1.00  0.27
ATOM   1045  HN   VAL  65   -3.363  -1.754   5.118  1.00  0.37
ATOM   1046  HA   VAL  65   -1.366  -2.207   3.208  1.00  0.29
ATOM   1047  HB   VAL  65   -3.265   0.098   3.647  1.00  0.37
ATOM   1048  1HG1 VAL  65   -0.997  -0.026   1.829  1.00  0.93
ATOM   1049  2HG1 VAL  65   -2.084   1.321   2.168  1.00  1.10
ATOM   1050  3HG1 VAL  65   -2.520   0.120   0.952  1.00  1.05
ATOM   1051  1HG2 VAL  65   -4.569  -1.669   2.962  1.00  0.98
ATOM   1052  2HG2 VAL  65   -3.230  -2.472   2.142  1.00  1.03
ATOM   1053  3HG2 VAL  65   -4.046  -1.111   1.373  1.00  1.06
ATOM   1054  N    GLY  66   -0.722   0.356   5.177  1.00  0.41
ATOM   1055  CA   GLY  66    0.379   1.244   5.634  1.00  0.48
ATOM   1056  C    GLY  66    1.573   0.381   6.023  1.00  0.48
ATOM   1057  O    GLY  66    2.693   0.644   5.633  1.00  0.50
ATOM   1058  HN   GLY  66   -1.593   0.384   5.624  1.00  0.41
ATOM   1059  1HA  GLY  66    0.056   1.812   6.489  1.00  0.52
ATOM   1060  2HA  GLY  66    0.659   1.914   4.834  1.00  0.49
ATOM   1061  N    ASP  67    1.342  -0.670   6.771  1.00  0.48
ATOM   1062  CA   ASP  67    2.471  -1.565   7.156  1.00  0.50
ATOM   1063  C    ASP  67    3.198  -1.973   5.878  1.00  0.47
ATOM   1064  O    ASP  67    4.399  -2.154   5.858  1.00  0.51
ATOM   1065  CB   ASP  67    1.930  -2.806   7.866  1.00  0.51
ATOM   1066  CG   ASP  67    1.976  -2.588   9.380  1.00  1.01
ATOM   1067  OD1  ASP  67    2.765  -3.253  10.031  1.00  1.56
ATOM   1068  OD2  ASP  67    1.222  -1.760   9.863  1.00  1.78
ATOM   1069  HN   ASP  67    0.429  -0.877   7.061  1.00  0.48
ATOM   1070  HA   ASP  67    3.150  -1.034   7.808  1.00  0.55
ATOM   1071  1HB  ASP  67    2.536  -3.662   7.609  1.00  0.76
ATOM   1072  2HB  ASP  67    0.911  -2.980   7.557  1.00  0.81
ATOM   1073  N    ALA  68    2.469  -2.080   4.799  1.00  0.42
ATOM   1074  CA   ALA  68    3.108  -2.431   3.504  1.00  0.41
ATOM   1075  C    ALA  68    4.102  -1.322   3.182  1.00  0.45
ATOM   1076  O    ALA  68    5.221  -1.563   2.769  1.00  0.49
ATOM   1077  CB   ALA  68    2.041  -2.512   2.409  1.00  0.37
ATOM   1078  HN   ALA  68    1.504  -1.901   4.839  1.00  0.40
```

FIG. 5A-14

| | | | | | | | | |
|---|---|---|---|---|---|---|---|---|
| ATOM | 1079 | HA | ALA | 68 | 3.624 | -3.374 | 3.592 | 1.00 | 0.42 |
| ATOM | 1080 | 1HB | ALA | 68 | 1.120 | -2.890 | 2.830 | 1.00 | 1.08 |
| ATOM | 1081 | 2HB | ALA | 68 | 2.377 | -3.177 | 1.627 | 1.00 | 1.05 |
| ATOM | 1082 | 3HB | ALA | 68 | 1.870 | -1.528 | 1.997 | 1.00 | 1.11 |
| ATOM | 1083 | N | VAL | 69 | 3.703 | -0.101 | 3.412 | 1.00 | 0.45 |
| ATOM | 1084 | CA | VAL | 69 | 4.620 | 1.040 | 3.169 | 1.00 | 0.50 |
| ATOM | 1085 | C | VAL | 69 | 5.814 | 0.870 | 4.119 | 1.00 | 0.56 |
| ATOM | 1086 | O | VAL | 69 | 6.964 | 0.971 | 3.730 | 1.00 | 0.62 |
| ATOM | 1087 | CB | VAL | 69 | 3.841 | 2.363 | 3.403 | 1.00 | 0.51 |
| ATOM | 1088 | CG1 | VAL | 69 | 4.347 | 3.137 | 4.631 | 1.00 | 0.55 |
| ATOM | 1089 | CG2 | VAL | 69 | 3.978 | 3.247 | 2.162 | 1.00 | 0.56 |
| ATOM | 1090 | HN | VAL | 69 | 2.805 | 0.058 | 3.773 | 1.00 | 0.43 |
| ATOM | 1091 | HA | VAL | 69 | 4.970 | 1.003 | 2.151 | 1.00 | 0.51 |
| ATOM | 1092 | HB | VAL | 69 | 2.796 | 2.128 | 3.548 | 1.00 | 0.51 |
| ATOM | 1093 | 1HG1 | VAL | 69 | 5.393 | 3.370 | 4.503 | 1.00 | 1.25 |
| ATOM | 1094 | 2HG1 | VAL | 69 | 4.218 | 2.531 | 5.516 | 1.00 | 0.95 |
| ATOM | 1095 | 3HG1 | VAL | 69 | 3.783 | 4.052 | 4.736 | 1.00 | 1.18 |
| ATOM | 1096 | 1HG2 | VAL | 69 | 4.964 | 3.687 | 2.139 | 1.00 | 1.18 |
| ATOM | 1097 | 2HG2 | VAL | 69 | 3.234 | 4.029 | 2.194 | 1.00 | 1.18 |
| ATOM | 1098 | 3HG2 | VAL | 69 | 3.829 | 2.648 | 1.277 | 1.00 | 1.13 |
| ATOM | 1099 | N | ASN | 70 | 5.534 | 0.571 | 5.358 | 1.00 | 0.57 |
| ATOM | 1100 | CA | ASN | 70 | 6.629 | 0.347 | 6.338 | 1.00 | 0.64 |
| ATOM | 1101 | C | ASN | 70 | 7.446 | -0.857 | 5.866 | 1.00 | 0.64 |
| ATOM | 1102 | O | ASN | 70 | 8.623 | -0.978 | 6.145 | 1.00 | 0.71 |
| ATOM | 1103 | CB | ASN | 70 | 6.031 | 0.053 | 7.716 | 1.00 | 0.67 |
| ATOM | 1104 | CG | ASN | 70 | 6.539 | 1.086 | 8.723 | 1.00 | 1.01 |
| ATOM | 1105 | OD1 | ASN | 70 | 5.774 | 1.617 | 9.504 | 1.00 | 1.73 |
| ATOM | 1106 | ND2 | ASN | 70 | 7.806 | 1.396 | 8.738 | 1.00 | 1.38 |
| ATOM | 1107 | HN | ASN | 70 | 4.600 | 0.468 | 5.635 | 1.00 | 0.56 |
| ATOM | 1108 | HA | ASN | 70 | 7.257 | 1.221 | 6.392 | 1.00 | 0.68 |
| ATOM | 1109 | 1HB | ASN | 70 | 6.330 | -0.934 | 8.035 | 1.00 | 0.87 |
| ATOM | 1110 | 2HB | ASN | 70 | 4.953 | 0.103 | 7.659 | 1.00 | 0.85 |
| ATOM | 1111 | 1HD2 | ASN | 70 | 8.423 | 0.967 | 8.108 | 1.00 | 1.81 |
| ATOM | 1112 | 2HD2 | ASN | 70 | 8.142 | 2.057 | 9.379 | 1.00 | 1.67 |
| ATOM | 1113 | N | TYR | 71 | 6.818 | -1.747 | 5.141 | 1.00 | 0.60 |
| ATOM | 1114 | CA | TYR | 71 | 7.529 | -2.950 | 4.629 | 1.00 | 0.62 |
| ATOM | 1115 | C | TYR | 71 | 8.618 | -2.519 | 3.646 | 1.00 | 0.66 |
| ATOM | 1116 | O | TYR | 71 | 9.677 | -3.110 | 3.577 | 1.00 | 0.74 |
| ATOM | 1117 | CB | TYR | 71 | 6.523 | -3.851 | 3.906 | 1.00 | 0.59 |
| ATOM | 1118 | CG | TYR | 71 | 6.898 | -5.299 | 4.100 | 1.00 | 0.61 |
| ATOM | 1119 | CD1 | TYR | 71 | 8.096 | -5.789 | 3.568 | 1.00 | 1.36 |
| ATOM | 1120 | CD2 | TYR | 71 | 6.046 | -6.153 | 4.811 | 1.00 | 1.33 |
| ATOM | 1121 | CE1 | TYR | 71 | 8.443 | -7.133 | 3.747 | 1.00 | 1.39 |
| ATOM | 1122 | CE2 | TYR | 71 | 6.393 | -7.497 | 4.990 | 1.00 | 1.38 |
| ATOM | 1123 | CZ | TYR | 71 | 7.592 | -7.987 | 4.459 | 1.00 | 0.77 |
| ATOM | 1124 | OH | TYR | 71 | 7.934 | -9.313 | 4.636 | 1.00 | 0.90 |
| ATOM | 1125 | HN | TYR | 71 | 5.870 | -1.621 | 4.930 | 1.00 | 0.57 |
| ATOM | 1126 | HA | TYR | 71 | 7.973 | -3.488 | 5.451 | 1.00 | 0.65 |
| ATOM | 1127 | 1HB | TYR | 71 | 6.526 | -3.618 | 2.851 | 1.00 | 0.61 |
| ATOM | 1128 | 2HB | TYR | 71 | 5.535 | -3.680 | 4.307 | 1.00 | 0.60 |
| ATOM | 1129 | HD1 | TYR | 71 | 8.751 | -5.130 | 3.018 | 1.00 | 2.21 |
| ATOM | 1130 | HD2 | TYR | 71 | 5.120 | -5.774 | 5.219 | 1.00 | 2.16 |
| ATOM | 1131 | HE1 | TYR | 71 | 9.368 | -7.512 | 3.337 | 1.00 | 2.24 |
| ATOM | 1132 | HE2 | TYR | 71 | 5.736 | -8.156 | 5.539 | 1.00 | 2.23 |
| ATOM | 1133 | HH | TYR | 71 | 8.247 | -9.653 | 3.794 | 1.00 | 0.96 |
| ATOM | 1134 | N | ILE | 72 | 8.361 | -1.496 | 2.878 | 1.00 | 0.64 |
| ATOM | 1135 | CA | ILE | 72 | 9.378 | -1.030 | 1.889 | 1.00 | 0.70 |
| ATOM | 1136 | C | ILE | 72 | 10.536 | -0.355 | 2.617 | 1.00 | 0.77 |
| ATOM | 1137 | O | ILE | 72 | 11.691 | -0.567 | 2.304 | 1.00 | 0.86 |
| ATOM | 1138 | CB | ILE | 72 | 8.753 | -0.013 | 0.930 | 1.00 | 0.67 |
| ATOM | 1139 | CG1 | ILE | 72 | 7.417 | -0.533 | 0.403 | 1.00 | 0.65 |
| ATOM | 1140 | CG2 | ILE | 72 | 9.699 | 0.228 | -0.249 | 1.00 | 0.76 |
| ATOM | 1141 | CD1 | ILE | 72 | 6.447 | 0.637 | 0.268 | 1.00 | 0.63 |
| ATOM | 1142 | HN | ILE | 72 | 7.496 | -1.039 | 2.947 | 1.00 | 0.61 |
| ATOM | 1143 | HA | ILE | 72 | 9.746 | -1.875 | 1.329 | 1.00 | 0.74 |
| ATOM | 1144 | HB | ILE | 72 | 8.594 | 0.919 | 1.454 | 1.00 | 0.65 |
| ATOM | 1145 | 1HG1 | ILE | 72 | 7.010 | -1.257 | 1.089 | 1.00 | 0.81 |
| ATOM | 1146 | 2HG1 | ILE | 72 | 7.566 | -0.991 | -0.563 | 1.00 | 0.80 |
| ATOM | 1147 | 1HG2 | ILE | 72 | 10.596 | 0.714 | 0.104 | 1.00 | 1.22 |
| ATOM | 1148 | 2HG2 | ILE | 72 | 9.211 | 0.859 | -0.978 | 1.00 | 1.24 |
| ATOM | 1149 | 3HG2 | ILE | 72 | 9.954 | -0.716 | -0.705 | 1.00 | 1.38 |
| ATOM | 1150 | 1HD1 | ILE | 72 | 5.439 | 0.287 | 0.424 | 1.00 | 1.17 |
| ATOM | 1151 | 2HD1 | ILE | 72 | 6.533 | 1.065 | -0.720 | 1.00 | 1.24 |
| ATOM | 1152 | 3HD1 | ILE | 72 | 6.686 | 1.389 | 1.007 | 1.00 | 1.22 |
| ATOM | 1153 | N | GLN | 73 | 10.235 | 0.467 | 3.579 | 1.00 | 0.76 |
| ATOM | 1154 | CA | GLN | 73 | 11.332 | 1.171 | 4.317 | 1.00 | 0.85 |
| ATOM | 1155 | C | GLN | 73 | 12.217 | 0.129 | 5.002 | 1.00 | 0.92 |

FIG. 5A-15

| ATOM | 1156 | O    | GLN | 73 | 13.399 | 0.333  | 5.193  | 1.00 | 1.03 |
|------|------|------|-----|----|--------|--------|--------|------|------|
| ATOM | 1157 | CB   | GLN | 73 | 10.789 | 2.142  | 5.389  | 1.00 | 0.88 |
| ATOM | 1158 | CG   | GLN | 73 | 9.338  | 2.558  | 5.107  | 1.00 | 1.08 |
| ATOM | 1159 | CD   | GLN | 73 | 9.185  | 3.028  | 3.659  | 1.00 | 1.11 |
| ATOM | 1160 | OE1  | GLN | 73 | 10.158 | 3.203  | 2.953  | 1.00 | 2.07 |
| ATOM | 1161 | NE2  | GLN | 73 | 7.986  | 3.238  | 3.187  | 1.00 | 0.83 |
| ATOM | 1162 | HN   | GLN | 73 | 9.295  | 0.622  | 3.803  | 1.00 | 0.71 |
| ATOM | 1163 | HA   | GLN | 73 | 11.931 | 1.725  | 3.608  | 1.00 | 0.89 |
| ATOM | 1164 | 1HB  | GLN | 73 | 11.411 | 3.025  | 5.409  | 1.00 | 1.16 |
| ATOM | 1165 | 2HB  | GLN | 73 | 10.833 | 1.661  | 6.354  | 1.00 | 1.09 |
| ATOM | 1166 | 1HG  | GLN | 73 | 9.061  | 3.362  | 5.773  | 1.00 | 1.61 |
| ATOM | 1167 | 2HG  | GLN | 73 | 8.690  | 1.715  | 5.276  | 1.00 | 1.71 |
| ATOM | 1168 | 1HE2 | GLN | 73 | 7.203  | 3.095  | 3.760  | 1.00 | 1.17 |
| ATOM | 1169 | 2HE2 | GLN | 73 | 7.866  | 3.535  | 2.264  | 1.00 | 1.07 |
| ATOM | 1170 | N    | ASN | 74 | 11.654 | -0.988 | 5.374  | 1.00 | 0.90 |
| ATOM | 1171 | CA   | ASN | 74 | 12.463 | -2.044 | 6.046  | 1.00 | 1.01 |
| ATOM | 1172 | C    | ASN | 74 | 13.479 | -2.616 | 5.054  | 1.00 | 1.06 |
| ATOM | 1173 | O    | ASN | 74 | 14.494 | -3.163 | 5.438  | 1.00 | 1.18 |
| ATOM | 1174 | CB   | ASN | 74 | 11.540 | -3.162 | 6.533  | 1.00 | 1.08 |
| ATOM | 1175 | CG   | ASN | 74 | 11.703 | -3.336 | 8.044  | 1.00 | 1.31 |
| ATOM | 1176 | OD1  | ASN | 74 | 11.348 | -2.462 | 8.810  | 1.00 | 1.90 |
| ATOM | 1177 | ND2  | ASN | 74 | 12.230 | -4.436 | 8.509  | 1.00 | 1.80 |
| ATOM | 1178 | HN   | ASN | 74 | 10.698 | -1.133 | 5.211  | 1.00 | 0.85 |
| ATOM | 1179 | HA   | ASN | 74 | 12.985 | -1.615 | 6.888  | 1.00 | 1.07 |
| ATOM | 1180 | 1HB  | ASN | 74 | 11.799 | -4.085 | 6.037  | 1.00 | 1.21 |
| ATOM | 1181 | 2HB  | ASN | 74 | 10.515 | -2.906 | 6.308  | 1.00 | 1.26 |
| ATOM | 1182 | 1HD2 | ASN | 74 | 12.517 | -5.141 | 7.892  | 1.00 | 2.30 |
| ATOM | 1183 | 2HD2 | ASN | 74 | 12.338 | -4.556 | 9.476  | 1.00 | 2.08 |
| ATOM | 1184 | N    | GLN | 75 | 13.216 | -2.493 | 3.782  | 1.00 | 1.08 |
| ATOM | 1185 | CA   | GLN | 75 | 14.169 | -3.029 | 2.771  | 1.00 | 1.22 |
| ATOM | 1186 | C    | GLN | 75 | 15.182 | -1.943 | 2.404  | 1.00 | 1.23 |
| ATOM | 1187 | O    | GLN | 75 | 16.286 | -2.226 | 1.984  | 1.00 | 1.40 |
| ATOM | 1188 | CB   | GLN | 75 | 13.399 | -3.456 | 1.520  | 1.00 | 1.31 |
| ATOM | 1189 | CG   | GLN | 75 | 12.566 | -4.700 | 1.835  | 1.00 | 1.54 |
| ATOM | 1190 | CD   | GLN | 75 | 13.222 | -5.927 | 1.200  | 1.00 | 1.98 |
| ATOM | 1191 | OE1  | GLN | 75 | 13.372 | -6.949 | 1.839  | 1.00 | 2.43 |
| ATOM | 1192 | NE2  | GLN | 75 | 13.622 | -5.869 | -0.041 | 1.00 | 2.55 |
| ATOM | 1193 | HN   | GLN | 75 | 12.393 | -2.048 | 3.491  | 1.00 | 1.09 |
| ATOM | 1194 | HA   | GLN | 75 | 14.689 | -3.881 | 3.183  | 1.00 | 1.35 |
| ATOM | 1195 | 1HB  | GLN | 75 | 14.097 | -3.684 | 0.728  | 1.00 | 1.65 |
| ATOM | 1196 | 2HB  | GLN | 75 | 12.747 | -2.654 | 1.207  | 1.00 | 1.73 |
| ATOM | 1197 | 1HG  | GLN | 75 | 11.571 | -4.578 | 1.435  | 1.00 | 1.95 |
| ATOM | 1198 | 2HG  | GLN | 75 | 12.511 | -4.834 | 2.906  | 1.00 | 1.75 |
| ATOM | 1199 | 1HE2 | GLN | 75 | 13.500 | -5.044 | -0.557 | 1.00 | 2.92 |
| ATOM | 1200 | 2HE2 | GLN | 75 | 14.042 | -6.650 | -0.457 | 1.00 | 2.94 |
| ATOM | 1201 | N    | GLN | 76 | 14.815 | -0.700 | 2.563  | 1.00 | 1.14 |
| ATOM | 1202 | CA   | GLN | 76 | 15.757 | 0.403  | 2.227  | 1.00 | 1.25 |
| ATOM | 1203 | C    | GLN | 76 | 16.763 | 0.577  | 3.366  | 1.00 | 1.67 |
| ATOM | 1204 | O    | GLN | 76 | 16.522 | 0.032  | 4.431  | 1.00 | 2.01 |
| ATOM | 1205 | CB   | GLN | 76 | 14.974 | 1.704  | 2.037  | 1.00 | 1.23 |
| ATOM | 1206 | CG   | GLN | 76 | 14.091 | 1.590  | 0.793  | 1.00 | 1.15 |
| ATOM | 1207 | CD   | GLN | 76 | 14.345 | 2.786  | -0.126 | 1.00 | 1.58 |
| ATOM | 1208 | OE1  | GLN | 76 | 14.865 | 3.797  | 0.304  | 1.00 | 2.23 |
| ATOM | 1209 | NE2  | GLN | 76 | 14.000 | 2.713  | -1.382 | 1.00 | 1.97 |
| ATOM | 1210 | OXT  | GLN | 76 | 17.757 | 1.252  | 3.155  | 1.00 | 2.36 |
| ATOM | 1211 | HN   | GLN | 76 | 13.919 | -0.494 | 2.905  | 1.00 | 1.10 |
| ATOM | 1212 | HA   | GLN | 76 | 16.283 | 0.163  | 1.315  | 1.00 | 1.55 |
| ATOM | 1213 | 1HB  | GLN | 76 | 15.664 | 2.525  | 1.912  | 1.00 | 1.74 |
| ATOM | 1214 | 2HB  | GLN | 76 | 14.355 | 1.881  | 2.905  | 1.00 | 1.68 |
| ATOM | 1215 | 1HG  | GLN | 76 | 13.052 | 1.580  | 1.088  | 1.00 | 1.43 |
| ATOM | 1216 | 2HG  | GLN | 76 | 14.326 | 0.675  | 0.269  | 1.00 | 1.35 |
| ATOM | 1217 | 1HE2 | GLN | 76 | 13.582 | 1.897  | -1.728 | 1.00 | 2.28 |
| ATOM | 1218 | 2HE2 | GLN | 76 | 14.159 | 3.474  | -1.979 | 1.00 | 2.36 |

END

METHODS FOR IDENTIFYING AGENTS THAT INTERACT WITH AN ACTIVE SITE OF ACYL CARRIER PROTEIN SYNTHASE-ACYL CARRIER PROTEIN COMPLEX

This application claims the benefit of U.S. Provisional Application No. 60/202,466 filed May 8, 2000.

FIELD OF THE INVENTION

The present invention relates to the crystal structure of the ACPS/ACP complex, as well as the three-dimensional solution structure of B. subtilis ACP. These structures are critical for the design and selection of potent and selective agents which interact with ACPS and ACP, and particularly, the design of novel antibiotics.

BACKGROUND OF THE INVENTION

Acyl Carrier Proteins (ACPs) play important roles in a number of biosynthetic pathways that are dependent upon acyl group transfers [1]. They are most often associated with the biosynthesis of fatty acids [2,3], but they are also utilized in the synthesis of polyketide antibiotics [4,5], non-ribosomal peptides [6,7], and of intermediates used in the synthesis of vitamins such as the protein-bound coenzymes, lipoic acid [8] and biotin [9]. The ACP in each of these pathways is composed of 80–100 residues and is either an integrated domain in a larger multi-functional protein (Type I synthase complex) or is a structurally independent protein that is part of a non-aggregated multi-enzyme system (Type II synthase complex). Type I synthases are found in mammals, fungi and certain Mycobacteria while type II ACPs are utilized by plants and most bacteria. The Escherichia coli ACP for fatty acid synthesis has been over-expressed [10] and purified [11,12], and the solution structure has been solved by NMR spectroscopy [13]. The fact that these proteins are essential for the maturation of the organism has led to their investigation as targets for the development of new anti-microbial agents [14–18].

ACPs require post-translational modification for activity. They are converted from an inactive apo-form to an active holo-form by the transfer of the 4'-phosphopantetheinyl (P-pant) moiety of coenzyme A to a conserved serine on the ACP. The β-hydroxy side chain of the serine residue serves as a nucleophilic group attacking the pyrophosphate linkage of CoA. Evidence now suggests [19] that each synthase that is dependent upon P-pant attachment for activation has its own partner enzyme responsible for this attachment.

The post-translational modification of the ACP subunit in the fatty acid synthase is performed by holo-[acyl carrier protein] synthase (hereinafter defined as "ACPS"; Enzyme Commission No. 2.7.8.7). The best characterized member of the ACPS family is the E. coli ACPS [20]. The enzyme produces holo-ACP by transferring the P-pant moiety to Ser-36 of the E. coli apo-ACP in a magnesium dependent reaction [20] as follows:

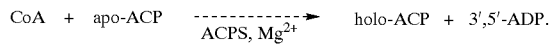

CoA + apo-ACP $\xrightarrow{\text{ACPS, Mg}^{2+}}$ holo-ACP + 3',5'-ADP.

The over-expression and purification of the E. coli ACPS has been described [21] and this protein is classified as a member of a new enzyme superfamily, the phosphopantetheinyl transferases [19]. Based on the size of the proteins, the P-pant transferase superfamily can be roughly divided into two subgroups [22]. Enzymes responsible for modifying the peptidyl carrier protein subunits of non-ribosomal peptide synthetases are good examples for the first subgroup, which are usually ~230 amino acids in size. The structure of one of this subgroup enzymes, the surfactin synthetase activating enzyme Sfp, has been solved recently and it consists of a 2-fold intramolecular pseudosymmetry with the CoA binding site at the interface of the symmetrical fold [22]. ACPS and other enzymes transfering the P-pant group onto domains of the fatty acid synthases are usually smaller, about ~120 residues, and belong to the second subgroup of the P-pant transferase superfamily. The sequence homology between these two subgroups is rather low, about 12–22% between E. coli ACPS and B. subtilis Sfp, for example, although both have been shown to possess P-pant transferase activity. Alignment [19] of some of these proteins show that two regions, residues 5–13 and 54–65 (E. coli ACPS numbering), are highly conserved with five of the residues in these regions identical.

While numerous members of the phosphopantetheinyl transferase superfamily have been identified and sequenced, until the present invention, the crystal structure of ACPS complexed with halo-ACP, and the three dimensional structure of the ACPS/ACP active site has not been determined. Further, prior to the present invention, the solution structure of B. subtilis ACP had not been determined.

SUMMARY OF THE INVENTION

The present invention relates to a crystallized complex comprising an acyl carrier protein synthase (ACPS) and an acyl carrier protein (ACP) (hereinafter referred to as "ACPS-ACP complex"). The invention is further directed to the three dimensional structure of the ACPS-ACP complex, as determined using crystallographic analysis (with or without sedimentation analysis) of the ACPS-ACP complex. Particularly, the invention is directed to the three dimensional structure of the ACP binding site present in ACPS and other ACPS-like P-pant transferases, alone, and as complexed with ACP or other agents that interact with the ACP binding site of said transferases. In addition, the invention is directed to the ACPS binding site on ACP. Identification of the three dimensional structure of the ACP binding site on ACPS and the ACPS binding site on ACP will be valuable for the design of antibiotics and other agents that interfere with P-pant attachment, thereby preventing activation of corresponding carrier proteins.

The invention additionally provides a method for identifying an agent that interacts with any active site of an ACPS-ACP complex, comprising the steps of determining a putative active site of an ACPS-ACP complex from a three dimensional model of the ACPS-ACP complex, and performing various computer fitting analyses to identify an agent which interacts with the putative active site. Again, such agents may act as inhibitors or activators of ACPS-ACP complex activity, as determined by obtaining the identified agent, contacting the same with ACPS-ACP complex, and measuring the agent's effect on ACPS-ACP complex activity.

In addition, the invention provides a solution comprising B. subtilis ACP having a three dimensional structure defined by the structural coordinates of FIG. 5 and 5-A1 to 5-A15,±a root mean square deviation from the backbone atoms of said amino acids of not more than 1.5 Å. Also provided by the invention is any active site of B. subtilis ACP that is defined by the structural coordinates of FIG. 5 and 5-A1 to 5-A15,±a root mean square deviation from the backbone atoms of said amino acids of not more than 1.5 Å. Further, the present invention provides a method for identifying an agent that interacts with any active site of *B. subtilis* ACP, comprising the steps of determining a putative active site of ACP from a three dimensional model of the ACP, and performing various computer fitting analyses to identify an agent which interacts with the putative active site. Again, such agents may act as inhibitors or activators of ACP activity, as determined by obtaining the identified agent, contacting the same with ACP, and measuring the agent's effect on ACP activity.

Yet another aspect of the present invention is a method for identifying an activator or inhibitor of any molecule or molecular complex which comprises an ACP binding site, including any member of the ACPS-like P-pant transferases, comprising the steps of generating a three dimensional model of said molecule or molecular complex using the relative structural coordinates according to FIGS. 3 and 3A-1 to 3A-79 of residues ARG14, MET18, ARG21, GLN22, ARG24, PHE25, ARG28, PHE54, GLU58, ILE68, GLY69, ALA70, SER73 and PHE74 from a first monomer of ACPS, and residue ARG45 from a second monomer of ACPS, or additionally, of residues ASP8, ILE9, THR10, GLU11, LEU12, ILE15, ALA16, SER17, ALA19, GLY20, ALA23, ALA26, GLU27, ILE29, ALA51, LYS57, SER61, LYS62, THR66, GLY67, GLN71, LEU72, GLN75, ASP76, ILE77 and LYS93 from the first monomer of ACPS and residues LEU41, SER42, LYS44, GLU48, GLN83, ASN84, HIS105, THR106 and ALA107 from the second monomer of ACPS, in each case±a root mean square deviation from the backbone atoms of said amino acids of not more than 1.5 Å, and then selecting or designing a candidate activator or inhibitor that interacts with said molecule or molecular complex using computer fitting analyses of interactions between the three dimensional model of the molecule or molecular complex and the candidate activator or inhibitor. The effect of the candidate activator or inhibitor may be evaluated by obtaining the candidate activator or inhibitor, contacting the same with the molecule or molecular complex, and measuring the effect of the candidate activator or inhibitor on molecular or molecular complex activity.

In addition, the present invention provides a method for identifying an activator or inhibitor of any molecule or molecular complex which comprises an ACPS binding site, comprising the steps of generating a three dimensional model of said molecule or molecular complex comprising an ACPS binding site using the relative structural coordinates according to FIGS. 3 and 3A-1 to 3A-79 or FIGS. 5 and 5-A1 to 5-A15 of residues ARG14, LYS29, ASP35, SER36, LEU37, ASP38, VAL40, GLU41, VAL43, MET44, GLU47, ASP48, ILE54, SER55, ASP56, GLU57 and GLU60, or additionally, of residues ASP13, LEU15, PHE28, GLU30, ASP31, LEU32, GLY33, ALA34, VAL39, LEU42, GLU45, LEU46, GLU49, MET52, GLU53, ASP58, ALA59, and LYS61, in each case±a root mean square deviation from the backbone atoms of said amino acids of not more than 1.5 Å, and then selecting or designing a candidate activator or inhibitor that interacts with said molecule or molecular complex using computer fitting analyses of interactions between the three dimensional model of the molecule or molecular complex and the candidate activator or inhibitor. The effect of the candidate activator or inhibitor may be evaluated by obtaining the candidate activator or inhibitor, contacting the same with the molecule or molecular complex, and measuring the effect of the candidate activator or inhibitor on molecular or molecular complex activity. Also provided by the present invention are the activators or inhibitors selected or designed using the above-noted methods.

Still further, the present invention is directed to a method of determining the three dimensional structure of a molecule or molecular complex whose structure is unknown, comprising the steps of first obtaining crystals of the molecule or molecular complex whose structure is unknown, and then generating X-ray diffraction data from the crystallized molecule or molecular complex. The X-ray diffraction data from the molecule or molecular complex is compared with the known three dimensional structures determined from the ACPS-ACP crystals of the present invention, and molecular replacement analysis is used to conform the known three dimensional structures to the X-ray diffraction data from the crystallized molecule or molecular complex.

In addition, the present invention provides the ACP active site of an ACPS-like P-pant transferase, including, but not limited to, an ACPS, comprising the structural coordinates according to FIGS. 3 and 3A-1 to 3A-79 of residues ARG14, MET18, ARG21, GLN22, ARG24, PHE25, ARG28, PHE54, GLU58, ILE68, GLY69, ALA70, SER73 and PHE74 from a first monomer of ACPS, and residue ARG45 from a second monomer of ACPS, in each case±a root mean square deviation from the backbone atoms of said amino acids of not more than 1.5 Å. In another embodiment, the active site may include, in addition to the structural coordinates above, the relative the structural coordinates according to FIGS. 3 and 3A-1 to 3A-79 of residues ASP8, ILE9, THR10, GLU11, LEU12, ILE15, ALA16, SER17, ALA19, GLY20, ALA23, ALA26, GLU27, ILE29, ALA51, LYS57, SER61, LYS62, THR66, GLY67, GLN71, LEU72, GLN75, ASP76, ILE77 and LYS93 from one monomer of ACPS and residues LEU41, SER42, LYS44, GLU48, GLN83, ASN84, HIS105, THR106 and ALA107 from a second monomer of ACPS, in each case±a root mean square deviation from the backbone atoms of said amino acids of not more than 1.5 Å.

Finally, the present invention provides the ACPS active site of ACP, comprising the structural coordinates according to FIGS. 3 and 3A-1 to 3A-79 or FIGS. 5 and 5-A1 to 5-A15 of residues ARG14, LYS29, ASP35, SER36, LEU37, ASP38, VAL40, GLU41, VAL43, MET44, GLU47, ASP48, ILE54, SER55, ASP56, GLU57 and GLU60, in each case±a root mean square deviation from the backbone atoms of said amino acids of not more than 1.5 Å. In another embodiment, the active site may include, in addition to the structural coordinates above, the relative structural coordinates according to FIGS. 3 and 3A-1 to 3A-79 or FIGS. 5 and 5-A1 to 5-A15 of residues ASP13, LEU15, PHE28, GLU30, ASP31, LEU32, GLY33, ALA34, VAL39, LEU42, GLU45, LEU46, GLU49, MET52, GLU53, ASP58, ALA59, and LYS61,±a root mean square deviation from the backbone atoms of said amino acids of not more than 1.5 Å.

BRIEF DESCRIPTION OF THE FIGURES

FIG. 1 depicts the amino acid sequences for the forms of ACP (SEQ ID NO:1) and ACPS (SEQ ID NO:2) used in the growth of ACP/ACPS complex crystals.

FIG. 2 illustrates the alignment of amino acid sequences for twelve members of the ACPS family, including the consensus sequence. Depicted are amino acid sequences for Aquifex (SEQ ID NO:3), Chlamydophila (SEQ ID NO:4), Helicobacter (SEQ ID NO:5), Staphylococcus (SEQ ID NO:6), Thermotoga (SEQ ID NO:7), Escherichia (SEQ ID NO:8), Rickettsia (SEQ ID NO:9), Streptomyces (SEQ ID NO:10), Treponema (SEQ ID NO:11), Bacillus (SEQ ID NO:12), Bradyrhizobium (SEQ ID NO:13), and Mycobacterium (SEQ ID NO:14).

FIGS. 3 and 3A-1 to 3A-79 provides the atomic structural coordinates for ACPS and ACP as derived by X-ray diffraction of an ACPS-ACP crystal. "Atom type" refers to the atom whose coordinates are being measured. "Residue" refers to the type of residue of which each measured atom is a part—i.e., amino acid, cofactor, ligand or solvent. The "x, y and z" coordinates indicate the Cartesian coordinates of each measured atom's location in the unit cell (Å). "Occ" indicates the occupancy factor. "B" indicates the "B-value", which is a measure of how mobile the atom is in the atomic structure (Å$^2$). "MOL" indicates the segment identification used to uniquely identify each molecule. Under "MOL", "A1", "B1" and "C1" refers to each molecule of ACPS, "AP1", "AP2" and "AP3" refers to each molecule of ACP, and "W" refers to water molecules.

FIG. 4 represents the sequence alignment of *B. subtilis* ACP, *E. coli* ACP (SEQ ID NO:15), and *Streptomyces coelicolor* A3(2) ACP (SEQ ID NO:16).

FIGS. 5 and 5-A1 to 5-A15 provides the atomic structural coordinates for the restrained minimized mean structure of *B. subtilis* ACP as derived by NMR spectroscopy. "Atom type" refers to the atom whose coordinates are being measured. "Residue" refers to the type of residue of which each measured atom is a part—i.e., amino acid, cofactor, ligand or solvent. The "x, y and z" coordinates indicate the Cartesian coordinates of each measured atom's location (Å). The last column indicates the temperature factor field, representing the rms deviation of the 22 individual NMR structures about the restrained minimized mean structure. All non-protein atoms are listed as HETATM instead of atoms using PDB conventions.

DETAILED DESCRIPTION OF THE INVENTION

As used herein, the following terms and phrases shall have the meanings set forth below:

"ACPS" includes acyl carrier protein synthases as well as "ACPS-like" P-pant transferases. Acyl carrier protein synthases produce a holo-fatty acid synthase ACP by transferring the P-pant moiety to Ser-36 (or equivalent Serine) of an apo-fatty acid synthase ACP in a magnesium dependent reaction. "ACPS-like" P-pant transferases are those enzymes having P-pant transferase activity (i.e., that transfer the 4'-phosphopantetheinyl moiety of CoA to a conserved serine on the corresponding target molecule) which form homodimers and activate the ACP domains or subunits of fatty acid synthases, polyketide synthases or other enzymes.

As used herein, "ACP" is the carrier of fatty acids during fatty acid biosynthesis, is responsible for acyl group activation and includes a 4'-phosphopantetheine (4'-PP) prosthetic group in which the 4'-PP moiety is attached through a phosphodiester linkage to a specific conserved serine residue. "ACP" also includes an active (holo) and inactive (apo) form where activation of ACP is mediated by Holo-acyl carier protein synthase (ACPS), and is preferably the active (holo) form.

Unless otherwise indicated, "protein" shall include a protein, protein domain, polypeptide or peptide.

"Structural coordinates" are the Cartesian coordinates corresponding to an atom's spatial relationship to other atoms in a molecule or molecular complex. Structural coordinates may be obtained using x-ray crystallography techniques or NMR techniques, or may be derived using molecular replacement analysis or homology modeling. Various software programs allow for the graphical representation of a set of structural coordinates to obtain a three dimensional representation of a molecule or molecular complex. The structural coordinates of the present invention may be modified from the original sets provided in FIGS. 3 and 3A-1 to 3A-79 or FIGS. 5 and 5-A1 to 5-A15 by mathematical manipulation, such as by inversion or integer additions or subtractions. As such, it is recognized that the structural coordinates of the present invention are relative, and are in no way specifically limited by the actual x, y, z coordinates of FIGS. 3 and 3A-1 to 3A-79 and FIGS. 5 and 5-A1 to 5-A15.

An "agent" shall include a protein, polypeptide, peptide, nucleic acid, including DNA or RNA, molecule, compound, antibiotic or drug.

"Root mean square deviation" is the square root of the arithmetic mean of the squares of the deviations from the mean, and is a way of expressing deviation or variation from the structural coordinates of ACPS and ACP described herein. The present invention includes all embodiments comprising conservative substitutions of the note amino acid residues resulting in same structural coordinates within the stated root mean square deviation.

It will be obvious to the skilled practitioner that the numbering of the amino acid residues in the various isoforms of ACPS, other ACPS-like P-pant transferases and ACP may be different than that set forth herein or may contain certain conservative amino acid substitutions that yield the same three dimensional structures as those defined in FIGS. 3 and 3A-1 to 3A-79 and FIGS. 5 and 5-A1 to 5-A15. Corresponding amino acids and conservative substitutions in other isoforms or analogues are easily identified by visual inspection of the relevant amino acid sequences or by using commercially available homology software programs (e.g., MODELLAR, MSI, San Diego, Calif.).

"Conservative substitutions" are those amino acid substitutions which are functionally equivalent to the substituted amino acid residue, either by way of having similar polarity, steric arrangement, or by belonging to the same class as the substituted residue (e.g., hydrophobic, acidic or basic) and includes substitutions having an inconsequential effect on the three dimensional structure of the ACPS-ACP complex, and the solution structure of *B. subtilis* ACP, with respect to the use of said structures for the identification and design of agents which interact with ACPS and ACP, for molecular replacement analyses and/or for homology modeling.

As used herein, an "active site" refers to a region of a molecule or molecular complex that, as a result of its shape and charge potential, favorably interacts or associates with another agent (including, without limitation, a protein, polypeptide, peptide, nucleic acid, including DNA or RNA, molecule, compound, antibiotic or drug) via various covalent and/or non-covalent binding forces.

As such, the active site of the ACPS-ACP complex may include both the actual site of ACP binding with ACPS, as well as accessory binding sites adjacent or proximal to the actual site of ACP binding that nonetheless may affect ACPS, ACPS-ACP or ACP activity upon interaction or association with a particular agent, either by direct interference with the actual site of ACP binding or by indirectly affecting the steric conformation or charge potential of the ACPS molecule and thereby preventing or reducing ACP binding to ACPS at the actual site of ACP binding. As used herein, an active site of ACPS-ACP also includes ACPS or ACPS analog residues which exhibit observable NMR perturbations in the presence of a binding ligand, such as ACP. While such residues exhibiting observable NMR perturbations may not necessarily be in direct contact with or immediately proximate to ligand binding residues, they may be critical to ACPS residues for rational drug design protocols.

The active site of ACP includes a region of ACP that, as a result of its shape and charge potential, favorably interacts or associates with another agent (including, without limitation, a protein, polypeptide, peptide, nucleic acid, including DNA or RNA, molecule, compound, antibiotic or drug) via various covalent and/or non-covalent binding forces. Preferably, the active site on ACP is the site of interaction with ACPS.

The present invention is directed to a crystallized ACPS-ACP complex that effectively diffracts X-rays for the determination of the structural coordinates of the ACPS-ACP complex. As used herein, the proteins used in the ACPS-ACP crystal complex of the present invention includes any ACPS or ACP protein (i.e., as used herein, any protein, polypeptide or peptide), isolated from any source (including, but not limited to, a protein isolated from Aquifex, Chlamydophila, Helicobacter, Staphylococcus, Thermotoga, Escherichia, Rickettsia, Streptomyces, Treponema, Bacillus, Bradyrhizobium, and Mycobacterium). In a preferred embodiment of the invention, ACPS and ACP are both cloned and isolated from *B. subtilis*, and overexpressed in a commercially available *E. coli* system.

The ACPS protein in the ACPS/ACP complex includes ACPS as well as proteins having ACPS-like P-pant transferase activity, including the consensus sequence shown in FIG. 2. More preferably, the ACPS protein or proteins having ACPS-like P-pant transferase activity, comprises the relative structural coordinates according to FIGS. 3 and 3A-1 to 3A-79 for the residues ARG14, MET18, ARG21, GLN22, ARG24, PHE25, ARG28, ARG45, PHE54, GLU58, ILE68, GLY69, ALA70, SER73 and PHE74, or conservative substitutions thereof, and additionally, the residues ASP8, ILE9, THR10, GLU11, LEU12, ILE15, ALA16, SER17, ALA19, GLY20, ALA23, ALA26, GLU27, ILE29, LEU41, SER42, ALA44, GLU48, ALA51, LYS57, SER61, LYS62, THR66, GLY67, GLN71, LEU72, GLN75, ASP76, ILE77, GLN83, ASN84, LYS93, HIS105, THR106 and ALA107, or conservative substitutions thereof. More particularly, the ACPS protein or proteins having ACPS-like P-pant transferase activity include an ACP binding site defined using the relative structural coordinates according to FIGS. 3 and 3A-1 to 3A-79 of residues ARG14, MET18, ARG21, GLN22, ARG24, PHE25, ARG28, PHE54, GLU58, ILE68, GLY69, ALA70, SER73 and PHE74 from a first monomer of ACPS, and residue ARG45 from a second monomer of ACPS, or additionally including the relative structural coordinates of residues ASP8, ILE9, THR10, GLU11, LEU12, ILE15, ALA16, SER17, ALA19, GLY20, ALA23, ALA26, GLU27, ILE29, ALA51, LYS57, SER61, LYS62, THR66, GLY67, GLN71, LEU72, GLN75, ASP76, ILE77 and LYS93 from the first monomer of ACPS and residues LEU 41, SER42, ALA44, GLU48, GLN83, ASN84, HIS105, THR106 and ALA107 from the second monomer of ACPS. In each case, the±a root mean square deviation from the backbone atoms of the amino acids is not more than 1.5 Å, more preferably not more than 1.0 Å, and most preferably, not more than 0.5 Å.

The ACP protein in the ACPS/ACP complex includes ACP and proteins having ACP activity, and preferably comprises the relative structural coordinates according to FIGS. 3 and 3A-1 to 3A-79 or FIGS. 5 and 5-A1 to 5-A15 for the residues ARG14, LYS29, ASP35, SER36, LEU37, ASP38, VAL40, GLU41, VAL43, MET44, GLU47, ASP48, ILE54, SER55, ASP56, GLU57 and GLU60, or conservative substitutions thereof, and additionally, the residues ASP13, LEU15, PHE28, LYS29, GLU30, ASP31, LEU32, GLY33, ALA34, ASP35, SER36, LEU37, ASP38, VAL39, LEU42, GLU45, LEU46, GLU49, MET52, GLU53, ASP58, ALA59 and LYS61, or conservative substitutions thereof, in each case±a root mean square deviation from the backbone atoms of said amino acids of not more than 1.5 Å, or more preferably not more than 1.0 Å, or most preferably, not more than 0.5 Å.

The crystals of the present invention may take a wide variety of forms, all of which are included in the present invention. However, in a preferred embodiment of the present invention, the ACPS-ACP crystallized complex is characterized as being in rod-shape form with space group $C222_1$, and having unit cell parameters of a=78.46 Å, b=122.03 Å and c=136.77 Å, and consists of three molecules of ACPS and three molecules of ACP in an asymmetric unit.

Once a crystal or crystal complex of the present invention is grown, X-ray diffraction data can be collected by a variety of means in order to obtain the atomic coordinates of the crystallized molecule or molecular complex. With the aid of specifically designed computer software, such crystallographic data can be used to generate a three dimensional structure of the molecule or molecular complex. Various methods used to generate and refine the three dimensional structure of a crystallized molecule or molecular structure are well known to those skilled in the art, and include, without limitation, multiwavelength anomalous dispersion (MAD), multiple isomorphous replacement, reciprocal space solvent flattening, molecular replacement, and single isomorphous replacement with anomalous scattering (SIRAS).

The present invention is also directed to an ACP active site of an ACPS-like P-pant transferase, including the active site of ACPS, and comprising the structural coordinates according to FIGS. 3 and 3A-1 to 3A-79 of residues ARG14, MET18, ARG21, GLN22, ARG24, PHE25, ARG28, PHE54, GLU58, ILE68, GLY69, ALA70, SER73 and PHE74 from one monomer of ACPS, and residue ARG45 from a second monomer of ACPS, in each case±a root mean square deviation from the backbone atoms of said amino acids of not more than 1.5 Å, or more preferably not more than 1.0 Å, or most preferably, not more than 0.5 Å. Alternatively, the active site may include, in addition to the structural coordinates define above, the structural coordinates according to FIGS. 3 and 3A-1 to 3A-79 of residues ASP8, ILE9, THR10, GLU11, LEU12, ILE15, ALA16, SER17, ALA19, GLY20, ALA23, ALA26, GLU27, ILE29, ALA51, LYS57, SER61, LYS62, THR66, GLY67, GLN71, LEU72, GLN75, ASP76, ILE77 and LYS93 from the first monomer of ACPS and residues LEU41, SER42, LYS44, GLU48, GLN83, ASN84, HIS105, THR106 and ALA107 from the second monomer of ACPS, in each case±a root mean square deviation from the backbone atoms of said amino acids of not more than 1.5 Å, or more preferably not more than 1.0 Å, or most preferably, not more than 0.5 Å. Preferably, the ACP active site corresponds to the configuration of the ACPS molecule in its state of association or inactivation with an agent, and preferably, ACP.

In addition, the present invention provides the ACPS active site of an ACP that comprises the structural coordinates according to FIGS. 3 and 3A-1 to 3A-79 or FIGS. 5 and 5-A1 to 5-A15 of residues ARG14, LYS29, ASP35, SER36, LEU37, ASP38, VAL40, GLU41, VAL43, MET44, SER47, ASP48, ILE54, SER55, ASP56, GLU57 and GLU60,±a root mean square deviation from the backbone atoms of said amino acids of not more than 1.5 Å, or more preferably not more than 1.0 Å, or most preferably, not more than 0.5 Å. Alternatively, the active site further includes, in addition to the coordinates defined above, the structural coordinates according to FIGS. 3 and 3A-1 to 3A-79 or FIGS. 5 and 5-A1 to 5-A15 of residues ASP13, LEU15, PHE28, GLU30, ASP31, LEU32, GLY33, ALA34, VAL39, LEU42, GLU45, LEU46, GLU49, MET52, GLU53, ASP58, ALA59, and LYS61,±a root mean square deviation from the backbone atoms of said amino acids of not more than 1.5 Å, or more preferably not more than 1.0 Å, or most preferably, not more than 0.5 Å. Preferably, the ACPS active site corresponds to the configuration of the ACP molecule in its state of association or inactivation with an agent, and preferably, ACPS.

Another aspect of the present invention is directed to a method for identifying an agent that interacts with an active site of an ACPS-ACP complex, comprising the steps of determining an active site of the ACPS-ACP complex from a three dimensional model of the ACPS-ACP complex and performing computer fitting analyses to identify an agent which interacts with said active site. Computer fitting analyses utilize various computer software programs that evaluate the "fit" between the putative active site and the identified agent, by (a) generating a three dimensional model of the putative active site of a molecule or molecular complex using homology modeling or the atomic structural coordinates of the active site, and (b) determining the degree of association between the putative active site and the identified agent. Three dimensional models of the putative active site may be generated using any one of a number of methods known in the art, and include, but are not limited to, homology modeling as well as computer analysis of raw data generated using crystallographic or spectroscopy data. Computer programs used to generate such three dimensional models and/or perform the necessary fitting analyses include, but are not limited to: GRID (Oxford University, Oxford, UK), MCSS (Molecular Simulations, San Diego, Calif.), AUTODOCK (Scripps Research Institute, La Jolla, Calif.), DOCK (University of California, San Francisco, Calif.), Flo99 (Thistlesoft, Morris Township, N.J.), Ludi (Molecular Simulations, San Diego, Calif.), QUANTA (Molecular Simulations, San Diego, Calif.), Insight (Molecular Simulations, San Diego, Calif.), SYBYL (TRIPOS, Inc., St. Louis. Mo.) and LEAPFROG (TRIPOS, Inc., St. Louis, Mo.).

The effect of such an agent identified by computer fitting analyses on ACPS-ACP complex activity may be further evaluated by contacting the identified agent with the ACPS-ACP complex and measuring the effect of the agent on ACPS-ACP complex activity. Depending upon the action of the agent on the active site of ACPS-ACP complex, the agent may act either as an inhibitor or activator of ACPS-ACP complex activity. Enzymatic assays may be performed and the results analyzed to determine whether the agent is an inhibitor of ACPS-ACP complex activity (i.e., the agent may reduce or prevent binding affinity between ACPS and ACP, and thereby reduce the level or rate of ACPS-ACP activity compared to baseline), or an activator of ACPS-ACP activity (i.e., the agent may increase binding affinity between ACPS and ACP, and thereby increase the level or rate of ACPS activity compared to baseline). Further tests may be performed to evaluate the effect of the identified agent on bacterial or eukaryotic cell populations, wherein an inhibitor of ACPS-ACP activity inhibits cell viability or reproduction.

The present invention is not limited to identifying agents which interact with an active site of the ACPS-ACP complex, but also is directed to a method for identifying an activator or inhibitor of any molecule or molecular complex comprising an ACP binding site or an ACPS binding site. The candidate activator or inhibitor is selected or designed by performing computer fitting analyses of said candidate agent with the three dimensional model of the molecule or molecular complex comprising the active site. Once the candidate activator or inhibitor is obtained, it may be contacted with the molecule or molecular complex in order to measure the effect the candidate activator or inhibitor has on said molecule or molecular complex.

In this regard, a potential activator or inhibitor of a molecule or molecular complex comprising an ACP binding site, is obtained by (a) generating a three dimensional model of said molecule or molecular complex comprising an ACP binding site using the relative structural coordinates according to FIGS. 3 and 3A-1 to 3A-79 of residues ARG14, MET18, ARG21, GLN22, ARG24, PHE25, ARG28, PHE54, GLU58, ILE68, GLY69, ALA70, SER73 and PHE74 from a first monomer of ACPS, and residue ARG45 from a second monomer of ACPS, and (b) selecting or designing a candidate activator or inhibitor by performing computer fitting analysis of the candidate activator or inhibitor with the three dimensional model generated in step (a). In another embodiment, the relative structural coordinates further include the relative structural coordinates according to FIGS. 3 and 3A-1 to 3A-79 of residues ASP8, ILE9, THR10, GLU11, LEU12, ILE15, ALA16, SER17, ALA19, GLY20, ALA23, ALA26, GLU27, ILE29, ALA51, LYS57, SER61, LYS62, THR66, GLY67, GLN71, LEU72, GLN75, ASP76, ILE77 and LYS93 from said first monomer of ACPS and residues LEU41, SER42, LYS44, GLU48, GLN83, ASN84, HIS105, THR106 and ALA107 from said second monomer of ACPS. In each case, the±a root mean square deviation from the backbone atoms of the amino acids is not more than 1.5 Å, preferably not more than 1.0 Å, and most preferably is not more than 0.5 Å.

A potential activator or inhibitor of a molecule or molecular complex comprising an ACPS binding site, may be obtained by (a) generating a three dimensional model of said molecule or molecular complex comprising an ACPS binding site using the relative structural coordinates according to FIGS. 3 and 3A-1 to 3A-79 or FIGS. 5 and 5-A1 to 5-A15 of residues ARG14, LYS29, ASP35, SER36, LEU37, ASP38, VAL40, GLU41, VAL43, MET44, GLU47, ASP48, ILE54, SER55, ASP56, GLU57 and GLU60, and (b) selecting or designing a candidate activator or inhibitor by performing computer fitting analysis of the candidate activator or inhibitor with the three dimensional model generated in step (a). In another embodiment, the relative structural coordinates further include the relative structural coordinates according to FIGS. 3 and 3A-1 to 3A-79 or FIGS. 5 and 5-A1 to 5-A15 of residues ASP13, LEU15, PHE28, GLU30, ASP31, LEU32, GLY33, ALA34, VAL39, LEU42, GLU45, LEU46, GLU49, MET52, GLU53, ASP58, ALA59, and LYS61. In each case, the±a root mean square deviation from the backbone atoms of the amino acids is not more than 1.5 Å, preferably not more than 1.0 Å, and most preferably is not more than 0.5 Å.

In addition, the invention provides a solution comprising B. subtilis ACP having a three dimensional structure defined by the structural coordinates of FIGS. 5 and 5-A1 to 5-A15,±a root mean square deviation from the backbone atoms of said amino acids of not more than 1.5 Å, more preferably not more than 1.0 Å, and most preferably not more than 0.5 Å. Also provided by the invention is any active site of B. subtilis ACP that is defined by the structural coordinates of FIGS. 5 and 5-A1 to 5-A15,±a root mean square deviation from the backbone atoms of said amino acids of not more than 1.5 Å, more preferably not more than 1.0 Å, and most preferably not more than 0.5 Å. In addition, the invention provides a method for identifying an agent that interacts with any active site of *B. subtilis* ACP, comprising the steps of determining a putative active site of ACP from a three dimensional model of the ACP, and performing various computer fitting analyses to identify an agent which interacts with the putative active site. Again, such agents may act as inhibitors or activators of ACP activity, as determined by obtaining the identified agent, contacting the same with ACP, and measuring the agent's effect on ACP activity. In the preferred embodiment, the three dimensional structure of *B. subtilis* ACP is defined by the relative structural coordinates of FIGS. 5 and 5-A1 to 5-A15,±a root mean square deviation from the backbone atoms of said amino acids of not more than 1.5 Å, or more preferably not more than 1.0 Å, or most preferably, not more than 0.5 Å. The use of the NMR solution structure of ACP for the identification of inhibitor binding sites on ACP, for the determination of the solution structure of ACP-inhibitor complexes, and for inhibitor design, is described further below in Examples 3–5.

Various molecular analysis and rational drug design techniques are further disclosed in U.S. Pat. Nos. 5,834,228, 5,939,528 and 5,865,116, as well as in PCT Application No. PCT/US98/16879, published WO 99/09148, the contents of which are hereby incorporated by reference.

The present invention is also directed to the agents, activators or inhibitors identified using the foregoing methods. Such agents, activators or inhibitors may be a protein, polypeptide, peptide, nucleic acid, including DNA or RNA, molecule, compound, antibiotic or drug.

Finally, the present invention is further directed to a method for determining the three dimensional structure of a molecule or molecular complex whose structure is unknown, comprising the steps of obtaining crystals of the molecule or molecular complex whose structure is unknown and generating X-ray diffraction data from the crystallized molecule or molecular complex. The X-ray diffraction data from the molecule or molecular complex is then compared with the known three dimensional structure determined from the ACPS-ACP crystals of the present invention. Then, the known three dimensional structure determined from the crystals of the present invention is "conformed" using molecular replacement analysis to the X-ray diffraction data from the crystallized molecule or molecular complex. Alternatively, spectroscopic data or homology modeling may be used to generate a putative three dimensional structure for the molecule or molecular complex, and the putative structure is refined by conformation to the known three dimensional structure determined from the ACPS-ACP crystals of the present invention.

The present invention may be better understood by reference to the following non-limiting Examples. The following Examples are presented in order to more fully illustrate the preferred embodiments of the invention, and should in no way be construed as limiting the scope of the present invention.

EXAMPLE 1

Crystal Structure of ACPS/ACP Complex

1. Material and Methods

Crystallization of ACPS with ACP. Purified ACP and ACPS were mixed at a 1:1.1 molar ratio and the mixture was loaded onto a gel filtration column. The resulting purified complex was dialyzed against a solution containing 50 mM Bis-Tris pH 6.4, 100 mM NaCl, 10 mM $MgCl_2$, and 10 mM DTT before concentrating the complex to ~10 mg/mL.

Crystallization conditions for the ACP/ACPS complex were also determined using the sparse matrix screens available from both Hampton Research and Emerald Biostructures. Screens were set up with 2 µL drops at both 18° C. and 4° C. Optimization of a crystalline hit (2M Potassium Formate, 20% PEG 3350) gave diffraction quality rod shaped crystals. Crystals could be obtained between 0.15M and 0.3M Potassium Formate and between 15 and 23% PEG 3350. The rate of growth seriously affected the quality of crystals with the optimal crystals being formed between 8 and 12 days after setup. The crystals were grown with a 1:2 drop ratio of protein to well solution at 18° C. These crystals belonged to space group $C222_1$ with unit cell parameters a=78.46, b=122.03, c=136.77 Å and contained three molecules of ACPS and three molecules of ACP in the asymmetric unit.

Data Collection. Data from the ACP/ACPS complex crystals were collected using a R-Axis IV mounted on a Rigaku RUH2R rotating anode operating at 5 kW from a single crystal, cooled to −180° C. The data to 2.3 Å were collected for the ACP/ACPS complex crystal using one-degree oscillations. The data were processed using DENZO and Scalepack [23] and the statistics from refinement are given in Table 2.

Model Building and Refinement. The structure of the ACP/ACPS complex was solved by molecular replacement using the program AMORE [24], with the trimer of ACPS as found in the ACPS/CoA structure as the probe. Prior to refinement, 10% of the data were randomly selected and designated as a $R_{free}$ test set to monitor the progress of the refinement. The structure of the ACPS trimer was then rebuilt using the X-BUILD feature in Quanta utilizing a series of omit maps. During this rebuilding, extra density was found in each active site that sharpened after each cycle of rebuilding. When the ACPS molecules had been rebuilt, the NMR structure of the *B. Subtilis* ACP was rotated into the density found in the active site. As a result of a large domain shift, a consequence of binding to ACPS, there were enough differences between the NMR structure and the X-Ray data that precluded using the NMR model as the starting point for refinement. Instead, the location of methionine 44 was noted from the NMR structure and the remainder of the ACP molecule was built into density using omit maps from that residue. Reference to the NMR structure as a source of secondary structure information allowed the structure of the three ACP molecules to be built into the electron density rapidly.

When roughly 80% of the ACP had been built into density, that ACP/ACPS model was then used as the initial model for refinement using the program CNS [25]. Following six cycles of refining and rebuilding the refinement converged with a model which contained 3 molecules of ACPS, 3 molecules of ACPS and 117 solvent molecules at an $R_{cryst}$ of 22.9% and $R_{free}$ of 28.0%. The refinement statistics are given in Table 3.

2. Results and Discussion

Needle-like crystals (0.1×0.1×0.5 mm) were grown using the hanging drop method from an equal molar solution of ACP and ACPS. These crystals belong to space group $C222_1$, with unit cell parameters a=78.46, b=122.03, c=136.77 Å and diffract to 2.3 Å using a R-Axis IV mounted on a Rigaku RUH2R rotating anode operating at 5 kW. These cell dimensions correspond to the asymmetric unit containing 3 molecules of ACPS and 3 molecules of ACP. The sequence of the ACP and ACPS used in obtaining these crystals is shown in FIG. 1. The phosphopantetheinyl group that is attached to the $O^\gamma$ of Ser-36 from ACP is not indicated in this figure.

The contacts between holo-ACP and ACPS are predominately hydrophilic in nature with almost all of the interactions occurring between helix α1 of ACPS and helix α2 of ACP. There are only two significant hydrophobic contacts and these both involve residues (Leu-37 and Met-44) from ACP protruding into hydrophobic pockets on ACPS. Leu-37 extends into a pocket formed by Met-18, Phe-25, Phe-54 and Ile-15 on ACP while Met-44 binds in a pocket formed by Phe-25 and the aliphatic portion of the side chains from Arg-28 and Gln-22. Table 1 details the hydrophilic interactions.

Examination of this structure suggests that a key residue in the binding of ACP to ACPS is Arg-14 from ACPS. Arg-14 forms a salt bridge with the residue just before the reactive serine (Asp-35) of ACP and is involved in hydrogen bonding with Asp-38, two residues after the reactive serine. These interactions serve to position the ACP molecule so that one end of helix α2 from ACP is placed at the bottom of the active site and correctly orients Ser-36. As shown in FIG. 2, Arg-14 is conserved in all ACPS proteins except that from Mycobacterium in which it is an aspartic acid. Another arginine, Arg-21, of ACPS forms a salt bridge with Glu-41 from ACP. The other end of helix α2 is positioned by the interactions of Arg-24 and Gln-22 from ACPS with Asp-48 of ACP. These interactions, along with the two hydrophobic "keys" described above, lock the ACP into place.

When the structure of ACPS/CoA and ACPS/ACP are superimposed (not shown), a loop consisting of residues 64 to 78 enlarges the active site by shifting 2 Å to accommodate helix α3 from ACP. Additionally, the dipole of the α2 helix of ACP is directed at the phosphate of the CoA that is to be transferred to ACP.

Since there is a significant rearrangement of ACP upon binding to ACPS and there are only limited interactions between the ACP and ACPS, it is not surprising that the B-values indicate the ACP molecules are very mobile. The average B of the main chain atoms of the three ACPS molecules is 40.1 Å$^3$ while that of the three ACP molecules is 72.3 Å$^3$.

TABLE 1

Hydrophilic Interactions between ACP and ACPS

| ACP Residue | ACPS Residue | Distance (Å) |
|---|---|---|
| Hydrophilic | | |
| 9 LYS NZ | 308 GLU OE1 | 3.15* |
| 35 ASP OD1 | 214 ARG NH2 | 2.81 |
| 35 ASP OD2 | 214 ARG NH1 | 2.50 |
| 35 ASP OD2 | 214 ARG NH2 | 3.05 |
| 38 ASP OD1 | 214 ARG NH2 | 3.05 |
| 38 ASP OD2 | 214 ARG NH2 | 3.20 |
| 41 GLU OE1 | 221 ARG NH2 | 2.66 |
| 41 GLU OE2 | 221 ARG NE | 2.91 |
| 48 ASP OD1 | 224 ARG NH1 | 2.95 |
| 54 ILE O | 228 ARG NH2 | 2.60 |
| 56 ASP OD2 | 273 SER OG | 2.50 |
| 56 ASP OD2 | 274 PHE N | 2.85 |
| 60 GLU OE2 | 270 ALA N | 2.97 |

*denotes a symmetry related molecule

TABLE 2

Residues of ACPS from FIG. 1 that were modeled as alanine due to poor electron density beyond Cβ for ACPS long chain residue

| Amino Acid | Chain A | Chain B | Chain C |
|---|---|---|---|
| Lys13 | Ala | Ala | Lys |
| Arg21 | Ala | Arg | Ala |
| Arg32 | Ala | Arg | Ala |
| Glu40 | Ala | Ala | Glu |
| Glu43 | Glu | Ala | Ala |
| Arg45 | Arg | Ala | Arg |
| Arg70 | Arg | Ala | Ala |
| Lys81 | Lys | Ala | Lys |
| Gln83 | Ala | Gln | Gln |
| Lys86 | Lys | Ala | Lys |
| Gln96 | Gln | Gln | Ala |
| Lys107 | Lys | Ala | Ala |

TABLE 3

Statistics for Data Collection, Phase Determination, and Refinement

| | ACP/ACPS |
|---|---|
| Data Collection | |
| Wavelength (Å) | λ = 1.54 |
| resolution range (Å) | 15–2.3 |
| R$_{merge}$$^a$ | 5.7% |
| | (56.0) |
| % complete | 97.7 |
| | (94.5) |
| total reflections | 270151 |
| unique reflections | 29694 |
| I/σ(I) | 26.6 |
| | (3.5) |
| Model Refinement | |
| Maximum Resolution (Å) | 2.3 |
| R$_{work}$$^b$ (%) | 22.9 |
| R$_{free}$ (%) | 28.0 |
| <B value> (Å$^3$) | 52.3 |
| R.m.s. Deviations from ideal geometry for | |
| Bonds (Å) | 0.0156 |
| Angles (°) | 1.80 |
| B values (Å$^2$) | 2.054 |
| Non-hydrogen Protein Atoms | 6972 |
| Water Molecules | 117 |
| Ions | none |
| Other Molecules | none |

$^a$R$_{merge}$ = ½I$_h$ − <I$_h$>1/2/I$_h$, where <I$_h$> is the average intensity over symmetry equivalents. Number in parentheses reflect statistics for the last shell
$^b$R$_{work}$ = ½½F$_{obs}$½− F$_{calc}$½/½F$_{obs}$½, R$_{free}$ is equivalent to R$_{work}$, but calculated for a randomly chosen 5% (or 10%) of reflections omitted from the refinement process.

TABLE 4

Residues from ACPS which are within 4Å of ACP.

From one molecule of ACPS:

Arg-14, Met-18, Arg-21, Gln-22, Arg-24, Phe-25, Arg-28, Phe-54, Glu-58, Ile-68, Gly-69, Ala-70, Ser-73, Phe-74
From a second molecule of ACPS:

Arg-45

Residues from ACP which are within 4Å of the ACPS dimer.

Arg-14, Lys-29, Asp-35, Ser-36, Leu-37, Asp-38, Val-40, Glu-41, Val-43, Met-44, Gly-47, Asp-48, Ile-54, Ser-55, Asp-56, Glu-57, Glu-60

TABLE 5

Residues from ACPS which are within 8Å of ACP.

From one molecule of ACPS:

Asp-8, Ile-9, Thr-10, Glu-11, Leu-12, Arg-14, Ile-15, Ala-16, Ser-17, Met-18 Ala-19, Gly-20, Arg-21, Gln-22, Ala-23, Arg-24, Phe-25, Ala-26, Glu-27, Arg-28, Ile-29, Ala-51, Phe-54, Lys-57, Glu-58, Ser-61, Lys-62, Thr-66, Gly-67, Ile-68, Gly-69, Ala-70, Gln-71, Leu-72, Ser-73, Phe-74, Gln-75, Asp-76, Ile-77, Lys-93

From a second molecule of ACPS:

Leu-41, Ser-42, Lys-44, Arg-45, Glu-48, Gln-83, Asn-84, His-105, Thr-106, Ala-107

Residues from ACP which are within 8Å of the ACPS dimer.

Asp-13, Arg-14, Leu-15, Phe-28, Lys-29, Glu-30, Asp-31, Leu-32, Gly-33, Ala-34, Asp-35, Ser-36, Leu-37, Asp-38, Val-39, Val-40, Glu-41, Leu-42, Val-43, Met-44, Glu-45, Leu-46, Glu-47, Asp-48, Glu-49, Met-52, Glu-53, Ile-54, Ser-55, Asp-56, Glu-57, Asp-58, Ala-59, Glu-60, Lys-61

EXAMPLE 2

Determination of NMR Solution Structure of ACP

1. Material and Methods

B. subtilis ACP Sample Preparation. The uniform 15N and 13C-labeled B. subtilis ACP was cloned into pGEX-6P-1 vector and expressed in E. coli strain BL21DE3 (pLysS) similar to the conditions previously reported for expression of ACPS [26], except that 0.5 mM IPTG was used for induction. Purification was done using the following procedure. Typically, 20 grams of cell pellet expressing GST-ACP fusion protein was resuspended in 300 ml breaking buffer consisting of 50 mM Tris.Cl (pH 8.0), 300 mM NaCl, 10 mM $MgCl_2$ and 2 mM of freshly prepared $MnCl_2$. Protease inhibitor tablets (Boehringer Mannheim GmbH, Mannheim, Germany), RNase H and DNase I (Sigma Chemical Co., St. Louis, Mo.) were added to the solution to prevent protease activity and to decrease viscosity of the solution. The cells were lysed by three passages through a Microfluidizer and the whole lysate was rocked at room temperature for one hour to enable the conversion of holo-ACP to apo-ACP by an endogenous ACP hydrolase from E. coli [27]. Once the incubation was finished, the lysate was centrifuged at 15,000 g for 20 minutes at 4° C. to remove the cell debris. Glutathione sepharose 4B resin (Amersham Pharmacia Biotech, Piscataway, N.J.) equilibrated with the same breaking buffer was added to the clear supernatent to a rough ratio of 1 ml resin slurry per 8 mg of GST fusion protein. The mixture was incubated at 4° C. for one hour by gentle rocking and centrifuged at 3,000 g for 10 minutes to remove excess supernatent prior to packing the resin into a suitable column. The column was then washed with 5 column volume of washing buffer containing 50 mM Tris.Cl (pH 8.0), 10 mM $MgCl_2$, 5 mM DTT. The GST-ACP was eluted with wash buffer plus 60 mM freshly prepared reduced glutathione. The resulting GST-ACP solution was dialyzed overnight with Prescission Protease Cleavage buffer consisting of 50 mM Tris.Cl (pH 8.0), 150 mM NaCl, 1 mM EDTA and 1 mM DTT. The fusion protein was cleaved with Prescission Protease (Amersham Pharmacia Biotech, Piscataway, N.J.) at room temperature for three hours at a ratio of 1U enzyme per 500 µg protein. The resulting protein mixture was loaded onto a MonoQ HR16/10 column (Amersham Pharmacia Biotech) equilibrated with 50 mM Tris.Cl; pH 8.0, 150 mM NaCl and 10 mM $MgCl_2$.

NMR Data Collection. The NMR sample is a mixture of $^{15}N$-, $^{13}C$-double labeled Apo- and Holo-ACP in 50 mM Bis-Tris (pH 6.4), 100 mM NaCl, 10 mM $MgCl_2$ and 10 mM DTT with 0.02% $NaN_3$ in 5% $D_2O$/95% $H_2O$ solution. The protein concentration was <1 mM.

All spectra were recorded at 25° C. on Varian Unity+ 600 spectrometer equipped with triple-resonance $^1H/^{13}C/^{15}N$ probe and an actively shielded z-gradient pulsed field accessories. 2D-$^1H$-$^{15}N$ HSQC and all triple-resonance 3D experiments were recorded with the enhanced-sensitivity pulsed field gradient approach [28]. This approach provides coherence transfer selection both to improve sensitivity and eliminate artifacts as well as for solvent suppression.

Data sets were typically processed and displayed on SGI workstation using the program packages NMRDraw and NMRPipe [29]. A skewed 60° phase-shifted sine-bell function and a single zero-filling was used in each of the all three dimensions prior to Fourier transformation. For triple-resonance 3D experiments, the time domain was extended by a factor of two using forward-backward linear prediction in the $^{15}N$ (t2) dimension and for constant-time $^1H$-$^{13}C$ correlation experiments, mirror image linear prediction was used prior to zero-filling to the double time-domain data points [30]. The programs PIPP and STAPP [31] were used for data analysis and semi-automatic assignments [30].

The complete assignments (>95%) of the $^1H$, $^{15}N$ and $^{13}C$ resonances were based on the following experiments: CBCA(CO)NNH, HNCACB, C(CC)TOCSY_NNH, H(CC)TOCSY_NNH, HAHB(CBCACO)NNH [28,32]. 2D $^{13}C$ (methyl)-1H HSQC and methyl relay experiments used for auxiliary methyl assignments of Ile, Val and Leu residues [33–35]. Some ambiguous resonances were further confirmed by simultaneous $^{15}N/^{13}C$-edited NOESY [36].

B. subtilis ACP Structure Calculation. The NMR solution structure is based on interproton distance constraints converted from observed NOEs in both the $^{15}N$-edited NOESY [37,38] and simultaneous $^{15}N/^{13}C$-edited NOESY experiments [36]. The NOEs were classified as either strong (1.8–2.7 Å), medium (1.8–3.3 Å) or weak (1.8–5.5 Å) constraints. φ and ψ torsion angle constraints were obtained from $^{15}N$, Hα, Cα and Cβ chemical shifts using the TALOS program [39]. Upper distance limits for distances involving methyl protons and non-stereospecifically assigned methylene protons were corrected appropriately for center averaging [40], and an additional 0.5 Å was added to upper distance limits for NOEs involving methyl protons [41,42].

The structures were calculated using the hybrid distance geometry-dynamical simulated annealing method of Nilges et al. (1988) [43] with minor modifications [44] using the program XPLOR [45], adapted to incorporate pseudopotential secondary $^{13}$Cα/$^{13}$Cβ chemical shift restraints [46] and a conformational database potential [47,48]. The target function that is minimized during restrained minimization and simulated annealing comprises only quadratic harmonic terms for covalent geometry and secondary $^{13}$Cα/$^{13}$Cβ chemical shift restraints, square-well quadratic potentials for the experimental distance and torsion angle restraints, and a quartic van der Waals term for non-bonded contacts. All peptide bonds were constrained to be planar and trans. There were no hydrogen-bonding, electrostatic or 6–12 Lennard-Jones empirical potential energy terms in the target function.

The structure of B. subtilis ACP was determined from a total of 1050 distance constraints comprising 337 intra-residue, 231 sequential, 188 medium, and 240 long range distance constraints, 54 hydrogen bond constraints and 92 torsion angles constraints comprised of 46 φ and 46 ψ dihedral constraints. The hydrogen bond constraints were based on the observation of slow exchanging NH protons in a $D_2O$ solution monitored by an $^1H$-$^{15}N$ HSQC spectrum.

The final ensemble of 22 structures contained no distance constraint violations greater than 0.2 Å and no torsion angle constraint violations greater than 2°. The NMR structures are well defined. This is evident by the atomic rms distribution of the 22 simulated annealing structures about the mean coordinate positions where the backbone and all atom rms is 0.45 Å and 0.93 Å, respectively. For residues only in secondary structure regions, the backbone and all atom rms is 0.35 Å and 0.84 Å, respectively. The *B. subtilis* ACP NMR structure is consistent with a good quality structure based on PROCHECK and Ramachandran analysis [49,50]. A Ramachandran plot of the minimized average structure shows a total of 83.1% of the residues are in the most favored region, 12.7% in the additional allowed, and 2.8% in the generously allowed regions with only one residue (Val17) in a disallowed region (based on residues 6–81 of ACP). Val17 is located in a long loop between helices 1 and 2 that corresponds to a very flexible region of the protein. PROCHECK analysis indicates an overall G-factor of −0.23, a hydrogen bond energy of 0.9 and only 2 bad contacts.

2. Results and Discussion

Introduction. The biosynthesis of fatty acids consists of a series of reactions catalyzed by specific enzymatic activities [51]. The organization of the enzymatic activity is significantly different between eukaryotic cells and prokaryotic and plants cells. In eukaryotic cells large multifunctional enzymes exist with distinct domains associated with a particular function. Conversely, in prokaryotic and plant cells, the various enzymatic activities is associated with individual proteins that are loosely associated with each other. Acyl carrier protein (ACP) is a discrete small acid protein (9 KDa) in prokaryotic and plant cells that plays an essential role in fatty acid biosynthesis; whereas, ACP is a subunit of fatty acid synthetase (FAS) in animal tissue. ACP is the carrier of fatty acids during fatty acid biosynthesis in prokaryotic and plant cells and is responsible for acyl group activation [51–53].

A unique feature of ACP is the presence of the 4'-phosphopantetheine (P-pant) prosthetic group. The P-pant moiety is attached through a phosphodiester linkage to a specific conserved serine residue found in all ACPs. ACP exists in both an active (holo) and inactive (apo) form where activation of ACP is mediated by Holo-acyl carier protein synthase (ACPS). ACPS transfers the P-pant moiety from CoA to Ser-36 of Apo-ACP to produce holo-ACP and 3',5'-ADP in a $Mg^{+2}$-dependent reaction. During biosynthesis of a long-chain fatty acid, the fatty acid chain is attached to ACP via a thioester linkage to the terminal cysteamine thiol of the P-pant prosthetic group where the fatty acid chain is then elongated by the fatty acid synthetase system. A potential function of the P-pant prosthetic group is to act as a tether to transfer the growing fatty acid chains between the various enzymes or active sites in the FAS system.

ACP is a central component and plays a fundamental role in fatty acid and other biosynthetic pathways that require acyl transfer steps [54, 55–58]. The activation of ACP by ACPS is critical to this function where ACPS was identified as critical for the viability of *E. coli* [59,60]. Furthermore both ACP and ACPS are viable targets for a drug discovery program since the enzymes are essentially unique to prokaryotic cells. Since the activation of ACP is mediated by its interaction with ACPS, interfering with either the activity of ACPS or the binding interaction of ACPS with ACP may prove to be a valuable approach for developing novel antibiotics.

NMR Data. NMR data was collected on both the apo- and holo-forms of ACP. While the NMR spectra indicate distinct chemical shifts for the NH proton and amide-$^{15}N$ resonances for residues in the vicinity of the 4'-PP prosthetic group, the NMR data indicate that the structures for apo-ACP and holo-ACP are effectively identical.

Uniqueness of the *B. subtilis* ACP NMR Structure. Structures for *E. coli* and *Streptomyces coelicolor* A3(2) ACP were reported in the literature prior to initiation of our efforts on the structure determination of *B. subtilis* ACP [61–63]. Amino acid sequence alignments indicate that *E. coli* ACP is highly homologous to *B. subtilis* ACP where 53 of 76 residues are identical residue types (46) and identical residue classes (7). Comparison of *Streptomyces coelicolor* A3(2) ACP with *B. subtilis* ACP indicate 38 of 76 residues are identical residue types (17) and identical residue classes (21). The overall sequence homology suggests that the three proteins should have a similar global fold (FIG. 4).

Comparison of the published structures for *E. coli* and *Streptomyces coelicolor* A3(2) ACP with *B. subtilis* ACP indicate similar secondary structure elements for the three proteins. The overall ACP structure consists of a four α-helical bundle where three α-helices are relatively long (6–15 residues) and one helix is short (0–6 residues). Despite the similarity in the secondary structure features the global fold for the three ACP structures is distinct. This is readily apparent by the superposition of the average-minimized three-dimensional structures for the three proteins (not shown). The atomic rms deviation of the Cα trace between *E. coli* and *B. subtilis* ACP is 2.32 Å. Similarly, the deviation of the Cα trace between *Streptomyces coelicolor* A3(2) and *B. subtilis* ACP is 2.31 Å. Although the previous structures of *E. coli* ACP and *Streptomyces coelicolor* A3(2) are of poor quality, the extremely large rms differences between *E. coli* ACP, *Streptomyces coelicolor* A3(2) and *B. subtilis* ACP indicate that each structure is relatively unique and that it would not be possible to predict the structure of *B. subtilis* ACP from the structures of *E. coli* ACP and *Streptomyces coelicolor* A3(2).

The observed large rms deviations between the three ACPS structures are located mainly in the short α-helix 3 and the long loop region between α-helix 1 and 2. The short α-helix 3 is not present in some models of both *E. coli* and *Streptomyces coelicolor* A3(2) ACP and is not present in the average minimized *Streptomyces coelicolor* A3(2) ACP structure. Some of the observed differences between the *B. subtilis* ACP structure and both the *E. coli* and *Streptomyces coelicolor* A3(2) ACP structures result from unusual features of the *E. coli* and *Streptomyces coelicolor* A3(2) ACP structures. An example of an unusual feature is the presence of a large kink in α-helix 1 for *E. coli* ACP that results in this helix being extremely distorted. The observation of distinct structures for the three ACP proteins is unexpected given the reasonable sequence homology and the obvious fact that the proteins are functionally identical. A potential cause for the structural difference may be a function of the structure determination process instead of a difference that may be attributed to the origin of the proteins.

The available structural information for ACP has been obtained by NMR methodologies over a span of ~12 years. During this time-period NMR technology has been vastly improved resulting in the ability to obtain high-resolution structures of increasingly larger proteins [64–66]. As a result, the methodology applied to determining the *B. subtilis* ACP structure is inherently superior to the techniques used for the *E. coli* and *Streptomyces coelicolor* A3(2) ACP structures. Invariably, the precision and accuracy of a protein structure determined by NMR is dependent on the number and reliability of the structural constraints interpreted from the NMR data [64,67]. The inherent reliability of the interpretation of the structural constraints is dependent on the number of available constraints. This relationship exists since a given structure has to be consistent with all the available constraints. So, the more constraints that are available for determining a structure the higher the likelihood that erroneous data will be identified by being inconsistent with the abundance of correct data. Additionally, the nature of the structural constraint is critical in relationship to the accuracy of the overall structure. Intra-residue constraints convey a localized structural effect usually contributing to the residues torsion angles whereas long-range inter-residue constraints will determine the overall fold of the protein. Therefore, a protein structure with an abundance of intra-residue constraints and a minimal number of long-range constraints will result in a relatively low-resolution structure.

The structures for *E. coli* and *Streptomyces coelicolor* A3(2) ACP were based on a minimal number of distance constraints, especially long-range distance constraints, relative to the *B. subtilis* ACP structure. *E. coli* ACP (77 residues) structure was based on a total of 478 distance constraints comprising 30 H-bond distance constraints, 101 intra-residue distance constraints and 205 sequential, 87 short-range and 55 long-range inter-residue constraints. The average number of distance constraints was only 6.2 constraints per residue. Similarly, the *Streptomyces coelicolor* A3(2) ACP (86 residues) structure was based on a total of 747 distance constraints comprising 48 H-bond distance constraints, 240 intra-residue constraints, 235 sequential, 131 short-range and 93 long-range distance constraints. The average number of distance constraints for *Streptomyces coelicolor* A3(2) ACP was only 8.7 constraints per residues. Conversely, our *B. subtilis* ACP (76 residues) structure is based on a total of 1050 distance constraints with an average of 13.8 constraints per residue. Similarly, the *B. subtilis* ACP structure is based on more $\phi$, $\psi$ dihedral angle constraints relative to both *E. coli* and *Streptomyces coelicolor* A3(2) ACP. A total of 92 $\phi$ and $\psi$ dihedral angle constraints were used for the *B. subtilis* ACP structure compared to 54 and 63 for the *E. coli* and *Streptomyces coelicolor* A3(2) ACP structures, respectively. In addition, the *B. subtilis* ACP structure was refined using both $C\alpha/C\beta$ chemical shifts constraints and a conformational database potential which were not used for determining the *E. coli* and *Streptomyces coelicolor* A3(2) ACP structures. In addition to the number of constraints, the quality of the ACP structures is also reflected by the rms difference between each structure in the ensemble relative to the average structure. Typically, a high resolution NMR structure exhibits a backbone rms of <0.5 Å [64]. As apparent in Table 5, the structures for *E. coli* and *Streptomyces coelicolor* A3(2) ACP have extremely high rms values suggestive of a low to poor quality structure, whereas, *B. subtilis* ACP conforms to a rms value consistent with a high quality structure.

TABLE 5

Atomic rms Differences (Å)[a]

|  | E. coli ACP | Streptomyces coelicolor A3(2) ACP[b] | B. subtilis ACP |
|---|---|---|---|
| All Residues |  |  |  |
| Backbone | 2.3 | 1.47 | 0.45 |
| All atoms | 3.3 | 1.84 | 0.93 |
| Secondary Structure |  |  |  |
| Backbone | N.D. | 1.01 | 0.35 |
| All atoms | N.D. | 1.45 | 0.84 |

[a]The NMR ensemble for the *E. coli*, *Streptomyces coelicolor* A3(2) and *B. subtilis* ACP structures consist of 7, 24 and 22; respectively.
[b]Only residues 5–86 were used for the rms.

There is additional evidence that indicates that the previous structural efforts related to ACP were problematic which may imply that the previous ACP structures may be inaccurate relative to the structure of *B. subtilis* ACP. The NMR structure for *E. coli* ACP was published in 1988, further modified in 1990 and finally released by the PDB in 1993 (PDB:1ACP). In fact, two separate models for *E. coli* ACP were deposited in the PDB, where one model is described as "Not Energetically Ideal" and the authors suggest multiple conformers. Structural information for Spinach ACP and the nodulation protein NodF from *Rhizobium leguminosarum*, which shares homology with ACP were also published, but the NMR data was of too low a quality to determine and release a three dimensional structure [68,69]. These results clearly suggest an inherent technical difficulty that was encountered with the previous ACPs structures that was not a factor in the *B. subtilis* ACP structure.

The uniqueness of the three structures and more critically the inherent value and accuracy of the *B. subtilis* ACP was also apparent from the molecular replacement efforts for solving the X-ray structure of the *B. subtilis* ACP-ACPS complex. It was not possible to solve the X-ray structure of ACP in the *B. subtilis* ACP-ACPS complex using the *E. coli* ACP structure. A solution to the X-ray structure of ACP in the *B. subtilis* ACP-ACPS complex was only obtained when the NMR *B. subtilis* ACP structure was used as part of a molecular replacement approach.

EXAMPLE 3

Identification of Inhibitor Binding Sites on ACP

Inhibitors of the ACPS conversion of apo-ACP to holo-ACP were analyzed for direct binding to either ACP or ACPS by NMR. Inhibitor binding to ACP was monitored by chemical shift perturbations in a 2D $^1$H-$^{15}$N HSQC spectra. The observation of chemical shift perturbations in a 2D $^1$H-$^{15}$N HSQC spectra indicate both an interaction between ACP and the inhibitor and the location of the inhibitor binding site. The NMR assignments for free ACP was utilized to identify which residues have changed in the ACP-inhibitor complex. Further identification of the binding site was obtained by superimposing the perturbed residues onto the NMR structure of ACP. All of the residues that experience chemical shift changes in the presence of the inhibitor occur on a loop region corresponding to residues 53–56. This loop is spatially proximal to the conserved serine (S36) that is attached through a phosphodiester linkage to the 4'phosphopantetheine (P-pant) prosthetic group. The identification of the location of the P-pant prosthetic group was determined by chemical shift differences between the apo- and holo-forms of ACP. The proximal location of the potential inhibitor-binding site with the P-pant binding site suggests two possible mechanisms for inhibition of the ACP-ACPS activity. The activity of the inhibitor could be attributed to disruption of the binding of ACP with ACPS or it may stericly prevent the addition of the P-pant prosthetic group to ACP from CoA.

Specificity for the inhibitor to ACP is also monitored by its ability to bind ACPS. Inhibitor binding to ACPS was monitored by line-width changes in one-dimensional $^1$H titration studies. An effect of the large molecular-weight difference between ACPS and a small molecular inhibitor is the corresponding difference in the observable NMR line-widths. If the small molecule binds ACPS, it will demonstrate an apparent molecular weight similar to ACPS resulting in a dramatic increase in the NMR line-widths for the small molecule. Inhibitors identified to affect the ACP-ACPS activity have been shown to bind either ACP or ACPS.

EXAMPLE 4

Use of the ACP NMR Structure to Determine the Solution Structure of ACP-Inhibitor Complexes When an appropriate ACP inhibitor has been identified, a structure for the ACP complexed to the inhibitor may be determined from the following procedure.

NMR Data Collection. NMR sample preparation and data collection and processing were as described in Example 2, with the addition of the inhibitor in either a molar excess or a 1:1 molar ratio with ACP.

NMR Assignments. The assignments of the 1H, $^{15}$N, and $^{13}$C resonances of ACP in the ACP-inhibitor complex are based on a minimal set of experiments: 2D $^1$H-$^{15}$N HSQC, 3D $^{15}$N-edited NOESY [37,38], CBCA(CO)NH [30], C(CO)NH [71], HC(CO)NH, [71], HNHA [72] and HNCA [73].

The nearly complete resonance assignments for ACP provided the starting point for the assignments of ACP in the new inhibitor complex. Three important observations facilitated these assignments and provided a simple "boot-strap" approach using a minimal set of NMR experiments. First, as apparent by the chemical shift perturbations in a 2D $^1$H-$^{15}$N HSQC spectra, >90% of the ACP residues are unperturbed by the presence of the new inhibitor. In fact, for inhibitors that bind ACP in a similar manner the resonance assignments for ACP in the complex will be very comparable and greatly facilitate the assignment process. This indicates that the majority of the ACP structure is unaffected and that only residues in close proximity to the new inhibitor may incur a significant chemical shift change. Therefore, the backbone assignments of residues in the vicinity of the inhibitor may be obtained by following sequential NOE connectivities in the 3D $^{15}$N-edited NOESY spectra by starting with unaffected residues sequential to perturbed residues.

Second, while significant $^1$H and $^{15}$N chemical shift perturbations occur for residues in the vicinity of the inhibitor, the general NOE pattern may be intact. Simple comparison of the 3D $^{15}$N-edited NOESY spectra of ACP and the new complex may readily identify the sequential and intra-residue NOEs in the ACP:Inhibitor spectra. This provides a straight-forward approach to side-chain $^1$H assignments. Third, $^{13}$C chemical shifts generally do not incur any significant chemical shift perturbations even for residues in close proximity to the new inhibitor.

The resonance assignments and bound conformation of the inhibitor in ACP-inhibitor complex are based on the 2D $^{12}$C/$^{12}$C-filtered NOESY [74,75], 2D $^{12}$C/$^{12}$C-filtered TOCSY [74,75] and $^{12}$C/$^{12}$C-filtered COSY experiments [76]. The ACP-inhibitor NMR sample is composed of $^{13}$C/$^{15}$N labeled ACP and unlabeled inhibitor. Thus, traditional 2D-NOESY, COSY and TOCSY spectra of the inhibitor in the presence of ACP were determined from 2D $^{12}$C-filtering experiments [74–76] where only crosspeaks between protons attached to $^{12}$C carbons are observed. This efficiently filters all protein resonances and allows for the straight-forward analysis of the inhibitor spectrum.

The ACP-inhibitor structure is based on the following series of spectra: HNHA [72], HNHB [77], 3D long-range $^{13}$C-$^{13}$C correlation [78], coupled CT-HCACO [79,80], HACAHB-COSY [81], 3D $^{15}$N- [37,38] and $^{13}$C-edited NOESY [82,83], 3D $^{13}$C-edited/$^{12}$C-filtered NOESY [84], 2D $^{12}$C/$^{12}$C-filtered NOESY [74,75] and $^{15}$N-edited ROESY [85]. The $^{15}$N-edited NOESY, $^{13}$C-edited NOESY, 2D $^{12}$C/$^{12}$C-filtered NOESY, 3D $^{13}$C-edited/$^{12}$C-filtered NOESY and $^{15}$N-edited ROESY experiments were collected with 100 msec, 120 msec, 100 msec, 110 msec and 40 msec mixing times, respectively.

The ACP-inhibitor structure is based on the observed intermolecular and intramolecular NOEs from the inhibitor observed in the 3D $^{15}$N-edited NOESY [37,38], 2D $^{12}$C/$^{12}$C-filtered NOESY [74,75], 3D $^{13}$C-edited/$^{12}$C-filtered NOESY [84].

Structure Calculations. The structure calculations and distance restraints are used as described in Example 2 with the following modifications. The restraints used for the refinement of the ACP-inhibitor NMR structure are amended with the distance restraints observed between ACP and the inhibitor from the 3D $^{13}$C-edited/$^{12}$C-filtered NOESY and 3D $^{15}$N-edited NOESY experiments and the intra-molecular restraints observed for the inhibitor from the 2D $^{12}$C-filtered NOESY experiment. Additionally, the ACP NMR restraints are modified as appropriate for residues in the vicinity of the active site. This permits the structure of the ACP active site to be determined primarily by the observed inter-molecular NOEs between ACP and the inhibitor. Also, the ACP-inhibitor complex may be refined using the $^3J_{NHa}$ coupling constants determined from the HNHA [72] experiment and secondary $^{13}$Cα/$^{13}$Cβ chemical shift restraints from the assignments for the complex.

Generation of the bound conformation of the inhibitor followed the general procedure described for ACP in Example 2 with the following modifications. The bound conformation for the inhibitor is generated using QUANTA97 and CHARMM (Molecular Simulations Inc., San Diego) and the XPLOR topology and parameter files is generated using XPLOR2D [86]. Generation of the bound conformation of the inhibitor follows the following general procedure. The initial inhibitor structure is created using the QUANTA97 2D-sketcher application and is subjected to 500 steps of CHARMM minimization. NOE restraints were created using the CHARMM distance/dihedral constraint option. The NOE scaling constant is set to 500 and the structure is subject to an additional 500 steps of CHARMM minimization.

The starting ACP-inhibitor complex structure for the simulated-annealing protocol is then obtained by manually docking the bound conformation of the inhibitor into the NMR structure determined for ACP using QUANTA97. The inhibitor was then subjected to a 1000 steps of restrained CHARMM minimization using the inhibitor intramolecular and intermolecular NOE restraints while keeping coordinates for ACP fixed. This approach approximates the positioning of the inhibitor in the active site of ACP without distorting the ACP structure. The final structure is exported as a PDB file and used as the starting point for the standard XPLOR simulated annealing protocol where all residues in the structure are free to move.

EXAMPLE 5

Inhibitor Design

General. There are a number of computational software packages that may be used for the analysis of protein NMR structures. In this case, the software packages Sybyl v.6.4+ to v.6.5+ from Tripos Associates and QUANTA97 (Version 97.1003) an XPLOR (Version 3.840) from MSI were the packages used. Once the coordinates have been determined by NMR a number of steps may be taken as listed below:

1. The original coordinates are read into the software package and the three-dimensional structure is analyzed graphically. In addition, programs within QUANTA check for the correctness of the NMR coordinates with regard to features such as bond and atom types.
2. The modified (if necessary) structure is energy minimized using the QUANTA/CHARM until all the structural parameters are at their equilibrium/optimal values.
3. The energy minimized structure is superimposed against the original NMR structure to ensure there are no significant deviations between the original and minimized coordinates.

4. The protein-native ligand complex is analyzed, the interactions between the native ligand and the protein are identified. The uncomplexed structure binding site is compared to the complexed structure's binding site for areas which may be exploited by a potential inhibitor.

5. The final protein structure bound to the inhibitor is modified by removing the inhibitor so only the protein and a few residues of the natural ligand are left for analysis of the binding site cavity. The natural ligand residues are docked into the uncomplexed structure's binding site to be used as templates for SYBYL/UNITY database searching.

6. SYBYL/UNITY is used to create excluded volume and distance constrained queries for searching structural databases. Structures qualifying as 'hits' are screened for activity.

7. Once specific inhibitor-protein interactions are determined between new inhibitors and the protein structure, docking studies may be carried out between the different series of in-house inhibitors and ACP. This part gives the initial modeled complexes of new inhibitors with ACP.

To check for the integrity of the modeled new ACP-inhibitor complexes, different procedures may be used. In this case, constrained conformational analysis is carried out using molecular dynamics methods. In this modeling process, both protein and the complexed ligand are allowed to sample different 3D conformational states until the most favorable state is reached or found to exist between protein and inhibitor. The final structure as proposed by the molecular dynamics analysis is analyzed visually to make sure the modeled complex is in accord with known experimental SAR based on measured binding affinities.

REFERENCES (1) Magnuson, K., et al., *Microbiological Reviews*, 57:522–542 (1993).
(2) Lynen, F., *Eur. J. Biochem.*, 112:431–442 (1980).
(3) Wakil, S. J., et al., *Annu. Rev. Biochem.*, 52:537–579 (1983).
(4) B. Shen, B., et al., *J. Bacteriol.*, 174:3818 (1992).
(5) Hopwood, D. A., and Sherman, D. H., *Annu. Rev. Genet.*, 24:37–66 (1990).
(6) Kleinkauf, H., and Von Dohren, H., *Eur. J. Biochem.*, 236:335–351 (1996).
(7) Marahiel, M. A., *FEBS Lett.*, 307:40 (1992).
(8) White, R. H., *Biochemistry*, 19:9–15 (1980).
(9) Sanyal, I., et al., *Am. Chem. Soc.*, 116:2637–2638 (1994).
(10) Rawlings, M. and J. E. J. Cronan, *FASEB J.*, 2:A1559 (1988).
(11) Hill, R. B., et al., *Protein Expression and Purification*, 6:394–400 (1995).
(12) Rock, C. O. and J. E. J. Cronan, *Anal. Biochem.*, 102:362–364 (1980).
(13) Holak, T. A., et al., *Eur. J. Biochem.*, 175:9–15 (1988).
(14) Furukawa, H., et al., *J. Bacteriol.*, 175:3723–3729 (1993).
(15) Bergler, H., et al., *J. Biol. Chem.*, 269, 5493–5496 (1994).
(16) Banerjee, A., et al., *Science*, 263:227–230 (1994).
(17) Dessen, A., et al., *Science*, 267:1638–1641 (1995).
(18) Quemard, A., et al., *Biochemistry*, 34:8235–8241 (1995).
(19) Lambalot, R. H., et al., *Chemistry & Biology*, 3:923–936 (1996).
(20) Elovson, J. and Vagelos, P. R., *J. Biol. Chem.*, 243:3603 (1968).
(21) Lambalot, R. H. and Walsh, C. T., *J. Biol. Chem.*, 270:24658–24661 (1995).
(22) Reuter, K., et al., *The EMBO Journal*, 18:6823–6831 (1999).
(23) Otwinowski, Z. and W. Minor, *Methods Enzymol.*, 276:307–326 (1997).
(24) Navaza, J., *Acta Crystallogr.*, A50:157–163 (1994).
(25) Brunger, A. T., et al., *Acta Crystallographica*, D54:905–921 (1998).
(26) Lambalot, R. H., and Walsh, C. T., *J. Biol. Chem.*, 270:24658–61 (1995).
(27) Fischl, A. S., and Kennedy, E. P., *J. Bacteriol.*, 172:5445–9 (1990).
(28) Kay, L. E., *Prog. Biophys. Molec. Biol.*, 63: 110–126 (1995).
(29) Delaglio, F., et al., *J. Biomol. NMR*, 6: 277–293 (1995).
(30) Zhu, G., and Bax, A., *J. Magn. Reson.*, 100: 202–7 (1992).
(31) Garrett, D. S., et al., *J. Magn. Reson.*, 95: 214–20 (1991).
(32) Muhandiram, D. R., and Kay, L. E., *J. Magn. Reson., Ser. B*, 103: 203–16 (1994).
(33) Grzesiek, S., et al., *J. Biomol. Nmr*, 3: 487–93 (1993).
(34) Bax, A., Max, D., and Zax, D., *J. Am. Chem. Soc.*, 114: 6923–5 (1992).
(35) Bax, A., et al., *J. Biomol. Nmr*, 4: 787–97 (1994).
(36) Pascal, S. M., et al., *J. Magn. Reson., Ser. B*, 103: 197–201 (1994).
(37) Marion, D., et al., *Biochemistry*, 28: 6150–6 (1989).
(38) Zuiderweg, E. R. P., and Fesik, S. W., *Biochemistry*, 28: 2387–91 (1989).
(39) Cornilescu, G., et al., *J. Biomol. NMR*, 13: 289–302 (1999).
(40) Wuthrich, K., et al., *J. Mol. Biol.*, 169: 949–961(1983).
(41) Clore, G. M., et al., *Biochemistry*, 26: 8012–23 (1987).
(42) Wagner, G., et al., *J. Mol. Biol*, 196: 611–39 (1987).
(43) Nilges, M., et al., *Protein Eng*, 2: 27–38 (1988).
(44) Clore, G. M., et al., *Biochemistry*, 29: 1689–96 (1990).
(45) Brunger, A. T. X-PLOR Version 3.1 Manual, Yale University, New Haven, Conn. (1993).
(46) Kuszewski, J., et al., *J. Magn. Reson., Ser. B*, 106: 92–6 (1995).
(47) Kuszewski, J., et al., *Protein Sci.*, 5: 1067–1080 (1996).
(48) Kuszewski, J., et al., *J. Magn. Reson.*, 125: 171–177 (1997).
(49) Laskowski, R. A., et al., *J. Appl. Cryst.* 26, 283–291 (1993).
(50) Laskowski, R., et al., *Biomol NMR*, 8: 477–486 (1996).
(51) Wakil, S. J., et al., *Annu. Rev. Biochem*, 52: 537–79 (1983).
(52) Majerus, P. W., and Vagelos, P. R., *Advan. Lipid Res*, 5: 1–33 (1967).
(53) Prescott, D. J., and Vagelos, P. R., *Advan. Enzymol. Relat. Areas Mol. Biol*, 36: 269–311 (1972).
(54) Shen, B., et al., *J. Bacteriol.*, 174: 3818–21 (1992).
(55) Baldwin, J. E., et al., *J. Antibiot.*, 44: 241–8 (1991).
(56) Rusnak, F., et al., *Biochemistry*, 30: 2916–27 (1991).
(57) Geiger, O., et al., *J. Bacteriol.*, 173: 2872–8 (1991).
(58) Issartel, J. P., et al., *Nature*, 351: 759–61 (1991).
(59) Takiff, H. E., et al., *J. Bacteriol.* 174: 1544–53 (1992).
(60) Lambalot, R. H., and Walsh, C. T., *J. Biol. Chem.*, 270: 24658–61 (1995).
(61) Crump, M. P., et al., *Biochemistry*, 36: 6000–6008 (1997).

(62) Holak, T. A., et al., *Biochemistry*, 27: 6135–42 (1988).
(63) Holak, T. A., et al., *FEBS Lett.*, 242: 218–24 (1989).
(64) Clore, G. M., and Gronenbom, A. M., *Protein Science*, 3:, 372–390 (1994).
(65) Arrowsmith, C. H., and Wu, Y.-S., *Prog. Nucl. Magn. Reson. Spectrosc.*, 32: 277–286 (1998).
(66) Clore, G. M., and Gronenbom, A. M., *Trends Biotechnol.*, 16: 22–34 (1998).
(67) Clore, G. M., et al., *J. Mol. Biol.*, 231: 82–102 (1993).
(68) Ghose, R., et al., *FEBS Lett.*, 388: 66–72 (1996).
(69) Oswood, M. C., et al., *Proteins: Struct., Funct., Genet.*, 27: 131–143 (1997).
(70) Grzesiek, S., and Bax, A., *J. Am. Chem. Soc*, 114: 6291–3 (1992).
(71) Grzesiek, S., et al., *J. Magn. Reson., Ser. B*, 101: 114–19 (1993).
(72) Vuister, G. W., and Bax, A., *J. Am. Chem. Soc*, 115: 7772–7 (1993).
(73) Kay, L. E., et al., *J. Magn. Reson*, 89: 496–514 (1990).
(74) Petros, A. M., et al., *FEBS Lett.*, 308: 309–14 (1992).
(75) Gemmecker, G., et al., *J. Magn. Reson.*, 96: 199–204 (1992).
(76) Ikura, M., and Bax, A., *J. Am. Chem. Soc.*, 114: 2433–40 (1992).
(77) Archer, S. J., et al., *J. Magn. Reson.*, 95: 636–41 (1991).
(78) Bax, A., and Pochapsky, S. S., *Journal of Magnetic Resonance*, 99: 638–643 (1992).
(79) Powers, R., et al., *J. Magn. Reson.*, 94: 209–13 (1991).
(80) Vuister, G. W., et al., *J. Am. Chem. Soc*, 114: 9674–5 (1992).
(81) Grzesiek, S., et al., *J. Am. Chem. Soc*, 117: 5312–15 (1995).
(82) Zuiderweg, E. R. P., et al., *J. Magn. Reson*, 86: 210–16 (1990).
(83) Ikura, M., et al., *J. Magn. Reson*, 86: 204–9 (1990).
(84) Lee, W., et al., *FEBS Lett.*, 350: 87–90 (1994).
(85) Clore, G. M., et al., *Biochemistry*, 29: 5671–6 (1990).
(86) Kleywegt, G. J., and Jones, T. A., *Methods Enzymol.*, 277: 208–230 (1997).

All publications mentioned herein above, whether to issued patents, pending applications, published articles, or otherwise, are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A method for identifying an agent that interacts with an active site of an acyl carrier protein synthase-acyl carrier protein (ACPS-ACP) complex, comprising the steps of:

(a) obtaining a crystallized complex comprising ACPS-ACP, wherein the crystallized complex is characterized as being in rod-shape form with space group C222$_1$, and having unit cell parameters of a=78.46 Å, b=122.03 Å and c=136.77 Å;

(b) obtaining the structural coordinates of amino acids of the crystallized complex of step (a), wherein the structural coordinates are set forth in FIGS. 3 and 3A-1 to 3A-79;

(c) generating a three dimensional model of ACPS-ACP using the structural coordinates of the amino acids generated in step (b), ±a root mean square deviation from the backbone atoms of said amino acids of not more than 1.5 Å;

(d) determining an active site of the ACPS-ACP complex from said three dimensional model; and (e) performing computer fitting analysis to identify an agent which interacts with said active site.

2. The method of claim 1, further comprising contacting the identified agent with ACPS-ACP complex in order to determine the effect the agent has on ACPS-ACP complex activity.

3. The method of claim 2, wherein the agent is an inhibitor of ACPS-ACP complex activity.

4. The method of claim 2, wherein the agent is an activator of ACPS-ACP complex activity.

5. The method of claim 1, wherein the active site of ACPS determined in step (d) comprises the structural coordinates according to FIGS. 3 and 3-A1 to 3-A79 of amino acid residues ARG14, MET18, ARG21, GLN22, ARG24, PHE25, ARG28, PHE54, GLU58, ILE68, GLY69, ALA70, SER73 and PHE74 from a first monomer of ACPS, and residue ARG45 from a second monomer of ACPS, in each case±a root mean square deviation from the backbone atoms of said amino acids of not more than 1.5 Å.

6. The method of claim 5, wherein the active site of ACPS further comprises the structural coordinates according to FIGS. 3 and 3-A1 to 3-A79 of amino acid residues ASP8, ILE9, THR10, GLU11, LEU12, ILE15, ALA16, SER17, ALA19, GLY20, ALA23, ALA26, GLU27, ILE29, ALA51, LYS57, SER61, LYS62, THR66, GLY67, GLN71, LEU72, GLN75, ASP76, ILE77 and LYS93 from said first monomer of ACPS and residues LEU41, SER42, LYS44, GLU48, GLN83, ASN84, HIS105, THR106 and ALA107 from said second monomer of ACPS, in each case±a root mean square deviation from the backbone atoms of said amino acids of not more than 1.5 Å.

7. The method of claim 1, wherein the active site of ACP determined in step (d) comprises the structural coordinates according to FIGS. 3 and 3-A1 to 3-A79 of amino acid residues ARG14, LYS29, ASP35, SER36, LEU37, ASP38, VAL40, GLU41, VAL43, MET44, GLU47, ASP48, ILE54, SER55, ASP56, GLU57 and GLU60,±a root mean square deviation from the backbone atoms of said amino acids of not more than 1.5 Å.

8. The method of claim 7, wherein the active site of ACP further comprises the structural coordinates according to FIGS. 3 and 3-A1 to 3A-79 of amino acid residues ASP13, LEU15, PHE28, GLU30, ASP31, LEU32, GLY33, ALA34, VAL39, LEU42, GLU45, LEU46, GLU49, MET52, GLU53, ASP58, ALA59, and LYS61, ±a root mean square deviation from the backbone atoms of said amino acids of not more than 1.5 Å.

9. The method of claim 1, wherein the±a root mean square deviation from the backbone atoms of said amino acids is not more than 1.0 Å.

10. The method of claim 9, wherein the±a root mean square deviation from the backbone atoms of said amino acids is not more than 0.5 Å.

11. The method of claim 5, wherein the±a root mean square deviation from the backbone atoms of said amino acids is not more than 1.0 Å.

12. The method of claim 11, wherein the±a root mean square deviation from the backbone atoms of said amino acids is not more than 0.5 Å.

13. The method of claim 6, wherein the±a root mean square deviation from the backbone atoms of said amino acids is not more than 1.0 Å.

14. The method of claim 13, wherein the±a root mean square deviation from the backbone atoms of said amino acids is not more than 0.5 Å.

15. The method of claim 7, wherein the±a root mean square deviation from the backbone atoms of said amino acids is not more than 1.0 Å.

16. The method of claim 15, wherein the±a root mean square deviation from the backbone atoms of said amino acids is not more than 0.5 Å.

17. The method of claim 8, wherein the±a root mean square deviation from the backbone atoms of said amino acids is not more than 1.0 Å.

18. The method of claim 17, wherein the±a root mean square deviation from the backbone atoms of said amino acids is not more than 0.5 Å.

19. A method for identifying an agent that interacts with an active site of an acyl carrier protein synthase-acyl carrier protein (ACPS-ACP) complex, comprising the steps of:

(a) obtaining a crystallized complex comprising ACPS-ACP, wherein the crystallized complex is characterized as being in rod-shape form with space group $C222_1$, and having unit cell parameters of a=78.46 Å, b=122.03 Å and c=136.77 Å;

(b) obtaining the structural coordinates of amino acids of the crystallized complex of step (a);

(c) generating a three dimensional model of ACPS-ACP using the structural coordinates of the amino acids generated in step (b),±a root mean square deviation from the backbone atoms of said amino acids of not more than 1.5 Å;

(d) determining an active site of the ACPS-ACP complex from said three dimensional model; and (e) performing computer fitting analysis to identify an agent which interacts with said active site.

20. The method of claim 19, further comprising contacting the identified agent with ACPS-ACP complex in order to determine the effect the agent has on ACPS-ACP complex activity.

21. The method of claim 20, wherein the agent is an inhibitor of ACPS-ACP complex activity.

22. The method of claim 20, wherein the agent is an activator of ACPS-ACP complex activity.

23. The method of claim 19, wherein the active site of ACPS determined in step (d) comprises the structural coordinates of amino acid residues ARG14, MET18, ARG21, GLN22, ARG24, PHE25, ARG28, PHE54, GLU58, ILE68, GLY69, ALA70, SER73 and PHE74 from a first monomer of ACPS, and residue ARG45 from a second monomer of ACPS, in each case±a root mean square deviation from the backbone atoms of said amino acids of not more than 1.5 Å.

24. The method of claim 23, wherein the active site of ACPS further comprises the structural coordinates of amino acid residues ASP8, ILE9, THR10, GLU11, LEU12, ILE15, ALA16, SER17, ALA19, GLY20, ALA23, ALA26, GLU27, ILE29, ALA51, LYS57, SER61, LYS62, THR66, GLY67, GLN71, LEU72, GLN75, ASP76, ILE77 and LYS93 from said first monomer of ACPS and residues LEU41, SER42, LYS44, GLU48, GLN83, ASN84, HIS105, THR106 and ALA107 from said second monomer of ACPS, in each case±a root mean square deviation from the backbone atoms of said amino acids of not more than 1.5 Å.

25. The method of claim 19, wherein the active site of ACP determined in step (d) comprises the structural coordinates of amino acid residues ARG14, LYS29, ASP35, SER36, LEU37, ASP38, VAL40, GLU41, VAL43, MET44, GLU47, ASP48, ILE54, SER55, ASP56, GLU57 and GLU60, ±a root mean square deviation from the backbone atoms of said amino acids of not more than 1.5 Å.

26. The method of claim 25, wherein the active site of ACP further comprises the structural coordinates of amino acid residues ASP13, LEU15, PHE28, GLU30, ASP31, LEU32, GLY33, ALA34, VAL39, LEU42, GLU45, LEU46, GLU49, MET52, GLU53, ASP58, ALA59, and LYS61,±a root mean square deviation from the backbone atoms of said amino acids of not more than 1.5 Å.

27. The method of claim 19, wherein the±a root mean square deviation from the backbone atoms of said amino acids is not more than 1.0 Å.

28. The method of claim 27, wherein the±a root mean square deviation from the backbone atoms of said amino acids is not more than 0.5 Å.

29. The method of claim 23, wherein the±a root mean square deviation from the backbone atoms of said amino acids is not more than 1.0 Å.

30. The method of claim 29, wherein the±a root mean square deviation from the backbone atoms of said amino acids is not more than 0.5 Å.

31. The method of claim 24, wherein the±a root mean square deviation from the backbone atoms of said amino acids is not more than 1.0 Å.

32. The method of claim 31, wherein the±a root mean square deviation from the backbone atoms of said amino acids is not more than 0.5 Å.

33. The method of claim 25, wherein the±a root mean square deviation from the backbone atoms of said amino acids is not more than 1.0 Å.

34. The method of claim 33, wherein the±a root mean square deviation from the backbone atoms of said amino acids is not more than 0.5 Å.

35. The method of claim 26, wherein the±a root mean square deviation from the backbone atoms of said amino acids is not more than 1.0 Å.

36. The method of claim 35, wherein the±a root mean square deviation from the backbone atoms of said amino acids is not more than 0.5 Å.

\* \* \* \* \*

SEQUENCE LISTING

```
<160> NUMBER OF SEQ ID NOS: 16

<210> SEQ ID NO 1
<211> LENGTH: 81
<212> TYPE: PRT
<213> ORGANISM: Bacillus subtilis

<400> SEQUENCE: 1

Gly Pro Leu Gly Ser Ala Asp Thr Leu Glu Arg Val Thr Lys Ile Ile
1               5                   10                  15

Val Asp Arg Leu Gly Val Asp Glu Ala Asp Val Lys Leu Glu Ala Ser
            20                  25                  30

Phe Lys Glu Asp Leu Gly Ala Asp Ser Leu Asp Val Val Glu Leu Val
        35                  40                  45

Met Glu Leu Glu Asp Glu Phe Asp Met Glu Ile Ser Asp Glu Asp Ala
    50                  55                  60

Glu Lys Ile Ala Thr Val Gly Asp Ala Val Asn Tyr Ile Gln Asn Gln
65                  70                  75                  80

Gln

<210> SEQ ID NO 2
<211> LENGTH: 120
<212> TYPE: PRT
<213> ORGANISM: Bacillus subtilis

<400> SEQUENCE: 2

Ala Tyr Gly Ile Gly Leu Asp Ile Thr Glu Leu Lys Arg Ile Ala Ser
1               5                   10                  15

Met Ala Gly Arg Gln Lys Arg Phe Ala Glu Arg Ile Leu Thr Arg Ser
            20                  25                  30

Glu Leu Asp Gln Tyr Tyr Glu Leu Ser Glu Lys Arg Lys Asn Glu Phe
        35                  40                  45

Leu Ala Gly Arg Phe Ala Ala Lys Glu Ala Phe Ser Lys Ala Phe Gly
    50                  55                  60
```

Thr Gly Ile Gly Arg Gln Leu Ser Phe Gln Asp Ile Glu Ile Arg Lys
65                  70                  75                  80

Asp Gln Asn Gly Lys Pro Tyr Ile Ile Cys Thr Lys Leu Ser Gln Ala
            85                  90                  95

Ala Val His Val Ser Ile Thr His Thr Lys Glu Tyr Ala Ala Ala Gln
            100                 105                 110

Val Val Ile Glu Arg Leu Ser Ser
            115                 120

<210> SEQ ID NO 3
<211> LENGTH: 122
<212> TYPE: PRT
<213> ORGANISM: Aquifex sp.

<400> SEQUENCE: 3

Met Ile Gly Val Asp Ile Val Lys Asn Glu Arg Ile Lys Asp Ala Leu
1               5                   10                  15

Glu Arg Phe Gly Asp Lys Phe Leu Asp Arg Ile Tyr Thr Lys Arg Glu
            20                  25                  30

Leu Glu Tyr Cys Tyr Ala His Cys Asp Phe Leu Pro Cys Leu Ala Ala
        35                  40                  45

Arg Trp Ala Gly Lys Glu Ala Val Leu Lys Ala Phe Tyr Thr Glu Phe
    50                  55                  60

Lys Ile Phe Leu Arg Phe Lys Glu Ile Glu Ile Leu Gly Asn Arg Gly
65                  70                  75                  80

Arg Pro Pro Thr Val Val Ile Asn Arg Glu Gly Val Glu Glu Ile Leu
            85                  90                  95

Lys Asn Tyr Glu Val Ile Val Ser Leu Ser His Glu Arg Asp Tyr Ser
            100                 105                 110

Val Ala Val Ala Tyr Ile Lys Lys Lys Ser
            115                 120

<210> SEQ ID NO 4
<211> LENGTH: 122
<212> TYPE: PRT
<213> ORGANISM: Chlamydophila sp.

<400> SEQUENCE: 4

Met Glu Ile Ile His Ile Gly Thr Asp Ile Ile Glu Ile Ser Arg Ile
1               5                   10                  15

Arg Glu Ala Ile Ala Thr His Gly Asn Arg Leu Leu Asn Arg Ile Phe
            20                  25                  30

Thr Glu Ala Glu Gln Lys Tyr Cys Leu Glu Lys Thr Asp Pro Ile Pro
        35                  40                  45

Ser Phe Ala Gly Arg Phe Ala Gly Lys Glu Ala Val Ala Lys Ala Leu
    50                  55                  60

Gly Thr Gly Ile Gly Ser Val Ala Trp Lys Asp Ile Glu Val Phe
65                  70                  75                  80

Lys Val Ser His Gly Pro Glu Val Leu Leu Pro Ser His Val Tyr Ala
            85                  90                  95

Lys Ile Gly Ile Ser Lys Val Ile Leu Ser Ile Ser His Cys Lys Glu
            100                 105                 110

Tyr Ala Thr Ala Thr Ala Ile Ala Leu Ala
            115                 120

<210> SEQ ID NO 5

```
<211> LENGTH: 119
<212> TYPE: PRT
<213> ORGANISM: Helicobacter sp.

<400> SEQUENCE: 5

Met Ile Gly Ile Asp Ile Val Ser Ile Ala Arg Ile Glu Lys Cys Val
1               5                   10                  15

Lys Arg Phe Lys Met Lys Phe Leu Glu Arg Phe Leu Ser Pro Ser Glu
            20                  25                  30

Ile Val Leu Cys Lys Asp Lys Ser Ser Ile Ala Gly Phe Phe Ala
        35                  40                  45

Leu Lys Glu Ala Cys Ser Lys Ala Leu Gln Val Gly Ile Gly Lys Glu
    50                  55                  60

Leu Ser Phe Leu Asp Ile Lys Ile Ser Lys Ser Pro Lys Asn Ala Pro
65                  70                  75                  80

Leu Ile Thr Leu Ser Lys Glu Lys Met Asp Tyr Phe Asn Ile Gln Ser
                85                  90                  95

Leu Ser Ala Ser Ile Ser His Asp Ala Gly Phe Ala Ile Ala Val Val
            100                 105                 110

Val Val Ser Ser Ser Asn Glu
        115

<210> SEQ ID NO 6
<211> LENGTH: 119
<212> TYPE: PRT
<213> ORGANISM: Staphylococcus sp.

<400> SEQUENCE: 6

Met Ile His Gly Ile Gly Val Asp Leu Ile Glu Ile Asp Arg Ile Gln
1               5                   10                  15

Ala Leu Tyr Ser Lys Gln Pro Lys Leu Val Glu Arg Ile Leu Thr Lys
            20                  25                  30

Asn Glu Gln His Lys Phe Asn Asn Phe Thr His Glu Gln Arg Lys Ile
            35                  40                  45

Glu Phe Leu Ala Gly Arg Phe Ala Thr Lys Glu Ala Phe Ser Lys Ala
    50                  55                  60

Leu Gly Thr Gly Leu Gly Lys His Val Ala Phe Asn Asp Ile Asp Cys
65                  70                  75                  80

Tyr Asn Asp Glu Leu Gly Lys Pro Lys Ile Asp Tyr Glu Gly Phe Ile
                85                  90                  95

Val His Val Ser Ile Ser His Thr Glu His Tyr Ala Met Ser Gln Val
            100                 105                 110

Val Leu Glu Lys Ser Ala Phe
        115

<210> SEQ ID NO 7
<211> LENGTH: 169
<212> TYPE: PRT
<213> ORGANISM: Thermotoga sp.

<400> SEQUENCE: 7

Met Ile Val Gly Val Gly Ile Asp Val Leu Glu Val Glu Arg Val Pro
1               5                   10                  15

Glu Lys Phe Ala Glu Arg Ile Leu Gly Glu Ser Glu Lys Arg Leu Phe
            20                  25                  30

Leu Thr Arg Lys Arg Arg Arg Glu Phe Ile Ala Gly Arg Phe Ala Leu
            35                  40                  45
```

```
Lys Glu Ala Phe Phe Lys Ala Leu Gly Thr Gly Leu Asn Gly His Ser
        50                  55                  60

Phe Thr Asp Val Glu Phe Leu Glu Ser Asn Gly Lys Pro Val Leu Cys
 65                  70                  75                  80

Val His Lys Asp Phe Gly Phe Phe Asn Tyr Ala His Val Ser Leu Ser
                    85                  90                  95

His Asp Arg Phe Ala Val Ala Leu Val Val Leu Glu Lys Arg Lys Gly
               100                 105                 110

Asp Ile Ile Val Glu Gly Asp Glu Ser Phe Leu Arg Lys Arg Phe Glu
               115                 120                 125

Val Leu Glu Arg Ser Val Glu Gly Trp Glu Ile Glu Thr Ser Leu Pro
        130                 135                 140

Pro Phe Thr Leu Lys Lys Leu Leu Glu Ser Ser Gly Cys Arg Leu Val
145                 150                 155                 160

Arg Tyr Gly Asn Ile Leu Ile Gly Glu
                    165

<210> SEQ ID NO 8
<211> LENGTH: 126
<212> TYPE: PRT
<213> ORGANISM: Escherichia coli

<400> SEQUENCE: 8

Met Ala Ile Leu Gly Leu Gly Thr Asp Ile Val Glu Ile Ala Arg Ile
  1               5                  10                  15

Glu Ala Val Ile Ala Arg Ser Gly Asp Arg Leu Ala Arg Arg Val Leu
                 20                  25                  30

Ser Asp Asn Glu Trp Ala Ile Trp Lys Thr His His Gln Pro Val Arg
             35                  40                  45

Phe Leu Ala Lys Arg Phe Ala Val Lys Glu Ala Ala Ala Lys Ala Phe
         50                  55                  60

Gly Thr Gly Ile Arg Asn Gly Leu Ala Phe Asn Gln Phe Glu Val Phe
 65                  70                  75                  80

Asn Asp Glu Leu Gly Lys Pro Arg Leu Arg Leu Trp Gly Glu Ala Leu
                 85                  90                  95

Lys Leu Ala Glu Lys Leu Gly Val Ala Asn Met His Val Thr Leu Ala
                100                 105                 110

Asp Glu Arg His Tyr Ala Cys Ala Thr Val Ile Ile Glu Ser
            115                 120                 125

<210> SEQ ID NO 9
<211> LENGTH: 126
<212> TYPE: PRT
<213> ORGANISM: Rickettsia sp.

<400> SEQUENCE: 9

Met Leu Ile Gly Val Gly Thr Asp Ile Val Gln Ile Pro Arg Ile Glu
  1               5                  10                  15

Lys Ile Leu Asn Ile Tyr Gln Glu Leu Phe Ala Lys Lys Ile Leu Ala
                 20                  25                  30

Leu Lys Glu Leu Lys Gln Phe Thr Leu Leu Asn Lys Thr Asn His Ala
             35                  40                  45

Thr Phe Leu Ala Lys Arg Phe Ser Ala Lys Glu Ala Val Ser Lys Ala
         50                  55                  60

Phe Gly Val Gly Ile Gly Arg Gly Ile Asn Phe Lys Asp Ile Thr Ile
 65                  70                  75                  80
```

-continued

```
Leu Asn Asp Asn Leu Gly Lys Pro Thr Val Glu Ile Ser Ser His Tyr
                85                  90                  95

Thr Asn Lys Leu Ala Pro Phe Asn Ile His Leu Ser Leu Ser Asp Asp
            100                 105                 110

Tyr Pro Ile Cys Ile Ala Phe Ala Ile Ile Glu Ser Asn Cys
        115                 120                 125

<210> SEQ ID NO 10
<211> LENGTH: 123
<212> TYPE: PRT
<213> ORGANISM: Streptomyces sp.

<400> SEQUENCE: 10

Met Ser Ile Ile Gly Val Gly Ile Asp Val Ala Glu Val Glu Arg Phe
1               5                   10                  15

Gly Ala Ala Leu Glu Arg Thr Pro Ala Leu Ala Gly Arg Leu Phe Leu
                20                  25                  30

Glu Ser Glu Leu Leu Leu Pro Gly Gly Glu Arg Arg Gly Val Ala Ser
            35                  40                  45

Leu Ala Ala Arg Phe Ala Ala Lys Glu Ala Leu Ala Lys Ala Leu Gly
        50                  55                  60

Ala Pro Ala Gly Leu Leu Trp Thr Asp Ala Glu Val Trp Val Glu Ala
65                  70                  75                  80

Gly Gly Arg Pro Arg Leu Arg Val Thr Gly Thr Val Ala Ala Arg Ala
                85                  90                  95

Ala Glu Leu Gly Val Ala Ser Trp His Val Ser Leu Ser His Asp Ala
            100                 105                 110

Gly Ile Ala Ser Ala Val Val Ile Ala Glu Gly
        115                 120

<210> SEQ ID NO 11
<211> LENGTH: 125
<212> TYPE: PRT
<213> ORGANISM: Treponema sp.

<400> SEQUENCE: 11

Met Ile Ile Gly Val Gly Ile Asp Ile Val Glu Ile Glu Arg Phe Val
1               5                   10                  15

Ser Trp Thr His Asn Val Arg Leu Leu Arg Arg Phe His Gln Glu
                20                  25                  30

Glu Ile Val Asp Phe Phe Lys Asn His Met Arg Ala Gln Phe Leu Ala
            35                  40                  45

Thr Arg Phe Ala Ala Lys Glu Ala Phe Gly Lys Ala Leu Gly Thr Gly
        50                  55                  60

Leu Arg Asn Met Glu Leu Arg Asn Ile Arg Val Cys Gln Asn Gly Trp
65                  70                  75                  80

Gly Lys Pro Arg Leu Glu Val Tyr Gly Ala Ala Gln Ala Met Leu Ala
                85                  90                  95

Ala Thr Gly Gly Thr His Ile Gln Val Ser Leu Thr His Glu Arg Glu
            100                 105                 110

Val Ala Ser Ala Ile Val Ile Glu Gly Glu Pro Leu
        115                 120                 125

<210> SEQ ID NO 12
<211> LENGTH: 121
<212> TYPE: PRT
<213> ORGANISM: Bacillus sp.
```

```
<400> SEQUENCE: 12

Met Ile Tyr Gly Ile Gly Leu Asp Ile Thr Glu Leu Lys Arg Ile Ala
 1               5                  10                  15

Ser Met Ala Gly Arg Gln Lys Arg Phe Ala Glu Arg Ile Leu Thr Arg
             20                  25                  30

Ser Glu Leu Asp Gln Tyr Tyr Glu Leu Ser Glu Lys Arg Lys Asn Glu
         35                  40                  45

Phe Leu Ala Gly Arg Phe Ala Ala Lys Glu Ala Phe Ser Lys Ala Phe
     50                  55                  60

Gly Thr Gly Ile Gly Arg Gln Leu Ser Phe Gln Asp Ile Glu Ile Arg
 65                  70                  75                  80

Lys Asp Gln Asn Gly Lys Pro Tyr Ile Ile Cys Thr Lys Leu Ser Gln
                 85                  90                  95

Ala Ala Val His Val Ser Ile Thr His Thr Lys Glu Tyr Ala Ala Ala
            100                 105                 110

Gln Val Val Ile Glu Arg Leu Ser Ser
            115                 120

<210> SEQ ID NO 13
<211> LENGTH: 139
<212> TYPE: PRT
<213> ORGANISM: Bradyrhizobium sp.

<400> SEQUENCE: 13

Met Ile Ile Gly Ile Gly Ser Asp Leu Ile Asp Ile Thr Arg Val Gly
 1               5                  10                  15

Lys Val Ile Glu Arg His Gly Glu Arg Phe Leu Asp Arg Ile Phe Thr
             20                  25                  30

Ala Ala Glu Arg Ala Lys Ala Glu Arg Arg Ala Lys Asn Glu Lys Met
         35                  40                  45

Val Val Ala Thr Tyr Ala Lys Arg Phe Ala Ala Lys Glu Ala Cys Ser
     50                  55                  60

Lys Ala Leu Gly Thr Gly Ile Arg Arg Gly Val Trp Trp Arg Asp Met
 65                  70                  75                  80

Gly Val Val Asn Leu Pro Gly Gly Arg Pro Thr Met Gln Leu Thr Gly
                 85                  90                  95

Gly Ala Leu Ala Arg Leu Gln Ala Leu Thr Pro Asp Gly Phe Glu Ala
            100                 105                 110

Arg Ile Asp Val Ser Ile Thr Asp Trp Pro Leu Ala Gln Ala Phe
            115                 120                 125

Val Ile Ile Ser Ala Val Pro Leu Ala Lys Ser
        130                 135

<210> SEQ ID NO 14
<211> LENGTH: 130
<212> TYPE: PRT
<213> ORGANISM: Mycobacterium sp.

<400> SEQUENCE: 14

Met Gly Ile Val Gly Val Gly Ile Asp Leu Val Ser Ile Pro Asp Phe
 1               5                  10                  15

Ala Glu Gln Val Ser Gln Pro Gly Thr Val Phe Met Thr Ile Phe Thr
             20                  25                  30

Pro Gly Glu Arg Arg Asp Ala Ser Val Lys Ser Ser Ala Val Cys
         35                  40                  45

His Leu Ala Ala Arg Trp Ala Val Lys Glu Ala Val Ile Lys Ala Trp
```

```
                    50                  55                  60
Ser Gly Ser Arg Phe Ala Gln Arg Pro Met Leu Pro Glu Asn Ile His
 65                  70                  75                  80

Arg Asp Ile Glu Val Val Asn Asp Met Trp Gly Arg Pro Arg Val Arg
                 85                  90                  95

Leu Thr Gly Ala Ile Ala Lys His Leu Thr Asp Val Thr Ile His Val
                100                 105                 110

Ser Leu Thr His Glu Gly Asp Ile Ala Ala Ala Val Val Ile Leu Glu
                115                 120                 125

Val Leu
    130

<210> SEQ ID NO 15
<211> LENGTH: 77
<212> TYPE: PRT
<213> ORGANISM: Escherichia coli

<400> SEQUENCE: 15

Ser Thr Ile Glu Glu Arg Val Lys Lys Ile Ile Gly Glu Gln Leu Gly
 1               5                  10                  15

Val Lys Gln Glu Glu Val Thr Asn Asn Ala Ser Phe Val Glu Asp Leu
                20                  25                  30

Gly Ala Asp Ser Leu Asp Thr Val Glu Leu Val Met Ala Leu Glu Glu
                35                  40                  45

Glu Phe Asp Thr Glu Ile Pro Asp Glu Glu Ala Glu Lys Ile Thr Thr
     50                  55                  60

Val Gln Ala Ala Ile Asp Tyr Ile Asn Gly His Gln Ala
 65                  70                  75

<210> SEQ ID NO 16
<211> LENGTH: 86
<212> TYPE: PRT
<213> ORGANISM: Streptomyces coelicolor

<400> SEQUENCE: 16

Met Ala Thr Leu Leu Thr Thr Asp Asp Leu Arg Arg Ala Leu Val Glu
 1               5                  10                  15

Cys Ala Gly Glu Thr Asp Gly Thr Asp Leu Ser Gly Asp Phe Leu Asp
                20                  25                  30

Leu Arg Phe Glu Asp Ile Gly Tyr Asp Ser Leu Ala Leu Met Glu Thr
                35                  40                  45

Ala Ala Arg Leu Glu Ser Arg Tyr Gly Val Ser Ile Pro Asp Asp Val
     50                  55                  60

Ala Gly Arg Val Asp Thr Pro Arg Glu Leu Leu Asp Leu Ile Asn Gly
 65                  70                  75                  80

Ala Leu Ala Glu Ala Ala
                85
```